(12) United States Patent
Boyd-Kirkup et al.

(10) Patent No.: US 11,780,933 B2
(45) Date of Patent: *Oct. 10, 2023

(54) HER3 ANTIGEN-BINDING MOLECULES

(71) Applicant: Hummingbird Bioscience Pte. Ltd., Singapore (SG)

(72) Inventors: Jerome Douglas Boyd-Kirkup, Singapore (SG); Piers Ingram, Singapore (SG); Dipti Thakkar, Singapore (SG); Zhihao Wu, Singapore (SG); Konrad Paszkiewicz, Singapore (SG); Vicente Sancenon, Singapore (SG); Siyu Guan, Singapore (SG)

(73) Assignee: Hummingbird Bioscience Pte. Ltd., Singapore (SG)

( * ) Notice: Subject to any disclaimer, the term of this patent is extended or adjusted under 35 U.S.C. 154(b) by 566 days.

This patent is subject to a terminal disclaimer.

(21) Appl. No.: 16/805,620

(22) Filed: Feb. 28, 2020

(65) Prior Publication Data
US 2020/0308275 A1   Oct. 1, 2020

Related U.S. Application Data

(63) Continuation of application No. 16/596,723, filed on Oct. 8, 2019, now Pat. No. 10,662,241, which is a continuation of application No. PCT/EP2019/058035, filed on Mar. 29, 2019.

(51) Int. Cl.
| | |
|---|---|
| *A61K 39/395* | (2006.01) |
| *C07K 16/32* | (2006.01) |
| *C07K 16/28* | (2006.01) |
| *A61P 35/00* | (2006.01) |
| *C07K 14/725* | (2006.01) |
| *C12N 15/62* | (2006.01) |
| *C12N 15/85* | (2006.01) |
| *A61K 39/00* | (2006.01) |

(52) U.S. Cl.
CPC ............. *C07K 16/32* (2013.01); *A61P 35/00* (2018.01); *C07K 14/7051* (2013.01); *C07K 16/28* (2013.01); *C12N 15/62* (2013.01); *C12N 15/85* (2013.01); *A61K 2039/505* (2013.01); *C07K 2317/24* (2013.01); *C07K 2317/33* (2013.01); *C07K 2317/522* (2013.01); *C07K 2317/524* (2013.01); *C07K 2317/526* (2013.01); *C07K 2317/565* (2013.01); *C07K 2317/622* (2013.01); *C07K 2317/72* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,625,558 B2 | 12/2009 | Greene et al. |
| 7,744,882 B2 | 6/2010 | Maihle et al. |
| 8,362,215 B2 | 1/2013 | Keyt |
| 8,735,551 B2 | 5/2014 | Garner et al. |
| 8,791,244 B2 | 7/2014 | Daly et al. |
| 8,895,001 B2 | 11/2014 | Moyo et al. |
| 9,127,065 B2 | 9/2015 | Chardes et al. |
| 9,725,512 B2 | 8/2017 | Bossenmaier et al. |
| 9,725,520 B2 | 8/2017 | Zhang et al. |
| 10,662,241 B1 | 5/2020 | Boyd-Kirkup et al. |
| 11,208,498 B2 | 12/2021 | Boyd-Kirkup et al. |
| 2004/0082510 A1 | 4/2004 | Ullrich et al. |
| 2014/0134170 A1 | 5/2014 | Garcia et al. |
| 2015/0152508 A1 | 6/2015 | Schneider et al. |
| 2016/0237162 A1 | 8/2016 | Chowdhury et al. |
| 2017/0037145 A1 | 2/2017 | Geuijen et al. |
| 2017/0166654 A1 | 6/2017 | Schneider et al. |
| 2017/0190788 A1 | 7/2017 | Lavallee et al. |
| 2017/0233490 A1 | 8/2017 | Bossenmaier et al. |
| 2017/0240648 A1 | 8/2017 | Schlessinger et al. |
| 2017/0291956 A1 | 10/2017 | Livingston et al. |
| 2017/0306049 A1 | 10/2017 | Yarden et al. |
| 2018/0171027 A1 | 6/2018 | Lavallee et al. |
| 2019/0300624 A1 | 10/2019 | Boyd-Kirkup et al. |
| 2021/0024651 A1 | 1/2021 | Boyd-Kirkup et al. |

FOREIGN PATENT DOCUMENTS

| | | |
|---|---|---|
| EP | 2 917 243 B1 | 3/2018 |
| WO | WO 2011/144749 A1 | 11/2011 |
| WO | WO 2013/084148 A2 | 6/2013 |
| WO | WO 2014/072305 A1 | 5/2014 |
| WO | WO 2014/072306 A1 | 5/2014 |
| WO | WO 2014/131019 A2 | 8/2014 |
| WO | WO 2015/173248 A1 | 11/2015 |

(Continued)

OTHER PUBLICATIONS

Boyd-Kirkup et al (Proceedings of the American Association for Cancer Research Annual Meeting, 2017: Apr. 1-5, 2017; Washington DC. Philadelphia (PA): AACR; Cancer Research, 2017; 77(13 Suppl); Abstract 24) (IDS).*
Thakker et al (European Journal of Cancer, Nov. 13, 2018; 103S1; e36-e37; Poster Session; abstract 87) (IDS).*
Edwards et al (Journal of Molecular Biology, 2003, 334:103-118).*
U.S. Appl. No. 16/170,370, filed Oct. 25, 2018, Boyd-Kirkup et al.
U.S. Appl. No. 16/596,723, filed Oct. 8, 2019, Boyd-Kirkup et al.
PCT/EP2018/058259, Sep. 21, 2018, International Search Report and Written Opinion.
PCT/EP2019/058035, May 29, 2019, International Search Report and Written Opinion.
Invitation to Pay Additional Fees for Application No. PCT/EP2018/058259, dated Jul. 30, 2018.

(Continued)

*Primary Examiner* — Laura B Goddard
(74) *Attorney, Agent, or Firm* — Wolf, Greenfield & Sacks, P.C.

(57) ABSTRACT

HER3 antigen-binding molecules are disclosed. Also disclosed are nucleic acids and expression vectors encoding, compositions comprising, and methods using, the HER3 antigen-binding molecules.

13 Claims, 105 Drawing Sheets

Specification includes a Sequence Listing.

(56) References Cited

FOREIGN PATENT DOCUMENTS

WO WO 2017/015008 A1 1/2017
WO WO 2017/214433 A1 12/2017
WO WO 2017/219995 A1 12/2017

OTHER PUBLICATIONS

International Preliminary Report on Patentability for Application No. PCT/EP2018/058259, dated Oct. 8, 2020.
International Preliminary Report on Patentability for Application No. PCT/EP2019/058035, dated Oct. 8, 2020.
Extended European Search Report for Application No. 20209917.2, dated Jun. 23, 2021.
Apantaku, Breast cancer diagnosis and screening. Am Fam Physician. Aug. 1, 2000;62(3):596-602, 605-6.
Martin et al., Genetic and hormonal risk factors in breast cancer. J Natl Cancer Inst. Jul. 19, 2000;92(14):1126-35. doi: 10.1093/jnci/92.14.1126.
International Search Report and Written Opinion for Application No. PCT/EP2018/058259, dated Sep. 21, 2018.
International Search Report and Written Opinion for Application No. PCT/EP2019/058035, dated May 29, 2019.
Aurisicchio et al., The promise of anti-ErbB3 monoclonals as new cancer therapeutics. Oncotarget. Aug. 2012;3(8):744-58.
Boyd-Kirkup et al., Abstract 24: HMBD001, a novel anti-ErbB3 antibody with a unique mechanism of action, effectively inhibits tumor growth in pre-clinical models of ErbB3+ solid tumors. Cancer Res. 2017;77(13 Suppl):Abstract nr 24. doi:10.1158/1538-7445.AM2017-24.
Boyd-Kirkup et al., HMBD001, a novel anti-ErbB3 antibody with a unique mechanism of action, effectively inhibits tumor growth in pre-clinical models of ErbB3+ solid tumors. Presented at AACR Annual Meeting Apr. 2, 2017. Abstract. 1 page.
Boyd-Kirkup et al., HMBD001, a novel anti-ErbB3 antibody with a unique mechanism of action, effectively inhibits tumor growth in pre-clinical models of ErbB3+ solid tumors. Presented at AACR Annual Meeting Apr. 2, 2017. Poster. 1 page.
Boyd-Kirkup et al., HMBD001-10D1, a novel humanized anti-HER3 antibody with a unique mechanism of action, demonstrates superior tumor inhibition in multiple tumor models compared to other EGFR family therapies. Abstracts, 30th EORTC-NCI-AARC Symposium. Eur. J. Cancer. Nov. 13, 2018;103S1(87(PB-038)):e36-e37.
Boyd-Kirkup et al., HMBD001-10D1, a novel humanized anti-HER3 antibody with a unique mechanism of action, demonstrates superior tumor inhibition in multiple tumor models compared to other EGFR family therapies. Presented at EORTC-NCI-AACR Symposium Nov. 13, 2018. Poster. 1 page.
Gaborit et al., Emerging anti-cancer antibodies and combination therapies targeting HER3/ERBB3. Hum Vaccin Immunother. Mar. 3, 2016;12(3):576-92. doi:10.1080/21645515.2015.1102809. Epub Nov. 3, 2015.
Garner et al., An antibody that locks HER3 in the inactive conformation inhibits tumor growth driven by HER2 or neuregulin. Cancer Res. Oct. 1, 2013;73(19):6024-35. doi:10.1158/0008-5472.CAN-13-1198. Epub Aug. 8, 2013.
Kim et al., ISU104, a fully human antibody targeting a specific epitope on the ErbB3, displays potent inhibition of tumor growth in multiple xenograft tumor models [abstract]. Proceedings of the American Association for Cancer Research Annual Meeting 2018, Chicago, IL. Cancer Research. Jul. 2018;78(13 Suppl):Abstract nr 830. doi: 10.1158/1538-7445.AM2018-830.
Lee et al., Inhibition of ErbB3 by a monoclonal antibody that locks the extracellular domain in an inactive configuration. Proc Natl Acad Sci U S A. Oct. 27, 2015;112(43):13225-30. doi: 10.1073/pnas.1518361112. Epub Oct. 12 2015.
Malm et al., Targeting HER3 using mono- and bispecific antibodies or alternative scaffolds. MAbs. Oct. 2016;8(7):1195-1209. Epub Aug. 17, 2016.
Singer et al., Identification of a heregulin binding site in HER3 extracellular domain. J Biol Chem. Nov. 23, 2001;276(47):44266-74. Epub Sep. 12, 2001.
Thakkar et al., HMBD001-10D1, a novel humanized anti-HER3 antibody with a unique mechanism of action, demonstrates superior tumor inhibition in multiple tumor models compared to other EGFR family therapies. European J. Cancer, Nov. 13, 2018;103(Suppl. 1):e36-e37.
Zhang et al., HER3/ErbB3, an emerging cancer therapeutic target. Acta Biochim Biophys Sin (Shanghai). Jan. 2016;48(1):39-48. doi: 10.1093/abbs/gmv103. Epub Oct. 24, 2015.
EP 20209917.2, Jun. 23, 2021, Extended European Search Report.

\* cited by examiner

| Cell line | \*RNA expression (RMA log2 LN) | | | | | | \*\*Protein expression (MFI fold over isotype) | |
|---|---|---|---|---|---|---|---|---|
| | HER1 | HER2 | HER3 | HER4 | IGF1R | MET | HER2 | HER3 |
| N87 | 7.08 | 13.18 | 9.67 | 3.83 | 4.08 | 4.22 | 358 | 618 | 5.6 |
| SNU16 | 6.88 | 7.8 | 11.06 | 4.04 | 3.78 | 4.26 | 13.6 | 28.3 | 1.87 |
| HT29 | 6.54 | 8.11 | 10.8 | 3.81 | 3.83 | 4.53 | 27.5 | 20.3 | 4.2 |
| FaDu | 7.99 | 7.36 | 8.35 | 4.01 | 3.89 | 4.96 | 65.1 | 11.6 | 1.5 |
| A549 | 7.29 | 6.79 | 5.18 | 3.85 | 4.2 | 8.81 | 19 | 17.7 | 7.4 |
| HCC95 | 7.33 | 7.06 | 7.31 | 3.85 | 4.19 | 11.24 | 100.8 | 44.5 | 8.2 |
| OvCAR8 | 6.19 | 6.72 | 8.24 | 3.86 | 4.72 | 6.65 | 44.5 | 130.5 | 4.7 |
| ACHN | 7.81 | 6.78 | 6.32 | 3.8 | 4.66 | 8.04 | 93.6 | 67.5 | 4 |

\*CCLE gene expression data is log2-transformed robust multi-array (RMA)-normalized data generated from Affymetrix gene chips. The expression values in rather are relative \*\* Median fluorescence intensity normalized to isotype calculated by FlowLogic.

Figure 16A

| Clones | Heavy Chain Homology | Light Chain Homology | Developability | | | | | | | pI_HC | pI_LC |
|---|---|---|---|---|---|---|---|---|---|---|---|
| | | | Deamidation (NS, NG, NH, NN) | Isomerization (DS, DG) | Protease Cleavage (DP) | Free Cys | Exposed M | Glycosylation | Immunogenicity (HC+LC) | | |
| 10D1_c75 | 82.5%(Hu) | 80.0%(Ma) | NG, | None | None | None | YES (CDR3) | NFT | 3+6 | 8.102 | 6.615 |
| 10D1_c76 | 83.5%(Hu) | 77.9%(Ma) | NG, | None | None | None | YES (CDR3) | NPS | 3+5 | 8.121 | 6.614 |
| 10D1_c77 | 83.5%(Hu) | 78.5%(Ma) | NG, | None | None | None | YES (CDR3) | NPS | 4+3 | 8.121 | 7.618 |
| 10D1_c78 | 83.5%(Hu) | 81.1%(Ma) | None | None | None | None | YES (CDR3) | NPS | 3+3 | 8.591 | 8.128 |
| V12b78L | 88.7%(Hu) | 81.1%(Ma) | None | None | None | None | YES (CDR3) | NPS | 3+3 | 8.453 | 8.128 |
| 10D1_c85 | 82.5%(Hu) | 81.1%(Ma) | None | None | None | None | YES (CDR3) | NPS | 1+3 | 8.952 | 8.578 |
| 10D1_c85_op_t1 | 83.5%(Hu) | 81.1%(Ma) | None | None | None | None | NO | NPS | 0+3 | 8.6 | 8.578 |
| 10D1_c85_op_t2 | 83.5%(Hu) | 80.0%(Ma) | None | None | None | None | NO | NPS | 0+3 | 8.952 | 8.578 |
| 10D1_c87 | 82.5%(Hu) | 85.3% (Hu/Ma) | NG, | None | None | None | YES (CDR3) | NPS | 3+5 | 8.113 | 4.646 |
| 10D1_c89 | 89.9%(Hu) | 80.0%(Ma) | None | None | None | None | YES (CDR3) | None | 3+4 | 7.965 | 6.545 |
| 10D1_c90 | 89.9%(Hu) | 80.0%(Ma) | None | None | None | None | YES (CDR3) | None | 3+4 | 7.965 | 5.380 |
| 10D1_c91 | 87.9%(Hu) | 84.2 (Hu/Ma) | None | None | None | None | YES (CDR3) | None | 3+3 | 7.935 | 7.469 |
| 10D1_c92 | 82.5%(Hu) | 78.9%(Ma) | None | None | None | None | YES (CDR3) | N.A. | 4+6 | 8.07 | 6.46 |
| 10D1_c93 | 82.5%(Hu) | 83.1%(Ma) | NG | None | None | None | YES (CDR3) | NPS | 3+5 | 8.13 | 7.535 |

Figure 37

$$k_{on} = 1.8e^5 M^{-1} s^{-1} \quad K_D = 34 \text{ nM} \quad k_{dis} = 0.61e^{-2} s^{-1}$$

| | | | | | | | | | |
|---|---|---|---|---|---|---|---|---|---|
| FcRn | Recycling (Increased affinity → Increased half life) | Medium | hgG1: 737<br>hgG2: 540<br>hgG3: 585<br>hgG4: 717 | 47.6 | 37.4 | 54.6 | 6.43 | 10.3 | 16.5 | 11.5 |
| FcgRIIIA (V158) CD16A | Cell activation | Medium | hgG1: 252-500<br>hgG2: 14286<br>hgG3: 102<br>hgG4: 4000 | 986 | 82.1 | ND | ND | ND | 705 | 7050 |
| FcgRIIIA (F158) CD16A | Cell activation | Low | hgG1: 655-454<br>hgG2: 33333<br>hgG3: 130<br>hgG4: 5000 | ND | 162 | ND | ND | ND | 5380 | ND |
| FcgRIIA (H167) CD32A | Cell activation | Low | hgG1: 192-4486<br>hgG2: 2222<br>hgG3: 1124<br>hgG4: 5862 | 1800 | 561 | ND | 670 | ND | 1460 | 222 |
| FcgRIIA (R167) CD32A | Cell activation | Low | hgG1: 226-1550<br>hgG2: 10000<br>hgG3: 1099<br>hgG4: 4762 | 978 | 400 | ND | ND | ND | 1900 | 243 |
| FcgRIIB CD32B | Cell inhibition | Low | hgG1: 500-3275<br>hgG2: 30000<br>hgG3: 5862<br>hgG4: 5000 | ND | 580 | ND | ND | ND | ND | 1440 |

Figure 41A

| | | | | | | | | | | |
|---|---|---|---|---|---|---|---|---|---|---|
| moFcRn | FCGRT | Recycling (increased affinity → increased half life) | Medium | mlgG1: 1157<br>mlgG2a: 490<br>mlgG2b: 545<br>mlgG3: 140 | hlgG1: 72<br>hlgG2: 63<br>hlgG3: 230<br>hlgG4: 116 | 14.6 | 15.2 | 13.7 | 7.33 | 1.9 | 12.8 | 8.69 |
| moFcgRIV | CD16-2 | Cell activation | High | mlgG1: ND<br>mlgG2a: 34.5<br>mlgG2b: 59<br>mlgG3: ND | hlgG1: 280<br>hlgG2: ND<br>hlgG3: 170<br>hlgG4: 260000 | 1,810 | 55.4 | ND | ND | ND | 70.1 | ND |
| moFcgRIII | CD16 | Cell activation | Low | mlgG1: 3200<br>mlgG2a: 1460<br>mlgG2b: 1555<br>mlgG3: ND | hlgG1: 9360<br>hlgG2: 9700<br>hlgG3: 1400<br>hlgG4: 210000 | ND | ND | ND | ND | ND | ND | ND |
| moFcgRIIb | CD32 | Cell inhibition | Low | mlgG1: 301<br>mlgG2a: 2390<br>mlgG2b: 448<br>mlgG3: ND | hlgG1: 1100<br>hlgG2: 7900<br>hlgG3: 700<br>hlgG4: 11000 | ND | ND | ND | ND | ND | ND | ND |

Figure 41B

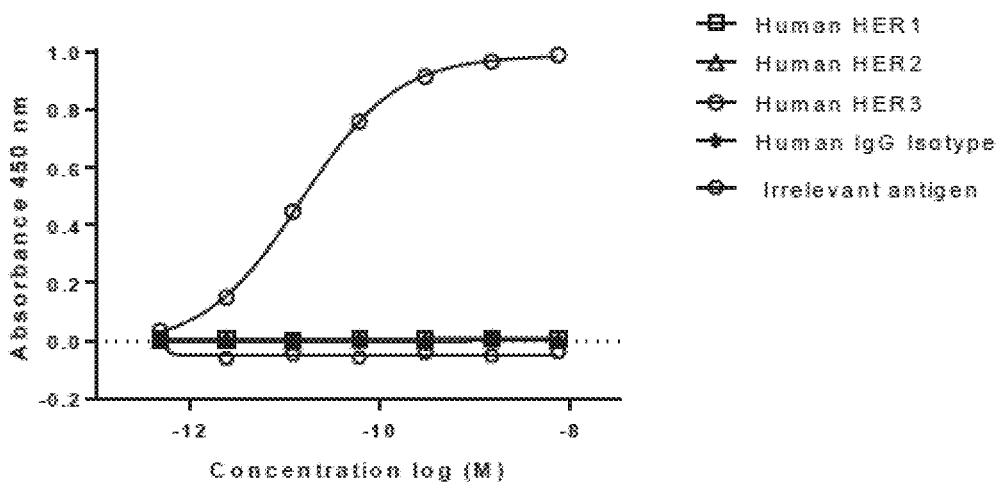
Figure 43
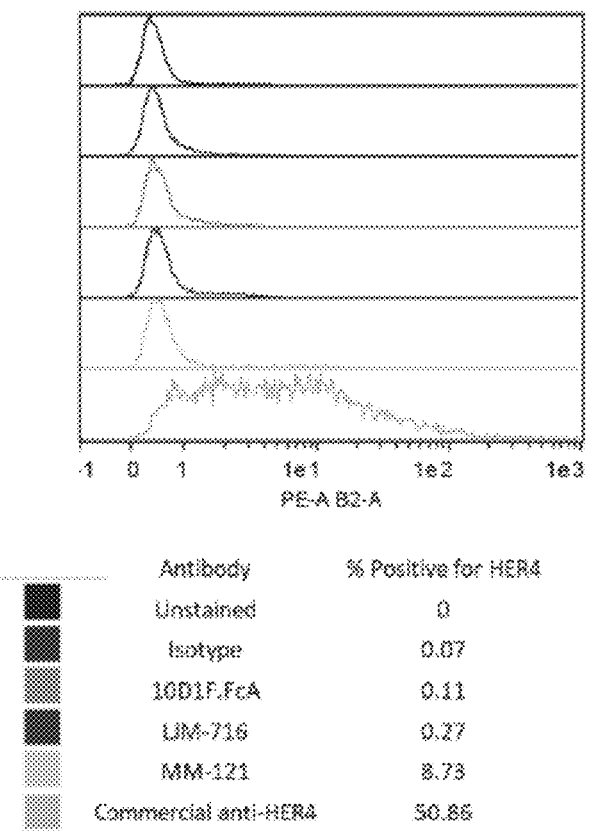
Figure 44

| Sourcing Antibody | Competing Antibody | | |
|---|---|---|---|
| | 1001 | Roche M-05-74 | Roche M-08-11 |
| 1001 | X | 0.5084 | 0.5614 |
| Roche M-05-74 | 0.5023 | X | 0.6424 |
| Roche M-08-11 | 0.4114 | x | x | s

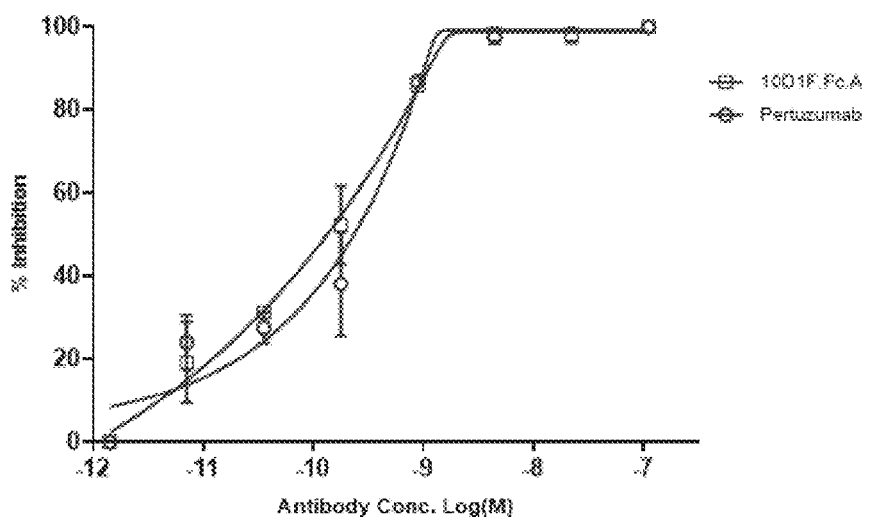
Figure 65
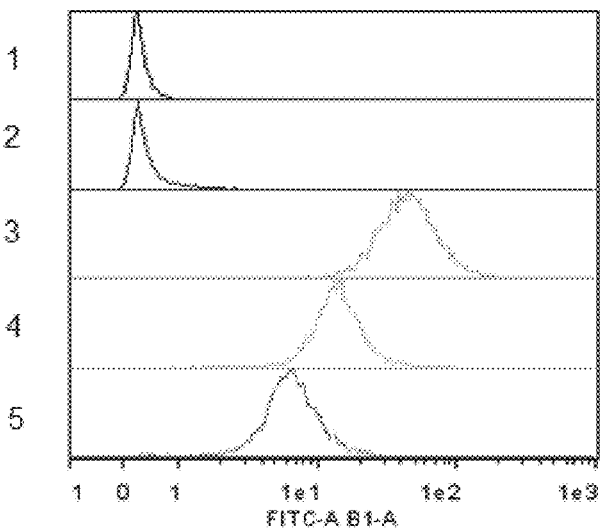
Figure 66A

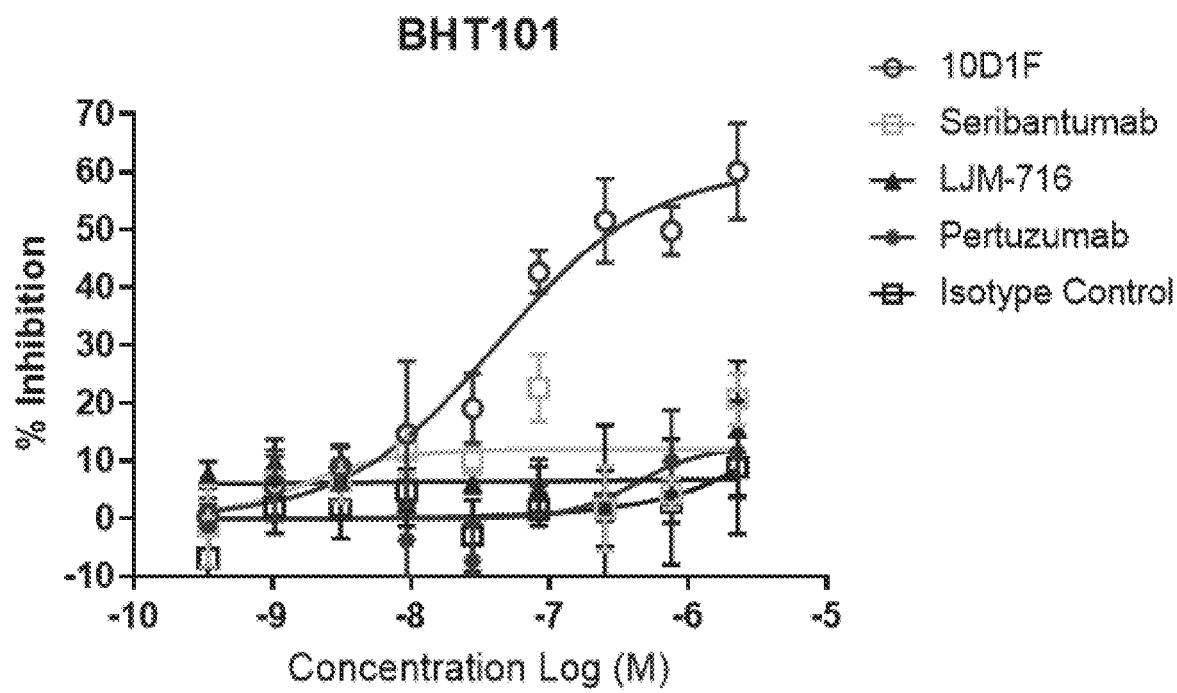
Figure 67A
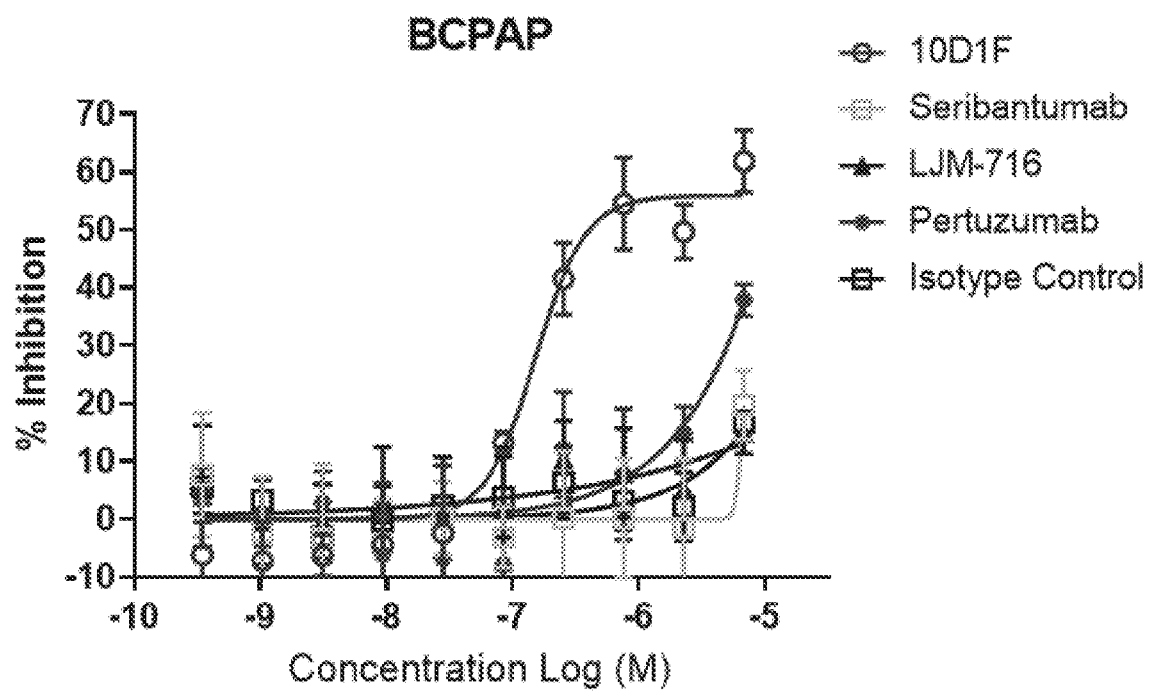

| Treatment Arm | Dose | Red Blood Cell | | | | | | Platelet count (10^9/L) |
|---|---|---|---|---|---|---|---|---|
| | | RBC Count (10^9/L) | Hemoglobin (g/dl) | Hematocrit (%) | Anemia Parameters | | | |
| | | | | | MCV (fml) | MCH (pg) | MCHC (g/dl) | |
| Vehicle | 0 | 10.59 | 17.075 | 52.9275 | 50 | 16.125 | 32.25 | 490.5 |
| Inhib | 10 mg/kg | 10.74 | 17.23 | 55.97 | 52.00 | 16.07 | 30.87 | 574.00 |
| | 25 mg/kg | 10.55 | 16.97 | 53.37 | 50.33 | 16.10 | 31.87 | 555.00 |
| | 100 mg/kg | 10.16 | 15.90 | 51.20 | 50.33 | 15.63 | 31.10 | 378.00 |
| | 250 mg/kg | 10.32 | 16.97 | 52.13 | 50.33 | 16.43 | 32.53 | 501.67 |

Figure 69A

| Treatment Arm | Dose | White Blood Cell | | | |
|---|---|---|---|---|---|
| | | WBC Count (10^9/L) | Lymphocyte Count (10^9/L) | Monocyte Count (10^9/L) | Neutrophil Count (10^9/L) |
| Vehicle | 0 | 7.43 | 5.58 | 0.30 | 1.55 |
| IDD1 | 10 mg/kg | 9.30 | 7.06 | 0.14 | 2.10 |
| | 25 mg/kg | 8.00 | 5.94 | 0.31 | 1.74 |
| | 100 mg/kg | 6.92 | 5.19 | 0.41 | 1.31 |
| | 250 mg/kg | 3.92 | 2.88 | 0.29 | 0.75 |

Figure 69B

| Treatment Arm | Dose | Biochemistry | | | |
|---|---|---|---|---|---|
| | | Liver (U/L) | | Kidney (mg/dL) | |
| | | ALT | ALP | CREA | BUN |
| Vehicle | 0 | 25.00 | 104.50 | 0.25 | 13.00 |
| IDD1 | 10 mg/kg | 22.67 | 109.33 | 0.30 | 11.33 |
| | 25 mg/kg | 48.67 | 131.00 | 0.23 | 12.33 |
| | 100 mg/kg | 27.00 | 101.33 | 0.23 | 11.00 |
| | 250 mg/kg | 53.00 | 101.33 | 0.27 | 16.33 |

| Treatment Arm | Dose | Biochemistry | | | | | |
|---|---|---|---|---|---|---|---|
| | | Pancreas | | Electrolytes | | | |
| | | GLU (mg/dL) | AMY (U/L) | NA (meq/L) | K (meq/L) | P (mg/dL) | CA (mg/dL) |
| Vehicle | 0 | 128.75 | 959.75 | 144.75 | 7.35 | 6.83 | 10.35 |
| IDD1 | 10 mg/kg | 91.00 | 904.67 | 143.00 | 8.07 | 6.67 | 10.30 |
| | 25 mg/kg | 109.67 | 938.00 | 144.33 | 7.30 | 6.50 | 10.77 |
| | 100 mg/kg | 119.00 | 862.00 | 148.33 | 7.47 | 5.53 | 10.57 |
| | 250 mg/kg | 139.00 | 1407.67 | 146.67 | 7.83 | 5.33 | 10.30 |

Figure 69C

| Treatment Arm | Time (hr) | Red Blood Cell | | | Anemia Parameters | | | Platelet count (10^9/L) |
|---|---|---|---|---|---|---|---|---|
| | | RBC Count (10^9/L) | Hemoglobin (g/dl) | Hematocrit (%) | MCV (fml) | MCH (pg) | MCHC (g/dl) | |
| Vehicle | 0 | 5.30 | 13.21 | 54.84 | 59.33 | 17.20 | 28.63 | 398.0 |
| | 6 | 4.55 | 8.97 | 51.38 | 60.67 | 16.77 | 29.90 | 362.0 |
| | 24 | 5.84 | 13.59 | 39.51 | 56.67 | 18.03 | 30.77 | 411.3 |
| | 96 | 7.76 | 10.87 | 52.41 | 60.67 | 17.60 | 30.23 | 488.7 |
| | 168 | 5.81 | 11.49 | 42.31 | 59.67 | 17.27 | 29.90 | 573.7 |
| | 336 | 7.51 | 16.41 | 49.23 | 60.67 | 16.83 | 29.03 | 685.0 |
| rhIT1 | 0 | 12.13 | 13.05 | 66.59 | 55.50 | 17.10 | 26.20 | 339.5 |
| | 6 | 11.96 | 12.95 | 66.88 | 57.00 | 17.35 | 25.90 | 392.0 |
| | 24 | 8.05 | 15.20 | 49.68 | 62.00 | 18.90 | 30.60 | 248.5 |
| | 96 | 8.07 | 15.65 | 49.34 | 61.00 | 19.40 | 31.80 | 337.5 |
| | 168 | 6.25 | 12.40 | 40.99 | 65.50 | 19.80 | 30.20 | 577.0 |
| | 336 | 7.35 | 13.60 | 47.13 | 64.00 | 18.25 | 28.40 | 440.0 |

Figure 70A

| Treatment Arm | Time (hr) | White Blood Cell | | | |
|---|---|---|---|---|---|
| | | WBC Count (10^9/L) | Lymphocyte Count (10^9/L) | Monocyte Count (10^9/L) | Neutrophil Count (10^9/L) |
| Vehicle | 0 | 13.22 | 10.12 | 1.43 | 3.08 |
| | 6 | 8.09 | 9.01 | 1.20 | 2.57 |
| | 24 | 9.82 | 9.08 | 0.89 | 2.08 |
| | 96 | 7.61 | 7.59 | 0.97 | 1.97 |
| | 168 | 11.02 | 9.23 | 1.24 | 2.05 |
| | 336 | 9.67 | 6.14 | 0.64 | 2.06 |
| rhIT1 | 0 | 10.61 | 2.87 | 0.27 | 2.47 |
| | 6 | 13.40 | 5.57 | 0.99 | 1.84 |
| | 24 | 10.70 | 7.55 | 0.84 | 2.32 |
| | 96 | 10.24 | 8.04 | 0.71 | 1.49 |
| | 168 | 4.68 | 3.45 | 0.18 | 1.05 |
| | 336 | 11.04 | 9.02 | 0.62 | 1.40 |

Figure 70B

| Treatment Arm | Time (hr) | Liver (U/L) | | Kidney (mg/dL) | |
|---|---|---|---|---|---|
| | | ALT | ALP | CREA | BUN |
| 1st Dose | 0 | 4.80 | 6.77 | 0.40 | 10.00 |
| | 6 | 5.03 | 6.37 | 0.37 | 12.00 |
| | 24 | 3.87 | 6.57 | 0.40 | 12.33 |
| | 96 | 3.93 | 6.63 | 0.40 | 12.00 |
| | 168 | 4.70 | 6.90 | 0.40 | 10.67 |
| | 336 | 4.97 | 6.53 | 0.33 | 13.33 |
| 3rd Dose | 0 | 5.05 | 5.55 | 0.30 | 13.50 |
| | 6 | 4.40 | 5.95 | 0.35 | 12.50 |
| | 24 | 4.30 | 7.40 | 0.40 | 12.50 |
| | 96 | 4.70 | 7.00 | 0.40 | 12.00 |
| | 168 | 5.00 | 6.50 | 0.55 | 13.50 |
| | 336 | 4.45 | 6.15 | 0.30 | 7.00 |

| Treatment Arm | Time (hr) | Pancreas | | Electrolytes | | | |
|---|---|---|---|---|---|---|---|
| | | GLU (mg/dL) | AMY (U/L) | NA (meq/L) | K (meq/L) | P (mg/dL) | CA (mg/dL) |
| 1st Dose | 0 | 119.3 | 514.3 | 138.3 | 6.87 | 6.87 | 11.50 |
| | 6 | 141.0 | 557.3 | 142.7 | 5.73 | 5.00 | 11.50 |
| | 24 | 130.3 | 594.3 | 139.7 | 5.37 | 7.43 | 11.53 |
| | 96 | 117.0 | 503.3 | 141.3 | 5.90 | 7.17 | 11.60 |
| | 168 | 122.7 | 562.7 | 144.0 | 7.10 | 6.93 | 11.30 |
| | 336 | 135.7 | 643.0 | 139.7 | 6.27 | 7.80 | 11.17 |
| 3rd Dose | 0 | 125.0 | 465.5 | 141.0 | 6.30 | 6.70 | 10.75 |
| | 6 | 123.5 | 521.0 | 143.5 | 6.00 | 7.25 | 11.05 |
| | 24 | 131.0 | 646.5 | 140.5 | 7.05 | 7.85 | 11.75 |
| | 96 | 111.0 | 632.5 | 140.0 | 6.85 | 8.05 | 11.85 |
| | 168 | 146.0 | 574.0 | 137.0 | 5.30 | 7.05 | 11.20 |
| | 336 | 100.5 | 821.5 | 139.0 | 5.35 | 7.30 | 11.45 |

Figure 70C

MFI

| | 0 min | 40 min | 80 min | 120 min | 240 min | 480 min |
|---|---|---|---|---|---|---|
| 80 nM 10D1F.A | 110 | 108 | 129 | 148 | 184 | 279 |
| 40 nM 10D1F.A | 104 | 114 | 129 | 145 | 178 | 204 |
| 20 nM 10D1F.A | 105 | 110 | 117 | 119 | 127 | 156 |
| 80 nM Trastuzumab | 133 | 270 | 393 | 435 | 528 | 802 |
| 40 nM Trastuzumab | 124 | 298 | 294 | 495 | 465 | 614 |
| 20 nM Trastuzumab | 115 | 194 | 266 | 305 | 354 | 578 |
| No Ab + 120 nM Zenon | 102 | 116 | 117 | 128 | 143 | 182 |

Percent of PE+ cells

| | 0 min | 40 min | 80 min | 120 min | 240 min | 480 min |
|---|---|---|---|---|---|---|
| 80 nM 10D1F.A | 0.13 % | 0 % | 0.26 % | 0.50 % | 0.97 % | 6.43 % |
| 40 nM 10D1F.A | 0.14 % | 0.21 % | 0.37 % | 0.38 % | 1.01 % | 1.72 % |
| 20 nM 10D1F.A | 0.093 % | 0.094 % | 0 % | 0.18 % | 0.22 % | 0.43 % |
| 80 nM Trastuzumab | 0.90 % | 9.64 % | 21.7 % | 26.9 % | 35.6 % | 56.0 % |
| 40 nM Trastuzumab | 0.49 % | 14.4 % | 13.2 % | 34.3 % | 31.4 % | 42.5 % |
| 20 nM Trastuzumab | 0.14 % | 3.73 % | 11.1 % | 15.2 % | 20.3 % | 41.8 % |
| No Ab + 120 nM Zenon | 0.039 % | 0.086 % | 0.35 % | 0.18 % | 0.26 % | 1.06 % |

Figure 73B

SEQUENCE LISTING

```
<160> NUMBER OF SEQ ID NOS: 231

<210> SEQ ID NO 1
<211> LENGTH: 1342
<212> TYPE: PRT
<213> ORGANISM: Homo sapiens
<220> FEATURE:
<221> NAME/KEY: MISC_FEATURE
<222> LOCATION: (1)..(1342)
<223> OTHER INFORMATION: HER3 Isoform 2

<400> SEQUENCE: 1

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125
```

```
His Ala Leu Arg Gln Leu Arg Leu Thr Gln Leu Thr Glu Ile Leu Ser
    130                 135                 140
Gly Gly Val Tyr Ile Glu Lys Asn Asp Lys Leu Cys His Met Asp Thr
145                 150                 155                 160
Ile Asp Trp Arg Asp Ile Val Arg Asp Arg Asp Ala Glu Ile Val Val
                165                 170                 175
Lys Asp Asn Gly Arg Ser Cys Pro Pro Cys His Glu Val Cys Lys Gly
                180                 185                 190
Arg Cys Trp Gly Pro Gly Ser Glu Asp Cys Gln Thr Leu Thr Lys Thr
                195                 200                 205
Ile Cys Ala Pro Gln Cys Asn Gly His Cys Phe Gly Pro Asn Pro Asn
210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
                245                 250                 255
Pro Arg Cys Pro Gln Pro Leu Val Tyr Asn Lys Leu Thr Phe Gln Leu
                260                 265                 270
Glu Pro Asn Pro His Thr Lys Tyr Gln Tyr Gly Gly Val Cys Val Ala
                275                 280                 285
Ser Cys Pro His Asn Phe Val Val Asp Gln Thr Ser Cys Val Arg Ala
290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                325                 330                 335
Gly Ser Arg Phe Gln Thr Val Asp Ser Ser Asn Ile Asp Gly Phe Val
                340                 345                 350
Asn Cys Thr Lys Ile Leu Gly Asn Leu Asp Phe Leu Ile Thr Gly Leu
        355                 360                 365
Asn Gly Asp Pro Trp His Lys Ile Pro Ala Leu Asp Pro Glu Lys Leu
        370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                405                 410                 415
Thr Ile Gly Gly Arg Ser Leu Tyr Asn Arg Gly Phe Ser Leu Leu Ile
                420                 425                 430
Met Lys Asn Leu Asn Val Thr Ser Leu Gly Phe Arg Ser Leu Lys Glu
        435                 440                 445
Ile Ser Ala Gly Arg Ile Tyr Ile Ser Ala Asn Arg Gln Leu Cys Tyr
450                 455                 460
His His Ser Leu Asn Trp Thr Lys Val Leu Arg Gly Pro Thr Glu Glu
465                 470                 475                 480
Arg Leu Asp Ile Lys His Asn Arg Pro Arg Arg Asp Cys Val Ala Glu
                485                 490                 495
Gly Lys Val Cys Asp Pro Leu Cys Ser Ser Gly Gly Cys Trp Gly Pro
                500                 505                 510
Gly Pro Gly Gln Cys Leu Ser Cys Arg Asn Tyr Ser Arg Gly Gly Val
                515                 520                 525
Cys Val Thr His Cys Asn Phe Leu Asn Gly Glu Pro Arg Glu Phe Ala
530                 535                 540
```

-continued

```
His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
    610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
                660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
        690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
930                 935                 940

Val Lys Cys Trp Met Ile Asp Glu Asn Ile Arg Pro Thr Phe Lys Glu
945                 950                 955                 960
```

```
Leu Ala Asn Glu Phe Thr Arg Met Ala Arg Asp Pro Pro Arg Tyr Leu
            965                 970                 975

Val Ile Lys Arg Glu Ser Gly Pro Gly Ile Ala Pro Gly Pro Glu Pro
            980                 985                 990

His Gly Leu Thr Asn Lys Lys Leu  Glu Glu Val Glu Leu  Glu Pro Glu
            995                1000                1005

Leu Asp  Leu Asp Leu Asp Leu  Glu Ala Glu Glu Asp  Asn Leu Ala
        1010                1015                1020

Thr Thr  Thr Leu Gly Ser Ala  Leu Ser Leu Pro Val  Gly Thr Leu
        1025                1030                1035

Asn Arg  Pro Arg Gly Ser Gln  Ser Leu Leu Ser Pro  Ser Ser Gly
        1040                1045                1050

Tyr Met  Pro Met Asn Gln Gly  Asn Leu Gly Glu Ser  Cys Gln Glu
        1055                1060                1065

Ser Ala  Val Ser Gly Ser Ser  Glu Arg Cys Pro Arg  Pro Val Ser
        1070                1075                1080

Leu His  Pro Met Pro Arg Gly  Cys Leu Ala Ser Glu  Ser Ser Glu
        1085                1090                1095

Gly His  Val Thr Gly Ser Glu  Ala Glu Leu Gln Glu  Lys Val Ser
        1100                1105                1110

Met Cys  Arg Ser Arg Ser Arg  Ser Arg Ser Pro Arg  Pro Arg Gly
        1115                1120                1125

Asp Ser  Ala Tyr His Ser Gln  Arg His Ser Leu Leu  Thr Pro Val
        1130                1135                1140

Thr Pro  Leu Ser Pro Pro Gly  Leu Glu Glu Glu Asp  Val Asn Gly
        1145                1150                1155

Tyr Val  Met Pro Asp Thr His  Leu Lys Gly Thr Pro  Ser Ser Arg
        1160                1165                1170

Glu Gly  Thr Leu Ser Ser Val  Gly Leu Ser Ser Val  Leu Gly Thr
        1175                1180                1185

Glu Glu  Glu Asp Glu Asp Glu  Glu Tyr Glu Tyr Met  Asn Arg Arg
        1190                1195                1200

Arg Arg  His Ser Pro Pro His  Pro Pro Arg Pro Ser  Ser Leu Glu
        1205                1210                1215

Glu Leu  Gly Tyr Glu Tyr Met  Asp Val Gly Ser Asp  Leu Ser Ala
        1220                1225                1230

Ser Leu  Gly Ser Thr Gln Ser  Cys Pro Leu His Pro  Val Pro Ile
        1235                1240                1245

Met Pro  Thr Ala Gly Thr Thr  Pro Asp Glu Asp Tyr  Glu Tyr Met
        1250                1255                1260

Asn Arg  Gln Arg Asp Gly Gly  Gly Pro Gly Gly Asp  Tyr Ala Ala
        1265                1270                1275

Met Gly  Ala Cys Pro Ala Ser  Glu Gln Gly Tyr Glu  Glu Met Arg
        1280                1285                1290

Ala Phe  Gln Gly Pro Gly His  Gln Ala Pro His Val  His Tyr Ala
        1295                1300                1305

Arg Leu  Lys Thr Leu Arg Ser  Leu Glu Ala Thr Asp  Ser Ala Phe
        1310                1315                1320

Asp Asn  Pro Asp Tyr Trp His  Ser Arg Leu Phe Pro  Lys Ala Asn
        1325                1330                1335

Ala Gln Arg Thr
        1340
```

```
<210> SEQ ID NO 2
<211> LENGTH: 183
<212> TYPE: PRT
<213> ORGANISM: Homo sapiens
<220> FEATURE:
<221> NAME/KEY: MISC_FEATURE
<222> LOCATION: (1)..(183)
<223> OTHER INFORMATION: HER3 isoform 2

<400> SEQUENCE: 2

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Gly Gln Phe Pro
    130                 135                 140

Met Val Pro Ser Gly Leu Thr Pro Gln Pro Ala Gln Asp Trp Tyr Leu
145                 150                 155                 160

Leu Asp Asp Asp Pro Arg Leu Leu Thr Leu Ser Ala Ser Ser Lys Val
                165                 170                 175

Pro Val Thr Leu Ala Ala Val
            180

<210> SEQ ID NO 3
<211> LENGTH: 331
<212> TYPE: PRT
<213> ORGANISM: Homo sapiens
<220> FEATURE:
<221> NAME/KEY: MISC_FEATURE
<222> LOCATION: (1)..(331)
<223> OTHER INFORMATION: HER 3 isoform 3

<400> SEQUENCE: 3

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95
```

Leu Pro Leu Pro Asn Leu Arg Val Val Arg Gly Thr Gln Val Tyr Asp
                100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
    195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
    275                 280                 285

Ser Cys Pro His Asn Phe Val Val Asp Gln Thr Ser Cys Val Arg Ala
290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Phe
                325                 330

<210> SEQ ID NO 4
<211> LENGTH: 1283
<212> TYPE: PRT
<213> ORGANISM: Homo sapiens
<220> FEATURE:
<221> NAME/KEY: MISC_FEATURE
<222> LOCATION: (1)..(1283)
<223> OTHER INFORMATION: HER3 isoform 4

<400> SEQUENCE: 4

Met Gly Asn Leu Glu Ile Val Leu Thr Gly His Asn Ala Asp Leu Ser
1               5                   10                  15

Phe Leu Gln Trp Ile Arg Glu Val Thr Gly Tyr Val Leu Val Ala Met
            20                  25                  30

Asn Glu Phe Ser Thr Leu Pro Leu Pro Asn Leu Arg Val Val Arg Gly
        35                  40                  45

Thr Gln Val Tyr Asp Gly Lys Phe Ala Ile Phe Val Met Leu Asn Tyr
    50                  55                  60

Asn Thr Asn Ser Ser His Ala Leu Arg Gln Leu Arg Leu Thr Gln Leu
65                  70                  75                  80

Thr Glu Ile Leu Ser Gly Gly Val Tyr Ile Glu Lys Asn Asp Lys Leu
                85                  90                  95

Cys His Met Asp Thr Ile Asp Trp Arg Asp Ile Val Arg Asp Arg Asp
            100                 105                 110

-continued

```
Ala Glu Ile Val Val Lys Asp Asn Gly Arg Ser Cys Pro Cys His
            115                 120                 125
Glu Val Cys Lys Gly Arg Cys Trp Gly Pro Gly Ser Glu Asp Cys Gln
130                 135                 140
Thr Leu Thr Lys Thr Ile Cys Ala Pro Gln Cys Asn Gly His Cys Phe
145                 150                 155                 160
Gly Pro Asn Pro Asn Gln Cys Cys His Asp Glu Cys Ala Gly Gly Cys
                165                 170                 175
Ser Gly Pro Gln Asp Thr Asp Cys Phe Ala Cys Arg His Phe Asn Asp
            180                 185                 190
Ser Gly Ala Cys Val Pro Arg Cys Pro Gln Pro Leu Val Tyr Asn Lys
            195                 200                 205
Leu Thr Phe Gln Leu Glu Pro Asn Pro His Thr Lys Tyr Gln Tyr Gly
210                 215                 220
Gly Val Cys Val Ala Ser Cys Pro His Asn Phe Val Val Asp Gln Thr
225                 230                 235                 240
Ser Cys Val Arg Ala Cys Pro Pro Asp Lys Met Glu Val Asp Lys Asn
            245                 250                 255
Gly Leu Lys Met Cys Glu Pro Cys Gly Gly Leu Cys Pro Lys Ala Cys
            260                 265                 270
Glu Gly Thr Gly Ser Gly Ser Arg Phe Gln Thr Val Asp Ser Ser Asn
            275                 280                 285
Ile Asp Gly Phe Val Asn Cys Thr Lys Ile Leu Gly Asn Leu Asp Phe
            290                 295                 300
Leu Ile Thr Gly Leu Asn Gly Asp Pro Trp His Lys Ile Pro Ala Leu
305                 310                 315                 320
Asp Pro Glu Lys Leu Asn Val Phe Arg Thr Val Arg Glu Ile Thr Gly
                325                 330                 335
Tyr Leu Asn Ile Gln Ser Trp Pro Pro His Met His Asn Phe Ser Val
            340                 345                 350
Phe Ser Asn Leu Thr Thr Ile Gly Gly Arg Ser Leu Tyr Asn Arg Gly
            355                 360                 365
Phe Ser Leu Leu Ile Met Lys Asn Leu Asn Val Thr Ser Leu Gly Phe
370                 375                 380
Arg Ser Leu Lys Glu Ile Ser Ala Gly Arg Ile Tyr Ile Ser Ala Asn
385                 390                 395                 400
Arg Gln Leu Cys Tyr His His Ser Leu Asn Trp Thr Lys Val Leu Arg
                405                 410                 415
Gly Pro Thr Glu Glu Arg Leu Asp Ile Lys His Asn Arg Pro Arg Arg
            420                 425                 430
Asp Cys Val Ala Glu Gly Lys Val Cys Asp Pro Leu Cys Ser Ser Gly
            435                 440                 445
Gly Cys Trp Gly Pro Gly Pro Gly Gln Cys Leu Ser Cys Arg Asn Tyr
            450                 455                 460
Ser Arg Gly Gly Val Cys Val Thr His Cys Asn Phe Leu Asn Gly Glu
465                 470                 475                 480
Pro Arg Glu Phe Ala His Glu Ala Glu Cys Phe Ser Cys His Pro Glu
                485                 490                 495
Cys Gln Pro Met Glu Gly Thr Ala Thr Cys Asn Gly Ser Gly Ser Asp
            500                 505                 510
Thr Cys Ala Gln Cys Ala His Phe Arg Asp Gly Pro His Cys Val Ser
            515                 520                 525
```

```
Ser Cys Pro His Gly Val Leu Gly Ala Lys Gly Pro Ile Tyr Lys Tyr
    530                 535                 540

Pro Asp Val Gln Asn Glu Cys Arg Pro Cys His Glu Asn Cys Thr Gln
545                 550                 555                 560

Gly Cys Lys Gly Pro Glu Leu Gln Asp Cys Leu Gly Gln Thr Leu Val
                565                 570                 575

Leu Ile Gly Lys Thr His Leu Thr Met Ala Leu Thr Val Ile Ala Gly
            580                 585                 590

Leu Val Val Ile Phe Met Met Leu Gly Gly Thr Phe Leu Tyr Trp Arg
        595                 600                 605

Gly Arg Arg Ile Gln Asn Lys Arg Ala Met Arg Arg Tyr Leu Glu Arg
    610                 615                 620

Gly Glu Ser Ile Glu Pro Leu Asp Pro Ser Glu Lys Ala Asn Lys Val
625                 630                 635                 640

Leu Ala Arg Ile Phe Lys Glu Thr Glu Leu Arg Lys Leu Lys Val Leu
                645                 650                 655

Gly Ser Gly Val Phe Gly Thr Val His Lys Gly Val Trp Ile Pro Glu
            660                 665                 670

Gly Glu Ser Ile Lys Ile Pro Val Cys Ile Lys Val Ile Glu Asp Lys
        675                 680                 685

Ser Gly Arg Gln Ser Phe Gln Ala Val Thr Asp His Met Leu Ala Ile
    690                 695                 700

Gly Ser Leu Asp His Ala His Ile Val Arg Leu Leu Gly Leu Cys Pro
705                 710                 715                 720

Gly Ser Ser Leu Gln Leu Val Thr Gln Tyr Leu Pro Leu Gly Ser Leu
                725                 730                 735

Leu Asp His Val Arg Gln His Arg Gly Ala Leu Gly Pro Gln Leu Leu
            740                 745                 750

Leu Asn Trp Gly Val Gln Ile Ala Lys Gly Met Tyr Tyr Leu Glu Glu
        755                 760                 765

His Gly Met Val His Arg Asn Leu Ala Ala Arg Asn Val Leu Leu Lys
    770                 775                 780

Ser Pro Ser Gln Val Gln Val Ala Asp Phe Gly Val Ala Asp Leu Leu
785                 790                 795                 800

Pro Pro Asp Asp Lys Gln Leu Leu Tyr Ser Glu Ala Lys Thr Pro Ile
                805                 810                 815

Lys Trp Met Ala Leu Glu Ser Ile His Phe Gly Lys Tyr Thr His Gln
            820                 825                 830

Ser Asp Val Trp Ser Tyr Gly Val Thr Val Trp Glu Leu Met Thr Phe
        835                 840                 845

Gly Ala Glu Pro Tyr Ala Gly Leu Arg Leu Ala Glu Val Pro Asp Leu
    850                 855                 860

Leu Glu Lys Gly Glu Arg Leu Ala Gln Pro Gln Ile Cys Thr Ile Asp
865                 870                 875                 880

Val Tyr Met Val Met Val Lys Cys Trp Met Ile Asp Glu Asn Ile Arg
                885                 890                 895

Pro Thr Phe Lys Glu Leu Ala Asn Glu Phe Thr Arg Met Ala Arg Asp
            900                 905                 910

Pro Pro Arg Tyr Leu Val Ile Lys Arg Glu Ser Gly Pro Gly Ile Ala
        915                 920                 925

Pro Gly Pro Glu Pro His Gly Leu Thr Asn Lys Lys Leu Glu Glu Val
    930                 935                 940
```

```
Glu Leu Glu Pro Glu Leu Asp Leu Asp Leu Glu Ala Glu
945                 950                 955                 960

Asp Asn Leu Ala Thr Thr Thr Leu Gly Ser Ala Leu Ser Leu Pro Val
                965                 970                 975

Gly Thr Leu Asn Arg Pro Arg Gly Ser Gln Ser Leu Leu Ser Pro Ser
                980                 985                 990

Ser Gly Tyr Met Pro Met Asn Gln Gly Asn Leu Gly Glu Ser Cys Gln
                995                 1000                1005

Glu Ser Ala Val Ser Gly Ser Ser Glu Arg Cys Pro Arg Pro Val
        1010                1015                1020

Ser Leu His Pro Met Pro Arg Gly Cys Leu Ala Ser Glu Ser Ser
        1025                1030                1035

Glu Gly His Val Thr Gly Ser Glu Ala Glu Leu Gln Glu Lys Val
        1040                1045                1050

Ser Met Cys Arg Ser Arg Ser Arg Ser Arg Ser Pro Arg Pro Arg
        1055                1060                1065

Gly Asp Ser Ala Tyr His Ser Gln Arg His Ser Leu Leu Thr Pro
        1070                1075                1080

Val Thr Pro Leu Ser Pro Pro Gly Leu Glu Glu Glu Asp Val Asn
        1085                1090                1095

Gly Tyr Val Met Pro Asp Thr His Leu Lys Gly Thr Pro Ser Ser
        1100                1105                1110

Arg Glu Gly Thr Leu Ser Ser Val Gly Leu Ser Ser Val Leu Gly
        1115                1120                1125

Thr Glu Glu Glu Asp Glu Asp Glu Glu Tyr Glu Tyr Met Asn Arg
        1130                1135                1140

Arg Arg Arg His Ser Pro Pro His Pro Pro Arg Pro Ser Ser Leu
        1145                1150                1155

Glu Glu Leu Gly Tyr Glu Tyr Met Asp Val Gly Ser Asp Leu Ser
        1160                1165                1170

Ala Ser Leu Gly Ser Thr Gln Ser Cys Pro Leu His Pro Val Pro
        1175                1180                1185

Ile Met Pro Thr Ala Gly Thr Thr Pro Asp Glu Asp Tyr Glu Tyr
        1190                1195                1200

Met Asn Arg Gln Arg Asp Gly Gly Pro Gly Gly Asp Tyr Ala
        1205                1210                1215

Ala Met Gly Ala Cys Pro Ala Ser Glu Gln Gly Tyr Glu Glu Met
        1220                1225                1230

Arg Ala Phe Gln Gly Pro Gly His Gln Ala Pro His Val His Tyr
        1235                1240                1245

Ala Arg Leu Lys Thr Leu Arg Ser Leu Glu Ala Thr Asp Ser Ala
        1250                1255                1260

Phe Asp Asn Pro Asp Tyr Trp His Ser Arg Leu Phe Pro Lys Ala
        1265                1270                1275

Asn Ala Gln Arg Thr
        1280

<210> SEQ ID NO 5
<211> LENGTH: 699
<212> TYPE: PRT
<213> ORGANISM: Homo sapiens
<220> FEATURE:
<221> NAME/KEY: Misc_feature
<222> LOCATION: (1)..(699)
<223> OTHER INFORMATION: HER3 isoform 5
```

```
<400> SEQUENCE: 5

Met Ala Leu Thr Val Ile Ala Gly Leu Val Val Ile Phe Met Met Leu
1               5                   10                  15

Gly Gly Thr Phe Leu Tyr Trp Arg Gly Arg Arg Ile Gln Asn Lys Arg
                20                  25                  30

Ala Met Arg Arg Tyr Leu Glu Arg Gly Glu Ser Ile Glu Pro Leu Asp
            35                  40                  45

Pro Ser Glu Lys Ala Asn Lys Val Leu Ala Arg Ile Phe Lys Glu Thr
        50                  55                  60

Glu Leu Arg Lys Leu Lys Val Leu Gly Ser Gly Val Phe Gly Thr Val
65                  70                  75                  80

His Lys Gly Val Trp Ile Pro Glu Gly Glu Ser Ile Lys Ile Pro Val
                85                  90                  95

Cys Ile Lys Val Ile Glu Asp Lys Ser Gly Arg Gln Ser Phe Gln Ala
            100                 105                 110

Val Thr Asp His Met Leu Ala Ile Gly Ser Leu Asp His Ala His Ile
        115                 120                 125

Val Arg Leu Leu Gly Leu Cys Pro Gly Ser Ser Leu Gln Leu Val Thr
130                 135                 140

Gln Tyr Leu Pro Leu Gly Ser Leu Leu Asp His Val Arg Gln His Arg
145                 150                 155                 160

Gly Ala Leu Gly Pro Gln Leu Leu Leu Asn Trp Gly Val Gln Ile Ala
                165                 170                 175

Lys Gly Met Tyr Tyr Leu Glu Glu His Gly Met Val His Arg Asn Leu
            180                 185                 190

Ala Ala Arg Asn Val Leu Leu Lys Ser Pro Ser Gln Val Gln Val Ala
        195                 200                 205

Asp Phe Gly Val Ala Asp Leu Leu Pro Pro Asp Lys Gln Leu Leu
210                 215                 220

Tyr Ser Glu Ala Lys Thr Pro Ile Lys Trp Met Ala Leu Glu Ser Ile
225                 230                 235                 240

His Phe Gly Lys Tyr Thr His Gln Ser Asp Val Trp Ser Tyr Gly Val
                245                 250                 255

Thr Val Trp Glu Leu Met Thr Phe Gly Ala Glu Pro Tyr Ala Gly Leu
            260                 265                 270

Arg Leu Ala Glu Val Pro Asp Leu Leu Glu Lys Gly Glu Arg Leu Ala
        275                 280                 285

Gln Pro Gln Ile Cys Thr Ile Asp Val Tyr Met Val Met Val Lys Cys
290                 295                 300

Trp Met Ile Asp Glu Asn Ile Arg Pro Thr Phe Lys Glu Leu Ala Asn
305                 310                 315                 320

Glu Phe Thr Arg Met Ala Arg Asp Pro Pro Arg Tyr Leu Val Ile Lys
                325                 330                 335

Arg Glu Ser Gly Pro Gly Ile Ala Pro Gly Pro Glu Pro His Gly Leu
            340                 345                 350

Thr Asn Lys Lys Leu Glu Glu Val Glu Leu Glu Pro Glu Leu Asp Leu
        355                 360                 365

Asp Leu Asp Leu Glu Ala Glu Asp Asn Leu Ala Thr Thr Thr Leu
370                 375                 380

Gly Ser Ala Leu Ser Leu Pro Val Gly Thr Leu Asn Arg Pro Arg Gly
385                 390                 395                 400

Ser Gln Ser Leu Leu Ser Pro Ser Ser Gly Tyr Met Pro Met Asn Gln
                405                 410                 415
```

-continued

```
Gly Asn Leu Gly Glu Ser Cys Gln Glu Ser Ala Val Ser Gly Ser Ser
            420                 425                 430

Glu Arg Cys Pro Arg Pro Val Ser Leu His Pro Met Pro Arg Gly Cys
        435                 440                 445

Leu Ala Ser Glu Ser Ser Glu Gly His Val Thr Gly Ser Glu Ala Glu
    450                 455                 460

Leu Gln Glu Lys Val Ser Met Cys Arg Ser Arg Ser Arg Ser Arg Ser
465                 470                 475                 480

Pro Arg Pro Arg Gly Asp Ser Ala Tyr His Ser Gln Arg His Ser Leu
                485                 490                 495

Leu Thr Pro Val Thr Pro Leu Ser Pro Pro Gly Leu Glu Glu Glu Asp
            500                 505                 510

Val Asn Gly Tyr Val Met Pro Asp Thr His Leu Lys Gly Thr Pro Ser
        515                 520                 525

Ser Arg Glu Gly Thr Leu Ser Ser Val Gly Leu Ser Ser Val Leu Gly
    530                 535                 540

Thr Glu Glu Glu Asp Glu Asp Glu Glu Tyr Glu Tyr Met Asn Arg Arg
545                 550                 555                 560

Arg Arg His Ser Pro Pro His Pro Pro Arg Pro Ser Ser Leu Glu Glu
                565                 570                 575

Leu Gly Tyr Glu Tyr Met Asp Val Gly Ser Asp Leu Ser Ala Ser Leu
            580                 585                 590

Gly Ser Thr Gln Ser Cys Pro Leu His Pro Val Pro Ile Met Pro Thr
        595                 600                 605

Ala Gly Thr Thr Pro Asp Glu Asp Tyr Glu Tyr Met Asn Arg Gln Arg
    610                 615                 620

Asp Gly Gly Pro Gly Gly Asp Tyr Ala Ala Met Gly Ala Cys Pro
625                 630                 635                 640

Ala Ser Glu Gln Gly Tyr Glu Glu Met Arg Ala Phe Gln Gly Pro Gly
                645                 650                 655

His Gln Ala Pro His Val His Tyr Ala Arg Leu Lys Thr Leu Arg Ser
            660                 665                 670

Leu Glu Ala Thr Asp Ser Ala Phe Asp Asn Pro Asp Tyr Trp His Ser
        675                 680                 685

Arg Leu Phe Pro Lys Ala Asn Ala Gln Arg Thr
    690                 695

<210> SEQ ID NO 6
<211> LENGTH: 1323
<212> TYPE: PRT
<213> ORGANISM: Homo sapiens
<220> FEATURE:
<221> NAME/KEY: Misc_feature
<222> LOCATION: (1)..(1323)
<223> OTHER INFORMATION: HER3 isoform 1

<400> SEQUENCE: 6

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
            20                  25                  30

Leu Tyr Glu Arg Cys Glu Val Val Met Gly Asn Leu Glu Ile Val Leu
        35                  40                  45

Thr Gly His Asn Ala Asp Leu Ser Phe Leu Gln Trp Ile Arg Glu Val
    50                  55                  60
```

-continued

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
            85                  90                  95

Ala Ile Phe Val Met Leu Asn Tyr Asn Thr Asn Ser Ser His Ala Leu
                100                 105                 110

Arg Gln Leu Arg Leu Thr Gln Leu Thr Glu Ile Leu Ser Gly Gly Val
            115                 120                 125

Tyr Ile Glu Lys Asn Asp Lys Leu Cys His Met Asp Thr Ile Asp Trp
130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
            195                 200                 205

His Asp Glu Cys Ala Gly Gly Cys Ser Gly Pro Gln Asp Thr Asp Cys
210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
            245                 250                 255

Pro His Thr Lys Tyr Gln Tyr Gly Gly Val Cys Val Ala Ser Cys Pro
            260                 265                 270

His Asn Phe Val Val Asp Gln Thr Ser Cys Val Arg Ala Cys Pro Pro
            275                 280                 285

Asp Lys Met Glu Val Asp Lys Asn Gly Leu Lys Met Cys Glu Pro Cys
290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
            325                 330                 335

Lys Ile Leu Gly Asn Leu Asp Phe Leu Ile Thr Gly Leu Asn Gly Asp
            340                 345                 350

Pro Trp His Lys Ile Pro Ala Leu Asp Pro Glu Lys Leu Asn Val Phe
            355                 360                 365

Arg Thr Val Arg Glu Ile Thr Gly Tyr Leu Asn Ile Gln Ser Trp Pro
370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
            405                 410                 415

Leu Asn Val Thr Ser Leu Gly Phe Arg Ser Leu Lys Glu Ile Ser Ala
            420                 425                 430

Gly Arg Ile Tyr Ile Ser Ala Asn Arg Gln Leu Cys Tyr His His Ser
            435                 440                 445

Leu Asn Trp Thr Lys Val Leu Arg Gly Pro Thr Glu Glu Arg Leu Asp
            450                 455                 460

Ile Lys His Asn Arg Pro Arg Arg Asp Cys Val Ala Glu Gly Lys Val
465                 470                 475                 480

```
Cys Asp Pro Leu Cys Ser Ser Gly Cys Trp Gly Pro Gly
                485             490             495

Gln Cys Leu Ser Cys Arg Asn Tyr Ser Arg Gly Val Cys Val Thr
            500             505             510

His Cys Asn Phe Leu Asn Gly Glu Pro Arg Glu Phe Ala His Glu Ala
        515             520             525

Glu Cys Phe Ser Cys His Pro Glu Cys Gln Pro Met Glu Gly Thr Ala
    530             535             540

Thr Cys Asn Gly Ser Gly Ser Asp Thr Cys Ala Gln Cys Ala His Phe
545             550             555             560

Arg Asp Gly Pro His Cys Val Ser Ser Cys Pro His Gly Val Leu Gly
                565             570             575

Ala Lys Gly Pro Ile Tyr Lys Tyr Pro Asp Val Gln Asn Glu Cys Arg
            580             585             590

Pro Cys His Glu Asn Cys Thr Gln Gly Cys Lys Gly Pro Glu Leu Gln
        595             600             605

Asp Cys Leu Gly Gln Thr Leu Val Leu Ile Gly Lys Thr His Leu Thr
    610             615             620

Met Ala Leu Thr Val Ile Ala Gly Leu Val Val Ile Phe Met Met Leu
625             630             635             640

Gly Gly Thr Phe Leu Tyr Trp Arg Gly Arg Arg Ile Gln Asn Lys Arg
                645             650             655

Ala Met Arg Arg Tyr Leu Glu Arg Gly Glu Ser Ile Glu Pro Leu Asp
            660             665             670

Pro Ser Glu Lys Ala Asn Lys Val Leu Ala Arg Ile Phe Lys Glu Thr
        675             680             685

Glu Leu Arg Lys Leu Lys Val Leu Gly Ser Gly Val Phe Gly Thr Val
    690             695             700

His Lys Gly Val Trp Ile Pro Glu Gly Glu Ser Ile Lys Ile Pro Val
705             710             715             720

Cys Ile Lys Val Ile Glu Asp Lys Ser Gly Arg Gln Ser Phe Gln Ala
                725             730             735

Val Thr Asp His Met Leu Ala Ile Gly Ser Leu Asp His Ala His Ile
            740             745             750

Val Arg Leu Leu Gly Leu Cys Pro Gly Ser Ser Leu Gln Leu Val Thr
        755             760             765

Gln Tyr Leu Pro Leu Gly Ser Leu Leu Asp His Val Arg Gln His Arg
    770             775             780

Gly Ala Leu Gly Pro Gln Leu Leu Leu Asn Trp Gly Val Gln Ile Ala
785             790             795             800

Lys Gly Met Tyr Tyr Leu Glu Glu His Gly Met Val His Arg Asn Leu
                805             810             815

Ala Ala Arg Asn Val Leu Leu Lys Ser Pro Ser Gln Val Gln Val Ala
            820             825             830

Asp Phe Gly Val Ala Asp Leu Leu Pro Pro Asp Lys Gln Leu Leu
        835             840             845

Tyr Ser Glu Ala Lys Thr Pro Ile Lys Trp Met Ala Leu Glu Ser Ile
    850             855             860

His Phe Gly Lys Tyr Thr His Gln Ser Asp Val Trp Ser Tyr Gly Val
865             870             875             880

Thr Val Trp Glu Leu Met Thr Phe Gly Ala Glu Pro Tyr Ala Gly Leu
                885             890             895
```

-continued

Arg Leu Ala Glu Val Pro Asp Leu Leu Glu Lys Gly Glu Arg Leu Ala
            900                 905                 910

Gln Pro Gln Ile Cys Thr Ile Asp Val Tyr Met Val Met Val Lys Cys
        915                 920                 925

Trp Met Ile Asp Glu Asn Ile Arg Pro Thr Phe Lys Glu Leu Ala Asn
    930                 935                 940

Glu Phe Thr Arg Met Ala Arg Asp Pro Pro Arg Tyr Leu Val Ile Lys
945                 950                 955                 960

Arg Glu Ser Gly Pro Gly Ile Ala Pro Gly Pro Glu Pro His Gly Leu
                965                 970                 975

Thr Asn Lys Lys Leu Glu Glu Val Glu Leu Glu Pro Glu Leu Asp Leu
            980                 985                 990

Asp Leu Asp Leu Glu Ala Glu Glu Asp Asn Leu Ala Thr Thr Thr Leu
        995                 1000                1005

Gly Ser Ala Leu Ser Leu Pro Val Gly Thr Leu Asn Arg Pro Arg
    1010            1015            1020

Gly Ser Gln Ser Leu Leu Ser Pro Ser Ser Gly Tyr Met Pro Met
    1025            1030            1035

Asn Gln Gly Asn Leu Gly Glu Ser Cys Gln Glu Ser Ala Val Ser
    1040            1045            1050

Gly Ser Ser Glu Arg Cys Pro Arg Pro Val Ser Leu His Pro Met
    1055            1060            1065

Pro Arg Gly Cys Leu Ala Ser Glu Ser Ser Glu Gly His Val Thr
    1070            1075            1080

Gly Ser Glu Ala Glu Leu Gln Glu Lys Val Ser Met Cys Arg Ser
    1085            1090            1095

Arg Ser Arg Ser Arg Ser Pro Arg Pro Arg Gly Asp Ser Ala Tyr
    1100            1105            1110

His Ser Gln Arg His Ser Leu Leu Thr Pro Val Thr Pro Leu Ser
    1115            1120            1125

Pro Pro Gly Leu Glu Glu Glu Asp Val Asn Gly Tyr Val Met Pro
    1130            1135            1140

Asp Thr His Leu Lys Gly Thr Pro Ser Ser Arg Glu Gly Thr Leu
    1145            1150            1155

Ser Ser Val Gly Leu Ser Ser Val Leu Gly Thr Glu Glu Glu Asp
    1160            1165            1170

Glu Asp Glu Glu Tyr Glu Tyr Met Asn Arg Arg Arg Arg His Ser
    1175            1180            1185

Pro Pro His Pro Pro Arg Pro Ser Ser Leu Glu Glu Leu Gly Tyr
    1190            1195            1200

Glu Tyr Met Asp Val Gly Ser Asp Leu Ser Ala Ser Leu Gly Ser
    1205            1210            1215

Thr Gln Ser Cys Pro Leu His Pro Val Pro Ile Met Pro Thr Ala
    1220            1225            1230

Gly Thr Thr Pro Asp Glu Asp Tyr Glu Tyr Met Asn Arg Gln Arg
    1235            1240            1245

Asp Gly Gly Pro Gly Gly Asp Tyr Ala Ala Met Gly Ala Cys
    1250            1255            1260

Pro Ala Ser Glu Gln Gly Tyr Glu Glu Met Arg Ala Phe Gln Gly
    1265            1270            1275

Pro Gly His Gln Ala Pro His Val His Tyr Ala Arg Leu Lys Thr
    1280            1285            1290

```
Leu Arg Ser Leu Glu Ala Thr Asp Ser Ala Phe Asp Asn Pro Asp
    1295                1300                1305

Tyr Trp His Ser Arg Leu Phe Pro Lys Ala Asn Ala Gln Arg Thr
    1310                1315                1320

<210> SEQ ID NO 7
<211> LENGTH: 164
<212> TYPE: PRT
<213> ORGANISM: Homo sapiens
<220> FEATURE:
<221> NAME/KEY: Misc_feature
<222> LOCATION: (1)..(164)
<223> OTHER INFORMATION: HER3 isoform 2

<400> SEQUENCE: 7

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
                20                  25                  30

Leu Tyr Glu Arg Cys Glu Val Val Met Gly Asn Leu Glu Ile Val Leu
            35                  40                  45

Thr Gly His Asn Ala Asp Leu Ser Phe Leu Gln Trp Ile Arg Glu Val
        50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Gly Gln Phe Pro Met Val Pro
        115                 120                 125

Ser Gly Leu Thr Pro Gln Pro Ala Gln Asp Trp Tyr Leu Leu Asp Asp
    130                 135                 140

Asp Pro Arg Leu Leu Thr Leu Ser Ala Ser Ser Lys Val Pro Val Thr
145                 150                 155                 160

Leu Ala Ala Val

<210> SEQ ID NO 8
<211> LENGTH: 312
<212> TYPE: PRT
<213> ORGANISM: Homo sapiens
<220> FEATURE:
<221> NAME/KEY: Misc_feature
<222> LOCATION: (1)..(312)
<223> OTHER INFORMATION: HER3 isoform 3

<400> SEQUENCE: 8

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
                20                  25                  30

Leu Tyr Glu Arg Cys Glu Val Val Met Gly Asn Leu Glu Ile Val Leu
            35                  40                  45

Thr Gly His Asn Ala Asp Leu Ser Phe Leu Gln Trp Ile Arg Glu Val
        50                  55                  60

Thr Gly Tyr Val Leu Val Ala Met Asn Glu Phe Ser Thr Leu Pro Leu
65                  70                  75                  80
```

```
Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
        115                 120                 125

Tyr Ile Glu Lys Asn Asp Lys Leu Cys His Met Asp Thr Ile Asp Trp
130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
        195                 200                 205

His Asp Glu Cys Ala Gly Gly Cys Ser Gly Pro Gln Asp Thr Asp Cys
210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270

His Asn Phe Val Val Asp Gln Thr Ser Cys Val Arg Ala Cys Pro Pro
        275                 280                 285

Asp Lys Met Glu Val Asp Lys Asn Gly Leu Lys Met Cys Glu Pro Cys
290                 295                 300

Gly Gly Leu Cys Pro Lys Ala Phe
305                 310

<210> SEQ ID NO 9
<211> LENGTH: 624
<212> TYPE: PRT
<213> ORGANISM: Homo sapiens
<220> FEATURE:
<221> NAME/KEY: Misc_feature
<222> LOCATION: (1)..(624)
<223> OTHER INFORMATION: HER3 isoform 1 exracellular region

<400> SEQUENCE: 9

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
            20                  25                  30

Leu Tyr Glu Arg Cys Glu Val Val Met Gly Asn Leu Glu Ile Val Leu
        35                  40                  45

Thr Gly His Asn Ala Asp Leu Ser Phe Leu Gln Trp Ile Arg Glu Val
    50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110
```

-continued

```
Arg Gln Leu Arg Leu Thr Gln Leu Thr Glu Ile Leu Ser Gly Gly Val
            115                 120                 125
Tyr Ile Glu Lys Asn Asp Lys Leu Cys His Met Asp Thr Ile Asp Trp
        130                 135                 140
Arg Asp Ile Val Arg Asp Arg Asp Ala Glu Ile Val Val Lys Asp Asn
145                 150                 155                 160
Gly Arg Ser Cys Pro Pro Cys His Glu Val Cys Lys Gly Arg Cys Trp
                165                 170                 175
Gly Pro Gly Ser Glu Asp Cys Gln Thr Leu Thr Lys Thr Ile Cys Ala
            180                 185                 190
Pro Gln Cys Asn Gly His Cys Phe Gly Pro Asn Pro Asn Gln Cys Cys
        195                 200                 205
His Asp Glu Cys Ala Gly Gly Cys Ser Gly Pro Gln Asp Thr Asp Cys
    210                 215                 220
Phe Ala Cys Arg His Phe Asn Asp Ser Gly Ala Cys Val Pro Arg Cys
225                 230                 235                 240
Pro Gln Pro Leu Val Tyr Asn Lys Leu Thr Phe Gln Leu Glu Pro Asn
                245                 250                 255
Pro His Thr Lys Tyr Gln Tyr Gly Gly Val Cys Val Ala Ser Cys Pro
            260                 265                 270
His Asn Phe Val Val Asp Gln Thr Ser Cys Val Arg Ala Cys Pro Pro
        275                 280                 285
Asp Lys Met Glu Val Asp Lys Asn Gly Leu Lys Met Cys Glu Pro Cys
    290                 295                 300
Gly Gly Leu Cys Pro Lys Ala Cys Glu Gly Thr Gly Ser Gly Ser Arg
305                 310                 315                 320
Phe Gln Thr Val Asp Ser Ser Asn Ile Asp Gly Phe Val Asn Cys Thr
                325                 330                 335
Lys Ile Leu Gly Asn Leu Asp Phe Leu Ile Thr Gly Leu Asn Gly Asp
            340                 345                 350
Pro Trp His Lys Ile Pro Ala Leu Asp Pro Glu Lys Leu Asn Val Phe
        355                 360                 365
Arg Thr Val Arg Glu Ile Thr Gly Tyr Leu Asn Ile Gln Ser Trp Pro
    370                 375                 380
Pro His Met His Asn Phe Ser Val Phe Ser Asn Leu Thr Thr Ile Gly
385                 390                 395                 400
Gly Arg Ser Leu Tyr Asn Arg Gly Phe Ser Leu Leu Ile Met Lys Asn
                405                 410                 415
Leu Asn Val Thr Ser Leu Gly Phe Arg Ser Leu Lys Glu Ile Ser Ala
            420                 425                 430
Gly Arg Ile Tyr Ile Ser Ala Asn Arg Gln Leu Cys Tyr His His Ser
        435                 440                 445
Leu Asn Trp Thr Lys Val Leu Arg Gly Pro Thr Glu Glu Arg Leu Asp
    450                 455                 460
Ile Lys His Asn Arg Pro Arg Arg Asp Cys Val Ala Glu Gly Lys Val
465                 470                 475                 480
Cys Asp Pro Leu Cys Ser Ser Gly Gly Cys Trp Gly Pro Gly Pro Gly
                485                 490                 495
Gln Cys Leu Ser Cys Arg Asn Tyr Ser Arg Gly Gly Val Cys Val Thr
            500                 505                 510
His Cys Asn Phe Leu Asn Gly Glu Pro Arg Glu Phe Ala His Glu Ala
        515                 520                 525
```

```
Glu Cys Phe Ser Cys His Pro Glu Cys Gln Pro Met Glu Gly Thr Ala
    530                 535                 540
Thr Cys Asn Gly Ser Gly Ser Asp Thr Cys Ala Gln Cys Ala His Phe
545                 550                 555                 560
Arg Asp Gly Pro His Cys Val Ser Ser Cys Pro His Gly Val Leu Gly
                565                 570                 575
Ala Lys Gly Pro Ile Tyr Lys Tyr Pro Asp Val Gln Asn Glu Cys Arg
            580                 585                 590
Pro Cys His Glu Asn Cys Thr Gln Gly Cys Lys Gly Pro Glu Leu Gln
        595                 600                 605
Asp Cys Leu Gly Gln Thr Leu Val Leu Ile Gly Lys Thr His Leu Thr
610                 615                 620

<210> SEQ ID NO 10
<211> LENGTH: 21
<212> TYPE: PRT
<213> ORGANISM: Homo sapiens
<220> FEATURE:
<221> NAME/KEY: Misc_feature
<222> LOCATION: (1)..(21)
<223> OTHER INFORMATION: HER3 isoform 1 transmembrane domain

<400> SEQUENCE: 10

Met Ala Leu Thr Val Ile Ala Gly Leu Val Val Ile Phe Met Met Leu
1               5                   10                  15
Gly Gly Thr Phe Leu
            20

<210> SEQ ID NO 11
<211> LENGTH: 678
<212> TYPE: PRT
<213> ORGANISM: Homo sapiens
<220> FEATURE:
<221> NAME/KEY: misc_feature
<222> LOCATION: (1)..(678)
<223> OTHER INFORMATION: HER3 isoform 1 cytoplasmic domain

<400> SEQUENCE: 11

Tyr Trp Arg Gly Arg Arg Ile Gln Asn Lys Arg Ala Met Arg Arg Tyr
1               5                   10                  15
Leu Glu Arg Gly Glu Ser Ile Glu Pro Leu Asp Pro Ser Glu Lys Ala
            20                  25                  30
Asn Lys Val Leu Ala Arg Ile Phe Lys Glu Thr Glu Leu Arg Lys Leu
        35                  40                  45
Lys Val Leu Gly Ser Gly Val Phe Gly Thr Val His Lys Gly Val Trp
    50                  55                  60
Ile Pro Glu Gly Glu Ser Ile Lys Ile Pro Val Cys Ile Lys Val Ile
65                  70                  75                  80
Glu Asp Lys Ser Gly Arg Gln Ser Phe Gln Ala Val Thr Asp His Met
                85                  90                  95
Leu Ala Ile Gly Ser Leu Asp His Ala His Ile Val Arg Leu Leu Gly
            100                 105                 110
Leu Cys Pro Gly Ser Ser Leu Gln Leu Val Thr Gln Tyr Leu Pro Leu
        115                 120                 125
Gly Ser Leu Leu Asp His Val Arg Gln His Arg Gly Ala Leu Gly Pro
    130                 135                 140
Gln Leu Leu Leu Asn Trp Gly Val Gln Ile Ala Lys Gly Met Tyr Tyr
145                 150                 155                 160
```

```
Leu Glu Glu His Gly Met Val His Arg Asn Leu Ala Ala Arg Asn Val
                165                 170                 175
Leu Leu Lys Ser Pro Ser Gln Val Gln Val Ala Asp Phe Gly Val Ala
            180                 185                 190
Asp Leu Leu Pro Pro Asp Asp Lys Gln Leu Leu Tyr Ser Glu Ala Lys
        195                 200                 205
Thr Pro Ile Lys Trp Met Ala Leu Glu Ser Ile His Phe Gly Lys Tyr
    210                 215                 220
Thr His Gln Ser Asp Val Trp Ser Tyr Gly Val Thr Val Trp Glu Leu
225                 230                 235                 240
Met Thr Phe Gly Ala Glu Pro Tyr Ala Gly Leu Arg Leu Ala Glu Val
                245                 250                 255
Pro Asp Leu Leu Glu Lys Gly Glu Arg Leu Ala Gln Pro Gln Ile Cys
            260                 265                 270
Thr Ile Asp Val Tyr Met Val Met Val Lys Cys Trp Met Ile Asp Glu
        275                 280                 285
Asn Ile Arg Pro Thr Phe Lys Glu Leu Ala Asn Glu Phe Thr Arg Met
    290                 295                 300
Ala Arg Asp Pro Pro Arg Tyr Leu Val Ile Lys Arg Glu Ser Gly Pro
305                 310                 315                 320
Gly Ile Ala Pro Gly Pro Glu Pro His Gly Leu Thr Asn Lys Lys Leu
                325                 330                 335
Glu Glu Val Glu Leu Glu Pro Glu Leu Asp Leu Asp Leu Asp Leu Glu
            340                 345                 350
Ala Glu Glu Asp Asn Leu Ala Thr Thr Thr Leu Gly Ser Ala Leu Ser
        355                 360                 365
Leu Pro Val Gly Thr Leu Asn Arg Pro Arg Gly Ser Gln Ser Leu Leu
    370                 375                 380
Ser Pro Ser Ser Gly Tyr Met Pro Met Asn Gln Gly Asn Leu Gly Glu
385                 390                 395                 400
Ser Cys Gln Glu Ser Ala Val Ser Gly Ser Ser Glu Arg Cys Pro Arg
                405                 410                 415
Pro Val Ser Leu His Pro Met Pro Arg Gly Cys Leu Ala Ser Glu Ser
            420                 425                 430
Ser Glu Gly His Val Thr Gly Ser Glu Ala Glu Leu Gln Glu Lys Val
        435                 440                 445
Ser Met Cys Arg Ser Arg Ser Arg Ser Arg Ser Pro Arg Pro Arg Gly
    450                 455                 460
Asp Ser Ala Tyr His Ser Gln Arg His Ser Leu Leu Thr Pro Val Thr
465                 470                 475                 480
Pro Leu Ser Pro Pro Gly Leu Glu Glu Glu Asp Val Asn Gly Tyr Val
                485                 490                 495
Met Pro Asp Thr His Leu Lys Gly Thr Pro Ser Ser Arg Glu Gly Thr
            500                 505                 510
Leu Ser Ser Val Gly Leu Ser Ser Val Leu Gly Thr Glu Glu Glu Asp
        515                 520                 525
Glu Asp Glu Glu Tyr Glu Tyr Met Asn Arg Arg Arg Arg His Ser Pro
    530                 535                 540
Pro His Pro Pro Arg Pro Ser Ser Leu Glu Glu Leu Gly Tyr Glu Tyr
545                 550                 555                 560
Met Asp Val Gly Ser Asp Leu Ser Ala Ser Leu Gly Ser Thr Gln Ser
                565                 570                 575
```

```
Cys Pro Leu His Pro Val Pro Ile Met Pro Thr Ala Gly Thr Thr Pro
            580                 585                 590

Asp Glu Asp Tyr Glu Tyr Met Asn Arg Gln Arg Asp Gly Gly Pro
        595                 600                 605

Gly Gly Asp Tyr Ala Ala Met Gly Ala Cys Pro Ala Ser Glu Gln Gly
        610                 615                 620

Tyr Glu Glu Met Arg Ala Phe Gln Gly Pro Gly His Gln Ala Pro His
625                 630                 635                 640

Val His Tyr Ala Arg Leu Lys Thr Leu Arg Ser Leu Glu Ala Thr Asp
                645                 650                 655

Ser Ala Phe Asp Asn Pro Asp Tyr Trp His Ser Arg Leu Phe Pro Lys
                660                 665                 670

Ala Asn Ala Gln Arg Thr
                675
```

<210> SEQ ID NO 12
<211> LENGTH: 44
<212> TYPE: PRT
<213> ORGANISM: Homo sapiens
<220> FEATURE:
<221> NAME/KEY: misc_feature
<222> LOCATION: (1)..(44)
<223> OTHER INFORMATION: HER3 isoform 1 juxtamembrane segment

<400> SEQUENCE: 12

```
Tyr Trp Arg Gly Arg Arg Ile Gln Asn Lys Arg Ala Met Arg Arg Tyr
1               5                   10                  15

Leu Glu Arg Gly Glu Ser Ile Glu Pro Leu Asp Pro Ser Glu Lys Ala
                20                  25                  30

Asn Lys Val Leu Ala Arg Ile Phe Lys Glu Thr Glu
                35                  40
```

<210> SEQ ID NO 13
<211> LENGTH: 258
<212> TYPE: PRT
<213> ORGANISM: Homo sapiens
<220> FEATURE:
<221> NAME/KEY: misc_feature
<222> LOCATION: (1)..(258)
<223> OTHER INFORMATION: HER3 isoform1 protein kinase domain

<400> SEQUENCE: 13

```
Leu Arg Lys Leu Lys Val Leu Gly Ser Gly Val Phe Gly Thr Val His
1               5                   10                  15

Lys Gly Val Trp Ile Pro Glu Gly Glu Ser Ile Lys Ile Pro Val Cys
                20                  25                  30

Ile Lys Val Ile Glu Asp Lys Ser Gly Arg Gln Ser Phe Gln Ala Val
                35                  40                  45

Thr Asp His Met Leu Ala Ile Gly Ser Leu Asp His Ala His Ile Val
            50                  55                  60

Arg Leu Leu Gly Leu Cys Pro Gly Ser Ser Leu Gln Leu Val Thr Gln
65                  70                  75                  80

Tyr Leu Pro Leu Gly Ser Leu Leu Asp His Val Arg Gln His Arg Gly
                85                  90                  95

Ala Leu Gly Pro Gln Leu Leu Leu Asn Trp Gly Val Gln Ile Ala Lys
                100                 105                 110

Gly Met Tyr Tyr Leu Glu Glu His Gly Met Val His Arg Asn Leu Ala
                115                 120                 125
```

```
Ala Arg Asn Val Leu Leu Lys Ser Pro Ser Gln Val Gln Val Ala Asp
    130                 135                 140

Phe Gly Val Ala Asp Leu Leu Pro Pro Asp Asp Lys Gln Leu Leu Tyr
145                 150                 155                 160

Ser Glu Ala Lys Thr Pro Ile Lys Trp Met Ala Leu Glu Ser Ile His
                165                 170                 175

Phe Gly Lys Tyr Thr His Gln Ser Asp Val Trp Ser Tyr Gly Val Thr
            180                 185                 190

Val Trp Glu Leu Met Thr Phe Gly Ala Glu Pro Tyr Ala Gly Leu Arg
        195                 200                 205

Leu Ala Glu Val Pro Asp Leu Leu Glu Lys Gly Glu Arg Leu Ala Gln
    210                 215                 220

Pro Gln Ile Cys Thr Ile Asp Val Tyr Met Val Met Val Lys Cys Trp
225                 230                 235                 240

Met Ile Asp Glu Asn Ile Arg Pro Thr Phe Lys Glu Leu Ala Asn Glu
                245                 250                 255

Phe Thr

<210> SEQ ID NO 14
<211> LENGTH: 376
<212> TYPE: PRT
<213> ORGANISM: Homo sapiens
<220> FEATURE:
<221> NAME/KEY: misc_feature
<222> LOCATION: (1)..(376)
<223> OTHER INFORMATION: HER3 isoform 1 C terminal segment

<400> SEQUENCE: 14

Arg Met Ala Arg Asp Pro Pro Arg Tyr Leu Val Ile Lys Arg Glu Ser
1               5                   10                  15

Gly Pro Gly Ile Ala Pro Gly Pro Glu Pro His Gly Leu Thr Asn Lys
            20                  25                  30

Lys Leu Glu Glu Val Glu Leu Glu Pro Glu Leu Asp Leu Asp Leu Asp
        35                  40                  45

Leu Glu Ala Glu Glu Asp Asn Leu Ala Thr Thr Thr Leu Gly Ser Ala
    50                  55                  60

Leu Ser Leu Pro Val Gly Thr Leu Asn Arg Pro Arg Gly Ser Gln Ser
65                  70                  75                  80

Leu Leu Ser Pro Ser Ser Gly Tyr Met Pro Met Asn Gln Gly Asn Leu
                85                  90                  95

Gly Glu Ser Cys Gln Glu Ser Ala Val Ser Gly Ser Ser Glu Arg Cys
            100                 105                 110

Pro Arg Pro Val Ser Leu His Pro Met Pro Arg Gly Cys Leu Ala Ser
        115                 120                 125

Glu Ser Ser Glu Gly His Val Thr Gly Ser Glu Ala Glu Leu Gln Glu
    130                 135                 140

Lys Val Ser Met Cys Arg Ser Arg Ser Arg Ser Arg Ser Pro Arg Pro
145                 150                 155                 160

Arg Gly Asp Ser Ala Tyr His Ser Gln Arg His Ser Leu Leu Thr Pro
                165                 170                 175

Val Thr Pro Leu Ser Pro Pro Gly Leu Glu Glu Glu Asp Val Asn Gly
            180                 185                 190

Tyr Val Met Pro Asp Thr His Leu Lys Gly Thr Pro Ser Ser Arg Glu
        195                 200                 205

Gly Thr Leu Ser Ser Val Gly Leu Ser Ser Val Leu Gly Thr Glu Glu
    210                 215                 220
```

-continued

Glu Asp Glu Asp Glu Glu Tyr Glu Tyr Met Asn Arg Arg Arg His
225                 230                 235                 240

Ser Pro Pro His Pro Pro Arg Pro Ser Ser Leu Glu Gly Leu Gly Tyr
            245                 250                 255

Glu Tyr Met Asp Val Gly Ser Asp Leu Ser Ala Ser Leu Gly Ser Thr
            260                 265                 270

Gln Ser Cys Pro Leu His Pro Val Pro Ile Met Pro Thr Ala Gly Thr
            275                 280                 285

Thr Pro Asp Glu Asp Tyr Glu Tyr Met Asn Arg Gln Arg Asp Gly Gly
290                 295                 300

Gly Pro Gly Gly Asp Tyr Ala Ala Met Gly Ala Cys Pro Ala Ser Glu
305                 310                 315                 320

Gln Gly Tyr Glu Glu Met Arg Ala Phe Gln Gly Pro Gly His Gln Ala
            325                 330                 335

Pro His Val His Tyr Ala Arg Leu Lys Thr Leu Arg Ser Leu Glu Ala
            340                 345                 350

Thr Asp Ser Ala Phe Asp Asn Pro Asp Tyr Trp His Ser Arg Leu Phe
            355                 360                 365

Pro Lys Ala Asn Ala Gln Arg Thr
370                 375

<210> SEQ ID NO 15
<211> LENGTH: 164
<212> TYPE: PRT
<213> ORGANISM: Homo sapiens
<220> FEATURE:
<221> NAME/KEY: misc_feature
<222> LOCATION: (1)..(164)
<223> OTHER INFORMATION: HER3 extracellular region subdomain I

<400> SEQUENCE: 15

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
            20                  25                  30

Leu Tyr Glu Arg Cys Glu Val Val Met Gly Asn Leu Glu Ile Val Leu
        35                  40                  45

Thr Gly His Asn Ala Asp Leu Ser Phe Leu Gln Trp Ile Arg Glu Val
50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
            85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
        115                 120                 125

Tyr Ile Glu Lys Asn Asp Lys Leu Cys His Met Asp Thr Ile Asp Trp
130                 135                 140

Arg Asp Ile Val Arg Asp Arg Asp Ala Glu Ile Val Val Lys Asp Asn
145                 150                 155                 160

Gly Arg Ser Cys

<210> SEQ ID NO 16
<211> LENGTH: 146
<212> TYPE: PRT

```
<213> ORGANISM: Homo sapiens
<220> FEATURE:
<221> NAME/KEY: misc_feature
<222> LOCATION: (1)..(146)
<223> OTHER INFORMATION: HER3 extracellular region subdomain II

<400> SEQUENCE: 16

Pro Pro Cys His Glu Val Cys Lys Gly Arg Cys Trp Gly Pro Gly Ser
1               5                   10                  15

Glu Asp Cys Gln Thr Leu Thr Lys Thr Ile Cys Ala Pro Gln Cys Asn
            20                  25                  30

Gly His Cys Phe Gly Pro Asn Pro Asn Gln Cys Cys His Asp Glu Cys
        35                  40                  45

Ala Gly Gly Cys Ser Gly Pro Gln Asp Thr Asp Cys Phe Ala Cys Arg
    50                  55                  60

His Phe Asn Asp Ser Gly Ala Cys Val Pro Arg Cys Pro Gln Pro Leu
65                  70                  75                  80

Val Tyr Asn Lys Leu Thr Phe Gln Leu Glu Pro Asn Pro His Thr Lys
                85                  90                  95

Tyr Gln Tyr Gly Gly Val Cys Val Ala Ser Cys Pro His Asn Phe Val
            100                 105                 110

Val Asp Gln Thr Ser Cys Val Arg Ala Cys Pro Pro Asp Lys Met Glu
        115                 120                 125

Val Asp Lys Asn Gly Leu Lys Met Cys Glu Pro Cys Gly Gly Leu Cys
    130                 135                 140

Pro Lys
145

<210> SEQ ID NO 17
<211> LENGTH: 166
<212> TYPE: PRT
<213> ORGANISM: Homo sapiens
<220> FEATURE:
<221> NAME/KEY: misc_feature
<222> LOCATION: (1)..(166)
<223> OTHER INFORMATION: HER3 extracellular region subdomain III

<400> SEQUENCE: 17

Ala Cys Glu Gly Thr Gly Ser Gly Ser Arg Phe Gln Thr Val Asp Ser
1               5                   10                  15

Ser Asn Ile Asp Gly Phe Val Asn Cys Thr Lys Ile Leu Gly Asn Leu
            20                  25                  30

Asp Phe Leu Ile Thr Gly Leu Asn Gly Asp Pro Trp His Lys Ile Pro
        35                  40                  45

Ala Leu Asp Pro Glu Lys Leu Asn Val Phe Arg Thr Val Arg Glu Ile
    50                  55                  60

Thr Gly Tyr Leu Asn Ile Gln Ser Trp Pro Pro His Met His Asn Phe
65                  70                  75                  80

Ser Val Phe Ser Asn Leu Thr Thr Ile Gly Gly Arg Ser Leu Tyr Asn
                85                  90                  95

Arg Gly Phe Ser Leu Leu Ile Met Lys Asn Leu Asn Val Thr Ser Leu
            100                 105                 110

Gly Phe Arg Ser Leu Lys Glu Ile Ser Ala Gly Arg Ile Tyr Ile Ser
        115                 120                 125

Ala Asn Arg Gln Leu Cys Tyr His His Ser Leu Asn Trp Thr Lys Val
    130                 135                 140

Leu Arg Gly Pro Thr Glu Glu Arg Leu Asp Ile Lys His Asn Arg Pro
145                 150                 155                 160
```

-continued

Arg Arg Asp Cys Val Ala
            165

<210> SEQ ID NO 18
<211> LENGTH: 148
<212> TYPE: PRT
<213> ORGANISM: Homo sapiens
<220> FEATURE:
<221> NAME/KEY: misc_feature
<222> LOCATION: (1)..(148)
<223> OTHER INFORMATION: HER3 extracellular region subdomain IV

<400> SEQUENCE: 18

Glu Gly Lys Val Cys Asp Pro Leu Cys Ser Ser Gly Gly Cys Trp Gly
1               5                   10                  15

Pro Gly Pro Gly Gln Cys Leu Ser Cys Arg Asn Tyr Ser Arg Gly Gly
            20                  25                  30

Val Cys Val Thr His Cys Asn Phe Leu Asn Gly Glu Pro Arg Glu Phe
        35                  40                  45

Ala His Glu Ala Glu Cys Phe Ser Cys His Pro Glu Cys Gln Pro Met
    50                  55                  60

Glu Gly Thr Ala Thr Cys Asn Gly Ser Gly Ser Asp Thr Cys Ala Gln
65                  70                  75                  80

Cys Ala His Phe Arg Asp Gly Pro His Cys Val Ser Ser Cys Pro His
                85                  90                  95

Gly Val Leu Gly Ala Lys Gly Pro Ile Tyr Lys Tyr Pro Asp Val Gln
            100                 105                 110

Asn Glu Cys Arg Pro Cys His Glu Asn Cys Thr Gln Gly Cys Lys Gly
        115                 120                 125

Pro Glu Leu Gln Asp Cys Leu Gly Gln Thr Leu Val Leu Ile Gly Lys
    130                 135                 140

Thr His Leu Thr
145

<210> SEQ ID NO 19
<211> LENGTH: 17
<212> TYPE: PRT
<213> ORGANISM: Homo sapiens
<220> FEATURE:
<221> NAME/KEY: misc_feature
<222> LOCATION: (1)..(17)
<223> OTHER INFORMATION: HER3 extracellular region subdomain II
      dimerisation loop

<400> SEQUENCE: 19

Gln Pro Leu Val Tyr Asn Lys Leu Thr Phe Gln Leu Glu Pro Asn Pro
1               5                   10                  15

His

<210> SEQ ID NO 20
<211> LENGTH: 1283
<212> TYPE: PRT
<213> ORGANISM: rhesus macaque
<220> FEATURE:
<221> NAME/KEY: misc_feature
<222> LOCATION: (1)..(1283)
<223> OTHER INFORMATION: HER3

<400> SEQUENCE: 20

Met Gly Asn Leu Glu Ile Val Leu Thr Gly His Asn Ala Asp Leu Ser
1               5                   10                  15

-continued

```
Phe Leu Gln Trp Ile Arg Glu Val Thr Gly Tyr Val Leu Val Ala Met
             20                  25                  30

Asn Glu Phe Ser Thr Leu Pro Leu Pro Asn Leu Arg Val Val Arg Gly
         35                  40                  45

Thr Gln Val Tyr Asp Gly Lys Phe Ala Ile Phe Val Met Leu Asn Tyr
 50                  55                  60

Asn Thr Asn Ser Ser His Ala Leu Arg Gln Leu Arg Leu Thr Gln Leu
 65                  70                  75                  80

Thr Glu Ile Leu Ser Gly Gly Val Tyr Ile Glu Lys Asn Asp Lys Leu
                 85                  90                  95

Cys His Met Asp Thr Ile Asp Trp Lys Asp Ile Val Arg Asp Gln Asp
            100                 105                 110

Ala Glu Ile Val Val Lys Asp Asn Gly Arg Ser Cys Pro Leu Cys His
            115                 120                 125

Glu Val Cys Lys Gly Arg Cys Trp Gly Pro Gly Pro Glu Asp Cys Gln
            130                 135                 140

Thr Leu Thr Lys Thr Ile Cys Ala Pro Gln Cys Asn Gly His Cys Phe
145                 150                 155                 160

Gly Pro Asn Pro Asn Gln Cys Cys His Asp Glu Cys Ala Gly Gly Cys
                165                 170                 175

Ser Gly Pro Gln Asp Thr Asp Cys Phe Ala Cys Arg His Phe Asn Asp
            180                 185                 190

Ser Gly Ala Cys Val Pro Arg Cys Pro Gln Pro Leu Val Tyr Asn Lys
            195                 200                 205

Leu Thr Phe Gln Leu Glu Pro Asn Pro His Thr Lys Tyr Gln Tyr Gly
210                 215                 220

Gly Val Cys Val Ala Ser Cys Pro His Asn Phe Val Val Asp Gln Thr
225                 230                 235                 240

Ser Cys Val Arg Ala Cys Pro Pro Asp Lys Met Glu Val Asp Lys Asn
            245                 250                 255

Gly Leu Lys Met Cys Glu Pro Cys Gly Gly Leu Cys Pro Lys Ala Cys
            260                 265                 270

Glu Gly Thr Gly Ser Gly Ser Arg Phe Gln Thr Val Asp Ser Ser Asn
            275                 280                 285

Ile Asp Gly Phe Val Asn Cys Thr Lys Ile Leu Gly Asn Leu Asp Phe
290                 295                 300

Leu Ile Thr Gly Leu Asn Gly Asp Pro Trp His Lys Ile Pro Ala Leu
305                 310                 315                 320

Asp Pro Glu Lys Leu Asn Val Phe Arg Thr Val Arg Glu Ile Thr Gly
            325                 330                 335

Tyr Leu Asn Ile Gln Ser Trp Pro Pro His Met Tyr Asn Phe Ser Val
            340                 345                 350

Phe Ser Asn Leu Thr Thr Ile Gly Gly Arg Ser Leu Tyr Asn Arg Gly
            355                 360                 365

Phe Ser Leu Leu Ile Met Lys Asn Leu Asn Val Thr Ser Leu Gly Phe
            370                 375                 380

Arg Ser Leu Lys Glu Ile Ser Ala Gly Arg Ile Tyr Ile Ser Ala Asn
385                 390                 395                 400

Arg Gln Leu Cys Tyr His His Ser Leu Asn Trp Thr Lys Val Leu Arg
            405                 410                 415

Gly Pro Thr Glu Glu Arg Leu Asp Ile Lys His Asn Arg Pro Arg Arg
            420                 425                 430
```

```
Asp Cys Val Ala Glu Gly Lys Val Cys Asp Pro Leu Cys Ser Ser Gly
        435                 440                 445

Gly Cys Trp Gly Pro Gly Pro Gly Gln Cys Leu Ser Cys Arg Asn Tyr
    450                 455                 460

Ser Arg Gly Gly Val Cys Val Thr His Cys Asn Phe Leu Asn Gly Glu
465                 470                 475                 480

Pro Arg Glu Phe Ala His Glu Ala Glu Cys Phe Ser Cys His Pro Glu
                485                 490                 495

Cys Gln Pro Met Glu Gly Thr Ala Thr Cys Asn Gly Ser Gly Ser Asp
            500                 505                 510

Thr Cys Ala Gln Cys Ala His Phe Arg Asp Gly Pro His Cys Val Ser
        515                 520                 525

Ser Cys Pro His Gly Val Leu Gly Ala Lys Gly Pro Ile Tyr Lys Tyr
    530                 535                 540

Pro Asp Val Gln Asn Glu Cys Arg Pro Cys His Glu Asn Cys Thr Gln
545                 550                 555                 560

Gly Cys Lys Gly Pro Glu Leu Gln Asp Cys Leu Gly Gln Thr Leu Val
                565                 570                 575

Leu Ile Gly Lys Thr His Leu Thr Met Ala Leu Thr Val Ile Ala Gly
            580                 585                 590

Leu Val Val Ile Phe Met Met Leu Gly Gly Thr Phe Leu Tyr Trp Arg
        595                 600                 605

Gly Arg Arg Ile Gln Asn Lys Arg Ala Met Arg Arg Tyr Leu Glu Arg
    610                 615                 620

Gly Glu Ser Ile Glu Pro Leu Asp Pro Ser Glu Lys Ala Asn Lys Val
625                 630                 635                 640

Leu Ala Arg Ile Phe Lys Glu Thr Glu Leu Arg Lys Leu Lys Val Leu
                645                 650                 655

Gly Ser Gly Val Phe Gly Thr Val His Lys Gly Val Trp Ile Pro Glu
            660                 665                 670

Gly Glu Ser Ile Lys Ile Pro Val Cys Ile Lys Ile Glu Asp Lys
        675                 680                 685

Ser Gly Arg Gln Ser Phe Gln Ala Val Thr Asp His Met Leu Ala Ile
    690                 695                 700

Gly Ser Leu Asp His Ala His Ile Val Arg Leu Leu Gly Leu Cys Pro
705                 710                 715                 720

Gly Ser Ser Leu Gln Leu Val Thr Gln Tyr Leu Pro Leu Gly Ser Leu
                725                 730                 735

Leu Asp His Val Arg Gln His Arg Gly Ala Leu Gly Pro Gln Leu Leu
            740                 745                 750

Leu Asn Trp Gly Val Gln Ile Ala Lys Gly Met Tyr Tyr Leu Glu Glu
        755                 760                 765

His Gly Met Val His Arg Asn Leu Ala Ala Arg Asn Val Leu Leu Lys
    770                 775                 780

Ser Pro Ser Gln Val Gln Val Ala Asp Phe Gly Val Ala Asp Leu Leu
785                 790                 795                 800

Pro Pro Asp Asp Lys Gln Leu Leu Tyr Ser Glu Ala Lys Thr Pro Ile
                805                 810                 815

Lys Trp Met Ala Leu Glu Ser Ile His Phe Gly Lys Tyr Thr His Gln
            820                 825                 830

Ser Asp Val Trp Ser Tyr Gly Val Thr Val Trp Glu Leu Met Thr Phe
        835                 840                 845
```

```
Gly Ala Glu Pro Tyr Ala Gly Leu Arg Leu Ala Glu Val Pro Asp Leu
    850                 855                 860

Leu Glu Lys Gly Glu Arg Leu Ala Gln Pro Gln Ile Cys Thr Ile Asp
865                 870                 875                 880

Val Tyr Met Val Met Val Lys Cys Trp Met Ile Asp Glu Asn Ile Arg
                885                 890                 895

Pro Thr Phe Lys Glu Leu Ala Asn Glu Phe Thr Arg Met Ala Arg Asp
                900                 905                 910

Pro Pro Arg Tyr Leu Val Ile Lys Arg Glu Ser Gly Pro Gly Ile Ala
            915                 920                 925

Pro Gly Pro Glu Pro His Gly Leu Thr Asn Lys Lys Leu Glu Glu Val
930                 935                 940

Glu Leu Glu Pro Glu Leu Asp Leu Asp Leu Asp Leu Glu Ala Glu Glu
945                 950                 955                 960

Asp Asn Leu Ala Thr Thr Thr Leu Gly Ser Ala Leu Ser Leu Pro Val
                965                 970                 975

Gly Thr Leu Asn Arg Pro Arg Gly Ser Gln Ser Leu Leu Ser Pro Ser
                980                 985                 990

Ser Gly Tyr Met Pro Met Asn Gln Gly Asn Leu Gly Glu Ala Phe Gln
            995                 1000                1005

Glu Ser Ala Val Ser Gly Ser Ser Glu Trp Cys Pro Arg Pro Val
    1010                1015                1020

Ser Leu His Pro Met Pro Arg Gly Cys Leu Ala Ser Glu Ser Ser
    1025                1030                1035

Glu Gly His Val Thr Gly Ser Glu Ala Glu Leu Gln Glu Lys Val
    1040                1045                1050

Ser Thr Cys Arg Ser Arg Ser Arg Ser Arg Ser Pro Arg Pro Arg
    1055                1060                1065

Gly Asp Ser Ala Tyr His Ser Gln Arg His Ser Leu Leu Thr Pro
    1070                1075                1080

Val Thr Pro Leu Ser Pro Pro Gly Leu Glu Glu Glu Asp Val Asn
    1085                1090                1095

Gly Tyr Val Met Pro Asp Thr His Leu Lys Gly Thr Pro Ser Ser
    1100                1105                1110

Arg Glu Gly Thr Leu Ser Ser Val Gly Leu Ser Ser Val Leu Gly
    1115                1120                1125

Thr Glu Glu Glu Asp Glu Asp Glu Glu Tyr Glu Tyr Met Asn Arg
    1130                1135                1140

Arg Arg Arg His Ser Pro Pro Arg Pro Pro Arg Pro Ser Ser Leu
    1145                1150                1155

Glu Glu Leu Gly Tyr Glu Tyr Met Asp Val Gly Ser Asp Leu Ser
    1160                1165                1170

Ala Ser Leu Gly Ser Thr Gln Ser Cys Pro Leu His Pro Val Pro
    1175                1180                1185

Val Met Pro Thr Ala Gly Thr Thr Pro Asp Glu Asp Tyr Glu Tyr
    1190                1195                1200

Met Asn Arg Gln Arg Gly Gly Ser Gly Pro Gly Gly Asp Tyr Ala
    1205                1210                1215

Ala Met Gly Ala Cys Pro Ala Ser Glu Gln Gly Tyr Glu Glu Met
    1220                1225                1230

Arg Ala Phe Gln Gly Pro Gly His Gln Ala Pro His Val His Tyr
    1235                1240                1245
```

-continued

Ala His Leu Lys Thr Leu Arg Ser Leu Glu Ala Thr Asp Ser Ala
    1250                1255                1260

Phe Asp Asn Pro Asp Tyr Trp His Ser Arg Leu Phe Pro Lys Ala
    1265                1270                1275

Asn Ala Gln Arg Thr
    1280

<210> SEQ ID NO 21
<211> LENGTH: 13
<212> TYPE: PRT
<213> ORGANISM: Artificial Sequence
<220> FEATURE:
<223> OTHER INFORMATION: Epitope recognised by anti-HER3 antibody clones
      10D1 and 10A6

<400> SEQUENCE: 21

Tyr Asn Lys Leu Thr Phe Gln Leu Glu Pro Asn Pro His
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Epitope recognised by anti-HER3 antibody clone
      4-35-B2 and 4-35-B4

<400> SEQUENCE: 22

Pro Arg Cys Pro Gln Pro Leu Val Tyr Asn Lys Leu Thr Phe
1               5                   10

<210> SEQ ID NO 23
<211> LENGTH: 21
<212> TYPE: PRT
<213> ORGANISM: Artificial Sequence
<220> FEATURE:
<223> OTHER INFORMATION: Composite sequence of epitopes recognised by
      anti-HER3 antibody clones 4-35-B2, 4-35-B4 10D1 and 10A6

<400> SEQUENCE: 23

Pro Arg Cys Pro Gln Pro Leu Val Tyr Asn Lys Leu Thr Phe Gln Leu
1               5                   10                  15

Glu Pro Asn Pro His
            20

<210> SEQ ID NO 24
<211> LENGTH: 120
<212> TYPE: PRT
<213> ORGANISM: Artificial Sequence
<220> FEATURE:
<223> OTHER INFORMATION: 10D1 heavy chain variable region

<400> SEQUENCE: 24

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
                20                  25                  30

Tyr Ser Trp His Trp Ile Arg Gln Phe Pro Gly Asn Lys Leu Glu Trp
            35                  40                  45

Met Gly Ser Ile His Tyr Ser Gly Gly Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

```
Leu Gln Leu Asn Ser Val Thr Glu Asp Thr Ala Thr Tyr Phe Cys
                85                  90                  95

Ala Arg Met Thr Thr Ala Pro Arg Tyr Pro Phe Asp Tyr Trp Gly Gln
            100                 105                 110

Gly Thr Thr Leu Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: 10D1_c75 heavy chain variable region

<400> SEQUENCE: 25

Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Ile Gly Ser Ile His Tyr Ser Gly Gly Thr Asn Tyr Asn Pro Thr Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser
        115                 120

<210> SEQ ID NO 26
<211> LENGTH: 120
<212> TYPE: PRT
<213> ORGANISM: Artificial Sequence
<220> FEATURE:
<223> OTHER INFORMATION: 10D1_c76 heavy chain variable region

<400> SEQUENCE: 26

Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Ile Gly Ser Ile His Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser
        115                 120
```

<210> SEQ ID NO 27
<211> LENGTH: 120
<212> TYPE: PRT
<213> ORGANISM: Artificial Sequence
<220> FEATURE:
<223> OTHER INFORMATION: 10D1_c77 heavy chain variable region

<400> SEQUENCE: 27

```
Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Ile Gly Ser Ile His Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser
        115                 120
```

<210> SEQ ID NO 28
<211> LENGTH: 120
<212> TYPE: PRT
<213> ORGANISM: Artificial Sequence
<220> FEATURE:
<223> OTHER INFORMATION: 10D1_c78v1 heavy chain variable region

<400> SEQUENCE: 28

```
Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Ile Gly Ser Ile His Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser
        115                 120
```

<210> SEQ ID NO 29
<211> LENGTH: 120
<212> TYPE: PRT
<213> ORGANISM: Artificial Sequence
<220> FEATURE:
<223> OTHER INFORMATION: 10D1_c78v2 heavy chain variable region

<400> SEQUENCE: 29

```
Asp Val Gln Leu Gln Glu Trp Gly Ala Gly Leu Leu Lys Pro Ser Glu
1               5                   10                  15
```

```
Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Lys Gly Leu Glu Trp
            35                  40                  45

Ile Gly Ser Ile His Tyr Ser Gly Gly Thr Asn Tyr Asn Pro Ser Leu
 50                  55                  60

Lys Ser Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Phe Cys
                 85                  90                  95

Ala Arg Met Thr Thr Ala Pro Arg Tyr Pro Phe Asp Tyr Trp Gly Gln
                100                 105                 110

Gly Thr Leu Val Thr Val Ser Ser
            115                 120

<210> SEQ ID NO 30
<211> LENGTH: 120
<212> TYPE: PRT
<213> ORGANISM: Artificial Sequence
<220> FEATURE:
<223> OTHER INFORMATION: 10D1_11B heavy chain variable region

<400> SEQUENCE: 30

Asp Val Gln Leu Gln Glu Trp Gly Ala Gly Leu Leu Lys Pro Ser Glu
 1               5                  10                  15

Thr Leu Ser Leu Thr Cys Ala Val Tyr Gly Tyr Ser Ile Thr Ser Gly
            20                  25                  30

Tyr Ser Trp His Trp Ile Arg Gln Pro Pro Gly Lys Gly Leu Glu Trp
            35                  40                  45

Ile Gly Ser Ile His Tyr Ser Gly Gly Thr Asn Tyr Asn Pro Ser Leu
 50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Met Thr Thr Ala Pro Arg Tyr Pro Phe Asp Tyr Trp Gly Gln
                100                 105                 110

Gly Thr Leu Val Thr Val Ser Ser
            115                 120

<210> SEQ ID NO 31
<211> LENGTH: 120
<212> TYPE: PRT
<213> ORGANISM: Artificial Sequence
<220> FEATURE:
<223> OTHER INFORMATION: 10D1_c85v1 heavy chain variable region

<400> SEQUENCE: 31

Asp Val Gln Leu Gln Glu Trp Gly Ala Gly Leu Leu Lys Pro Ser Glu
 1               5                  10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
            35                  40                  45

Ile Gly Ser Ile Arg Tyr Ser Gly Gly Thr Asn Tyr Asn Pro Ser Leu
 50                  55                  60
```

```
Lys Ser Arg Ile Thr Ile Ser Arg Asp Thr Ser Lys Asn Gln Phe Ser
 65                  70                  75                  80

Leu Lys Leu Gly Ser Val Thr Ala Ala Asp Thr Ala Val Tyr Phe Cys
                 85                  90                  95

Ala Arg Met Thr Thr Ala Pro Arg Tyr Pro Phe Asp Tyr Trp Gly Gln
            100                 105                 110

Gly Thr Leu Val Thr Val Ser Ser
        115                 120

<210> SEQ ID NO 32
<211> LENGTH: 120
<212> TYPE: PRT
<213> ORGANISM: Artificial Sequence
<220> FEATURE:
<223> OTHER INFORMATION: 10D1_c85v2 heavy chain variable region

<400> SEQUENCE: 32

Asp Val Gln Leu Gln Glu Trp Gly Ala Gly Leu Leu Lys Pro Ser Glu
  1               5                  10                  15

Thr Leu Ser Leu Thr Cys Ala Val Thr Gly Tyr Ser Ile Thr Ser Gly
                 20                  25                  30

Tyr Ser Trp His Trp Ile Arg Gln Phe Pro Gly Lys Gly Leu Glu Trp
             35                  40                  45

Ile Gly Ser Ile Arg Tyr Ser Gly Gly Thr Asn Tyr Asn Pro Ser Leu
         50                  55                  60

Lys Ser Arg Ile Thr Ile Ser Arg Asp Thr Ser Lys Asn Gln Phe Ser
 65                  70                  75                  80

Leu Lys Leu Gly Ser Val Thr Ala Ala Asp Thr Ala Val Tyr Phe Cys
                 85                  90                  95

Ala Arg Met Thr Thr Ala Pro Arg Tyr Pro Phe Asp Tyr Trp Gly Gln
            100                 105                 110

Gly Thr Leu Val Thr Val Ser Ser
        115                 120

<210> SEQ ID NO 33
<211> LENGTH: 120
<212> TYPE: PRT
<213> ORGANISM: Artificial Sequence
<220> FEATURE:
<223> OTHER INFORMATION: 10D1_c85o1 heavy chain variable region

<400> SEQUENCE: 33

Asp Val Gln Leu Gln Glu Trp Gly Ala Gly Leu Leu Lys Pro Ser Glu
  1               5                  10                  15

Thr Leu Ser Leu Thr Cys Ala Val Thr Gly Tyr Ser Ile Thr Ser Gly
                 20                  25                  30

Tyr Ser Trp His Trp Ile Arg Gln Phe Pro Gly Lys Gly Leu Glu Trp
             35                  40                  45

Ile Gly Ser Ile Arg Tyr Ser Gly Gly Thr Asn Tyr Asn Pro Ser Leu
         50                  55                  60

Lys Ser Arg Ile Thr Ile Ser Arg Asp Thr Ser Lys Asn Gln Phe Ser
 65                  70                  75                  80

Leu Lys Leu Gly Ser Val Thr Ala Ala Asp Thr Ala Val Tyr Phe Cys
                 85                  90                  95

Ala Arg Glu Thr Thr Ala Pro Arg Tyr Pro Phe Asp Tyr Trp Gly Gln
            100                 105                 110
```

```
Gly Thr Leu Val Thr Val Ser Ser
        115                 120

<210> SEQ ID NO 34
<211> LENGTH: 120
<212> TYPE: PRT
<213> ORGANISM: Artificial Sequence
<220> FEATURE:
<223> OTHER INFORMATION: 10D1_c85o2 heavy chain variable region

<400> SEQUENCE: 34

Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Lys Gly Leu Glu Trp
        35                  40                  45

Ile Gly Ser Ile Arg Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Gly Ser Val Thr Ala Ala Asp Thr Ala Val Tyr Phe Cys
                85                  90                  95

Ala Arg Gly Thr Thr Ala Pro Arg Tyr Pro Phe Asp Tyr Trp Gly Gln
            100                 105                 110

Gly Thr Leu Val Thr Val Ser Ser
        115                 120

<210> SEQ ID NO 35
<211> LENGTH: 120
<212> TYPE: PRT
<213> ORGANISM: Artificial Sequence
<220> FEATURE:
<223> OTHER INFORMATION: 10D1_c87 heavy chain variable region

<400> SEQUENCE: 35

Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Ile Gly Ser Ile His Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Arg Leu Ser Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser
        115                 120

<210> SEQ ID NO 36
<211> LENGTH: 120
<212> TYPE: PRT
<213> ORGANISM: Artificial Sequence
<220> FEATURE:
<223> OTHER INFORMATION: 10D1_c89 heavy chain variable region
```

<400> SEQUENCE: 36

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Ile Gly Ser Ile Arg Tyr Ser Gly Gly Thr Asp Tyr Asn Pro Ser Leu
    50                  55                  60

Lys Ser Leu Val Thr Ile Ser Ala Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Thr Thr Ala Pro Trp Tyr Pro Phe Asp Tyr Trp Gly Gln
            100                 105                 110

Gly Thr Thr Val Thr Val Ser Ser
            115                 120

<210> SEQ ID NO 37
<211> LENGTH: 120
<212> TYPE: PRT
<213> ORGANISM: Artificial Sequence
<220> FEATURE:
<223> OTHER INFORMATION: 10D1_c90 heavy chain variable region

<400> SEQUENCE: 37

Gln Val Gln Leu Gln Glu Ser Gly Pro Gly Leu Val Lys Pro Ser Gln
1               5                   10                  15

Thr Leu Phe Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Ile Gly Ser Ile Arg Tyr Ser Gly Gly Thr Asp Tyr Asn Pro Ser Leu
    50                  55                  60

Lys Ser Leu Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Thr Thr Ala Pro Trp Tyr Pro Phe Asp Tyr Trp Gly Gln
            100                 105                 110

Gly Thr Thr Val Thr Val Ser Ser
            115                 120

<210> SEQ ID NO 38
<211> LENGTH: 120
<212> TYPE: PRT
<213> ORGANISM: Artificial Sequence
<220> FEATURE:
<223> OTHER INFORMATION: 10D1_c91 heavy chain variable region

<400> SEQUENCE: 38

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Tyr Ile Thr Ser Gly
            20                  25                  30

Tyr Ser Trp His Trp Ile Arg Gln His Pro Gly Lys Gly Leu Glu Trp
        35                  40                  45

Ile Gly Ser Ile Arg Tyr Ser Gly Gly Thr Asp Tyr Asn Pro Ser Leu
            50                  55                  60

Lys Ser Leu Ala Thr Ile Ser Ala Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Met Thr Thr Ala Pro Trp Tyr Pro Phe Asp Tyr Trp Gly Gln
               100                 105                 110

Gly Thr Ala Val Thr Val Ser Ser
            115                 120

<210> SEQ ID NO 39
<211> LENGTH: 120
<212> TYPE: PRT
<213> ORGANISM: Artificial Sequence
<220> FEATURE:
<223> OTHER INFORMATION: 10D1_c92 heavy chain variable region

<400> SEQUENCE: 39

Asp Val Gln Leu Gln Glu Trp Gly Ala Gly Leu Leu Lys Pro Ser Glu
 1               5                  10                  15

Thr Leu Ser Leu Thr Cys Ala Val Thr Gly Tyr Ser Ile Thr Ser Gly
                 20                  25                  30

Tyr Ser Trp His Trp Ile Arg Gln Phe Pro Gly Asn Gly Leu Glu Trp
             35                  40                  45

Ile Gly Ser Ile His Tyr Ser Gly Gly Thr Asn Tyr Asn Pro Thr Leu
            50                  55                  60

Lys Ser Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Phe Cys
                 85                  90                  95

Ala Arg Met Thr Thr Ala Pro Arg Tyr Pro Phe Asp Tyr Trp Gly Gln
               100                 105                 110

Gly Thr Leu Val Thr Val Ser Ser
            115                 120

<210> SEQ ID NO 40
<211> LENGTH: 120
<212> TYPE: PRT
<213> ORGANISM: Artificial Sequence
<220> FEATURE:
<223> OTHER INFORMATION: 10D1_c93 heavy chain variable region

<400> SEQUENCE: 40

Asp Val Gln Leu Gln Glu Trp Gly Ala Gly Leu Leu Lys Pro Ser Glu
 1               5                  10                  15

Thr Leu Ser Leu Thr Cys Ala Val Thr Gly Tyr Ser Ile Thr Ser Gly
                 20                  25                  30

Tyr Ser Trp His Trp Ile Arg Gln Phe Pro Gly Asn Gly Leu Glu Trp
             35                  40                  45

Ile Gly Ser Ile His Tyr Ser Gly Gly Thr Asn Tyr Asn Pro Ser Leu
            50                  55                  60

Lys Ser Arg Ile Thr Ile Ser Arg Asp Thr Ser Lys Asn Gln Phe Ser
 65                  70                  75                  80

Leu Arg Leu Ser Ser Val Thr Ala Ala Asp Thr Ala Val Tyr Phe Cys
                 85                  90                  95

Ala Arg Met Thr Thr Ala Pro Arg Tyr Pro Phe Asp Tyr Trp Gly Gln
            100                 105                 110

Gly Thr Leu Val Thr Val Ser Ser
        115                 120

<210> SEQ ID NO 41
<211> LENGTH: 9
<212> TYPE: PRT
<213> ORGANISM: Artificial Sequence
<220> FEATURE:
<223> OTHER INFORMATION: 10D1, 10D1_c75, 10D1_c76, 10D1_c77, 10D1_c78v1,
      10D1_c78v2, 10D1_11B, 10D1_c85v1,10D1_c85v2, 10D1_c85o1,
      10D1_c85o2, 10D1_c87, 10D1_c89, 10D1_c90, 10D1_c92, 10D1_c93 heavy
      chain CDR1

<400> SEQUENCE: 41

Gly Tyr Ser Ile Thr Ser Gly Tyr Ser
1               5

<210> SEQ ID NO 42
<211> LENGTH: 9
<212> TYPE: PRT
<213> ORGANISM: Artificial Sequence
<220> FEATURE:
<223> OTHER INFORMATION: 10D1_c91 heavy chain CDR1

<400> SEQUENCE: 42

Gly Tyr Tyr Ile Thr Ser Gly Tyr Ser
1               5

<210> SEQ ID NO 43
<211> LENGTH: 9
<212> TYPE: PRT
<213> ORGANISM: Artificial Sequence
<220> FEATURE:
<223> OTHER INFORMATION: 10D1 derived consensus heavy chain CDR1
<220> FEATURE:
<221> NAME/KEY: MISC_FEATURE
<222> LOCATION: (3)..(3)
<223> OTHER INFORMATION: Xaa = S or Y

<400> SEQUENCE: 43

Gly Tyr Xaa Ile Thr Ser Gly Tyr Ser
1               5

<210> SEQ ID NO 44
<211> LENGTH: 7
<212> TYPE: PRT
<213> ORGANISM: Artificial Sequence
<220> FEATURE:
<223> OTHER INFORMATION: 10D1, 10D1_c75, 10D1_c76, 10D1_c77, 10D1_c78v1,
      10D1_c78v2, 10D1_11B, 10D1_c87, 10D1_c92, 10D1_c93 heavy chain
      CDR2

<400> SEQUENCE: 44

Ile His Tyr Ser Gly Gly Thr
1               5

<210> SEQ ID NO 45
<211> LENGTH: 7
<212> TYPE: PRT
<213> ORGANISM: Artificial Sequence
<220> FEATURE:
<223> OTHER INFORMATION: 10D1_c85v1, 10D1_c85v2,10D1_c85o1, 10D1_c85o2,
      10D1_c89, 10D1_c90, 10D1_c91 heavy chain CDR2

```
<400> SEQUENCE: 45

Ile Arg Tyr Ser Gly Gly Thr
1               5

<210> SEQ ID NO 46
<211> LENGTH: 7
<212> TYPE: PRT
<213> ORGANISM: Artificial Sequence
<220> FEATURE:
<223> OTHER INFORMATION: 10D1 derived consensus heavy chain CDR2
<220> FEATURE:
<221> NAME/KEY: MISC_FEATURE
<222> LOCATION: (2)..(2)
<223> OTHER INFORMATION: Xaa = H or R

<400> SEQUENCE: 46

Ile Xaa Tyr Ser Gly Gly Thr
1               5

<210> SEQ ID NO 47
<211> LENGTH: 13
<212> TYPE: PRT
<213> ORGANISM: Artificial Sequence
<220> FEATURE:
<223> OTHER INFORMATION: 10D1, 10D1_c75, 10D1_c76, 10D1_c77, 10D1_c78v1,
      10D1_c78v2, 10D1_11B, 10D1_c85v1,10D1_c85v2, 10D1_c87, 10D1_c92,
      10D1_c93 heavy chain CDR3

<400> SEQUENCE: 47

Ala Arg Met Thr Thr Ala Pro Arg Tyr Pro Phe Asp Tyr
1               5                   10

<210> SEQ ID NO 48
<211> LENGTH: 13
<212> TYPE: PRT
<213> ORGANISM: Artificial Sequence
<220> FEATURE:
<223> OTHER INFORMATION: 10D1_c89, 10D1_c90, 10D1_c91 heavy chain CDR3

<400> SEQUENCE: 48

Ala Arg Met Thr Thr Ala Pro Trp Tyr Pro Phe Asp Tyr
1               5                   10

<210> SEQ ID NO 49
<211> LENGTH: 13
<212> TYPE: PRT
<213> ORGANISM: Artificial Sequence
<220> FEATURE:
<223> OTHER INFORMATION: 10D1_c85o1 heavy chain CDR3

<400> SEQUENCE: 49

Ala Arg Glu Thr Thr Ala Pro Arg Tyr Pro Phe Asp Tyr
1               5                   10

<210> SEQ ID NO 50
<211> LENGTH: 13
<212> TYPE: PRT
<213> ORGANISM: Artificial Sequence
<220> FEATURE:
<223> OTHER INFORMATION: 10D1_c85o2 heavy chain CDR3

<400> SEQUENCE: 50

Ala Arg Gly Thr Thr Ala Pro Arg Tyr Pro Phe Asp Tyr
1               5                   10

<210> SEQ ID NO 51
```

```
<211> LENGTH: 13
<212> TYPE: PRT
<213> ORGANISM: Artificial Sequence
<220> FEATURE:
<223> OTHER INFORMATION: 10D1 derived consensus heavy chain CDR3
<220> FEATURE:
<221> NAME/KEY: MISC_FEATURE
<222> LOCATION: (3)..(3)
<223> OTHER INFORMATION: Xaa = M, E or G
<220> FEATURE:
<221> NAME/KEY: MISC_FEATURE
<222> LOCATION: (8)..(8)
<223> OTHER INFORMATION: Xaa = R or W

<400> SEQUENCE: 51

Ala Arg Xaa Thr Thr Ala Pro Xaa Tyr Pro Phe Asp Tyr
1               5                   10

<210> SEQ ID NO 52
<211> LENGTH: 25
<212> TYPE: PRT
<213> ORGANISM: Artificial Sequence
<220> FEATURE:
<223> OTHER INFORMATION: 10D1_c75, 10D1_c76, 10D1_c77, 10D1_c78v1,
      10D1_c78v2, 10D1_c85v1,10D1_c85v2, 10D1_c85o1, 10D1_c85o2,
      10D1_c87, 10D1_c92, 10D1_c93 heavy chain FR1

<400> SEQUENCE: 52

Asp Val Gln Leu Gln Glu Trp Gly Ala Gly Leu Leu Lys Pro Ser Glu
1               5                   10                  15

Thr Leu Ser Leu Thr Cys Ala Val Thr
            20                  25

<210> SEQ ID NO 53
<211> LENGTH: 25
<212> TYPE: PRT
<213> ORGANISM: Artificial Sequence
<220> FEATURE:
<223> OTHER INFORMATION: 110D1_c89, 10D1_c91 heavy chain FR1

<400> SEQUENCE: 53

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 54
<211> LENGTH: 25
<212> TYPE: PRT
<213> ORGANISM: Artificial Sequence
<220> FEATURE:
<223> OTHER INFORMATION: 10D1_c90 heavy chain FR1

<400> SEQUENCE: 54

Gln Val Gln Leu Gln Glu Ser Gly Pro Gly Leu Val Lys Pro Ser Gln
1               5                   10                  15

Thr Leu Phe Leu Thr Cys Thr Val Ser
            20                  25

<210> SEQ ID NO 55
<211> LENGTH: 25
<212> TYPE: PRT
<213> ORGANISM: Artificial Sequence
<220> FEATURE:
<223> OTHER INFORMATION: 10D1 heavy chain FR1
```

<400> SEQUENCE: 55

Asp Val Gln Leu Gln Glu Ser Gly Pro Asp Leu Val Lys Pro Ser Gln
1               5                   10                  15

Ser Leu Ser Leu Thr Cys Thr Val Thr
            20                  25

<210> SEQ ID NO 56
<211> LENGTH: 17
<212> TYPE: PRT
<213> ORGANISM: Artificial Sequence
<220> FEATURE:
<223> OTHER INFORMATION: 10D1_c75, 10D1_c76, 10D1_c77, 10D1_c78v1,
      0D1_c85v1, 10D1_c87, 10D1_c92, 10D1_c93 heavy chain FR2

<400> SEQUENCE: 56

Trp His Trp Ile Arg Gln Phe Pro Gly Asn Gly Leu Glu Trp Ile Gly
1               5                   10                  15

Ser

<210> SEQ ID NO 57
<211> LENGTH: 17
<212> TYPE: PRT
<213> ORGANISM: Artificial Sequence
<220> FEATURE:
<223> OTHER INFORMATION: 10D1_c78v2, 10D1_c85v2, 10D1_c85o1, 10D1_c85o2
      heavy chain FR2

<400> SEQUENCE: 57

Trp His Trp Ile Arg Gln Phe Pro Gly Lys Gly Leu Glu Trp Ile Gly
1               5                   10                  15

Ser

<210> SEQ ID NO 58
<211> LENGTH: 17
<212> TYPE: PRT
<213> ORGANISM: Artificial Sequence
<220> FEATURE:
<223> OTHER INFORMATION: 10D1 heavy chain FR2

<400> SEQUENCE: 58

Trp His Trp Ile Arg Gln Phe Pro Gly Asn Lys Leu Glu Trp Met Gly
1               5                   10                  15

Ser

<210> SEQ ID NO 59
<211> LENGTH: 17
<212> TYPE: PRT
<213> ORGANISM: Artificial Sequence
<220> FEATURE:
<223> OTHER INFORMATION: 10D1_c89, 10D1_c90, 10D1_c91 heavy chain FR2

<400> SEQUENCE: 59

Trp His Trp Ile Arg Gln His Pro Gly Lys Gly Leu Glu Trp Ile Gly
1               5                   10                  15

Ser

<210> SEQ ID NO 60
<211> LENGTH: 17
<212> TYPE: PRT
<213> ORGANISM: Artificial Sequence
<220> FEATURE:
<223> OTHER INFORMATION: 10D1_11B heavy chain FR2

```
<400> SEQUENCE: 60

Trp His Trp Ile Arg Gln Pro Pro Gly Lys Gly Leu Glu Trp Ile Gly
1               5                   10                  15

Ser

<210> SEQ ID NO 61
<211> LENGTH: 38
<212> TYPE: PRT
<213> ORGANISM: Artificial Sequence
<220> FEATURE:
<223> OTHER INFORMATION: 10D1_c75, 10D1_c92 heavy chain FR3

<400> SEQUENCE: 61

Asn Tyr Asn Pro Thr Leu Lys Ser Arg Ile Thr Ile Ser Arg Asp Thr
1               5                   10                  15

Ser Lys Asn Gln Phe Ser Leu Lys Leu Ser Ser Val Thr Ala Ala Asp
            20                  25                  30

Thr Ala Val Tyr Phe Cys
        35

<210> SEQ ID NO 62
<211> LENGTH: 38
<212> TYPE: PRT
<213> ORGANISM: Artificial Sequence
<220> FEATURE:
<223> OTHER INFORMATION: 10D1_c76, 10D1_c77, 10D1_c78v1, 10D1_c78v2
      heavy chain FR3

<400> SEQUENCE: 62

Asn Tyr Asn Pro Ser Leu Lys Ser Arg Ile Thr Ile Ser Arg Asp Thr
1               5                   10                  15

Ser Lys Asn Gln Phe Ser Leu Lys Leu Ser Ser Val Thr Ala Ala Asp
            20                  25                  30

Thr Ala Val Tyr Phe Cys
        35

<210> SEQ ID NO 63
<211> LENGTH: 38
<212> TYPE: PRT
<213> ORGANISM: Artificial Sequence
<220> FEATURE:
<223> OTHER INFORMATION: 10D1_11B heavy chain FR3

<400> SEQUENCE: 63

Asn Tyr Asn Pro Ser Leu Lys Ser Arg Val Thr Ile Ser Arg Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
        35

<210> SEQ ID NO 64
<211> LENGTH: 38
<212> TYPE: PRT
<213> ORGANISM: Artificial Sequence
<220> FEATURE:
<223> OTHER INFORMATION: 10D1_c85v1,10D1_c85v2, 10D1_c85o1, 10D1_c85o2
      heavy chain FR3

<400> SEQUENCE: 64

Asn Tyr Asn Pro Ser Leu Lys Ser Arg Ile Thr Ile Ser Arg Asp Thr
1               5                   10                  15
```

```
Ser Lys Asn Gln Phe Ser Leu Lys Leu Gly Ser Val Thr Ala Ala Asp
            20                  25                  30

Thr Ala Val Tyr Phe Cys
        35

<210> SEQ ID NO 65
<211> LENGTH: 38
<212> TYPE: PRT
<213> ORGANISM: Artificial Sequence
<220> FEATURE:
<223> OTHER INFORMATION: 10D1_c87, 10D1_c93 heavy chain FR3

<400> SEQUENCE: 65

Asn Tyr Asn Pro Ser Leu Lys Ser Arg Ile Thr Ile Ser Arg Asp Thr
1               5                   10                  15

Ser Lys Asn Gln Phe Ser Leu Arg Leu Ser Ser Val Thr Ala Ala Asp
            20                  25                  30

Thr Ala Val Tyr Phe Cys
        35

<210> SEQ ID NO 66
<211> LENGTH: 38
<212> TYPE: PRT
<213> ORGANISM: Artificial Sequence
<220> FEATURE:
<223> OTHER INFORMATION: 10D1_c89 heavy chain FR3

<400> SEQUENCE: 66

Asp Tyr Asn Pro Ser Leu Lys Ser Leu Val Thr Ile Ser Ala Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
        35

<210> SEQ ID NO 67
<211> LENGTH: 38
<212> TYPE: PRT
<213> ORGANISM: Artificial Sequence
<220> FEATURE:
<223> OTHER INFORMATION: 10D1_c90 heavy chain FR3

<400> SEQUENCE: 67

Asp Tyr Asn Pro Ser Leu Lys Ser Leu Val Thr Ile Ser Val Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
        35

<210> SEQ ID NO 68
<211> LENGTH: 38
<212> TYPE: PRT
<213> ORGANISM: Artificial Sequence
<220> FEATURE:
<223> OTHER INFORMATION: 10D1_c91 heavy chain FR3

<400> SEQUENCE: 68

Asp Tyr Asn Pro Ser Leu Lys Ser Leu Ala Thr Ile Ser Ala Asp Thr
1               5                   10                  15

Ser Lys Asn Gln Phe Ser Leu Lys Leu Ser Ser Val Thr Ala Ala Asp
            20                  25                  30
```

Thr Ala Val Tyr Tyr Cys
        35

<210> SEQ ID NO 69
<211> LENGTH: 38
<212> TYPE: PRT
<213> ORGANISM: Artificial Sequence
<220> FEATURE:
<223> OTHER INFORMATION: 10D1 heavy chain FR3

<400> SEQUENCE: 69

Asn Tyr Asn Pro Ser Leu Lys Ser Arg Ile Ser Ile Thr Arg Asp Thr
1               5                   10                  15

Ser Lys Asn Gln Phe Phe Leu Gln Leu Asn Ser Val Thr Thr Glu Asp
            20                  25                  30

Thr Ala Thr Tyr Phe Cys
        35

<210> SEQ ID NO 70
<211> LENGTH: 11
<212> TYPE: PRT
<213> ORGANISM: Artificial Sequence
<220> FEATURE:
<223> OTHER INFORMATION: 10D1_c75, 10D1_c76, 10D1_c77, 10D1_c78v1,
      10D1_c78v2, 10D1_11B, 10D1_c85v1, 10D1_c85v2, 10D1_c85o1,
      10D1_c85o2, 10D1_c87, 10D1_c92, 10D1_c93 heavy chain FR4

<400> SEQUENCE: 70

Trp Gly Gln Gly Thr Leu Val Thr Val Ser Ser
1               5                   10

<210> SEQ ID NO 71
<211> LENGTH: 11
<212> TYPE: PRT
<213> ORGANISM: Artificial Sequence
<220> FEATURE:
<223> OTHER INFORMATION: 10D1_c89, 10D1_c90 heavy chain FR4

<400> SEQUENCE: 71

Trp Gly Gln Gly Thr Thr Val Thr Val Ser Ser
1               5                   10

<210> SEQ ID NO 72
<211> LENGTH: 11
<212> TYPE: PRT
<213> ORGANISM: Artificial Sequence
<220> FEATURE:
<223> OTHER INFORMATION: 10D1_c91 heavy chain FR4

<400> SEQUENCE: 72

Trp Gly Gln Gly Thr Ala Val Thr Val Ser Ser
1               5                   10

<210> SEQ ID NO 73
<211> LENGTH: 11
<212> TYPE: PRT
<213> ORGANISM: Artificial Sequence
<220> FEATURE:
<223> OTHER INFORMATION: 10D1, 4-35-B4, 10A6 heavy chain FR4

<400> SEQUENCE: 73

Trp Gly Gln Gly Thr Thr Leu Thr Val Ser Ser
1               5                   10

<210> SEQ ID NO 74
<211> LENGTH: 107

```
<212> TYPE: PRT
<213> ORGANISM: Artificial Sequence
<220> FEATURE:
<223> OTHER INFORMATION: 10D1 light chain variable region

<400> SEQUENCE: 74

Asp Ile Val Met Thr Gln Ser Gln Lys Phe Met Ser Thr Ser Val Gly
1               5                   10                  15

Asp Arg Val Ser Val Thr Cys Lys Ala Ser Gln Ile Val Gly Ser Asn
            20                  25                  30

Val Ala Trp Tyr Gln Gln Lys Pro Gly Gln Ser Pro Lys Pro Leu Ile
        35                  40                  45

Tyr Ser Ala Ser Tyr Arg Tyr Ser Gly Val Pro Asp Arg Phe Thr Ala
50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Ser Ser His Pro Leu
                85                  90                  95

Thr Phe Gly Ala Gly Thr Lys Leu Glu Leu Lys
            100                 105

<210> SEQ ID NO 75
<211> LENGTH: 107
<212> TYPE: PRT
<213> ORGANISM: Artificial Sequence
<220> FEATURE:
<223> OTHER INFORMATION: 10D1_c75 light chain variable region

<400> SEQUENCE: 75

Asp Ile Val Met Thr Gln Ser Pro Ser Ser Leu Ser Ala Ser Val Gly
1               5                   10                  15

Asp Leu Val Thr Ile Thr Cys Lys Ala Ser Gln Ile Val Gly Ser Asn
            20                  25                  30

Val Ala Trp Tyr Gln Met Lys Pro Gly Lys Ser Pro Lys Pro Leu Ile
        35                  40                  45

Tyr Ser Ala Ser Tyr Leu Tyr Phe Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Glu Tyr Phe Cys Gln Gln Tyr Ser Ser His Pro Leu
                85                  90                  95

Thr Phe Gly Pro Gly Thr Lys Val Glu Ile Lys
            100                 105

<210> SEQ ID NO 76
<211> LENGTH: 107
<212> TYPE: PRT
<213> ORGANISM: Artificial Sequence
<220> FEATURE:
<223> OTHER INFORMATION: 10D1_c76 light chain variable region

<400> SEQUENCE: 76

Asp Ile Val Met Thr Gln Ser Pro Ser Ser Leu Ser Ala Ser Gly Gly
1               5                   10                  15

Asp Arg Val Thr Ile Thr Cys Lys Ala Ser Gln Ile Val Gly Tyr Asn
            20                  25                  30

Val Ala Trp Tyr Gln Gln Lys Pro Gly Lys Ser Pro Lys Pro Leu Ile
        35                  40                  45
```

```
Tyr Ser Ala Ser Tyr Leu Tyr Ser Asp Val Pro Ser Arg Phe Ser Ala
        50                  55                  60

Ser Gly Ser Gly Thr Asp Phe Thr Leu Thr Ile Ser Ser Leu Gln Pro
 65                  70                  75                  80

Glu Asp Val Ala Glu Tyr Phe Cys Gln Gln Tyr Ser Ser His Pro Leu
                 85                  90                  95

Thr Phe Gly Pro Gly Thr Lys Val Glu Ile Lys
            100                 105

<210> SEQ ID NO 77
<211> LENGTH: 107
<212> TYPE: PRT
<213> ORGANISM: Artificial Sequence
<220> FEATURE:
<223> OTHER INFORMATION: 10D1_c77 light chain variable region

<400> SEQUENCE: 77

Val Ile Val Met Thr Gln Ser Pro Ser Ser Leu Ser Ala Ser Val Gly
  1               5                  10                  15

Asp Arg Val Thr Ile Thr Cys Lys Ala Ser Gln Ile Val Gly Pro Asn
             20                  25                  30

Val Ala Trp Tyr Gln Gln Lys Pro Gly Lys Ser Pro Lys Pro Leu Ile
         35                  40                  45

Tyr Ser Ala Ser Tyr Gly Tyr Ser Asp Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Val Ala Glu Tyr Phe Cys Gln Gln Tyr Ser Thr His Pro Leu
                 85                  90                  95

Thr Phe Gly Pro Gly Thr Lys Val Glu Ile Lys
            100                 105

<210> SEQ ID NO 78
<211> LENGTH: 107
<212> TYPE: PRT
<213> ORGANISM: Artificial Sequence
<220> FEATURE:
<223> OTHER INFORMATION: 10D1_c78v1, 10D1_c78v2, 10D1_11B light chain
      variable region

<400> SEQUENCE: 78

Asp Ile Val Met Thr Gln Ser Pro Ser Ser Leu Ser Ala Ser Val Gly
  1               5                  10                  15

Asp Arg Val Thr Ile Thr Cys Lys Ala Ser Gln Ile Val Gly Ser Asn
             20                  25                  30

Val Ala Trp Tyr Gln Gln Lys Pro Gly Lys Ser Pro Lys Pro Leu Ile
         35                  40                  45

Tyr Ser Ala Ser Tyr Gly Tyr Ser Asp Val Pro Ser Arg Phe Ser Gly
     50                  55                  60

Ser Gly Ser Gly Thr Asp Phe Thr Leu Thr Ile Ser Ser Leu Arg Pro
 65                  70                  75                  80

Glu Asp Val Ala Thr Tyr Tyr Cys Gln Gln Tyr Ser Ser His Pro Leu
                 85                  90                  95

Thr Phe Gly Pro Gly Thr Lys Val Glu Ile Lys
            100                 105

<210> SEQ ID NO 79
<211> LENGTH: 107
```

```
<212> TYPE: PRT
<213> ORGANISM: Artificial Sequence
<220> FEATURE:
<223> OTHER INFORMATION: 10D1_c85v1, 10D1_c85v2 light chain variable
      region

<400> SEQUENCE: 79

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ile Val Gly Ser Asn
            20                  25                  30

Val Ala Trp Tyr Gln Gln Lys Pro Gly Lys Ser Pro Lys Pro Leu Ile
        35                  40                  45

Tyr Ser Ala Arg Tyr Gln Tyr Ser Gly Val Pro Phe Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser His Pro Leu
                85                  90                  95

Thr Phe Gly Pro Gly Thr Lys Val Glu Ile Lys
            100                 105

<210> SEQ ID NO 80
<211> LENGTH: 107
<212> TYPE: PRT
<213> ORGANISM: Artificial Sequence
<220> FEATURE:
<223> OTHER INFORMATION: 10D1_c85o1 light chain variable region

<400> SEQUENCE: 80

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ile Val Gly Ser Asn
            20                  25                  30

Val Ala Trp Tyr Gln Gln Lys Pro Gly Lys Ser Pro Lys Pro Leu Ile
        35                  40                  45

Tyr Ser Ala Arg Tyr Gln Tyr Ser Gly Val Pro Phe Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser His Pro Leu
                85                  90                  95

Thr Phe Gly Pro Gly Thr Lys Val Glu Ile Lys
            100                 105

<210> SEQ ID NO 81
<211> LENGTH: 107
<212> TYPE: PRT
<213> ORGANISM: Artificial Sequence
<220> FEATURE:
<223> OTHER INFORMATION: 10D1_c85o2 light chain variable region

<400> SEQUENCE: 81

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ile Val Gly Ser Asn
            20                  25                  30

Val Ala Trp Tyr Gln Gln Lys Pro Gly Lys Ser Pro Lys Pro Leu Ile
        35                  40                  45
```

-continued

```
Tyr Ser Ala Arg Tyr Gln Tyr Ser Gly Val Pro Phe Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser His Pro Leu
                85                  90                  95

Thr Phe Gly Pro Gly Thr Lys Val Glu Ile Lys
            100                 105

<210> SEQ ID NO 82
<211> LENGTH: 107
<212> TYPE: PRT
<213> ORGANISM: Artificial Sequence
<220> FEATURE:
<223> OTHER INFORMATION: 10D1_c87 light chain variable region

<400> SEQUENCE: 82

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ile Val Gly Ser Asn
                20                  25                  30

Val Ala Trp Tyr Gln Gln Met Pro Gly Lys Ser Pro Glu Pro Leu Ile
            35                  40                  45

Tyr Ser Ala Ser Tyr Leu Tyr Ser Asp Val Pro Ser Arg Phe Ser Gly
    50                  55                  60

Ser Gly Ser Gly Thr Asp Phe Thr Met Thr Ile Ser Ser Leu Gln Pro
65                  70                  75                  80

Glu Asp Val Ala Thr Tyr Tyr Cys Gln Gln Tyr Ser Ser His Pro Leu
                85                  90                  95

Thr Phe Gly Pro Gly Thr Lys Val Glu Ile Lys
            100                 105

<210> SEQ ID NO 83
<211> LENGTH: 107
<212> TYPE: PRT
<213> ORGANISM: Artificial Sequence
<220> FEATURE:
<223> OTHER INFORMATION: 10D1_c89 light chain variable region

<400> SEQUENCE: 83

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Ile Val Gly Ser Asn
                20                  25                  30

Val Ala Trp Tyr Gln Gln Lys Pro Gly Lys Ala Pro Glu Pro Leu Ile
            35                  40                  45

Tyr Ser Ala Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser His Pro Leu
                85                  90                  95

Thr Phe Gly Gln Gly Thr Lys Leu Glu Ile Lys
            100                 105

<210> SEQ ID NO 84
<211> LENGTH: 107
<212> TYPE: PRT
<213> ORGANISM: Artificial Sequence
```

<220> FEATURE:
<223> OTHER INFORMATION: 10D1_c90 light chain variable region

<400> SEQUENCE: 84

Asp Ile Gln Met Thr Gln Ser Pro Ser Ser Val Ser Ala Ser Val Gly
1               5                   10                  15

Asp Arg Val Thr Phe Thr Cys Lys Ala Ser Gln Ile Val Gly Ser Asn
            20                  25                  30

Val Ala Trp Tyr Gln Gln Lys Pro Gly Lys Ala Pro Glu Pro Leu Ile
        35                  40                  45

Tyr Ser Ala Ser Tyr Leu Tyr Ser Ser Val Pro Ser Arg Phe Ser Gly
    50                  55                  60

Ser Gly Ser Gly Thr Glu Phe Thr Met Thr Ile Ser Ser Leu Glu Pro
65                  70                  75                  80

Glu Asp Phe Ala Thr Tyr Tyr Cys Gln Gln Tyr Thr Thr His Pro Leu
                85                  90                  95

Thr Phe Gly Pro Gly Thr Lys Val Glu Ile Lys
            100                 105

<210> SEQ ID NO 85
<211> LENGTH: 107
<212> TYPE: PRT
<213> ORGANISM: Artificial Sequence
<220> FEATURE:
<223> OTHER INFORMATION: 10D1_c91 light chain variable region

<400> SEQUENCE: 85

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Ile Val Gly Ser Asn
            20                  25                  30

Val Ala Trp Tyr Gln Gln Lys Pro Gly Lys Ala Pro Met Pro Leu Ile
        35                  40                  45

Tyr Ser Ala Ser Tyr Gly Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser His Pro Leu
                85                  90                  95

Thr Phe Gly Gln Gly Thr Lys Leu Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: 10D1_c92 light chain variable region

<400> SEQUENCE: 86

Asp Ile Val Met Thr Gln Ser Pro Ser Ser Leu Ser Ala Ser Val Gly
1               5                   10                  15

Asp Leu Val Thr Ile Thr Cys Lys Ala Ser Gln Ile Val Gly Ser Asn
            20                  25                  30

Val Ala Trp Tyr Gln Met Lys Leu Gly Lys Ser Pro Lys Pro Leu Ile
        35                  40                  45

Tyr Ser Ala Ser Tyr Leu Tyr Phe Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Val Ala Glu Tyr Phe Cys Gln Gln Tyr Phe Ser His Pro Leu
                 85                  90                  95

Thr Phe Gly Pro Gly Thr Lys Val Glu Ile Lys
            100                 105

<210> SEQ ID NO 87
<211> LENGTH: 107
<212> TYPE: PRT
<213> ORGANISM: Artificial Sequence
<220> FEATURE:
<223> OTHER INFORMATION: 10D1_c93 light chain variable region

<400> SEQUENCE: 87

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ile Val Gly Ser Asn
                20                  25                  30

Val Ala Trp Tyr Gln Gln Lys Pro Gly Lys Ser Pro Lys Pro Leu Ile
            35                  40                  45

Tyr Ser Ala Ser Tyr Leu Tyr Ser Asp Val Pro Ser Arg Phe Ser Gly
 50                 55                  60

Ser Gly Ser Gly Thr Asp Phe Thr Met Thr Ile Ser Ser Leu Gln Pro
 65                 70                  75                  80

Glu Asp Val Ala Thr Tyr Tyr Cys Gln Gln Tyr Ser Ser His Pro Leu
                85                  90                  95

Thr Phe Gly Pro Gly Thr Lys Val Glu Ile Lys
            100                 105

<210> SEQ ID NO 88
<211> LENGTH: 6
<212> TYPE: PRT
<213> ORGANISM: Artificial Sequence
<220> FEATURE:
<223> OTHER INFORMATION: 10D1, 10D1_c75, 10D1_c78v1, 10D1_c78v2,
      10D1_11B, 10D1_c85v1, 10D1_c85v2, 10D1_c85o1, 10D1_c85o2,
      10D1_c87, 10D1_c89, 10D1_c90, 10D1_c91, 10D1_c92, 10D1_c93 light
      chain CDR1

<400> SEQUENCE: 88

Gln Ile Val Gly Ser Asn
1               5

<210> SEQ ID NO 89
<211> LENGTH: 6
<212> TYPE: PRT
<213> ORGANISM: Artificial Sequence
<220> FEATURE:
<223> OTHER INFORMATION: 10D1_c76 light chain CDR1

<400> SEQUENCE: 89

Gln Ile Val Gly Ser Asn
1               5

<210> SEQ ID NO 90
<211> LENGTH: 6
<212> TYPE: PRT
<213> ORGANISM: Artificial Sequence
<220> FEATURE:
<223> OTHER INFORMATION: 10D1_c77 light chain CDR1
```

<400> SEQUENCE: 90

Gln Ile Val Gly Pro Asn
1               5

<210> SEQ ID NO 91
<211> LENGTH: 6
<212> TYPE: PRT
<213> ORGANISM: Artificial Sequence
<220> FEATURE:
<223> OTHER INFORMATION: 10D1 derived consensus light chain CDR1
<220> FEATURE:
<221> NAME/KEY: MISC_FEATURE
<222> LOCATION: (5)..(5)
<223> OTHER INFORMATION: Xaa is S, Y or P

<400> SEQUENCE: 91

Gln Ile Val Gly Xaa Asn
1               5

<210> SEQ ID NO 92
<211> LENGTH: 3
<212> TYPE: PRT
<213> ORGANISM: Artificial Sequence
<220> FEATURE:
<223> OTHER INFORMATION: 10D1,  10D1_c75, 10D1_c76, 10D1_c77,
      10D1_c78v1, 10D1_c78v2, 10D1_11B, 10D1_c87, 10D1_c89, 10D1_c90,
      10D1_c91, 10D1_c92, 10D1_c93 light chain CDR2

<400> SEQUENCE: 92

Ser Ala Ser
1

<210> SEQ ID NO 93
<211> LENGTH: 3
<212> TYPE: PRT
<213> ORGANISM: Artificial Sequence
<220> FEATURE:
<223> OTHER INFORMATION: 10D1_c85v1, 10D1_c85v2, 10D1_c85o1, 10D1_c85o2
      light chain CDR2

<400> SEQUENCE: 93

Ser Ala Arg
1

<210> SEQ ID NO 94
<211> LENGTH: 3
<212> TYPE: PRT
<213> ORGANISM: Artificial Sequence
<220> FEATURE:
<223> OTHER INFORMATION: 10D1 derived consensus light chain CDR2
<220> FEATURE:
<221> NAME/KEY: MISC_FEATURE
<222> LOCATION: (3)..(3)
<223> OTHER INFORMATION: Xaa is S or R

<400> SEQUENCE: 94

Ser Ala Xaa
1

<210> SEQ ID NO 95
<211> LENGTH: 9
<212> TYPE: PRT
<213> ORGANISM: Artificial Sequence
<220> FEATURE:
<223> OTHER INFORMATION: 10D1, 10D1_c75, 10D1_c76, 10D1_c78v1,
      10D1_c78v2, 10D1_11B, 10D1_c85v1, 10D1_c85v2, 10D1_c85o1,
      10D1_c85o2, 10D1_c87, 10D1_c89, 10D1_c91, 10D1_c93 light chain
      CDR3

<400> SEQUENCE: 95

Gln Gln Tyr Ser Ser His Pro Leu Thr
1               5

<210> SEQ ID NO 96
<211> LENGTH: 9
<212> TYPE: PRT
<213> ORGANISM: Artificial Sequence
<220> FEATURE:
<223> OTHER INFORMATION: 10D1_c77 light chain CDR3

<400> SEQUENCE: 96

Gln Gln Tyr Ser Thr His Pro Leu Thr
1               5

<210> SEQ ID NO 97
<211> LENGTH: 9
<212> TYPE: PRT
<213> ORGANISM: Artificial Sequence
<220> FEATURE:
<223> OTHER INFORMATION: 10D1_c90 light chain CDR3

<400> SEQUENCE: 97

Gln Gln Tyr Thr Thr His Pro Leu Thr
1               5

<210> SEQ ID NO 98
<211> LENGTH: 9
<212> TYPE: PRT
<213> ORGANISM: Artificial Sequence
<220> FEATURE:
<223> OTHER INFORMATION: 10D1_c92 light chain CDR3

<400> SEQUENCE: 98

Gln Gln Tyr Phe Ser His Pro Leu Thr
1               5

<210> SEQ ID NO 99
<211> LENGTH: 9
<212> TYPE: PRT
<213> ORGANISM: Artificial Sequence
<220> FEATURE:
<223> OTHER INFORMATION: 10D1 derived consensus light chain CDR3
<220> FEATURE:
<221> NAME/KEY: MISC_FEATURE
<222> LOCATION: (4)..(4)
<223> OTHER INFORMATION: Xaa is S, T or F
<220> FEATURE:
<221> NAME/KEY: MISC_FEATURE
<222> LOCATION: (5)..(5)
<223> OTHER INFORMATION: Xaa is S or T

<400> SEQUENCE: 99

Gln Gln Tyr Xaa Xaa His Pro Leu Thr
1               5

<210> SEQ ID NO 100
<211> LENGTH: 26
<212> TYPE: PRT
<213> ORGANISM: Artificial Sequence
<220> FEATURE:
<223> OTHER INFORMATION: 10D1_c75, 10D1_c92 light chain FR1

<400> SEQUENCE: 100

Asp Ile Val Met Thr Gln Ser Pro Ser Ser Leu Ser Ala Ser Val Gly
1               5                   10                  15

Asp Leu Val Thr Ile Thr Cys Lys Ala Ser
            20                  25

<210> SEQ ID NO 101
<211> LENGTH: 26
<212> TYPE: PRT
<213> ORGANISM: Artificial Sequence
<220> FEATURE:
<223> OTHER INFORMATION: 10D1_c76 light chain FR1

<400> SEQUENCE: 101

Asp Ile Val Met Thr Gln Ser Pro Ser Ser Leu Ser Ala Ser Gly Gly
1               5                   10                  15

Asp Arg Val Thr Ile Thr Cys Lys Ala Ser
            20                  25

<210> SEQ ID NO 102
<211> LENGTH: 26
<212> TYPE: PRT
<213> ORGANISM: Artificial Sequence
<220> FEATURE:
<223> OTHER INFORMATION: 10D1_c77 light chain FR1

<400> SEQUENCE: 102

Val Ile Val Met Thr Gln Ser Pro Ser Ser Leu Ser Ala Ser Val Gly
1               5                   10                  15

Asp Arg Val Thr Ile Thr Cys Lys Ala Ser
            20                  25

<210> SEQ ID NO 103
<211> LENGTH: 26
<212> TYPE: PRT
<213> ORGANISM: Artificial Sequence
<220> FEATURE:
<223> OTHER INFORMATION: 10D1_c78v1, 10D1_c78v2, 10D1_11B, 10D1_c85v1,
      10D1_c85v2, 10D1_c85o1, 10D1_c85o2, 10D1_c87, 10D1_c93 light chain
      FR1

<400> SEQUENCE: 103

Asp Ile Val Met Thr Gln Ser Pro Ser Ser Leu Ser Ala Ser Val Gly
1               5                   10                  15

Asp Arg Val Thr Ile Thr Cys Lys Ala Ser
            20                  25

<210> SEQ ID NO 104
<211> LENGTH: 26
<212> TYPE: PRT
<213> ORGANISM: Artificial Sequence
<220> FEATURE:
<223> OTHER INFORMATION: 10D1_c89, 10D1_c91 light chain FR1

<400> SEQUENCE: 104

Asp Ile Gln Met Thr Gln Ser Pro Ser Ser Val Ser Ala Ser Val Gly
1               5                   10                  15

Asp Arg Val Thr Ile Thr Cys Lys Ala Ser
            20                  25

<210> SEQ ID NO 105
<211> LENGTH: 26
<212> TYPE: PRT
<213> ORGANISM: Artificial Sequence
<220> FEATURE:
<223> OTHER INFORMATION: 10D1_c90 light chain FR1

```
<400> SEQUENCE: 105

Asp Ile Gln Met Thr Gln Ser Pro Ser Ser Val Ser Ala Ser Val Gly
1               5                   10                  15

Asp Arg Val Thr Phe Thr Cys Lys Ala Ser
            20                  25

<210> SEQ ID NO 106
<211> LENGTH: 26
<212> TYPE: PRT
<213> ORGANISM: Artificial Sequence
<220> FEATURE:
<223> OTHER INFORMATION: 10D1 light chain FR1

<400> SEQUENCE: 106

Asp Ile Val Met Thr Gln Ser Gln Lys Phe Met Ser Thr Ser Val Gly
1               5                   10                  15

Asp Arg Val Ser Val Thr Cys Lys Ala Ser
            20                  25

<210> SEQ ID NO 107
<211> LENGTH: 17
<212> TYPE: PRT
<213> ORGANISM: Artificial Sequence
<220> FEATURE:
<223> OTHER INFORMATION: 10D1_c75 light chain FR2

<400> SEQUENCE: 107

Val Ala Trp Tyr Gln Met Lys Pro Gly Lys Ser Pro Lys Pro Leu Ile
1               5                   10                  15

Tyr

<210> SEQ ID NO 108
<211> LENGTH: 17
<212> TYPE: PRT
<213> ORGANISM: Artificial Sequence
<220> FEATURE:
<223> OTHER INFORMATION: 10D1_c76, 10D1_c77, 10D1_c78v1, 10D1_c78v2,
      10D1_11B, 10D1_c85v1, 10D1_c85v2, 10D1_c85o1, 10D1_c85o2, 10D1_c93
      light chain FR2

<400> SEQUENCE: 108

Val Ala Trp Tyr Gln Gln Lys Pro Gly Lys Ser Pro Lys Pro Leu Ile
1               5                   10                  15

Tyr

<210> SEQ ID NO 109
<211> LENGTH: 17
<212> TYPE: PRT
<213> ORGANISM: Artificial Sequence
<220> FEATURE:
<223> OTHER INFORMATION: 10D1_c87 light chain FR2

<400> SEQUENCE: 109

Val Ala Trp Tyr Gln Gln Met Pro Gly Lys Ser Pro Glu Pro Leu Ile
1               5                   10                  15

Tyr

<210> SEQ ID NO 110
<211> LENGTH: 17
<212> TYPE: PRT
<213> ORGANISM: Artificial Sequence
<220> FEATURE:
<223> OTHER INFORMATION: 10D1_c89, 10D1_c90 light chain FR2
```

```
<400> SEQUENCE: 110

Val Ala Trp Tyr Gln Gln Lys Pro Gly Lys Ala Pro Glu Pro Leu Ile
1               5                   10                  15

Tyr

<210> SEQ ID NO 111
<211> LENGTH: 17
<212> TYPE: PRT
<213> ORGANISM: Artificial Sequence
<220> FEATURE:
<223> OTHER INFORMATION: 10D1_c91 light chain FR2

<400> SEQUENCE: 111

Val Ala Trp Tyr Gln Gln Lys Pro Gly Lys Ala Pro Met Pro Leu Ile
1               5                   10                  15

Tyr

<210> SEQ ID NO 112
<211> LENGTH: 17
<212> TYPE: PRT
<213> ORGANISM: Artificial Sequence
<220> FEATURE:
<223> OTHER INFORMATION: 10D1_c92 light chain FR2

<400> SEQUENCE: 112

Val Ala Trp Tyr Gln Met Lys Leu Gly Lys Ser Pro Lys Pro Leu Ile
1               5                   10                  15

Tyr

<210> SEQ ID NO 113
<211> LENGTH: 17
<212> TYPE: PRT
<213> ORGANISM: Artificial Sequence
<220> FEATURE:
<223> OTHER INFORMATION: 10D1 light chain FR2

<400> SEQUENCE: 113

Val Ala Trp Tyr Gln Gln Lys Pro Gly Gln Ser Pro Lys Pro Leu Ile
1               5                   10                  15

Tyr

<210> SEQ ID NO 114
<211> LENGTH: 36
<212> TYPE: PRT
<213> ORGANISM: Artificial Sequence
<220> FEATURE:
<223> OTHER INFORMATION: 10D1_c75, 10D1_c92 light chain FR3

<400> SEQUENCE: 114

Tyr Leu Tyr Phe Gly Val Pro Ser Arg Phe Ser Gly Ser Gly Ser Gly
1               5                   10                  15

Thr Asp Phe Thr Leu Thr Ile Ser Ser Leu Gln Pro Glu Asp Val Ala
            20                  25                  30

Glu Tyr Phe Cys
        35

<210> SEQ ID NO 115
<211> LENGTH: 36
<212> TYPE: PRT
<213> ORGANISM: Artificial Sequence
<220> FEATURE:
<223> OTHER INFORMATION: 10D1_c76 light chain FR3
```

```
<400> SEQUENCE: 115

Tyr Leu Tyr Ser Asp Val Pro Ser Arg Phe Ser Ala Ser Gly Ser Gly
1               5                   10                  15

Thr Asp Phe Thr Leu Thr Ile Ser Ser Leu Gln Pro Glu Asp Val Ala
            20                  25                  30

Glu Tyr Phe Cys
        35

<210> SEQ ID NO 116
<211> LENGTH: 36
<212> TYPE: PRT
<213> ORGANISM: Artificial Sequence
<220> FEATURE:
<223> OTHER INFORMATION: 10D1_c77 light chain FR3

<400> SEQUENCE: 116

Tyr Gly Tyr Ser Asp Val Pro Ser Arg Phe Ser Gly Ser Gly Ser Gly
1               5                   10                  15

Thr Asp Phe Thr Leu Thr Ile Ser Ser Leu Gln Pro Glu Asp Val Ala
            20                  25                  30

Glu Tyr Phe Cys
        35

<210> SEQ ID NO 117
<211> LENGTH: 36
<212> TYPE: PRT
<213> ORGANISM: Artificial Sequence
<220> FEATURE:
<223> OTHER INFORMATION: 10D1_c78v1, 10D1_c78v2, 10D1_11B light chain
      FR3

<400> SEQUENCE: 117

Tyr Gly Tyr Ser Asp Val Pro Ser Arg Phe Ser Gly Ser Gly Ser Gly
1               5                   10                  15

Thr Asp Phe Thr Leu Thr Ile Ser Ser Leu Arg Pro Glu Asp Val Ala
            20                  25                  30

Thr Tyr Tyr Cys
        35

<210> SEQ ID NO 118
<211> LENGTH: 36
<212> TYPE: PRT
<213> ORGANISM: Artificial Sequence
<220> FEATURE:
<223> OTHER INFORMATION: 10D1_c85v1, 10D1_c85v2, 10D1_c85o1, 10D1_c85o2
      light chain FR3

<400> SEQUENCE: 118

Tyr Gln Tyr Ser Gly Val Pro Phe Arg Phe Ser Gly Ser Gly Ser Gly
1               5                   10                  15

Thr Asp Phe Thr Leu Thr Ile Ser Ser Leu Gln Pro Glu Asp Val Ala
            20                  25                  30

Thr Tyr Tyr Cys
        35

<210> SEQ ID NO 119
<211> LENGTH: 36
<212> TYPE: PRT
<213> ORGANISM: Artificial Sequence
<220> FEATURE:
<223> OTHER INFORMATION: 10D1_c87, 10D1_c93 light chain FR3
```

```
<400> SEQUENCE: 119

Tyr Leu Tyr Ser Asp Val Pro Ser Arg Phe Ser Gly Ser Gly Ser Gly
1               5                   10                  15

Thr Asp Phe Thr Met Thr Ile Ser Ser Leu Gln Pro Glu Asp Val Ala
            20                  25                  30

Thr Tyr Tyr Cys
        35

<210> SEQ ID NO 120
<211> LENGTH: 36
<212> TYPE: PRT
<213> ORGANISM: Artificial Sequence
<220> FEATURE:
<223> OTHER INFORMATION: 10D1_c89 light chain FR3

<400> SEQUENCE: 120

Tyr Leu Tyr Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 121
<211> LENGTH: 36
<212> TYPE: PRT
<213> ORGANISM: Artificial Sequence
<220> FEATURE:
<223> OTHER INFORMATION: 10D1_c90 light chain FR3

<400> SEQUENCE: 121

Tyr Leu Tyr Ser Ser Val Pro Ser Arg Phe Ser Gly Ser Gly Ser Gly
1               5                   10                  15

Thr Glu Phe Thr Met Thr Ile Ser Ser Leu Glu Pro Glu Asp Phe Ala
            20                  25                  30

Thr Tyr Tyr Cys
        35

<210> SEQ ID NO 122
<211> LENGTH: 36
<212> TYPE: PRT
<213> ORGANISM: Artificial Sequence
<220> FEATURE:
<223> OTHER INFORMATION: 10D1_c91 light chain FR3

<400> SEQUENCE: 122

Tyr Gly Tyr Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 123
<211> LENGTH: 36
<212> TYPE: PRT
<213> ORGANISM: Artificial Sequence
<220> FEATURE:
<223> OTHER INFORMATION: 10D1 light chain FR3
```

<400> SEQUENCE: 123

Tyr Arg Tyr Ser Gly Val Pro Asp Arg Phe Thr Ala Ser Gly Ser Gly
1               5                   10                  15

Thr Asp Phe Thr Leu Thr Ile Thr Asn Val Gln Ser Glu Asp Leu Ala
            20                  25                  30

Glu Tyr Phe Cys
        35

<210> SEQ ID NO 124
<211> LENGTH: 10
<212> TYPE: PRT
<213> ORGANISM: Artificial Sequence
<220> FEATURE:
<223> OTHER INFORMATION: 10D1_c75, 10D1_c76, 10D1_c77, 10D1_c78v1,
    10D1_c78v2, 10D1_11B, 10D1_c85v1, 10D1_c85v2, 10D1_c85o1,
    10D1_c85o2, 10D1_c87, 10D1_c90, 10D1_c92, 10D1_c93 light chain FR4

<400> SEQUENCE: 124

Phe Gly Pro Gly Thr Lys Val Glu Ile Lys
1               5                   10

<210> SEQ ID NO 125
<211> LENGTH: 10
<212> TYPE: PRT
<213> ORGANISM: Artificial Sequence
<220> FEATURE:
<223> OTHER INFORMATION: 10D1_c89, 10D1_c91 light chain FR4

<400> SEQUENCE: 125

Phe Gly Gln Gly Thr Lys Leu Glu Ile Lys
1               5                   10

<210> SEQ ID NO 126
<211> LENGTH: 10
<212> TYPE: PRT
<213> ORGANISM: Artificial Sequence
<220> FEATURE:
<223> OTHER INFORMATION: 10D1 light chain FR4

<400> SEQUENCE: 126

Phe Gly Ala Gly Thr Lys Leu Glu Leu Lys
1               5                   10

<210> SEQ ID NO 127
<211> LENGTH: 117
<212> TYPE: PRT
<213> ORGANISM: Artificial Sequence
<220> FEATURE:
<223> OTHER INFORMATION: 4-35-B2 heavy chain variable region

<400> SEQUENCE: 127

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Asn Met Tyr Trp Val Lys Gln Ser His Gly Lys Ser Leu Glu Trp Ile
        35                  40                  45

Gly His Ile Asn Pro Tyr Asn Gly Gly Thr Tyr Asn Gln Lys Phe
    50                  55                  60

Lys Gly Arg Ala Thr Leu Thr Val Asp Lys Ser Ser Ser Thr Ala Phe
65                  70                  75                  80

```
Met His Leu Asn Ser Leu Thr Ser Glu Asp Ser Ala Val Tyr Phe Cys
             85                  90                  95

Val Ser Leu Arg Trp Gly Ala Met Asp Tyr Trp Gly Gln Gly Thr Ser
            100                 105                 110

Val Thr Val Ser Ser
        115

<210> SEQ ID NO 128
<211> LENGTH: 8
<212> TYPE: PRT
<213> ORGANISM: Artificial Sequence
<220> FEATURE:
<223> OTHER INFORMATION: 4-35-B2 heavy chain CDR1

<400> SEQUENCE: 128

Gly Tyr Ser Phe Thr Asp Tyr Asn
1               5

<210> SEQ ID NO 129
<211> LENGTH: 8
<212> TYPE: PRT
<213> ORGANISM: Artificial Sequence
<220> FEATURE:
<223> OTHER INFORMATION: 4-35-B2 heavy chain CDR2

<400> SEQUENCE: 129

Ile Asn Pro Tyr Asn Gly Gly Thr
1               5

<210> SEQ ID NO 130
<211> LENGTH: 10
<212> TYPE: PRT
<213> ORGANISM: Artificial Sequence
<220> FEATURE:
<223> OTHER INFORMATION: 4-35-B2 heavy chain CDR3

<400> SEQUENCE: 130

Val Ser Leu Arg Trp Gly Ala Met Asp Tyr
1               5                   10

<210> SEQ ID NO 131
<211> LENGTH: 25
<212> TYPE: PRT
<213> ORGANISM: Artificial Sequence
<220> FEATURE:
<223> OTHER INFORMATION: 4-35-B2 heavy chain FR1

<400> SEQUENCE: 131

Glu Ile Gln Leu Gln Gln Ser Gly Pro Glu Leu Val Lys Pro Gly Ala
1               5                   10                  15

Ser Val Lys Val Ser Cys Lys Ala Ser
            20                  25

<210> SEQ ID NO 132
<211> LENGTH: 17
<212> TYPE: PRT
<213> ORGANISM: Artificial Sequence
<220> FEATURE:
<223> OTHER INFORMATION: 4-35-B2 heavy chain FR2

<400> SEQUENCE: 132

Met Tyr Trp Val Lys Gln Ser His Gly Lys Ser Leu Glu Trp Ile Gly
1               5                   10                  15

His
```

```
<210> SEQ ID NO 133
<211> LENGTH: 38
<212> TYPE: PRT
<213> ORGANISM: Artificial Sequence
<220> FEATURE:
<223> OTHER INFORMATION: 4-35-B2 heavy chain FR3

<400> SEQUENCE: 133

Thr Tyr Asn Gln Lys Phe Lys Gly Arg Ala Thr Leu Thr Val Asp Lys
1               5                   10                  15

Ser Ser Ser Thr Ala Phe Met His Leu Asn Ser Leu Thr Ser Glu Asp
            20                  25                  30

Ser Ala Val Tyr Phe Cys
        35

<210> SEQ ID NO 134
<211> LENGTH: 11
<212> TYPE: PRT
<213> ORGANISM: Artificial Sequence
<220> FEATURE:
<223> OTHER INFORMATION: 4-35-B2 heavy chain FR4

<400> SEQUENCE: 134

Trp Gly Gln Gly Thr Ser Val Thr Val Ser Ser
1               5                   10

<210> SEQ ID NO 135
<211> LENGTH: 106
<212> TYPE: PRT
<213> ORGANISM: Artificial Sequence
<220> FEATURE:
<223> OTHER INFORMATION: 4-35-B2 light chain variable region

<400> SEQUENCE: 135

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser Asn Pro Tyr Thr
                85                  90                  95

Phe Gly Gly Gly Thr Lys Leu Glu Ile Lys
            100                 105

<210> SEQ ID NO 136
<211> LENGTH: 5
<212> TYPE: PRT
<213> ORGANISM: Artificial Sequence
<220> FEATURE:
<223> OTHER INFORMATION: 4-35-B2 light chain CDR1

<400> SEQUENCE: 136

Ser Ser Val Ser Tyr
1               5

<210> SEQ ID NO 137
```

```
<211> LENGTH: 3
<212> TYPE: PRT
<213> ORGANISM: Artificial Sequence
<220> FEATURE:
<223> OTHER INFORMATION: 4-35-B2 light chain CDR2

<400> SEQUENCE: 137

Leu Thr Ser
1

<210> SEQ ID NO 138
<211> LENGTH: 9
<212> TYPE: PRT
<213> ORGANISM: Artificial Sequence
<220> FEATURE:
<223> OTHER INFORMATION: 4-35-B2 light chain CDR3

<400> SEQUENCE: 138

Gln Gln Trp Asn Ser Asn Pro Tyr Thr
1               5

<210> SEQ ID NO 139
<211> LENGTH: 26
<212> TYPE: PRT
<213> ORGANISM: Artificial Sequence
<220> FEATURE:
<223> OTHER INFORMATION: 4-35-B2 light chain FR1

<400> SEQUENCE: 139

Gln Ile Val Leu Thr Gln Ser Pro Ala Leu Met Ser Ala Ser Pro Gly
1               5                   10                  15

Glu Lys Val Thr Met Thr Cys Ser Ala Ser
            20                  25

<210> SEQ ID NO 140
<211> LENGTH: 17
<212> TYPE: PRT
<213> ORGANISM: Artificial Sequence
<220> FEATURE:
<223> OTHER INFORMATION: 4-35-B2 light chain FR2

<400> SEQUENCE: 140

Met Tyr Trp Tyr Gln Gln Lys Pro Arg Ser Ser Pro Lys Pro Trp Ile
1               5                   10                  15

Tyr

<210> SEQ ID NO 141
<211> LENGTH: 36
<212> TYPE: PRT
<213> ORGANISM: Artificial Sequence
<220> FEATURE:
<223> OTHER INFORMATION: 4-35-B2 light chain FR3

<400> SEQUENCE: 141

Asn Leu Ala Ser Gly Val Pro Ala Arg Phe Ser Gly Ser Gly Ser Gly
1               5                   10                  15

Thr Ser Tyr Ser Leu Thr Ile Ser Ser Met Glu Ala Glu Asp Ala Ala
            20                  25                  30

Thr Tyr Tyr Cys
            35

<210> SEQ ID NO 142
<211> LENGTH: 10
<212> TYPE: PRT
<213> ORGANISM: Artificial Sequence
```

```
<220> FEATURE:
<223> OTHER INFORMATION: 4-35-B2, 4-35-B4, 10A6 light chain FR4

<400> SEQUENCE: 142

Phe Gly Gly Gly Thr Lys Leu Glu Ile Lys
1               5                   10

<210> SEQ ID NO 143
<211> LENGTH: 113
<212> TYPE: PRT
<213> ORGANISM: Artificial Sequence
<220> FEATURE:
<223> OTHER INFORMATION: 4-35-B4 heavy chain variable region

<400> SEQUENCE: 143

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Asp Gln Gly Leu Glu Trp Ile
        35                  40                  45

Gly Lys Ile Ile Asp Pro Ala Asn Gly Asn Thr Asn Tyr Asp Pro Lys
    50                  55                  60

Phe Gln Gly Lys Ala Thr Ile Thr Ala Asp Thr Ser Ser Asn Thr Ala
65                  70                  75                  80

Tyr Leu Gln Leu Ser Ser Leu Ser Ser Glu Asp Thr Ala Val Tyr Phe
                85                  90                  95

Cys Ala Arg Gly Leu His Trp Gly Gln Gly Thr Thr Leu Thr Val Ser
            100                 105                 110

Ser

<210> SEQ ID NO 144
<211> LENGTH: 8
<212> TYPE: PRT
<213> ORGANISM: Artificial Sequence
<220> FEATURE:
<223> OTHER INFORMATION: 4-35-B4 heavy chain CDR1

<400> SEQUENCE: 144

Gly Phe Asn Ile Lys Asp Thr Tyr
1               5

<210> SEQ ID NO 145
<211> LENGTH: 8
<212> TYPE: PRT
<213> ORGANISM: Artificial Sequence
<220> FEATURE:
<223> OTHER INFORMATION: 4-35-B4 heavy chain CDR2

<400> SEQUENCE: 145

Ile Asp Pro Ala Asn Gly Asn Thr
1               5

<210> SEQ ID NO 146
<211> LENGTH: 5
<212> TYPE: PRT
<213> ORGANISM: Artificial Sequence
<220> FEATURE:
<223> OTHER INFORMATION: 4-35-B4 heavy chain CDR3

<400> SEQUENCE: 146

Ala Arg Gly Leu His
1               5
```

<210> SEQ ID NO 147
<211> LENGTH: 25
<212> TYPE: PRT
<213> ORGANISM: Artificial Sequence
<220> FEATURE:
<223> OTHER INFORMATION: 4-35-B4 heavy chain FR1

<400> SEQUENCE: 147

Glu Val Gln Leu Gln Gln Ser Gly Ala Glu Leu Val Lys Pro Gly Ala
1               5                   10                  15

Ser Val Lys Leu Ser Cys Thr Ala Ser
            20                  25

<210> SEQ ID NO 148
<211> LENGTH: 17
<212> TYPE: PRT
<213> ORGANISM: Artificial Sequence
<220> FEATURE:
<223> OTHER INFORMATION: 4-35-B4 heavy chain FR2

<400> SEQUENCE: 148

Ile His Trp Val Lys Gln Arg Pro Asp Gln Gly Leu Glu Trp Ile Gly
1               5                   10                  15

Lys

<210> SEQ ID NO 149
<211> LENGTH: 38
<212> TYPE: PRT
<213> ORGANISM: Artificial Sequence
<220> FEATURE:
<223> OTHER INFORMATION: 4-35-B4 heavy chain FR3

<400> SEQUENCE: 149

Asn Tyr Asp Pro Lys Phe Gln Gly Lys Ala Thr Ile Thr Ala Asp Thr
1               5                   10                  15

Ser Ser Asn Thr Ala Tyr Leu Gln Leu Ser Ser Leu Ser Glu Asp
            20                  25                  30

Thr Ala Val Tyr Phe Cys
        35

<210> SEQ ID NO 150
<211> LENGTH: 111
<212> TYPE: PRT
<213> ORGANISM: Artificial Sequence
<220> FEATURE:
<223> OTHER INFORMATION: 4-35-B4 light chain variable region

<400> SEQUENCE: 150

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys
            100                 105                 110

<210> SEQ ID NO 151
<211> LENGTH: 10
<212> TYPE: PRT
<213> ORGANISM: Artificial Sequence
<220> FEATURE:
<223> OTHER INFORMATION: 4-35-B4 light chain CDR1

<400> SEQUENCE: 151

Lys Ser Val Ser Thr Ser Gly Tyr Ser Tyr
1               5                   10

<210> SEQ ID NO 152
<211> LENGTH: 3
<212> TYPE: PRT
<213> ORGANISM: Artificial Sequence
<220> FEATURE:
<223> OTHER INFORMATION: 4-35-B4 light chain CDR2

<400> SEQUENCE: 152

Leu Ala Ser
1

<210> SEQ ID NO 153
<211> LENGTH: 9
<212> TYPE: PRT
<213> ORGANISM: Artificial Sequence
<220> FEATURE:
<223> OTHER INFORMATION: 4-35-B4 light chain CDR3

<400> SEQUENCE: 153

Gln His Ser Arg Glu Leu Pro Tyr Thr
1               5

<210> SEQ ID NO 154
<211> LENGTH: 26
<212> TYPE: PRT
<213> ORGANISM: Artificial Sequence
<220> FEATURE:
<223> OTHER INFORMATION: 4-35-B4 light chain FR1

<400> SEQUENCE: 154

Asp Ile Val Leu Thr Gln Ser Pro Ala Ser Leu Ala Val Ser Leu Gly
1               5                   10                  15

Gln Arg Ala Thr Ile Ser Cys Arg Ala Ser
            20                  25

<210> SEQ ID NO 155
<211> LENGTH: 17
<212> TYPE: PRT
<213> ORGANISM: Artificial Sequence
<220> FEATURE:
<223> OTHER INFORMATION: 4-35-B4 light chain FR2

<400> SEQUENCE: 155

Met His Trp Tyr Gln Gln Lys Pro Gly Gln Pro Pro Lys Leu Leu Ile
1               5                   10                  15

Tyr

<210> SEQ ID NO 156
<211> LENGTH: 36
<212> TYPE: PRT
<213> ORGANISM: Artificial Sequence
<220> FEATURE:

<223> OTHER INFORMATION: 4-35-B4 light chain FR3

<400> SEQUENCE: 156

Asn Leu Glu Ser Gly Val Pro Ala Arg Phe Ser Gly Ser Gly Ser Gly
1               5                   10                  15

Thr Asp Phe Thr Leu Asn Ile His Pro Val Glu Glu Glu Asp Ala Ala
            20                  25                  30

Thr Tyr Tyr Cys
        35

<210> SEQ ID NO 157
<211> LENGTH: 118
<212> TYPE: PRT
<213> ORGANISM: Artificial Sequence
<220> FEATURE:
<223> OTHER INFORMATION: 10A6 heavy chain variable region

<400> SEQUENCE: 157

Asp Val Gln Leu Gln Glu Ser Gly Pro Gly Leu Val Lys Pro Ser Gln
1               5                   10                  15

Ser Leu Ser Leu Thr Cys Ser Val Thr Gly Asn Phe Ile Thr Ser Gly
            20                  25                  30

Tyr Phe Trp Asn Trp Ile Arg Gln Phe Pro Gly Asn Lys Leu Glu Trp
        35                  40                  45

Met Gly Phe Ile Ser Tyr Asp Gly Ser Asn Asn Tyr Lys Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Asn Tyr Gly Phe Gly Phe Asp Tyr Trp Gly Gln Gly Thr
            100                 105                 110

Thr Leu Thr Val Ser Ser
        115

<210> SEQ ID NO 158
<211> LENGTH: 9
<212> TYPE: PRT
<213> ORGANISM: Artificial Sequence
<220> FEATURE:
<223> OTHER INFORMATION: 10A6 heavy chain CDR1

<400> SEQUENCE: 158

Gly Asn Phe Ile Thr Ser Gly Tyr Phe
1               5

<210> SEQ ID NO 159
<211> LENGTH: 7
<212> TYPE: PRT
<213> ORGANISM: Artificial Sequence
<220> FEATURE:
<223> OTHER INFORMATION: 10A6 heavy chain CDR2

<400> SEQUENCE: 159

Ile Ser Tyr Asp Gly Ser Asn
1               5

<210> SEQ ID NO 160
<211> LENGTH: 11
<212> TYPE: PRT
<213> ORGANISM: Artificial Sequence
<220> FEATURE:

<223> OTHER INFORMATION: 10A6 heavy chain CDR3

<400> SEQUENCE: 160

Ala Arg Glu Asn Tyr Gly Phe Gly Phe Asp Tyr
1               5                   10

<210> SEQ ID NO 161
<211> LENGTH: 25
<212> TYPE: PRT
<213> ORGANISM: Artificial Sequence
<220> FEATURE:
<223> OTHER INFORMATION: 10A6 heavy chain FR1

<400> SEQUENCE: 161

Asp Val Gln Leu Gln Glu Ser Gly Pro Gly Leu Val Lys Pro Ser Gln
1               5                   10                  15

Ser Leu Ser Leu Thr Cys Ser Val Thr
            20                  25

<210> SEQ ID NO 162
<211> LENGTH: 17
<212> TYPE: PRT
<213> ORGANISM: Artificial Sequence
<220> FEATURE:
<223> OTHER INFORMATION: 10A6 heavy chain FR2

<400> SEQUENCE: 162

Trp Asn Trp Ile Arg Gln Phe Pro Gly Asn Lys Leu Glu Trp Met Gly
1               5                   10                  15

Phe

<210> SEQ ID NO 163
<211> LENGTH: 38
<212> TYPE: PRT
<213> ORGANISM: Artificial Sequence
<220> FEATURE:
<223> OTHER INFORMATION: 10A6 heavy chain FR3

<400> SEQUENCE: 163

Asn Tyr Lys Pro Ser Leu Lys Asn Arg Ile Ser Ile Thr Arg Asp Thr
1               5                   10                  15

Ser Lys Asn Gln Phe Phe Leu Lys Leu Asn Ser Val Thr Thr Glu Asp
            20                  25                  30

Thr Ala Thr Tyr Tyr Cys
        35

<210> SEQ ID NO 164
<211> LENGTH: 113
<212> TYPE: PRT
<213> ORGANISM: Artificial Sequence
<220> FEATURE:
<223> OTHER INFORMATION: 10A6 light chain variable region

<400> SEQUENCE: 164

Asp Ile Val Leu Thr Gln Ser Pro Ser Ser Leu Pro Val Ser Ile Gly
1               5                   10                  15

Glu Lys Val Thr Met Ser Cys Lys Ser Ser Gln Ser Leu Leu Tyr Ser
            20                  25                  30

Asp Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Trp Lys Ser Gly Val
    50                  55                  60

```
Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Phe Thr Phe Pro Trp Thr Phe Gly Gly Gly Thr Lys Leu Glu Ile
            100                 105                 110

Lys

<210> SEQ ID NO 165
<211> LENGTH: 12
<212> TYPE: PRT
<213> ORGANISM: Artificial Sequence
<220> FEATURE:
<223> OTHER INFORMATION: 10A6 light chain CDR1

<400> SEQUENCE: 165

Gln Ser Leu Leu Tyr Ser Asp Asn Gln Lys Asn Tyr
1               5                   10

<210> SEQ ID NO 166
<211> LENGTH: 3
<212> TYPE: PRT
<213> ORGANISM: Artificial Sequence
<220> FEATURE:
<223> OTHER INFORMATION: 10A6 light chain CDR2

<400> SEQUENCE: 166

Trp Ala Ser
1

<210> SEQ ID NO 167
<211> LENGTH: 9
<212> TYPE: PRT
<213> ORGANISM: Artificial Sequence
<220> FEATURE:
<223> OTHER INFORMATION: 10A6 light chain CDR3

<400> SEQUENCE: 167

Gln Gln Tyr Phe Thr Phe Pro Trp Thr
1               5

<210> SEQ ID NO 168
<211> LENGTH: 26
<212> TYPE: PRT
<213> ORGANISM: Artificial Sequence
<220> FEATURE:
<223> OTHER INFORMATION: 10A6 light chain FR1

<400> SEQUENCE: 168

Asp Ile Val Leu Thr Gln Ser Pro Ser Ser Leu Pro Val Ser Ile Gly
1               5                   10                  15

Glu Lys Val Thr Met Ser Cys Lys Ser Ser
            20                  25

<210> SEQ ID NO 169
<211> LENGTH: 17
<212> TYPE: PRT
<213> ORGANISM: Artificial Sequence
<220> FEATURE:
<223> OTHER INFORMATION: 10A6 light chain FR2
```

```
<400> SEQUENCE: 169

Leu Ala Trp Tyr Gln Gln Lys Pro Gly Gln Ser Pro Lys Leu Leu Ile
1               5                   10                  15

Tyr

<210> SEQ ID NO 170
<211> LENGTH: 36
<212> TYPE: PRT
<213> ORGANISM: Artificial Sequence
<220> FEATURE:
<223> OTHER INFORMATION: 10A6 light chain FR3

<400> SEQUENCE: 170

Thr Trp Lys Ser Gly Val Pro Asp Arg Phe Thr Gly Ser Gly Ser Gly
1               5                   10                  15

Thr Asp Phe Thr Leu Thr Ile Ser Ser Val Lys Ala Glu Asp Leu Ala
                20                  25                  30

Val Tyr Tyr Cys
            35

<210> SEQ ID NO 171
<211> LENGTH: 330
<212> TYPE: PRT
<213> ORGANISM: Artificial Sequence
<220> FEATURE:
<223> OTHER INFORMATION: Human IgG1 constant region (IGHG1;
      UniProt:P01857-1, v1)

<400> SEQUENCE: 171

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 172
<211> LENGTH: 98
<212> TYPE: PRT
<213> ORGANISM: Artificial Sequence
<220> FEATURE:
<223> OTHER INFORMATION: CH1 IgG1 (positions 1-98 of P01857-1, v1)

<400> SEQUENCE: 172

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 173
<211> LENGTH: 12
<212> TYPE: PRT
<213> ORGANISM: Artificial Sequence
<220> FEATURE:
<223> OTHER INFORMATION: Hinge IgG1 (positions 99-110 of P01857-1, v1)

<400> SEQUENCE: 173

Glu Pro Lys Ser Cys Asp Lys Thr His Thr Cys Pro
1               5                   10

<210> SEQ ID NO 174
<211> LENGTH: 113
<212> TYPE: PRT
<213> ORGANISM: Artificial Sequence
<220> FEATURE:
<223> OTHER INFORMATION: CH2 IgG1 (positions 111-223 of P01857-1, v1)

<400> SEQUENCE: 174

Pro Cys Pro Ala Pro Glu Leu Leu Gly Gly Pro Ser Val Phe Leu Phe
1               5                   10                  15

```
Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
 50                      55                  60

Arg Glu Glu Gln Tyr Asn Ser Thr Tyr Arg Val Val Ser Val Leu Thr
 65                      70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 175
<211> LENGTH: 107
<212> TYPE: PRT
<213> ORGANISM: Artificial Sequence
<220> FEATURE:
<223> OTHER INFORMATION: CH3 IgG1 (positions 224-330 of P01857-1, v1)

<400> SEQUENCE: 175

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
         35                     40                  45

Asn Asn Tyr Lys Thr Thr Pro Pro Val Leu Asp Ser Asp Gly Ser Phe
 50                      55                  60

Phe Leu Tyr Ser Lys Leu Thr Val Asp Lys Ser Arg Trp Gln Gln Gly
 65                      70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 176
<211> LENGTH: 107
<212> TYPE: PRT
<213> ORGANISM: Artificial Sequence
<220> FEATURE:
<223> OTHER INFORMATION: CH3 (D356E, L358M; positions numbered according
      to EU numbering)

<400> SEQUENCE: 176

Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
         35                     40                  45

Asn Asn Tyr Lys Thr Thr Pro Pro Val Leu Asp Ser Asp Gly Ser Phe
 50                      55                  60

Phe Leu Tyr Ser Lys Leu Thr Val Asp Lys Ser Arg Trp Gln Gln Gly
 65                      70                  75                  80
```

Asn Val Phe Ser Cys Ser Val Met His Glu Ala Leu His Asn His Tyr
            85                  90                  95

Thr Gln Lys Ser Leu Ser Leu Ser Pro Gly Lys
            100                 105

<210> SEQ ID NO 177
<211> LENGTH: 107
<212> TYPE: PRT
<213> ORGANISM: Artificial Sequence
<220> FEATURE:
<223> OTHER INFORMATION: C? CL (IGCK; UniProt: P01834-1, v2)

<400> SEQUENCE: 177

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 178
<211> LENGTH: 18
<212> TYPE: PRT
<213> ORGANISM: Artificial Sequence
<220> FEATURE:
<223> OTHER INFORMATION: 10A6 heavy chain SignalP

<400> SEQUENCE: 178

Met Lys Val Leu Ser Leu Leu Tyr Leu Leu Thr Ala Ile Pro Gly Ile
1               5                   10                  15

Leu Ser

<210> SEQ ID NO 179
<211> LENGTH: 18
<212> TYPE: PRT
<213> ORGANISM: Artificial Sequence
<220> FEATURE:
<223> OTHER INFORMATION: 10D1 heavy chain SignalP

<400> SEQUENCE: 179

Met Arg Val Leu Ile Leu Leu Cys Leu Phe Thr Ala Phe Pro Gly Ile
1               5                   10                  15

Leu Ser

<210> SEQ ID NO 180
<211> LENGTH: 20
<212> TYPE: PRT
<213> ORGANISM: Artificial Sequence
<220> FEATURE:
<223> OTHER INFORMATION: 10D1 light chain SignalP -continued

<400> SEQUENCE: 180

Met Glu Ser Gln Thr Gln Val Phe Val Tyr Met Leu Leu Trp Leu Ser
1               5                   10                  15

Gly Val Asp Gly
            20

<210> SEQ ID NO 181
<211> LENGTH: 19
<212> TYPE: PRT
<213> ORGANISM: Artificial Sequence
<220> FEATURE:
<223> OTHER INFORMATION: 4-35-B2 heavy chain SignalP

<400> SEQUENCE: 181

Met Glu Trp Ser Trp Ile Phe Leu Phe Leu Leu Ser Gly Thr Thr Gly
1               5                   10                  15

Val His Ser

<210> SEQ ID NO 182
<211> LENGTH: 22
<212> TYPE: PRT
<213> ORGANISM: Artificial Sequence
<220> FEATURE:
<223> OTHER INFORMATION: 4-35-B2 light chain SignalP

<400> SEQUENCE: 182

Met Asp Phe Gln Val Gln Ile Phe Ser Phe Leu Leu Met Ser Ala Ser
1               5                   10                  15

Val Met Met Ser Arg Gly
            20

<210> SEQ ID NO 183
<211> LENGTH: 19
<212> TYPE: PRT
<213> ORGANISM: Artificial Sequence
<220> FEATURE:
<223> OTHER INFORMATION: 4-35-B4 heavy chain SignalP

<400> SEQUENCE: 183

Met Lys Cys Ser Trp Val Ile Phe Phe Leu Met Ala Val Val Thr Gly
1               5                   10                  15

Val Asn Ser

<210> SEQ ID NO 184
<211> LENGTH: 20
<212> TYPE: PRT
<213> ORGANISM: Artificial Sequence
<220> FEATURE:
<223> OTHER INFORMATION: 4-35-B4 light chain SignalP

<400> SEQUENCE: 184

Met Glu Thr Asp Thr Leu Leu Leu Trp Val Leu Leu Leu Trp Val Pro
1               5                   10                  15

Gly Ser Thr Gly
            20

<210> SEQ ID NO 185
<211> LENGTH: 19
<212> TYPE: PRT
<213> ORGANISM: Artificial Sequence
<220> FEATURE:
<223> OTHER INFORMATION: 10D1_c75, 10D1_c76, 10D1_c77, 10D1_c78v1,
      10D1_c78v2, 10D1_11B, 10D1_c85v1, 10D1_c85v2, 10D1_c85o1, 10D1_c85o2, 10D1_c87, 10D1_c89, 10D1_c90, 10D1_c91, 10D1_c92,
10D1_c93 heavy chain SignalP

<400> SEQUENCE: 185

Met Glu Leu Gly Leu Arg Trp Val Phe Leu Ile Ala Thr Leu Ala Gly
1               5                   10                  15

Ala Arg Cys

<210> SEQ ID NO 186
<211> LENGTH: 22
<212> TYPE: PRT
<213> ORGANISM: Artificial Sequence
<220> FEATURE:
<223> OTHER INFORMATION: 10D1_c75, 10D1_c76, 10D1_c77, 10D1_c78v1,
10D1_c78v2, 10D1_11B, 10D1_c85v1, 10D1_c85v2, 10D1_c85o1,
10D1_c85o2, 10D1_c87, 10D1_c89, 10D1_c90, 10D1_c91, 10D1_c92,
10D1_c93 light chain SignalP

<400> SEQUENCE: 186

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 187
<211> LENGTH: 450
<212> TYPE: PRT
<213> ORGANISM: Artificial Sequence
<220> FEATURE:
<223> OTHER INFORMATION: 10D1_c75 VH-CH1-CH2-CH3

<400> SEQUENCE: 187

Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
                20                  25                  30

Tyr Ser Trp His Trp Ile Arg Gln Phe Pro Gly Asn Gly Leu Glu Trp
            35                  40                  45

Ile Gly Ser Ile His Tyr Ser Gly Gly Thr Asn Tyr Asn Pro Thr Leu
        50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

-continued

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 188
<211> LENGTH: 214
<212> TYPE: PRT
<213> ORGANISM: Artificial Sequence
<220> FEATURE:
<223> OTHER INFORMATION: 10D1_c75 VL-Ckappa

<400> SEQUENCE: 188

Asp Ile Val Met Thr Gln Ser Pro Ser Ser Leu Ser Ala Ser Val Gly
1               5                   10                  15

Asp Leu Val Thr Ile Thr Cys Lys Ala Ser Gln Ile Val Gly Ser Asn
            20                  25                  30

Val Ala Trp Tyr Gln Met Lys Pro Gly Lys Ser Pro Lys Pro Leu Ile
        35                  40                  45

Tyr Ser Ala Ser Tyr Leu Tyr Phe Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Glu Tyr Phe Cys Gln Gln Tyr Ser Ser His Pro Leu
                85                  90                  95

Thr Phe Gly Pro Gly Thr Lys Val Glu Ile Lys Arg Thr Val Ala Ala
            100                 105                 110
```

```
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 189
<211> LENGTH: 450
<212> TYPE: PRT
<213> ORGANISM: Artificial Sequence
<220> FEATURE:
<223> OTHER INFORMATION: 10D1_c76 VH-CH1-CH2-CH3

<400> SEQUENCE: 189

```
Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Ile Gly Ser Ile His Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 190
<211> LENGTH: 214
<212> TYPE: PRT
<213> ORGANISM: Artificial Sequence
<220> FEATURE:
<223> OTHER INFORMATION: 10D1_c76 VL-Ckappa

<400> SEQUENCE: 190

Asp Ile Val Met Thr Gln Ser Pro Ser Ser Leu Ser Ala Ser Gly Gly
1               5                   10                  15

Asp Arg Val Thr Ile Thr Cys Lys Ala Ser Gln Ile Val Gly Tyr Asn
            20                  25                  30

Val Ala Trp Tyr Gln Gln Lys Pro Gly Lys Ser Pro Lys Pro Leu Ile
        35                  40                  45

Tyr Ser Ala Ser Tyr Leu Tyr Ser Asp Val Pro Ser Arg Phe Ser Ala
50                  55                  60

Ser Gly Ser Gly Thr Asp Phe Thr Leu Thr Ile Ser Ser Leu Gln Pro
65                  70                  75                  80

Glu Asp Val Ala Glu Tyr Phe Cys Gln Gln Tyr Ser Ser His Pro Leu
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 191
<211> LENGTH: 450
<212> TYPE: PRT
<213> ORGANISM: Artificial Sequence
<220> FEATURE:
<223> OTHER INFORMATION: 10D1_c77 VH-CH1-CH2-CH3

<400> SEQUENCE: 191

```
Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Ile Gly Ser Ile His Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 192
<211> LENGTH: 214
<212> TYPE: PRT
<213> ORGANISM: Artificial Sequence
<220> FEATURE:
<223> OTHER INFORMATION: 10D1_c77 VL-Ckappa

<400> SEQUENCE: 192

Val Ile Val Met Thr Gln Ser Pro Ser Ser Leu Ser Ala Ser Val Gly
1               5                   10                  15

Asp Arg Val Thr Ile Thr Cys Lys Ala Ser Gln Ile Val Gly Pro Asn
            20                  25                  30

Val Ala Trp Tyr Gln Gln Lys Pro Gly Lys Ser Pro Lys Pro Leu Ile
        35                  40                  45

Tyr Ser Ala Ser Tyr Gly Tyr Ser Asp Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Glu Tyr Phe Cys Gln Gln Tyr Ser Thr His Pro Leu
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 193
<211> LENGTH: 450
<212> TYPE: PRT
<213> ORGANISM: Artificial Sequence
<220> FEATURE:
<223> OTHER INFORMATION: 10D1_c78v1 VH-CH1-CH2-CH3

<400> SEQUENCE: 193

Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Ile Gly Ser Ile His Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 194
<211> LENGTH: 450
<212> TYPE: PRT
<213> ORGANISM: Artificial Sequence
<220> FEATURE:
<223> OTHER INFORMATION: 10D1_c78v2 VH-CH1-CH2-CH3

<400> SEQUENCE: 194

Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Lys Gly Leu Glu Trp
        35                  40                  45

Ile Gly Ser Ile His Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 195
<211> LENGTH: 214
<212> TYPE: PRT
<213> ORGANISM: Artificial Sequence
<220> FEATURE:
<223> OTHER INFORMATION: 10D1_c78v1, 10D1_c78v2, 10D1_11B VL-Ckappa

<400> SEQUENCE: 195

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ile Val Gly Ser Asn
            20                  25                  30

Val Ala Trp Tyr Gln Gln Lys Pro Gly Lys Ser Pro Lys Pro Leu Ile
        35                  40                  45

Tyr Ser Ala Ser Tyr Gly Tyr Ser Asp Val Pro Ser Arg Phe Ser Gly
    50                  55                  60

Ser Gly Ser Gly Thr Asp Phe Thr Leu Thr Ile Ser Ser Leu Arg Pro
65                  70                  75                  80

Glu Asp Val Ala Thr Tyr Tyr Cys Gln Gln Tyr Ser Ser His Pro Leu
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 196
<211> LENGTH: 450
<212> TYPE: PRT
<213> ORGANISM: Artificial Sequence
<220> FEATURE:
<223> OTHER INFORMATION: 10D1_11B VH-CH1-CH2-CH3

<400> SEQUENCE: 196

Asp Val Gln Leu Gln Glu Trp Gly Ala Gly Leu Leu Lys Pro Ser Glu
1               5                   10                  15

Thr Leu Ser Leu Thr Cys Ala Val Tyr Gly Tyr Ser Ile Thr Ser Gly
            20                  25                  30

Tyr Ser Trp His Trp Ile Arg Gln Pro Pro Gly Lys Gly Leu Glu Trp
        35                  40                  45

Ile Gly Ser Ile His Tyr Ser Gly Gly Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 197
<211> LENGTH: 450
<212> TYPE: PRT
<213> ORGANISM: Artificial Sequence
<220> FEATURE:
<223> OTHER INFORMATION: 10D1_c85v1 VH-CH1-CH2-CH3

<400> SEQUENCE: 197

Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Ile Gly Ser Ile Arg Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Gly Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 198
<211> LENGTH: 450
<212> TYPE: PRT
<213> ORGANISM: Artificial Sequence
<220> FEATURE:
<223> OTHER INFORMATION: 10D1_c85v2 VH-CH1-CH2-CH3

<400> SEQUENCE: 198

Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Lys Gly Leu Glu Trp
        35                  40                  45

Ile Gly Ser Ile Arg Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Gly Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110
```

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 199
<211> LENGTH: 214
<212> TYPE: PRT
<213> ORGANISM: Artificial Sequence
<220> FEATURE:
<223> OTHER INFORMATION: 10D1_c85v1, 10D1_c85v2 VL-Ckappa

<400> SEQUENCE: 199

Asp Ile Val Met Thr Gln Ser Pro Ser Ser Leu Ser Ala Ser Val Gly
1               5                   10                  15

```
Asp Arg Val Thr Ile Thr Cys Lys Ala Ser Gln Ile Val Gly Ser Asn
            20                  25                  30

Val Ala Trp Tyr Gln Gln Lys Pro Gly Lys Ser Pro Lys Pro Leu Ile
        35                  40                  45

Tyr Ser Ala Arg Tyr Gln Tyr Ser Gly Val Pro Phe Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser His Pro Leu
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 200
<211> LENGTH: 450
<212> TYPE: PRT
<213> ORGANISM: Artificial Sequence
<220> FEATURE:
<223> OTHER INFORMATION: 10D1_c85o1 VH-CH1-CH2-CH3

<400> SEQUENCE: 200

Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Lys Gly Leu Glu Trp
        35                  40                  45

Ile Gly Ser Ile Arg Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Gly Ser Val Thr Ala Ala Asp Thr Ala Val Tyr Phe Cys
                85                  90                  95

Ala Arg Glu Thr Thr Ala Pro Arg Tyr Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 201
<211> LENGTH: 214
<212> TYPE: PRT
<213> ORGANISM: Artificial Sequence
<220> FEATURE:
<223> OTHER INFORMATION: 10D1_c85o1 VL-Ckappa

<400> SEQUENCE: 201

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ile Val Gly Ser Asn
            20                  25                  30

Val Ala Trp Tyr Gln Gln Lys Pro Gly Lys Ser Pro Lys Pro Leu Ile
        35                  40                  45

Tyr Ser Ala Arg Tyr Gln Tyr Ser Gly Val Pro Phe Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Tyr Ser Ser His Pro Leu
                 85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 202
<211> LENGTH: 450
<212> TYPE: PRT
<213> ORGANISM: Artificial Sequence
<220> FEATURE:
<223> OTHER INFORMATION: 10D1_c85o2 VH-CH1-CH2-CH3

<400> SEQUENCE: 202

```
Asp Val Gln Leu Gln Glu Trp Gly Ala Gly Leu Leu Lys Pro Ser Glu
  1               5                  10                  15

Thr Leu Ser Leu Thr Cys Ala Val Thr Gly Tyr Ser Ile Thr Ser Gly
             20                  25                  30

Tyr Ser Trp His Trp Ile Arg Gln Phe Pro Gly Lys Gly Leu Glu Trp
         35                  40                  45

Ile Gly Ser Ile Arg Tyr Ser Gly Gly Thr Asn Tyr Asn Pro Ser Leu
 50                  55                  60

Lys Ser Arg Ile Thr Ile Ser Arg Asp Thr Ser Lys Asn Gln Phe Ser
 65                  70                  75                  80

Leu Lys Leu Gly Ser Val Thr Ala Ala Asp Thr Ala Val Tyr Phe Cys
                 85                  90                  95

Ala Arg Gly Thr Thr Ala Pro Arg Tyr Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 203
<211> LENGTH: 214
<212> TYPE: PRT
<213> ORGANISM: Artificial Sequence
<220> FEATURE:
<223> OTHER INFORMATION: 10D1_c85o2 VL-Ckappa

<400> SEQUENCE: 203

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ile Val Gly Ser Asn
            20                  25                  30

Val Ala Trp Tyr Gln Gln Lys Pro Gly Lys Ser Pro Lys Pro Leu Ile
        35                  40                  45

Tyr Ser Ala Arg Tyr Gln Tyr Ser Gly Val Pro Phe Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser His Pro Leu
                85                  90                  95

Thr Phe Gly Pro Gly Thr Lys Val Glu Ile Lys Arg Thr Val Ala Ala
            100                 105                 110
```

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 204
<211> LENGTH: 450
<212> TYPE: PRT
<213> ORGANISM: Artificial Sequence
<220> FEATURE:
<223> OTHER INFORMATION: 10D1_c87 VH-CH1-CH2-CH3

<400> SEQUENCE: 204

Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Ile Gly Ser Ile His Tyr Ser Gly Gly Thr Asn Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Arg Leu Ser Ser Val Thr Ala Ala Asp Thr Ala Val Tyr Phe Cys
                85                  90                  95

Ala Arg Met Thr Thr Ala Pro Arg Tyr Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 205
<211> LENGTH: 214
<212> TYPE: PRT
<213> ORGANISM: Artificial Sequence
<220> FEATURE:
<223> OTHER INFORMATION: 10D1_c87 VL-Ckappa

<400> SEQUENCE: 205

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ile Val Gly Ser Asn
            20                  25                  30

Val Ala Trp Tyr Gln Gln Met Pro Gly Lys Ser Pro Glu Pro Leu Ile
        35                  40                  45

Tyr Ser Ala Ser Tyr Leu Tyr Ser Asp Val Pro Ser Arg Phe Ser Gly
    50                  55                  60

Ser Gly Ser Gly Thr Asp Phe Thr Met Thr Ile Ser Ser Leu Gln Pro
65                  70                  75                  80

Glu Asp Val Ala Thr Tyr Tyr Cys Gln Gln Tyr Ser Ser His Pro Leu
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 206
<211> LENGTH: 450
<212> TYPE: PRT
<213> ORGANISM: Artificial Sequence
<220> FEATURE:
<223> OTHER INFORMATION: 10D1_c89 VH-CH1-CH2-CH3

<400> SEQUENCE: 206

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Ile Gly Ser Ile Arg Tyr Ser Gly Gly Thr Asp Tyr Asn Pro Ser Leu
    50                  55                  60

Lys Ser Leu Val Thr Ile Ser Ala Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Thr Thr Ala Pro Trp Tyr Pro Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 207
<211> LENGTH: 214
<212> TYPE: PRT
<213> ORGANISM: Artificial Sequence
<220> FEATURE:
<223> OTHER INFORMATION: 10D1_c89 VL-Ckappa

<400> SEQUENCE: 207

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Ile Val Gly Ser Asn
            20                  25                  30

Val Ala Trp Tyr Gln Gln Lys Pro Gly Lys Ala Pro Glu Pro Leu Ile
        35                  40                  45

Tyr Ser Ala Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser His Pro Leu
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

```
Phe Asn Arg Gly Glu Cys
    210

<210> SEQ ID NO 208
<211> LENGTH: 450
<212> TYPE: PRT
<213> ORGANISM: Artificial Sequence
<220> FEATURE:
<223> OTHER INFORMATION: 10D1_c90 VH-CH1-CH2-CH3

<400> SEQUENCE: 208

Gln Val Gln Leu Gln Glu Ser Gly Pro Gly Leu Val Lys Pro Ser Gln
1               5                   10                  15

Thr Leu Phe Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Ile Gly Ser Ile Arg Tyr Ser Gly Gly Thr Asp Tyr Asn Pro Ser Leu
    50                  55                  60

Lys Ser Leu Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Thr Thr Ala Pro Trp Tyr Pro Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 209
<211> LENGTH: 214
<212> TYPE: PRT
<213> ORGANISM: Artificial Sequence
<220> FEATURE:
<223> OTHER INFORMATION: 10D1_c90 VL-Ckappa

<400> SEQUENCE: 209

Asp Ile Gln Met Thr Gln Ser Pro Ser Ser Val Ser Ala Ser Val Gly
1               5                   10                  15

Asp Arg Val Thr Phe Thr Cys Lys Ala Ser Gln Ile Val Gly Ser Asn
            20                  25                  30

Val Ala Trp Tyr Gln Gln Lys Pro Gly Lys Ala Pro Glu Pro Leu Ile
        35                  40                  45

Tyr Ser Ala Ser Tyr Leu Tyr Ser Ser Val Pro Ser Arg Phe Ser Gly
50                  55                  60

Ser Gly Ser Gly Thr Glu Phe Thr Met Thr Ile Ser Ser Leu Glu Pro
65                  70                  75                  80

Glu Asp Phe Ala Thr Tyr Tyr Cys Gln Gln Tyr Thr Thr His Pro Leu
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 210
<211> LENGTH: 450
<212> TYPE: PRT
<213> ORGANISM: Artificial Sequence
```

<220> FEATURE:
<223> OTHER INFORMATION: 10D1_c91 VH-CH1-CH2-CH3

<400> SEQUENCE: 210

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Tyr Ile Thr Ser Gly
            20                  25                  30

Tyr Ser Trp His Trp Ile Arg Gln His Pro Gly Lys Gly Leu Glu Trp
        35                  40                  45

Ile Gly Ser Ile Arg Tyr Ser Gly Gly Thr Asp Tyr Asn Pro Ser Leu
    50                  55                  60

Lys Ser Leu Ala Thr Ile Ser Ala Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Thr Thr Ala Pro Trp Tyr Pro Phe Asp Tyr Trp Gly Gln
            100                 105                 110

Gly Thr Ala Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

-continued

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 211
<211> LENGTH: 214
<212> TYPE: PRT
<213> ORGANISM: Artificial Sequence
<220> FEATURE:
<223> OTHER INFORMATION: 10D1_c91 VL-Ckappa

<400> SEQUENCE: 211

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Ile Val Gly Ser Asn
            20                  25                  30

Val Ala Trp Tyr Gln Gln Lys Pro Gly Lys Ala Pro Met Pro Leu Ile
        35                  40                  45

Tyr Ser Ala Ser Tyr Gly Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser His Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 212
<211> LENGTH: 450
<212> TYPE: PRT
<213> ORGANISM: Artificial Sequence
<220> FEATURE:
<223> OTHER INFORMATION: 10D1_c92 VH-CH1-CH2-CH3

<400> SEQUENCE: 212

Asp Val Gln Leu Gln Glu Trp Gly Ala Gly Leu Leu Lys Pro Ser Glu
1               5                   10                  15

-continued

```
Thr Leu Ser Leu Thr Cys Ala Val Thr Gly Tyr Ser Ile Thr Ser Gly
             20                  25                  30

Tyr Ser Trp His Trp Ile Arg Gln Phe Pro Gly Asn Gly Leu Glu Trp
             35                  40                  45

Ile Gly Ser Ile His Tyr Ser Gly Gly Thr Asn Tyr Asn Pro Thr Leu
 50                  55                  60

Lys Ser Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Phe Cys
             85                  90                  95

Ala Arg Met Thr Thr Ala Pro Arg Tyr Pro Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430
```

-continued

Glu Ala Leu His Asn His Tyr Thr Gln Lys Ser Leu Ser Leu Ser Pro
                435                 440                 445
Gly Lys
    450

<210> SEQ ID NO 213
<211> LENGTH: 214
<212> TYPE: PRT
<213> ORGANISM: Artificial Sequence
<220> FEATURE:
<223> OTHER INFORMATION: 10D1_c92 VL-Ckappa

<400> SEQUENCE: 213

Asp Ile Val Met Thr Gln Ser Pro Ser Ser Leu Ser Ala Ser Val Gly
1               5                   10                  15

Asp Leu Val Thr Ile Thr Cys Lys Ala Ser Gln Ile Val Gly Ser Asn
            20                  25                  30

Val Ala Trp Tyr Gln Met Lys Leu Gly Lys Ser Pro Lys Pro Leu Ile
        35                  40                  45

Tyr Ser Ala Ser Tyr Leu Tyr Phe Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Glu Tyr Phe Cys Gln Gln Tyr Phe Ser His Pro Leu
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 214
<211> LENGTH: 450
<212> TYPE: PRT
<213> ORGANISM: Artificial Sequence
<220> FEATURE:
<223> OTHER INFORMATION: 10D1_c93 VH-CH1-CH2-CH3

<400> SEQUENCE: 214

Asp Val Gln Leu Gln Glu Trp Gly Ala Gly Leu Leu Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Ile Gly Ser Ile His Tyr Ser Gly Gly Thr Asn Tyr Asn Pro Ser Leu
    50                  55                  60

```
Lys Ser Arg Ile Thr Ile Ser Arg Asp Thr Ser Lys Asn Gln Phe Ser
 65                  70                  75                  80

Leu Arg Leu Ser Ser Val Thr Ala Ala Asp Thr Ala Val Tyr Phe Cys
                 85                  90                  95

Ala Arg Met Thr Thr Ala Pro Arg Tyr Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 215
<211> LENGTH: 214
```

```
<212> TYPE: PRT
<213> ORGANISM: Artificial Sequence
<220> FEATURE:
<223> OTHER INFORMATION: 10D1_c93 VL-Ckappa

<400> SEQUENCE: 215

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ile Val Gly Ser Asn
            20                  25                  30

Val Ala Trp Tyr Gln Gln Lys Pro Gly Lys Ser Pro Lys Pro Leu Ile
        35                  40                  45

Tyr Ser Ala Ser Tyr Leu Tyr Ser Asp Val Pro Ser Arg Phe Ser Gly
    50                  55                  60

Ser Gly Ser Gly Thr Asp Phe Thr Met Thr Ile Ser Ser Leu Gln Pro
65                  70                  75                  80

Glu Asp Val Ala Thr Tyr Tyr Cys Gln Gln Tyr Ser Ser His Pro Leu
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 216
<211> LENGTH: 450
<212> TYPE: PRT
<213> ORGANISM: Artificial Sequence
<220> FEATURE:
<223> OTHER INFORMATION: 10D1 VH-CH1-CH2-CH3

<400> SEQUENCE: 216

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Ser Ile His Tyr Ser Gly Gly Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95

Ala Arg Met Thr Thr Ala Pro Arg Tyr Pro Phe Asp Tyr Trp Gly Gln
            100                 105                 110
```

```
Gly Thr Thr Leu Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 217
<211> LENGTH: 214
<212> TYPE: PRT
<213> ORGANISM: Artificial Sequence
<220> FEATURE:
<223> OTHER INFORMATION: 10D1 VL-Ckappa

<400> SEQUENCE: 217

Asp Ile Val Met Thr Gln Ser Gln Lys Phe Met Ser Thr Ser Val Gly
1               5                   10                  15
```

Asp Arg Val Ser Val Thr Cys Lys Ala Ser Gln Ile Val Gly Ser Asn
            20                  25                  30

Val Ala Trp Tyr Gln Lys Pro Gly Gln Ser Pro Lys Pro Leu Ile
        35                  40                  45

Tyr Ser Ala Ser Tyr Arg Tyr Ser Gly Val Pro Asp Arg Phe Thr Ala
50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Ser Ser His Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 218
<211> LENGTH: 447
<212> TYPE: PRT
<213> ORGANISM: Artificial Sequence
<220> FEATURE:
<223> OTHER INFORMATION: 4-35-B2 VH-CH1-CH2-CH3

<400> SEQUENCE: 218

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Asn Met Tyr Trp Val Lys Gln Ser His Gly Lys Ser Leu Glu Trp Ile
        35                  40                  45

Gly His Ile Asn Pro Tyr Asn Gly Gly Thr Thr Tyr Asn Gln Lys Phe
50                  55                  60

Lys Gly Arg Ala Thr Leu Thr Val Asp Lys Ser Ser Thr Ala Phe
65                  70                  75                  80

Met His Leu Asn Ser Leu Thr Ser Glu Asp Ser Ala Val Tyr Phe Cys
                85                  90                  95

Val Ser Leu Arg Trp Gly Ala Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 219
<211> LENGTH: 213
<212> TYPE: PRT
<213> ORGANISM: Artificial Sequence
<220> FEATURE:
<223> OTHER INFORMATION: 4-35-B2 VL-Ckappa

<400> SEQUENCE: 219

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

```
Asp Ala Ala Thr Tyr Tyr Cys Gln Gln Trp Asn Ser Asn Pro Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 220
<211> LENGTH: 443
<212> TYPE: PRT
<213> ORGANISM: Artificial Sequence
<220> FEATURE:
<223> OTHER INFORMATION: 4-35-B4 VH-CH1-CH2-CH3

<400> SEQUENCE: 220

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Asp Gln Gly Leu Glu Trp Ile
        35                  40                  45

Gly Lys Ile Ile Asp Pro Ala Asn Gly Asn Thr Asn Tyr Asp Pro Lys
    50                  55                  60

Phe Gln Gly Lys Ala Thr Ile Thr Ala Asp Thr Ser Ser Asn Thr Ala
65                  70                  75                  80

Tyr Leu Gln Leu Ser Ser Leu Ser Glu Asp Thr Ala Val Tyr Phe
                85                  90                  95

Cys Ala Arg Gly Leu His Trp Gly Gln Gly Thr Thr Leu Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220
```

```
Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 221
<211> LENGTH: 218
<212> TYPE: PRT
<213> ORGANISM: Artificial Sequence
<220> FEATURE:
<223> OTHER INFORMATION: 4-35-B4 VL-Ckappa

<400> SEQUENCE: 221

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140
```

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
        180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 222
<211> LENGTH: 448
<212> TYPE: PRT
<213> ORGANISM: Artificial Sequence
<220> FEATURE:
<223> OTHER INFORMATION: 10A6 VH-CH1-CH2-CH3

<400> SEQUENCE: 222

Asp Val Gln Leu Gln Glu Ser Gly Pro Gly Leu Val Lys Pro Ser Gln
1               5                   10                  15

Ser Leu Ser Leu Thr Cys Ser Val Thr Gly Asn Phe Ile Thr Ser Gly
            20                  25                  30

Tyr Phe Trp Asn Trp Ile Arg Gln Phe Pro Gly Asn Lys Leu Glu Trp
        35                  40                  45

Met Gly Phe Ile Ser Tyr Asp Gly Ser Asn Asn Tyr Lys Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Asn Tyr Gly Phe Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 223
<211> LENGTH: 220
<212> TYPE: PRT
<213> ORGANISM: Artificial Sequence
<220> FEATURE:
<223> OTHER INFORMATION: 10A6 VL-Ckappa

<400> SEQUENCE: 223

Asp Ile Val Leu Thr Gln Ser Pro Ser Ser Leu Pro Val Ser Ile Gly
1               5                   10                  15

Glu Lys Val Thr Met Ser Cys Lys Ser Ser Gln Ser Leu Leu Tyr Ser
            20                  25                  30

Asp Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Trp Lys Ser Gly Val
50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Phe Thr Phe Pro Trp Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

```
Ser Pro Val Thr Lys Ser Phe Asn Arg Gly Glu Cys
    210                 215                 220

<210> SEQ ID NO 224
<211> LENGTH: 25
<212> TYPE: PRT
<213> ORGANISM: Artificial Sequence
<220> FEATURE:
<223> OTHER INFORMATION: 10D1_11B heavy chain FR1

<400> SEQUENCE: 224

Asp Val Gln Leu Gln Glu Trp Gly Ala Gly Leu Leu Lys Pro Ser Glu
1               5                   10                  15

Thr Leu Ser Leu Thr Cys Ala Val Tyr
            20                  25

<210> SEQ ID NO 225
<211> LENGTH: 450
<212> TYPE: PRT
<213> ORGANISM: Artificial Sequence
<220> FEATURE:
<223> OTHER INFORMATION: 10D1F.FcA VH-CH1-CH2-Ch3 (GASDALIE; LCKC)
      (10D1F.FcB)

<400> SEQUENCE: 225

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Ile Gly Ser Ile Arg Tyr Ser Gly Gly Thr Asp Tyr Asn Pro Ser Leu
    50                  55                  60

Lys Ser Leu Val Thr Ile Ser Ala Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Thr Thr Ala Pro Trp Tyr Pro Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Ala Gly
225                 230                 235                 240

Pro Asp Val Phe Cys Phe Pro Pro Lys Pro Lys Asp Thr Leu Met Ile
                245                 250                 255
```

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Leu Pro Glu Glu
                325                 330                 335

Cys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
   450

<210> SEQ ID NO 226
<211> LENGTH: 450
<212> TYPE: PRT
<213> ORGANISM: Artificial Sequence
<220> FEATURE:
<223> OTHER INFORMATION: 10D1F.FcA VH-CH1-CH2-CH3 (N297Q)

<400> SEQUENCE: 226

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln His Pro Gly Lys Gly Leu Glu Trp
        35                  40                  45

Ile Gly Ser Ile Arg Tyr Ser Gly Gly Thr Asp Tyr Asn Pro Ser Leu
    50                  55                  60

Lys Ser Leu Val Thr Ile Ser Ala Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Met Thr Thr Ala Pro Trp Tyr Pro Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 227
<211> LENGTH: 450
<212> TYPE: PRT
<213> ORGANISM: Artificial Sequence
<220> FEATURE:
<223> OTHER INFORMATION: 10D1 VH-CH1-CH2-CH3 (GASDALIE; LCKC)

<400> SEQUENCE: 227

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Ser Ile His Tyr Ser Gly Gly Thr Asn Tyr Asn Pro Ser Leu
    50                  55                  60
```

```
Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Phe Cys
             85                  90                  95

Ala Arg Met Thr Thr Ala Pro Arg Tyr Pro Phe Asp Tyr Trp Gly Gln
            100                 105                 110

Gly Thr Thr Leu Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Ala Gly
225                 230                 235                 240

Pro Asp Val Phe Cys Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Leu Pro Glu Glu
                325                 330                 335

Cys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 228
<211> LENGTH: 450
<212> TYPE: PRT
```

<213> ORGANISM: Artificial Sequence
<220> FEATURE:
<223> OTHER INFORMATION: 10D1 VH-CH1-CH2-CH3 (GASD)

<400> SEQUENCE: 228

| | | | | | | | | | | | | | | |
|---|---|---|---|---|---|---|---|---|---|---|---|---|---|---|
| Asp | Val | Gln | Leu | Gln | Glu | Ser | Gly | Pro | Asp | Leu | Val | Lys | Pro | Ser | Gln |
| 1 | | | | 5 | | | | | 10 | | | | | 15 | |
| Ser | Leu | Ser | Leu | Thr | Cys | Thr | Val | Thr | Gly | Tyr | Ser | Ile | Thr | Ser | Gly |
| | | | 20 | | | | | 25 | | | | | 30 | | |
| Tyr | Ser | Trp | His | Trp | Ile | Arg | Gln | Phe | Pro | Gly | Asn | Lys | Leu | Glu | Trp |
| | | 35 | | | | | 40 | | | | | 45 | | | |
| Met | Gly | Ser | Ile | His | Tyr | Ser | Gly | Gly | Thr | Asn | Tyr | Asn | Pro | Ser | Leu |
| 50 | | | | | 55 | | | | | 60 | | | | | |
| Lys | Ser | Arg | Ile | Ser | Ile | Thr | Arg | Asp | Thr | Ser | Lys | Asn | Gln | Phe | Phe |
| 65 | | | | 70 | | | | | 75 | | | | | 80 | |
| Leu | Gln | Leu | Asn | Ser | Val | Thr | Thr | Glu | Asp | Thr | Ala | Thr | Tyr | Phe | Cys |
| | | | | 85 | | | | | 90 | | | | | 95 | |
| Ala | Arg | Met | Thr | Thr | Ala | Pro | Arg | Tyr | Pro | Phe | Asp | Tyr | Trp | Gly | Gln |
| | | | 100 | | | | | 105 | | | | | 110 | | |
| Gly | Thr | Thr | Leu | Thr | Val | Ser | Ser | Ala | Ser | Thr | Lys | Gly | Pro | Ser | Val |
| | | 115 | | | | | 120 | | | | | 125 | | | |
| Phe | Pro | Leu | Ala | Pro | Ser | Ser | Lys | Ser | Thr | Ser | Gly | Gly | Thr | Ala | Ala |
| 130 | | | | | 135 | | | | | 140 | | | | | |
| Leu | Gly | Cys | Leu | Val | Lys | Asp | Tyr | Phe | Pro | Glu | Pro | Val | Thr | Val | Ser |
| 145 | | | | 150 | | | | | 155 | | | | | 160 | |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | 195 | | | | | 200 | | | | | 205 | | | |
| Pro | Ser | Asn | Thr | Lys | Val | Asp | Lys | Lys | Val | Glu | Pro | Lys | Ser | Cys | Asp |
| 210 | | | | | 215 | | | | | 220 | | | | | |
| Lys | Thr | His | Thr | Cys | Pro | Pro | Cys | Pro | Ala | Pro | Glu | Leu | Leu | Ala | Gly |
| 225 | | | | 230 | | | | | 235 | | | | | 240 | |
| Pro | Asp | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | 275 | | | | | 280 | | | | | 285 | | | |
| Asn | Ala | Lys | Thr | Lys | Pro | Arg | Glu | Glu | Gln | Tyr | Asn | Ser | Thr | Tyr | Arg |
| 290 | | | | | 295 | | | | | 300 | | | | | |
| Val | Val | Ser | Val | Leu | Thr | Val | Leu | His | Gln | Asp | Trp | Leu | Asn | Gly | Lys |
| 305 | | | | 310 | | | | | 315 | | | | | 320 | |
| Glu | Tyr | Lys | Cys | Lys | Val | Ser | Asn | Lys | Ala | Leu | Pro | Ala | Pro | Ile | Glu |
| | | | 325 | | | | | 330 | | | | | 335 | | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Arg | Asp | Glu | Leu | Thr | Lys | Asn | Gln | Val | Ser | Leu |
| | | | 355 | | | | | 360 | | | | | 365 | | |
| Thr | Cys | Leu | Val | Lys | Gly | Phe | Tyr | Pro | Ser | Asp | Ile | Ala | Val | Glu | Trp |
| | | | 370 | | | | | 375 | | | | | 380 | | |

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 229
<211> LENGTH: 18
<212> TYPE: PRT
<213> ORGANISM: Artificial Sequence
<220> FEATURE:
<223> OTHER INFORMATION: HER3 binding site for 10D1-derived clones

<400> SEQUENCE: 229

Cys Phe Gly Pro Asn Pro Asn Gln Cys Cys His Asp Glu Cys Ala Gly
1               5                   10                  15

Gly Cys

<210> SEQ ID NO 230
<211> LENGTH: 5
<212> TYPE: PRT
<213> ORGANISM: Artificial Sequence
<220> FEATURE:
<223> OTHER INFORMATION: 10D1 binding site motif 1

<400> SEQUENCE: 230

Pro Asn Pro Asn Gln
1               5

<210> SEQ ID NO 231
<211> LENGTH: 5
<212> TYPE: PRT
<213> ORGANISM: Artificial Sequence
<220> FEATURE:
<223> OTHER INFORMATION: 10D1 binding site motif 2

<400> SEQUENCE: 231

Asp Glu Cys Ala Gly
1               5
```

HER3 ANTIGEN-BINDING MOLECULES

RELATED APPLICATIONS

This application is a continuation of U.S. patent application Ser. No. 16/596,723, filed Oct. 8, 2019, which is a continuation of International Patent Application No. PCT/EP2019/058035, filed Mar. 29, 2019, the contents and elements of each of which are herein incorporated by reference for all purpose.

FIELD OF THE INVENTION

The present invention relates to the fields of molecular biology, more specifically antibody technology. The present invention also relates to methods of medical treatment and prophylaxis.

BACKGROUND TO THE INVENTION

Increased HER3 expression is linked to poor prognosis in multiple solid tumors, including breast, gastric, head & neck, pancreatic, ovarian, and lung cancers. HER3-mediated signalling has adverse consequences for tumour progression; HER3 upregulation is associated with resistance to anti-HER2 and anti-EGFR therapy, and solid tumors refractory to anti-PD-1 therapy have been shown to have higher HER3 expression compared to responders to anti-PD-1 therapy.

HER3-binding antibodies are described e.g. in Zhang et al., Acta Biochimica et Biophysica Sinica (2016) 48(1): 39-48. The anti-HER3 antibody LJM-716 binds to an epitope on subdomains II and IV of the HER3 extracellular domain, locking HER3 in the inactive conformation (Garner et al., Cancer Res (2013) 73: 6024-6035). MM-121 (also known as seribantumab) has been shown to inhibit HER3-mediated signalling by blocking binding of heregulin (HRG) to HER3 (Schoeberl et al., Sci. Signal. (2009) 2(77): ra31). Patritumab (also known as U-1287 and AMG-888) also blocks binding of heregulins to HER3 (see e.g. Shimizu et al. Cancer Chemother Pharmacol. (2017) 79(3):489-495. RG7116 (also known as lumretuzumab and RO-5479599) recognises an epitope in subdomain I of the HER3 extracellular domain (see e.g. Mirschberger et al. Cancer Research (2013) 73(16) 5183-5194). KTN3379 binds to HER3 through interaction with amino acid residues in subdomain III (corresponding to the following positions of SEQ ID NO:1: Gly476, Pro477, Arg481, Gly452, Arg475, Ser450, Gly420, Ala451, Gly419, Arg421, Thr394, Leu423, Arg426, Gly427, Lys356, Leu358, Leu358, Lys356, Ala330, Lys329 and Gly337), and Met310, Glu311 and Pro328 of subdomain II (see Lee et al., Proc Natl Acad Sci USA. 2015 Oct. 27; 112(43):13225). AV-203 (also known as CAN-017) has been shown to block binding of NRG1 to HER3 and to promote HER3 degradation (see Meetze et al., Eur J Cancer 2012; 48:126). REGN1400 also inhibits binding of ligand to HER3 (see Zhang et al., Mol Cancer Ther (2014) 13:1345-1355). RG7597 (duligotuzumab) is a dual action Fab (DAF) capable of binding to both HER3 and EGFR, and binds to subdomain III of HER3 (see Schaefer et al., Cancer Cell (2011) 20(4):472-486). MM-111 and MM-141 are bispecific antibodies having HER3-binding arms which inhibit HRG ligand binding to HER3 (see McDonagh et al. Mol Cancer Ther (2012) 11:582-593 and Fitzgerald et al., Mol Cancer Ther (2014) 13:410-425).

SUMMARY OF THE INVENTION

In a first aspect the present invention provides an antigen-binding molecule, optionally isolated, which is capable of binding to HER3 in extracellular region subdomain II.

In some embodiments the antigen-binding molecule inhibits interaction between HER3 and an interaction partner for HER3.

In some embodiments the antigen-binding molecule is capable of binding to a polypeptide comprising or consisting of the amino acid sequence of SEQ ID NO:16.

In some embodiments the antigen-binding molecule is capable of binding to a polypeptide comprising the amino acid sequence of SEQ ID NO:229.

In some embodiments the antigen-binding molecule is capable of binding to a polypeptide comprising the amino acid sequences of SEQ ID NO:230 and 231.

In some embodiments the antigen-binding molecule is capable of binding to a polypeptide comprising the amino acid sequence of SEQ ID NO:230.

In some embodiments the antigen-binding molecule is capable of binding to a polypeptide comprising the amino acid sequence of SEQ ID NO:231.

In some embodiments the antigen-binding molecule is capable of binding to a polypeptide comprising the amino acid sequence of SEQ ID NO:23.

In some embodiments the antigen-binding molecule is capable of binding to a polypeptide comprising the amino acid sequence of SEQ ID NO:21.

In some embodiments the antigen-binding molecule comprises:
(i) a heavy chain variable (VH) region incorporating the following CDRs:
    HC-CDR1 having the amino acid sequence of SEQ ID NO:43
    HC-CDR2 having the amino acid sequence of SEQ ID NO:46
    HC-CDR3 having the amino acid sequence of SEQ ID NO:51; and
(ii) a light chain variable (VL) region incorporating the following CDRs:
    LC-CDR1 having the amino acid sequence of SEQ ID NO:91
    LC-CDR2 having the amino acid sequence of SEQ ID NO:94
    LC-CDR3 having the amino acid sequence of SEQ ID NO:99.

In some embodiments the antigen-binding molecule comprises:
(i) a heavy chain variable (VH) region incorporating the following CDRs:
    HC-CDR1 having the amino acid sequence of SEQ ID NO:41
    HC-CDR2 having the amino acid sequence of SEQ ID NO:44
    HC-CDR3 having the amino acid sequence of SEQ ID NO:47; and
(ii) a light chain variable (VL) region incorporating the following CDRs:
    LC-CDR1 having the amino acid sequence of SEQ ID NO:88
    LC-CDR2 having the amino acid sequence of SEQ ID NO:92
    LC-CDR3 having the amino acid sequence of SEQ ID NO:95.

In some embodiments the antigen-binding molecule comprises:
- (i) a heavy chain variable (VH) region incorporating the following CDRs:
  - HC-CDR1 having the amino acid sequence of SEQ ID NO:41
  - HC-CDR2 having the amino acid sequence of SEQ ID NO:44
  - HC-CDR3 having the amino acid sequence of SEQ ID NO:47; and
- (ii) a light chain variable (VL) region incorporating the following CDRs:
  - LC-CDR1 having the amino acid sequence of SEQ ID NO:89
  - LC-CDR2 having the amino acid sequence of SEQ ID NO:92
  - LC-CDR3 having the amino acid sequence of SEQ ID NO:95.

In some embodiments the antigen-binding molecule comprises:
- (i) a heavy chain variable (VH) region incorporating the following CDRs:
  - HC-CDR1 having the amino acid sequence of SEQ ID NO:41
  - HC-CDR2 having the amino acid sequence of SEQ ID NO:44
  - HC-CDR3 having the amino acid sequence of SEQ ID NO:47; and
- (ii) a light chain variable (VL) region incorporating the following CDRs:
  - LC-CDR1 having the amino acid sequence of SEQ ID NO:90
  - LC-CDR2 having the amino acid sequence of SEQ ID NO:92
  - LC-CDR3 having the amino acid sequence of SEQ ID NO:96.

In some embodiments the antigen-binding molecule comprises:
- (i) a heavy chain variable (VH) region incorporating the following CDRs:
  - HC-CDR1 having the amino acid sequence of SEQ ID NO:41
  - HC-CDR2 having the amino acid sequence of SEQ ID NO:44
  - HC-CDR3 having the amino acid sequence of SEQ ID NO:47; and
- (ii) a light chain variable (VL) region incorporating the following CDRs:
  - LC-CDR1 having the amino acid sequence of SEQ ID NO:88
  - LC-CDR2 having the amino acid sequence of SEQ ID NO:92
  - LC-CDR3 having the amino acid sequence of SEQ ID NO:98.

In some embodiments the antigen-binding molecule comprises:
- (i) a heavy chain variable (VH) region incorporating the following CDRs:
  - HC-CDR1 having the amino acid sequence of SEQ ID NO:41
  - HC-CDR2 having the amino acid sequence of SEQ ID NO:45
  - HC-CDR3 having the amino acid sequence of SEQ ID NO:47; and
- (ii) a light chain variable (VL) region incorporating the following CDRs:
  - LC-CDR1 having the amino acid sequence of SEQ ID NO:88
  - LC-CDR2 having the amino acid sequence of SEQ ID NO:93
  - LC-CDR3 having the amino acid sequence of SEQ ID NO:95.

In some embodiments the antigen-binding molecule comprises:
- (i) a heavy chain variable (VH) region incorporating the following CDRs;
  - HC-CDR1 having the amino acid sequence of SEQ ID NO:41
  - HC-CDR2 having the amino acid sequence of SEQ ID NO:45
  - HC-CDR3 having the amino acid sequence of SEQ ID NO:49; and
- (ii) a light chain variable (VL) region incorporating the following CDRs:
  - LC-CDR1 having the amino acid sequence of SEQ ID NO:88
  - LC-CDR2 having the amino acid sequence of SEQ ID NO:93
  - LC-CDR3 having the amino acid sequence of SEQ ID NO:95.

In some embodiments the antigen-binding molecule comprises:
- (i) a heavy chain variable (VH) region incorporating the following CDRs:
  - HC-CDR1 having the amino acid sequence of SEQ ID NO:41
  - HC-CDR2 having the amino acid sequence of SEQ ID NO:45
  - HC-CDR3 having the amino acid sequence of SEQ ID NO:50; and
- (ii) a light chain variable (VL) region incorporating the following CDRs:
  - LC-CDR1 having the amino acid sequence of SEQ ID NO:88
  - LC-CDR2 having the amino acid sequence of SEQ ID NO:93
  - LC-CDR3 having the amino acid sequence of SEQ ID NO:95.

In some embodiments the antigen-binding molecule comprises:
- (i) a heavy chain variable (VH) region incorporating the following CDRs:
  - HC-CDR1 having the amino acid sequence of SEQ ID NO:41
  - HC-CDR2 having the amino acid sequence of SEQ ID NO:45
  - HC-CDR3 having the amino acid sequence of SEQ ID NO:48; and
- (ii) a light chain variable (VL) region incorporating the following CDRs:
  - LC-CDR1 having the amino acid sequence of SEQ ID NO:88
  - LC-CDR2 having the amino acid sequence of SEQ ID NO:92
  - LC-CDR3 having the amino acid sequence of SEQ ID NO:95.

In some embodiments the antigen-binding molecule comprises:
- (i) a heavy chain variable (VH) region incorporating the following CDRs:
  - HC-CDR1 having the amino acid sequence of SEQ ID NO:41

HC-CDR2 having the amino acid sequence of SEQ ID NO:45
HC-CDR3 having the amino acid sequence of SEQ ID NO:48; and
(ii) a light chain variable (VL) region incorporating the following CDRs:
LC-CDR1 having the amino acid sequence of SEQ ID NO:88
LC-CDR2 having the amino acid sequence of SEQ ID NO:92
LC-CDR3 having the amino acid sequence of SEQ ID NO:97.

In some embodiments the antigen-binding molecule comprises;
(i) a heavy chain variable (VH) region incorporating the following CDRs:
HC-CDR1 having the amino acid sequence of SEQ ID NO:42
HC-CDR2 having the amino acid sequence of SEQ ID NO:45
HC-CDR3 having the amino acid sequence of SEQ ID NO:48; and
(ii) a light chain variable (VL) region incorporating the following CDRs:
LC-CDR1 having the amino acid sequence of SEQ ID NO:88
LC-CDR2 having the amino acid sequence of SEQ ID NO:92
LC-CDR3 having the amino acid sequence of SEQ ID NO:95.

In some embodiments the antigen-binding molecule comprises:
(i) a heavy chain variable (VH) region incorporating the following CDRs:
HC-CDR1 having the amino acid sequence of SEQ ID NO:158
HC-CDR2 having the amino acid sequence of SEQ ID NO:159
HC-CDR3 having the amino acid sequence of SEQ ID NO:160; and
(ii) a light chain variable (VL) region incorporating the following CDRs:
LC-CDR1 having the amino acid sequence of SEQ ID NO:165
LC-CDR2 having the amino acid sequence of SEQ ID NO:166
LC-CDR3 having the amino acid sequence of SEQ ID NO:167.

In some embodiments the antigen-binding molecule is capable of binding to a polypeptide comprising the amino acid sequence of SEQ ID NO:22.

In some embodiments the antigen-binding molecule comprises:
(i) a heavy chain variable (VH) region incorporating the following CDRs:
HC-CDR1 having the amino acid sequence of SEQ ID NO:128
HC-CDR2 having the amino acid sequence of SEQ ID NO:129
HC-CDR3 having the amino acid sequence of SEQ ID NO:130; and
(ii) a light chain variable (VL) region incorporating the following CDRs:
LC-CDR1 having the amino acid sequence of SEQ ID NO:136
LC-CDR2 having the amino acid sequence of SEQ ID NO:137
LC-CDR3 having the amino acid sequence of SEQ ID NO:138.

In some embodiments the antigen-binding molecule comprises:
(i) a heavy chain variable (VH) region incorporating the following CDRs:
HC-CDR1 having the amino acid sequence of SEQ ID NO:144
HC-CDR2 having the amino acid sequence of SEQ ID NO:145
HC-CDR3 having the amino acid sequence of SEQ ID NO:146; and
(ii) a light chain variable (VL) region incorporating the following CDRs:
LC-CDR1 having the amino acid sequence of SEQ ID NO:151
LC-CDR2 having the amino acid sequence of SEQ ID NO:152
LC-CDR3 having the amino acid sequence of SEQ ID NO:153.

In particular embodiments the antigen-binding molecule comprises:
(i) a heavy chain variable (VH) region incorporating the following CDRs:
HC-CDR1 having the amino acid sequence of SEQ ID NO:41
HC-CDR2 having the amino acid sequence of SEQ ID NO:45
HC-CDR3 having the amino acid sequence of SEQ ID NO:48; and
(ii) a light chain variable (VL) region incorporating the following CDRs:
LC-CDR1 having the amino acid sequence of SEQ ID NO:88
LC-CDR2 having the amino acid sequence of SEQ ID NO:92
LC-CDR3 having the amino acid sequence of SEQ ID NO:95;
or
(i) a heavy chain variable (VH) region incorporating the following CDRs:
HC-CDR1 having the amino acid sequence of SEQ ID NO:41
HC-CDR2 having the amino acid sequence of SEQ ID NO:45
HC-CDR3 having the amino acid sequence of SEQ ID NO:48; and
(ii) a light chain variable (VL) region incorporating the following CDRs:
LC-CDR1 having the amino acid sequence of SEQ ID NO:88
LC-CDR2 having the amino acid sequence of SEQ ID NO:92
LC-CDR3 having the amino acid sequence of SEQ ID NO:97;
or
(i) a heavy chain variable (VH) region incorporating the following CDRs:
HC-CDR1 having the amino acid sequence of SEQ ID NO:42
HC-CDR2 having the amino acid sequence of SEQ ID NO:45
HC-CDR3 having the amino acid sequence of SEQ ID NO:48; and (ii) a light chain variable (VL) region incorporating the following CDRs:
LC-CDR1 having the amino acid sequence of SEQ ID NO:88
LC-CDR2 having the amino acid sequence of SEQ ID NO:92
LC-CDR3 having the amino acid sequence of SEQ ID NO:95.

In some embodiments the antigen-binding molecule comprises:
(i) a VH region comprising an amino acid sequence having at least 70% sequence identity to the amino acid sequence of SEQ ID NO:24; and
a VL region comprising an amino acid sequence having at least 70% sequence identity to the amino acid sequence of SEQ ID NO:74;
or
(ii) a VH region comprising an amino acid sequence having at least 70% sequence identity to the amino acid sequence of SEQ ID NO:25; and
a VL region comprising an amino acid sequence having at least 70% sequence identity to the amino acid sequence of SEQ ID NO:75;
or
(iii) a VH region comprising an amino acid sequence having at least 70% sequence identity to the amino acid sequence of SEQ ID NO:26; and
a VL region comprising an amino acid sequence having at least 70% sequence identity to the amino acid sequence of SEQ ID NO:78;
or
(iv) a VH region comprising an amino acid sequence having at least 70% sequence identity to the amino acid sequence of SEQ ID NO:27; and
a VL region comprising an amino acid sequence having at least 70% sequence identity to the amino acid sequence of SEQ ID NO:77;
or
(v) a VH region comprising an amino acid sequence having at least 70% sequence identity to the amino acid sequence of SEQ ID NO:28; and
a VL region comprising an amino acid sequence having at least 70% sequence identity to the amino acid sequence of SEQ ID NO:78;
or
(vi) a VH region comprising an amino acid sequence having at least 70% sequence identity to the amino acid sequence of SEQ ID NO:29; and
a VL region comprising an amino acid sequence having at least 70% sequence identity to the amino acid sequence of SEQ ID NO:78;
or
(vii) a VH region comprising an amino acid sequence having at least 70% sequence identity to the amino acid sequence of SEQ ID NO:30; and
a VL region comprising an amino acid sequence having at least 70% sequence identity to the amino acid sequence of SEQ ID NO:78;
or
(viii) a VH region comprising an amino acid sequence having at least 70% sequence identity to the amino acid sequence of SEQ ID NO:31; and
a VL region comprising an amino acid sequence having at least 70% sequence identity to the amino acid sequence of SEQ ID NO:79;
or
(ix) a VH region comprising an amino acid sequence having at least 70% sequence identity to the amino acid sequence of SEQ ID NO:32; and
a VL region comprising an amino acid sequence having at least 70% sequence identity to the amino acid sequence of SEQ ID NO:79;
or
(x) a VH region comprising an amino acid sequence having at least 70% sequence identity to the amino acid sequence of SEQ ID NO:33; and
a VL region comprising an amino acid sequence having at least 70% sequence identity to the amino acid sequence of SEQ ID NO:80;
or
(xi) a VH region comprising an amino acid sequence having at least 70% sequence identity to the amino acid sequence of SEQ ID NO:34; and
a VL region comprising an amino acid sequence having at least 70% sequence identity to the amino acid sequence of SEQ ID NO:81;
or
(xii) a VH region comprising an amino acid sequence having at least 70% sequence identity to the amino acid sequence of SEQ ID NO:35; and
a VL region comprising an amino acid sequence having at least 70% sequence identity to the amino acid sequence of SEQ ID NO:82;
or
(xiii) a VH region comprising an amino acid sequence having at least 70% sequence identity to the amino acid sequence of SEQ ID NO:36; and
a VL region comprising an amino acid sequence having at least 70% sequence identity to the amino acid sequence of SEQ ID NO:83;
or
(xiv) a VH region comprising an amino acid sequence having at least 70% sequence identity to the amino acid sequence of SEQ ID NO:37; and
a VL region comprising an amino acid sequence having at least 70% sequence identity to the amino acid sequence of SEQ ID NO:84;
or
(xv) a VH region comprising an amino acid sequence having at least 70% sequence identity to the amino acid sequence of SEQ ID NO:38; and
a VL region comprising an amino acid sequence having at least 70% sequence identity to the amino acid sequence of SEQ ID NO:85;
or
(xvi) a VH region comprising an amino acid sequence having at least 70% sequence identity to the amino acid sequence of SEQ ID NO:39; and
a VL region comprising an amino acid sequence having at least 70% sequence identity to the amino acid sequence of SEQ ID NO:86;
or
(xvii) a VH region comprising an amino acid sequence having at least 70% sequence identity to the amino acid sequence of SEQ ID NO:40; and
a VL region comprising an amino acid sequence having at least 70% sequence identity to the amino acid sequence of SEQ ID NO:87;
or
(xviii) a VH region comprising an amino acid sequence having at least 70% sequence identity to the amino acid sequence of SEQ ID NO:127; and a VL region comprising an amino acid sequence having at least 70% sequence identity to the amino acid sequence of SEQ ID NO:135:

or (xix) a VH region comprising an amino acid sequence having at least 70% sequence identity to the amino acid sequence of SEQ ID NO:143; and
a VL region comprising an amino acid sequence having at least 70% sequence identity to the amino acid sequence of SEQ ID NO:150;

or (xx) a VH region comprising an amino acid sequence having at least 70% sequence identity to the amino acid sequence of SEQ ID NO:157; and
a VL region comprising an amino acid sequence having at least 70% sequence identity to the amino acid sequence of SEQ ID NO:164.

In particular embodiments the antigen-binding molecule comprises:

(i) a VH region comprising an amino acid sequence having at least 70% sequence identity to the amino acid sequence of SEQ ID NO:36; and
a VL region comprising an amino acid sequence having at least 70% sequence identity to the amino acid sequence of SEQ ID NO:83;

or (ii) a VH region comprising an amino acid sequence having at least 70% sequence identity to the amino acid sequence of SEQ ID NO:37; and
a VL region comprising an amino acid sequence having at least 70% sequence identity to the amino acid sequence of SEQ ID NO:84;

or (iii) a VH region comprising an amino acid sequence having at least 70% sequence identity to the amino acid sequence of SEQ ID NO:38; and
a VL region comprising an amino acid sequence having at least 70% sequence identity to the amino acid sequence of SEQ ID NO:85.

In some embodiments the antigen-binding molecule is capable of binding to human HER3 and one or more of mouse HER3, rat HER3 and cynomolgous macaque HER3.

Also provided is an antigen-binding molecule, optionally isolated, comprising (i) an antigen-binding molecule according to the invention, and (ii) an antigen-binding molecule capable of binding to an antigen other than HER3.

In some embodiments the antigen-binding molecule is capable of binding to cells expressing HER3 at the cell surface.

In some embodiments the antigen-binding molecule is capable of inhibiting HER3-mediated signalling.

In some embodiments the antigen-binding molecule comprises an Fc region, the Fc region comprising a polypeptide having: (i) C at the position corresponding to position 242, and C at the position corresponding to position 334, and (ii) one or more of: A at the position corresponding to position 236, D at the position corresponding to position 239, E at the position corresponding to position 332, L at the position corresponding to position 330, K at the position corresponding to position 345, and G at the position corresponding to position 430. In some embodiments the Fc region comprises a polypeptide having C at the position corresponding to position 242, C at the position corresponding to position 334, A at the position corresponding to position 236, D at the position corresponding to position 239, E at the position corresponding to position 332, and L at the position corresponding to position 330.

Also provided is a chimeric antigen receptor (CAR) comprising an antigen-binding molecule according to the present invention.

Also provided is a nucleic acid, or a plurality of nucleic acids, optionally isolated, encoding an antigen-binding molecule or a CAR according to the present invention.

Also provided is an expression vector, or a plurality of expression vectors, comprising a nucleic acid or a plurality of nucleic acids according to the present invention.

Also provided is a cell comprising an antigen-binding molecule, a CAR, a nucleic acid or a plurality of nucleic acids, or an expression vector or a plurality of expression vectors according to the present invention.

Also provided is a method comprising culturing a cell comprising a nucleic acid or a plurality of nucleic acids or an expression vector or a plurality of expression vectors according to the present invention, under conditions suitable for expression of the antigen-binding molecule or CAR from the nucleic acid(s) or expression vector(s).

Also provided is a composition comprising an antigen-binding molecule, a CAR, a nucleic acid or a plurality of nucleic acids, an expression vector or a plurality of expression vectors, or a cell according to the present invention.

Also provided is an antigen-binding molecule, a CAR, a nucleic acid or a plurality of nucleic acids, an expression vector or a plurality of expression vectors, a cell, or a composition according to the present invention for use in a method of medical treatment or prophylaxis.

Also provided is an antigen-binding molecule, a CAR, a nucleic acid or a plurality of nucleic acids, an expression vector or a plurality of expression vectors, a cell, or a composition according to the present invention for use in a method of treatment or prevention of a cancer.

Also provided is the use of an antigen-binding molecule, a CAR, a nucleic acid or a plurality of nucleic acids, an expression vector or a plurality of expression vectors, a cell, or a composition according to the present invention in the manufacture of a medicament for use in a method of treatment or prevention of a cancer.

Also provided is a method of treating or preventing a cancer, comprising administering to a subject a therapeutically or prophylactically effective amount of an antigen-binding molecule, a CAR, a nucleic acid or a plurality of nucleic acids, an expression vector or a plurality of expression vectors, a cell, or a composition according to the present invention.

In some embodiments in accordance with various aspects of the present invention, the method additionally comprises administration of an inhibitor of signalling mediated by an EGFR family member, optionally wherein the inhibitor of signalling mediated by an EGFR family member is an inhibitor of signalling mediated by HER2 and/or EGFR.

In some embodiments the cancer is selected from: a cancer comprising cells expressing an EGFR family member, a cancer comprising cells expressing HER3, a solid tumor, breast cancer, breast carcinoma, ductal carcinoma, gastric cancer, gastric carcinoma, gastric adenocarcinoma, colorectal cancer, colorectal carcinoma, colorectal adenocarcinoma, head and neck cancer, squamous cell carcinoma of the head and neck (SCCHN), lung cancer, lung adenocarcinoma, squamous cell lung carcinoma, ovarian cancer, ovarian carcinoma, ovarian serous adenocarcinoma, kidney cancer, renal cell carcinoma, renal clear cell carcinoma, renal cell adenocarcinoma, renal papillary cell carcinoma, pancreatic cancer, pancreatic adenocarcinoma, pancreatic ductal adenocarcinoma, cervical cancer, cervical squamous cell carcinoma, skin cancer, melanoma, esophageal cancer, esophageal adenocarcinoma, liver cancer, hepatocellular carcinoma, cholangiocarcinoma, uterine cancer, uterine corpus endometrial carcinoma, thyroid cancer, thyroid carcinoma, pheochromocytoma, paraganglioma, bladder cancer, bladder urothelial carcinoma, prostate cancer, prostate adenocarcinoma, sarcoma and thymoma.

Also provided is a method of inhibiting HER3-mediated signalling, comprising contacting HER3-expressing cells with an antigen-binding molecule according to the present invention.

Also provided is a method of reducing the number or activity of HER3-expressing cells, the method comprising contacting HER3-expressing cells with an antigen-binding molecule according to the present invention.

Also provided is an in vitro complex, optionally isolated, comprising an antigen-binding molecule according to the present invention bound to HER3.

Also provided is a method comprising contacting a sample containing, or suspected to contain, HER3 with an antigen-binding molecule according to the present invention, and detecting the formation of a complex of the antigen-binding molecule with HER3.

Also provided is a method of selecting or stratifying a subject for treatment with a HER3-targeted agent, the method comprising contacting, in vitro, a sample from the subject with an antigen-binding molecule according to the present invention and detecting the formation of a complex of the antigen-binding molecule with HER3.

Also provided is the use of an antigen-binding molecule according to the present invention as an in vitro or in vivo diagnostic or prognostic agent.

Also provided is the use of an antigen-binding molecule according to the present invention in a method for detecting, localizing or imaging a cancer, optionally wherein the cancer is selected from: a cancer comprising cells expressing an EGFR family member, a cancer comprising cells expressing HER3, a sold tumor, breast cancer, breast carcinoma, ductal carcinoma, gastric cancer, gastric carcinoma, gastric adenocarcinoma, colorectal cancer, colorectal carcinoma, colorectal adenocarcinoma, head and neck cancer, squamous cell carcinoma of the head and neck (SCCHN), lung cancer, lung adenocarcinoma, squamous cell lung carcinoma, ovarian cancer, ovarian carcinoma, ovarian serous adenocarcinoma, kidney cancer, renal cell carcinoma, renal clear cell carcinoma, renal cell adenocarcinoma, renal papillary cell carcinoma, pancreatic cancer, pancreatic adenocarcinoma, pancreatic ductal adenocarcinoma, cervical cancer, cervical squamous cell carcinoma, skin cancer, melanoma, esophageal cancer, esophageal adenocarcinoma, liver cancer, hepatocellular carcinoma, cholangiocarcinoma, uterine cancer, uterine corpus endometrial carcinoma, thyroid cancer, thyroid carcinoma, pheochromocytoma, paraganglioma, bladder cancer, bladder urothelial carcinoma, prostate cancer, prostate adenocarcinoma, sarcoma and thymoma.

DESCRIPTION

The present invention relates to novel HER3-binding molecules having improved properties as compared to known anti-HER3 antibodies.

The inventors undertook the targeted generation of antigen-binding molecules which bind to particular regions of interest in the extracellular region of HER3. The HER3-binding molecules of the present invention are provided with combinations of desirable biophysical and/or functional properties as compared to antigen-binding molecules disclosed in the prior art.

In embodiments of the present invention the antigen binding molecules are capable of binding to the subdomain II of the extracellular region of HER3 (SEQ ID NO:16), and inhibit association of the bound HER3 molecule with interaction partners.

In particular, HER3-binding antigen-binding molecules described herein are demonstrated to bind to an epitope of HER3 providing for potent inhibition of association of HER3 with interaction partners, strong inhibition of downstream signalling and exceptional anti-cancer activity against a wide range of cancers.

HER3

HER3 (also known e.g. as ERBB3 LCCS2, MDA-BF-1) is the protein identified by UniProt P21860. Alternative splicing of mRNA encoded by the human ERBB3 gene yields five different isoforms: isoform 1 (UniProt; P21860-1, v1; SEQ ID NO:1); isoform 2 (UniProt: P21860-2, SEQ ID NO:2), which comprises a different sequence to SEQ ID NO:1 from position 141, and which lacks amino acid sequence corresponding to positions 183 to 1342 of SEQ ID NO:1; isoform 3 (UniProt: P21860-3; SEQ ID NO:3), which comprises the substitution C331F relative to SEQ ID NO:1, and which lacks the amino acid sequence corresponding to positions 332 to 1342 of SEQ ID NO:1; isoform 4 (UniProt: P21860-4; SEQ 10 NO:4), which lacks the amino acid sequence corresponding to positions 1 to 59 of SEQ ID NO:1; and isoform 5 (UniProt: P21360-5; SEQ ID NO:5), which lacks the amino acid sequence corresponding to positions 1 to 643 of SEQ ID NO:1.

The N-terminal 19 amino acids of SEQ ID NOs:1 to 3 constitute a signal peptide, and so the mature form of HER3 isoforms 1, 2 and 3 (i.e. after processing to remove the signal peptide) have the amino acid sequences shown in SEQ ID NOs:6, 7 and 8, respectively.

The structure and function of HER3 is described e.g. in Cho and Leahy Science (2002) 297 (5585):1330-1333, Singer et al., Journal of Biological Chemistry (2001) 276, 44266-44274, Roskoski et al., Pharmacol. Res. (2014) 79: 34-74, Bazley and Gullick Endocrine-Related Cancer (2005) S17-S27 and Mujoo et al., Oncotarget (2014) 5(21):10222-10236, each of which are hereby incorporated by reference in their entirety. HER3 is a single-pass transmembrane ErbB receptor tyrosine kinase having an N-terminal extracellular region (SEQ ID NO:9) comprising two leucine-rich subdomains (domains I and III, shown in SEQ ID NOs:15 and 17, respectively) and two cysteine-rich subdomains (domains II and IV, shown in SEQ ID NOs:16 and 18, respectively). Domain II comprises a β hairpin dimerisation loop (SEQ ID NO:19) which is involved in intermolecular interaction with other HER receptor molecules. The extracellular region is linked via a transmembrane region (SEQ ID NO:10) to a cytoplasmic region (SEQ ID NO:11). The cytoplasmic region comprises a juxtamembrane segment (SEQ ID NO:12), a protein kinase domain (SEQ ID NO:13), and a C-terminal segment (SEQ ID NO:14).

Signalling through HER3 involves receptor homodimerisation (i.e. with other HER3 receptors) or heterodimerisation (with other HER receptors, e.g. HER2) and consequent autophosphotylation by the protein kinase domain of tyrosines of the cytoplasmic region. The phosphotylated tyrosine residues recruit adaptor/effector proteins (e.g. Grb2 and phospholipase Cγ (PLCγ), containing src homology domain 2 (SH2) or phosphotyrosine binding (PTB) domains.

Signalling through HER3 can be activated in a ligand-dependent or ligand-independent manner. In the absence of ligand, HER3 receptor molecules are normally expressed at the cell surface as monomers with a conformation which prevents receptor dimerisation in which the dimerisation loop of subdomain II makes intramolecular contact with a pocket on subdomain IV. Binding of a HER3 ligand such as a neuregulin (NRG), e.g. NRG1 (also known as heregulin, HRG) or NRG2 to subdomains I and III of the extracellular region causes a conformational change which results in the exposure of the dimerisation loop of subdomain II, facilitating receptor dimerisation and signalling. Some cancer-associated mutations in HER3 may disrupt interaction of subdomains II and IV required for the formation of the inactive 'closed' conformation and thereby cause constitutive presentation of the dimerisation loop and activation of HER3-mediated signalling in the absence of ligand binding (see e.g. in Jaiswal et al., Cancer Cell (2013) 23(5): 603-617).

In this specification "HER3" refers to HER3 from any species and includes HER3 isoforms, fragments, variants (including mutants) or homologues from any species.

As used herein, a "fragment", "variant" or "homologue" of a protein may optionally be characterised as having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of the reference protein (e.g. a reference isoform). In some embodiments fragments, variants, isoforms and homologues of a reference protein may be characterised by ability to perform a function performed by the reference protein.

A "fragment" generally refers to a fraction of the reference protein. A "variant" generally refers to a protein having an amino acid sequence comprising one or more amino acid substitutions, insertions, deletions or other modifications relative to the amino acid sequence of the reference protein, but retaining a considerable degree of sequence identity (e.g. at least 60%) to the amino acid sequence of the reference protein. An "isoform" generally refers to a variant of the reference protein expressed by the same species as the species of the reference protein (e.g. HER3 isoforms 1 to 5 are all isoforms of one another). A "homologue" generally refers to a variant of the reference protein produced by a different species as compared to the species of the reference protein. For example, human HER3 isoform 1 (P21860-1, v1; SEQ ID NO:1) and Rhesus macaque HER3 (UniProt; F7HEH3-1, v2; SEQ ID NO:20) are homologues of one another. Homologues include orthologues.

A "fragment" of a reference protein may be of any length (by number of amino acids), although may optionally be at least 20% of the length of the reference protein (that is, the protein from which the fragment is derived) and may have a maximum length of one of 50%, 75%, 80%, 85%, 90%, 91%, 92%, 93%, 94%, 95%, 96%, 97%, 98%, or 99% of the length of the reference protein.

A fragment of HER3 may have a minimum length of one of 10, 20, 30, 40, 50, 100, 150, 200, 250, 300, 350, 400, 450, 500, 600, 700, 800, 900, 1000, 1100, 1200 amino acids, and may have a maximum length of one of 20, 30, 40, 50, 100, 150, 200, 250, 300, 350, 400, 450, 500, 600, 700, 800, 900, 1000, 1100, 1200, or 1300 amino acids.

In some embodiments, the HER3 is HER3 from a mammal (e.g. a primate (rhesus, cynomolgus, non-human primate or human) and/or a rodent (e.g. rat or murine) HER3). Isoforms, fragments, variants or homologues of HER3 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature HER3 isoform from a given species, e.g. human.

Isoforms, fragments, variants or homologues may optionally be functional isoforms, fragments, variants or homologues, e.g. having a functional property/activity of the reference HER3 (e.g. human HER3 isoform 1), as determined by analysis by a suitable assay for the functional property/activity. For example, an isoform, fragment, variant or homologue of HER3 may display association with one or more of: HER2, NRG1 (type I, II, III, IV, V or VI) or NRG2 (α or β).

In some embodiments, the HER3 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to one of SEQ ID NOs:1 to 8.

In some embodiments, a fragment of HER3 comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to one of SEQ ID NOs:9 to 19, e.g. one of 9, 16 or 19.

Regions of Particular Interest on the Target Molecule

The antigen-binding molecules of the present invention were specifically designed to target regions of HER3 of particular interest. In a two-step approach, HER3 regions to be targeted were selected following analysis for predicted antigenicity, function and safety. Antibodies specific for the target regions of HER3 were then prepared using peptides corresponding to the target regions as immunogens to raise specific monoclonal antibodies, and subsequent screening identified antibodies capable of binding to HER3 in the native state. This approach provides exquisite control over the antibody epitope.

The antigen-binding molecules of the present invention may be defined by reference to the region of HER3 to which they bind. The antigen-binding molecules of the present invention may bind to a particular region of interest of HER3. In some embodiments the antigen-binding molecule may bind to a linear epitope of HER3, consisting of a contiguous sequence of amino acids (i.e. an amino acid primary sequence). In some embodiments, the antigen-binding molecule may bind to a conformational epitope of HER3, consisting of a discontinuous sequence of amino acids of the amino acid sequence.

In some embodiments, the antigen-binding molecule of the present invention binds to HER3. In some embodiments, the antigen-binding molecule binds to the extracellular region of HER3 (e.g. the region shown in SEQ ID NO:9). In some embodiments, the antigen-binding molecule binds to subdomain II of the extracellular region of HER3 (e.g. the region shown in SEQ ID NO:16).

In some embodiments, the antigen-binding molecule binds to the region of HER3 shown in SEQ ID NO:229. In some embodiments the antigen-binding molecule contacts one or more amino acid residues of the region of HER3 shown in SEQ ID NO:229. In some embodiments, the antigen-binding molecule binds to the regions of HER3 shown in SEQ ID NOs:230 and 231. In some embodiments the antigen-binding molecule contacts one or more amino acid residues of the regions of HER3 shown in SEQ ID NOs:230 and 231. In some embodiments, the antigen-binding molecule binds to the region of HER3 shown in SEQ ID NO:230. In some embodiments the antigen-binding molecule contacts one or more amino acid residues of the region of HER3 shown in SEQ ID NO:230. In some embodiments, the antigen-binding molecule binds to the region of HER3 shown in SEQ ID NO:231. In some embodiments the antigen-binding molecule contacts one or more amino acid residues of the region of HER3 shown in SEQ ID NO:231.

In some embodiments, the antigen-binding molecule binds to the region of HER3 shown in SEQ ID NO:23. In some embodiments the antigen-binding molecule contacts one or more amino acid residues of the region of HER3 shown in SEQ ID NO:23. In some embodiments, the antigen-binding molecule binds to the region of HER3 shown in SEQ ID NO:21. In some embodiments the antigen-binding molecule contacts one or more amino acid residues of the region of HER3 shown in SEQ ID NO:21. In some embodiments the antigen-binding molecule binds to the region of HER3 shown in SEQ ID NO:19. In some embodiments the antigen-binding molecule contacts one or more amino acid residues of the region of HER3 shown in SEQ ID NO:19. In some embodiments, the antigen-binding molecule binds to the region of HER3 shown in SEQ ID NO:22. In some embodiments the antigen-binding molecule contacts one or more amino acid residues of the region of HER3 shown in SEQ ID NO:22.

In some embodiments, the antigen-binding molecule does not bind to the region of HER3 corresponding to positions 260 to 279 of SEQ ID NO:1. In some embodiments the antigen-binding molecule does not contact an amino acid residue of the region of HER3 corresponding to positions 260 to 279 of SEQ ID NO:1. In some embodiments, the antigen-binding molecule does not bind to the region of HER3 shown in SEQ ID NO:23. In some embodiments the antigen-binding molecule does not contact an amino acid residue of the region of HER3 shown in SEQ ID NO:23.

The region of a peptide/polypeptide to which an antibody binds can be determined by the skilled person using various methods well known in the art, including X-ray co-crystallography analysis of antibody-antigen complexes, peptide scanning, mutagenesis mapping, hydrogen-deuterium exchange analysis by mass spectrometry, phage display, competition ELISA and proteolysis-based 'protection' methods. Such methods are described, for example, in Gershoni et al., BioDrugs, 2007, 21(3):145-156, which is hereby incorporated by reference in its entirety.

In some embodiments the antigen-binding molecule is capable of binding the same region of HER3, or an overlapping region of HER3, to the region of HER3 which is bound by an antibody comprising the VH and VL sequences of one of antibody clones 10D1, 10D1_c75, 10D1_c76, 10D1_c77, 10D1_c78v1, 10D1_c78v2, 10D1_11B, 10D1_c85v1, 10D1_c85v2, 10D1_c85o1, 10D1_c85o2, 10D1_c87, 10D1_c89, 10D1_c90, 10D1_c91, 10D1_c92, 10D1_c93, 10A6, 4-35-B2 or 4-35-84 described herein. In some embodiments the antigen-binding molecule is capable of binding the same region of HER3, or an overlapping region of HER3, to the region of HER3 which is bound by an antibody comprising the VH and VL sequences of one of antibody clones 10D1_c89, 10D1_c90 or 10D1_c91. In some embodiments the antigen-binding molecule is capable of binding the same region of HER3, or an overlapping region of HER3, to the region of HER3 which is bound by an antibody comprising the VH and VL sequences of antibody clone 10D1_c89.

As used herein, a "peptide" refers to a chain of two or more amino acid monomers linked by peptide bonds. A peptide typically has a length in the region of about 2 to 50 amino acids. "polypeptide" is a polymer chain of two or more peptides. Polypeptides typically have a length greater than about 50 amino acids.

In some embodiments, the antigen-binding molecule of the present invention is capable of binding to a polypeptide comprising, or consisting of, the amino acid sequence of one of SEQ ID NOs:1, 3, 4, 6 or 8.

In some embodiments, the antigen-binding molecule is capable of binding to a polypeptide comprising, or consisting of, the amino acid sequence of SEQ ID NO:9. In some embodiments, the antigen-binding molecule is capable of binding to a polypeptide comprising, or consisting of, the amino acid sequence of SEQ ID NO:16.

In some embodiments, the antigen-binding molecule is capable of binding to a peptide/polypeptide comprising, or consisting of, the amino acid sequence of SEQ ID NO:229. In some embodiments, the antigen-binding molecule is capable of binding to a peptide/polypeptide comprising, or consisting of, the amino acid sequences of SEQ ID NOs:230 and 231. In some embodiments, the antigen-binding molecule is capable of binding to a peptide/polypeptide comprising, or consisting of, the amino acid sequence of SEQ ID NO:230. In some embodiments, the antigen-binding molecule is capable of binding to a peptide; polypeptide comprising, or consisting of, the amino acid sequence of SEQ ID NO:231. In some embodiments, the antigen-binding molecule is capable of binding to a peptide/polypeptide comprising, or consisting of, the amino acid sequence of SEQ ID NO:23. In some embodiments, the antigen-binding molecule is capable of binding to a peptide/polypeptide comprising, or consisting of, the amino acid sequence of SEQ ID NO:21. In some embodiments, the antigen-binding molecule is capable of binding to a peptide/polypeptide comprising, or consisting of, the amino acid sequence of SEQ ID NO:19. In some embodiments, the antigen-binding molecule is capable of binding to a peptide/polypeptide comprising, or consisting of, the amino acid sequence of SEQ ID NO:22.

In some embodiments, the antigen-binding molecule is not capable of binding to a peptide consisting of the amino acid sequence corresponding to positions 260 to 279 of SEQ ID NO:1. In some embodiments, the antigen-binding molecule is not capable of binding to a peptide consisting of the amino acid sequence of SEQ 110 NO:23.

The ability of an antigen-binding molecule to bind to a given peptide/polypeptide can be analysed by methods well known to the skilled person, including analysis by ELISA, immunoblot (e.g. western blot), immunoprecipitation, Surface Plasmon Resonance (SPR; see e.g. Hearty et al., Methods Mol Biol (2012) 907:411-442) or Bio-Layer Interferometry (see e.g. Lad et al., (2015) J Biomol Screen 20(4): 498-507).

In embodiments where the antigen binding molecule is capable of binding to a peptide/polypeptide comprising a reference amino acid sequence, the peptide/polypeptide may comprise one or more additional amino acids at one or both ends of the reference amino acid sequence. In some embodiments the peptide/polypeptide comprises e.g. 1-5, 1-10, 1-20, 1-30, 1-40, 1-50, 5-10, 5-20, 5-30, 5-40, 5-50, 10-20, 10-30, 10-40, 10-50, 20-30, 20-40 or 20-50 additional amino acids at one or both ends of the reference amino acid sequence.

In some embodiments the additional amino acid(s) provided at one or both ends (i.e. the N-terminal and C-terminal ends) of the reference sequence correspond to the positions at the ends of the reference sequence in the context of the amino acid sequence of HER3. By way of example, where the antigen-binding molecule is capable of binding to a peptide comprising the sequence of SEQ ID NO:23 and an additional two amino acids at the C-terminal end of SEQ ID NO:23, the additional two amino acids may be threonine and lysine, corresponding to positions 278 and 279 of SEQ ID NO:1.

In some embodiments the antigen-binding molecule is capable of binding to a peptide/polypeptide which is bound by an antibody comprising the VH and VL sequences of one of antibody clones 10D1, 10D1_c75, 10D1_c76, 10D1_c77, 10D1_c78v1, 10D1_c78v2, 10D1_11B, 10D1_c85v1, 10D1_c85v2, 10D1_c85o1, 10D1_c85o2, 10D1_c87, 10D1_c89, 10D1_c90, 10D1_c91, 10D1_c92, 10D1_c93, 10A6, 4-35-B2 or 4-35-B4 described herein. In some embodiments the antigen-binding molecule is capable of binding to a peptide/polypeptide which is bound by an antibody comprising the VH and VL sequences of one of antibody clones 10D1_c89, 10D1_c90 or 10D1_c91. In some embodiments the antigen-binding molecule is capable of binding to a peptide/polypeptide which is bound by an antibody comprising the VH and VL sequences of antibody clone 10D1_c89.

Antigen-Binding Molecules

The present invention provides antigen-binding molecules capable of binding to HER3.

An "antigen-binding molecule" refers to a molecule which is capable of binding to a target antigen, and encompasses monoclonal antibodies, polyclonal antibodies, monospecific and multispecific antibodies (e.g., bispecific antibodies), and antibody fragments (e.g. Fv, scFv, Fab, scFab, F(ab')$_2$, Fab$_2$, diabodies, triabodies, scFv-Fc, minibodies, single domain antibodies (e.g. VhH), etc.), as long as they display binding to the relevant target molecule(s).

The antigen-binding molecule of the present invention comprises a moiety capable of binding to a target antigen(s). In some embodiments, the moiety capable of binding to a target antigen comprises an antibody heavy chain variable region (VH) and an antibody light chain variable region (VL) of an antibody capable of specific binding to the target antigen. In some embodiments, the moiety capable of binding to a target antigen comprises or consists of an aptamer capable of binding to the target antigen, e.g., a nucleic acid aptamer (reviewed, for example, in Zhou and Rossi Nat Rev Drug Discov, 2017 16(3):181-202). In some embodiments, the moiety capable of binding to a target antigen comprises or consists of a antigen-binding peptide/polypeptide, e.g. a peptide aptamer, thioredoxin, monobody, anticalin, Kunitz domain, avimer, knottin, fynomer, atrimer, DARPin, affibody, nanobody (i.e. a single-domain antibody (sdAb)) affilin, armadillo repeat protein (ArmRP), OBody or fibronectin—reviewed e.g. in Reverdatto et al., Curr Top Med Chem. 2015; 15(12): 1082-1101, which is hereby incorporated by reference in its entirety (see also e.g. Boersma et al., J Biol Chem (2011) 286:41273-85 and Emanuel et al., Mabs (2011) 3:38-48).

The antigen-binding molecules of the present invention generally comprise an antigen-binding domain comprising a VH and a VL of an antibody capable of specific binding to the target antigen. The antigen-binding domain formed by a VH and a VL may also be referred to herein as an Fv region.

An antigen-binding molecule may be, or may comprise, an antigen-binding polypeptide, or an antigen-binding polypeptide complex. An antigen-binding molecule may comprise more than one polypeptide which together form an antigen-binding domain. The polypeptides may associate covalently or non-covalently. In some embodiments the polypeptides form part of a larger polypeptide comprising the polypeptides (e.g. in the case of scFv comprising VH and VL, or in the case of scFab comprising VH-CH1 and VL-CL).

An antigen-binding molecule may refer to a non-covalent or covalent complex of more than one polypeptide (e.g. 2, 3, 4, 6, or 8 polypeptides), e.g. an IgG-like antigen-binding molecule comprising two heavy chain polypeptides and two light chain polypeptides.

The antigen-binding molecules of the present invention may be designed and prepared using the sequences of monoclonal antibodies (mAbs) capable of binding to HER3. Antigen-binding regions of antibodies, such as single chain variable fragment (scFv), Fab and F(ab')$_2$ fragments may also be used/provided. An "antigen-binding region" is any fragment of an antibody which is capable of binding to the target for which the given antibody is specific.

Antibodies generally comprise six complementarity-determining regions CDRs; three in the heavy chain variable (VH) region: HC-CDR1, HC-CDR2 and HC-CDR3, and three in the light chain variable (VL) region: LC-CDR1, LC-CDR2, and LC-CDR3. The six CDRs together define the paratope of the antibody, which is the part of the antibody which binds to the target antigen.

The VH region and VL region comprise framework regions (FRs) either side of each CDR, which provide a scaffold for the CDRs. From N-terminus to C-terminus, VH regions comprise the following structure: N term-[HC-FR1]-[HC-CDR1]-[HC-FR2]-[HC-CDR2]-[HC-FR3]-[HC-CDR3]-[HC-FR4]-C term; and VL regions comprise the following structure: N term-[LC-FR1]-[LC-CDR1]-[LCFR2]-[LC-CDR2]-[LC-FR3]-[LC-CDR3]-[LC-FR4]-C term.

There are several different conventions for defining antibody OCRs and FRs, such as those described in Rabat et al., Sequences of Proteins of Immunological Interest, 5th Ed. Public Health Service, National Institutes of Health, Bethesda, Md. (1991), Chothia et al., J. Mol. Biol. 196:901-917 (1987), and VBASE2, as described in Reiter et al., Nucl. Acids Res. (2005) 33 (suppl 1): D671-D674. The CDRs and FRs of the VH regions and VL regions of the antibody clones described herein were defined according to the international IMGT (ImMunoGeneTics) information system (LeFranc et al., Nucleic Acids Res. (2015) 43 (Database issue):D413-22), which uses the IMGT V-DOMAIN numbering rules as described in Lefranc et al., Dev. Comp. Immunol. (2003) 27:55-77.

In some embodiments, the antigen-binding molecule comprises the CDRs of an antigen-binding molecule which is capable of binding to HER3. In some embodiments, the antigen-binding molecule comprises the FRs of an antigen-binding molecule which is capable of binding to HER3. In some embodiments, the antigen-binding molecule comprises the CDRs and the FRs of an antigen-binding molecule which is capable of binding to HER3. That is, in some embodiments the antigen-binding molecule comprises the VH region and the VL region of an antigen-binding molecule which is capable of binding to HER3.

In some embodiments the antigen-binding molecule comprises a VH region and a VL region which is, or which is derived from, the VH/VL region of a HER3-binding antibody clone described herein (i.e. anti-HER3 antibody clones 10D1_c75, 10D1_c76, 10D1_c77, 10D1_c76v1, 10D1_c78v2, 10D1_11B, 10D1_c85v1, 10D1_c85v2, 10D1_c85o1, 10D1_c85o2, 10D1_c87, 10D1_c89, 10D1_c90, 10D1_c91, 10D1_c92, 10D1_c93, 10D1, 10A6, 4-35-B2 or 4-35-B4; e.g. 10D1_c89, 10D1_c90 or 10D1_c91; e.g. 10D1_c89).

In some embodiments the antigen-binding molecule comprises a VH region according to one of (1) to (10) below:

(1) (10D1 derived) a VH region incorporating the following CDRs:
HC-CDR1 having the amino acid sequence of SEQ ID NO:43
HC-CDR2 having the amino acid sequence of SEQ ID NO:46
HC-CDR3 having the amino acid sequence of SEQ ID NO:51,
or a variant thereof in which one or two or three amino acids in one or more of HC-CDR1, HC-CDR2, or HC-CDR3 are substituted with another amino acid.

(2) (10D1, 10D1_c75, 10D1_c76, 10D1_c77, 10D1_c78v1, 10D1_c78v2, 10D1_11B, 10D1_c87, 10D1_c92, 10D1_c93) a VH region incorporating the following CDRs:
HC-CDR1 having the amino acid sequence of SEQ ID NO:41
HC-CDR2 having the amino acid sequence of SEQ ID NO:44
HC-CDR3 having the amino acid sequence of SEQ ID NO:47,
or a variant thereof in which one or two or three amino acids in one or more of HC-CDR1, HC-CDR2, or HC-CDR3 are substituted with another amino acid.

(3) (10D1_c85v1, 10D1_c85v2) a VH region incorporating the following CDRs:
HC-CDR1 having the amino acid sequence of SEQ ID NO:41
HC-CDR2 having the amino acid sequence of SEQ ID NO:45
HC-CDR3 having the amino acid sequence of SEQ ID NO:47,
or a variant thereof in which one or two or three amino acids in one or more of HC-CDR1, HC-CDR2, or HC-CDR3 are substituted with another amino acid.

(4) (10D1_c85o1) a VH region incorporating the following CDRs:
HC-CDR1 having the amino acid sequence of SEQ ID NO:41
HC-CDR2 having the amino acid sequence of SEQ ID NO:45
HC-CDR3 having the amino acid sequence of SEQ ID NO:49,
or a variant thereof in which one or two or three amino acids in one or more of HC-CDR1, HC-CDR2, or HC-CDR3 are substituted with another amino acid.

(5) (10D1_c85o2) a VH region incorporating the following CDRS:
HC-CDR1 having the amino acid sequence of SEQ ID NO:41
HC-CDR2 having the amino acid sequence of SEQ ID NO:45
HC-CDR3 having the amino acid sequence of SEQ ID NO:50,
or a variant thereof in which one or two or three amino acids in one or more of HC-CDR1, HC-CDR2, or HC-CDR3 are substituted with another amino acid.

(6) (10D1_c89, 10D1_c90) a VH region incorporating the following CDRs:
HC-CDR1 having the amino acid sequence of SEQ ID NO:41
HC-CDR2 having the amino acid sequence of SEQ ID NO:45
HC-CDR3 having the amino acid sequence of SEQ ID NO:48,
or a variant thereof in which one or two or three amino acids in one or more of HC-CDR1, HC-CDR2, or HC-CDR3 are substituted with another amino acid.

(7) (10D1_c91) a VH region incorporating the following CDRs:
HC-CDR1 having the amino acid sequence of SEQ ID NO:42
HC-CDR2 having the amino acid sequence of SEQ ID NO:45
HC-CDR3 having the amino acid sequence of SEQ ID NO:48,
or a variant thereof in which one or two or three amino acids in one or more of HC-CDR1, HC-CDR2, or HC-CDR3 are substituted with another amino acid.

(8) (10A6) a VH region incorporating the following CDRs:
HC-CDR1 having the amino acid sequence of SEQ ID NO:158
HC-CDR2 having the amino acid sequence of SEQ ID NO:159
HC-CDR3 having the amino acid sequence of SEQ ID NO:160,
or a variant thereof in which one or two or three amino acids in one or more of HC-CDR1, HC-CDR2, or HC-CDR3 are substituted with another amino acid.

(9) (4-35-B2) a VH region incorporating the following CDRs:
HC-CDR1 having the amino acid sequence of SEQ ID NO:128
HC-CDR2 having the amino acid sequence of SEQ ID NO:129
HC-CDR3 having the amino acid sequence of SEQ ID NO:130,
or a variant thereof in which one or two or three amino acids in one or more of HC-CDR1, HC-CDR2, or HC-CDR3 are substituted with another amino acid.

(10) (4-35-B4) a VH region incorporating the following CDRs:
HC-CDR1 having the amino acid sequence of SEQ ID NO:144
HC-CDR2 having the amino acid sequence of SEQ ID NO:145
HC-CDR3 having the amino acid sequence of SEQ ID NO:146,
or a variant thereof in which one or two or three amino acids in one or more of HC-CDR1, HC-CDR2, or HC-CDR3 are substituted with another amino acid.

In some embodiments the antigen-binding molecule comprises a VH region according to one of (11) to (24) below:
(11) (10D1) a VH region incorporating the following FRs:
HC-FR1 having the amino acid sequence of SEQ ID NO:55
HC-FR2 having the amino acid sequence of SEQ ID NO:58
HC-FR3 having the amino acid sequence of SEQ ID NO:69
HC-FR4 having the amino acid sequence of SEQ ID NO:73,
or a variant thereof in which one or two or three amino acids in one or more of HC-FR1, HC-FR2, HC-FR3, or HC-FR4 are substituted with another amino acid.

(12) (10D1_c75, 10D1_c92) a VH region incorporating the following FRs:
HC-FR1 having the amino acid sequence of SEQ ID NO:52
HC-FR2 having the amino acid sequence of SEQ ID NO:56

HC-FR3 having the amino acid sequence of SEQ ID NO:61
HC-FR4 having the amino acid sequence of SEQ ID NO:70,
or a variant thereof in which one or two or three amino acids in one or more of HC-FR1, HC-FR2, HC-FR3, or HC-FR4 are substituted with another amino add.

(13) (10D1_c76, 10D1_c77, 10D1_c78v1) a VH region incorporating the following FRs:
HC-FR1 having the amino acid sequence of SEQ ID NO:52
HC-FR2 having the amino acid sequence of SEQ ID NO:56
HC-FR3 having the amino acid sequence of SEQ ID NO:62
HC-FR4 having the amino acid sequence of SEQ ID NO:70,
or a variant thereof in which one or two or three amino acids in one or more of HC-FR1, HC-FR2, HC-FR3, or HC-FR4 are substituted with another amino acid.

(14) (10D1_c78v2) a VH region incorporating the following FRs:
HC-FR1 having the amino acid sequence of SEQ ID NO:52
HC-FR2 having the amino acid sequence of SEQ ID NO:57
HC-FR3 having the amino acid sequence of SEQ ID NO:62
HC-FR4 having the amino acid sequence of SEQ ID NO:70,
or a variant thereof in which one or two or three amino acids in one or more of HC-FR1, HC-FR2, HC-FR3, or HC-FR4 are substituted with another amino acid.

(15) (10D1_11B) a VH region incorporating the following FRs:
HC-FR1 having the amino acid sequence of SEQ ID NO:224
HC-FR2 having the amino acid sequence of SEQ ID NO:60
HC-FR3 having the amino acid sequence of SEQ ID NO:83
HC-FR4 having the amino acid sequence of SEQ ID NO:70,
or a variant thereof in which one or two or three amino acids in one or more of HC-FR1, HC-FR2, HC-FR3, or HC-FR4 are substituted with another amino acid.

(16) (10D1_c85v1) a VH region incorporating the following FRs:
HC-FR1 having the amino acid sequence of SEQ ID NO:52
HC-FR2 having the amino acid sequence of SEQ ID NO:56
HC-FR3 having the amino acid sequence of SEQ ID NO:64
HC-FR4 having the amino acid sequence of SEQ ID NO:70,
or a variant thereof in which one or two or three amino acids in one or more of HC-FR1, HC-FR2, HC-FR3, or HC-FR4 are substituted with another amino acid.

(17) (10D1_c85v2, 10D1_c85o1, 10D1_c85o2) a VH region incorporating the following FRs:
HC-FR1 having the amino acid sequence of SEQ ID NO:52
HC-FR2 having the amino acid sequence of SEQ ID NO:57
HC-FR3 having the amino acid sequence of SEQ ID NO:64
HC-FR4 having the amino acid sequence of SEQ ID NO:70,
or a variant thereof in which one or two or three amino acids in one or more of HC-FR1, HC-FR2, HC-FR3, or HC-FR4 are substituted with another amino acid.

(18) (10D1_c87, 10D1_c93) a VH region incorporating the following FRs:
HC-FR1 having the amino acid sequence of SEQ ID NO:52
HC-FR2 having the amino acid sequence of SEQ ID NO:56
HC-FR3 having the amino acid sequence of SEQ ID NO:65
HC-FR4 having the amino acid sequence of SEQ ID NO:70,
or a variant thereof in which one or two or three amino acids in one or more of HC-FR1, HC-FR2, HC-FR3, or HC-FR4 are substituted with another amino acid.

(19) (10D1_c89) a VH region incorporating the following FRs:
HC-FR1 having the amino acid sequence of SEQ ID NO:53
HC-FR2 having the amino acid sequence of SEQ ID NO:59
HC-FR3 having the amino acid sequence of SEQ ID NO:66
HC-FR4 having the amino acid sequence of SEQ ID NO:71,
or a variant thereof in which one or two or three amino acids in one or more of HC-FR1, HC-FR2, HC-FR3, or HC-FR4 are substituted with another amino acid.

(20) (10D1_c90) a VH region incorporating the following FRs:
HC-FR1 having the amino acid sequence of SEQ ID NO:54
HC-FR2 having the amino acid sequence of SEQ ID NO:59
HC-FR3 having the amino acid sequence of SEQ ID NO:67
HC-FR4 having the amino acid sequence of SEQ ID NO:71,
or a variant thereof in which one or two or three amino acids in one or more of HC-FR1, HC-FR2, HC-FR3, or HC-FR4 are substituted with another amino acid.

(21) (10D1_c91) a VH region incorporating the following FRs:
HC-FR1 having the amino acid sequence of SEQ ID NO:53
HC-FR2 having the amino acid sequence of SEQ ID NO:59
HC-FR3 having the amino acid sequence of SEQ ID NO:68
HC-FR4 having the amino acid sequence of SEQ ID NO:72,
or a variant thereof in which one or two or three amino acids in one or more of HC-FR1, HC-FR2, HC-FR3, or HC-FR4 are substituted with another amino acid.

(22) (10A6) a VH region incorporating the following FRs:
HC-FR1 having the amino acid sequence of SEQ ID NO:161
HC-FR2 having the amino acid sequence of SEQ ID NO:162
HC-FR3 having the amino acid sequence of SEQ ID NO:163
HC-FR4 having the amino acid sequence of SEQ ID NO:73, or a variant thereof in which one or two or three amino acids in one or more of HC-FR1, HC-FR2, HC-FR3, or HC-FR4 are substituted with another amino acid.

(23) (4-35-B2) a VH region incorporating the following FRs:
  HC-FR1 having the amino acid sequence of SEQ ID NO:131
  HC-FR2 having the amino acid sequence of SEQ ID NO:132
  HC-FR3 having the amino acid sequence of SEQ ID NO:133
  HC-FR4 having the amino acid sequence of SEQ ID NO:134,
  or a variant thereof in which one or two or three amino acids in one or more of HC-FR1, HC-FR2, HC-FR3, or HC-FR4 are substituted with another amino acid.

(24) (4-35-B4) a VH region incorporating the following FRs:
  HC-FR1 having the amino acid sequence of SEQ ID NO:147
  HC-FR2 having the amino acid sequence of SEQ ID NO:148
  HC-FR3 having the amino acid sequence of SEQ ID NO:149
  HC-FR4 having the amino acid sequence of SEQ ID NO:73,
  or a variant thereof in which one or two or three amino acids in one or more of HC-FR1, HC-FR2, HC-FR3, or HC-FR4 are substituted with another amino acid.

In some embodiments the antigen-binding molecule comprises a VH region comprising the CDRs according to one of (1) to (10) above, and the FRs according to one of (11) to (24) above.

In some embodiments the antigen-binding molecule comprises a VH region according to one of (25) to (41) below:
  (25) a VH region comprising the CDRs according to (1) and the FRs according to (11), (12), (13), (14), (15), (16), (17), (18), (19), (20) or (21).
  (26) a VH region comprising the CDRs according to (2) and the FRs according to (11).
  (27) a VH region comprising the CDRs according to (2) and the FRs according to (12).
  (28) a VH region comprising the CDRs according to (2) and the FRs according to (13).
  (29) a VH region comprising the CDRs according to (2) and the FRs according to (14).
  (30) a VH region comprising the CDRs according to (2) and the FRs according to (15).
  (31) a VH region comprising the CDRs according to (2) and the FRs according to (18).
  (32) a VH region comprising the CDRs according to (3) and the FRs according to (16).
  (33) a VH region comprising the CDRs according to (3) and the FRs according to (17).
  (34) a VH region comprising the CDRs according to (4) and the FRs according to (17).
  (35) a VH region comprising the CDRs according to (5) and the FRs according to (17).
  (36) a VH region comprising the CDRs according to (6) and the FRs according to (19).
  (37) a VH region comprising the CDRs according to (6) and the FRs according to (20).
  (38) a VH region comprising the CDRs according to (7) and the FRs according to (21).
  (39) a VH region comprising the CDRs according to (8) and the FRs according to (22).
  (40) a VH region comprising the CDRs according to (9) and the FRs according to (23).
  (41) a VH region comprising the CDRs according to (10) and the FRs according to (24).

In some embodiments the antigen-binding molecule comprises a VH region according to one of (42) to (61) below:
  (42) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:24.
  (43) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:25.
  (44) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:26.
  (45) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:27.
  (46) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:28.
  (47) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:29.
  (48) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:30.
  (49) a VH region comprising an amino acid sequence having at least 70% sequence identity more preferably one of at least 75%, 80%, 85%, 86%, 87%, 8830, 89%, 90%, 91%, 92%, 93%, 94%, 95%, 96%, 97%, 98%, 99%, or 100%, sequence identity to the amino acid sequence of SEQ ID NO:31.
  (50) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:32.
  (51) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:33.

(52) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:34.

(53) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:35.

(54) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:36.

(55) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:37.

(56) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:38.

(57) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:39.

(58) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:40.

(59) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:127.

(60) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:143.

(61) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:157.

In some embodiments the antigen-binding molecule comprises a VL region according to one of (62) to (71) below:

(62) (10D1 derived) a VL region incorporating the following CDRs:
 LC-CDR1 having the amino acid sequence of SEQ ID NO:91
 LC-CDR2 having the amino acid sequence of SEQ ID NO:94
 LC-CDR3 having the amino acid sequence of SEQ ID NO:99;
 or a variant thereof in which one or two or three amino acids in one or more of LC-CDR1, LC-CDR2 or LC-CDR3 are substituted with another amino acid.

(63) (10D1, 10D1_c75, 10D1_c78v1, 10D1_c78v2, 10D1_11B, 10D1_c87, 10D1_c89, 10D1_c91, 10D1_c93) a VL region incorporating the following CDRs:
 LC-CDR1 having the amino acid sequence of SEQ ID NO:88
 LC-CDR2 having the amino acid sequence of SEQ ID NO:92
 LC-CDR3 having the amino acid sequence of SEQ ID NO:95;
 or a variant thereof in which one or two or three amino acids in one or more of LC-CDR1, LC-CDR2 or LC-CDR3 are substituted with another amino acid.

(64) (10D1_c76) a VL region incorporating the following CDRs:
 LC-CDR1 having the amino acid sequence of SEQ ID NO:89
 LC-CDR2 having the amino acid sequence of SEQ ID NO:92
 LC-CDR3 having the amino acid sequence of SEQ ID NO:95;
 or a variant thereof in which one or two or three amino acids in one or more of LC-CDR1, LC-CDR2 or LC-CDR3 are substituted with another amino acid.

(65) (10D1_c77) a VL region incorporating the following CDRs:
 LC-CDR1 having the amino acid sequence of SEQ ID NO:90
 LC-CDR2 having the amino acid sequence of SEQ ID NO:92
 LC-CDR3 having the amino acid sequence of SEQ ID NO:96;
 or a variant thereof in which one or two or three amino acids in one or more of LC-CDR1, LC-CDR2 or LC-CDR3 are substituted with another amino acid.

(66) (10D1_c85v1, 10D1_c85v2, 10D1_c85o1, 10D1_c85o2) a VL region incorporating the following CDRs:
 LC-CDR1 having the amino acid sequence of SEQ ID NO:88
 LC-CDR2 having the amino acid sequence of SEQ ID NO:93
 LC-CDR3 having the amino acid sequence of SEQ ID NO:95;
 or a variant thereof in which one or two or three amino acids in one or more of LC-CDR1 LC-CDR2 or LC-CDR3 are substituted with another amino acid.

(67) (10D1_c90) a VL region incorporating the following CDRs:
 LC-CDR1 having the amino acid sequence of SEQ ID NO:88
 LC-CDR2 having the amino acid sequence of SEQ ID NO:92
 LC-CDR3 having the amino acid sequence of SEQ ID NO:97;
 or a variant thereof in which one or two or three amino acids in one or more of LC-CDR1, LC-CDR2 or LC-CDR3 are substituted with another amino acid.

(68) (10D1_c92) a VL region incorporating the following CDRs:
- LC-CDR1 having the amino acid sequence of SEQ ID NO:88
- LC-CDR2 having the amino acid sequence of SEQ ID NO:92
- LC-CDR3 having the amino acid sequence of SEQ ID NO:98;
- or a variant thereof in which one or two or three amino acids in one or more of LC-CDR1, LC-CDR2 or LC-CDR3 are substituted with another amino acid.

(69) (10A6) a VL region incorporating the following CDRs;
- LC-CDR1 having the amino acid sequence of SEQ ID NO:165
- LC-CDR2 having the amino acid sequence of SEQ ID NO:166
- LC-CDR3 having the amino acid sequence of SEQ ID NO:167;
- or a variant thereof in which one or two or three amino acids in one or more of LC-CDR1 LC-CDR2 or LC-CDR3 are substituted with another amino acid.

(70) (4-35-B2) a VL region incorporating the following CDRs:
- LC-CDR1 having the amino acid sequence of SEQ ID NO:136
- LC-CDR2 having the amino acid sequence of SEQ ID NO:137
- LC-CDR3 having the amino acid sequence of SEQ ID NO:138,
- or a variant thereof in which one or two or three amino acids in one or more of LC-CDR1, LC-CDR2 or LC-CDR3 are substituted with another amino acid.

(71) (4-35-B4) a VL region incorporating the following CDRs:
- LC-CDR1 having the amino acid sequence of SEQ ID NO:151
- LC-CDR2 having the amino acid sequence of SEQ ID NO:152
- LC-CDR3 having the amino acid sequence of SEQ ID NO:153;
- or a variant thereof in which one or two or three amino acids in one or more of LC-CDR1. LC-CDR2 or LC-CDR3 are substituted with another amino acid.

In some embodiments the antigen-binding molecule comprises a VL region according to one of (72) to (86) below;

(72) (10D1) a VL region incorporating the following FRs:
- LC-FR1 having the amino acid sequence of SEQ ID NO:106
- LC-FR2 having the amino acid sequence of SEQ ID NO:113
- LC-FR3 having the amino acid sequence of SEQ ID NO:123
- LC-FR4 having the amino acid sequence of SEQ ID NO:126,
- or a variant thereof in which one or two or three amino acids in one or more of LC-FR1, LC-FR2, LC-FR3, or LC-FR4 are substituted with another amino acid.

(73) (10D1_c75) a VL region incorporating the following FRs;
- LC-FR1 having the amino acid sequence of SEQ ID NO:100
- LC-FR2 having the amino acid sequence of SEQ ID NO:107
- LC-FR3 having the amino acid sequence of SEQ ID NO:114
- LC-FR4 having the amino acid sequence of SEQ ID NO:124,
- or a variant thereof in which one or two or three amino acids in one or more of LC-FR1, LC-FR2, LC-FR3, or LC-FR4 are substituted with another amino acid.

(74) (10D1_c76) a VL region incorporating the following FRs:
- LC-FR1 having the amino acid sequence of SEQ ID NO:101
- LC-FR2 having the amino acid sequence of SEQ ID NO:108
- LC-FR3 having the amino acid sequence of SEQ ID NO:115
- LC-FR4 having the amino acid sequence of SEQ ID NO:124,
- or a variant thereof in which one or two or three amino acids in one or more of LC-FR1, LC-FR2, LC-FR3, or LC-FR4 are substituted with another amino acid.

(75) (10D1_c77) a VL region incorporating the following FRs:
- LC-FR1 having the amino acid sequence of SEQ ID NO:102
- LC-FR2 having the amino acid sequence of SEQ ID NO:108
- LC-FR3 having the amino acid sequence of SEQ ID NO:116
- LC-FR4 having the amino acid sequence of SEQ ID NO:124,
- or a variant thereof in which one or two or three amino acids in one or more of LC-FR1, LC-FR2, LC-FR3, or LC-FR4 are substituted with another amino acid.

(76) (10D1_c78v1, 10D1_c78v2, 10D1_11B) a VL region incorporating the following FRs:
- LC-FR1 having the amino acid sequence of SEQ ID NO:103
- LC-FR2 having the amino acid sequence of SEQ ID NO:108
- LC-FR3 having the amino acid sequence of SEQ ID NO:117
- LC-FR4 having the amino acid sequence of SEQ ID NO:124,
- or a variant thereof in which one or two or three amino acids in one or more of LC-FR1, LC-FR2, LC-FR3, or LC-FR4 are substituted with another amino acid.

(77) (10D1_c85v1, 10D1_c85v2, 10D1_c85o1, 10D1_c85o2) a VL region incorporating the following FRs:
- LC-FR1 having the amino acid sequence of SEQ ID NO:103
- LC-FR2 having the amino acid sequence of SEQ ID NO:108
- LC-FR3 having the amino acid sequence of SEQ ID NO:118
- LC-FR4 having the amino acid sequence of SEQ ID NO:124,
- or a variant thereof in which one or two or three amino acids in one or more of LC-FR1, LC-FR2, LC-FR3, or LC-FR4 are substituted with another amino acid.

(78) (10D1_c87) a VL region incorporating the following FRs:
- LC-FR1 having the amino acid sequence of SEQ ID NO:103
- LC-FR2 having the amino acid sequence of SEQ ID NO:109
- LC-FR3 having the amino acid sequence of SEQ ID NO:119
- LC-FR4 having the amino acid sequence of SEQ ID NO:124, or a variant thereof in which one or two or three amino acids in one or more of LC-FR1, LC-FR2, LC-FR3, or LC-FR4 are substituted with another amino acid.

(79) (10D1_c89) a VL region incorporating the following FRs:
LC-FR1 having the amino acid sequence of SEQ ID NO:104
LC-FR2 having the amino acid sequence of SEQ ID NO:110
LC-FR3 having the amino acid sequence of SEQ ID NO:120
LC-FR4 having the amino acid sequence of SEQ ID NO:125,
or a variant thereof in which one or two or three amino acids in one or more of LC-FR1, LC-FR2, LC-FR3, or LC-FR4 are substituted with another amino acid.

(80) (10D1_c90) a VL region incorporating the following FRs:
LC-FR1 having the amino acid sequence of SEQ ID NO:105
LC-FR2 having the amino acid sequence of SEQ ID NO:110
LC-FR3 having the amino acid sequence of SEQ ID NO:121
LC-FR4 having the amino acid sequence of SEQ ID NO:124,
or a variant thereof in which one or two or three amino acids in one or more of LC-FR1, LC-FR2, LC-FR3, or LC-FR4 are substituted with another amino acid.

(81) (10D1_c91) a VL region incorporating the following FRs:
LC-FR1 having the amino acid sequence of SEQ ID NO:104
LC-FR2 having the amino acid sequence of SEQ ID NO:111
LC-FR3 having the amino acid sequence of SEQ ID NO:122
LC-FR4 having the amino acid sequence of SEQ ID NO:125,
or a variant thereof in which one or two or three amino acids in one or more of LC-FR1 LC-FR2, LC-FR3, or LC-FR4 are substituted with another amino acid.

(82) (10D1_c92) a VL region incorporating the following FRs:
LC-FR1 having the amino acid sequence of SEQ ID NO:100
LC-FR2 having the amino acid sequence of SEQ ID NO:112
LC-FR3 having the amino acid sequence of SEQ ID NO:114
LC-FR4 having the amino acid sequence of SEQ ID NO:124,
or a variant thereof in which one or two or three amino acids in one or more of LC-FR1, LC-FR2, LC-FR3, or LC-FR4 are substituted with another amino acid.

(83) (10D1_c93) a VL region incorporating the following FRs:
LC-FR1 having the amino acid sequence of SEQ ID NO:103
LC-FR2 having the amino acid sequence of SEQ ID NO:108
LC-FR3 having the amino acid sequence of SEQ ID NO:119
LC-FR4 having the amino acid sequence of SEQ ID NO:124,
or a variant thereof in which one or two or three amino acids in one or more of LC-FR1, LC-FR2, LC-FR3, or LC-FR4 are substituted with another amino acid.

(84) (10A6) a VL region incorporating the following FRs:
LC-FR1 having the amino acid sequence of SEQ ID NO:168
LC-FR2 having the amino acid sequence of SEQ ID NO:169
LC-FR3 having the amino acid sequence of SEQ ID NO:170
LC-FR4 having the amino acid sequence of SEQ ID NO:142,
or a variant thereof in which one or two or three amino acids in one or more of LC-FR1, LC-FR2, LC-FR3, or LC-FR4 are substituted with another amino acid.

(85) (4-35-B2) a VL region incorporating the following FRs:
LC-FR1 having the amino acid sequence of SEQ ID NO:139
LC-FR2 having the amino acid sequence of SEQ ID NO:140
LC-FR3 having the amino acid sequence of SEQ ID NO:141
LC-FR4 having the amino acid sequence of SEQ ID NO:142,
or a variant thereof in which one or two or three amino acids in one or more of LC-FR1, LC-FR2, LC-FR3, or LC-FR4 are substituted with another amino acid.

(86) (4-35-B4) a VL region incorporating the following FRs:
LC-FR1 having the amino acid sequence of SEQ ID NO:154
LC-FR2 having the amino acid sequence of SEQ ID NO:155
LC-FR3 having the amino acid sequence of SEQ ID NO:156
LC-FR4 having the amino acid sequence of SEQ ID NO:142,
or a variant thereof in which one or two or three amino acids in one or more of LC-FR1. LC-FR2, LC-FR3, or LC-FR4 are substituted with another amino acid.

In some embodiments the antigen-binding molecule comprises a VL region comprising the CDRs according to one of (62) to (71) above, and the FRs according to one of (72) to (86) above.

In some embodiments the antigen-binding molecule comprises a VL region according to one of (87) to (102) below:

(87) a VL region comprising the CDRs according to (62) and the FRs according to (72), (73), (74), (75), (76), (77), (78), (79), (80), (81), (82), or (83).

(88) a VL region comprising the CDRs according to (63) and the FRs according to (72).

(89) a VL region comprising the CDRs according to (63) and the FRs according to (73).

(90) a VL region comprising the CDRs according to (63) and the FRs according to (76).

(91) a VL region comprising the CDRs according to (63) and the FRs according to (78).

(92) a VL region comprising the CDRs according to (63) and the FRs according to (79).

(93) a VL region comprising the CDRs according to (63) and the FRs according to (81).

(94) a VL region comprising the CDRs according to (63) and the FRs according to (83).

(95) a VL region comprising the CDRs according to (64) and the FRs according to (74).

(96) a VL region comprising the CDRs according to (65) and the FRs according to (75).

(97) a VL region comprising the CDRs according to (66) and the FRs according to (77).

(98) a VL region comprising the CDRs according to (67) and the FRs according to (80).

(99) a VL region comprising the CDRs according to (68) and the FRs according to (82).

(100) a VL region comprising the CDRs according to (69) and the FRs according to (84).

(101) a VL region comprising the CDRs according to (70) and the FRs according to (85).

(102) a VL region comprising the CDRs according to (71) and the FRs according to (86).

In some embodiments the antigen-binding molecule comprises a VL region according to one of (103) to (119) below:

(103) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:74.

(104) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:75.

(105) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:76.

(106) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:77.

(107) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 93%, 99%, or 100%, sequence identity to the amino acid sequence of SEQ ID NO:78.

(108) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:79.

(109) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:80.

(110) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:81.

(111) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:82.

(112) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:83.

(113) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:84.

(114) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:85.

(115) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:86.

(116) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:87.

(117) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:135.

(118) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:150.

(119) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:164.

In some embodiments the antigen-binding molecule comprises a VH region according to any one of (1) to (61) above, and a VL region according to any one of (62) to (119) above.

In embodiments in accordance with the present invention in which one or more amino acids are substituted with another amino acid, the substitutions may be conservative substitutions, for example according to the following Table. In some embodiments, amino acids in the same block in the middle column are substituted. In some embodiments, amino acids in the same line in the rightmost column are substituted:

| ALIPHATIC | Non-polar | G A P |
| | | I L V |

| | | |
|---|---|---|
| | Polar - uncharged | C S T M N Q |
| | Polar - charged | D E K R |
| AROMATIC | | H F W Y |

In some embodiments, substitution(s) may be functionally conservative. That is, in some embodiments the substitution may not affect (or may not substantially affect) one or more functional properties (e.g. target binding) of the antigen-binding molecule comprising the substitution as compared to the equivalent unsubstituted molecule.

The VH and VL region of an antigen-binding region of an antibody together constitute the Fv region. In some embodiments, the antigen-binding molecule according to the present invention comprises, or consists of, an Fv region which binds to HER3. In some embodiments the VH and VL regions of the Fv are provided as single polypeptide joined by a linker region, i.e. a single chain Fv (scFv).

In some embodiments the antigen-binding molecule of the present invention comprises one or more regions of an immunoglobulin heavy chain constant sequence. In some embodiments the immunoglobulin heavy chain constant sequence is, or is derived from, the heavy chain constant sequence of an IgG (e.g. IgG1, IgG2, IgG3, IgG4), IgA (e.g. IgA1, IgA2), IgD, IgE or IgM.

In some embodiments the immunoglobulin heavy chain constant sequence is human immunoglobulin G 1 constant (IGHG1; UniProt, P01857-1, v1; SEQ ID NO:171). Positions 1 to 98 of SEQ ID NO:171 form the CH1 region (SEQ ID NO:172). Positions 99 to 110 of SEQ ID NO:171 form a hinge region between CH1 and CH2 regions (SEQ ID NO:173). Positions 111 to 223 of SEQ ID NO:171 form the CH2 region (SEQ ID NO:174). Positions 224 to 330 of SEQ ID NO:171 form the CH3 region (SEQ ID NO:175).

The exemplified antigen-binding molecules may be prepared using pFUSE-CHIg-hG1, which comprises the substitutions D356E, L358M (positions numbered according to EU numbering) in the CH3 region. The amino acid sequence of the CH3 region encoded by pFUSE-CHIg-hG1 is shown in SEQ ID NO:176. It will be appreciated that CH3 regions may be provided with further substitutions in accordance with modification to an Fc region of the antigen-binding molecule as described herein.

In some embodiments a CH1 region comprises or consists of the sequence of SEQ ID NO:172, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:172. In some embodiments a CH1-CH2 hinge region comprises or consists of the sequence of SEQ ID NO:173, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:173. In some embodiments a CH2 region comprises or consists of the sequence of SEQ ID NO:174, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:174. In some embodiments a CH3 region comprises or consists of the sequence of SEQ ID NO:175 or 176, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:175 or 176.

In some embodiments the antigen-binding molecule of the present invention comprises one or more regions of an immunoglobulin light chain constant sequence. In some embodiments the immunoglobulin light chain constant sequence is human immunoglobulin kappa constant (IGKC; Cκ; UniProt: P01834-1, v2; SEQ ID NO:177). In some embodiments the immunoglobulin light chain constant sequence is a human immunoglobulin lambda constant (IGLC; Cλ), e.g. IGLC1, IGLC2, IGLC3, IGLC6 or IGLC7. In some embodiments a CL region comprises or consists of the sequence of SEQ ID NO:177, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:177.

The VL and light chain constant (CL) region, and the VH region and heavy chain constant 1 (CH1) region of an antigen-binding region of an antibody together constitute the Fab region. In some embodiments the antigen-binding molecule comprises a Fab region comprising a VH, a CH1, a VL and a CL (e.g. Cκ or Cλ). In some embodiments the Fab region comprises a polypeptide comprising a VH and a CH1 (e.g. a VH-CH1 fusion polypeptide), and a polypeptide comprising a VL and a CL (e.g. a VL-CL fusion polypeptide). In some embodiments the Fab region comprises a polypeptide comprising a VH and a CL (e.g. a VH-CL fusion polypeptide) and a polypeptide comprising a VL and a CH (e.g. a VL-CH1 fusion polypeptide), that is, in some embodiments the Fab region is a CrossFab region. In some embodiments the VH, CH1, VL and CL regions of the Fab or CrossFab are provided as single polypeptide joined by linker regions, i.e. as a single chain Fab (scFab) or a single chain CrossFab (scCrossFab).

In some embodiments, the antigen-binding molecule of the present invention comprises, or consists of, a Fab region which binds to HER3.

In some embodiments, the antigen-binding molecule described herein comprises, or consists of, a whole antibody which binds to HER3. As used herein, "whole antibody" refers to an antibody having a structure which is substantially similar to the structure of an immunoglobulin (Ig). Different kinds of immunoglobulins and their structures are described e.g. in Schroeder and Cavacini J Allergy Clin Immunol. (2010) 125(202): S41-S52, which is hereby incorporated by reference in its entirety.

Immunoglobulins of type G (i.e. IgG) are ~150 kDa glycoproteins comprising two heavy chains and two light chains. From N- to C-terminus, the heavy chains comprise a VH followed by a heavy chain constant region comprising three constant domains (CH1, CH2, and CH3), and similarly the light chain comprise a VL followed by a CL. Depending on the heavy chain, immunoglobulins may be classed as IgG (e.g. IgG1, IgG2, IgG3, IgG4), IgA (e.g. IgA1, IgA2), IgE, or IgM. The light chain may be kappa (κ) or lambda (λ).

In some embodiments, the antigen-binding molecule described herein comprises, or consists of, an IgG (e.g. IgG1, IgG2, IgG3, IgG4), IgA (e.g. IgA1, IgA2), IgD, IgE, or IgM which binds to HER3.

In some embodiments, the antigen-binding molecule of the present invention is at least monovalent binding for HER3. Binding valency refers to the number of binding sites in an antigen-binding molecule for a given antigenic determinant. Accordingly, in some embodiments the antigen-binding molecule comprises at least one binding site for HER3.

In some embodiments the antigen-binding molecule comprises more than one binding site for HER3, e.g. 2, 3 or 4 binding sites. The binding sites may be the same or different. In some embodiments the antigen-binding molecule is e.g. bivalent, trivalent or tetravalent for HER3.

Aspects of the present invention relate to multispecific antigen-binding molecules. By "multispecific" it is meant that the antigen-binding molecule displays specific binding to more than one target. In some embodiments the antigen-binding molecule is a bispecific antigen-binding molecule. In some embodiments the antigen-binding molecule comprises at least two different antigen-binding domains (i.e. at least two antigen-binding domains, e.g. comprising non-identical VHs and VLs).

In some embodiments the antigen-binding molecule binds to HER3 and another target (e.g. an antigen other than HER3), and so is at least bispecific. The term "bispecific" means that the antigen-binding molecule is able to bind specifically to at least two distinct antigenic determinants.

It will be appreciated that an antigen-binding molecule according to the present invention (e.g. a multispecific antigen-binding molecule) may comprise antigen-binding molecules capable of binding to the targets for which the antigen-binding molecule is specific. For example, an antigen-binding molecule which is capable of binding to HER3 and an antigen other than HER3 may comprise: (i) an antigen-binding molecule which is capable of binding to HER3, and (ii) an antigen-binding molecule which is capable of binding to an antigen other than HER3.

It will also be appreciated that an antigen-binding molecule according to the present invention (e.g. a multispecific antigen-binding molecule) may comprise antigen-binding polypeptides or antigen-binding polypeptide complexes capable of binding to the targets for which the antigen-binding molecule is specific. For example, an antigen-binding molecule according to the invention may comprise e.g. (i) an antigen-binding polypeptide complex capable of binding to HER3, comprising a light chain polypeptide (comprising the structure VL-CL) and a heavy chain polypeptide (comprising the structure VH-CH1-CH2-CH3), and (ii) an antigen-binding polypeptide complex capable of binding to an antigen other than HER3, comprising a light chain polypeptide (comprising the structure VL-CL) and a heavy chain polypeptide (comprising the structure VH-CH1-CH2-CH3).

In some embodiments, a component antigen-binding molecule of a larger antigen-binding molecule (e.g. a multispecific antigen-biding molecule) may be referred to e.g. as an "antigen-binding domain" or "antigen-binding region" of the larger antigen-binding molecule.

In some embodiments the antigen-binding molecule comprises an antigen-binding molecule capable of binding to HER3, and an antigen-binding molecule capable of binding to an antigen other than HER3. In some embodiments, the antigen other than HER3 is an immune cell surface molecule. In some embodiments, the antigen other than HER3 is a cancer cell antigen. In some embodiments the antigen other than HER3 is a receptor molecule, e.g. a cell surface receptor. In some embodiments the antigen other than HER3 is a cell signalling molecule, e.g. a cytokine, chemokine, interferon, interleukin or lymphokine. In some embodiments the antigen other than HER3 is a growth factor or a hormone.

A cancer cell antigen is an antigen which is expressed or over-expressed by a cancer cell. A cancer cell antigen may be any peptide polypeptide, glycoprotein, lipoprotein, glycan, glycolipid, lipid, or fragment thereof. A cancer cell antigen's expression may be associated with a cancer. A cancer cell antigen may be abnormally expressed by a cancer cell (e.g. the cancer cell antigen may be expressed with abnormal localisation), or may be expressed with an abnormal structure by a cancer cell. A cancer cell antigen may be capable of eliciting an immune response. In some embodiments, the antigen is expressed at the cell surface of the cancer cell (i.e. the cancer cell antigen is a cancer cell surface antigen). In some embodiments, the part of the antigen which is bound by the antigen-binding molecule described herein is displayed on the external surface of the cancer cell (i.e. is extracellular). The cancer cell antigen may be a cancer-associated antigen. In some embodiments the cancer cell antigen is an antigen whose expression is associated with the development, progression or severity of symptoms of a cancer. The cancer-associated antigen may be associated with the cause or pathology of the cancer, or may be expressed abnormally as a consequence of the cancer. In some embodiments, the cancer cell antigen is an antigen whose expression is upregulated (e.g. at the RNA and/or protein level) by cells of a cancer, e.g. as compared to the level of expression by comparable noncancerous cells (e.g. non-cancerous cells derived from the same tissue/cell type). In some embodiments, the cancer-associated antigen may be preferentially expressed by cancerous cells, and not expressed by comparable non-cancerous cells (e.g. non-cancerous cells derived from the same tissue/cell type). In some embodiments, the cancer-associated antigen may be the product of a mutated oncogene or mutated tumor suppressor gene. In some embodiments, the cancer-associated antigen may be the product of an overexpressed cellular protein, a cancer antigen produced by an oncogenic virus, an oncofetal antigen, or a cell surface glycolipid or glycoprotein.

In some embodiments the antigen other than HER3 is an antigen expressed by cells of a HER3-associated cancer. A HER3-associated cancer may be a cancer expressing HER3 (e.g. expressing HER3 protein at the cell surface): such cancers may be referred to as "HER3-positive" cancers. HER3-associated cancers include cancers for which HER3 gene/protein expression is a risk factor for, and/or is positively associated with, the onset, development, progression or severity of symptoms of the cancer, and/or metastasis. HER3-associated cancers include those described in Zhang et al., Acta Biochimica et Biophysica Sinica (2016) 48(1): 39-48 and Sithanandam and Anderson Cancer Gene Ther (2003) 15(7):413-448, both of which are hereby incorporated by reference in their entirety. In some embodiments a HER3-associated cancer may be a lung cancer (e.g. NSCLC), melanoma, breast cancer, pancreatic cancer, prostate cancer, ovarian cancer, gastric cancer, colon cancer or oral cavity cancer.

An immune cell surface molecule may be any peptide/polypeptide, glycoprotein, lipoprotein, glycan, glycolipid, lipid, or fragment thereof expressed at or on the cell surface of an immune cell. In some embodiments, the part of the immune cell surface molecule which is bound by the antigen-binding molecule of the present invention is on the external surface of the immune cell (i.e. is extracellular). The immune cell surface molecule may be expressed at the cell surface of any immune cell. In some embodiments, the immune cell may be a cell of hematopoietic origin, e.g. a neutrophil, eosinophil, basophil, dendritic cell, lymphocyte, or monocyte. The lymphocyte may be e.g. a T cell, B cell, natural killer (NK) cell, NKT cell or innate lymphoid cell (ILO), or a precursor thereof (e.g. a thymocyte or pre-B cell). In some embodiments the immune cell surface molecule may be a costimulatory molecule (e.g. CD28, OX40, 4-1BB, ICOS or CD27) or a ligand thereof. In some embodiments the immune cell surface molecule may be a checkpoint molecule (e.g. PD-1, CTLA-4, LAG-3, TIM-3, VISTA, TIGIT or BTLA) or a ligand thereof.

Multispecific antigen-binding molecules according to the invention may be provided in any suitable format, such as those formats described in described in Brinkmann and Kontermann MAbs (2017) 9(2): 182-212, which is hereby incorporated by reference in its entirety. Suitable formats include those shown in FIG. 2 of Brinkmann and Kontermann MAbs (2017) 9(2): 182-212: antibody conjugates, e.g. IgG$_2$, F(ab')$_2$ or CovX-Body: IgG or IgG-like molecules, e.g. IgG, chimeric IgG, κλ-body common HC; CH1/CL fusion proteins, e.g. scFv2-CH1/CL, VHH2-CH1/CL: 'variable domain only' bispecific antigen-binding molecules, e.g. tandem scFv (taFV), triplebodies, diabodies (Db), dsDb, Db(kih), DART, scDB, dsFv-dsFv, tandAbs, triple heads, tandem dAb/VHH, tetravalent dAb.VHH; Non-Ig fusion proteins, e.g. scFv$_2$-albumin, scDb-albumin, taFv-albumin, taFv-toxin, miniantibody, DNL-Fab$_2$, DNL-Fab$_2$-scFv, DNL-Fab$_2$-IgG-cytokine$_2$, ImmTAC (TCR-scFv); modified Fc and CH3 fusion proteins, e.g. scFv-Fc(kih), scFv-Fc(CH3 charge pairs), scFv-Fc (EW-RVT), scFv-fc (HA-TF), scFv-Fc (SEEDbody), taFv-Fc(kih), scFv-Fc(kih)-Fv, Fab-Fc (kih)-scFv, Fab-scFv-Fc(kih), Fab-scFv-Fc(BEAT), Fab-scFv-Fc (SEEDbody), DART-Fc, scFv-CH3(kih), TriFabs; Fc fusions, e.g. Di-diabody, scDb-Fc, taFv-Fc, scFv-Fc-scFv, HCAb-VHH, Fab-scFv-Fc, scFv$_4$-Ig, scFv2-Fcab; CH3 fusions, e.g. Dia-diabody, scDb-CH3; IgE/IgM CH2 fusions, e.g. scFv-EHD2-scFv, scFvMHD2-scFv; Fab fusion proteins, e.g. Fab-scFv (bibody), Fab-scFv2 (tribody), Fab-Fv, Fab-dsFv, Fab-VHH, orthogonal Fab-Fab; non-Ig fusion proteins, e.g. DNL-Fab$_3$, DNL-Fab$_2$-scFv, DNL-Fab$_2$-IgG-cytokine$_2$; asymmetric IgG or IgG-like molecules, e.g. IgG (kih), IgG(kih) common LC, ZW1 IgG common LC, BicIonics common LC, CrossMab, CrossMab(kih), scFab-IgG(kih), Fab-scFab-IgG(kih), orthogonal Fab IgG(kih), DuetMab, CH3 charge pairs+CH1/CL charge pairs, hinge/CH3 charge pairs, SEED-body, Duobody, four-in-one-CrossMab(kih), LUZ-Y common LC; LUZ-Y scFab-IgG, FcFc*; appended and Fc-modified IgGs, e.g. IgG(kih)-Fv, IgG HA-TF-Fv, IgG(kih)scFab, scFab-Fc(kih)-scFv2, scFab-Fc(kih)-scFv, half DVD-Ig, DVI-Ig (four-in-one), CrossMab-Fab; modified Fc and CH3 fusion proteins, e.g. Fab-Fc(kih)-scFv, Fab-scFv-Fc(kih), Fab-scFv-Fc(BEAT), Fab-scFv-Fc-SEEDbody, TriFab; appended IgGs-HC fusions, e.g. IgG-HC, scFv, IgG-dAb, IgG-taFV, IgG-Cross-Fab, IgG-orthogonal Fab, IgG-(CαCβ) Fab, scFv-HC-IgG, tandem Fab-IgG (orthogonal Fab) Fab-IgG(CαCβ Fab), Fab-IgG(CR3), Fab-hinge-IgG(CR3); appended IgGs-LC fusions, e.g. IgG-scFv(LC), scFv(LC)-IgG, dAb-IgG; appended IgGs-HC and LC fusions, e.g. DVD-Ig, TVD-Ig, CODV-Ig, scFv$_4$-IgG, Zybody; Fc fusions, e.g. Fab-scFv-Fc, scFv$_4$-Ig; F(ab')2 fusions, e.g. F(ab')$_2$-scFv$_2$; CH1/CL fusion proteins e.g. scFv$_2$-CH1-hinge/CL; modified IgGs, e.g. DAF (two-in one-IgG), DutaMab, Mab$^2$; and non-Ig fusions, e.g. DNL-Fab$_4$-IgG.

The skilled person is able to design and prepare bispecific antigen-binding molecules. Methods for producing bispecific antigen-binding molecules include chemically cross-linking of antigen-binding molecules or antibody fragments, e.g. with reducible disulphide or non-reducible thioether bonds, for example as described in Segal and Bast, 2001. Production of Bispecific Antigen-binding molecules. Current Protocols in Immunology. 14:IV:2.13:2.13.1-2.13.16, which is hereby incorporated by reference in its entirety. For example, N-succinimidyl-3-(−2-pyridyldithio)-propionate (SPDP) can be used to chemically crosslink e.g. Fab fragments via hinge region SH— groups, to create disulfide-linked bispecific F(ab)$_2$ heterodimers.

Other methods for producing bispecific antigen-binding molecules include fusing antibody-producing hybridomas e.g. with polyethylene glycol, to produce a quadroma cell capable of secreting bispecific antibody, for example as described in D. M. and Bast, B. J. 2001. Production of Bispecific Antigen-binding molecules. Current Protocols in Immunology. 14:IV:2.13:2.13.1-2.13.16.

Bispecific antigen-binding molecules according to the present invention can also be produced recombinantly, by expression from e.g. a nucleic acid construct encoding polypeptides for the antigen-binding molecules, for example as described in Antibody Engineering: Methods and Protocols, Second Edition (Humana Press, 2012), at Chapter 40: Production of Bispecific Antigen-binding molecules: Diabodies and Tandem scFv (Hornig and Färber-Schwarz), or French, How to make bispecific antigen-binding molecules, Methods Mol. Med. 2000; 40:333-339, the entire contents of both of which are hereby incorporated by reference. For example, a DNA construct encoding the light and heavy chain variable domains for the two antigen-binding fragments (i.e. the light and heavy chain variable domains for the antigen-binding fragment capable of binding HER3, and the light and heavy chain variable domains for the antigen-binding fragment capable of binding to another target protein), and including sequences encoding a suitable linker or dimerization domain between the antigen-binding fragments can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Fc Regions

In some embodiments the antigen-binding molecules of the present invention comprise an Fc region.

In IgG, IgA and IgD isotypes an Fc region is composed of CH2 and CH3 regions from one polypeptide, and CH2 and CH3 regions from another polypeptide. The CH2 and CH3 regions from the two polypeptides together form the Fc region. In IgM and IgE isotypes the Fc regions contain three constant domains (CH2, CH3 and CH4), and CH2 to CH4 from the two polypeptides together form the Fc region.

In preferred embodiments in accordance with the various aspects of the present disclosure an Fc region comprises two polypeptides, each polypeptide comprising a CH2 region and a CH3 region.

In some embodiments, the antigen-binding molecule of the present invention comprises an Fc region comprising modification in one or more of the CH2 and CH3 regions promoting association of the Fc region. Recombinant co-expression of constituent polypeptides of an antigen-binding molecule and subsequent association leads to several possible combinations. To improve the yield of the desired combinations of polypeptides in antigen-binding molecules in recombinant production, it is advantageous to introduce in the Fc regions modification(s) promoting association of the desired combination of heavy chain polypeptides. Modifications may promote e.g. hydrophobic and/or electrostatic interaction between CH2 and/or CH3 regions of different polypeptide chains. Suitable modifications are described e.g. in Ha et al., Front. Immnol (2016) 7:394, which is hereby incorporated by reference in its entirety.

In some embodiments the antigen-binding molecule of the present invention comprises an Fc region comprising paired substitutions in the CH3 regions of the Fr region according to one of the following formats, as shown in Table 1 of Ha et al., Front. Immnol (2016) 7:394: KiH, KiH$_{s\text{-}s}$, HA-TF, ZW1, 7.8.60 DD-KK, EW-RVT, EW-RVT$_{s\text{-}s}$, SEED or A107.

In some embodiments, the Fc region comprises the "knob-into-hole" or "KiH" modification, e.g. as described e.g. in U.S. Pat. No. 7,695,936 and Carter, J Immunol Meth 248, 7-15 (2001). In such embodiments, one of the CH3 regions of the Fc region comprises a "knob" modification, and the other CH3 region comprises a "hole" modification. The "knob" and "hole" modifications are positioned within the respective CH3 regions so that the "knob" can be positioned in the "hole" in order to promote heterodimerisation (and inhibit homodimerisation) of the polypeptides and/or stabilise heterodimers. Knobs are constructed by substituting amino acids having small chains with those having larger side chains (e.g. tyrosine or tryptophan). Holes are created by substituting amino acids having large side chains with those having smaller side chains (e.g. alanine or threonine).

In some embodiments, one of the CH3 regions of the Fc region of the antigen-binding molecule of the present invention comprises the substitution (numbering of positions/substitutions in the Fc, CH2 and CH3 regions herein is according to the EU numbering system as described in Kabat et al., Sequences of Proteins of Immunological Interest, 5th Ed. Public Health Service, National Institutes of Health, Bethesda, Md., 1991) T366W, and the other CH3 region of the Fc region comprises the substitution Y407V. In some embodiments, one of the CH3 regions of the Fc region of the antigen-binding molecule comprises the substitution T366W, and the other CH3 region of the Fc region comprises the substitutions T366S and L368A. In some embodiments, one of the CH3 regions of the Fc region of the antigen-binding molecule comprises the substitution T366W, and the other CH3 region of the Fc region comprises the substitutions Y407V, T366S and L368A.

In some embodiments, the Fc region comprises the "DD-KK" modification as described e.g. in WO 2014/131694 A1. In some embodiments, one of the CH3 regions comprises the substitutions K392D and K409D, and the other CH3 region of the Fc region comprises the substitutions E356K and D399K. The modifications promote electrostatic interaction between the CH3 regions.

In some embodiments, the antigen-binding molecule of the present invention comprises an Fc region modified as described in Labrijn et al., Proc Natl Acad Sci USA. (2013) 110(13):5145-50, referred to as 'Duobody' format. In some embodiments one of the CH3 regions comprises the substitution K409R, and the other CH3 region of the Fc region comprises the substitution K405L.

In some embodiments, the antigen-binding molecule of the present invention comprises an Fc region comprising the "EEE-RRR" modification as described in Strop et al., J Mol Biol. (2012) 420(3):204-19. In some embodiments one of the CH3 regions comprises the substitutions D221E, P228E and L368E, and the other CH3 region of the Fc region comprises the substitutions D221R, P228R and K409R.

In some embodiments, the antigen-binding molecule comprises an Fc region comprising the "EW-RVT" modification described in Choi et al., Mol Cancer Ther (2013) 12(12):2748-59. In some embodiments one of the CH3 regions comprises the substitutions K360E and K409W, and the other CH3 region of the Fc region comprises the substitutions Q347R, D399V and F405T.

In some embodiments, one of the CH3 regions comprises the substitution S354C, and the other CH3 region of the Fc region comprises the substitution Y349C. Introduction of these cysteine residues results in formation of a disulphide bridge between the two CH3 regions of the Fc region, fruitier stabilizing the heterodimer (Carter (2001), J Immunol Methods 248, 7-15).

In some embodiments, the Fc region comprises the "KiH$_{s\text{-}s}$" modification. In some embodiments one of the CH3 regions comprises the substitutions T366W and S354C, and the other CH3 region of the Fc region comprises the substitutions T366S, L368A, Y407V and Y349C.

In some embodiments, the antigen-binding molecule of the present invention comprises an Fc region comprising the "SEED" modification as described in Davis et al., Protein Eng Des Sel (2010) 23(4):195-202, in which β-strand segments of human IgG1 CH3 and IgA CH3 are exchanged.

In some embodiments, one of the CH3 regions comprises the substitutions S364H and F405A, and the other CH3 region of the Fc region comprises the substitutions Y349T and T394F (see e.g. Moore et al., MAbs (2011) 3(6):546-57).

In some embodiments, one of the CH3 regions comprises the substitutions T350V, L351Y, F405A and Y407V, and the other CH3 region of the Fc region comprises the substitutions T350V, T366L, K392L and T394W (see e.g. Von Kreudenstein et al., MAbs (2013) 5(5):646-54).

In some embodiments, one of the CH3 regions comprises the substitutions K360D, D399M and Y407A, and the other CH3 region of the Fc region comprises the substitutions E345R, Q347R, T366V and K409V (see e.g. Leaver-Fay et al., Structure (2016) 24(4):641-51).

In some embodiments, one of the CH3 regions comprises the substitutions K370E and K409W, and the other CH3 region of the Fc region comprises the substitutions E357N, D399V and F405T (see e.g. Choi et al., PLoS One (2015) 10(12):e0145349).

Fc-mediated functions include Fc receptor binding, antibody-dependent cellular cytotoxicity (ADCC), antibody-dependent cell-mediated phagocytosis (ADCP), complement-dependent cytotoxicity (CDC), formation of the membrane attack complex (MAC), cell degranulation, cytokine and/or chemokine production, and antigen processing and presentation.

Modifications to antibody Fc regions that influence Fc-mediated functions are known in the art, such as those described e.g. in Wang et al., Protein Cell (2018) 9(1):63-73, which is hereby incorporated by reference in its entirety. Exemplary Fc region modifications known to influence antibody effector function are summarised in Table 1 of Wang et al., Protein Cell (2018) 9(1):63-73.

The combination of substitutions F243L/R292P/Y300L/V305I/P396L is described in Stavenhagen et al. Cancer Res. (2007) to increase binding to FcγRIIIa, and thereby enhance ADCC. The combination of substitutions S239D/I332E or S239D/I332E/A330L is described in Lazar et al., Proc Natl Acad Sci USA. (2006) 103:4005-4010 to increase binding to FcγRIIIa, and thereby increase ADCC. The combination of substitutions S239D/I332E/A330L is also described to decrease binding to FcγRIIb, and thereby increase ADCC. The combination of substitutions S298A/E333A/K334A is described in Shields et al., J Biol Chem. (2001) 276:6591-6604 to increase binding to FcγRIIIa, and thereby increase ADCC. The combination of substitutions L234Y/L235Q/G236W/S239M/H268D/D270E/S298A in one heavy chain, and the combination of substitutions D270E/K326D/A330M/K334E in the other heavy chain, is described in Mimoto et al., MAbs. (2013): 5:229-236 to increase binding to FcγRIIIa, and thereby increase ADCC. The combination of substitutions G236A/S239D/I332E is described in Richards et al., Mol Cancer Ther. (2008) 7:2517-2527 to increase binding to FcγRIIa and to increase binding to FcγRIIIa, and thereby increase ADCP.

The combination of substitutions K326W/E333S is described in Idusogie et al. J Immunol. (2001) 166(4):2571-5 to increase binding to C1q, and thereby increase CDC. The combination of substitutions S267E/H268F/S324T is described in Moore et al. MAbs. (2010) 2(2):181-9 to increase binding to C1q, and thereby increase CDC. The combination of substitutions described in Natsume et al., Cancer Res. (2008) 68(10):3863-72 is reported to increase binding to C1q, and thereby increase CDC. The combination of substitutions E345R/E430G/S440Y is described in Dieboider et al. Science (2014) 343(6176):1260-3 to increase hexamerisation, and thereby increase CDC.

The combination of substitutions M252Y/S254T/T256E is described in Dall'Acqua et al. J Immunol. (2002) 169:5171-5180 to increase binding to FcRn at pH 6.0, and thereby increase antigen-binding molecule half-life. The combination of substitutions M428L/N434S is described in Zalevsky et al. Nat Biotechnol. (2010) 28:157-159 to increase binding to FcRn at pH 6.0, and thereby increase antigen-binding molecule half-life.

Where a heavy chain constant region/Fc region/CH2-CH3 region/CH2 region/CH3 region is described herein as comprising position(s)/substitution(s) "corresponding to" reference positions) sub equivalent position(s)/substitution(s) in homologous heavy chain constant regions/Fc regions/CH2-CH3 regions/CH2 regions/CH3 regions are contemplated.

Where an Fc region is described as comprising specific position(s)/substitution(s), the position(s)/substitution(s) may be present in one or both of the polypeptide chains which together form the Fc region.

Unless otherwise specified, positions herein refer to positions of human immunoglobulin constant region amino acid sequences numbered according to the EU numbering system as described in Kabat et al., Sequences of Proteins of Immunological Interest, 5th Ed. Public Health Service, National Institutes of Health, Bethesda, Md., 1991. By way of illustration, the substitutions L242C and K334C in human IgG1 correspond to L>C substitution at position 125, and K>C substitution at position 217 of the human IgG1 constant region numbered according to SEQ ID NO:171.

Homologous heavy chain constant regions are heavy chain constant regions comprising an amino acid sequence having at least 60%, preferably one of 70%, 75%, 80%, 85%, 90%, 91%, 92%, 93%, 94%, 95%, 96%, 97%, 98%, 99% or 100% amino acid sequence identity to the heavy chain constant region of Human IgG1 (i.e. the amino acid sequence shown in SEQ ID NO:171). Homologous Fc regions are Fc regions comprised of polypeptides comprising an amino acid sequence having at least 60%, preferably one of 70%, 75%, 80%, 85%, 90%, 91%, 92%, 93%, 94%, 95%, 96%, 97%, 98%, 99% or 100% amino acid sequence identity to CH2-CH3 region of Human IgG1 (i.e. the amino acid sequences shown in SEQ ID NO:174 and 175). Homologous CH2 regions are CH2 regions comprising an amino acid sequence having at least 60%, preferably one of 70%, 75%, 80%, 85%, 90%, 91%, 92%, 93%, 94%, 95%, 96%, 97%, 98%, 99% or 100% amino acid sequence identity to CH2 region of Human IgG1 (i.e. the amino acid sequence shown in SEQ ID NO:174). Homologous CH3 regions are CH3 regions comprising an amino acid sequence having at least 60%, preferably one of 70%, 75%, 80%, 85%, 90%, 91%, 92%, 93%, 94%, 95%, 96%, 97%, 98%, 99% or 100% amino acid sequence identity to CH3 region of Human IgG1 (i.e. the amino acid sequence shown in SEQ ID NO:175).

Corresponding positions to those identified in human IgG1 can be identified by sequence alignment which can be performed e.g. using sequence alignment software such as ClustalOmega (Söding, J. 2005, Bioinformatics 21, 951-960).

In some embodiments the antigen-binding molecule of the present invention comprises an Fc region comprising modification to increase an Fc-mediated function. In some embodiments the Fc region comprises modification to increase ADCC. In some embodiments the Fc region comprises modification to increase ADCP. In some embodiments the Fc region comprises modification to increase CDC. An antigen-binding molecule comprising an Fc region comprising modification to increase an Fc-mediated function (e.g. ADCC, ADCP, CDC) induces an increased level of the relevant effector function as compared to an antigen-binding molecule comprising the corresponding unmodified Fc region.

In some embodiments, the antigen-binding molecule of the present invention comprises an Fc region comprising modification to increase affinity for one or more Fc receptors (e.g. FcγRIIa, FcγRIIIa). Modifications increasing affinity for Fc receptors can increase Fc-mediated effector function such as antibody-dependent cellular cytotoxicity (ADCC) and/or antibody-dependent cellular phagocytosis (ADCP). In some embodiments, the antigen-binding molecule of the present invention comprises an Fc region comprising modification to reduce affinity for C1q; such modification reducing complement-dependent cytotoxicity (CDC), which can be desirable. In some embodiments, the antigen-binding molecule of the present invention comprises an Fc region comprising modification to increase hexamer formation. Modifications to the Fc region capable of increasing affinity for one or more Fc receptors, reducing affinity for C1q and/or increasing hexamer formation are described e.g. in Saxena and Wu Front Immunol. (2016) 7:580, which is hereby incorporated by reference in its entirety. In some embodiments the antigen-binding molecule of the present invention comprises an Fc region comprising CH2/CH3 comprising one or more of the substitutions shown in Table 1 of Saxena and Wu Front Immunol. (2016) 7:580.

In some embodiments the antigen-binding molecule of the present invention comprises an Fc comprising modification to increase binding to an Fc receptor. In some embodiments the Fc region comprises modification to increase binding to an Fcγ receptor. In some embodiments the Fc region comprises modification to increase binding to one or more of FcγRI, FcγRIIa, FcγRIIb, FcγRIIc, FcγRIIIa and FcγRIIIb. In some embodiments the Fc region comprises modification to increase binding to FcγRIIIa. In some embodiments the Fc region comprises modification to increase binding to FcγRIIa. In some embodiments the Fc region comprises modification to increase binding to FcγRIIb. In some embodiments the Fc region comprises modification to increase binding to FcRn. In some embodiments the Fc region comprises modification to increase binding to a complement protein. In some embodiments the Fc region comprises modification to increase or reduce binding to C1q. In some embodiments the Fc region comprises modification to promote hexamerisation of the antigen-binding molecule. In some embodiments the Fc region comprises modification to increase antigen-binding molecule half-life. In some embodiments the Fc region comprises modification to increase co-engagement.

In this specification an "Fcγ receptor" may be from any species, and includes isoforms, fragments, variants (including mutants) or homologues from any species. Similarly, "FcγRI", "FcγRIIa", "FcγRIIb", "FcγRIIc", "FcγRIIIa" and "FcγRIIIb" refer respectively to FcγRI/FcγRIIa/FcγRIIb/FcγRIIc/FcγRIIIa/FcγRIIIb from any species, and include isoforms, fragments, variants (including mutants) or homologues from any species. Humans have six different classes of Fcγ receptor (mouse orthologues are shown in brackets): FcγRI (mFcγRI), FcγRIIa (mFcγRIII), FcγRIIb (mFcγRIIb), FcγRIIc, FcγRIIIa (mFcγRIV) and FcγRIIIb. Variant Fcγ receptors include e.g. the 158V and 158F polymorphs of human FcγRIIIa, and the 167H and 167R polymorphs of human FcγRIIa.

In some embodiments the antigen-binding molecule of the present invention comprises an Fc region comprising (e.g. comprising one more polypeptides comprising a heavy chain constant region, or a CH2-CH3 region, comprising) one or more (e.g. 1, 2, 3, 4, 5, 6, 7 or 8) of the following: C at the position corresponding to position 242; C at the position corresponding to position 334; A at the position corresponding to position 236; D at the position corresponding to position 239; E at the position corresponding to position 332; L at the position corresponding to position 330; K at the position corresponding to position 345; and G at the position corresponding to position 430.

In some embodiments the antigen-binding molecule of the present invention comprises an Fc region comprising (e.g. comprising one more polypeptides comprising a heavy chain constant region, or a CH2-CH3 region, comprising) one or more (e.g. 1, 2, 3, 4, 5, 6, 7 or 8) of the following substitutions (or corresponding substitutions): L242C, K334C, G236A, S239D, I332E, A330L, E345K, and E430G.

In some embodiments the antigen-binding molecule comprises an Fc region comprising (e.g. comprising one more polypeptides comprising a heavy chain constant region, a CH2-CH3 region, or a CH2 region, comprising) a C at the position corresponding to position 242. In some embodiments the Fc region comprises (e.g. comprises one more polypeptides comprising a heavy chain constant region, a CH2-CH3 region, or a CH2 region, comprising) a C at the position corresponding to position 334. In some embodiments the Fc region comprises (e.g. comprises one more polypeptides comprising a heavy chain constant region, a CH2-CH3 region, or a CH2 region, comprising) a C at the position corresponding to position 242 and a C at the position corresponding to position 334.

In some embodiments the antigen-binding molecule comprises an Fc region comprising (e.g. comprising one more polypeptides comprising a heavy chain constant region, a CH2-GFH region, or a CH2 region, comprising) an A at the position corresponding to position 236. In some embodiments the Fc region comprises (e.g. comprises one more polypeptides comprising a heavy chain constant region, a CH2-CH3 region, or a CH2 region, comprising) a D at the position corresponding to position 239. In some embodiments the Fc region comprises (e.g. comprises one more polypeptides comprising a heavy chain constant region, a CH2-CH3 region, or a CH2 region, comprising) an A at the position corresponding to position 236, and a D at the position corresponding to position 239.

In some embodiments the antigen-binding molecule comprises an Fc region comprising (e.g. comprising one more polypeptides comprising a heavy chain constant region, a CH2-CH3 region, or a CH2 region, comprising) an E at the position corresponding to position 332. In some embodiments the Fc region comprises (e.g. comprises one more polypeptides comprising a heavy chain constant region, a CH2-CH3 region, or a CH2 region, comprising) an A at the position corresponding to position 236, a D at the position corresponding to position 239, and an E at the position corresponding to position 332.

In some embodiments the antigen-binding molecule comprises an Fc region comprising (e.g. comprising one more polypeptides comprising a heavy chain constant region, a CH2-CH3 region, or a CH2 region, comprising) an L at the position corresponding to position 330. In some embodiments the Fc region comprises (e.g. comprises one more polypeptides comprising a heavy chain constant region, a CH2-CH3 region, or a CH2 region, comprising) an A at the position corresponding to position 236, a D at the position corresponding to position 239, an E at the position corresponding to position 332, and an L at the position corresponding to position 330.

In some embodiments the antigen-binding molecule comprises an Fc region comprising (e.g. comprising one more polypeptides comprising a heavy chain constant region, a CH2-CH3 region, or a CH3 region, comprising) a K at the position corresponding to position 345. In some embodiments the Fc region comprises (e.g. comprises one more polypeptides comprising a heavy chain constant region, a CH2-CH3 region, or a CH3 region, comprising) a G at the position corresponding to position 430. In some embodiments the Fc region comprises (e.g. comprises one more polypeptides comprising a heavy chain constant region, a CH2-CH3 region, or a CH2 region, comprising) a K at the position corresponding to position 345, and a G at the position corresponding to position 430.

In some embodiments the antigen-binding molecule comprises an Fc region comprising (e.g. comprising one more polypeptides comprising a heavy chain constant region, a CH2-CH3 region, or a CH2 region, comprising) a C at the position corresponding to position 242, a C at the position corresponding to position 334, an A at the position corresponding to position 236, and a D at the position corresponding to position 239.

In some embodiments the antigen-binding molecule comprises an Fc region comprising (e.g. comprising one more polypeptides comprising a heavy chain constant region, a CH2-CH3 region, or a CH2 region, comprising) a C at the position corresponding to position 242, a C at the position corresponding to position 334, an A at the position corresponding to position 236, a D at the position corresponding to position 239, and an E at the position corresponding to position 332.

In some embodiments the antigen-binding molecule comprises an Fc region comprising (e.g. comprising one more polypeptides comprising a heavy chain constant region, a CH2-CH3 region, or a CH2 region, comprising) a C at the position corresponding to position 242, a C at the position corresponding to position 334, an A at the position corresponding to position 236, a D at the position corresponding to position 239, an E at the position corresponding to position 332, and an L at the position corresponding to position 330.

In some embodiments the antigen-binding molecule comprises an Fc region comprising (e.g. comprising one more polypeptides comprising a heavy chain constant region, or a CH2-CH3 region, comprising) a C at the position corresponding to position 242, a C at the position corresponding to position 334, a K at the position corresponding to position 345, and a G at the position corresponding to position 430.

In some embodiments the antigen-binding molecule comprises an Fc region comprising (e.g. comprising one more polypeptides comprising a heavy chain constant region, a CH2-CH3 region, or a CH2 region, comprising) the substitution L242C (or an equivalent substitution). In some embodiments the Fc region comprises (e.g. comprises one more polypeptides comprising a heavy chain constant region, a CH2-CH3 region, or a CH2 region, comprising) the substitution K334C (or an equivalent substitution). In some embodiments the Fc region comprises (e.g, comprises one more polypeptides comprising a heavy chain constant region, a CH2-CH3 region, or a CH2 region, comprising) the substitution L242C (or an equivalent substitution) and the substitution K334C (or an equivalent substitution).

In some embodiments the antigen-binding molecule comprises an Fc region comprising (e.g. comprising one more polypeptides comprising a heavy chain constant region, a CH2-CH3 region, or a CH2 region, comprising) the substitution G236A (or an equivalent substitution). In some embodiments the Fc region comprises (e.g. comprises one more polypeptides comprising a heavy chain constant region, a CH2-CH3 region, or a CH2 region, comprising) the substitution S239D (or an equivalent substitution). In some embodiments the Fc region comprises (e.g. comprises one more polypeptides comprising a heavy chain constant region, a CH2-CH3 region, or a CH2 region, comprising) the substitution G236A (or an equivalent substitution), and the substitution S239D (or an equivalent substitution).

In some embodiments the antigen-binding molecule comprises an Fc region comprising (e.g. comprising one more polypeptides comprising a heavy chain constant region, a CH2-CH3 region, or a CH2 region, comprising) the substitution I332E (or an equivalent substitution). In some embodiments the Fc region comprises (e.g. comprises one more polypeptides comprising a heavy chain constant region, a CH2-CH3 region, or a CH2 region, comprising) the substitution G236A (or an equivalent substitution), the substitution S239D (or an equivalent substitution), and the substitution I332E (or an equivalent substitution).

In some embodiments the antigen-binding molecule comprises an Fc region comprising (e.g, comprising one more polypeptides comprising a heavy chain constant region, a CH2-CH3 region, or a CH2 region, comprising) the substitution A330L (or an equivalent substitution). In some embodiments the Fc region comprises (e.g. comprises one more polypeptides comprising a heavy chain constant region, a CH2-CH3 region, or a CH2 region, comprising) the substitution G236A (or an equivalent substitution), the substitution S239D (or an equivalent substitution), the substitution I332E (or an equivalent substitution), and the substitution A330L (or an equivalent substitution).

In some embodiments the antigen-binding molecule comprises an Fc region comprising (e.g. comprising one more polypeptides comprising a heavy chain constant region, a CH2-CH3 region, or a CH3 region, comprising) the substitution E345K (or an equivalent substitution). In some embodiments the Fc region comprises (e.g. comprises one more polypeptides comprising a heavy chain constant region, a CH2-CH3 region, or a CH3 region, comprising) the substitution E430G (or an equivalent substitution). In some embodiments the Fc region comprises (e.g. comprises one more polypeptides comprising a heavy chain constant region, a CH2-CH3 region, or a CH2 region, comprising) the substitution E345K (or an equivalent substitution), and the substitution E430G (or an equivalent substitution).

In some embodiments the antigen-binding molecule comprises an Fc region comprising (e.g. comprising one more polypeptides comprising a heavy chain constant region, a CH2-CH3 region, or a CH2 region, comprising) the substitution L242C (or an equivalent substitution), the substitution K334C (or an equivalent substitution), the substitution G236A (or an equivalent substitution), and the substitution S239D (or an equivalent substitution).

In some embodiments the antigen-binding molecule comprises an Fc region comprising (e.g. comprising one more polypeptides comprising a heavy chain constant region, a CH2-CH3 region, or a CH2 region, comprising) the substitution L242C (or an equivalent substitution), the substitution K334C (or an equivalent substitution), the substitution G236A (or an equivalent substitution), the substitution S239D (or an equivalent substitution), and the substitution I332E (or an equivalent substitution).

In some embodiments the antigen-binding molecule comprises an Fc region comprising (e.g. comprising one more polypeptides comprising a heavy chain constant region, a CH2-CH3 region, or a CH2 region, comprising) the substitution L242C (or an equivalent substitution), the substitution K334C (or an equivalent substitution), the substitution G236A (or an equivalent substitution), the substitution S239D (or an equivalent substitution), the substitution I332E (or an equivalent substitution), and the substitution A330L (or an equivalent substitution).

In some embodiments the antigen-binding molecule comprises an Fc region comprising (e.g. comprising one more polypeptides comprising a heavy chain constant region, or a CH2-CH3 region, comprising) the substitution L242C (or an equivalent substitution), the substitution K334C (or an equivalent substitution), the substitution E345K (or an equivalent substitution), and the substitution E430G (or an equivalent substitution).

In some embodiments the antigen-binding molecule comprises an Fc region comprising (e.g. comprising one more polypeptides comprising a heavy chain constant region, or a CH2-CH3 region, comprising) one or more (e.g. 1, 2, 3, 4, 5, 6, 7, 8, 9, 10, 11 or 12) of the following: L at the position corresponding to position 243, P at the position corresponding to position 292, L at the position corresponding to position 300, 1 at the position corresponding to position 305 and L at the position corresponding to position 396; at the position corresponding to position 239 and E at the position corresponding to position 332; 0 at the position corresponding to position 239, E at the position corresponding to position 332 and L at the position corresponding to position 330; A at the position corresponding to position 298, A at the position corresponding to position 333 and A at the position corresponding to position 334; Y at the position corresponding to position 234, Q at the position corresponding to position 235, W at the position corresponding to position 236, M at the position corresponding to position 239, D at the position corresponding to position 268, E at the position corresponding to position 270 and A at the position corresponding to position 298; E at the position corresponding to position 270, D at the position corresponding to position 326, M at the position corresponding to position 330 and E at the position corresponding to position 334; A at the position corresponding to position 236, D at the position corresponding to position 239 and E at the position corresponding to position 332; W at the position corresponding to position 326 and S at the position corresponding to position 333; E at the position corresponding to position 267, F at the position corresponding to position 268 and T at the position corresponding to position 324; R at the position corresponding to position 345, G at the position corresponding to position 430 and Y at the position corresponding to position 440; Y at the position corresponding to position 252, T at the position corresponding to position 254 and E at the position corresponding to position 256, and L at the position corresponding to position 428 and S at the position corresponding to position 434.

In some embodiments the antigen-binding molecule comprises an Fc region comprising (e.g. comprising one more polypeptides comprising a heavy chain constant region, or a CH2-CH3 region, comprising) one or more (e.g. 1, 2, 3, 4, 5, 6, 7, 8, 9, 10, 11 or 12) of the following combinations of substitutions (or corresponding substitutions): F243L/R292P/Y300L/V305I/P396L; S239D/I332E; S239D/I332E/A330L; S298A/E333A/K334A; L234Y/L235Q/G236W/S239M/H268D/D270E/S298A; D270E/K326D/A330M/K334E; G238A/S239D/I332E; K326W/E333S; S287E/H288F/S324T; E345R/E430G/S440Y; M252Y/S254T/T256E; and M428L/N434S.

Polypeptides

The present invention also provides polypeptide constituents of antigen-binding molecules. The polypeptides may be provided in isolated or substantially purified form.

The antigen-binding molecule of the present invention may be, or may comprise, a complex of polypeptides.

In the present specification where a polypeptide comprises more than one domain or region, it will be appreciated that the plural domains/regions are preferably present in the same polypeptide chain. That is, the polypeptide comprises more than one domain or region is a fusion polypeptide comprising the domains/regions.

In some embodiments a polypeptide according to the present invention comprises, or consists of, a VH as described herein. In some embodiments a polypeptide according to the present invention comprises, or consists of, a VL as described herein.

In some embodiments, the polypeptide additionally comprises one or more antibody heavy chain constant regions (CH). In some embodiments, the polypeptide additionally comprises one or more antibody light chain constant regions (CL). In some embodiments, the polypeptide comprises a CH1, CH2 region and/or a CH3 region of an immunoglobulin (Ig).

In some embodiments the polypeptide comprises one or more regions of an immunoglobulin heavy chain constant sequence. In some embodiments the polypeptide comprises a CH1 region as described herein. In some embodiments the polypeptide comprises a CH1-CH2 hinge region as described herein. In some embodiments the polypeptide comprises a CH2 region as described herein. In some embodiments the polypeptide comprises a CH3 region as described herein. In some embodiments the polypeptide comprises a CH2-CH3 region as described herein.

In some embodiments the polypeptide comprises a CH3 region comprising any one of the following amino acid substitutions/combinations of amino acid substitutions (shown e.g. in Table 1 of Ha et al., Front. Immnol (2016) 7:394, incorporated by reference hereinabove): T366W; T366S, L368A and Y407V; T366W and S354C; T366S, L368A, Y407V and Y349C; S364H and F405A; Y349T and T394F, T350V, L351Y, F405A and Y407V; T350V, T366L, K392L and T394W: K360D, D399M and Y407A; E345R, Q347R, T366V and K409V; K409D and K392D; D399K and E356K; K360E and K409W; Q347R, D399V and F405T; K360E, K409W and Y349C; Q347R, D399V, F405T and S354C; K370E and K409W, and E357N, D399V and F405T.

In some embodiments the CH2 and/or CH3 regions of the polypeptide comprise one or more amino acid substitutions for promoting association of the polypeptide with another polypeptide comprising a CH2 and/or CH3 region.

In some embodiments the polypeptide comprises one or more regions of an immunoglobulin light chain constant sequence. In some embodiments the polypeptide comprises a CL region as described herein.

In some embodiments, the polypeptide according to the present invention comprises a structure from N- to C-terminus according to one of the following:

(i) VH
(ii) VL
(iii) VH-CH1
(iv) VL-CL
(v) VL-CH1
(vi) VH-CL
(vii) VH-CH1-CH2-CH3
(viii) VL-CL-CH2-CH3
(ix) VL-CH1-CH2-CH3
(x) VH-CL-CH2-CH3

Also provided by the present invention are antigen-binding molecules composed of the polypeptides of the present invention. In some embodiments, the antigen-binding molecule of the present invention comprises one of the following combinations of polypeptides:

(A) VH+VL
(B) VH-CH1+VL-CL
(C) VL-CH1+VH-CL
(D) VH-CH1-CH2-CH3+VL-CL
(E) VH-CL-CH2-CH3+VL-CH1
(F) VL-CH1-CH2-CH3+VH-CL
(G) VL-CL-CH2-CH3+VH-CH1
(H) VH-CH1-CH2-CH3+VL-CL-CH2-CH3
(I) VH-CL-CH2-CH3+VL-CH1-CH2-CH3

In some embodiments the antigen-binding molecule comprises more than one of a polypeptide of the combinations shown in (A) to (I) above. By way of example, with reference to (D) above, in some embodiments the antigen-binding molecule comprises two polypeptides comprising the structure VH-CH1-CH2-CH3, and two polypeptides comprising the structure VL-CL.

In some embodiments, the antigen-binding molecule of the present invention comprises one of the following combinations of polypeptides:

(J) VH (anti-HER3)+VL (anti-HER3)
(K) VH (anti-HER3)-CH1+VL (anti-HER3)-CL
(L) VL (anti-HER3)-CH1+VH (anti-HER3)-CL
(M) VH (anti-HER3)-CH1-CH2-CH3+VL (anti-HER3)-CL
(N) VH (anti-HER3)-CL-CH2-CH3+VL (anti-HER3)-CH1
(O) VL (anti-HER3)-CH1-CH2-CH3+VH (anti-HER3)-CL
(P) VL (anti-HER3)-CL-CH2-CH3+VH (anti-HER3)-CH1
(Q) VH (anti-HER3)-CH1-CH2-CH3+VL (anti-HER3)-CL-CH2-CH3
(R) VH (anti-HER3)-CL-CH2-CH3+VL (anti-HER3)-CH1-CH2-CH3

Wherein: "VH(anti-HER3)" refers to the VH of an antigen-binding molecule capable of binding to HER3 as described herein, e.g. as defined in one of (1) to (61) above; "VL(anti-HER3)" refers to the VL of an antigen-binding molecule capable of binding to HER3 as described herein, e.g. as defined in one of (62) to (119) above.

In some embodiments the polypeptide comprises or consists of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of one of SEQ ID NOs:187 to 223.

Linkers and Additional Sequences

In some embodiments the antigen-binding molecules and polypeptides of the present invention comprise a hinge region. In some embodiments a hinge region is provided between a CH1 region and a CH2 region. In some embodiments a hinge region is provided between a CL region and a CH2 region. In some embodiments the hinge region comprises, or consists of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:173.

In some embodiments the antigen-binding molecules and polypeptides of the present invention comprise one or more linker sequences between amino acid sequences. A linker sequence may be provided at one or both ends of one or more of a VH, VL, CH1-CH2 hinge region, CH2 region and a CH3 region of the antigen-binding molecule/polypeptide.

Linker sequences are known to the skilled person, and are described, for example in Chen et al., Adv Drug Deliv Rev (2013) 65(10): 1357-136$, which is hereby incorporated by reference in its entirety. In some embodiments, a linker sequence may be a flexible linker sequence. Flexible linker sequences allow for relative movement of the amino acid sequences which are linked by the linker sequence. Flexible linkers are known to the skilled person, and several are identified in Chen et al., Adv Drug Deliv Rev (2013) 65(10): 1357-1369. Flexible linker sequences often comprise high proportions of glycine and/or serine residues.

In some embodiments, the linker sequence comprises at least one glycine residue and/or at least one serine residue. In some embodiments the linker sequence consists of glycine and serine residues. In some embodiments, the linker sequence has a length of 1-2, 1-3, 1-4, 1-5 or 1-10 amino acids.

The antigen-binding molecules and polypeptides of the present invention may additionally comprise further amino acids or sequences of amino acids. For example, the antigen-binding molecules and polypeptides may comprise amino acid sequence(s) to facilitate expression, folding, trafficking, processing, purification or detection of the antigen-binding molecule/polypeptide. For example, the antigen-binding molecule/polypeptide may comprise a sequence encoding a His, (e.g. 6×His), Myc, GST, MBP, FLAG, HA, E, or Biotin tag, optionally at the N- or C-terminus of the antigen-binding molecule/polypeptide. In some embodiments the antigen-binding molecule/polypeptide comprises a detectable moiety, e.g. a fluorescent, luminescent, immuno-detectable, radio, chemical, nucleic acid or enzymatic label.

The antigen-binding molecules and polypeptides of the present invention may additionally comprise a signal peptide (also known as a leader sequence or signal sequence). Signal peptides normally consist of a sequence of 5-30 hydrophobic amino acids, which form a single alpha helix. Secreted proteins and proteins expressed at the cell surface often comprise signal peptides.

The signal peptide may be present at the N-terminus of the antigen-binding molecule/polypeptide, and may be present in the newly synthesised antigen-binding molecule/polypeptide. The signal peptide provides for efficient trafficking and secretion of the antigen-binding molecule/polypeptide. Signal peptides are often removed by cleavage, and thus are not comprised in the mature antigen-binding molecule/polypeptide secreted from the cell expressing the antigen-binding molecule/polypeptide.

Signal peptides are known for many proteins, and are recorded in databases such as GenBank, UniProt, Swiss-Prot, TrEMBL, Protein Information Resource, Protein Data Bank, Ensembl, and InterPro, and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

In some embodiments, the signal peptide of the antigen-binding molecule/polypeptide of the present invention comprises, or consists of, an amino acid sequence having at least 80%, 85% 86%, 87%, 88%, 89%, 90%, 91%, 92%, 93%, 94%, 95%, 96%, 97%, 98%, 99%, or 100% sequence identity to the amino acid sequence of one of SEQ ID NOs:178 to 186.

Labels and Conjugates

In some embodiments the antigen-binding molecules of the present invention additionally comprise a detectable moiety.

In some embodiments the antigen-binding molecule comprises a detectable moiety, e.g. a fluorescent label, phosphorescent label, luminescent label, immuno-detectable label (e.g. an epitope tag), radiolabel, chemical, nucleic acid or enzymatic label. The antigen-binding molecule may be covalently or non-covalently labelled with the detectable moiety.

Fluorescent labels include e.g. fluorescein, rhodamine, allophycocyanin, eosine and NDB, green fluorescent protein (GFP) chelates of rare earths such as europium (Eu), terbium (Tb) and samarium (Sm), tetramethyl rhodamine, Texas Red, 4-methyl umbelliferone, 7-amino-4-methyl coumarin, Cy3, and Cy5. Radiolabels include radioisotopes such as $Iodine^{123}$, $Iodine^{125}$, $Iodine^{126}$, $Iodine^{131}$, $Iodine^{133}$, $Bromine^{77}$, $Technetium^{99m}$, $Indium^{111}$, $Indium^{113m}$, $Gallium^{67}$, $Gallium^{68}$, $Ruthenium^{95}$, $Ruthenium^{97}$, $Ruthenium^{103}$, $Ruthenium^{105}$, $Mercury^{207}$, $Mercury^{203}$, $Rhenium^{99m}$, $Rhenium^{101}$, $Rhenium^{105}$, $Scandium^{47}$, $Tellurium^{121m}$, $Tellurium^{122m}$, $Tellurium^{125m}$, $Thulium^{165}$, $Thulium^{167}$, $Thulium^{168}$, $Copper^{67}$, $Fluorine^{18}$, $Yttrium^{90}$, $Palladium^{100}$, $Bismuth^{217}$ and $Antimony^{211}$. Luminescent labels include as radioluminescent, chemiluminescent (e.g. acridinium ester, luminal, isoluminol) and bioluminescent labels. Immuno-detectable labels include haptens, peptides/polypeptides, antibodies, receptors and ligands such as biotin, avidin, streptavidin or digoxigenin. Nucleic acid labels include aptamers. Enzymatic labels include e.g. peroxidase, alkaline phosphatase, glucose oxidase, beta-galactosidase and luciferase.

In some embodiments the antigen-binding molecules of the present invention are conjugated to a chemical moiety. The chemical moiety may be a moiety for providing a therapeutic effect. Antibody-drug conjugates are reviewed e.g. in Parslow et al., Biomedicines. 2016 September; 4(3): 14. In some embodiments, the chemical moiety may be a drug moiety (e.g. a cytotoxic agent). In some embodiments, the drug moiety may be a chemotherapeutic agent. In some embodiments, the drug moiety is selected from calicheamicin, DM1, DM4, monomethylauristatin E (MMAE), monomethylauristatin F (MMAF), SN-38, doxorubicin, duocarmycin, D6.5 and PBD.

Particular Exemplary Embodiments of the Antigen-Binding Molecules

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:187, and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:188.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:189; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:190.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:191; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:192.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:193; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:195.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:194; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:195.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:196; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:195.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:197; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:199.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:198; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:199.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:200; and
- (ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:201.

In some embodiments the antigen-binding molecule comprises, or consists of:
- (i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:202; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:203.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:204, and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:205.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:206; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:207.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:208; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:209.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:210; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:211.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:212; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:213.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:214, and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:215.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:216; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:217.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:218; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:219.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:220; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:221.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:222; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:223.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:225, and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:207.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:226; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:207.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:227; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:217.

In some embodiments the antigen-binding molecule comprises, or consists of:
(i) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:228; and
(ii) two polypeptides comprising, or consisting of, an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of NO:217.

Functional Properties of the Antigen-Binding Molecules

The antigen-binding molecules described herein may be characterised by reference to certain functional properties. In some embodiments, the antigen-binding molecule described herein may possess one or more of the following properties:

binds to HER3 (e.g. human, mouse, rat or cynomolgus macaque HER3);
does not bind to EGFR and/or HER2;
binds to HER3-expressing cells;
binds to subdomain II of the extracellular region of HER3;
binds to HER3 when HER3 is in open and closed conformations:
binds to HER3 independently of NRG;
does not compete with MM-121 and/or LJM-716 for binding to HER3;
does not compete with M-05-74 and/or M-08-11 for binding to HER3;
inhibits interaction between HER3 and an interaction partner for HER3 (e.g. HER3, HER2, EGFR, HER4, HGFR, IGF1R and/or cMet);
inhibits HER3-mediated signalling;
inhibits proliferation of HER3-expressing cells (e.g. in response to stimulation with NRG);
inhibits PI3K/AKT/mTOR and/or MAPK signalling by HER3-expressing cells (e.g. in response to stimulation with NRG);
binds to an activatory Fcγ receptor (e.g. FcγRIIIa);
increased binding to an activatory Fcγ receptor;
increased binding to an activatory Fcγ receptor as compared to an equivalent antigen-binding molecule having an Fc region comprised of CH2-CH3 having the amino acid sequence of SEQ ID NO:174-175;
decreased binding to an inhibitory Fcγ receptor as compared to an equivalent antigen-binding molecule having an Fc region comprised of CH2-CH3 having the amino acid sequence of SEQ ID NO:174-175;
increased binding to an activatory Fcγ receptor over an inhibitory Fcγ receptor as compared to an equivalent antigen-binding molecule having an Fc region comprised of CH2-CH3 having the amino acid sequence of SEQ ID NO:174-175;
increased or decreased binding to a complement protein (e.g. C1q) as compared to an equivalent antigen-binding molecule having an Fc region comprised of CH2-CH3 having the amino acid sequence of SEQ ID NO:174-175;
increased hexamerisation as compared to an equivalent antigen-binding molecule having an Fc region comprised of CH2-CH3 having the amino acid sequence of SEQ ID NO:174-175;
increased ADCC activity as compared to an equivalent antigen-binding molecule having an Fc region comprised of CH2-CH3 having the amino acid sequence of SEQ ID NO:174-175;
increased ADCP activity as compared to an equivalent antigen-binding molecule having an Fc region comprised of CH2-CH3 having the amino acid sequence of SEQ ID NO:174-175;

increased or decreased CDC activity as compared to an equivalent antigen-binding molecule having an Fc region comprised of CH2-CH3 having the amino acid sequence of SEQ ID NO:174-175;

similar or increased thermostability as compared to an equivalent antigen-binding molecule having an Fc region comprised of CH2-CH3 having the amino acid sequence of SEQ ID NO:174-175;

increases killing of HER3-expressing cells;

reduces the number/proportion of HER3-expressing cells; and inhibits the development and/or progression of cancer in vivo.

The antigen-binding molecules described herein preferably display specific binding to HER3. As used herein, "specific binding" refers to binding which is selective for the antigen, and which can be discriminated from non-specific binding to non-target antigen. An antigen-binding molecule that specifically binds to a target molecule preferably binds the target with greater affinity, and/or with greater duration than it binds to other, non-target molecules.

The ability of a given polypeptide to bind specifically to a given molecule can be determined by analysis according to methods known in the art, such as by ELISA, Surface Plasmon Resonance (SPR; see e.g. Hearty et al., Methods Mol Biol (2012) 907:411-442). Bio-Layer interferometry (see e.g. Lad et al., (2015) J Biomol Screen 20(4): 498-507), flow cytometry, or by a radiolabeled antigen-binding assay (RIA) enzyme-linked immunosorbent assay. Through such analysis binding to a given molecule can be measured and quantified. In some embodiments, the binding may be the response detected in a given assay.

In some embodiments, the extent of binding of the antigen-binding molecule to an non-target molecule is less than about 10% of the binding of the antibody to the target molecule as measured, e.g. by ELISA, SPR, Bio-Layer Interferometry or by RIA. Alternatively, binding specificity may be reflected in terms of binding affinity where the antigen-binding molecule binds with a dissociation constant ($K_D$) that is at least 0.1 order of magnitude (i.e. $0.1\times10^{\circ}$, where n is an integer representing the order of magnitude) greater than the $K_D$ of the antigen-binding molecule towards a non-target molecule. This may optionally be one of at least 0.2, 0.3, 0.4, 0.5, 0.6, 0.7, 0.8, 0.9, 1.0, 1.5, or 2.0.

In some embodiments, the antigen-binding molecule displays binding to human HER3, mouse HER3, rat HER3 and/or cynomolgus macaque (*Macaca fascicularis*) HER3. That is, in some embodiments the antigen-binding molecule is cross-reactive for human HER3, mouse HER3, rat HER3 and/or cynomolgus macaque HER3. In some embodiments the antigen-binding molecule of the present invention displays cross-reactivity with HER3 of a non-human primate. Cross-reactivity to HER3 in model species allows in vivo exploration of efficacy in syngeneic models without relying on surrogate molecules.

In some embodiments the antigen-binding molecule binds to human HER3, mouse HER3, rat HER3 and/or cynomolgus macaque HER3; and does not bind to HER2 and/or EGFR (e.g. human HER2 and/or human EGFR).

In some embodiments, the antigen-binding molecule does not display specific binding to EGFR human EGFR). In some embodiments, the antigen-binding molecule does not display specific binding to HER2 (e.g. human HER2). In some embodiments, the antigen-binding molecule does not display specific binding to (i.e. does not cross-react with) a member of the EGFR family of proteins other than HER3.

In some embodiments, the antigen-binding molecule does not display specific binding to EGFR, HER2 and/or HER4.

In some embodiments, the antigen-binding molecule of the invention binds to HER3 (e.g. human HER3) with a $K_D$ of 10 µM or less, preferably one of ≤5 µM, ≤52 µM, ≤1 µM, ≤500 nM, ≤400 nM, ≤300 nM, ≤200 nM, ≤100 nM, ≤95 nM, ≤90 nM, ≤85 nM, ≤80 nM, ≤75 nM, ≤70 nM, ≤65 nM, ≤60 nM, ≤55 nM, ≤50 nM, ≤45 nM, ≤40 nM, ≤35 nM, ≤30 nM, ≤25 nM, ≤20 nM, ≤15 nM, ≤12.5 nM, ≤10 nM, ≤9 nM, ≤3 nM, ≤7 nM, nM, ≤5 nM, ≤4 nM ≤3 nM, ≤2 nM, ≤1 nM, ≤900 pM, ≤800 pM, ≤700 pM, ≤600 pM, ≤500 pM, ≤400 pM, ≤300 pM, ≤200 pM, ≤100 pM, ≤90 pM, ≤80 pM, ≤70 pM, ≤60 pM, ≤50 pM, ≤40 pM, ≤30 pM, ≤20 pM, ≤10 pM, ≤9 pM, ≤8 pM, ≤7 pM, ≤6 pM, ≤5 pM, ≤4 pM, ≤3 pM, ≤2 pM, ≤1 pM.

The antigen-binding molecules of the present invention may bind to a particular region of interest of HER3. The antigen-binding region of an antigen-binding molecule according to the present invention may bind to a linear epitope of HER3, consisting of a contiguous sequence of amino acids (i.e. an amino acid primary sequence). In some embodiments, the antigen-binding molecule may bind to a conformational epitope of HER3, consisting of a discontinuous sequence of amino acids of the amino acid sequence.

In some embodiments, the antigen-binding molecule of the present invention binds to HER3. In some embodiments, the antigen-binding molecule binds to the extracellular region of HER3 (e.g. the region shown in SEQ ID NO:9). In some embodiments, the antigen-binding molecule binds to subdomain H of the extracellular region of HER3 (e.g. the region shown in SEQ ID NO:16).

In some embodiments, the antigen-binding molecule binds to the region of HER3 shown in SEQ ID NO:229. In some embodiments the antigen-binding molecule contacts one or more amino acid residues of the region of HER3 shown in SEQ ID NO:229. In some embodiments, the antigen-binding molecule binds to the regions of HER3 shown in SEQ ID NOs:230 and 231. In some embodiments the antigen-binding molecule contacts one or more amino acid residues of the regions of HER3 shown in SEQ ID NOs:230 and 231. In some embodiments, the antigen-binding molecule binds to the region of HER3 shown in SEQ ID NO:230. In some embodiments the antigen-binding molecule contacts one or more amino acid residues of the region of HER3 shown in SEQ ID NO:230, in some embodiments, the antigen-binding molecule binds to the region of HER3 shown in SEQ ID NO:231. In some embodiments the antigen-binding molecule contacts one or more amino acid residues of the region of HER3 shown in SEQ ID NO:231. In some embodiments, the antigen-binding molecule binds to the region of HER3 shown in SEQ ID NO:23. In some embodiments the antigen-binding molecule contacts one or more amino acid residues of the region of HER3 shown in SEQ ID NO:23. In some embodiments, the antigen-binding molecule binds to the region of HER3 shown in SEQ ID NO:21. In some embodiments the antigen-binding molecule contacts one or more amino acid residues of the region of HER3 shown in SEQ ID NO:21. In some embodiments the antigen-binding molecule binds to the region of HER3 shown in SEQ ID NO:19. In some embodiments the antigen-binding molecule contacts one or more amino acid residues of the region of HER3 shown in SEQ ID NO:19. In some embodiments, the antigen-binding molecule binds to the region of HER3 shown in SEQ ID NO:22. In some embodiments the antigen-binding molecule contacts one or more amino acid residues of the region of HER3 shown in SEQ ID NO:22.

In some embodiments, the antigen-binding molecule of the present invention is capable of binding to a polypeptide comprising, or consisting of, the amino acid sequence of one of SEQ ID NOs:1, 3, 4, 6 or 8. In some embodiments, the antigen-binding molecule is capable of binding to a polypeptide comprising, or consisting of, the amino acid sequence of SEQ ID NO:9. In some embodiments, the antigen-binding molecule is capable of binding to a polypeptide comprising, or consisting of, the amino acid sequence of SEQ ID NO:16. In some embodiments, the antigen-binding molecule is capable of binding to a peptide/polypeptide comprising, or consisting of, the amino acid sequence of SEQ ID NO:229. In some embodiments, the antigen-binding molecule is capable of binding to a peptide/polypeptide comprising, or consisting of, the amino acid sequences of SEQ ID NO230 and 231. In some embodiments, the antigen-binding molecule is capable of binding to a peptide/polypeptide comprising, or consisting of, the amino acid sequence of SEQ ID NO:230. In some embodiments, the antigen-binding molecule is capable of binding to a peptide/polypeptide comprising, or consisting of, the amino acid sequence of SEQ ID NO:231. In some embodiments, the antigen-binding molecule is capable of binding to a peptide/polypeptide comprising, or consisting of, the amino acid sequence of SEQ ID NO:23. In some embodiments, the antigen-binding molecule is capable of binding to a peptide/polypeptide comprising, or consisting of, the amino acid sequence of SEQ ID NO:21. In some embodiments, the antigen-binding molecule is capable of binding to a peptide/polypeptide comprising, or consisting of, the amino acid sequence of SEQ ID NO:19. In some embodiments, the antigen-binding molecule is capable of binding to a peptide/polypeptide comprising, or consisting of, the amino acid sequence of SEQ ID NO:22.

In some embodiments, the antigen-binding molecule does not bind to the region of HER3 corresponding to positions 260 to 279 of SEQ ID NO:1. In some embodiments the antigen-binding molecule does not contact an amino acid residue of the region of HER3 corresponding to positions 260 to 279 of SEQ ID NO:1. In some embodiments, the antigen-binding molecule does not bind to the region of HER3 shown in SEQ ID NO:23. In some embodiments the antigen-binding molecule does not contact an amino acid residue of the region of HER3 shown in SEQ ID NO:23. In some embodiments, the antigen-binding molecule is not capable of binding to a peptide consisting of the amino acid sequence corresponding to positions 260 to 279 of SEQ ID NO:1. In some embodiments, the antigen-binding molecule is not capable of binding to a peptide consisting of the amino acid sequence of SEQ ID NO:23.

As used herein, a "peptide" refers to a chain of two or more amino acid monomers linked by peptide bonds. A peptide typically has a length in the region of about 2 to 50 amino acids. A "polypeptide" is a polymer chain of two or more peptides. Polypeptides typically have a length greater than about 50 amino acids.

The ability of an antigen-binding molecule to bind to a given peptide/polypeptide can be analysed by methods well known to the skilled person, including analysis by ELISA, immunoblot (e.g. western blot), immunoprecipitation, surface plasmon resonance and biolayer interferometry.

Ligand binding to HER3 promotes conformational changes that enables HER3 to homo- or heterodimerise, resulting in activation of downstream pathways. HER3 demonstrates 'closed' and 'open' conformations. By closed conformation it is meant that HER3 is in a tethered conformation and is unavailable for receptor homo- or heterodimerisation. By open conformation it is meant that HER3 is in an extended conformation and is available for receptor homo- or heterodimerisation.

In some embodiments the antigen-binding molecule is capable of binding to HER3 when HER3 is in the open conformation. In some embodiments the antigen-binding molecule is capable of binding to HER3 when HER3 is in the closed conformation. In some embodiments the antigen-binding molecule is capable of binding to HER3 when HER3 is in the open and/or closed conformation. In some embodiments the antigen-binding molecule is capable of binding to the HER3 ectodomain when HER3 is in the open and/or closed conformation. In some embodiments the antigen-binding molecule is capable of binding to the HER3 dimerisation arm when HER3 is in the open and/or closed conformation. Binding to the dimerisation arm enables an antigen-binding molecule to prevent interaction between HER3 and an interaction partner for HER3, e.g. as described herein.

In some embodiments the antigen-binding molecule is capable of binding to HER3 in the presence and/or absence of a ligand for HER3. In some embodiments the antigen-binding molecule is capable of binding to HER3 independently of a ligand for HER3. In some embodiments the ligand is NRG, NRG-1 and/or NRG-2 HER3 is activated by ligand binding to its extracellular domain which promotes conformational changes that enables HER3 to homo- or heterodimerise. Binding of an antigen-binding molecule to HER3 independently of ligand binding allows the antigen-binding molecule to inhibit the action of HER3 in both ligand-absent and ligand-present conformational states. In some embodiments the antigen-binding molecule does not compete with ligand binding to HER3. In some embodiments the antigen-binding molecule does not bind to HER3 at the ligand binding site.

In some embodiments the antigen-binding molecule is capable of binding the same region of HER3, or an overlapping region of HER3, to the region of HER3 which is bound by an antibody comprising the VH and VL sequences of one of clones 10D1, 10D1_c75, 10D1_c76, 10D1_c77, 10D1_c78v1, 10D1_c78v2, 10D1_11E, 10D1_c85v1, 10D1_c85v2, 10D1_c85o1, 10D1_c85o2, 10D1_c87, 10D1_c89, 10D1_c90, 10D1_c91, 10D1_c92, 10D1_c93, 10A6, 4-35-B2 or 4-35-B4. In some embodiments the antigen-binding molecule is capable of binding the same region of HER3, or an overlapping region of HER3, to the region of HER3 which is bound by an antibody comprising the VH and VL sequences of one of clones 10D1_c89, 10D1_c90 or 10D1_c91. In some embodiments the antigen-binding molecule is capable of binding the same region of HER3, or an overlapping region of HER3, to the region of HER3 which is bound by an antibody comprising the VH and VL sequences of clone 10D1_c59.

The region of a peptide/polypeptide to which an antibody binds can be determined by the skilled person using various methods well known in the art, including X-ray co-crystallography analysis of antibody-antigen complexes, peptide scanning, mutagenesis mapping, hydrogen-deuterium exchange analysis by mass spectrometry, phage display, competition ELISA and proteolysis-based 'protection' methods. Such methods are described, for example, in Gershoni et al., BioDrugs, 2007, 21(3):145-156, which is hereby incorporated by reference in its entirety. Such methods can also be used to determine whether an antigen-binding molecule is capable of binding to proteins in different conformations.

In some embodiments the antigen-binding molecule of the present invention does not bind to HER3 in the same region of HER3, or an overlapping region of HER3, as an antibody comprising the VH and VL sequences of anti-HER3 antibody clone MM-121 (described e.g. in Schoeberl et al., Sci. Signal. (2009) 2(77): ra31) and/or LJM-716 (described e.g. Garner et al., Cancer Res (2013) 73: 6024-6035). In some embodiments the antigen-binding molecule of the present invention does not display competition with an antibody comprising the VH and VL sequences of anti-HER3 antibody clone MM-121 and/or LJM-716 for binding to HER3, e.g. as determined by SPR analysis.

In some embodiments the antigen-binding molecule of the present invention binds to HER3 in a region which is accessible to an antigen-binding molecule (i.e., an extracellular antigen-binding molecule) when HER3 is expressed at the cell surface (i.e. in or at the cell membrane). In some embodiments the antigen-binding molecule is capable of binding to HER3 expressed at the cell surface of a cell expressing HER3. In some embodiments the antigen-binding molecule is capable of binding to HER3-expressing cells (e.g. HER3+ cells, e.g. HER3+ cancer cells).

The ability of an antigen-binding molecule to bind to a given cell type can be analysed by contacting cells with the antigen-binding molecule, and detecting antigen-binding molecule bound to the cells, e.g. after a washing step to remove unbound antigen-binding molecule. The ability of an antigen-binding molecule to bind to immune cell surface molecule-expressing cells and/or cancer cell antigen-expressing cells can be analysed by methods such as flow cytometry and immunofluorescence microscopy.

The antigen-binding molecule of the present invention may be an antagonist of HER3. In some embodiments, the antigen-binding molecule is capable of inhibiting a function or process (e.g. interaction, signalling or other activity) mediated by HER3 and/or a binding partner for HER3 (e.g. HER3 (i.e. in the case of homodimerisation), HER2, EGFR, HER4, HGFR, IGF1R and/or cMet). Herein, 'inhibition' refers to a reduction, decrease or lessening relative to a control condition.

In some embodiments the antigen-binding molecule of the present invention is capable of inhibiting interaction between HER3 and an interaction partner for HER3. An interaction partner for HER3 may be expressed by the same cell as the HER3. An interaction partner or HER3 may be expressed at the cell surface (i.e. in or at the cell membrane). In some embodiments an interaction partner for HER3 may be a member of the EGFR family of proteins, e.g. HER3, HER2, EGFR, HER4, HGFR, IGF1R and/or cMet. In some embodiments an interaction partner for HER3 may be IGF1R and/or cMet. Interaction between HER3 and an interaction partner for HER3 may result in the formation of a polypeptide complex. Interaction between HER3 and an interaction partner for HER3 to form a polypeptide complex may be referred to as multimerisation. Where multimerisation is between polypeptide monomers multimerisation may be referred to as dimerisation.

In some embodiments the antigen-binding molecule is capable of inhibiting interaction between HER3 monomers. In some embodiments the antigen-binding molecule is capable of inhibiting interaction between HER3 and HER2. In some embodiments the antigen-binding molecule is capable of inhibiting interaction between HER3 and EGFR. In some embodiments the antigen-binding molecule is capable of inhibiting interaction between HER3 and HER4. In some embodiments the antigen-binding molecule is capable of inhibiting interaction between HER3 and HGFR. In some embodiments the antigen-binding molecule is capable of inhibiting interaction between HER3 and IGF1R. In some embodiments the antigen-binding molecule is capable of inhibiting interaction between HER3 and cMet.

Inhibition of interaction may be achieved by binding of the antigen-binding molecule to a region of HER3 required for interaction between HER3 and an interaction partner for HER3 (e.g. the dimerisation loop of HER3 shown in SEQ ID NO:19). In some embodiments the antigen-binding molecule contacts one or more residues of HER3 necessary for interaction between HER3 and an interaction partner for HER3; in this way the antigen-binding molecule makes the region unavailable, thereby inhibiting interaction. In some embodiments the antigen-binding molecule binds to HER3 in a manner which inhibits/prevents interaction between HER3 and an interaction partner for HER3. In some embodiments the antigen-binding molecule inhibits/prevents access of the interaction partner for HER3 to the region of HER3 required for interaction between HER3 and the interaction partner for HER3; this may be achieved in cases even where the antigen-binding molecule does not contact the region of HER3 required for interaction between HER3 and the interaction partner for HER3, e.g. through steric inhibition of access of the interaction partner for HER3 to the region of HER3 required for interaction between HER3 and the interaction partner.

In some embodiments the antigen-binding molecule is capable of inhibiting homodimerisation of HER3 monomers. In some embodiments the antigen-binding molecule is capable of inhibiting dimerisation between HER3 and HER2. In some embodiments the antigen-binding molecule is capable of inhibiting dimerisation between HER3 and EGFR. In some embodiments the antigen-binding molecule is capable of inhibiting dimerisation between HER3 and HER4. In some embodiments the antigen-binding molecule is capable of inhibiting dimerisation between HER3 and HGFR. In some embodiments the antigen-binding molecule is capable of inhibiting dimerisation between HER3 and IGF1R. In some embodiments the antigen-binding molecule is capable of inhibiting dimerisation between HER3 and cMet.

The ability of an antigen-binding molecule to inhibit interaction between two factors can be determined for example by analysis of interaction in the presence of, or following incubation of one or both of the interaction partners with, the antibody/fragment. Assays for determining whether a given antigen-binding molecule is capable of inhibiting interaction between two interaction partners include competition ELISA assays and analysis by SPR. In some embodiments the antigen-binding molecule is a competitive inhibitor of interaction between HER3 and an interaction partner for HER3.

In some embodiments, the antigen-binding molecule of the present invention is capable of inhibiting interaction between HER3 and an interaction partner for HER3 (e.g. HER3, HER2, EGFR, HER4, HGFR, IGF1R and/or cMet) to less than less than 1 times, e.g. $\leq 0.99$ times, $\leq 0.95$ times, $\leq 0.9$ times, $\leq 0.85$ times, $\leq 0.8$ times, $\leq 0.75$ times, $\leq 0.7$ times, $\leq 0.65$ times, $\leq 0.6$ times, $\leq 0.55$ times, $\leq 0.5$ times, $\leq 0.45$ times, $\leq 0.4$ times, $\leq 0.35$ times, $\leq 0.3$ times, $\leq 0.25$ times, $\leq 0.2$ times, $\leq 0.15$ times, $\leq 0.1$ times, $\leq 0.05$ times, or $\leq 0.01$ times the level of interaction between HER3 and the interaction partner for HER3 in the absence of the antigen-binding molecule (or in the presence of an appropriate control antigen-binding molecule), in a suitable assay.

The ability of an antigen-binding molecule to inhibit interaction between interaction partners can also be determined by analysis of the downstream functional consequences of such interaction. For example, downstream functional consequences of interaction between HER3 and interaction partners for HER3 include PI3K/AKT/mTOR and/or MAPK signalling. For example, the ability of an antigen-binding molecule to inhibit interaction of HER3 and an interaction partner for HER3 may be determined by analysis of PI3K/AKT/mTOR and/or MAPK signalling following treatment with NRG in the presence of the antigen-binding molecule. PI3K/AKT/mTOR and/or MAPK signalling can be detected and quantified e.g. using antibodies capable of detecting phosphorylated members of the signal transduction pathways.

The ability of an antigen-binding molecule to inhibit interaction of HER3 and an interaction partner for HER3 can also be determined by analysing proliferation of cells expressing HER3 following treatment with NRG in the presence of the antigen-binding molecule. Cell proliferation can be determined e.g. by detecting changes in number of cells over time, or by in vitro analysis of incorporation of $^3$H-thymidine or by CFSE dilution assay, e.g. as described in Fulcher and Wong, Immunol Cell Biol (1999) 77(6): 559-564, hereby incorporated by reference in entirety.

In some embodiments, the antigen-binding molecule of the present invention is capable of inhibiting proliferation of cells harbouring mutation to BRAF V600, e.g. cells comprising the BRAF V600E or V600K mutation (see Example 10).

In some embodiments the antigen-binding molecule inhibits HER3-mediated signalling. HER3-mediated signalling can be analysed e.g. using an assay of a correlate of HER3-mediated signalling, e.g. cell proliferation, and/or phosphorylation of one or more signal transduction molecules of the PI3K/AKT/mTOR and/or MAPK signal transduction pathways.

In some embodiments, the antigen-binding molecule of the present invention is capable of inhibiting PI3K/AKT/mTOR and/or MAPK signalling by HER3-expressing cells. The level of PI3K/AKT/mTOR and/or MAPK signalling may be analysed by detection and quantification of the level of phosphorylation of one or more of the components of the PI3K/AKT/mTOR and/or MAPK pathways, e.g. following stimulation with NRG (see Example 4.3).

In some embodiments, the antigen-binding molecule of the present invention is capable of inhibiting proliferation of HER3-expressing cells, e.g. in response to stimulation with NRG. In some embodiments, the antigen-binding molecule of the present invention is capable of inhibiting proliferation of HER3-expressing cells to less than less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of proliferation of HER3-expressing cells in the absence of the antigen-binding molecule (or in the presence of an appropriate control antigen-binding molecule), in a suitable assay.

In some embodiments, the antigen-binding molecule of the present invention is capable of inhibiting PI3K/AKT/mTOR and/or MAPK signalling by HER3-expressing cells to less than less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of signalling by HER3-expressing cells in the absence of the antigen-binding molecule (or in the presence of an appropriate control antigen-binding molecule), in a suitable assay.

HER3-mediated signalling can be investigated in vitro, e.g. as described in Example 8.9, or in vivo, e.g. as described in Example 11.

ADCC activity can be analysed e.g. according to the methods described in Yamashita et al., Scientific Reports (2016) 6:19772 (hereby incorporated by reference in its entirety), or by $^{51}$Cr release assay as described e.g. in Jedema et al., Blood (2004) 103: 2677-82 (hereby incorporated by reference in its entirety). ADCC activity can also be analysed using the Pierce LDH Cytotoxicity Assay Kit, in accordance with the manufacturer's instructions (as described in Example 5 herein).

ADCP can be analysed e.g. according to the method described in Kamen et al., J Immunol (2017) 198 (1 Supplement) 157.17 (hereby incorporated by reference in its entirety).

The ability to induce CDC can be analysed e.g. using a C1q binding assay, e.g. as described in Schlothauer et al., Protein Engineering, Design and Selection (2016), 29(10): 457-466 (hereby incorporated by reference in its entirety).

Thermostability of antigen-binding molecules can be analysed by methods well known to the skilled person, including Differential Scanning Fluorimetry and Differential Scanning calorimetry (DSC), which are described e.g. in He et al., J Pharm Sci. (2010) which is hereby incorporated by reference in its entirety. Thermostability may be reflected in terms of a melting temperature ($T_m$), unfolding temperature or disassembly temperature (expressed e.g. in ° C. or ° F.).

In some embodiments, an antigen-binding molecule comprising an Fc region as described herein binds to an activatory Fcγ receptor (e.g. hFcγRIIa (e.g. hFcγRIIa167H, hFcγRIIa167R), hFcγRIIIa (e.g. hFcγRIIIa158V, hFcγRIIIa158F), mFcγRIV, mFcγRIII) with an affinity of binding which is greater than 1 times, e.g. greater than 2, 3, 4, 5, 6, 7, 8, 9, 10, 15, or greater than 20 times the affinity of binding to the activatory Fcγ receptor by an equivalent antigen-binding molecule having an Fc region comprised of CH2-CH3 having the amino acid sequence of SEQ ID NO:174-175. In some embodiments the $K_D$ of the antigen-binding molecule comprising an Fc region described herein for binding to the activatory Fcγ receptor is less than 1 times, e.g. less than 0.9, 0.8, 0.7, 0.6, 0.5, 0.4, 0.3, 0.2, 0.1, 0.09, 0.08, 0.07, 0.06 or less than 0.05 times the $K_D$ of an equivalent antigen-binding molecule having an Fc region comprised of CH2-CH3 having the amino acid sequence of SEQ ID NO:174-175 for the activatory Fcγ receptor.

In some embodiments, the antigen-binding molecule comprising an Fc region as described herein binds to an activatory Fcγ receptor (e.g. hFcγRIIa (e.g. hFcγRIIa167H, hFcγRIIa167R), hFcγRIIIa (e.g. hFcγRIIIa158V, hFcγRIIIa158F), mFcγRIV, mFcγRIII) with a $K_D$ of 1000 nM or less, preferably one of ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, nM, ≤7 nM, ≤6 nM, ≤5 nM, ≤4 nM ≤3 nM, ≤2 nM or ≤1 nM.

In some embodiments, an antigen-binding molecule comprising an Fc region as described herein binds to an FcRn (e.g. hFcRn, mFcRn) with an affinity of binding which is greater than 1 times, e.g. greater than 2, 3, 4, 5, 6, 7, 8, 9, 10, 15, or greater than 20 times the affinity of binding to the FcRn by an equivalent antigen-binding molecule having an Fc region comprised of CH2-CH3 having the amino acid sequence of SEQ ID NO:174-175. In some embodiments the $K_D$ of the antigen-binding molecule comprising an Fc region described herein for binding to the FcRn is less than 1 times, e.g. less than 0.9, 0.8, 0.7, 0.6, 0.5, 0.4, 0.3, 0.2, 0.1, 0.09, 0.08, 0.07, 0.06 or less than 0.05 times the $K_D$ of an equivalent antigen-binding molecule having an Fc region comprised of CH2-CH3 having the amino acid sequence of SEQ ID NO:174-175 for the FcRn.

In some embodiments, the antigen-binding molecule comprising an Fc region as described herein binds to an FcRn (e.g. hFcRn, mFcRn) with a $K_D$ of 1000 nM or less, preferably one of ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM or ≤1 nM.

In some embodiments, an antigen-binding molecule comprising an Fc region as described herein binds to an inhibitory Fcγ receptor (e.g. hFcγRIIb mFcγRIIb) with an affinity of binding which is less than 1 times, e.g. less than 0.9, 0.8, 0.7, 0.8, 0.5, 0.4, 0.3, 0.2, or less than 0.1 times the affinity of binding to the inhibitory Fcγ receptor by an equivalent antigen-binding molecule having an Fc region comprised of CH2-CH3 having the amino acid sequence of SEQ ID NO:174-175. In some embodiments the $K_D$ of the antigen-binding molecule comprising an Fc region described herein for binding to the inhibitory Fcγ receptor is greater than 1 times, e.g. greater than 2, 3, 4, 5, 6, 7, 8, 9 or greater than 10 times the $K_D$ of an equivalent antigen-binding molecule having an Fc region comprised of CH2-CH3 having the amino acid sequence of SEQ ID NO:174-175 for the inhibitory Fcγ receptor.

In some embodiments, the antigen-binding molecule comprising an Fc region as described herein binds to an inhibitory Fcγ receptor (e.g. hFcγRIIb mFcγRIIb) with a $K_D$ 1 nM or greater, preferably one of ≥5 nM, ≥10 nM, ≥50 nM, ≥100 nM, ≥500 nM, ≥1000 nM, ≥2000 nM, ≥3000 nM, ≥4000 nM or ≥5000 nM.

In some embodiments the selectivity of binding for an activatory Fcγ receptor (e.g. hFcγRIIa; relative to an inhibitory Fcγ receptor (e.g. hFcγRIIb) for an antigen-binding molecule comprising an Fc region as described herein is greater than 1 times, e.g. greater than 2, 3, 4, 5, 6, 7, 8, 9, 10, 15, or greater than 20 times selectivity of binding displayed by an equivalent antigen-binding molecule having an Fc region comprised of CH2-CH3 having the amino acid sequence of SEQ ID NO:174-175.

In some embodiments, an antigen-binding molecule comprising an Fc region as described herein displays ADCC which is greater than 1 times, e.g. greater than 2, 3, 4, 5, 6, 7, 8, 9, 10, 15, or greater than 20 times the ADCC displayed by an equivalent antigen-binding molecule having an Fc region comprised of CH2-CH3 having the amino acid sequence of SEQ ID NO:174-175.

In some embodiments, the EC50 (ng/mil determined for an antigen-binding molecule comprising an Fc region as described herein in an assay of ADCC activity less than 1 times, e.g. less than 0.9, 0.8, 0.7, 0.6, 0.5, 0.4, 0.3, 0.2, or less than 0.1 times the EC50 determined for an equivalent antigen-binding molecule having an Fc region comprised of CH2-CH3 having the amino acid sequence of SEQ ID NO:174-175.

In some embodiments, the EC50 (ng/ml) for an antigen-binding molecule comprising an Fc region as described herein in an assay of ADCC activity is 500 ng/ml or less, preferably one of ≤400 ng/ml, ≤300 ng/ml, ≤200 ng/ml, ≤100 ng/ml, ≤90 ng/ml, ≤80 ng/ml, ≤70 ng/ml, ≤60 ng/ml, ≤50 ng/ml, ≤40 ng/ml, ≤30 ng/ml, ≤20 ng/ml, or ≤10 ng/ml.

In some embodiments, an antigen-binding molecule comprising an Fc region as described herein may have a melting temperature, unfolding temperature or disassembly temperature which is which is ≥0.75 times and ≤1.25 times, e.g. ≥0.8 times and ≤1.2 times, ≥0.85 times and ≤1.15 times, ≥0.9 times and ≤1.1 times, ≥0.91 times and ≤1.09 times, ≥0.92 times and ≤1.08 times, ≥0.93 times and ≤1.07 times, ≥0.94 times and ≤1.06 times, ≥0.95 times and ≤1.05 times, ≥0.96 times and ≤1.04 times, ≥0.97 times and ≤1.03 times, ≥0.98 times and ≤1.02 times, or ≥0.99 times and ≤1.01 times the melting temperature, unfolding temperature or disassembly temperature of an equivalent antigen-binding molecule having an Fc region comprised of CH2-CH3 having the amino acid sequence of SEQ ID NO:174-175.

In some embodiments, the antigen-binding molecule of the present invention is capable of increasing killing of HER3-expressing cells. Killing of HER3-expressing cells may be increased through an effector function of the antigen-binding molecule. In embodiments wherein antigen-binding molecule comprises an Fc region the antigen-binding molecule may increasing killing of HER3-expressing cells through one or more of complement dependent cytotoxicity (CDC), antibody-dependent cell-mediated cytotoxicity (ADCC) and antibody-dependent cellular phagocytosis (ADCP).

An antigen-binding molecule which is capable of increasing killing of HER3-expressing cells can be identified by observation of an increased level of killing of HER3-expressing cells in the presence of or following incubation of the HER3-expressing cells with the antigen-binding molecule, as compared to the level of cell killing detected in the absence of the antigen-binding molecule (or in the presence of an appropriate control antigen-binding molecule), in an appropriate assay. Assays of CDC, ADCC and ADCP are well known the skilled person. The level of killing of HER3-expressing cells can also be determined by measuring the number/proportion of viable and/or non-viable HER3-expressing cells following exposure to different treatment conditions.

In some embodiments, the antigen-binding molecule of the present invention is capable of increasing killing of HER3-expressing cells (e.g. HER3-expressing cancer cells) to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level of killing observed in the absence of the antigen-binding molecule (or in the presence of an appropriate control antigen-binding molecule).

In some embodiments, the antigen-binding molecule of the present invention is capable of reducing the number of HER3-expressing cells (e.g. HER3-expressing cancer cells) to less than less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the number of HER3-expressing cells (e.g. HER3-expressing cancer cells) detected following incubation in the absence of the antigen-binding molecule (or following incubation in the presence of an appropriate control antigen-binding molecule), in a comparable assay.

In some embodiments, the antigen-binding molecule of the present invention inhibits the development and/or progression of cancer in vivo.

In some embodiments the antigen-binding molecule causes an increase in the killing of cancer cells, by effector immune cells. In some embodiments the antigen-binding molecule causes a reduction in the number of cancer cells in vivo, e.g. as compared to an appropriate control condition. In some embodiments the antigen-binding molecule inhibits tumor growth, e.g. as determined by measuring tumor size/volume over time.

The antigen-binding molecule of the present invention may be analysed for the ability to inhibit development and/or progression of cancer in an appropriate in vivo model, e.g. cell line-derived xenograft model. The cell line-derived xenograft model may be derived from HER3-expressing cancer cells. In some embodiments the model is an N87 cell-derived model, a SNU16 cell-derived model, a FaDu cell-derived model, an OvCAR8 cell-derived model, a HCC95 cell-derived model, an A549 cell-derived model, an ACHN cell-derived model or a HT29 cell-derived model.

The cancer may be a HER3-associated cancer as described herein (i.e. cancers for which HER3 gene/protein expression is a risk factor for, and/or is positively associated with, the onset, development, progression or severity of symptoms of the cancer, and/or metastasis). The cancer may comprise HER3-expressing cells. In some embodiments the cancer comprises a HER3+ tumor.

In some embodiments, administration of an antigen-binding molecule according to the present invention may cause one or more of: inhibition of the development/progression of the cancer, a delay to/prevention of onset of the cancer, a reduction in/delay to/prevention of tumor growth, a reduction in/delay to/prevention of metastasis, a reduction in the severity of the symptoms of the cancer, a reduction in the number of cancer cells, a reduction in tumour size/volume, and/or an increase in survival (e.g. progression free survival), e.g. as determined in an appropriate HER3-expressing cancer cell line-derived xenograft model.

In some embodiments, the antigen-binding molecule of the present invention is capable of inhibiting tumor growth in a HER3-expressing cancer cell line-derived xenograft model to less than less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the tumor growth observed in the absence of treatment with the antigen-binding molecule (or following treatment with an appropriate negative control antigen-binding molecule).

Chimeric Antigen Receptors (CARs)

The present invention also provides Chimeric Antigen Receptors (CARs) comprising the antigen-binding molecules or polypeptides of the present invention.

CARs are recombinant receptors that provide both antigen-binding and T cell activating functions. CAR structure and engineering is reviewed, for example, in Dotti et al., Immunol Rev (2014) 257(1), hereby incorporated by reference in its entirety. CARs comprise an antigen-binding region linked to a cell membrane anchor region and a signalling region. An optional hinge region may provide separation between the antigen-binding region and cell membrane anchor region, and may act as a flexible linker.

The CAR of the present invention comprises an antigen-binding region which comprises or consists of the antigen-binding molecule of the present invention, or which comprises or consists of a polypeptide according to the invention.

The cell membrane anchor region is provided between the antigen-binding region and the signalling region of the CAR and provides for anchoring the CAR to the cell membrane of a cell expressing a CAR, with the antigen-binding region in the extracellular space, and signalling region inside the cell. In some embodiments, the CAR comprises a cell membrane anchor region comprising or consisting of an amino acid sequence which comprises, consists of, or is derived from, the transmembrane region amino acid sequence for one of CD3-ζ, CD4, CD8 or CD28. As used herein, a region which is 'derived from' a reference amino acid sequence comprises an amino acid sequence having at least 60%, e.g. one of at least 65%, 70%, 75%, 80%, 85%, 90%, 91%, 92%, 93%, 94%, 95%, 96%, 97%, 98%, 99% or 100% sequence identity to the reference sequence.

The signalling region of a CAR allows for activation of the T cell. The CAR signalling regions may comprise the amino acid sequence of the intracellular domain of CD3-ζ, which provides immunoreceptor tyrosine-based activation motifs (ITAMs) for phosphorylation and activation of the CAR-expressing T cell. Signalling regions comprising sequences of other ITAM-containing proteins such as FcγRI have also been employed in CARs (Haynes et al., 2001 J Immunol 166(1):182-187). Signalling regions of CARs may also comprise co-stimulatory sequences derived from the signalling region of co-stimulatory molecules, to facilitate activation of CAR-expressing T cells upon binding to the target protein. Suitable co-stimulatory molecules include CD28, OX40, 4-1BB, ICOS and CD27. In some cases CARs are engineered to provide for co-stimulation of different intracellular signalling pathways. For example, signalling associated with CD28 costimulation preferentially activates the phosphatidylinositol 3-kinase (P13K) pathway, whereas the 4-1BB-mediated signalling is through TNF receptor associated factor (TRAF) adaptor proteins. Signalling regions of CARs therefore sometimes contain co-stimulatory sequences derived from signalling regions of more than one co-stimulatory molecule. In some embodiments, the CAR of the present invention comprises one or more co-stimulatory sequences comprising or consisting of an amino acid sequence which comprises, consists of, or is derived from, the amino acid sequence of the intracellular domain of one or more of CD28, OX40, 4-1BB, ICOS and CD27.

An optional hinge region may provide separation between the antigen-binding domain and the transmembrane domain, and may act as a flexible linker. Hinge regions may be derived from IgG1. In some embodiments, the CAR of the present invention comprises a hinge region comprising or consisting of an amino acid sequence which comprises, consists of, or is derived from, the amino acid sequence of the hinge region of IgG1.

Also provided is a cell comprising a CAR according to the invention. The CAR according to the present invention may be used to generate CAR-expressing immune cells, e.g. CAR-T or CAR-NK cells. Engineering of CARS into immune cells may be performed during culture, in vitro.

The antigen-binding region of the CAR of the present invention may be provided with any suitable format, e.g. scFv, scFab, etc.

Nucleic Acids and Vectors

The present invention provides a nucleic acid, or a plurality of nucleic acids, encoding an antigen-binding molecule, polypeptide or CAR according to the present invention.

In some embodiments, the nucleic acid is purified or isolated, e.g. from other nucleic acid, or naturally-occurring biological material. In some embodiments the nucleic acid(s) comprise or consist of DNA and/or RNA.

The present invention also provides a vector, or plurality of vectors, comprising the nucleic acid or plurality of nucleic acids according to the present invention.

The nucleotide sequence may be contained in a vector, e.g. an expression vector. A "vector" as used herein is a nucleic acid molecule used as a vehicle to transfer exogenous nucleic acid into a cell. The vector may be a vector for expression of the nucleic acid in the cell. Such vectors may include a promoter sequence operably linked to the nucleotide sequence encoding the sequence to be expressed. A vector may also include a termination codon and expression enhancers. Any suitable vectors, promoters, enhancers and termination codons known in the art may be used to express a peptide or polypeptide from a vector according to the invention.

The term "operably linked" may include the situation where a selected nucleic acid sequence and regulatory nucleic acid sequence (e.g. promoter and/or enhancer) are covalently linked in such a way as to place the expression of nucleic acid sequence under the influence or control of the regulatory sequence (thereby forming an expression cassette). Thus a regulatory sequence is operably linked to the selected nucleic acid sequence if the regulatory sequence is capable of effecting transcription of the nucleic acid sequence. The resulting transcripts) may then be translated into a desired peptide(s)/polypeptide(s).

Suitable vectors include plasmids, binary vectors, DNA vectors, mRNA vectors, viral vectors (e.g. gammaretroviral vectors (e.g. murine Leukemia virus (MLV)-derived vectors), lentiviral vectors, adenovirus vectors, adeno-associated virus vectors, vaccinia virus vectors and herpesvirus vectors), transposon-based vectors, and artificial chromosomes (e.g. yeast artificial chromosomes).

In some embodiments, the vector may be a eukaryotic vector, e.g. a vector comprising the elements necessary for expression of protein from the vector in a eukaryotic cell. In some embodiments, the vector may be a mammalian vector, e.g. comprising a cytomegalovirus (CMV) or SV40 promoter to drive protein expression.

Constituent polypeptides of an antigen-binding molecule according to the present invention may be encoded by different nucleic acids of the plurality of nucleic acids, or by different vectors of the plurality of vectors.

Cells Comprising/Expressing the Antigen-Binding Molecules and Polypeptides

The present invention also provides a cell comprising or expressing an antigen-binding molecule, polypeptide or CAR according to the present invention. Also provided is a cell comprising or expressing a nucleic acid, a plurality of nucleic acids, a vector or a plurality of vectors according to the invention.

The cell may be a eukaryotic cell, e.g. a mammalian cell. The mammal may be a primate (rhesus, cynomolgous, non-human primate or human) or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

The present invention also provides a method for producing a cell comprising a nucleic acid(s) or vector(s) according to the present invention, comprising introducing a nucleic acid, a plurality of nucleic acids, a vector or a plurality of vectors according to the present invention into a cell. In some embodiments, introducing an isolated nucleic acid(s) vector(s) according to the invention into a cell comprises transformation, transfection, electroporation or transduction (e.g. retroviral transduction).

The present invention also provides a method for producing a cell expressing/comprising an antigen-binding molecule, polypeptide or CAR according to the present invention, comprising introducing a nucleic acid, a plurality of nucleic acids, a vector or a plurality of vectors according to the present invention in a cell. In some embodiments, the methods additionally comprise culturing the cell under conditions suitable for expression of the nucleic acid(s) or vector(s) by the cell. In some embodiments, the methods are performed in vitro.

The present invention also provides cells obtained or obtainable by the methods according to the present invention.

Producing the Antigen-Binding Molecules and Polypeptides

Antigen-binding molecules and polypeptides according to the invention may be prepared according to methods for the production of polypeptides known to the skilled person.

Polypeptides may be prepared by chemical synthesis, e.g. liquid or solid phase synthesis. For example, peptides/polypeptides can by synthesised using the methods described in, for example, Chandrudu et al., Molecules (2013), 18: 4373-4388, which is hereby incorporated by reference in its entirety.

Alternatively, antigen-binding molecules and polypeptides may be produced by recombinant expression. Molecular biology techniques suitable for recombinant production of polypeptides are well known in the art, such as those set out in Green and Sambrook, Molecular Cloning: A Laboratory Manual (4th Edition), Cold Spring Harbor Press, 2012, and in Nat Methods. (2008); 5(2): 135-146 both of which are hereby incorporated by reference in their entirety. Methods for the recombinant production of antigen-binding molecules are also described in Frenzel et al., Front Immunol. (2013); 4: 217 and Kunert and Reinhart, Appl Microbiol Biotechnol. (2016) 100: 3451-3461, both of which are hereby incorporated by reference in their entirety.

In some cases the antigen-binding molecule of the present invention are comprised of more than one polypeptide chain. In such cases, production of the antigen-binding molecules may comprise transcription and translation of more than one polypeptide, and subsequent association of the polypeptide chains to form the antigen-binding molecule.

For recombinant production according to the invention, any cell suitable for the expression of polypeptides may be used. The cell may be a prokaryote or eukaryote. In some embodiments the cell is a prokaryotic cell, such as a cell of archaea or bacteria. In some embodiments the bacteria may be Gram-negative bacteria such as bacteria of the family Enterobacteriaceae, for example *Escherichia coli*. In some embodiments, the cell is a eukaryotic cell such as a yeast cell, a plant cell, insect cell or a mammalian cell, e.g. CHO, HEK (e.g. HEK293), HeLa or COS cells. In some embodiments, the cell is a CHO cell that transiently or stably expresses the polypeptides.

In some cases the cell is not a prokaryotic cell because some prokaryotic cells do not allow for the same folding or post-translational modifications as eukaryotic cells. In addition, very high expression levels are possible in eukaryotes and proteins can be easier to purify from eukaryotes using appropriate tags. Specific plasmids may also be utilised which enhance secretion of the protein into the media.

In some embodiments polypeptides may be prepared by cell-free-protein synthesis (CFPS), according using a system described in Zemella et al. Chembiochem (2015) 16(17): 2420-2431, which is hereby incorporated by reference in its entirety.

Production may involve culture or fermentation of a eukaryotic cell modified to express the polypeptide(s) of interest. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide(s). Culture, fermentation and separation techniques are well known to those of skill in the art, and are described, for example, in Green and Sambrook, Molecular Cloning; A Laboratory Manual (4th Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culturing the cells that express the antigen-binding molecule/polypeptide(s), the polypeptide(s) of interest may be isolated. Any suitable method for separating proteins from cells known in the art may be used. In order to isolate the polypeptide it may be necessary to separate the cells from nutrient medium. If the polypeptide(s) are secreted from the cells, the cells may be separated by centrifugation from the culture media that contains the secreted polypeptide(s) of interest. If the polypeptide(s) of interest collect within the cell, protein isolation may comprise centrifugation to separate cells from cell culture medium, treatment of the cell pellet with a lysis buffer, and cell disruption e.g. by sonification, rapid freeze-thaw or osmotic lysis.

It may then be desirable to isolate the polypeptide(s) of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. These may be used as an alternative to precipitation, or may be performed subsequently to precipitation.

Once the polypeptide(s) of interest have been isolated from culture it may be desired or necessary to concentrate the polypeptide(s). A number of methods for concentrating proteins are known in the art, such as ultrafiltration or lyophilisation.

Compositions

The present invention also provides compositions comprising the antigen-binding molecules, polypeptides, CARs, nucleic acids, expression vectors and cells described herein.

The antigen-binding molecules, polypeptides, CARs, nucleic acids, expression vectors and cells described herein may be formulated as pharmaceutical compositions or medicaments for clinical use and may comprise a pharmaceutically acceptable carrier, diluent, excipient or adjuvant. The composition may be formulated for topical, parenteral, systemic, intracavitary, intravenous, intra-arterial, intramuscular, intrathecal, intraocular, intraconjunctival, intratumoral, subcutaneous, intradermal, intrathecal, oral or transdermal routes of administration which may include injection or infusion.

Suitable formulations may comprise the antigen-binding molecule in a sterile or isotonic medium. Medicaments and pharmaceutical compositions may be formulated in fluid, including gel, form. Fluid formulations may be formulated for administration by injection or infusion (e.g. via catheter) to a selected region of the human or animal body.

In some embodiments the composition is formulated for injection or infusion, e.g. into a blood vessel or tumor.

In accordance with the invention described herein methods are also provided for the production of pharmaceutically useful compositions, such methods of production may comprise one or more steps selected from: producing an antigen-binding molecule, polypeptide, CAR, nucleic acid (or plurality thereof), expression vector (or plurality thereof) or cell described herein; isolating an antigen-binding molecule, polypeptide, CAR, nucleic acid (or plurality thereof), expression vector (or plurality thereof) or cell described herein; and/or mixing an antigen-binding molecule, polypeptide, CAR, nucleic acid (or plurality thereof), expression vector (or plurality thereof) or cell described herein with a pharmaceutically acceptable carder, adjuvant, excipient or diluent.

For example, a further aspect the invention described herein relates to a method of formulating or producing a medicament or pharmaceutical composition for use in the treatment of a disease/condition (e.g. a cancer), the method comprising formulating a pharmaceutical composition or medicament by mixing an antigen-binding molecule, polypeptide, CAR, nucleic acid (or plurality thereof), expression vector (or plurality thereof) or cell described herein with a pharmaceutically acceptable carrier, adjuvant, excipient or diluent.

Therapeutic and Prophylactic Applications

The antigen-binding molecules, polypeptides, CARs, nucleic acids, expression vectors, cells and compositions described herein find use in therapeutic and prophylactic methods.

The present invention provides an antigen-binding molecule, polypeptide, CAR, nucleic acid (or plurality thereof), expression vector (or plurality thereof), cell or composition described herein for use in a method of medical treatment or prophylaxis. Also provided is the use of an antigen-binding molecule, polypeptide, CAR, nucleic acid (or plurality thereof), expression vector (or plurality thereof), cell or composition described herein in the manufacture of a medicament for treating or preventing a disease or condition. Also provided is a method of treating or preventing a disease or condition, comprising administering to a subject a therapeutically or prophylactically effective amount of an antigen-binding molecule, polypeptide, CAR, nucleic acid (or plurality thereof), expression vector (or plurality thereof), cell or composition described herein.

The methods may be effective to reduce the development or progression of a disease/condition, alleviation of the symptoms of a disease/condition or reduction in the pathology of a disease/condition. The methods may be effective to prevent progression of the disease/condition, e.g. to prevent worsening of, or to slow the rate of development of, the disease/condition. In some embodiments the methods may lead to an improvement in the disease/condition, e.g. a reduction in the symptoms of the disease/condition or reduction in some other correlate of the severity/activity of the disease/condition. In some embodiments the methods may prevent development of the disease/condition a later stage (e.g. a chronic stage or metastasis).

It will be appreciated that the articles of the present invention may be used for the treatment/prevention of any disease/condition that would derive therapeutic or prophylactic benefit from a reduction in the number and/or activity of cells expressing HER3. For example, the disease/condition may be a disease/condition in which cells expressing HER3 are pathologically implicated, e.g. a disease/condition in which an increased number/proportion of cells expressing HER3 is positively associated with the onset, development or progression of the disease/condition, and/or severity of one or more symptoms of the disease/condition, or for which an increased number/proportion of cells expressing HER3, is a risk factor for the onset, development or progression of the disease/condition.

In some embodiments, the disease/condition to be treated/prevented in accordance with the present invention is a disease/condition characterised by an increase in the number/proportion/activity of cells expressing HER3, e.g. as compared to the number/proportion/activity of cells expressing HER3 in the absence of the disease/condition.

In some embodiments the disease/condition to be treated/prevented is a cancer.

The cancer may be any unwanted cell proliferation (or any disease manifesting itself by unwanted cell proliferation), neoplasm or tumor. The cancer may be benign or malignant and may be primary or secondary (metastatic). A neoplasm or tumor may be any abnormal growth or proliferation of cells and may be located in any tissue. The cancer may be of tissues/cells derived from e.g. the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal gland, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, and/or white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, hematologic cancer and sarcoma.

HER3 and its association with and role in cancer is reviewed e.g. in Karachaliou et al., BioDrugs. (2017) 31(1): 83-73 and Zhang et al., Acta Biochimica et Biophysica Sinica (2016) 43(1): 39-48, both of which are hereby incorporated by reference in their entirety.

In some embodiments, a cancer is selected from: a cancer comprising cells expressing HER3, a solid tumor, breast cancer, breast carcinoma, ductal carcinoma, gastric cancer, gastric carcinoma, gastric adenocarcinoma, colorectal cancer, colorectal carcinoma, colorectal adenocarcinoma, head and neck cancer, squamous cell carcinoma of the head and neck (SCCHN), lung cancer, lung adenocarcinoma, squamous cell lung carcinoma, ovarian cancer, ovarian carcinoma, ovarian serous adenocarcinoma, kidney cancer, renal cell carcinoma, renal clear cell carcinoma, renal cell adenocarcinoma, renal papillary cell carcinoma, pancreatic cancer, pancreatic adenocarcinoma, pancreatic ductal adenocarcinoma, cervical cancer, cervical squamous cell carcinoma, skin cancer, melanoma, esophageal cancer, esophageal adenocarcinoma, liver cancer, hepatocellular carcinoma, cholangiocarcinoma, uterine cancer, uterine corpus endometrial carcinoma, thyroid cancer, thyroid carcinoma, pheochromocytoma, paraganglioma, bladder cancer, bladder urothelial carcinoma, prostate cancer, prostate adenocarcinoma, sarcoma and thymoma.

In some embodiments the cancer to be treated in accordance with the present invention is selected from: a HER3-expressing cancer, gastric cancer (e.g. gastric carcinoma, gastric adenocarcinoma, gastrointestinal adenocarcinoma), head and neck cancer (e.g. head and neck squamous cell carcinoma), breast cancer, ovarian cancer (e.g. ovarian carcinoma), lung cancer (e.g. NSCLC, lung adenocarcinoma, squamous lung cell carcinoma), melanoma, prostate cancer, oral cavity cancer (e.g. oropharyngeal cancer), renal cancer (e.g. renal cell carcinoma) or colorectal cancer (e.g. colorectal carcinoma), oesophageal cancer, pancreatic cancer, a solid cancer and/or a liquid cancer.

The treatment/prevention may be aimed at one or more of: delaying/preventing the onset/progression of symptoms of the cancer, reducing the severity of symptoms of the cancer, reducing the survival/growth/invasion/metastasis of cells of the cancer, reducing the number of cells of the cancer and/or increasing survival of the subject.

In some embodiments, the cancer to be treated/prevented comprises cells expressing an EGFR family member (e.g. HER3, EGFR, HER2 or HER4), and/or cells expressing a ligand for an EGFR family member. In some embodiments, the cancer to be treated/prevented is a cancer which is positive for an EGFR family member. In some embodiments, the cancer over-expresses an EGFR family member and/or a ligand for an EGFR family member. Overexpression of can be determined by detection of a level of expression which is greater than the level of expression by equivalent non-cancerous cells/non-tumor tissue.

Expression may be determined by any suitable means. Expression may be gene expression or protein expression. Gene expression can be determined e.g. by detection of mRNA encoding HER3, for example by quantitative real-time PCR (gRT-PCR). Protein expression can be determined e.g. by for example by antibody-based methods, for example by western blot, immunohistochemistry, immunocytochemistry, flow cytometry, or ELISA.

In some embodiments, the cancer to be treated/prevented comprises cells expressing HER3. In some embodiments, the cancer to be treated/prevented is a cancer which is positive for HER3. In some embodiments, the cancer over-expresses HER3. Overexpression of HER3 can be determined by detection of a level of expression of HER3 which is greater than the level of expression by equivalent non-cancerous cells/non-tumor tissue.

In some embodiments, a patient may be selected for treatment described herein based on the detection of a cancer expressing HER3, or overexpressing HER3, e.g. in a sample obtained from the subject.

In some embodiments, the cancer to be treated/prevented comprises cells expressing a ligand for HER3 (e.g. NRG1 and/or NRG2). In some embodiments, the cancer to be treated/prevented comprises cells expressing a level of expression of NRG1 and/or NRG2 which is greater than the level of expression by equivalent non-cancerous cells/non-tumor tissue.

Administration of the articles of the present invention is preferably in a "therapeutically effective" or "prophylactically effective" amount, this being sufficient to show therapeutic or prophylactic benefit to the subject. The actual amount administered, and rate and time-course of administration, will depend on the nature and severity of the disease/condition and the particular article administered. Prescription of treatment, e.g. decisions on dosage etc., is within the responsibility of general practitioners and other medical doctors, and typically takes account of the disease/disorder to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Administration may be alone or in combination with other treatments, either simultaneously or sequentially dependent upon the condition to be treated. The antigen-binding molecule or composition described herein and a therapeutic agent may be administered simultaneously or sequentially.

In some embodiments, the methods comprise additional therapeutic or prophylactic intervention, e.g. for the treatment/prevention of a cancer. In some embodiments, the therapeutic or prophylactic intervention is selected from chemotherapy, immunotherapy, radiotherapy, surgery, vaccination and/or hormone therapy. In some embodiments, the therapeutic or prophylactic intervention comprises leukapheresis. In some embodiments the therapeutic or prophylactic intervention comprises a stem cell transplant.

In some embodiments the antigen-binding molecule is administered in combination with an agent capable of inhibiting signalling mediated by an EGFR family member.

Accordingly, the invention provides compositions comprising an article according to the present invention (e.g. an antigen-binding molecule according to the invention) and another agent capable of inhibiting signalling mediated by an EGFR family member (e.g. EGFR, HER2, HER3 or HER4). Also provided is the use of such compositions in methods of medical treatment and prophylaxis of diseases/conditions described herein.

Also provided are methods for treating/preventing diseases/conditions described herein comprising administering articles of the present invention an article according to the present invention (e.g. an antigen-binding molecule according to the invention) and another agent capable of inhibiting signalling mediated by an EGFR family member.

Agents capable of inhibiting signalling mediated by EGFR family members are known in the art, and include e.g. small molecule inhibitor's (e.g. tyrosine kinase inhibitors), monoclonal antibodies (and antigen-binding fragments thereof), peptide/polypeptide inhibitors (e.g. decoy ligands; receptors or peptide aptamers) and nucleic acids (e.g. antisense nucleic acid, splice-switching nucleic acids or nucleic acid aptamers). Inhibitors of signalling mediated by EGFR family members include agents that inhibit signalling through a direct effect on an EGFR family member, an interaction partner therefore, and/or a downstream factor involved in signalling mediated by the EGFR family member.

In some embodiments the antagonist of signalling mediated by an EGFR family member inhibits signalling mediated by one or more of EGFR, HER2, HER4 and HER3. Inhibitors of signalling mediated by EGFR family members are described e.g. in Yamaoka et al., Int. J. Mol. Sci. (2018), 19, 3491, which is hereby incorporated by reference in its entirety. In some embodiments the antagonist is a pan-ErbB inhibitor. In some embodiments the antagonist is an inhibitor of signalling mediated by EGFR (e.g. cetuximab, panitumumab, gefitinib, erlotinib, lapatinib, afatinib, brigatinib, icotinib, osimertinib, zalutumuniab, vandetanib, necitunimab, nimotuzumab, dacomitinib, duligotuzumab or matuzumab). In some embodiments the antagonist is an inhibitor of signalling mediated by HER2 (e.g. trastuzumab, pertuzumab, lapatinib, neratinib, afatinib, dacomitinib, MM-111, MCLA-128 or margetuximab). In some embodiments the antagonist is an inhibitor of signalling mediated by HER3 (e.g. seribantumab, lumretuzumab, elgemtumab, KTN3379, AV-203, GSK2849330, REGN1400, MP-RM-1, EV20, duligotuzumab, MM-111, istiratumab, MCLA-128, patritumab, EZN-3920, RB200 or U3-1402). In some embodiments the antagonist is an inhibitor of signalling mediated by HER4 (e.g. lapatinib, ibrutinib, afatinib, dacomitinib or neratinib).

In some embodiments the antagonist of signalling mediated by an EGFR family member inhibits a downstream effector of signalling by an EGFR family member. Downstream effectors of signalling by an EGFR family members include e.g. PI3K, AKT, KRAS, BRAF, MEK/ERK and mTOR. In some embodiments, the antagonist of signalling mediated by an EGFR family member is an inhibitor of the MAPK/ERK pathway. In some embodiments, the antagonist of signalling mediated by an EGFR family member is an inhibitor of the PI3K/ATK/mTOR pathway. In some embodiments the antagonist is a PI3K inhibitor (e.g. pictilisib, buparlisib, idelalisib, copanlisib or duvelisib). In some embodiments the antagonist is an AKT inhibitor (e.g. MK-2206, AZD5363, ipatasertib, VQD-002, perifosine or miltefosine). In some embodiments the antagonist is a BRAF inhibitor (e.g. vemurafenib, dabrafenib, SB590885, XL281, RAF265, encorafenib, GDC-0879, PLX-4720, sorafenib, or LGX818). In some embodiments the antagonist is a MEK/ERK inhibitor (e.g. trametinib, cobimetinib, binimetinib, selumetinib, RD-325901 CI-1040, PD035901, or TAK-733). In some embodiments the antagonist is a mTOR inhibitor (e.g. rapamycin, deforolimus, temsirolimus, everolimus, ridaforolimus or sapanisertib).

In some embodiments, the cancer to be treated in accordance with an aspect of the present invention (including monotherapy or combination therapy) is a cancer which is resistant to treatment with an antagonist of signalling mediated by an EGFR family member (e.g. EGFR, HER2, HER4 and/or HER3), e.g. an antagonist as described in the preceding three paragraphs. In some embodiments the subject to be treated has a cancer which is resistant to treatment with an antagonist of signalling mediated by an EGFR family member. In some embodiments the subject to be treated has a cancer which has developed resistance to treatment with an antagonist of signalling mediated by an EGFR family member. In some embodiments the subject to be treated has a cancer which previously responded to treatment with an antagonist of signalling mediated by an EGFR family member, and which is now resistant to treatment with the antagonist. In some embodiments the subject to be treated has a cancer which has relapsed and/or progressed following treatment with an antagonist of signalling mediated by an EGFR family member. In some embodiments the subject to be treated has a cancer which initially responded to treatment with an antagonist of signalling mediated by an EGFR family member, but later progressed on said treatment.

The skilled person is readily able to identify cancers and subjects according to the preceding paragraph. Such cancers and subjects may be identified e.g. through monitoring of the development/progression of the cancer (and/or correlates thereof) over time e.g. during the course of treatment with an antagonist of signalling mediated by an EGFR family member. In some embodiments, identification of such subjects/cancers may comprise analysis of a sample (e.g. a biopsy), e.g. in vitro. In some embodiments the cancer may be determined to comprise cells having a mutation which is associated with reduced susceptibility and/or resistance to treatment with the antagonist. In some embodiments the cancer may be determined to comprise cells having upregulated expression of an EGFR family member.

In particular embodiments, the cancer to be treated is a cancer which is resistant to treatment with an antagonist of signalling mediated by EGFR and/or HER2. In some embodiments the subject to be treated has a cancer which is resistant to treatment with an antagonist of signalling mediated by EGFR and/or HER2. In some embodiments the subject to be treated has a cancer which has developed resistance to treatment with an antagonist of signalling mediated by EGFR and/or HER2. In some embodiments the subject to be treated has a cancer which previously responded to treatment with an antagonist of signalling mediated by EGFR and/or HER2, and which is now resistant to treatment with the antagonist. In some embodiments the subject to be treated has a cancer which has relapsed and/or progressed following treatment with an antagonist of signalling mediated by EGFR and/or HER2. In some embodiments the subject to be treated has a cancer which initially responded to treatment with an antagonist of signalling mediated by EGFR and/or HER2, but later progressed on said treatment.

In particular embodiments, the cancer to be treated comprises mutation conferring resistance to treatment with an inhibitor of BRAF. In some embodiments, the mutation is mutation at BRAF V600. In some embodiments, the mutation is BRAF V600E or V600K.

In particular embodiments, the cancer to be treated comprises mutation conferring resistance to treatment with an inhibitor of BRAF (e.g. mutation at BRAF V600), and the treatment comprises administration of vemurafenib or darafenib.

In some embodiments the antigen-binding molecule is administered in combination with an agent capable of inhibiting signalling mediated by an immune checkpoint molecule. In some embodiments the immune checkpoint molecule is e.g. PD-1, CTLA-4, LAG-3, VISTA, TIM-3, TIGIT or BTLA. In some embodiments the antigen-binding molecule is administered in combination with an agent capable of promoting signalling mediated by a costimulatory receptor. In some embodiments the costimulatory receptor is e.g. CD28, CD80, CD40L, CD86, OX40, 4-1 BB, CD27 or ICOS.

Accordingly, the invention provides compositions comprising an article according to the present invention (e.g. an antigen-binding molecule according to the invention) and an agent capable of inhibiting signalling mediated by an immune checkpoint molecule. Also provided are compositions comprising the articles of the present invention and an agent capable of promoting signalling mediated by a costimulatory receptor. Also provided is the use of such compositions in methods of medical treatment and prophylaxis of diseases/conditions described herein.

Also provided are methods for treating/preventing diseases/conditions described herein comprising administering articles of the present invention an article according to the present invention (e.g. an antigen-binding molecule according to the invention) and an agent capable of inhibiting signalling mediated by an immune checkpoint molecule. Also provided are methods for treating/preventing diseases/conditions described herein comprising administering articles of the present invention an article according to the present invention (e.g. an antigen-binding molecule according to the intention)) and an agent capable of promoting signalling mediated by a costimulatory receptor.

Agents capable of inhibiting signalling mediated by immune checkpoint molecules are known in the art, and include e.g. antibodies capable of binding to immune checkpoint molecules or their ligands, and inhibiting signalling mediated by the immune checkpoint molecule. Other agents capable of inhibiting signalling mediated by an immune checkpoint molecule include agents capable of reducing gene/protein expression of the immune checkpoint molecule or a ligand for the immune checkpoint molecule (e.g. through inhibiting transcription of the gene(s) encoding the immune checkpoint molecule/ligand, inhibiting post-transcriptional processing of RNA encoding the immune checkpoint molecule/ligand, reducing stability of RNA encoding the immune checkpoint molecule/ligand, promoting degradation of RNA encoding the immune checkpoint molecule/ligand, inhibiting post-translational processing of the immune checkpoint molecule/ligand, reducing stability the immune checkpoint molecule/ligand, or promoting degradation of the immune checkpoint molecule/ligand), and small molecule inhibitors.

Agents capable of promoting signalling mediated by costimulatory receptors are known in the art, and include e.g. agonist antibodies capable of binding to costimulatory receptors and triggering or increasing signalling mediated by the costimulatory receptor. Other agents capable of promoting signalling mediated by costimulatory receptors include agents capable of increasing gene/protein expression of the costimulatory receptor or a ligand for the costimulatory receptor (e.g. through promoting transcription of the gene(s) encoding the costimulatory receptor/ligand, promoting post-transcriptional processing of RNA encoding the costimulatory receptor/ligand, increasing stability of RNA encoding the costimulatory receptor/ligand, inhibiting degradation of RNA encoding the costimulatory receptor/ligand, promoting post-translational processing of the costimulatory receptor/ligand, increasing stability the costimulatory receptor/ligand, or inhibiting degradation of the costimulatory receptor/ligand), and small molecule agonists.

In particular embodiments the antigen-binding molecule of the present invention is administered in combination with an agent capable of inhibiting signalling mediated by PD-1. The agent capable of inhibiting signalling mediated by PD-1 may be a PD-1- or PD-L1-targeted agent. The agent capable of inhibiting signalling mediated by PD-1 may e.g. be an antibody capable of binding to PD-1 or PD-L1 and inhibiting PD-1-mediated signalling.

In some embodiments, the antigen-binding molecule of the present invention is administered in combination with an agent capable of inhibiting signalling mediated by CTLA-4. The agent capable of inhibiting signalling mediated by CTLA-4 may be a CTLA-4-targeted agent, or an agent targeted against a ligand for CTLA-4 such as CD80 or CD86. In some embodiments, the agent capable of inhibiting signalling mediated by CTLA-4 may e.g. be an antibody capable of binding to CTLA-4, CD80 or CD86 and inhibiting CTLA-4-mediated signalling.

In some embodiments, the antigen-binding molecule of the present invention is administered in combination with an agent capable of inhibiting signalling mediated by LAG-3. The agent capable of inhibiting signalling mediated by LAG-3 may be a LAG-3-targeted agent, or an agent targeted against a ligand for LAG-3 such as MHC class II. In some embodiments, the agent capable of inhibiting signalling mediated by LAG-3 may e.g. be an antibody capable of binding to LAG-3 or MHC class II and inhibiting LAG-3-mediated signalling.

In some embodiments, the antigen-binding molecule of the present invention is administered in combination with an agent capable of inhibiting signalling mediated by VISTA. The agent capable of inhibiting signalling mediated by VISTA may be a VISTA-targeted agent, or an agent targeted against a ligand for VISTA such as VSIG-3 or VSIG-8. In some embodiments, the agent capable of inhibiting signalling mediated by VISTA may e.g. be an antibody capable of binding to VISTA, VS1G-3 or VS1G-8 and inhibiting VISTA-mediated signalling.

In some embodiments, the antigen-binding molecule of the present invention is administered in combination with an agent capable of inhibiting signalling mediated by TIM-3. The agent capable of inhibiting signalling mediated by TIM-3 may be a TIM-3-targeted agent, or an agent targeted against a ligand for TIM-3 such as Galectin 9. In some embodiments, the agent capable of inhibiting signalling mediated by TIM-3 may e.g. be an antibody capable of binding to TIM-3 or Galectin 9 and inhibiting TIM-3-mediated signalling.

In some embodiments, the antigen-binding molecule of the present invention is administered in combination with an agent capable of inhibiting signalling mediated by TIGIT. The agent capable of inhibiting signalling mediated by TIGIT may be a TIGIT-targeted agent, or an agent targeted against a ligand for TIGIT such as CD113, CD112 or CD155. In some embodiments, the agent capable of inhibiting signalling mediated by TIGIT may e.g. be an antibody capable of binding to TIGIT, CD113, CD112 or CD155 and inhibiting TIGIT-mediated signalling.

In some embodiments, the antigen-binding molecule of the present invention is administered in combination with an agent capable of inhibiting signalling mediated by BTLA. The agent capable of inhibiting signalling mediated by BTLA may be a BTLA-targeted agent, or an agent targeted against a ligand for BTLA such as HVEM. In some embodiments, the agent capable of inhibiting signalling mediated by BTLA may e.g. be an antibody capable of binding to BTLA or HVEM and inhibiting BTLA-mediated signalling.

In some embodiments methods employing a combination of an antigen-binding molecule of the present invention and an agent capable of inhibiting signalling mediated by an immune checkpoint molecule (e.g. PD-1) provide an improved treatment effect as compared to the effect observed when either agent is used as a monotherapy. In some embodiments the combination of an antigen-binding molecule of the present invention and an agent capable of inhibiting signalling mediated by an immune checkpoint molecule (e.g. PD-1) provide a synergistic (i.e. super-additive) treatment effect.

Simultaneous administration refers to administration of the antigen-binding molecule, polypeptide, CAR, nucleic acid (or plurality thereof), expression vector (or plurality thereof), cell or composition and therapeutic agent together, for example as a pharmaceutical composition containing both agents (combined preparation), or immediately after each other and optionally via the same route of administration, e.g. to the same artery, vein or other blood vessel. Sequential administration refers to administration of one of the antigen-binding molecule/composition or therapeutic agent followed after a given time interval by separate administration of the other agent. It is not required that the two agents are administered by the same route, although this is the case in some embodiments. The time interval may be any time interval.

Chemotherapy and radiotherapy respectively refer to treatment of a cancer with a drug or with ionising radiation (e.g. radiotherapy using X-rays or γ-rays). The drug may be a chemical entity, e.g. small molecule pharmaceutical, antibiotic, DNA intercalator, protein inhibitor (e.g. kinase inhibitor), or a biological agent, e.g. antibody, antibody fragment, aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a pre-determined timetable, plan, scheme or schedule of chemotherapy administration which may be prepared by a physician or medical practitioner and may be tailored to suit the patient requiring treatment. The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs may be selected from; Abemaciclib, Abiraterone Acetate, Abitrexate (Methotrexate), Abraxane (Paclitaxel Albumin-stabilized Nanoparticle Formulation), ABVD, ABVE, ABVE-PC, AC, Acalabrutinib, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemluzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochiorin (Chlorambucil), Ambociorin (Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Atezolizumab, Avastin (Bevacizumab), Avelumab, Axicabtagene Ciloleucel, Axitinib, Azacitidine, Bavencio (Ayelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Calquence (Acalabrutinib), Campath (Alemluzumab), Camptosar (Irinotecan Hydrochloride), Capecitabine, CAPOX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fiudarabine Phosphate), Fludarabine Phosphate, Fluoroplex (Fluorouracil—Topical), Fluorouracil injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), [No Entries], Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Lahergarepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq (Atezolizumab), Temodar (Temozolomide), Temozolomide, Temsirolimus, Thalidomide, Thalomid (Thalidomide), Thioguanine, Thiotepa, Tisagenlecieucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Valrubicin, Valstar (Valrubicin), Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xaikori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yescarta (Axicabtagene Ciloleucel), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib) and Zytiga (Abiraterone Acetate).

In some embodiments the antigen-binding molecule of the invention is administered in combination with one or more of: trastuzumab, cetuximab, cisplatin, 5-FU or capecitabine. In some embodiments the antigen-binding molecule of the invention is administered in combination with trastuzumab and cisplatin, and 5-FU or capecitabine.

In some embodiments the antigen-binding molecule of the invention is administered in combination with cetuximab. Administration in combination with cetuximab is contemplated in particular for the treatment of head and neck cancer (e.g. head and neck squamous cell carcinoma).

Multiple doses of the antigen-binding molecule, polypeptide, CAR, nucleic acid (or plurality thereof), expression vector (or plurality thereof), cell or composition may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

Methods of Detection

The invention also provides the articles of the present invention for use in methods for detecting, localizing or imaging HER3, or cells expressing HER3.

The antigen-binding molecules described herein may be used in methods that involve the antigen-binding molecule to HER3. Such methods may involve detection of the bound complex of the antigen-binding molecule and HER3.

As such, a method is provided, comprising contacting a sample containing, or suspected to contain, HER3, and detecting the formation of a complex of the antigen-binding molecule and HER3. Also provided is a method comprising contacting a sample containing, or suspected to contain, a cell expressing HER3, and detecting the formation of a complex of the antigen-binding molecule and a cell expressing HER3.

Suitable method formats are well known in the art, including immunoassays such as sandwich assays, e.g. ELISA. The methods may involve labelling the antigen-binding molecule, or target(s), or both, with a detectable moiety, e.g. a fluorescent label, phosphorescent label, luminescent label, immuno-detectable label, radiolabel, chemical, nucleic acid or enzymatic label as described herein. Detection techniques are well known to those of skill in the art and can be selected to correspond with the labelling agent.

Methods of this kind may provide the basis of methods for the diagnostic and/or prognostic evaluation of a disease or condition, e.g. a cancer. Such methods may be performed in vitro on a patient sample, or following processing of a patient sample. Once the sample is collected, the patient is not required to be present for the in vitro method to be performed, and therefore the method may be one which is not practised on the human or animal body. In some embodiments the method is performed in vivo.

Detection in a sample may be used for the purpose of diagnosis of a disease/condition (e.g. a cancer), predisposition to a disease/condition, or for providing a prognosis (prognosticating) for a disease/condition, e.g. a disease/condition described herein. The diagnosis or prognosis may relate to an existing (previously diagnosed) disease/condition.

Such methods may involve detecting or quantifying HER3 or cells expressing HER3, e.g. in a patient sample. Where the method comprises quantifying the relevant factor, the method may further comprise comparing the determined amount against a standard or reference value as part of the diagnostic or prognostic evaluation. Other diagnostic/prognostic tests may be used in conjunction with those described herein to enhance the accuracy of the diagnosis or prognosis or to confirm a result obtained by using the tests described herein.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; pleural fluid; cerebrospinal fluid (CSF); or cells isolated from said individual. In some embodiments, the sample may be obtained or derived from a tissue or tissues which are affected by the disease/condition (e.g. tissue or tissues in which symptoms of the disease manifest, or which are involved in the pathogenesis of the disease/condition).

The present invention also provides methods for selecting/stratifying a subject for treatment with a HER3-targeted agent. In some embodiments a subject is selected for treatment/prevention in accordance with the invention, or is identified as a subject which would benefit from such treatment/prevention, based on detection/quantification of HER3, or cells expressing HER3, e.g. in a sample obtained from the individual.

Subjects

The subject in accordance with aspects the invention described herein may be any animal or human. The subject is preferably mammalian, more preferably human. The subject may be a non-human mammal, but is more preferably human. The subject may be male or female. The subject may be a patient. A subject may have been diagnosed with a disease or condition requiring treatment (e.g. a cancer), may be suspected of having such a disease/condition, or may be at risk of developing/contracting such a disease/condition.

In embodiments according to the present invention the subject is preferably a human subject. In some embodiments, the subject to be treated according to a therapeutic; or prophylactic method of the invention herein is a subject having, or at risk of developing, a cancer. In embodiments according to the present invention, a subject may be selected for treatment according to the methods based on characterisation for certain markers of such disease/condition.

Kits

In some aspects of the invention described herein a kit of parts is provided. In some embodiments the kit may have at least one container having a predetermined quantity of an antigen-binding molecule, polypeptide, CAR, nucleic acid (or plurality thereof), expression vector (or plurality thereof), cell or composition described herein.

In some embodiments, the kit may comprise materials for producing an antigen-binding molecule, polypeptide, CAR, nucleic acid (or plurality thereof), expression vector (or plurality thereof), cell or composition described herein.

The kit may provide the antigen-binding molecule, polypeptide, CAR, nucleic acid (or plurality thereof), expression vector (or plurality thereof), cell or composition together with instructions for administration to a patient in order to treat a specified disease/condition.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Sequence Identity

As used herein, "sequence identity" refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using publicly available computer software such as ClustalOmega (Boding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

Sequences

| SEQ ID NO: | DESCRIPTION | SEQUENCE |
|---|---|---|
| 1 | Human HER3 isoform 1 (UniProt: P21860-1, v1) | MRANDALQVLGLLFSLARGSEVGNSQAVCPGTLNGLSVTGDAENQYQTLYKLYERCEVVMGNLE IVLTGHNADLSFLQWIREVTGYVLVAMNEFSTLPLPNLRVVRGTQVDGKFAIFVMLNYNTNSSHA LRQLRLTQLTEILSGGVYIEKNDKLCHMDTIDWRDIVRDRDAEIVVKDNGRSCPPCHEVCKGRCW GPGSEDCQTLTKTICAPQCNGHCFGPNPNQCCHDECAGGCSGPQDTDCFACRHFNDSGACVP RCPQPLVYNKLTCLEPNPHTKYQYGGVCVASCPHNFVVDQTSCVRACPPDKMEVDKNGLKMC EPCGGLCPKACEGTGSGSRFQTVDSSNIDGFVNCTKILGNLDFLITGLNGDPWHKIPALDPEKLNV FRTVREITGYLNIQSWPPHMHNFSVFSNLTTIGGRSLYNRGFSLLIMKNLNVTSLGFRSLKEISAGR IYISANRQLCYHHSLNWTKVLRGPTEERLDIKHNRPRRDCVAEGKVCDPLCSSGGCWGRGPGQC LSCRNYSRGGVCVTHCNFLNGEPREFAHEAECFSCHPECQPMEGTATCNGSGSDTCAQCAHFR DGPHCVSSCPHGVLGAKGPIYKYPDVQNECRPCHENCTQGCKGPELQDCLGQTLVLIGKTHLTM ALTVIAGLVVIFMMLGGTFLYWRGRRIQNKRAMRRYLERGESIEPLDPSEKANKVLARIFKETELRK LKVLGSGVFGTVHKGVWIPEGESIKIPVCIKVIEDKSGRQSFQAVTDHMLAIGSLDHAHIVRLLGLC PGSSLQLVTQYLPLGSLLDHVRQHRGALGPQLLLNWGVQIAKGMYYLEEHGMVHRNLAARNVLL KSPSQVQVADFGVADLLPPDDKQLLYSEAKTPIKWMALESIHFGKYTHQSDVWSYGVTVWELMT FGAEPYAGLRLAEVPDLLEKGERLAQPQICTIDVYMVMVKCWMIDENIRPTFKELANEFTRMARDP |

| SEQ ID NO: | DESCRIPTION | SEQUENCE |
|---|---|---|
| | | PRYLVIKRESGPGIAPGPEPHGLTNKKLEEVELEPELDLDLDLEAEEDNLATTTLGSALSLPVGTLN
RPRGSQSLLSPSSGYMPMVQGNLGESCQESAVSGSSERCPRPVSLHPMPRGCLASESSEGHVT
GSEAELQEKVSMCRSRSRSRSPRPRGDSAYHSQRHSLLTPVTPLSPPGLEEEDVNGYVMPDTHL
KGTPSSREGTLSSVGLSSVLGTEEEDEDEEYEYMNRRRRHSPPHPPRPSSLEELGYEYMDVGSD
LSASLGSTQSCPLHPVPIMPTAGTTPDEDYEYMNRQRDGGGPGGDYAMAGACPASEQGYEEMR
AFQGPGHQAPHVHYARLKTLRSLEATDSAFDNPDYWHSRLFPKANAQRT |
| 2 | Human HER3 isoform 2 (UniProt: P21860-2) | MRANDALQVLGLLFSLARGSEVGNSQAVCPGTLNGLSVTGDAENQYQTLYKLYERCEVVMGNLE
IVLTGHNADLSFLQWIREVTGYVLVAMNEFSTLPLPNLRVVRGTQWDGKFAIFVMLNYNTNSSHA
LRQLRLTQLTGQFPMVPSGLTPQPAQDWYLLDDDPRLLTLSASSKVPVTLAAV |
| 3 | Human HER3 isoform 3 (UnniProt: P21860-3) | MRANDALQVLGLLFSLARGSEVGNSQAVCPGTLNGLSVTGDAENGYQTLYKLYERCEVVMGNLE
IVLTGHNADLSFLQWIREVTGYVLVAMNEFSTLPLPNLRVVRGTQVYDGKFAIFVMLNYNTNSSHA
LRQLRLTQLTEILSGGVYIEKNDKLCHMDTIDWRDIVRDRDAEIVVKDNGRSCPPCHEVCKGRCW
GPGSEDCQTLTKTICAPQCNGHCFGPNPNQCCHDECAGGCSGPQDTDCFACRHFNDSGACVP
RCPQPLVYNKLTFQLERNPHTKYQYGGVCVASCPHNFVVDQTSCVRACPPDKMEVDKNGLKMC
EPCGGLCPKAF |
| 4 | Human HER3 isoform 4 (UniProt: P21860-4 | MGNLEIVLTGHNADLSFLQWIREVTGYVLVAMNEFSTLPLPNLRVVRGTQVYDGKFAIFVMLNYNT
NSSHALRQLRLTQLTEILSGGVYIEKNDKLCHMDTIDWRDIVRDRDAEIVVKDNGRSCPPCHEVCK
GRCWGPGSEDCQTLTKTICAPQCNGHCFGPNPNQCCHDECAGGCSGPQDTDCFACRHFNDSG
ACVPRCPQRLVYNKLTFQLEPNPHTKYQYGGVCVASCPHNFVVDQTSCVRACPPDKMEVDKNG
LKMCEPCGGLCPKACEGTSGSRFQTVDSSNIDGFVNCTKILGNLDFLITGLNGDPWHKIPALDP
EKLNVFRTVREITGYLNIQSWPPHMHNFSVFSNLTTIGGRSLYNRGFSLLIMKNLNVTSLGFRSLKE
ISAGRIYISANRQLCYHHSLNWTKVLRGPTEERLDIKHNRPRRDCVAEGKVCDPLCSSGGCWGP
GPGQCLSCRNYSRGGVCVTHCNFLNGEPREFAHEAECFSCHPECQPMEGTATCNGSGSDTCA
QCAHFRDGPHCVSSCPHGVLGAKGPIYKYPDVQNECRPCHENCTQGCKGPELQDCLGQTLVLIG
KTHLTMALTVIAGLVVIFMMLGGTFLYWRGRRIQNKRAMRRYLERGESIEPLDPSEKANKVLARIF
KETELRKLKVLGSGVFGTHKGVWIPEGESIKIPVCIKVIEDKSGRQSFQAVTDHMLAIGLDHAHI
VRLLGLCPGSSLQLVTQYLPLGSLLDHVRQHRGALGPQLLLNWGVQIAKGMYYLEEHGMVHRNL
AARNVLLKSPSQVQVADFGVADLLPPDDKQLLYSEAKTPIKWMALESIHFGKYTHQSDVWSYGVT
VWELMTFGAEPYAGLRLAEVPDLLEKGERLAQPQICTIDVYMVMVKCWMIDENIRPTFKELANEFT
RMARDPPRYLVIKRESGPGIAPGREPHGLTNKKLEEVELEPELDLDLDLEAEEDNLATTTLGSALS
LPVGTLNRPRGSQSLLSPSSGYMPMNQGNLGESCQESAVSGSSERCPRPVSLHPMPRGCLASE
SSEGHVTGSEAELQEKVSMCRSRSRSRSPRPRGDSAYHSQRHSLLTPVTPLSPPGLEEEDVNGY
VMPDTHLKGTPSSREGTLSSVGLSSVLGTEEEDEDEEYEYMNRRRRHSPPHPPRPSSLEELGYE
YMDVGSDLSASLGSTQSCPLHPVPIMPTAGTTPDEDYEYMNRQRDGGGPGGDYAAMGACPASE
QGYEEMRAFQGPGHQAPHVHYARLKTLRSLEATDSAFDNPDYWHSRLFPKANAQRT |
| 5 | Human HER3 isoform 5 (UniProt: P21860-5) | MALTVIAGLVVIFMMLGGTFLYWRGRRIQNKRAMRRYLERGESIEPLDPSEKANKVLARIFKETEL
RKLKVLGSGVFGTVHKGVWIPEGESIKIPVCIKVIEDKSGRQSFQAVTDHMLAIGSLDHAHIVRLLG
LCPGSSLQLVTQYLPLGSLLDHVRQHRGALGPQLLLNWGVQIAKGMYYLEEHGMVHRNLAARNV
LLKSPSQVQVADFGVADLLPPDDKQLLYSEAKTPIKWMALESIHFGKYTHQSDVWSYGVTVWEL
MTFGAERYAGLRLAEVPDLLEKGERLAQPQICTIDVYMVMVKCWMIDENIRPTFKELANEFTRMA
RDPPRYLVIKRESGPGIAPGPEPHGLTNKKLEEVELEPELDLDLDLEAEEDNLATTTLGSALSLPVG
TLNRPRGSQSLLSPSSGYMPMNQGNLGESCQESAVSGSSERCPRPVSLHPMPRGCLASESSEG
HVTGSEAELQEKVSMCRSRSRSRSPRPRGDSAYHSQPHSLLTPVTPLSPPGLEEEDVNGYVMP
DTHLKGTPSSREGTLSSVGLSSVLGTEEEDEDEEYEYMNRRRPHSPPHPPRPSSLEELGYEYMD
VGSDLSASLGSTQSCPLHPVPIMPTAGTTPDEDYEYMNPQRDGGGPGGDYAAMGACPASEQGY
EEMRAFQGPGHQAPHVHYARLKTLRSLEATDSAFDNPDYWHSRLFPKANAQRT |
| 6 | Mature human HER3 isoform 1 (UniProt: P21860-1, v1 positions 20 to 1342) | SEVGNSQAVCPGTLNGLSVTGDAENQYQTLYKLYERCEVVMGNLEIVLTGHNADLSFLQWIREVT
GYVLVAMNEFSTLPLPNLRVVRGTQVYDGKFAIFVMLNYNTNSSHALRQLRLTQLTEILSGGVYIE
KNDKLCHMDTDWRDIVRDRDAEIVVKDNGRSCPPCHEVCKGRCWGPGSEDCQTLIKTICAPQC
NGHCFGPNPNQCCHDECAGGCSGPQDTDCFACRHFNDSGACVPRCPQPLVYNKLTFQLEPNP
HTKYQYGGVCVASCPHNFVVDQTSCVRACPPDKMEVDKNGLKMCEPCGGLCPKACEGTSGSG
RFQTVDSSNIDGFVNCTKILGNLDFLITGLNGDPWHKIPALDPEKLNVFRTVREITGYLNIQSWPPH
MHNFSVFSNLTTIGGRSLYNRGFSLLIMKNLNVTSLGFRSLKEISAGRIYISANRQLCYHHSLNWTK
VLRGPTEERLDIKHNRPRRDCVAEGKVCDPLCSSGGCWGPGPGQCLSCRNYSRGGVCTHCNF
LNGEPREFAHEAECFSCHPECQPMEGTATCNGSGSDTCAQCAHFRDGPHCVSSCPHGVLGAK
GPIYKYPDVQNECRPCHENCTQGCKGPELQDCLGQTLVLIGKTHLTMALTVIAGLVVIFMMLGGTF
LYWRGRRIQNKRAMRRYLERGESIEPLDPSEKANKVLARIFKETELRKLKVLGSGVFGTVHKGVWI
PEGESIKIPVCIKVIEDKSGRQSFQAVTDHMLAIGSLDHAHIVRLLGLCPGSSLQLVTQYLPLGSLLD
HVRQHRGALGPQLLLNWGVQIAKGMYYLEEHGMVHRNLAARNVLLKSPSQVQVADFGVADLLPP
DDKQLLYSEAKTPIKWMALESIHFGKYTHQSDVWSYGVTVWELMTFGAEPYAGLRLAEVPDLLEK
GERLAQPQICTIDVYMVMVKCWMIDENIRPTFKELANEFTRMARDPPRYLVIKRESGPGIAPGPEP
HGLTNKKLEEVELEPELDLDLDLEAEEDNLATTTLGSALSLPVGTLNRPRGSQSLLSPSSGYMPM
NQGNLGESCQESAVSGSSERCPRPVSLHPMPRGCLASESSEGHVTGSEAELQEKVSMCRSRS
RSRSPRPRGDSAYHSQRHSLLTPVTPLSPPGLEEEDVNGYVMPDTHLKGTPSSREGTLSSVGLSS
VLGTEEEDEDEEYEYMNRRRRHSPPHPPRPSSLEELGYEYMDVGSDLSASLGSTQSCPLHPVPI
MPTAGTTPDEDYEYMNRQRDGGGPGGDYAAMGACPASEQGYEEMRAFQGPGHQAPHVHYAR
LKTLRSLEATDSAFDNPDYWHSRLFPKANAQRT |

| SEQ ID NO: | DESCRIPTION | SEQUENCE |
|---|---|---|
| 7 | Mature human HER3 isoform 2 (UniProt: P21860-2 positions 20 to 133) | SEVGNSQAVCPGTLNGLSVTGDAENQYQTLYKLYERCEVVMGNLEIVLTGHNADLSFLQWIREVT GYVLVAMNEFSTLPLPNLRVVRGTQVYDGKFAIFVMLNYNTNSSHALRQLRLTQLTGQFPMVPSG LTPQPAQDWYLLDDDPRLLTLSASSKVPVTLAAV |
| 8 | Mature human HER3 isoform 2 (UniProt: P21860-3 positions 20 to 331) | SEVGNSQAVCPGTLNGLSVTGDAENQYQTLYKLYERCEVVMGNLEIVLTGHNADLSFLQWIREVT GYVLVAMNEFSTLPLPNLPVVRGTQVYDGKFAIFVMLNYNTNSSHALRQLRLTQLTEILSGGVYIE KNDKLCHMDTIDWRDIVRDRDAEIVVKDNGRSCPPCHEVCKGRCWGPGSEDCQTLTKTICAPQC NGHCFGPNPNQCCHDECAGGCSGPQDTDCFACRHFNDSGACVPRCPQPLVYNKLITQLEPNP HTKYQYGGVCVASCPHNFVVDQTSCVRACPPDKMEVDKNGLKMCEPCGGLCPKAF |
| 9 | Human HER3 isoform 1 extracellular region (UniProt: P21360-1, v1 positions 20 to 643) | SEVGNSQAVCPGTLNGLSVTGDAENQYQTLYKLYERCEVVMGNLEIVLTGHNADLSFLQWIREVT GYVLVAMNEFSTLPLPNLRVVRGTQVYDGKFAIFVMLNYNTNSSHALRQLPLTQLTEILSGGVYIE KNDKLCHMDTIDWRDIVRDRDAEIVVKDNGRSCPPCHEVCKGRCWGPGSEDCQTLTKTICAPQC NGHCFGPNPNQCCHDECAGGCSGPQDTDCFACRHFNDSGACVPRCPQPLVYNKLTEQLEPNP HTKYQYGGVCVASCPHNFVVDQTSCVRACPPDKMEVDKNGLKMCEPCGGLCPKACEGTGSGS RFQTVDSSNIDGFVNCTKILGNLDFLITGLNGDPWHKIPALDPEKLAVERTVREITGYLNIQSWPPH MHNFSVFSNLTTIGGRSLYNRGESLLIMKNLNVTSLGFRSLKEISAGRIYISANRQLCYHHSLNWTK VLRGPTEERLDIKHNRPRPDCVAEGKVCDPLCSSGGCWGPGPGQCLSCRNYSRGGVCVTHCNF LNGEPREFAHEAECFSCHPECQPMEGTATCNGSGSDTCAQCAHFRDGPHCVSSCPHGVLGAK GPIYKYPDVQNECRPCHENCTQGCKGPELQDCLGQTLVLIGKTHLT |
| 10 | Human HER3 isoform 1 transmembrane domain (UniProt: P21860-1, v1 positions 644 to 664) | MALTVIAGLVVIFMMLGGTFL |
| 11 | Human HER3 isoform 1 cytoplasmic domain (UniProt: P21360-1, v1 positions 665 to 1342) | YWRGRRIQNKRAMRRYLERGESIEPLDPSEKANKVLARIFKETELRKLKVLGSGVFGTVHKGVWI PEGESIKIPVCIKVIEDKSGRQSFQAVTDHMLAIGSLDHAHIVRLLGLCPGSSLQLVTQYLPLGSLLD HVRQHRGALGPQLLLNWGVQIAKGMYYLEEHGMVHRNLAARNVLLKSPSQVQVADFGVADLLPP DDKQLLYSEAKTPIKWMALESIHFGKYTHQSDVWSYGVTVWELMTFGAEPYAGLRLAEVPDLLEK GERLAQPQICTIDVYMVMKCWMIDENIRPTFKELANEFTMARDPPRYLVIKRESGPGIAPGPEP HGLTNKKLEEVELEPELDLDLDLEAEEDNLATTTLGSALSLPVGTLNRPRGSQSLLSPSSGYMPM NQGNLGESCQESAVSGSSERCPRPVSLHPMPRGCLASESSEGHVTGSEAELQEKVSMCRSRSR SRSPRPRGDSAYHSQRHSLLTPVTPLSPPGLEEEDVNGYVMPDTHLKGTPSSREGTLSSVGLSS VLGTEEEDEDEEYEYMNRRRRHSPPHPPRPSSLEELGYEYMDVGSDLSASLGSTQSCPLHPVPI MPTAGTTPDEDYEYMNRQRDGGGPGGDYAAMGACPASEQGYEEMRAFQGPGHQAPHVHYAR LKTLRSLEATDSAFDNNPDYWHSRLFPKANAQRT |
| 12 | Human HER3 isoform 1 juxtamembrane segment (UniProt: P21360-1, v1 positions 665 to 708) | YVVRGRRIQNKRAMRRYLERGESIEPLDPSEKANKYLARIFKETE |
| 13 | Human HER3 isoform 1 protein kinase domain (UniProt: P21860-1, v1 positions 709 to 966) | LRKLKVLGSGVFGTVHKGVWIPEGESIKIPVCIKVIEDKSGRQSFQAVTDHMLAIGSLDH AHIVRLLGLCPGSSLQLVTQYLPLGSLLDHVRQHRGALGPQLLLNWGVQIAKGMYYLEEH GMVHRNLAARNVLLKSPSQVQVADFGVADLLPPDDKQLLYSEAKTPIKWMALESIHFGKY THQSDVWSYGVTVWELMTFGAEPYAGLRLAEVPDLLEKGERLAQPQICTIDVYMVMKCW MIDENIRPTFKELANEFT |
| 14 | Human HER3 isoform 1 C terminal segment (UniProt: P21860-1, v1 positions 967 to 1342) | RMARDPPRYLVIKRESGPGIAPGPEPHGLTNKKLEEVELEPELDLDLDLEAEEDNLATTTLGSALS LPVGTLNRPRGSQSLLSPSSGYMPMNQGNLGESCQESAVSGSSERCPRPVSLHPMPRGCLASE SSEGHVTGSEAELQEKVSMCRSRSRSRSPRPRGDSAYHSQRHSLLTPVTPLSPPGLEEEDVNGY VMPDTHLKGTPSSREGTLSSVGLSSVLGTEEEDEDEEYEYMNRRRRHSPPHPPRPSSLEELGYE YMDVGSDLSASLGSTQSCPLHPVPIMPTAGTTPDEDYEYMNRQRDGGGPGGDYAAMGACPASE QGYEEMRAFQGPGHQAPHVHYARLKTLRSLEATDSAFDNPDYWHSRLFPKANAQRT |
| 15 | Human HER3 extracellular region subdomain I (UniProt: P21360-1, v1 positions 20 to 183) | SEVGNSQAVCPGTLNGLSVTGDAENQYQTLYKLYERCEVVMGNLEIVLTGHNADLSFLQWIREVT GYVLVAMNEFSTLPLPNLRVVRGTQVYDGKFAIFVMLNYNTNSSHALRQLRLTQLTEILSGGVYIE KNDKLCHMDTIDWRDIVRDRDAEIVVKDNGRSC |

-continued

Sequences

| SEQ ID NO: | DESCRIPTION | SEQUENCE |
|---|---|---|
| 16 | Human HER3 extracellular region subdomain II (UniProt: P21860-1, v1 positions 184 to 329) | PPCHEVCKGRCWGPGSEDCQTLTKTICAPQCNGHCFGPNPNQCCHDECAGGCSGPQDTDCFA CRHFNDSGACVPRCPQPLVYNKLTFQLEPNPHTKYQYGGVCVASCPHNFVVDQTSCVRACPPD KMEVDKNGLKMCEPCGGLCPK |
| 17 | Human HER3 extracellar region subdomain III (UniProt: P21860-1, v1 positions 330 to 495) | ACEGTGSGSRFQTVDSSNIDGFVNCTKILGNLDFLITGLNGDPWHKIPALDPEKLNVFRTVREITGY LNIQSWPPHMHNFSVFSNLTTIGGRSLYNRGFSLLIMKNLNVTSLGFRSLKEISAGRIYISANRQLC YHHSLNWTKVLRGPTEERLDIKHNRPRRDCVA |
| 18 | Human HER3 extracellular region subdomain IV (UniProt: P21360-1, v1 positions 496 to 643) | EGKVCDPLCSSGGCWGPGPGQCLSCRNYSRGGVCVTHCNFLNGEPREFAHEAECFSCHPECQ PMEGTATCNGSGSDTCAQCAHFRDGPHCVSSCPHGVLGAKGPIYKYPDVQNECRPCHENCTQ GCKGPELQDCLGQTLVLIGKTHLT |
| 19 | Human HER3 extracellular region subdomain II dimerisation loop (UniProt: P21860-1, v1 positions 261 to 278) | QPLVYNKLTFQLEPNPH |
| 20 | Rhesus macaque HER3 (UniProt: F7HEH3-1, v2) | MGNLEIVLTGHNADLSFLQWIREVTGYVLVAMNEFSTLPLPNLRVVRGTQVYDGKFAIFVMLNYNT NSSHALRQLRLTQLTEILSGGVYIEKNDKLCHMDTIDWKDIVRDQDAEIVVKDNGRSCPLCHEVCK GRCWGPGPEDCQTLTKTICAPQCNGHCFGPNPNQCCHDECAGGCSGPQDTDCFACRHFNDSG ACVPRCPQPLVYNKLTFQLEPNPHTKYQYGGVCVASCPHNFVVDQTSCVRACPPDKMEVDKNG LKMCEPCGGLCPKACEGTGSGSRFQTVDSSNIDGFVNCTKILGNLDFLITGLNGDPWHKIPALDP EKLNVFRTVREITGYLNIQSWPPHMYNFSVFSNLTTIGGRSLYNRGFSLLIMKNLNVTSLGFRSLKE ISAGRIYISANRQLCYHHSLNWTKVLRGPTEERLDIKHNRPRRDCVAEGKVCDPLCSSGGCWGP GPGQCLSCRNYSRGGVCVTHCNFLNGEPREFAHEAECFSCHPECQPMEGTATCNGSGSQTCA QCAHFRDGPHCVSSCPHGVLGAKGPIYKYPDVQNECRPCHENCTQGCKGPELQDCLGQTLVLIG KTHLTMALTVIAGLVVIFMMLGGTFLYWRGRRIQNKRAMRRYLERGESIEPLDPSEKANKVLARIF KETELRKLKVLGSGVFGTVHKGVWIPEGESIKIPVCIKIIEDKSGRQSFQAVTDHMLAIGSLDHAIV RLLGLCPGSSLQLVTQYLPLGSLLDHVRQHRGALGPQLLLNWGVQIAKGMYYLEEHGMVHRNLA ARNVLLKSPSQVQVADFGVADLLPPDDKQLLYSEAKTPIKWMALESIHFGKYTHQSDVWSYGVTV WELMTFGAEPYAGLRLAEVPDLLEKGERLAQPQICTIDWMVMVKCWMIDENIRPTFKELANEFTR MARDPPRYLVIKRESGPGIAPGPEPHGLINKKLEEVELEPELDLDLDLEAEEDNLATTTLGSALSLP VGTLNRPRGSQSLLSPSSGYMPMNQGNLGEAFQESAVSGSSEWCPRPVSLHPMPRGCLASESS EGHVTGSEAELQEKVSTCRSRSRSRSPRPRGDSAYHSQRHSLLTPVTPLSPPGLEEEDVNGYVM PDTHLKGTPSSREGTLSSVGLSSVLGTEEEDEDEEYEYMNRRRRHSPPRPPRPSSLEELGYEYM DVGSDLSASLGSTQSCPLHPVPVMPTAGTTPDEDYEYMNRQRGGSGPGGDYAAMGACPASEQ GYEEMRAFQGPGHQAPHVHYAHLKTLRSLEATDSAFDNPDYWHSRLFPKANAQRT |
| 21 | Epitope recognised by anti-HER3 antibody done 10A6 | YNKLTFQLEPNPH |
| 22 | Epitope recognised by anti-HER3 antibody clone 4-35-B2 and 4-35-64 | PRCPQPLVYNKLIT |
| 23 | Composite sequence epitopes recognised by anti-HER3 antibody clones 4-35-62, 4-35-64 and 10A6 | PRCPQPLVYNKLTFQLEPNPH |
| 24 | 10D1 heavy chain variable region | DVQLQESGPDLVKPSQSLSLTCTVTGYSITSGYSWHWIRQFPGNKLEWMGSIHYSGGTNYNPSL KSRISITRDTSKNQFFLQLNSVTTEDTATYFCARMTTAPRYPFDYWGQGTTLTVSS |

-continued

| SEQ ID NO: | DESCRIPTION | SEQUENCE |
|---|---|---|
| 25 | 10D1_c75 heavy chain variable region | DVQLQEWGAGLIKPSETLSLTCAVTGYSITSGYSWHWIRQFPGNGLEWIGSIHYSGGTNYNPTLK SRITISRDTSKNQFSLKLSSVTAADTAVYFCARMTTAPRYPFDYWGQGTLVTVSS |
| 26 | 10D1_c76 heavy chain variable region | DVQLQEWGAGLLYPSETLSLTCAVTGYSITSGYSWHWIRQFPGNGLEWIGSIHYSGGTNYNPSLK SRITISRDTSKNQFSLKLSSVTAADTAVYFCARMTTAPRYPFDYWGOGTLVTVSS |
| 27 | 10D1_c77 heavy chain variable region | DVQLQEWGAGLLKPSETLSLTCAVTGYSITSGYSWHWIRQFPGNGLEWIGSIHYSGGTNYNPSLK SRITISRDTSKNQFSLKLSSVTAADTAVYFCARMTTAPRYPFDYWGOGTLVTVSS |
| 28 | 10D1_c78v1 heavy chain variable region | DVQLQEWGAGLLKPSETLSLTCAVTGYSITSGYSWHWIRQFPGNGLEWIGSIHYSGGTNYNPSLK SRITISRDTSKNQFSLKLSSVTAADTAVYFCARMTTAPRYPFDYWGOGTLVTVSS |
| 29 | 10D1_c76v2 heavy chain variable region | DVQLQEWGAGLLKPSETLSLTCAVTGYSITSGYSWHWIRQFPGkGLEWIGSIHYSGGTNYNPSLK SRITISRDTSKNQFSLKLSSVTAADTAVYFCARMTTAPRYPFDYWGOGTLVTVSS |
| 30 | 10D1_11B heavy chain variable region | DVQLQEWGAGLLKPSETLSLTCAVTGYSITSGYSWHWIRQPPGKGLEWIGSIHYSGGTNYNPSLK SRVTISRDTSKNQFSLKLSSVTAADTAVYYCARMTTAPRYPFDYWGQGTLVTVSS |
| 31 | 10D1_c85v1 heavy chain variable legion | DVQLQEWGAGLLKPSETLSLTCAVTGYSITSGYSWHWIRQFPGNGLEWIGSIRYSGGTNYNPSLK SRITISRDTSKNQFSLKLGSVTAADTAVYFCARMTTAPRYPFDYWGQGTLVTVSS |
| 32 | 10D1_c85v2 heavy chain variable region | DVQLQEWGAGLLKPSETLSLTCAVTGYSITSGYSWHWIRQFPGKGLEWIGSIRYSGGTNYNPSLK SRITISRDTSKNQFSLKLGSVTAADTAVYFCARMTTAPRYPFDYWGQGTLVTVSS |
| 33 | 10D1_c85o1 heavy chain variable region | DVQLQEWGAGLLKPSETLSLTCAVTGYSITSGYSWHWIRQFPGKGLEWIGSIRYSGGTNYNPSLK SRITISRDTSKNQFSLKLGSVTAADTAVYFCARETTAPRYPEDYWGQGTLVTVSS |
| 34 | 10D1_c85o2 heavy chain variable region | DVQLQEWGAGLLKPSETLSLTCAVTGYSITSGYSWHWIRQFPGKGLEWIGSIRYSGGTNYNPSLK SRITISRDTSKNQFSLKLGSVTAADTAVYFCARGTTAPRYPEDYWGQGTLVTVSS |
| 35 | 10D1_c87 heavy chain variable region | DVOLQEWGAGLLKPSETLSLTCAVTGYSITSGYSWHWIRQFPGNGLEWIGSIHYSGGTNYNPSLK SRITISRDTSKNQFSLRLSSVTAADTAVYFCARMTTAPRYPFDYWGQGILVIVSS |
| 36 | 10D1_c89 heavy chain variable region | QVQLQESGPGLVKPSQTLSLTCTVSGYSITSGYSWHWIRQHPGKGLEWIGSIRYSGGTDYNPSLK SLVTISADTSKNQESLKLSSVTAADTAVYYCARMTTAPWYPFDYWGQGTTVTVSS |
| 37 | 10D1_c90 heavy chain variable region | QVQLQESGPGLVKPSQTLFLTCTVSGYSITSGYSWHWIRQHPGKGLEWIGSIRYSGGTDYNPSLK SLVTISVDTSKNQFSLKLSSVTAADTAVYYCARMTTARNYPFDYWGQGTTVRTSS |
| 38 | 10D1_c91 heavy chain variable region | QVQLQESGPGLVKPSQTLSLTCTVSGYYITSGYSWHWIRQHPGKGLEWIGSIRYSGGTDYNPSLK SLATISADTSKNQFSLKLSSVTAADTAVYYCARMTTAPWYPFDYWGQGTAVTVSS |
| 39 | 10D1_c92 heavy chain variable region | DVQLQEWGAGLLKPSETLSLTCTVSGYSITSGYSWHWIRQFPGNGLEWIGSIHYSGGTNYNPTLK SRITISRDTSKNQFSLKLBSVTAADTAVYFCARMTTAPRYPFDYWGQGTLVTVSS |
| 40 | 10D1_c93 heavy chain variable region | DVQLQEWGAGLLKPSETLSLTCAVTGYSITSGYSWHWIRQFPGNGLEWIGSIHYSGGTNYNPSLK SRITISRDTSKNQFSLRLSSVTAADTAVYFCARMTTAPRYPFDYWGQGTLVTVSS |
| 41 | 10D1, 10D1_c75, 10D1_c76, 10D1_c77, 10D1_c78v1, 10D1_c78v2, 10D1_11B, 10D1_c85v1, | GYSITSGYS |

| | | |
|---|---|---|
| SEQ ID NO: | DESCRIPTION | SEQUENCE |
| | 10D1_c85v2, 10D1_c85o1, 10D1_c85o2, 10D1_c87, 10D1_c89, 10D1_c90, 10D1_c92, 10D1_c93 heavy chain CDR1 | |
| 42 | 10D1_c91 heavy chain CDR1 | GYYITSGYS |
| 43 | 10D1 derived consensus heavy chain CDR1 | GYX$_1$ITSGYS wherein X$_1$ = S or Y |
| 44 | 10D1, 10D1_c75, 10D1_c76, 10D1_c77, 10D1_c78v1, 10D1_c78v2, 10D1_11B, 10D1_c87, 10D1_c92, 10D1_c93 heavy chain CDR2 | IHYSGGT |
| 45 | 10D1_c85v1, 10D1_c85v2, 10D1_c85o1, 10D1_c85o2, 10D1_c99, 10D1_c90, 10D1_c91 heavy chain CDR2 | IRYSGGT |
| 46 | 10D1 derived consensus heavy chain CDR2 | IX$_2$YSGGT wherein X$_2$ = H or R |
| 47 | 10D1, 10D1_c75, 10D1_c76, 10D1_c77, 10D1_c78v1, 10D1_c78v2, 10D1_11B, 10D1_c85v1, 10D1_c85v2, 10D1_c87, 10D1_c92, 10D1_c93 heavy chain CDR3 | ARMTTAPRYPFDY |
| 48 | 10D1_c89, 10D1_c90, 10D1_c91 heavy chain CDR3 | ARMTTAPWYPFDY |
| 49 | 10D1_c85o1 chain CDR3 | ARETTAPRYPFDY |
| 50 | 10D1_c85o2 heavy chain CDR3 | ARGTTAPRYPFDY |
| 51 | 10D1 derived consensus heavy chain CDR3 | ARX$_3$TTAPX$_4$YPFDY wherein X$_3$ = M, E or G; X$_4$ = R or W |
| 52 | 10D1_c75 10D1_c76, | DVQLQEWGAGLLKPSETLSLTCAVT |

-continued

| SEQ ID NO: | DESCRIPTION | SEQUENCE |
|---|---|---|
| | 10D1_c77, 10D1_c78v1, 10D1_c78v2, 10D1_c85v1, 10D1_c85v2, 10D1_c85o1, 10D1_c85o2, 10D1_c87, 10D1_c92, 10D1_c93 heavy chain FR1 | |
| 53 | 10D1_c89, 10D1_c91 heavy chain FR1 | QVQLQESGPGLVKPSQTLSLTCTVS |
| 54 | 10D1_c90 heavy chain FR1 | QVQLQESGPGLVKPSQTLFLTCTVS |
| 55 | 10D1 heavy chain FR1 | DVQLQESGPDLVKPSQSLSLTCTVT |
| 56 | 10D1_c75, 10D1_c76, 10D1_c77, 10D1_c78v1, 10a1_c85v1, 10D1_c87, 10D1_c92, 10D1_c93 heavy chain FR2 | WHWIRQFPGNGLEWIGS |
| 57 | 10D1_c78v2, 10D1_c85v2, 10D1_c85o1, 10D1_c85o2 heavy chain FR2 | WHWIRQFPGKGLEWIGS |
| 58 | 10D1 heavy chain FR2 | WHWIRQFPGNKLEWMGS |
| 59 | 10D1_c89, 10D1_c90, 10D1_c91 heavy chain FR2 | WHWIRQARGKGLEWIGS |
| 60 | 10D1_11B heavy chain FR2 | WHWIRQFPGKGLEWIGS |
| 61 | 10D1_c75, 10D1_c92 heavy chain FR3 | NYNPTLKSRITISRDTSKNQFSLKLSSVTAADTAVYFC |
| 62 | 10D1_c76, 10D1_c77, 10D1_c78v1, 10D1_c78v2 heavy chain FR3 | NYNPSLKSRITISRDTSKNQFSLKLSSVTAADTAVYFC |
| 63 | 10D1_11B heavy chain FR3 | NYNPSLKSRVTISRDTSKNQFSLKLSSVTAADTAVYYC |
| 64 | 10D1_085v1, 10D1_c85v2, 10D1_c85o1, 10D1_c85o2 heavy chain FR3 | NYNPSLKSRITISRDTSKNQFSLKLGSVTAADTAVYFC |
| 65 | 10D1_c87, 10D1_c93 chain FR3 | NYNPSLKSRITISRDTSKNQFSLRLSSVTAADTAVYFC |

-continued

| SEQ ID NO: | DESCRIPTION | SEQUENCE |
|---|---|---|
| 66 | 10D1_c89 heavy chain FR3 | DYNPSLKSLVTISADTSKNQFSLKLSSVFAADTAVYYC |
| 67 | 10D1_c90 heavy chain FR3 | DYNPSLKSLVTISVDTSKNQFSLKLSSVTAADTAVYYC |
| 68 | 10D1_c91 heavy chain FR3 | DYNPSLKSLATISADTSKNQFSLKLSSVTAADTAVYYC |
| 69 | 10a1 heavy chain FR3 | NYNPSLKSRISITRDTSKNQFFLQLNSVTTEDTATYFC |
| 70 | 10D1_c75, 10D1_c76, 10D1_c77, 10D1_c78v1, 10D1_c78v2, 10D1_11B, 10D1_c85v1, 10D1_c85v2, 10D1_c85o1, 10D1_c85o2, 10D1_c87, 10D1_c92, 10D1_c93 heavy chain FR4 | WGQGTLVTVSS |
| 71 | 10D1_c89, 10D1_c90 heavy chain FR4 | WGQGTTLTVSS |
| 72 | 10D1_c91 heavy chain FR4 | WGQGTAVTVSS |
| 73 | 10D1, 4-35-F34, 10A6 heavy chain FR4 | WGQGTTLTVSS |
| 74 | 10D1 light chain variable region | DIVMTQSQKFMSTSVGDRVSVTCKASQIVGSNVAWYQQKPGQSPKPLIYSASYRYSGVPDRFTASGSGTDFTLTITNVQSEDLAEYFCQQYSSHPLTFGAGTKLELK |
| 75 | 10D1_c75 light chain variable region | DIVMTQSPSSLSASVGDLVTITCKASQIVGSNVAWYQMKPGKSPKPLIYSASYLYFGVPSRFSGSGSGTDFTLTISSLQPEDVAEYFCQQYSSHPLTFGPGIKVEIK |
| 76 | 10D1_c78 light chain variable region | DIVMTQSPSSLSASGGDRVTITCKASQIVGYNVAWYQQKPGKSPKPLIYSASYLYSDVPSRFSASGSGTDFTLTISSLQPEDVAEYFCQQYSSHPLTFGPGTKVEIK |
| 77 | 10D1_c77 light chain variable region | VIVMTQSPSSLSASVGDRVTITCKASQIVGPNVAWYQQKPGKSPKPLIYSASYGYSDVPSRFSGSGSGTDFTLTISSLQPEDVAEYFCQQYSTHPLTFGPGTKVEIK |
| 78 | 10D1_c78v1, 10D1_c78v2, 10D1_11B light chain variable region | DIVMTQSPSSLSASVGDRVTITCKASQIVGSNVAWYQQKPGKSPKPLIYSASYGYSDVPSRFSGSGSGTDFTLTISSLRPEDVATYYCQQYSSHPLTFGRGTKVEIK |
| 79 | 10D1_c85v1, 10D1_c85v2 light chain variable region | DIVMTQSPSSLSASVGDRVTITCKASQIVGENVAWYQQKPGKSPKPLIYSARYQYSGVPFRFSGSGSGTDFTLTISSLQPEDVATYYCQQYSSHPLTFGPGTKVEIK |
| 80 | 10D1_c35o1 light chain variable region | DIVMTQSPSSLSASVGDRVTITCKASQIVGSNVAWYQQKPGKSPKPLIYSARYQYSGVPFRFSGSGSGTDFTLTISSLQPEDVATYYCQQYSSHPLTFGPGTKVEIK |
| 81 | 10D1_c85o2 light chain variable region | DIVMTQSPSSLSASVGDRVTITCKASQIVGENVAWYQQKPGKSPKPLIYSARYQYSGVPFRFSGSGSGTDFTLTISSLQPEDVATYYCQQYSSHPLTFGPGTKVEIK |

| SEQ ID NO: | DESCRIPTION | SEQUENCE |
|---|---|---|
| 82 | 10D1_c37 light chain variable region | DIVMTQSPSSLSASVGDRVTITCKASQIVGSNVAWYQQMPGKSPEPLIYSASYLYSDVPSRFSGS GSGTDFTMTISSLQPEDVATYYCQQYSSHPLTFGPGTKVEIK |
| 83 | 10D1_c89 light chain variable region | DIQMTQSPSSVSASVGDRVTITCKASQIVGSNVAWYQQKPGKAPEPLIYSASYLYSGVPSRFSGS GSGTDFTLTISSLQPEDFATYYCQQYSSHPLIFGQGTKLEIK |
| 84 | 10D1_c90 light chain variable region | DIQMTQSPSSVSASVGDRVTITCKASQIVGSNVAWYQQKPGKAPEPLIYSASYLYSSVPSRFSGS GSGTEFTMTISSLEPEDFATYYCQQYTTHPLTFGRGTKVEIK |
| 85 | 10D1_c91 light chain variable region | DIQMTQSPSSVSASVGDRVTITCKASQIVGSNVAWYQQKPGKAPMPLIYSASYGYSGVPSRFSGS GSGTDFTLTISSLQPEDFATYYCQQYSSIIPLTFGQGTKLEIK |
| 86 | 10D1_c92 light chain variable region | DIVMTQSPSSVSASVGDLVTITCKASQIVGSNVAWYQMKLGKSPKPLIYSASYLYFGVPSRFSGSG SGTDFTLITSSLQPEDVAEYFCQQYFSHPLTFGPGTKVEIK |
| 87 | 10D1_c93 light chain Variable region | DIVMTQSPSSLSASVGDRVTITCKASQIVGSNVAWYQQKPGKSPKPLIYSASYLYSDVPSRFSGS GSGTDFTMTISSMPEDVATYYCQQYSSHPLTFGRGTKVEIK |
| 88 | 10D1, 10D1_c75, 10D1_c78v1, 10D1_c78v2, 10D1_11B, 10D1_c35v1, 10D1_c65v2, 10D1_c65o1, 10D1_c85o2, 10D1_c87, 10D1_c89, 10D1_c90, 10D1_c91, 10D1_c92, 10D1_c93 light chain CDR1 | QIVGSN |
| 89 | 10D1_c76 light chain CDR1 | QIVGYN |
| 90 | 10D1_c77 light chain CDR1 | QIVGPN |
| 91 | 10D1 derived consensus light chain CDR1 | QIVGX$_5$N wherein X$_5$ = S, Y or P |
| 92 | 10D1, c75, 10D1_c76, 10D1_c77, 10D1_c78v1, 10D1_c78v2, 10D1_11B, 10D1_c87, 10D1_c89, 10D1_c90, 10D1_c91, 10D1_c92, 10D1_c93 light chain CDR2 | SAS |
| 93 | 10D1_c85v1, 10D1_c85v2, 10D1_c85o1, 10D1_c85o2 light chain CDR2 | SAR |

| SEQ ID NO: | DESCRIPTION | SEQUENCE |
|---|---|---|
| 94 | 10D1 derived consensus light chain CDR2 | SAX$_6$ wherein X$_6$ = S or R |
| 95 | 10D1, 10D1_c75, 10D1_c76, 10D1_c78v1, 10D1_c73v2, 10D1_116, 10D1_c85v1, 10D1_c85v2, 10D1_c85o1, 10D1_c85o2, 10D1_c87, 10D1_c39, 10D1_c91, 10D1_c93 light chain CDR3 | QQYSSHRLT |
| 96 | 10D1_c77 light chain CDR3 | QQYSTHPLT |
| 97 | 10D1_c90 light chain CDR3 | QQYTTHPLT |
| 98 | 10D1_c92 light chain CDR3 | QQYFSHPLT |
| 99 | 10D1 derived consensus light chain CDR3 | QQYX$_7$X$_8$HPLT wherein X$_7$ = S, T or F; X$_8$ = S or T |
| 100 | 10D1_c75, 10D1_c92 light chain FR1 | DIVMTQSPSSLSASVGDLVTITCKAS |
| 101 | 10D1_c76 light chain FR1 | DIVMTQSPSSLSASGGDRVTITCKAS |
| 102 | 10D1_c77 light chain FR1 | VIVMTQSRSSLSASVGDRVTITCKAS |
| 103 | 10D1_c78v1, 10D1_c78v2, 10D1_11B, 10D1_c85v1, 10D1_c85v2, 10D1_c85o1, 10D1_c85o2, 10D1_c87, 10D1_c93 light chain FR1 | DIVMTQSPSSLSASVGDRVTITCKAS |
| 104 | 10D1_c89, 10D1_c91 chain FR1 | DIQMTQSPSSVSASVGDRVTITCKAS |
| 105 | 10D1_c90 light chain FR1 | DIQMTQSPSSVSASVGDRVTFTCKAS |
| 106 | 10D1 light chain FR1 | DIVMTQSQKFMSTSVGDRVSVTCKAS |
| 107 | 10D1_c75 light chain FR2 | VAWYQMKPGKSPKPLIY |
| 108 | 10D1_c76, 10D1_c77, 10D1_c78v1, 10D1_c78v2, 10D1_11B, | VAWYQQKPGKSPKPLIY |

-continued

| SEQ ID NO: | DESCRIPTION | SEQUENCE |
|---|---|---|
| | 10D1_c85v1, 10D1_c85v2, 10D1_c85o1, 10D1_c85o2, 10D1_c93 light chain FR2 | |
| 109 | 10D1_c87 light chain FR2 | VAWYQQMPGKSPEPLIY |
| 110 | 10D1_c89, 10D1_c90 light chain FR2 | VAWYQQKPGKAPEPLIY |
| 111 | 10D1_c91 light chain FR2 | VAWYQQKPGKAPMPLIY |
| 112 | 10D1_c92 light chain FR2 | VAWYQMKLGKSPKPLIY |
| 113 | 10D1 light chain FR2 | VAWYQQKPGQSPKPLIY |
| 114 | 10D1_c75, 10D1_c92 light chain FRS | YLYFGVPSRFSGSGSGTDFTLTISSLQPEDVAEYFC |
| 115 | 10D1_c76 light chain FR3 | YLYSDVPSRFSASGSGTDFTLTISSLQPEDVAEYFC |
| 116 | 10D1_c77 light chain FR3 | YGYSDVPSRFSGSGSGTDFTLTISSLQPEDVAEYFC |
| 117 | 10D1_c78v1 10D1_c78v2, 10D1_11B light chain FR3 | YGYSDVPSRFSGSGSGTDFTLTISSLRPEDVATYYC |
| 118 | 10D1_c85v1, 10D1_c85v2, 10D1_c85o1, 10D1_c85o2 light chain FR3 | YQYSGVPFRFSGSGSGTDFTLTISSLQPEDVATYYC |
| 119 | 10D1_c87, 10D1_c93 light chain FR3 | YLYSDVPSRFSGSGSGTDFTMTISSLQPEDVATYYC |
| 120 | 10D1_c89 light chain FR3 | YLYSGVPSRFSGSGSGTDFTLTISSLQPEDFATYYD |
| 121 | 10D1_c90 light chain FR3 | YLYSSVPSRFSGSGSGTEFTMTISSLEPEDFATYYC |
| 122 | 10D1_c91 light chain FR3 | YGYSGVPSRFSGSGSGTDFTLTISSLQPEDFATYYC |
| 123 | 10D1 light chain FR3 | YRYSGVPDRFTASGSGIDFTLATINVQSEDLAEYFC |
| 124 | 10D1_c75, 10D1_c76, 10D1_c77, 10D1_c78v1, 10D1_c78v2, 10D1_11B, 10D1_c85v1, 10D1_c65v2, 10a1_c65o1, 10D1_c85o2, 10D1_c87, 10D1_c90, 10D1_c92, | FGPGTKVEIK |

| SEQ ID NO: | DESCRIPTION | SEQUENCE |
|---|---|---|
| | 10D1_c93 light chain FR4 | |
| 125 | 10D1_c69, 10D1_c91 light chain FR4 | FGQGTKLEIK |
| 126 | 10D1 light chain FR4 | FGAGTKLELK |
| 127 | 4-35-B2 heavy chain variable region | EIQLQQSGPELVKPGASVKVSCKASGYSFTDYNMYWVKQSHGKSLEWIGHINPYNGGTTYNQKF KGRATLTVDKSSSTAFMHLNSLTSEDSAVYFCVSLRWGAMDYWGQGTSVTVSS |
| 128 | 4-35-B2 heavy chain CDR1 | GYSFTDYN |
| 129 | 4-35-B2 heavy chain CDR2 | INRYNGGT |
| 130 | 4-35-B2 heavy chain CDR3 | VSLRWGAMDY |
| 131 | 4-35-B2 heavy chain FR1 | EIQLQQSGPELVKPGASVKVSCKAS |
| 132 | 4-35-B2 heavy chain FR2 | MYWVKQSHGKSLEWIGH |
| 133 | 4-35-B2 heavy chain FR3 | TYNQKFKGRATLTVDKSSSTAFMHLNSLTSEDSAVYFC |
| 134 | 4-35-B2 heavy chain FR4 | WGQGTSVTVSS |
| 135 | 4-35-B2 light chain variable region | QIVLTQSPALMSASPGEKVTMTCSASSSVSYMYWYQQKPRSSPKPWIYLTSNLASGVPARFSGS GSGTSYSLTISSMEAEDAATYYCQQWNSNPYTFGGGTKLEIK |
| 136 | 4-35-B2 light chain CDR1 | SSVSY |
| 137 | 4-35-B2 light chain CDR2 | LTS |
| 138 | 4-35-B2 light chain CDR3 | QQWNSNPYT |
| 139 | 4-35-B2 light chain FR1 | QIVLTQSPALMSASPGEKVTMTCSAS |
| 140 | 4-35-B2 light chain FR2 | MYWYQQKPRSSPKPWIY |
| 141 | 4-35-B2 light chain FR3 | NLASGVPARFSGSGSGTSYSLTISSMEAEDAATYYC |
| 142 | 4-35-B2, 4-35-B4, 10A6 light chain FR4 | FGGGTKLEK |
| 143 | 4-35-B4 heavy chain variable region | EVQLQQSGAELVKPGASVKLSCTASGNIKDTYIHWVKQRPDQGLEWIGKIIDPANGNTNYDPKF QGKATITADTSSNTAYLQLSSLSSEDTAWFCARGLHWGQGTTLTVSS |
| 144 | 4-35-B4 heavy chain CDR1 | GFNIKDTY |
| 145 | 4-35-B4 heavy chain CDR2 | IDPANGNT |
| 146 | 4-35-B4 heavy chain CDR3 | ARGLH |

-continued

| SEQ ID NO: | DESCRIPTION | SEQUENCE |
|---|---|---|
| 147 | 4-35-B4 heavy chain FR1 | EVQLQQSGAELVKPGASVKLSCTAS |
| 148 | 4-35-B4 heavy chain FR2 | IHWVKQRPDQGLEWIGK |
| 149 | 4-35-B4 heavy chain FR3 | NYDPKFQGKATITADTSSNTAYLQLSSLSSEDTAVYFC |
| 150 | 4-35-B4 light chain variable region | DIVLTQSPASLAVSLGQRATISCRASKSVSTSGYSYMHWYQQKPGQPPKLLYLASNLESGVPARF SGSGSGTDFTLNIHRVEEEDAATYYCQHSRELPYTFGGGTKLEIK |
| 151 | 4-35-B4 light chain CDR1 | KSVSTSGYSY |
| 152 | 4-35-B4 light chain CDR2 | LAS |
| 153 | 4-35-B4 light chain CDR3 | QHSRELPYT |
| 154 | 4-35-B4 light chan FR1 | DIVLTQSPASLAVSLGQRATISCRAS |
| 155 | 4-35-B4 light chain FR2 | MHWYQQKPGQPPKLLIY |
| 156 | 4-35-B4 light chain FR3 | NLESGVPARFSGSGSGTDFTLNIHPVEEEDAATYYC |
| 157 | 4-35-B4 light chain variable region | DVQLQESGPGLVKPSQSLSLTCSVTGNFITSGYFWNWIRQFPGNKLEWMGHSYDGSNNYKPSL KNRISITRDTSKNQFFLKLNSVTTEDTATYYCARENYGFGFDYWGQGTTLTVSS |
| 158 | 10A6 heavy chain CDR1 | GNFITSGYF |
| 159 | 10A6 heavy chain CDR2 | ISYDGSN |
| 160 | 10A6 heavy chain CDR3 | ARENYGFGFDY |
| 161 | 10A6 heavy chain FR1 | DVQLQESGPGLVKPSQSLSLTCSVT |
| 162 | 10A6 heavy chain FR2 | WNWIRQFPGNKLEWMGF |
| 163 | 10A6 heavy chain FR3 | NYKPSLKNRISITRDTSKNQFFLKLNSVTTEDTATYYC |
| 164 | 10A6 light chain variable region | DIVLTQSPSSLPVSIGEKVTMSCKSSQSLLYSDNQKNYLAWYQQKPGQSPKLLIYWASTWKSGVP DRFTGSGSGIDFTLTISSVKAEDLAVYYCQQYFTFPWIFGGGTKLEIK |
| 165 | 10A6 light chain CDR1 | QSLLYSDNQKNY |
| 166 | 10A6 light chain CDR2 | WAS |
| 167 | 10A6 light chain CDR3 | QQYFTFPWT |
| 168 | 10A6 light chain FR1 | DIVLTQSPSSLPVSIGEKVTMSCKSS |
| 169 | 10A6 light chain FR2 | LAVWQQKPGQSPKLLIY |
| 170 | 10A6 light chain FR3 | TWKSGVPDRFTGSGSGTDFTLTISSVKAEDLAVYYC |

| SEQ ID NO: | DESCRIPTION | SEQUENCE |
|---|---|---|
| 171 | Human IgG1 constant region (IGHG1; UniProt: P01857-1, v1) | ASTKGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQVSLTCLVKGFYPSDI AVEWESNGDPENNYKTTPPVLDSDGSFFLYSKLTVDKSRWQQGNVFSCSVMHEALHNHYTQKS LSLSPGK |
| 172 | CH1 IgG1 (positions 1-98 of P01857-1, v1) | ASTKGPSVFPLAPSSKSTSGGTAALGCLVKDYFPEPVTVSWNSGALTSGVHTFFAVLQSSGLYSL SSVVTVPSSSLGTQTYICNVNHKPSNTKVDKKV |
| 173 | Hinge IgG1 (positions 99-110 of P01857-1, v1) | EPKSCDKTHTCP |
| 174 | HC2 IgG1 (positions 111-223 of P01357-1, v1) | PCPAPELLGGPSVFLFPPKPKDTLMISRTPEVTCVWDVSHEDPEVKFNWYVDGVEVHNAKTKPR EEQYNSTYRVVSVLTVLHQDWLNGKEYKCKVSNKALPAPIEKTISKAK |
| 175 | CH3 IgG1 (positions 224-330 of P01857-1, v1) | GQPREPQVYTLPPSRDELTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 176 | CH3 (D3563, L358M; positions numbered according to EU numbering) | GQPREPQVYTLPPSREEMTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 177 | Cκ CL (IGCK: UniProt: P01834-1, v2) | RTVAAPSVFIFPPSDEQLKSGTASVVCLLNNFYPREAKVQWKVDNALQSGNSQESVTEQDSKDS TYSLSSTLTLSKADYEKHKWACEVTHQGLSSPVTKSFNRGEC |
| 178 | 10A6 heavy chain signalP | MKVLSLLYLLTAIPGILS |
| 179 | 10D1 heavy chan SignalP | MRVLILLCLFTAFPGILS |
| 180 | 10D1 light chain SignalP | MESQTQVFVYMLLWLSGVDG |
| 181 | 4-35-B2 heavy chain SignalP | MEWSWIFLFLLSGTTGVHS |
| 182 | 4-35-B2 light chain SignalP | MDFQVQIF6FLLMSASVMMSRG |
| 183 | 4-35-B4 heavy chain SignalP | MKCSWVIFFLMAVVTGVNB |
| 184 | 4-35-B4 light chain SignalP | METDTLLLWVLLLWVPGSTG |
| 185 | 10D1_c75, 10D1_c76, 10D1_c77, 10D1_c78v1, 10D1_c78v2, 10D1_11B, 10D1_c85v1, 10D1_c85v2, 10D1_c85o1, 10D1_c85o2, 10D1_c87, 10D1_c89, 10D1_c90, 10D1_c91, 10D1_c92, 10D1_c93 heavy chain SignalP | MELGLRVWFLIATLAGARC |

-continued

| SEQ ID NO: | DESCRIPTION | SEQUENCE |
|---|---|---|
| 186 | 10D1_c75, 10D1_c76, 10D1_c77, 10D1_c76v1, 10D1_c78v2, 10D1_11B, 10D1_c85v1, 10D1_c85v2, 10D1_c85o1, 10D1_c85o2, 10D1_c67, 10D1_c69, 10D1_c90, 10D1_c91, 10D1_c92, 10D1_c93 light chain SignalP | MDMRVPAQLLGLLLLWLRGARC |
| 187 | 10D1_c75 VH-CH1-CH2-CH3 | DVQLQEWGAGLLKPSETLSLTCAVTGYSITSGYSWHWIRQFPGNGLEWIGSIHYSGGTNYNPTLK SRITISRDTSKNQPSLKLSSVTAADTAVYFCARMTTAPRYPFDYWGQGLVTVSSASTKGPSVFPL APSSKSTSGGTAALGCLVKDYFREPVTVSWNSGALTSGVHTFPAVLQBSGLYSLBSVVTVPSSSL GTQTYICNVNHKPSNTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRWSVLTVLHQDWLNGKEYKCK VSNKALPAPIEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLSPGK |
| 188 | 10D1_c75 VL-Cκ | DIVMTQSPSSLSASVGDLVTITCKASQIVGSNVAWYQMKPGKSPKPLIYSASYLYFGVPSRFSGSG SGTDFTLTISSLQPEDVAEYFCQQYSSHPLTFGPGTKVEIKRTVAAPSVFIFPPSDEQLKSGTASVV CLLNNFYPREAKVQWKVDNALQSGNSQESVTEQDSKDSTYSLSSTLTLSKADYEKHKVYACEVT HQGLSSPVTKSFNRGEC |
| 189 | 10D1_c76 VH1-CH1-CH2-CH3 | DVQLQEWGAGLLKPSETLSLTCAVTGYSITSGYSWHWIRQFPGNGLEWIGSHYSGGTNYNPSLK SRIIISRDTSKNQFSLKLSSVTAADTAVYFCARMTTAPRYPFDYWGQGTLVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRWSVLTVLHQDWLNGKEYKCK VSNKALPAPIEKTISKAKGQPREPQVYTLPPSRDELTKNQVSLTCLVKGFYPSDIAVEWESNGQPE NNYKTTPPVLDSDGSFFLYSKLTVDKERWQQGNVFSCSVMHEALHNHYTQKSLBISPGK |
| 190 | 10D1_c76 VL-Cκ | DIVMTQSPSSLSASGGDRVTITCKASQIVGYNVAMQKPGKSPKPLIYBASYLYBDVPSRFSAS GSGTDFTLTISSLQPEDVAEYFCQQYSSHPLTIGPGTKVEIKRTVAAPSVFIFPPSDEQLKSGTAS VVCLLNNFYPREAKVQWKVDNALQSGNSQESVTEQDSKDSTYSLSSTLTISKADYEKHKVYACE VTHQGLSSPVTKSFNRGEC |
| 191 | 10D1_c77 VH1-CH1-CH2-CH3 | DVQLQEWGAGLLKPBETLSLTCAVTGYSITSGYSWHWIRQFPGNGLEWIGSIHYSGGTNYNPSLK SRITISRDTSKNQFSLKLSSVTAADTAVYFCARMTTAPRYPFDYWGQGTLVTVSSASTKGPSVFPL APSSKSTSGGTAALGCLVKDYFPEPVTVSWNSGALTSGVHTFPAVLQSSGLYSLSSWTVPSSSL GTQTYICNVNHKPSNTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLSPGK |
| 192 | 10Da_c77 VL-Cκ | VIVMTQSPSSLSASVGDRVTITCKASQIVGPNVAWYQQKPGKSPKPLIYSASYGYSDVPSRFSGS GSGTDFTLTISSLQPEDVAEYFCQQYSTHPLTFGPGTKVEIKRTVAAPSVFIFPPSDEQLKSGTASV VCLLNNFYPREAKVQWKVDNALQSGNSQESVTEQDSKDSTYSLSSILTLSKADYEKHKVYACEV THQGLSSPVTKSFNRGEC |
| 193 | 10D1_c78v1 VH-CH1-CH2-CH3 | DVQLQEWGAGLLKPSETLSLTCAVTGYSITSGYSWHWIRQFPGNGLEWIGSIHYSGGTNYNPSLK SRITISRDTSKNQFSLKLSSVTAADTAVYFCARMTTAPRYPFDYWGQGTLVTVSSASTKGPSVFPL APSSKSTSGGTAALGCLVKDYFPEPVTVSWNSGALTSGVHTFPAVLQSSGLYSLSSVVTTVPSSSL GTQTYICNVNHKPSNTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRVVSVLTVLHQDWLNGKEYKEK VSNKALPAPIEKTISKAKGQPREPQWTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLSPGK |
| 194 | 10D1_c78v2 VH-CH1-CH2-CH3 | DVQLQEWGAGLLKPSETLSLTCAVTGYSITSGYSWHWIRQFPGkGLEWIGSIHYSGGTNYNPSLK SRITISRDTSKNQFSLKLSSVTAADTAVYFCARMTTAPRYPFDYWGQGTLVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRWSVLTVLHQDWLNGKEYKCK VSNKALPAPIEKTISKAKGQPREPQVYTLPPSRDELTKNQVSLTCLVKGFYPSDIAVEWESNGQPE NNYKTTPPVLDSDGSFFLYSKLTVDKERWQQGNVFSCSVMHEALHNHYTQKSLSLSPGK |

-continued

| SEQ ID NO: | DESCRIPTION | SEQUENCE |
| --- | --- | --- |
| 195 | 10D1_c78v1, 10D1_c78v2, 10D1_11B VL-Cκ | DIVMTQSPSSLSASVGDRVTITCKASQIVGSNVAWYQQKPGKSPKPLIYSASYGYSDVPSRFSGS GSGTDFTLTISSLRPEDVATYYCQQYSSHPLTFGPGTKVEIKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 196 | 10D1_11B VH-CH1-CH2-CH3 | DVQLQEWGAGLLKPSETLSLTCAVYGYSITSGYSWHWIRQFPGKGLEWIGSHYSGGTNYNPSLK SRVTISRDTSKNQFSLKLSSVTAADTAVYYCARMTTAPRYPFDYWGQGTLVTVSSASTKGPSVFP LAPSSKSTSGGTAALGCLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTVLHQDWLNGKEYKC KVSNKALPAPIEKTISKAKGQPREPQWTLPPSRDELTKNQVSLTCLVKGFYPSDIAVEWESNGQP ENNYKTTPPVLDSDGSFFLYSKLTVDKSRWQQGNVFSCSVMHEALHNHYTQKSLSLSPGK |
| 197 | 10D1_c85v1 VH-CH1-CH2-CH3 | DVQLQEWGAGLLKPSETLSLTCAVTGYSITSGYSWHWIRQFPGNGLEWIGSRYSGGTNYNPSLK SRITISRDTSKNQFSLKLGSVTAADTAVYFCARMTTAPRYPFDYWGQGTLVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLSPGK |
| 198 | 10D1_c85v2 VH-CH1-CH2-CH3 | DVQLQEWGAGLLKPSETLSLTCAVTGYSITSGYSWHWIRQFPGKGLEWIGSIRYSGGTNYNPSLK SRITISRDTSKNQFSLKLGSVTAADTAVYFCARMTTAPRYPFDYWGQGTLVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKKVFPKSCDKTHTCPPCPAPELLGGPSVFLFPPKPKDTLMISRTPEV TCVVVDVSHEDPEVKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLSPGK |
| 199 | 10D1_c85v1, 10D1_c85v2 VL-Cκ | DIVMTQSPSSLSASVGDRVTEICKASQIVGSNVAWYQQKPGKSPKPLIYSARYQYSGVPFRFSGS GSGTDFTLTISSLQPEDVATYYCQQYSSHPLTFGPGTKVEIKRTVAAPSVFIFPPSDEQLKSGTAS VVCLLNNFYPREAKVQWKVDNALQSGNSQESVTEQDSKDSTYSLSSTLTLSKADYEKHKVYACE VTHQGLSSPVTKSFNRGEC |
| 200 | 10D1_c85o1 VH-CH1-CH2-CH3 | DVQLQEWGAGLLKPSETLSLTCAVTGYSITSGYSWHWIRQFPGKGLEWIGSIRYSGGTNYNPSLK SRITISFRDTSKNQFSLKLGSVTAADTAVYFCARETTAPRYPFDYWGQGTLVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLSPGK |
| 201 | 10D1_c85o1 VL-Cκ | DIVMTQSPSSLSASVGDRVTITCKASQIVGSNVAWYQQKPGKSPKPLIYSARYQYSGVPFRFSGS GSGTDFTLTISSLQPEDVATYYCQQYSSHPLTFGPGTKVEIKRTVAAPSVFIFPPSDEQLKSGTAS VVCLLNNFYPREAKVQWKVDNALQSGNSQESVTEQDSKDSTYSLSSTLTLSKADYEKHKVYACE VTHQGLSSPVTKSFNRGEC |
| 202 | 10D1_c85o2 VH-CH1-CH2-CH3 | DVQLQEWGAGLLKPSETLSLCAVTGYSITSGYSWHWIRQFPGKGLEWIGSIRYSGGTNYNPSLK SRITISRDTSKNQFSLKLGSVTAADTAVYFCARGTTAPRYPFDYWGQGTLVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVOKKVEPKSCDKTHICPPCPAPELLGGPSVFLFPPKPKDTLMISRTPEV TCVVVDVSHEDPEVKFNWYVDGVEVHNAKTKPREEQYNSTYRVVSVLTVLHQDWLNGKEYKEK VSNKALPAREKTISKAKGQPREPQVYTLPPSRDELTKNQVSLTCLVKGEYPSDIAVEWESNGQPE NNYKTTPPVLDSDGSFELYSKLTVDKSRWQQGNVESCSVMHEALHNHYTQKSISLSPGK |
| 203 | 10D1_c85o2 VL-Cκ | DIVMTQSPSSLSASVGDRVTITCKASOIVGSNVAVVYQQKPGKSPKPLEYSARYQYSGVPFRFSGS GSGTDFTLTISSLQPEDVATYYCQQYSSHPLTFGPGTKVEIKRTVAAPSVFIFPPSDEQLKSGTAS VVCLLNNFYPREAKVQWKVDNALQSGNSQESVTEQDSKDSTYSLSSTLTLSKADYEKHKVYACE VTHQGLSSPVTKSPNRGEC |
| 204 | 10D1_c87 VH-CH1-CH2-CH3 | DVQLQEWGAGLLKPSETLSLTCAVTGYSITSGYSWHWIRQFPGNGLEWIGSIHYSGGTNYNPSLK SRITISRDTSKNQFSLRLSSVTAADTAVYPCARMTTAPRYPFDYWGQGTLVTVSSASTKGPSVFPL APSSKSTSGGTAALGCLVKDYFPEPVTVSWNSGALTSGVHTFPAVLQSSGLYSLSSVVTVPSSSL TCVVVDVSHEDPEVKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLSPGK |
| 205 | 10D1_c87 VL-Cκ | DIVMTOSPSSLSASVGDRVTITCKASQIVGSNVAWYQQMPGKSPEPLIYSASYLYSDVPSRFSGS GSGTDFTMTISLQPEDVATYYCQQYSSHPLTFGPGTKVEIKRTVAAPSVFIFPPSDEQLKSGTAS VVCLLNNFYPREAKVQWKVDNALQSGNSQESVTEQDSKDSTYSLSSTLTLSKADYEKHKVYACE VTHQGLSSPVTKSFNRGEC |

-continued

| SEQ ID NO: | DESCRIPTION | SEQUENCE |
|---|---|---|
| 206 | 10D1_c89 VH-CH1-CH2-CH3 | QVQLQESGPGLVKPSQTLSLTCTVSGYSITSGYSWHWIRQHPGKGLEWIGSIRYSGGTDYNPSLK SLVTISADTSKNQFSLKLSSVTAADTAVYYCARMTTAPWYPFDYWGQGTTVTVSSASTKGPSVFP LAPSSKSTSGGTAALGCLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVFLEPPKPKDTLMSRTPE VTCVVVDVSHEDPEVKFNWWDGVEVHNAKTKPREEQYNSTYRWSVLTVLHQDWLNGKEYKC KVSNKALPAPIEKTISKAKGQPREPQVYTLPPSRDELTKNQVSLTCLVKGFYPSDIAVEWESNGQP ENNYKTTPPVLDSDGSPFLYSKLTVDKSRWQQGNVFSCSVMHEALHNHYTQKSLSLSPGK |
| 207 | 10D1_c89 VL-Cκ | DIQMTQSPSSVSASVGDRVTITCKASQIGSNVAWYQQKPGKAPEPLYSASYLYSGVPSRFSGS GSGTDFTLTISSLQPEDFATYYCQQYSSHPLTPGQGTKLEIKRTVAAPSVFIFPPSDEQLKSGTASV VCLLNNFYPREAKVQWKVDNALQSGNSQESVTEQDSKDSTYSLSSILTLSKADYEKHKVYACEV THQGLSSPVTKSFNRGEC |
| 205 | 10D1_c90 VH-CH1-CH2-CH3 | QVQLQESGPGLVKPSQTLFLTCTVSGYSITSGYSWHWIRQHPGKGLEWIGSIRYSGGTDYNPSLK SLVTISVDTSKNQFSLKLSSVTAADTAVYYCARMTTAPWYPFDYWGQGTTVTVSSASTKGPSVFP LAPSSKSTSGGTAALGCLVKDYFPEPVTVSWNSGALTSGVHTFPAVLQSSGLYSLSSVVTVPSSS LGQTYICNVNHKPSNTKVDKKVEPKSCDKTHTEPPCPAPELLGGPSVFLPPPKPKDTLMISRTPE VTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNHYTQKSLSLSPGK |
| 209 | 10D1_c90 VL-Cκ | DIQMTQSPSSVSASVGDRVTFTCKASQIVGSNVAWYQQKPGKAPEPLIYSASYLYSSVPSRFSGS GSGTEFTMTISSLEPEDFATYYCQQYTTHPLTFGPGTKVEIKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSFNRGEC |
| 210 | 10D1_c91 VH-CH1-CH2-CH3 | QVQLQESGPGLVKPSQTLSLTCTVSGYYITSGYSWHWIRQHPGKGLEWIGSIRYSGGTDYNPSLK SLATISADTSKNQFSLKLSSVTAADTAVYYCARMTTAPWYPFDYWGQGTAVTVSSASTKGPSVFP LAPSSKSTSGGTAALGCLVKDYFPEPVTVSWNSGLTSGVHTFPAVLQSSGLYSLSSVVTVPSSS LGTQTYICNVNHKPSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRWSVLTVLHQDWLNGKEYKC KVSNKALPAPIEKTISKAKGQPREPQVYTLPPSRDELTKNQVSLTCLVKGPYPSDIAVEWESNGQP ENNYKTTPPVLDSDGSFELYSKLTVDKSRWQQGNVFSCSVMHEALHNHYTQKSLSLSPGK |
| 211 | 10D1_c91 VL-Cκ | DIQMTQSPSSVSASVGDRVTITCKASQIVGSNVAWYQQKPGKAPMPLIYSASYGYSGVPSRFSGS GSGTDFTLTISSLQPEDFATYYCQQYSSHPLTFGQGTKLEIKRTVAAPSVFIFPPSDEQLKSGTASV VCLLNNFYPREAKVQWKVDNALQSGNSQESVTEQDSKDSTYSLSSTLTLSKADYEKHKVYACEV THQGLSSPVTKSPNRGEC |
| 212 | 10D1_c92 VH-CH1-CH2-CH3 | DVQLQEWGAGLLKPSETLSLTCAVTGYSITSGYSWHWRQFPGNGLEWIGSIHYSGGTNYNPTLK SRITISRDTSKNQFSLKLSSVTAADTAVYFCARMTTAPRYPFDYWGQGTLVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLSPGK |
| 213 | 10D1_c92 VL-Cκ | DIVMTQSPSSLSASVGDLVTITCKASQNGSNVAWYQMKLGKSPKPLIYSASYLYFGVPSRFSGSG SGTDFTLTISSLQPEDVAEYFCQQYFSHPLTFGPGTKVEIKRTVAAPSVFIFPPSDEQLKSGTASVV CLLNNFYPREAKVQWKVDNALQSGNSQESVTEQDSKDSTYSLSSTLTLSKADYEKHKVYACEVT HQGLSSPVTKSFNRGEC |
| 214 | 10D1_c93 VH-CH1-CH2-EH3 | DVQLQEWGAGLLKPSETLSLTCAVTGYSITSGYSWHWIRQFPGNGLEWIGSHYSGGTNYNPSLK SRITISRDTSKNQFSLRLSSVTAADTAWFCARMTTAPRYPFDYWGQGTLVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKKVEPKSCDKIHTCPPCPAPELLGGPSVFLFPPKPKDTLMISRIPEV TCVVVDVSHEDPEVKFNWYVDGVEVHNAKTKPREEQYNSTYRWSVLTVLHODWLNGKEYKCK VSNKALPAPIEKTISKAKGQPREPQVYTIPPSRDELIKNQVSLTCLVKGFYPSDIAVEWESNGQPE NNYKTTPPVLDSDGSPFLYSKLTVDKSRWQQGNVFSCSVMHEALHNHYTQKSLSISPGK |
| 215 | 10D1_c93 VL-Cκ | DIVMTQSPSSLSASVGDRVTITCKASQIVGSNVAWYQQKPGKSPKPLIYSASYLYSDVPSRFSGS GSGTDFTMTISSLQPEDVATYYCQQYSSHPLTFGPGTKVEIKRTVAAPSVFIFPPSDEQLKSGTAS VVCLLNNFYPREAKVQWKVDNALQSGNSQESVTEQDSKDSTYSLSSTLTLSKADYEKHKVYACE VTHQGLSSPVTKSFNRGEC |
| 216 | 10D1 VH-CH1-CH2-CH3 | DVQLQESGPDLVKPSQSLSLTCTVTGYSITSGYSWHWIRQFPGNKLEWMGSIHYSGGTNYNPSL KSRISITRDTSKNQFFLQLNSVTTEDTATYFCARMTTAPRYPFDYWGQGTTLVTVSSASTKGPSVFP LAPSSKSTSGGTAALGCLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNHYTQKSLSLSPGK |

| SEQ ID NO: | DESCRIPTION | SEQUENCE |
|---|---|---|
| 217 | 10D1 VL-Cκ | DIVMTQSQKFMSTSVGDRVSVTCKASQIVGSNVAWYQQKPGQSPKPLIYSASYRYSGVPDRFTA SGSGTDFTLTITNVQSEDLAEYFCQQYSSHPLTFGAGTKLELKRTVAAPSVFIFPPSDEQLKSGTA SVVCLLNNFYPREAKVQWKVDNALQSGNSQESVTEQCSKDSTYSLSSTLTLSKADYEKHKVYAC EVTHQGLSSRVTKSFNRGEC |
| 218 | 4-35-B2 VH-CH1-CH2-CH3 | EIQLQQSGPELVKPGASVKVSCKASGYSFTDYWVYWVKQSHGKSLEWIGHINPYNGGTTYNQKF KGRATLTVDKSSSTAFMHLNSLTSEDSAVYFCVSLRVVGAMDYWGQGTSVTVSSASTKGPSVFPL APSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKRKDTLMISRTREV TCVVVDVSHEDPEVKFNWYVDGVEVHNAKTKPREEQYNSTYRVVSVLTVLHQDWLNGKEYKCK VSNKALPAPIEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLSPGK |
| 219 | 4-35-B2 VL-Cκ | QIVLTQSPALMSASPGEKVTMTCSASSSVSYMYWYQQKPRSSPKPWIYLTSNLASGVPARFSGS GSGTSYSLTISSMEAEDAATYYCQWWSNPYTFGGGTKLEIKRTVAAPSVFIFPPSDEQLKSGTA SVVCLLNNFYPREAKVQWKVDNALQSGNSQESVTEQDSKDSTYSLSSTLTLSKADYEKHKVYAC EVTHQGLSSPVTKSFNRGEC |
| 220 | 4-35-B4 VH-CH1-CH2-CH3 | EVQLQQSGAELVKPGASVKLSCTASGFNIKDTYIHWVKQRPDQGLEWIGKIIDPANGNTNYDPKF QGKATITADTSSNTAYLQLSSLSSEDTAVYFCARGLHVVGQGTTLTVSSASTKGPSVPPLAPSSKS TSGGTAALGCLVKDYFFEPVTVSWNSGALTSGVHTFPAVWSSGLYSLSSVVTVPSSSLGTQTYI CNVNHKPSNTKVDKKVEPKSCDKTHTCPPCPAPELLGGPSVFLFPPFKPKDTLMISRTPEVTCVVV DVSHEDPEVKFNWYVDGVEVHNAKTKPREEQYNSTYRVVSVLTVLHQDWLNGKEYKCKVSNKA LPAPIEKTISKAKGQPREPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLSLSPGK |
| 221 | 4-35-B4 VL-Cκ | DIVLTQSPASLAVSLGQRATISCRASKSVSTSGYSYMHWYQQKPGQPPKLLIYLASNLESGVPARF SGSGSGTDFTLNIHPVEEEDAATYYCQHSRELPYTFGGGTKLEIKRTVAAPSVFIFPPSDEQLKSG TASVVCLLNNFYPPEAKVQWKVDNALQSGNSQESVTEQDSKDSTYSLSSTLTLSKADYEKHKVY ACEVTHQGLSSPVTKSFNRGEC |
| 222 | 10A6 VH-CH1-CH2-CH3 | DVQLQESGPGLVKPSQSLSLTCSVTGNFITSGYFWNWIRQFPGNKLEWMGFISYDGSNNYKPSL KNRISITRDTSKNQFFLKLNSVTTEDTATYYCARENYGFGFDYWGQGTTLTVSSASTKGPSVFPLA PSSKSTSGGTAALGCLVKDYFPEPVTVSWNSGALTSGVHTFPAVLQSSGLYSLSSVVTVPSSSLG TQTYICNVNHKPSNTKVDKKVEPKSCDKTHTCPPCPARELLGGPSVFLFPPKPKDTLMISRTPEVT CVVVDVSHEDPEVKFNWYVDGVEVHNAKTKPREEQYNSTYRVVSVLTVLHQDWLNGKEYKCKV SNKALPAPIEKTISKAKGQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQKSLSLSPGK |
| 223 | 10A6 VL-Cκ | DIVLTQSPSSLPVSIGEKVTMSCKSSQSLLYSDNQKNYLAWYQQKPGQSPKLLIYWASTWKSGVP DRFTGSGSGTDFTLTISSVKAEDLAVYYCQQYFTFPWTFGGGTKLEIKRTVAARSVFIFPPSDEQL KSGTASVVCLLNNFYPREAKVQWKVDNALQSGNSQESVTEQDSKDSTYSLSSTLTLSKADYEKH KVYACEVTHQGLSSPVTKSFNRGEC |
| 224 | 10D1_11B heavy chain FR1 | DVQLQEWGAGLLKPSETLSLTCAVY |
| 225 | 10D1F VH-CH1-CH2-CH3 (GASDALIE; LCKC) (10D1F.FcB) | QVQLQESGPGLVKPSQTLSLTCTVSGYSITSGYSWHWIRQHPGKGLWIGSIRYSGGTDYNPSLK SLVTISADTSKNQRSLKLSSVTAADTAVYYCARMTTARWYPFDYANGQGTIVTVSSASTKGPSVFP LAPSSKSTSGGTAALGCLVKDYFREPVTVSANNSGALTSGVHTFRAVLQSSGLYSLSSVVTVPSSS LGTQTYTCNVNHKRSNTKVDKKVEPKSCDKTHTCPPCPAPELLAGPDVFCFPPKRKDTLMISRTRE VTCVVVDVSHEDPEVKFNWYVDGVEVHNAKTKPREEQYNSTYRVVSVLTVLHQDWLNGKEYKC KVSNKALPLEECTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGK |
| 226 | 10D1F VH-CH1-CH2-CH3 (N297Q) | QVQLQESGPGLVKPSQTLSLTCTVSGYSITSGYSWHIMRQHPGKGLEWIGSIRYSGGTDYNPSLK SLVTISADTSKNQFSLKLSSVTAADTAVYYCARMTTAPWYPFDYWGQGTTVTVSSASTKGPSVFP LAPSSKSTSGGTAALGCLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVFLFPPKPKDTLMISRTPE VTCVVVDVSHEDPEVKFNWYVDGVEVHNAKTKPREEQYQSTYRVVSVLTVLHQDWLNGKEYKC KVSNKALPAPIEKTISKAKGQPREPQVYTLPPSRDELTKNQVSLTCLVKGFYPSDIAVEWESNGQP ENNYKTTPRVLDSDGSFFLYSKLTVDKSRWQQGNVFSCSVMHEALHNHYTQKSLSLSPGK |
| 227 | 10D1 VH-CH1-CH2-CH3 (GASDALIE; LCKC) | DVQLQESGPDLVKPSQSLSLTCTVTGYSITSGYSWHIMRQFPGNKLEWMGSIHYSGGTNYNPSL KSRISITRDTSKNQFFLQLNSVTTEDTATYFCARMTTAPRYPFDYWGQGTTLTVSSASTKGPSVFP LAPSSKSTSGGTAALGCLVKDYFPEPVTVSWNSGALTSGVHTFPAVLQSSGLYSLSSVVTVPSSS LGTQTYICNVNHKPSNTKVDKKVERKSCDKTHTCPPCPARELLAGRDVFCFPPKPKDTLMISRIPE VTCVVVDVSHEDPEVKFNWYVDGVEVHNAKTKPREEQYNSTYRVVSVLTVLHQDWLNGKEYKC KVSNKALPLEECTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSISLSPGK |

Sequences

| SEQ ID NO: | DESCRIPTION | SEQUENCE |
|---|---|---|
| 228 | 10D1 VH-CH1-CH2-CH3 (GASD) | DVQLQESGPDLVKPSQSLSLTCTVTGYSITSGYSWHWIRQFPGNKLEMAGSEHYSGGTNYNPSL KSRISITRDTSKNQFFLQLNSVTTEDTATYFCARMTTAPRYPFDYWGQGTTLTVSSASTKGPSVFP LAPSSKSTSGGTAALGCLVKDYFPEPVTVSWNSGALTSGVHTFPAVLQSSGLYSLSSVVTVPSSS LGTQTYICNVNHKPSNTKVDKKVEPKSCDKTHTCPPCPAPELLAGPDVFLFPPKPKDTLMISRTPE VTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNHYTQKSLSLSPGK |
| 229 | HER3 binding site for 10D1-derived clones | CFGPNPNQCCHDECAGGC |
| 230 | Binding site motif 1 | PNPNQ |
| 231 | Binding site motif 2 | DECAG |

Numbered Paragraphs

The following numbered paragraphs (paras) provide further statements of features and combinations of features which are contemplated in connection with the present invention:

1. An antigen-binding molecule, optionally isolated, which is capable of binding to HER3 in extracellular region subdomain II.

2. The antigen-binding molecule according to para 1, wherein the antigen-binding molecule inhibits interaction between HER3 and an interaction partner for HER3.

3. The antigen-binding molecule according to para 1 or para 2, wherein the antigen-binding molecule is capable of binding to a polypeptide comprising or consisting of the amino acid sequence of SEQ ID NO:16.

4. The antigen-binding molecule according to any one of paras 1 to 3, wherein the antigen-binding molecule is capable of binding to a polypeptide comprising the amino acid sequence of SEQ ID NO:23 or SEQ ID NO:229.

5. The antigen-binding molecule according to any one of paras 1 to 4, wherein the antigen-binding molecule is capable of binding to a polypeptide comprising the amino acid sequence of SEQ ID NO:21 or SEQ ID NO:229.

6. The antigen-binding molecule according to any one of paras 1 to 5, wherein the antigen-binding molecule comprises:
   (i) a heavy chain variable (VH) region incorporating the following CDRs:
      HC-CDR1 having the amino acid sequence of SEQ ID NO:43
      HC-CDR2 having the amino acid sequence of SEQ ID NO:46
      HC-CDR3 having the amino acid sequence of SEQ ID NO:51; and
   (ii) a light chain variable (VL) region incorporating the following CDRs:
      LC-CDR1 having the amino acid sequence of SEQ ID NO:91
      LC-CDR2 having the amino acid sequence of SEQ ID NO:94
      LC-CDR3 having the amino acid sequence of SEQ ID NO:99.

7. The antigen-binding molecule according to any one of paras 1 to 6, wherein the antigen-binding molecule comprises:
   (i) a heavy chain variable (VH) region incorporating the following CDRs:
      HC-CDR1 having the amino acid sequence of SEQ ID NO:41
      HC-CDR2 having the amino acid sequence of SEQ ID NO:44
      HC-CDR3 having the amino acid sequence of SEQ ID NO:47; and
   (ii) a light chain variable (VL) region incorporating the following CDRs:
      LC-CDR1 having the amino acid sequence of SEQ ID NO:88
      LC-CDR2 having the amino acid sequence of SEQ ID NO:92
      LC-CDR3 having the amino acid sequence of SEQ ID NO:95.

8. The antigen-binding molecule according to any one of paras 1 to 6, wherein the antigen-binding molecule comprises:
   (i) a heavy chain variable (VH) region incorporating the following CDRs:
      HC-CDR1 having the amino acid sequence of SEQ ID NO:41
      HC-CDR2 having the amino acid sequence of SEQ ID NO:44
      HC-CDR3 having the amino acid sequence of SEQ ID NO:47; and
   (ii) a light chain variable (VL) region incorporating the following CDRs:
      LC-CDR1 having the amino acid sequence of SEQ ID NO:89
      LC-CDR2 having the amino acid sequence of SEQ ID NO:92
      LC-CDR3 having the amino acid sequence of SEQ ID NO:95.

9. The antigen-binding molecule according to any one of paras 1 to 6, wherein the antigen-binding molecule comprises:

(i) a heavy chain variable (VH) region incorporating the following CDRs:
  HC-CDR1 having the amino acid sequence of SEQ ID NO:41
  HC-CDR2 having the amino acid sequence of SEQ ID NO:44
  HC-CDR3 having the amino acid sequence of SEQ ID NO:47; and
(ii) a light chain variable (VL) region incorporating the following CDRs:
  LC-CDR1 having the amino acid sequence of SEQ ID NO:90
  LC-CDR2 having the amino acid sequence of SEQ ID NO:92
  LC-CDR3 having the amino acid sequence of SEQ ID NO:96.

10. The antigen-binding molecule according to any one of paras 1 to 6, wherein the antigen-binding molecule comprises;
(i) a heavy chain variable (VH) region incorporating the following CDRs:
  HC-CDR1 having the amino acid sequence of SEQ ID NO:41
  HC-CDR2 having the amino acid sequence of SEQ ID NO:44
  HC-CDR3 having the amino acid sequence of SEQ ID NO:47; and
(ii) a light chain variable (VL) region incorporating the following CDRs:
  LC-CDR1 having the amino acid sequence of SEQ ID NO:88
  LC-CDR2 having the amino acid sequence of SEQ ID NO:92
  LC-CDR3 having the amino acid sequence of SEQ ID NO:98.

11. The antigen-binding molecule according to any one of paras 1 to 6, wherein the antigen-binding molecule comprises:
(i) a heavy chain variable (VH) region incorporating the following CDRs:
  HC-CDR1 having the amino acid sequence of SEQ ID NO:41
  HC-CDR2 having the amino acid sequence of SEQ ID NO:45
  HC-CDR3 having the amino acid sequence of SEQ ID NO:47; and
(ii) a light chain variable (VL) region incorporating the following CDRs:
  LC-CDR1 having the amino acid sequence of SEQ ID NO:88
  LC-CDR2 having the amino acid sequence of SEQ ID NO:93
  LC-CDR3 having the amino acid sequence of SEQ ID NO:95.

12. The antigen-binding molecule according to any one of paras 1 to 6, wherein the antigen-binding molecule comprises:
(i) a heavy chain variable (VH) region incorporating the following CDRs:
  HC-CDR1 having the amino acid sequence of SEQ ID NO:41
  HC-CDR2 having the amino acid sequence of SEQ ID NO:45
  HC-CDR3 having the amino acid sequence of SEQ ID NO:49; and
(ii) a light chain variable (VL) region incorporating the following CDRs:
  LC-CDR1 having the amino acid sequence of SEQ ID NO:88
  LC-CDR2 having the amino acid sequence of SEQ ID NO:93
  LC-CDR3 having the amino acid sequence of SEQ ID NO:95.

13. The antigen-binding molecule according to any one of paras 1 to 6, wherein the antigen-binding molecule comprises:
(i) a heavy chain variable (VH) region incorporating the following CDRs:
  HC-CDR1 having the amino acid sequence of SEQ ID NO:41
  HC-CDR2 having the amino acid sequence of SEQ ID NO:45
  HC-CDR3 having the amino acid sequence of SEQ ID NO:50; and
(ii) a light chain variable (VL) region incorporating the following CDRs:
  LC-CDR1 having the amino acid sequence of SEQ ID NO:88
  LC-CDR2 having the amino acid sequence of SEQ ID NO:93
  LC-CDR3 having the amino acid sequence of SEQ ID NO:95.

14. The antigen-binding molecule according to any one of paras 1 to 6, wherein the antigen-binding molecule comprises:
(i) a heavy chain variable (VH) region incorporating the following CDRs:
  HC-CDR1 having the amino acid sequence of SEQ ID NO:41
  HC-CDR2 having the amino acid sequence of SEQ ID NO:45
  HC-CDR3 having the amino acid sequence of SEQ ID NO:48; and
(ii) a light chain variable (VL) region incorporating the following CDRs:
  LC-CDR1 having the amino acid sequence of SEQ ID NO:88
  LC-CDR2 having the amino acid sequence of SEQ ID NO:92
  LC-CDR3 having the amino acid sequence of SEQ ID NO:95.

15. The antigen-binding molecule according to any one of paras 1 to 6, wherein the antigen-binding molecule comprises:
(i) a heavy chain variable (VH) region incorporating the following CDRs:
  HC-CDR1 having the amino acid sequence of SEQ ID NO:41
  HC-CDR2 having the amino acid sequence of SEQ ID NO:45
  HC-CDR3 having the amino acid sequence of SEQ ID NO:48; and
(ii) a light chain variable (VL) region incorporating the following CDRs:
  LC-CDR1 having the amino acid sequence of SEQ ID NO:88
  LC-CDR2 having the amino acid sequence of SEQ ID NO:92
  LC-CDR3 having the amino acid sequence of SEQ ID NO:97.

16. The antigen-binding molecule according to any one of paras 1 to 6, wherein the antigen-binding molecule comprises:
  (i) a heavy chain variable (VH) region incorporating the following CDRs:
    HC-CDR1 having the amino acid sequence of SEQ ID NO:42
    HC-CDR2 having the amino acid sequence of SEQ ID NO:45
    HC-CDR3 having the amino acid sequence of SEQ ID NO:48; and
  (ii) a light chain variable (VL) region incorporating the following CDRs:
    LC-CDR1 having the amino acid sequence of SEQ ID NO:88
    LC-CDR2 having the amino acid sequence of SEQ ID NO:92
    LC-CDR3 having the amino acid sequence of SEQ ID NO:95.

17. The antigen-binding molecule according to any one of paras 1 to 5, wherein the antigen-binding molecule comprises:
  (i) a heavy chain variable (VH) region incorporating the following CDRs:
    HC-CDR1 having the amino acid sequence of SEQ ID NO:158
    HC-CDR2 having the amino acid sequence of SEQ ID NO:159
    HC-CDR3 having the amino acid sequence of SEQ ID NO:160; and
  (ii) a light chain variable (VL) region incorporating the following CDRs:
    LC-CDR1 having the amino acid sequence of SEQ ID NO:165
    LC-CDR2 having the amino acid sequence of SEQ ID NO:166
    LC-CDR3 having the amino acid sequence of SEQ ID NO:167.

18. The antigen-binding molecule according to any one of paras 1 to 4, wherein the antigen-binding molecule is capable of binding to a polypeptide comprising the amino acid sequence of SEQ ID NO:22.

19. The antigen-binding molecule according to any one of paras 1 to 4 or para 18 wherein the antigen-binding molecule comprises:
  (i) a heavy chain variable (VH) region incorporating the following CDRs:
    HC-CDR1 having the amino acid sequence of SEQ ID NO:128
    HC-CDR2 having the amino acid sequence of SEQ ID NO:129
    HC-CDR3 having the amino acid sequence of SEQ ID NO:130; and
  (ii) a light chain variable (VL) region incorporating the following CDRs:
    LC-CDR1 having the amino acid sequence of SEQ ID NO:136
    LC-CDR2 having the amino acid sequence of SEQ ID NO:137
    LC-CDR3 having the amino acid sequence of SEQ ID NO:138.

20. The antigen-binding molecule according to any one of paras 1 to 4 or para 18 wherein the antigen-binding molecule comprises:
  (i) a heavy chain variable (VH) region incorporating the following CDRs:
    HC-CDR1 having the amino acid sequence of SEQ ID NO:144
    HC-CDR2 having the amino acid sequence of SEQ ID NO:145
    HC-CDR3 having the amino acid sequence of SEQ ID NO:146; and
  (ii) a light chain variable (VL) region incorporating the following CDRs:
    LC-CDR1 having the amino acid sequence of SEQ ID NO:151
    LC-CDR2 having the amino acid sequence of SEQ ID NO:152
    LC-CDR3 having the amino acid sequence of SEQ ID NO:153.

21. The antigen-binding molecule according to any one of paras 1 to 4, wherein the antigen-binding molecule comprises:
  (i) a VH region comprising an amino acid sequence having at least 70% sequence identity to the amino acid sequence of SEQ ID NO:24; and
    a VL region comprising an amino acid sequence having at least 70% sequence identity to the amino acid sequence of SEQ ID NO:74;
  or
  (ii) a VH region comprising an amino acid sequence having at least 70% sequence identity to the amino acid sequence of SEQ ID NO:25; and
    a VL region comprising an amino acid sequence having at least 70% sequence identity to the amino acid sequence of SEQ ID NO:75;
  or
  (iii) a VH region comprising an amino acid sequence having at least 70% sequence identity to the amino acid sequence of SEQ ID NO:26; and
    a VL region comprising an amino acid sequence having at least 70% sequence identity to the amino acid sequence of SEQ ID NO:76;
  or
  (iv) a VH region comprising an amino acid sequence having at least 70% sequence identity to the amino acid sequence of SEQ ID NO:27; and
    a VL region comprising an amino acid sequence having at least 70% sequence identity to the amino acid sequence of SEQ ID NO:77;
  or
  (v) a VH region comprising an amino acid sequence having at least 70% sequence identity to the amino acid sequence of SEQ ID NO:28; and
    a VL region comprising an amino acid sequence having at least 70% sequence identity to the amino acid sequence of SEQ ID NO:78;
  or
  (vi) a VH region comprising an amino acid sequence having at least 70% sequence identity to the amino acid sequence of SEQ ID NO:29; and
    a VL region comprising an amino acid sequence having at least 70% sequence identity to the amino acid sequence of SEQ ID NO:78;
  or
  (vii) a VH region comprising an amino acid sequence having at least 70% sequence identity to the amino acid sequence of SEQ ID NO:30; and
    a VL region comprising an amino acid sequence having at least 70% sequence identity to the amino acid sequence of SEQ ID NO:78;

or
(viii) a VH region comprising an amino acid sequence having at least 70% sequence identity to the amino acid sequence of SEQ ID NO:31; and
a VL region comprising an amino acid sequence having at least 70% sequence identity to the amino acid sequence of SEQ ID NO:79;
or
(ix) a VH region comprising an amino acid sequence having at least 70% sequence identity to the amino acid sequence of SEQ ID NO:32; and
a VL region comprising an amino acid sequence having at least 70% sequence identity to the amino acid sequence of SEQ ID NO:79;
or
(x) a VH region comprising an amino acid sequence having at least 70% sequence identity to the amino acid sequence of SEQ ID NO:33; and
a VL region comprising an amino acid sequence having at least 70% sequence identity to the amino acid sequence of SEQ ID NO:80;
or
(xi) a VH region comprising an amino acid sequence having at least 70% sequence identity to the amino acid sequence of SEQ ID NO:34; and
a VL region comprising an amino acid sequence having at least 70% sequence identity to the amino acid sequence of SEQ ID NO:81;
or
(xii) a VH region comprising an amino acid sequence having at least 70% sequence identity to the amino acid sequence of SEQ ID NO:35; and
a VL region comprising an amino acid sequence having at least 70% sequence identity to the amino acid sequence of SEQ ID NO:82;
or
(xiii) a VH region comprising an amino acid sequence having at least 70% sequence identity to the amino acid sequence of SEQ ID NO:36; and
a VL region comprising an amino acid sequence having at least 70% sequence identity to the amino acid sequence of SEQ ID NO:83;
or
(xiv) a VH region comprising an amino acid sequence having at least 70% sequence identity to the amino acid sequence of SEQ ID NO:37; and
a VL region comprising an amino acid sequence having at least 70% sequence identity to the amino acid sequence of SEQ ID NO:84;
or
(xv) a VH region comprising an amino acid sequence having at least 70% sequence identity to the amino acid sequence of SEQ ID NO:38; and
a VL region comprising an amino acid sequence having at least 70% sequence identity to the amino acid sequence of SEQ ID NO:85;
or
(xvi) a VH region comprising an amino acid sequence having at least 70% sequence identity to the amino acid sequence of SEQ ID NO:39; and
a VL region comprising an amino acid sequence having at least 70% sequence identity to the amino acid sequence of SEQ ID NO:86;
or
(xvii) a VH region comprising an amino acid sequence having at least 70% sequence identity to the amino acid sequence of SEQ ID NO:40; and
a VL region comprising an amino acid sequence having at least 70% sequence identity to the amino acid sequence of SEQ ID NO:87;
or
(xviii) a VH region comprising an amino acid sequence having at least 70% sequence identity to the amino acid sequence of SEQ ID NO:127; and
a VL region comprising an amino acid sequence having at least 70% sequence identity to the amino acid sequence of SEQ ID NO:135;
or
(xix) a VH region comprising an amino acid sequence having at least 70% sequence identity to the amino acid sequence of SEQ ID NO:143; and
a VL region comprising an amino acid sequence having at least 70% sequence identity to the amino acid sequence of SEQ ID NO:150;
or
(xx) a VH region comprising an amino acid sequence having at least 70% sequence identity to the amino acid sequence of SEQ ID NO:157; and
a VL region comprising an amino acid sequence having at least 70% sequence identity to the amino acid sequence of SEQ ID NO:164.

22. The antigen-binding molecule according to any one of paras 1 to 21, wherein the antigen-binding molecule is capable of binding to human HER3 and one or more of mouse HER3, rat HER3 and cynomolgous macaque HER3.

23. An antigen-binding molecule, optionally isolated, comprising (i) an antigen-binding molecule according to any one of paras 1 to 22, and (ii) an antigen-binding molecule capable of binding to an antigen other than HER3.

24. The antigen-binding molecule according to any one of paras 1 to 23, wherein the antigen-binding molecule is capable of binding to cells expressing HER3 at the cell surface.

25. The antigen-binding molecule according to any one of paras 1 to 24, wherein the antigen-binding molecule is capable of inhibiting HER3-mediated signalling.

26. The antigen-binding molecule according to any one of paras 1 to 25, wherein the antigen-binding molecule comprises an Fc region, the Fc region comprising a polypeptide having: (i) C at the position corresponding to position 242, and C at the position corresponding to position 334, and (ii) one or more of: A at the position corresponding to position 236, at the position corresponding to position 239, E at the position corresponding to position 332, L at the position corresponding to position 330, K at the position corresponding to position 345, and G at the position corresponding to position 430.

27. The antigen-binding molecule according to para 26 wherein the Fc region comprises a polypeptide having C at the position corresponding to position 242, C at the position corresponding to position 334, A at the position corresponding to position 236, D at the position corresponding to position 239, E at the position corresponding to position 332, and L at the position corresponding to position 330.

28. A chimeric antigen receptor (CAR) comprising an antigen-binding molecule according to any one of paras 1 to 27.

29. A nucleic add, or a plurality of nucleic adds, optionally isolated, encoding an antigen-binding molecule according to any one of paras 1 to 27 or a CAR according to para 28.

30. An expression vector, or a plurality of expression vectors, comprising a nucleic add or a plurality of nucleic adds according to para 29.

31. A cell comprising an antigen-binding molecule according to any one of paras 1 to 27, a CAR according to para 28, a nucleic add or a plurality of nucleic adds according to para 29, or an expression vector or a plurality of expression vectors according to para 30.

32. A method comprising culturing a cell comprising a nucleic add or a plurality of nucleic adds according to para 29, or an expression vector or a plurality of expression vectors according to para 30, under conditions suitable for expression of the antigen-binding molecule or CAR from the nucleic acid(s) or expression vector(s).

33. A composition comprising an antigen-binding molecule according to any one of paras 1 to 27, a CAR according to para 28, a nucleic acid or a plurality of nucleic acids according to para 29, an expression vector or a plurality of expression vectors according to para 30, or a cell according to para 31.

34. An antigen-binding molecule according to any one of paras 1 to 27, a CAR according to para 28, a nucleic acid or a plurality of nucleic acids according to para 29, an expression vector or a plurality of expression vectors according to para 30, a cell according to para 31, or a composition according to para 33 for use in a method of medical treatment or prophylaxis.

35. An antigen-binding molecule according to any one of paras 1 to 27, a CAR according to para 28, a nucleic acid or a plurality of nucleic acids according to para 29, an expression vector or a plurality of expression vectors according to para 30, a cell according to para 31, or a composition according to para 33, for use in a method of treatment or prevention of a cancer.

36. Use of an antigen-binding molecule according to any one of paras 1 to 27, a CAR according to para 28, a nucleic acid or a plurality of nucleic acids according to para 29, an expression vector or a plurality of expression vectors according to para 30, a cell according to para 31, or a composition according to para 33, in the manufacture of a medicament for use in a method of treatment or prevention of a cancer.

37. A method of treating or preventing a cancer, comprising administering to a subject a therapeutically or prophylactically effective amount of an antigen-binding molecule according to any one of paras 1 to 27, a CAR according to para 28, a nucleic acid or a plurality of nucleic acids according to para 29, an expression vector or a plurality of expression vectors according to para 30, a cell according to para 31, or a composition according to para 33.

38. The antigen-binding molecule, CAR, nucleic acid or plurality of nucleic acids, expression vector or plurality of expression vectors, cell or composition for use according to para 34 or para 35, the use according to para 36 or the method according to para 37, wherein the method additionally comprises administration of an inhibitor of signalling mediated by an EGFR family member, optionally wherein the inhibitor of signalling mediated by an EGFR family member is an inhibitor of signalling mediated by HER2 and/or EGFR.

39. The antigen-binding molecule, CAR, nucleic: acid or plurality of nucleic acids, expression vector or plurality of expression vectors, cell or composition for use, the use or the method according to any one of paras 34 to para 38, wherein the cancer is selected from: a cancer comprising cells expressing an EGFR family member, a cancer comprising cells expressing HER3, a solid tumor, breast cancer, breast carcinoma, ductal carcinoma, gastric cancer, gastric carcinoma, gastric adenocarcinoma, colorectal cancer, colorectal carcinoma, colorectal adenocarcinoma, head and neck cancer, squamous carcinoma of the head and neck (SCCHN), lung cancer, lung adenocarcinoma, squamous cell lung carcinoma, ovarian cancer, ovarian carcinoma, ovarian serous adenocarcinoma, kidney cancer, renal cell carcinoma, renal clear cell carcinoma, renal cell adenocarcinoma, renal papillary cell carcinoma, pancreatic cancer, pancreatic adenocarcinoma, pancreatic ductal adenocarcinoma, cervical cancer, cervical squamous cell carcinoma, skin cancer, melanoma, esophageal cancer, esophageal adenocarcinoma, liver cancer, hepatocellular carcinoma, cholangiocarcinoma, uterine cancer, uterine corpus endometrial carcinoma, thyroid cancer, thyroid carcinoma, pheochromocytoma, paraganglioma, bladder cancer, bladder urothelial carcinoma, prostate cancer, prostate adenocarcinoma, sarcoma and thymoma.

40. A method of inhibiting HER3-mediated signalling, comprising contacting HER3-expressing cells with an antigen-binding molecule according to any one of paras 1 to 27.

41. A method of reducing the number or activity of HER3-expressing cells, the method comprising contacting HER3-expressing cells with an antigen-binding molecule according to any one of paras 1 to 27.

42. An in vitro complex, optionally isolated, comprising an antigen-binding molecule according to any one of paras 1 to 27 bound to HER3.

43. A method comprising contacting a sample containing, or suspected to contain, HER3 with an antigen-binding molecule according to any one of paras 1 to 27, and detecting the formation of a complex of the antigen-binding molecule with HER3.

44. A method of selecting or stratifying a subject for treatment with a HER3-targeted agent, the method comprising contacting, in vitro, a sample from the subject with an antigen-binding molecule according to any one of paras 1 to 27 and detecting the formation of a complex of the antigen-binding molecule with HER3.

45. Use of an antigen-binding molecule according to any one of paras 1 to 27 as an in vitro or in vivo diagnostic or prognostic agent.

46. Use of an antigen-binding molecule according to any one of paras 1 to 27 in a method for detecting, localizing or imaging a cancer, optionally wherein the cancer is selected from: a cancer comprising cells expressing an EGFR family member, a cancer comprising cells expressing HER3, a solid tumor, breast cancer, breast carcinoma, ductal carcinoma, gastric cancer, gastric carcinoma, gastric adenocarcinoma, colorectal cancer, colorectal carcinoma, colorectal adenocarcinoma, head and neck cancer, squamous cell carcinoma of the head and neck (SCCHN), lung cancer, lung adenocarcinoma, squamous cell lung carcinoma, ovarian cancer, ovarian carcinoma, ovarian serous adenocarcinoma, kidney cancer, renal cell carcinoma, renal dear cell carcinoma, renal cell adenocarcinoma, renal papillary cell carcinoma, pancreatic cancer, pancreatic adenocarcinoma, pancreatic ductal adenocarcinoma, cervical cancer, cervical squamous cell carcinoma, skin cancer, melanoma, esophageal cancer, esophageal adenocarcinoma, liver cancer, hepatocellular carcinoma, cholangiocarcinoma, uterine cancer, uterine corpus endometrial carcinoma, thyroid cancer, thyroid carcinoma, pheochromocytoma, paraganglioma, bladder cancer, bladder urothelial carcinoma, prostate cancer, prostate adenocarcinoma, sarcoma and thymoma.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a" "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Where a nucleic acid sequence is disclosed herein, the reverse complement thereof is also expressly contemplated.

Methods described herein may preferably performed in vitro. The term "in vitro" is intended to encompass procedures performed with cells in culture whereas the term "in vivo" is intended to encompass procedures with/on intact multi-cellular organisms.

BRIEF DESCRIPTION OF THE FIGURES

Embodiments and experiments illustrating the principles of the invention will now be discussed with reference to the accompanying figures.

FIGS. 16A and 16B. Table and histograms showing gene and protein expression of EGFR protein family members and their ligands by different cancer cell lines.

FIG. 37. Table summarising properties of anti-HER3 antibody 10D1 variant clones relevant to safety and developability.

FIGS. 41A and 41B. Tables showing the binding affinity for mouse and human Fc receptors of anti-HER3 antibody clones 10D1F.FcA and 10D1F.FcB (GASDALIE-LCKC variant) compared to silent variant N297Q, isoform variants, and commercially available antibodies. ND=$K_D$ Not Determined due to low binding affinity.

FIG. 43. Graph showing the results of ELISA analysis of binding of anti-HER3 antibody clone 10D1F.FcA to human EGFR (HER1) and human HER2. $EC_{50}$ values are shown.

FIG. 44. Histogram showing staining of cells by anti-HER3 and anti-HER4 antibodies as determined by flow cytometry. Histogram shows staining of HEK293 HER4 overexpressing cells by anti-HER3 antibody clone 10D1F.FcA, anti-HER3 antibodies LJM-716 and MM-121, and commercial anti-HER4 antibody.

FIG. 65. Graph showing the results of analysis of inhibiting of HER2:HER3 interaction by 10D1F.FcA or pertuzumab, as determined by PathHunter Pertuzumab Bioassay. IC50 (M) values are shown.

FIGS. 66A to 66C. Histograms showing the results of analysis of expression of EGFR, HER2 and HER3 by (66A) BCPAP (66B) BHT101 and (66C) SW1736 cells. 1=unstained cells, 2=isotype control, 3=cetuximab, 4=trastuzumab, and 5=10D1F.FcA.

FIGS. 67A to 67C. Graphs showing the results of analysis of the ability of different anti-ErbB antibodies to inhibit proliferation of BRAF$^{V600E}$ mutant thyroid cancer cell lines in vitro. 67A shows the results obtained for BHT101 cells, 687 shows the results obtained for BCPAP cells, and 67C shows the results obtained for SW1736 cells.

FIGS. 69A to 69C. Tables showing representative hematological profiles of BALB/c mice following administration of 10 mg/kg, 25 mg/kg, 100 mg/kg or 250 mg/kg of 10D1F.FcA or an equal volume of PBS. 69A shows results of analysis of the red blood cell compartment, 69B shows results of analysis of the white blood cell compartment, and 69C shows results of analysis of correlates of liver, kidney and pancreas function, and levels of electrolytes. RBC=red blood cell, MVC=mean corpuscular volume, MCH=mean corpuscular haemoglobin, MCHC=mean corpuscular haemoglobin concentration, WBC=white blood cell, ALT=alanine aminotransferase, ALP=alkaline phosphatase, CREA=creatinine, BUN=blood urea nitrogen, GLU=glucagon, AMY=amylase, NA=sodium, K=potassium, P=phosphorus and CA=calcium.

FIGS. 70A to 70C. Tables showing representative hematological profiles of SD rats at the indicated time points, following administration of 250 mg/kg 10D1F.FcA or an equal volume of PBS. 70A shows results of analysis of the red blood cell compartment, 70B shows results of analysis of the white blood cell compartment, and 70C shows results of analysis of correlates of liver, kidney and pancreas function, and levels of electrolytes. RBC=red blood cell, MVC=mean corpuscular volume, MCH=mean corpuscular haemoglobin, MCHC=mean corpuscular haemoglobin concentration, WBC=white blood cell, ALT=alanine aminotransferase, ALP=alkaline phosphatase, CREA=creatinine, BUN=blood urea nitrogen, GLU=glucagon, AMY=amylase, NA=sodium, K=potassium, P=phosphorus and CA=calcium.

FIGS. 73A and 73B. Histograms and tables showing the results of analysis of internalisation of 10D1F.FcA or trastuzumab by the indicated cell lines at different time points, as determined by flow cytometry. 73B shows median fluorescence intensity and percentages of PE-positive cells determined from the histograms shown in 73A.

EXAMPLES

Figure 1A:
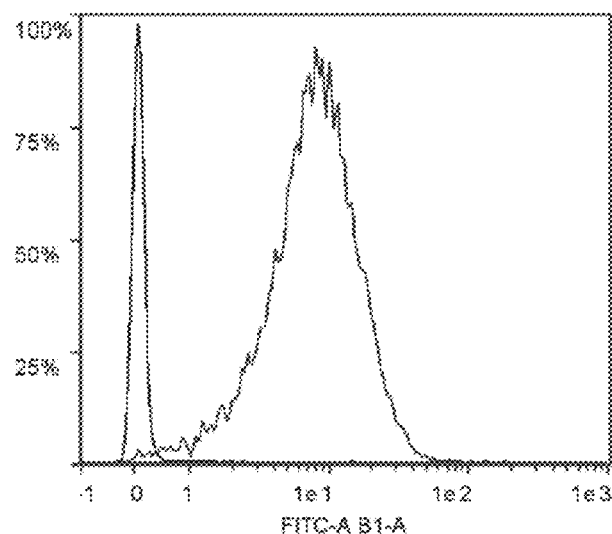
FIGS. 1A and 1B. Histograms showing staining of cells by anti-HER3 antibodies as determined by flow cytometry. Histograms show staining of HEK293 cells (which do not express HER3), or HEK293 HER3 overexpressing cells (HEK293 HER3 O/E) by (1A, 1B) anti-HER3 antibody clone 10D1 and (1B) anti-HER3 antibody clone LJM716.
Figure 1B:
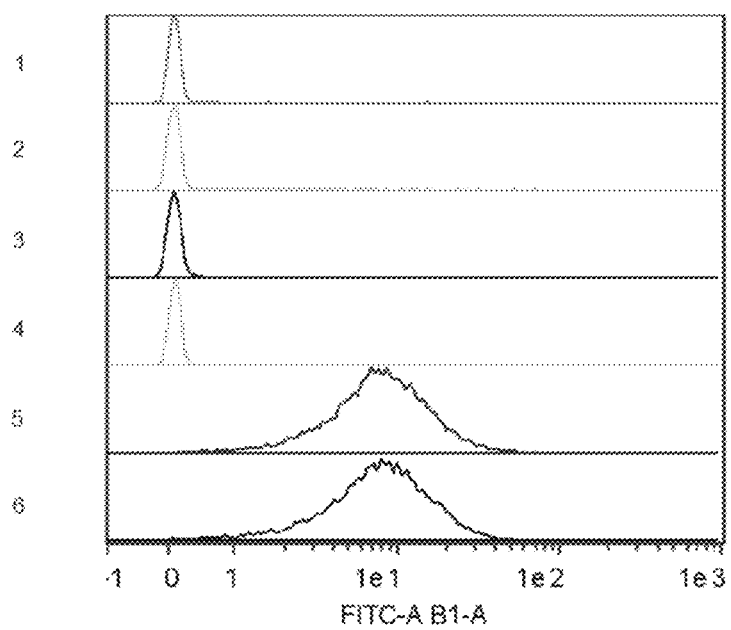
Figure 2A:
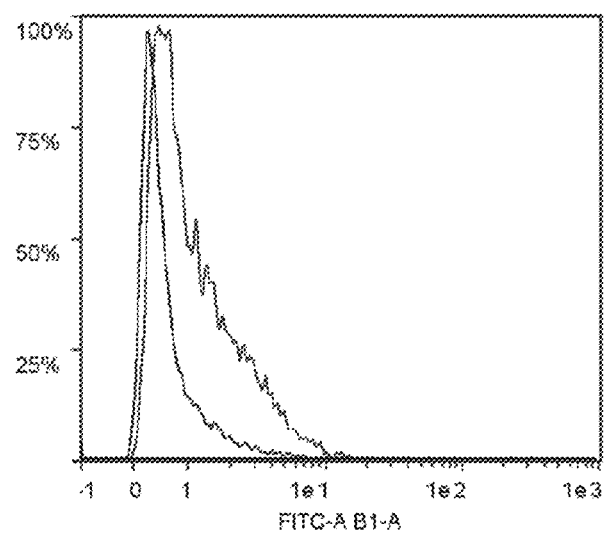
FIGS. 2A and 2B. Histograms showing staining of cells by anti-HER3 antibodies as determined by flow cytometry. Histograms show staining of HEK293 cells (which do not express HER3), or HEK293 HER3 overexpressing cells (HEK293 HER3 O/E) by (2A, 2B) anti-HER3 antibody clone 4-35-B2 and (2B) anti-HER3 antibody clone LJM716.
Figure 2B:
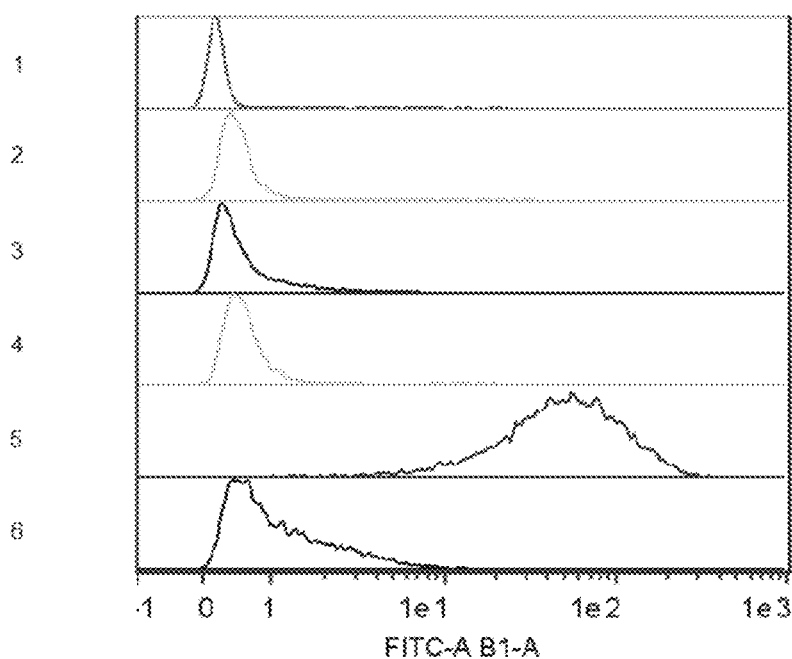
Figure 3A:
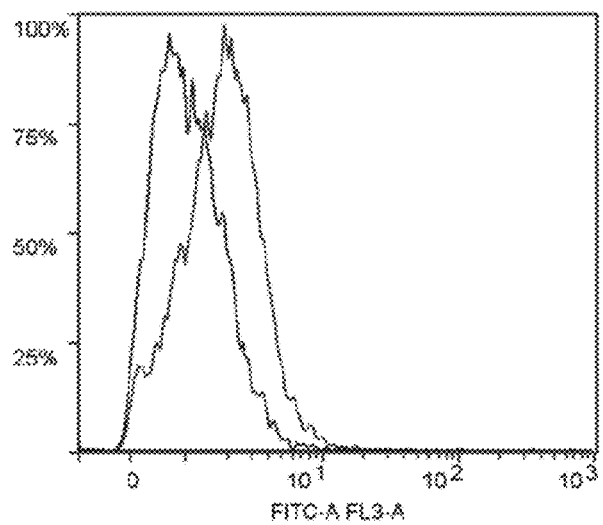
FIGS. 3A and 3B. Histograms showing staining of cells by anti-HER3 antibodies as determined by flow cytometry. Histograms show staining of HEK293 cells (which do not express HER3), or HEK293 HER3 overexpressing cells (HEK293 HER3 O/E) by (3A, 3B) anti-HER3 antibody clone 4-35-B4 and (3B) anti-HER3 antibody clone LJM716.
Figure 3B:
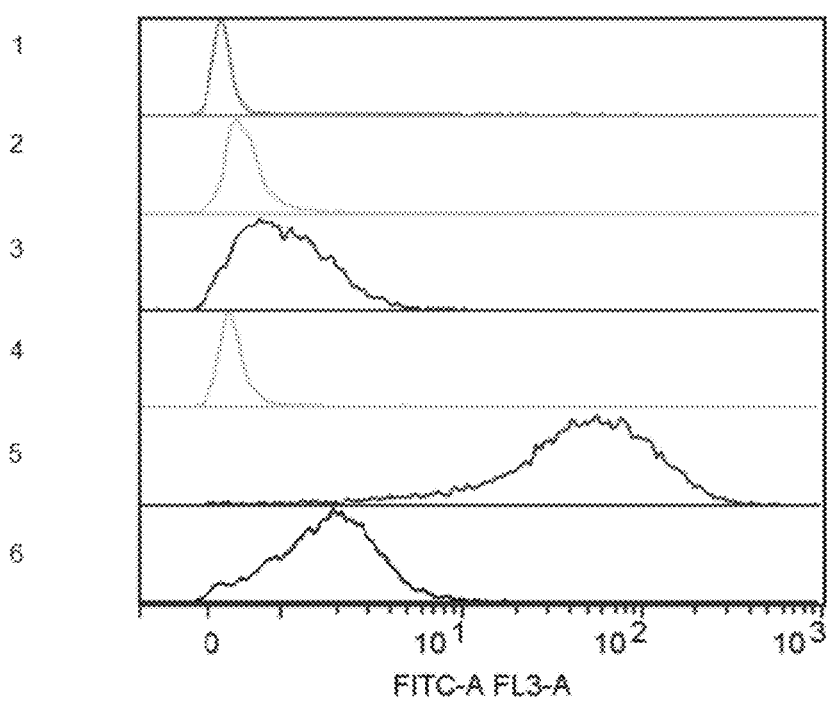
Figure 4:
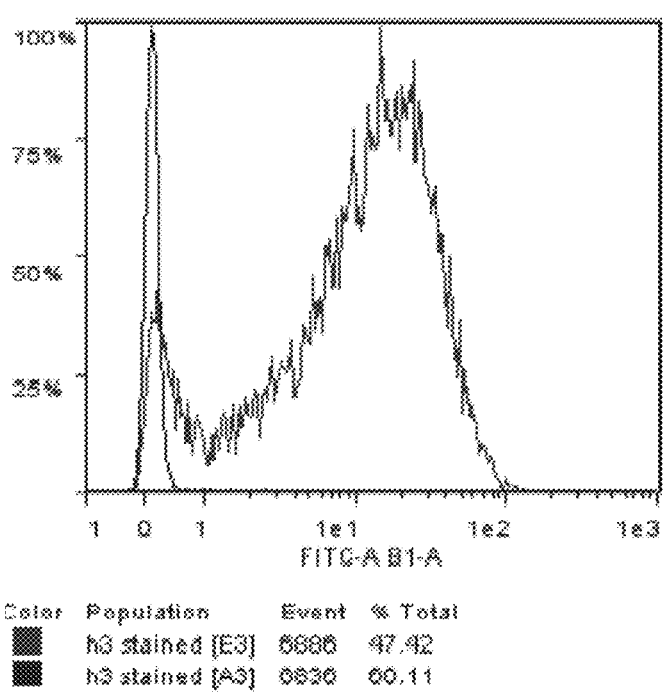
FIG. 4. Histograms showing staining of cells by anti-HER3 antibodies as determined by flow cytometry. Histograms show staining of HEK293 cells (which do not express HER3), or HEK293 HER3 overexpressing cells (HEK293 HER3 O/E) by anti-HER3 antibody clone 10A6.

In the following Examples, the inventors describe the generation of novel anti-HER3 antibody clones targeted to specific regions of interest in the HER3 molecule, and the biophysical and functional characterisation and therapeutic evaluation of these antigen-binding molecules.

Example 1

HER3 Target Design and Anti-HER3 Antibody Hybridoma Production

The inventors selected two regions in the extracellular region of human HER3 (SEQ ID NO:9) for raising HER3-binding monoclonal antibodies.

1.1 Hybridoma Production

Approximately 6 week old female BALE/c mice were obtained from InVivos (Singapore). Animals were housed under specific pathogen-free conditions and were treated in compliance with the Institutional Animal Care and Use Committee (IACUC) guidelines.

For hybridoma production, mice were immunized with proprietary mixtures of antigenic peptide, recombinant target protein or cells expressing the target protein.

Prior to harvesting the spleen for fusion, mice were either boosted with antigen mixture for three consecutive days or only for a single day. 24 h after the final boost total splenocytes were isolated and fused with the myeloma cell line P3X63.Ag8.653 (ATCC, USA), with PEG using Clona-Cell-HY Hybridoma Cloning Kit, in accordance with the manufacturer's instructions (Stemcell Technologies, Canada).

Fused cells were cultured in ClonaCell-HY Medium C (Stemcell Technologies, Canada) overnight at 37° C. in a 5% CO$_2$ incubator. The next day, fused cells were centrifuged and resuspended in 10 ml of ClonaCell-HY Medium C and then gently mixed with 90 ml of semisolid methylcellulose-based ClonaCell-HY Medium C (StemCell Technologies, Canada) containing HAT components, which combines the hybridoma selection and cloning into one step.

The fused cells were then plated into 96 well plates and allowed to grow at 37° C. in a 5% CO$_2$ incubator. After 7-10 days, single hybridoma clones were isolated and antibody producing hybridomas were selected by screening the supernatants by Enzyme-linked immunosorbent assay (ELISA) and Fluorescence-activated cell sorting (FACS).

1.2 Antibody Variable Region Amplification and Sequencing

Total RNA was extracted from hybridoma cells using TRIzol reagent (Life Technologies, Inc., USA) using manufacturer's protocol. Double-stranded cDNA was synthesized using SMARTer RACE 5'/3' Kit (Clontech™, USA) in accordance with the manufacturer's instructions. Briefly, 1 μg total RNA was used to generate full-length cDNA using 5'-RACE CDS primer (provided in the kit), and the 5' adaptor (SMARTer II A primer) was then incorporated into each cDNA according to manufacturers instructions. cDNA synthesis reactions contained, 5× First-Strand Buffer, DTT (20 mM), dNTP Mix (10 mM), RNase Inhibitor (40 U/μl) and SMARTScribe Reverse Transcriptase (100 U/μl).

The race-ready cDNAs were amplified using SegAmp DNA Polymerase (Clontech™, USA). Amplification reactions contained SeqAmp DNA Polymerase, 2× Seq AMP buffer, 5' universal primer provided in the 5' SMARTer Race kit, that is complement to the adaptor sequence, and 3' primers that anneal to respective heavy chain or light chain constant region primer. The 5' constant region were designed based on previously reported primer mix either by Krebber et al. J. Immunol. Methods 1997; 201: 35-55, Wang et al. Journal of Immunological Methods 2000, 233; 167-177 or Tiller et al. Journal of Immunological Methods 2009; 350: 183-193. The following thermal protocol was used: pre-denature cycle at 94° C. for 1 min; 35 cycles of 94° C., 30 s, 55° C., 30 s and 72° C., 45 s; final extension at 72° C. for 3 min.

The resulting VH and VL PCR products, approximately 550 bp, were cloned into pJET1.2/blunt vector using CloneJET PCR Cloning Kit (Thermo Scientific, USA) and used to transform highly competent E. coli DH5α. From the resulting transformants, plasmid DNA was prepared using Miniprep Kb (Eugene, Germany) and sequenced. DNA sequencing was carried out by AITbiotech. These sequencing data were analyzed using the international IMGT (ImMunoGeneTics) information system (LeFranc et al., Nucleic Acids Res. (2015) 43 (Database issue):D413-22) to characterize the individual CDRs and framework sequences. The signal peptide at 5' end of the VH and VL was identified by SignalP (v 4.1; Nielsen, in Kihara, D (ed): Protein Function Prediction (Methods in Molecular Biology vol. 1611) 59-73, Springer 2017).

Four monoclonal anti-HER3 antibody clones were selected for further development; 10D1, 10A6, 4-35-B2, and 4-35-B4.

Humanised versions of 10D1 were designed in silico by grafting of complementarity determining regions (CDRs) into VH and VL comprising human antibody framework regions, and were further optimized for antigen binding by yeast display method.

For yeast display, humanized sequences were converted into single-chain fragment variable (scFv) format by polymerase chain reaction (PCR) and used as templates to generate mutant libraries by random mutagenesis. Mutant PCR libraries were then electroporated into yeast together with linearized pCTcon2 vector to generate yeast libraries. The libraries were stained with human HER3 antigen and sorted for top binders. After 4-5 rounds of sorting, individual yeast clones were sequenced to identify unique antibody sequences.

| Antibody done | VH/VL sequence |
|---|---|
| 10A6 | VH = SEQ ID NO: 157 |
| | VL = SEQ ID NO: 164 |

| Antibody done | VH/VL sequence |
|---|---|
| 10D1 | VH = SEQ ID NO: 24 |
| | VL = SEQ ID NO: 74 |
| 10D1_c75 | VH = SEQ ID NO: 25 |
| | VL = SEQ ID NO: 75 |
| 10D1_c76 | VH = SEQ ID NO: 26 |
| | VL = SEQ ID NO: 76 |
| 10D1_c77 | VH = SEQ ID NO: 27 |
| | VL = SEQ ID NO: 77 |
| 10D1_c78v1 | VH = SEQ ID NO: 28 |
| | VL = SEQ ID NO: 78 |
| 10D1_c78v2 | VH = SEQ ID NO: 29 |
| | VL = SEQ ID NO: 78 |
| 10D1_c11B | VH = SEQ ID NO: 30 |
| | VL = SEQ ID NO: 78 |
| 10D1_c85v1 | VH = SEQ ID NO: 31 |
| | VL = SEQ ID NO: 79 |
| 10D1_c85v2 | VH = SEQ ID NO: 32 |
| | VL = SEQ ID NO: 79 |
| 10D1_c85o1 | VH = SEQ ID NO: 33 |
| | VL = SEQ ID NO: 80 |
| 10D1_c85o2 | VH = SEQ ID NO: 34 |
| | VL = SEQ ID NO: 81 |
| 10D1_c87 | VH = SEQ ID NO: 35 |
| | VL = SEQ ID NO: 82 |
| 10D1_c89 | VH = SEQ ID NO: 36 |
| | VL = SEQ ID NO: 83 |
| 10D1_c90 | VH = SEQ ID NO: 37 |
| | VL = SEQ ID NO: 84 |
| 10D1_c91 | VH = SEQ ID NO: 38 |
| | VL = SEQ ID NO: 85 |
| 10D1_c92 | VH = SEQ ID NO: 39 |
| | VL = SEQ ID NO: 86 |
| 10D1_c93 | VH = SEQ ID NO: 40 |
| | VL = SEQ ID NO: 87 |
| 4-35-B2 | VH = SEQ ID NO: 127 |
| | VL = SEQ ID NO: 135 |
| 4-35-B4 | VH = SEQ ID NO: 143 |
| | VL = SEQ ID NO: 150 |

Example 2

Antibody Production and Purification 2.1 Cloning VH and VL Into Expression Vectors:

DNA sequences encoding the heavy and light chain variable regions of the anti-HER3 antibody clones were subcloned into the pmAbaZ_IgG1_CH and pmAbDZ_IgG1_CL (InvivoGen, USA) eukaryotic expression vectors for construction of human-mouse chimeric antibodies.

Alternatively, DNA sequence encoding the heavy and light chain variable regions of the anti-HER3 antibody clones were subcloned into the pFUSE-CHIg-hG1 and pFUSE2ss-CLIg-hk (InvivoGen, USA) eukaryotic expression vectors for construction of human-mouse chimeric antibodies. Human IgG1 constant region encoded by pFUSE-CHIg-hG1 comprises the substitutions D356E, L358M (positions numbered according to EU numbering) in the CH3 region relative to Human IgG1 constant region (IGHG1; UniProt:P01857-1, v1; SEQ ID NO:176). pFUSE2ss-CLIg-hk encodes human IgG1 light chain kappa constant region (IGCK: UniProt: P01834-1, v2).

Variable regions along with the signal peptides were amplified from the cloning vector using SeqAmp enzyme (Clontech™, USA) following the manufacturer's protocol. Forward and reverse primers having 15-20 bp overlap with the appropriate regions within VH or VL plus 6 bp at 5' end as restriction sites were used. The DNA insert and the vector were digested with restriction enzyme recommended by the manufacturer to ensure no frameshift was introduced and ligated into its respective plasmid using T4 ligase enzyme (Thermo Scientific, USA). The molar ratio of 3:1 of DNA insert to vector was used for ligation.

2.2 Expression of Antibodies in Mammalian Cells

Antibodies were expressed using either 1) Expi293 Transient Expression System Kit (Life Technologies, USA), or 2) HEK293-6E Transient Expression System (CNRC-NRC, Canada) following the manufacturer's instructions.

1) Expi293 Transient Expression System:

Cell Line Maintenance:

HEK293F cells (Expi293F) were obtained from Life Technologies, Inc (USA). Cells were cultured in serum-free, protein-free, chemically defined medium (Expi293 Expression Medium, Thermo Fisher, USA), supplemented with 50 IU/ml penicillin and 50 μg/ml streptomycine (Gibco, USA) at 37° C. in 8% $CO_2$ and 80% humidified incubators with shaking platform.

Transfection:

Expi293F cells were transfected with expression plasmids using ExpiFectamine 293 Reagent kit (Gibed, USA) according to its manufacturer's protocol. Briefly, cells at maintenance were subjected to a media exchange to remove antibiotics by spinning down the culture, cell pellets were re-suspended in fresh media without antibiotics at 1 day before transfection. On the day of transfection, $2.5 \times 10^6$/ml of viable cells were seeded in shaker flasks for each transfection. DNA-ExpiFectamine complexes were formed in serum-reduced medium, Opti-MEM (Gibco, USA), for 25 min at room temperature before being added to the cells. Enhancers were added to the transfected cells at 16-18 h post transfection. An equal amount of media was topped up to the transfectants at day 4 post-transfection to prevent cell aggregation. Transfectants were harvested at day 7 by centrifugation at 4000×g for 15 min, and filtered through 0.22 μm sterile filter units.

2) HEK293-6E Transient Expression System

Cell Line Maintenance:

HEK293-6E cells were obtained from National Research Council Canada. Cells were cultured in serum-free, protein-free, chemically defined Freestyle F17 Medium (Invitrogen, USA), supplemented with 0.1% Kolliphor-P188 and 4 mM L-Glutamine (Gibco, USA) and 25 μg/ml G-418 at 37° C., in 5% $CO_2$ and 80% humidified incubators with shaking platform.

Transfection:

HEK293-6E cells were transfected with expression plasmids using PEIpro™ (Polyplus, USA) according to its manufacturer's protocol. Briefly, cells at maintenance were subjected to a media exchange to remove antibiotics by centrifugation, cell pellets were re-suspended with fresh media without antibiotics at 1 day before transfection. On the day of transfection, $1.5-2 \times 10^5$ cells/ml of viable cells were seeded in shaker flasks for each transfection. DNA and PEIpro™ were mixed to a ratio of 1:1 and the complexes were allowed to form in F17 medium for 5 min at RT before adding to the cells. 0.5% (w/v) of Tryptone N1 was fed to transfectants at 24-48 h post transfection. Transfectants were harvested at day 6-7 by centrifugation at 4000×g for 15 min and the supernatant was filtered through 0.22 μm sterile filter units.

Cells were transfected with vectors encoding the following combinations of polypeptides:

| Antigen-biding molecule | Polypeptides | Antibody |
|---|---|---|
| [1] | 10D1 VH-CH1-CH2-CH3 (SEQ ID NO: 216) + 10D1 VL-Cκ (SEQ ID NO: 217) | anti-HER3 clone 10D1 IgG1 |
| [2] | 10A6 VH-CH1-CH2-CH3 (SEQ ID NO: 222) + 10A6 VL-Cκ (SEQ ID NO: 223) | anti-HER3 clone 10A6 IgG1 |
| [3] | 4-35-B2 VH-CH1-CH2-CH3 (SEQ ID NO: 218) + 4-35-B2 VL-Cκ (SEQ ID NO: 219) | anti-HER3 clone 4-35-B2 IgG1 |
| [4] | 4-35-B4 VH-CH1-CH2-CH3 (SEQ ID NO: 220) + 4-35-B4 VL-Cκ (SEQ ID NO: 221) | anti-HER3 clone 4-35-B4 IgG1 |
| [5] | 10D1_c75 VH-CH1-CH2-CH3 (SEQ ID NO: 187) + 10D1_c75 VL-Cκ (SEQ ID NO: 188) | anti-HER3 clone 10D1_c75 IgG1 |
| [6] | 10D1_c76 VH-CH1-CH2-CH3 (SEQ ID NO: 189) + 10D1_c76 VL-Cκ (SEQ ID NO: 190) | anti-HER3 clone 10D1_c76 IgG1 |
| [7] | 10D1_c77 VH-CH1-CH2-CH3 (SEQ ID NO: 191) + 10D1_c77 VL-Cκ (SEQ ID NO: 192) | anti-HER3 clone 10D1_c77 IgG1 |
| [8] | 10D1_c78v1 VH-CH1-CH2-CH3 (SEQ ID NO: 193) + 10D1_c78v1 VL-Cκ (SEQ ID NO: 195) | anti-HER3 clone 10D1_c78v1 IgG1 |
| [9] | 10D1_c78v1 VH-CH1-CH2-CH3 (SEQ ID NO: 194) + 10D1_c78v2 VL-Cκ (SEQ ID NO: 195) | anti-HER3 clone 10D1_c78v2 IgG1 |
| [10] | 10D1_11B VH-CH1-CH2-CH3 (SEQ ID NO: 196) + 10D1_11B VL-Cκ (SEQ ID NO: 195) | anti-HER3 clone 10D1_11B IgG1 |
| [11] | 1QD1_c85v1 VH-CH1-CH2-CH3 (SEQ ID NO: 197) + 10D1_c85v1 VL-Cκ (SEQ ID NO: 199) | anti-HER3 clone 10D1_c85v1 IgG1 |
| [12] | 10D1_c85v2 VH-CH1-CH2-CH3 (SEQ ID NO: 198) + 10D1_c85v2 VL-Cκ (SEQ ID NO: 199) | anti-HER3 clone 10D1_c85v2 IgG1 |
| [13] | 10D1_c85o1 VH-CH1-CH2-CH3 (SEQ ID NO: 200) + 10D1_c85o1 VL-Cκ (SEQ ID NO: 201) | anti-HER3 clone 10D1_c85o1 IgG1 |
| [14] | 10D1_c85o2 VH-CH1-CH2-CH3 (SEQ ID NO: 202) + 10D1_c85o2 VL-Cκ (SEQ ID NO: 203) | anti-HER3 clone 10D1_c85o2 IgG1 |
| [15] | 10D1_c87 VH-CH1-CH2-CH3 (SEQ ID NO: 204) + 10D1_c87 VL-Cκ (SEQ ID NO: 205) | anti-HER3 clone 10D1_c87 IgG1 |
| [16] | 10D1_c89 VH-CH1-CH2-CH3 (SEQ ID NO: 206) + 10D1_c89 VL-Cκ (SEQ ID NO: 207) | anti-HER3 clone 10D1_c89 IgG1 |
| [17] | 10D1_c90 VH-CH1-CH2-CH3 (SEQ ID NO: 208) + 10D1_c90 VL-Cκ (SEQ ID NO: 209) | anti-HER3 clone 10D1_c90 IgG1 |

-continued

| Antigen-binding molecule | Polypeptides | Antibody |
|---|---|---|
| [18] | 10D1_c91 VH-CH1-CH2-CH3 (SEQ ID NO: 210) + 10D1_c91 VL-Cκ (SEQ ID NO: 211) | anti-HER3 clone 10D1_c91 IgG1 |
| [19] | 10D1_c92 VH-CH1-CH2-CH3 (SEQ ID NO: 212) + 10D1_c92 VL-Cκ (SEQ ID NO: 213) | anti-HER3 clone 10D1_c92 IgG1 |
| [20] | 10D1_c93 VH-CH1-CH2-CH3 (SEQ ID NO: 214) + 10D1_c93 VL-Cκ (SEQ ID NO: 215) | anti-HER3 clone 10D1_c93 IgG1 |

2.3 Antibody Purification

Affinity Purification, Buffer Exchange and Storage:

Antibodies secreted by the transfected cells into the culture supernatant were purified using liquid chromatography system AKTA Start (GE Healthcare, UK). Specifically, supernatants were loaded onto HiTrap Protein G column (GE Healthcare, UK) at a binding rate of 5 ml/min, followed by washing the column with 10 column volumes of washing buffer (20 mM sodium phosphate, pH 7.0). Bound mAbs were eluted with elution buffer (0.1 M glycine, pH 2.7) and the eluents were fractionated to collection tubes which contain appropriate amount of neutralization buffer (1 M Tris, pH 9). Neutralised elution buffer containing purified mAb were exchanged into PBS using 30K MWCO protein concentrators (Thermo Fisher, USA) or 3.5K MWCO dialysis cassettes (Thermo Fisher, USA). Monoclonal antibodies were sterilized by passing through 0.22 μm filter, aliquoted and snap-frozen in −80° C. for storage.

2.4 Antibody-Purity Analysis

Size Exclusion Chromatography (SEC):

Antibody purity was analysed by size exclusion chromatography (SEC) using Superdex 200 10/30 GL columns (GE Healthcare, UK) in PBS running buffer, on a AKTA Explorer liquid chromatography system (GE Healthcare, UK). 150 μg of antibody in 500 μl PBS pH 7.2 was injected to the column at a flow rate of 0.75 ml/min at room temperature. Proteins were eluted according to their molecular weights.

Figure 12:
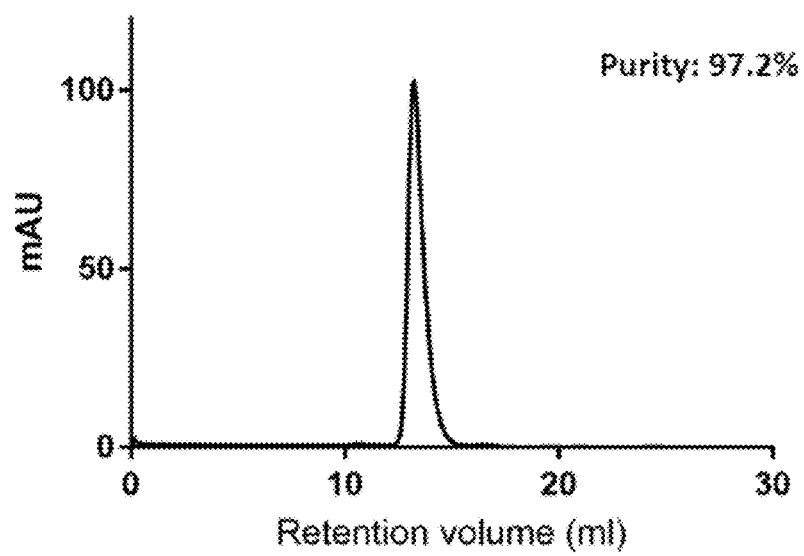
FIG. 12. Graph showing the results of the analysis of recombinantly-expressed anti-HER3 antibody clone 10D1 by size exclusion chromatography.

The result for anti-HER3 antibody clone 10D1 ([1] of Example 2.2) is shown in FIG. 12.

Figure 34A:
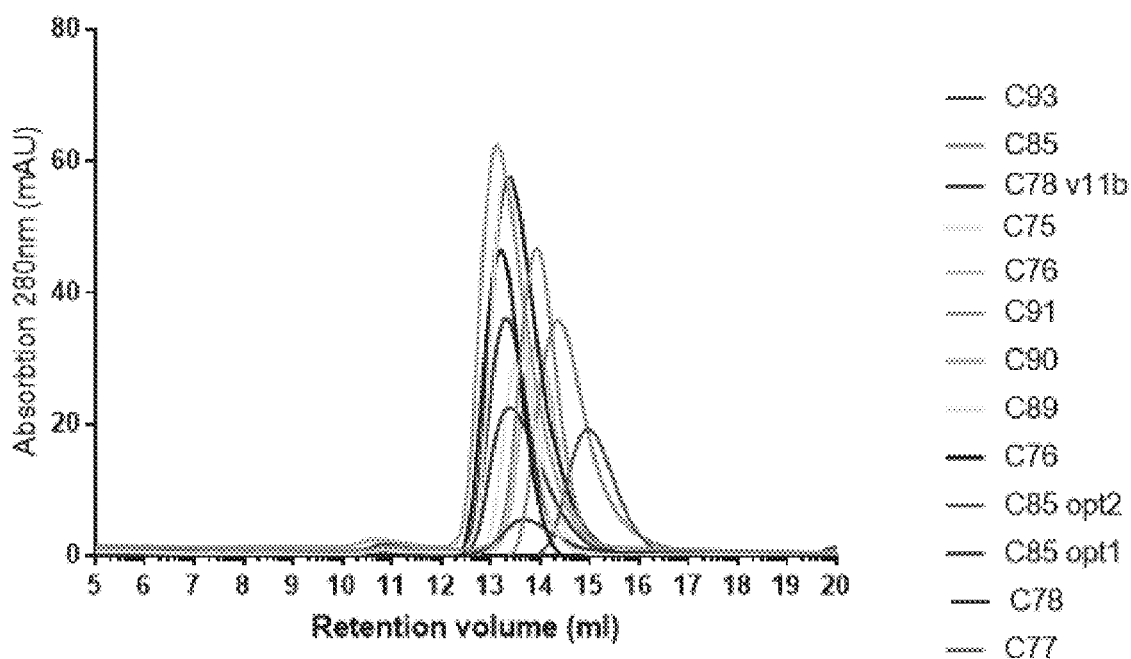
FIGS. 34A and 34B. Graphs showing the results of the analysis of recombinantly-expressed anti-HER3 antibody 10D1 variant clones by size exclusion chromatography. (34A) shows results for anti-HER3 antibody clones 10D1_c93, 10D1_c75, 10D1_c76, 10D1_c77, 10D1_c78, 10D1_11B (referred to as C78 v11b), 10D1_c85, 10D1_c85o1, 10D1_c85o2, 10D1_c89, 10D1_c90, 10D1_c91 and 10D1_c93. (34B) shows the same data as 33A, but for clones 10D1_c89, 10D1_c90, 10D1_c91 and only.
Figure 34B:
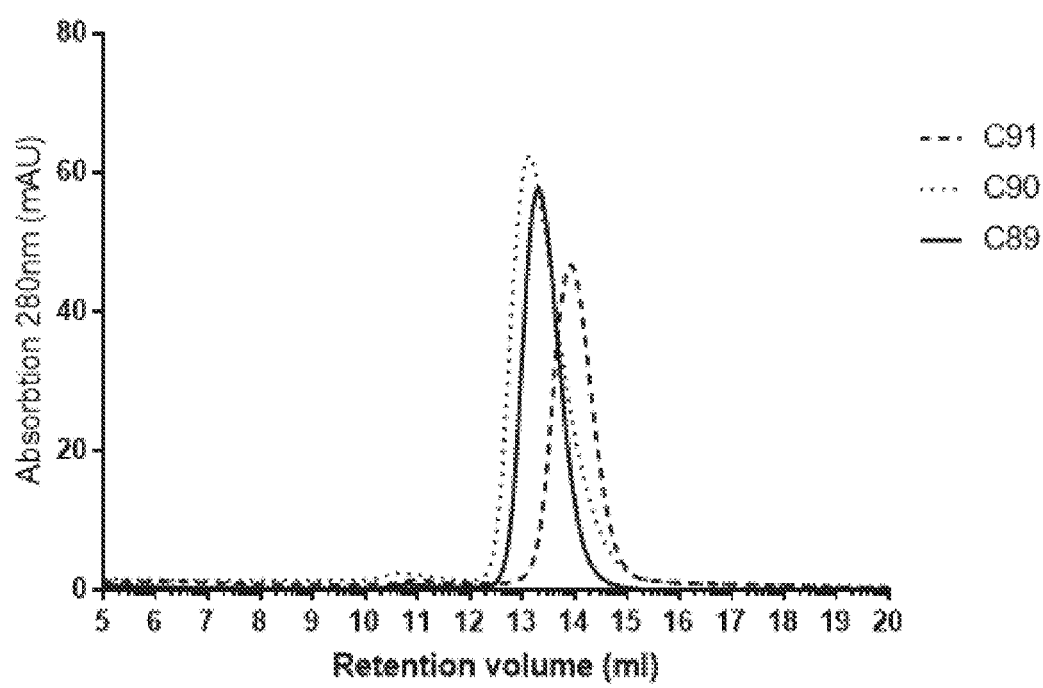

The results obtained for the different 10D1 variant clones are shown in FIG. 34.

Sodium-Dodecyl Sulfate Polyacrylamide Gel Electrophoresis (SDS-PAGE):

Antibody purity was also analysed by SDS-PAGE under reducing and non-reducing conditions according to standard methods. Briefly, 4%-20% TGX protein gels (Bio-Rad, USA) were used to resolve proteins using a Mini-Protean Electrophoresis System (Bio-Rad, USA). For non-reducing condition, protein samples were denatured by mixing with 2× Laemmli sample buffer (Bio-Rad, USA) and boiled at 95° C. for 5-10 min before loading to the gel. For reducing conditions, 2× sample buffer containing 5% of β-mercaptoethanol (βME), or 40 mM DTT (dithiothreitol) was used. Electrophoresis was carded out at a constant voltage of 150V for 1 h in SDS running buffer (25 mM Tris, 192 mM glycine, 1% SDS, pH 8.3).

Western Blot:

Protein samples (30 μg) were fractionated by SDS-PAGE as described above and transferred to nitrocellulose membranes. Membranes were then blocked and immunoblotted with antibodies overnight at 4° C. After washing three times in PBS-Tween the membranes were then incubated for 1 h at room temperature with horseradish peroxidase (HRP)-conjugated secondary antibodies. The results were visualized via a chemiluminescent Pierce ECL Substrate Western blot detection system (Thermo Scientific, USA) and exposure to autoradiography film (Kodak XAR film).

The primary antibodies used for detection were goat anti-human IgG-HRP (GenScript Cat No. A00166) and goat anti-human kappa-HRP (SouterhnBiotech Cat No. 2060-05).

Figure 13:
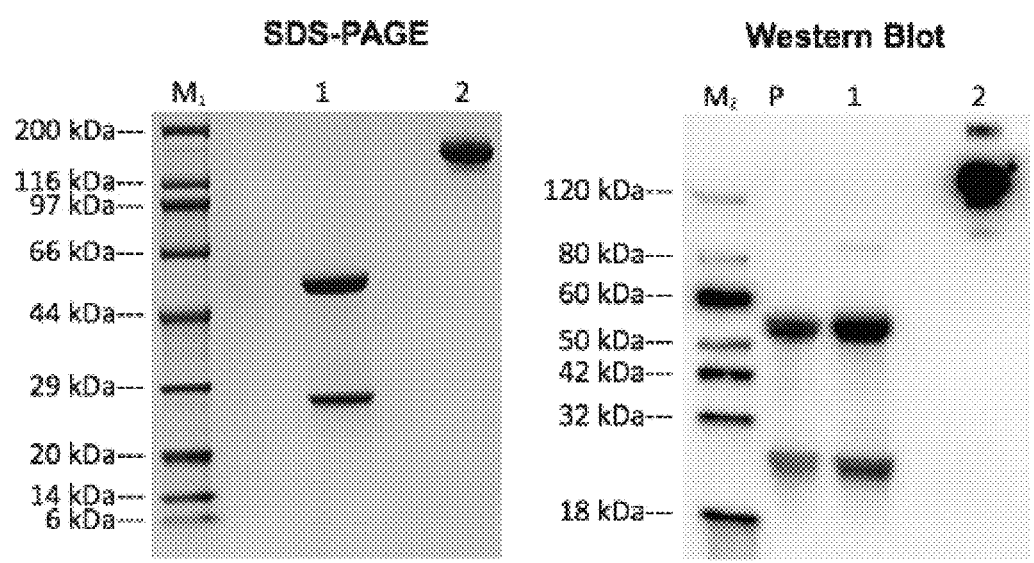
FIG. 13. Images showing the results of the analysis of anti-HER3 antibody clone 10D1 expression by SDS-PAGE and western blot. Lanes: M1=TaKaRa protein marker Cat. No. 3452; M2=GenScript protein marker Cat. No. M00521; 1=reducing conditions; 2=non-reducing conditions; P=positive control: human IgG1, Kappa (Sigma Cat. No. I5154). For western blot, the primary antibodies used were goat anti-human IgG-HRP (GenScript Cat No. A00166) and goat anti-human kappa-HRP (SouterhnBiotech Cat No. 2060-05).

The result for anti-HER3 antibody clone 10D1 ([1] of Example 2.2) is shown in FIG. 13. 10D1 was easily expressed, purified and processed at high concentrations.

Example 3

Biophysical Characterisation 3. 1 Analysis of Cell Surface Antigen-Binding by Flow Cytometry Wildtype HEK293 cells (which do not express high levels of HER3) and HEK293 cells transfected with vector encoding human HER3 (i.e. HEK 293 HER O/E cells) were incubated with 20 μg/ml of anti-HER3 antibody or isotype control antibody at 4° C. for 1.5 hr. The anti-HER3 antibody clone LJM716 (described e.g. in Garner et al., Cancer Res (2013) 73: 6024-6035) was included in the analysis as a positive control.

The cells were washed thrice with FACS buffer (PBS with 5 mM EDTA and 0.5% BSA) and resuspended in FITC-conjugated anti-FC antibody (Invitrogen, USA) for 40 min at 2-8° C. Cells were washed again and resuspended in 200 μL of FACS flow buffer (PBS with 5 mM EDTA) for flow cytometric analysis using MACSQuant 10 (Miltenyi Biotec, Germany). After acquisition, all raw data were analyzed using Flowlogic software. Cells were gated using forward and side scatter profile percentage of positive cells was determined for native and overexpressing cell populations.

The results are shown in FIGS. 1 to 4 and 30 to 32. The anti-HER3 antibodies were shown to bind to human HER3 with high specificity. 10D1 and LJM716 were shown to bind to human HER3-expressing cells to a similar extent.

3.2 ELISAs for Determining Antibody Specificity and Cross-Reactivity

ELISAs were used to determine the binding specificity of the antibodies. The antibodies were analysed for binding to human HER3 polypeptide, as well as respective mouse, rat and monkey homologues of HER3 (Sino Biological Inc., China). The antibodies were also analysed for their ability to bind to human EGFR and human HER2 (Sino Biological Inc., China).

ELISAs were carded out according to standard protocols. Briefly, 96-well plates (Nunc, Denmark) were coated with 0.1 μg/ml of target polypeptide in phosphate-buffered saline (PBS) for 16 h at 4° C. After blocking for 1 h with 1% BSA in Tris buffer saline (TBS) at room temperature, the anti-HER3 antibody was serially diluted with the highest concentration being 10 µg/ml, and added to the plate. Post 1 h incubation at room temperature, plates were washed three times with TBS containing 0.05% Tween 20 (TBS-T) and were then incubated with a HRP-conjugated anti-His antibody (Life Technologies, Inc., USA) for 1 h at room temperature. After washing, plates were developed with colorimetric detection substrate 3,3',5,5'-tetramethylbenzidine (Turbo-TMB; Pierce, USA) for 10 min. The reaction was stopped with 2M $H_2SO_4$, and OD was measured at 450 nM.

The results of the ELISAs are shown in FIGS. 5 to 7 and FIG. 33.

Figure 5A:
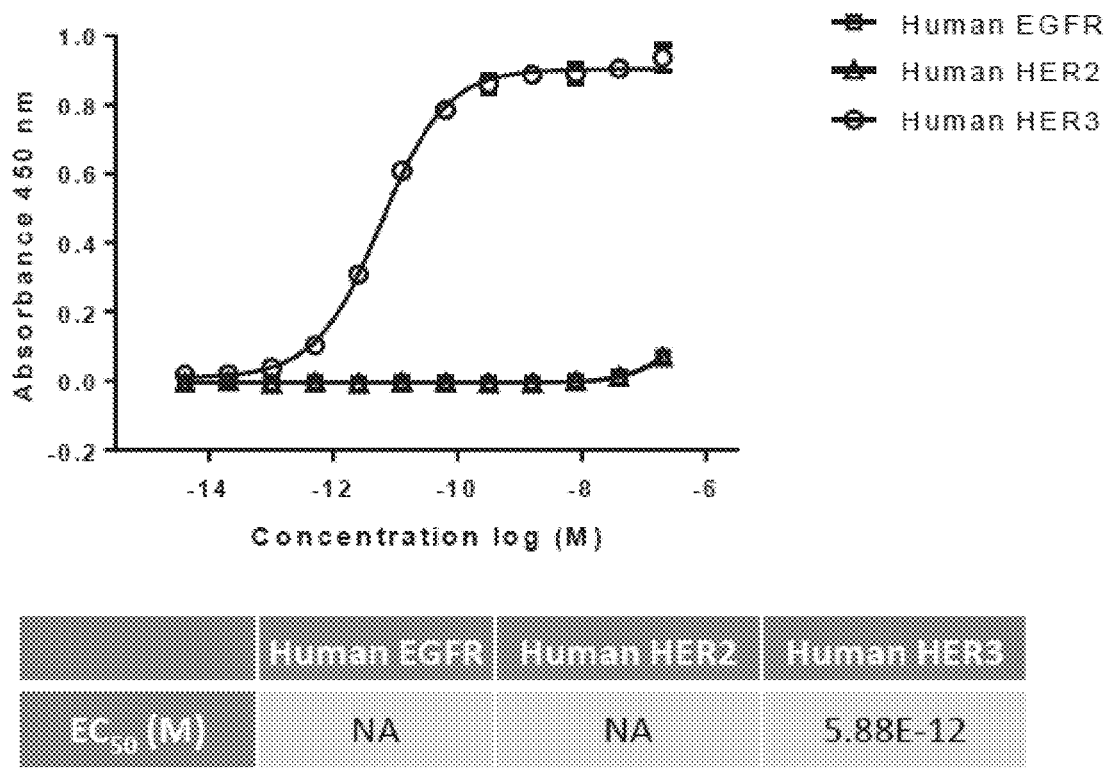
FIGS. 5A and 5B. Graphs showing the results of ELISA analysis of binding of anti-HER3 antibody clone 10D1 to (5A) human, mouse, rat and cynomolgus macaque HER3, and (5B) human EGFR and human HER2. $EC_{50}$ values are shown.
Figure 5B:
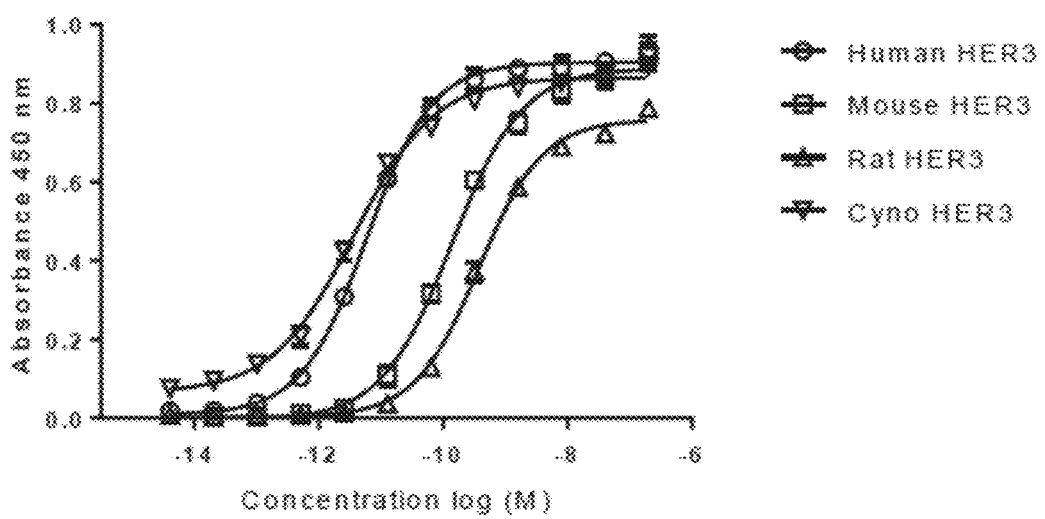

Anti-HER3 antibody clone 10D1 was found not to bind to human HER2 or human EGFR even at high concentrations of the antibody (FIG. 5A). Anti-HER3 antibody clone 10D1 was also found to display substantial cross-reactivity with mouse HER3, rat HER3 and cynomolgus macaque HER3 (FIG. 5B).

Figure 6A:
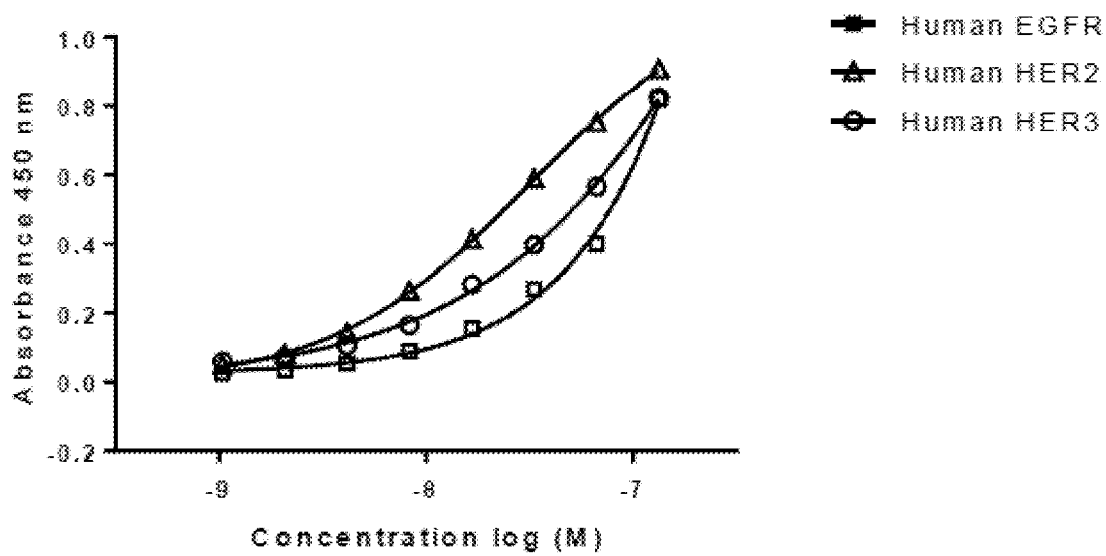
FIGS. 6A and 6B. Graphs showing the results of ELISA analysis of binding of anti-HER3 antibody clone 4-35-B2 to (6A) human, mouse, rat and cynomolgus macaque HER3, and (6B) human EGFR and human HER2.
Figure 6B:
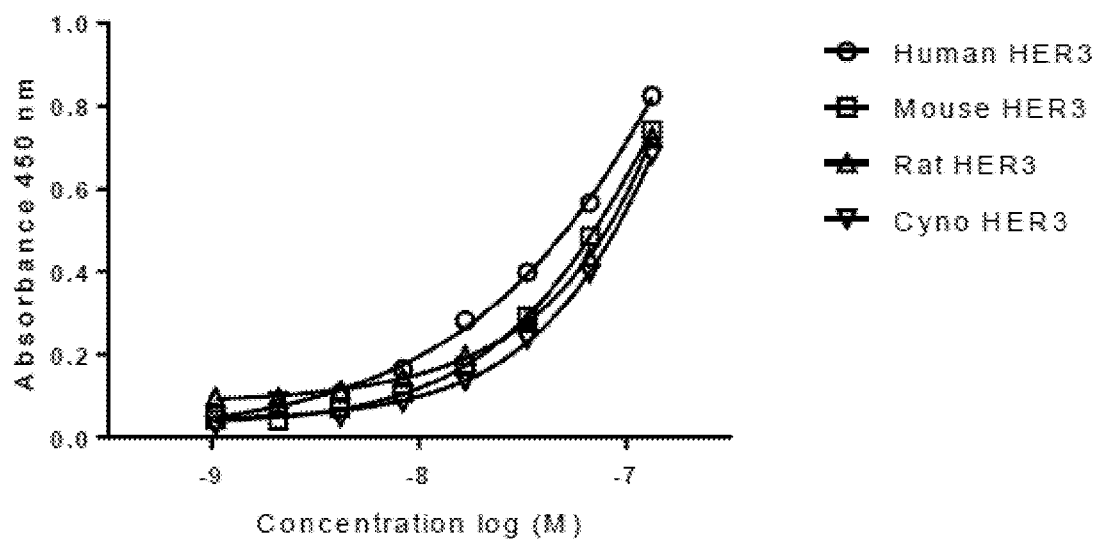

Anti-HER3 antibody clone 4-35-B2 was found to bind to human HER2 and human EGFR (FIG. 6A). Anti-HER3 antibody clone 4-35-B2 also displayed substantial cross-reactivity with mouse HER3, rat HER3 and cynomolgus macaque HER3 (FIG. 6B).

Figure 7A:
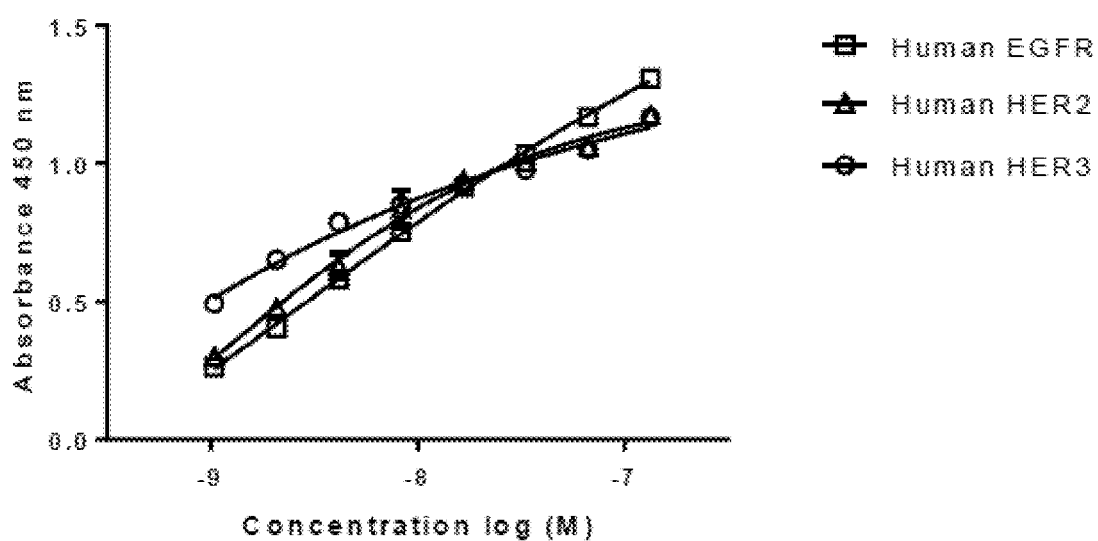
FIGS. 7A and 7B. Graphs showing the results of ELISA analysis of binding of anti-HER3 antibody cone 4-35-B4 to (7A) human HER3, human EGFR and human HER2, and (7B) human, mouse, rat and cynomolgus macaque HER3.
Figure 7B:
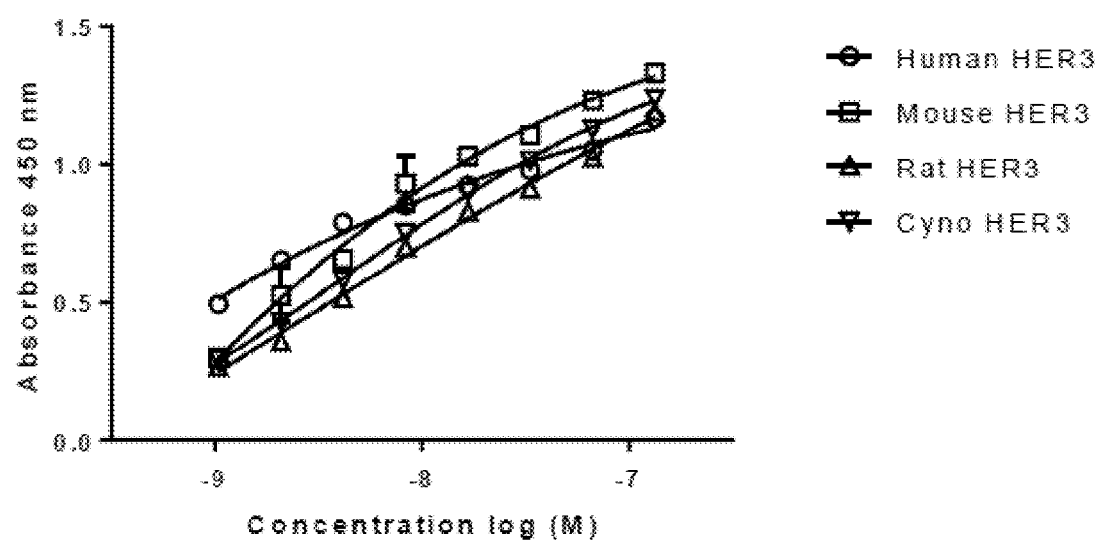

Anti-HER3 antibody clone 4-35-B4 was found to bind to human HER2 and human EGFR (FIG. 7A). Anti-HER3 antibody clone 4-35-B4 also displayed substantial cross-reactivity with mouse HER3, rat HER3 and cynomolgus macaque HER3 (FIG. 7B).

Figure 33A:
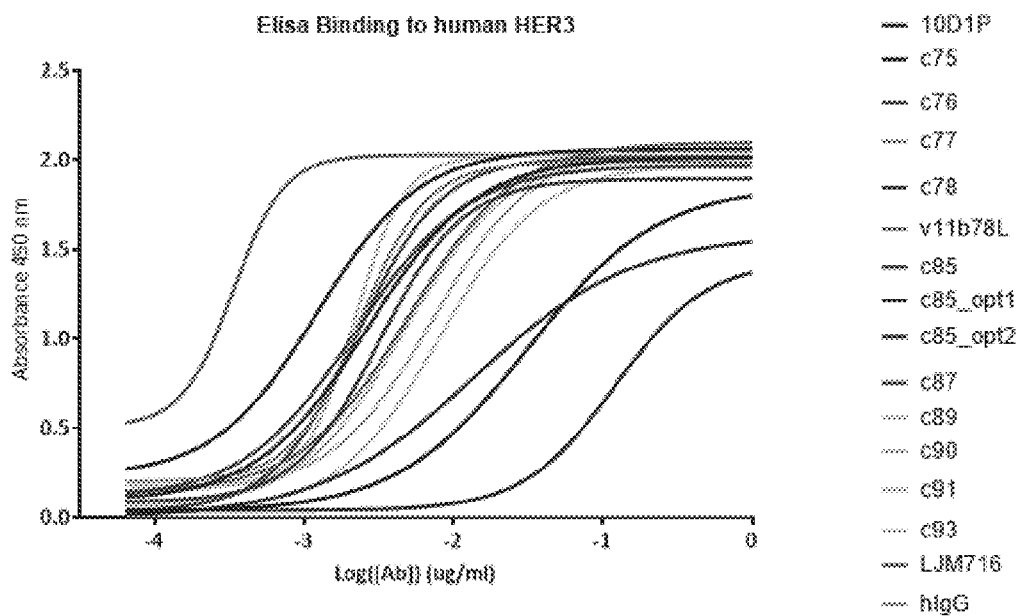
FIGS. 33A and 33B. Graphs showing the results of ELISA analysis of binding of anti-HER3 antibody 10D1 variant clones to human HER3. (33A) shows binding of anti-HER3 antibody clones 10D1 (referred to as 10D1P), 10D1_c75, 10D1_c76, 10D1_c77, 10D1_c78, 10D1_11B (referred to as v11b78L), 10D1_c85, 10D1_c85o1, 10D1_c85o2, 10D1_c87, 10D1_c89, 10D1_c90, 10D1_c91, 10D1_c93, LJM716 and hIgG (negative control). (33B) shows the same data as 33A, but for clones 10D1_c89, 10D1_c90, 10D1_c91 and LJM716 only.
Figure 33B:
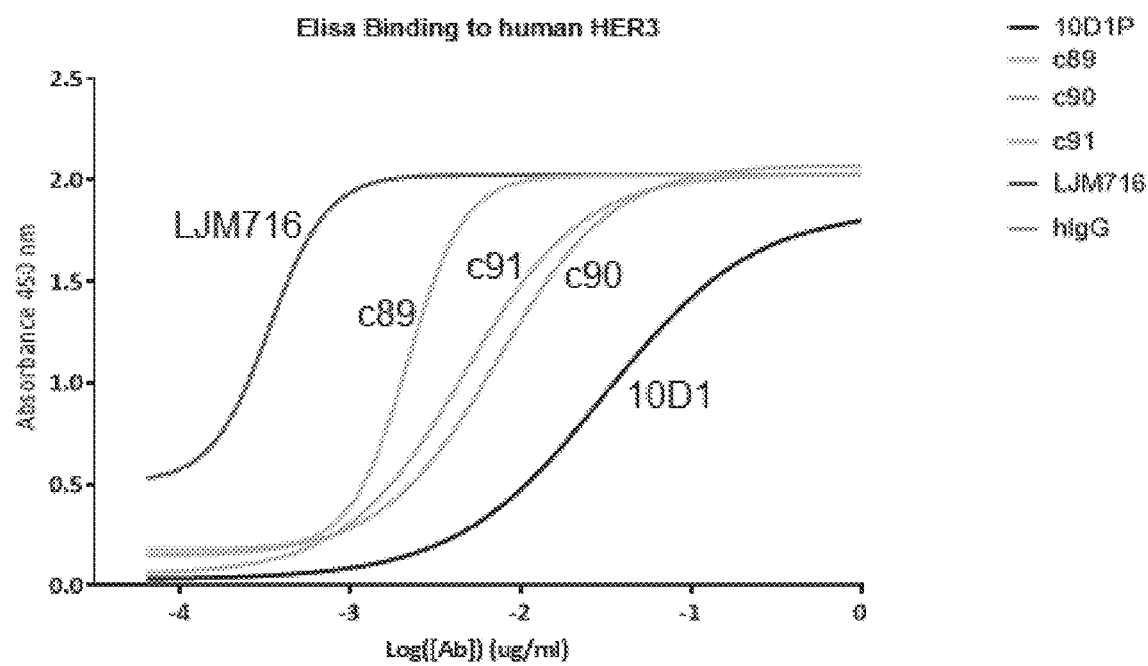

All of the 10D1 variants were demonstrated to bind to human HER3 (FIGS. 33A and 33B).

3.3 Global Affinity Study Using Octet QK384 System

The anti-HER3 antibody clones in IgG1 format were analysed for binding affinity to human HER3.

Bio-Layer Interferometry (BLE) experiments were performed using the Octet QK384 system (ForteBio). anti-Human IgG Capture (AHC) Octet sensor tips (Pall ForteBio, USA) were used to anti-HER3 antibodies (25 nM). All measurements were performed at 25° C. with agitation at 1000 rpm. Kinetic measurements for antigen binding were performed by loading His-tagged human HER3 antigens at different concentrations for 120 s, followed by a 120 s dissociation time by transferring the biosensors into assay buffer containing wells. Sensograms were referenced for buffer effects and then fitted using the Octet QK364 user software (Pall ForteBio, USA). Kinetic responses were subjected to a global fitting using a one site binding model to obtain values for association ($K_{on}$), dissociation ($K_{off}$) rate constants and the equilibrium dissociation constant ($K_D$). Only curves that could be reliably fitted with the software ($R^2 > 0.90$) were included in the analysis.

Figure 8:
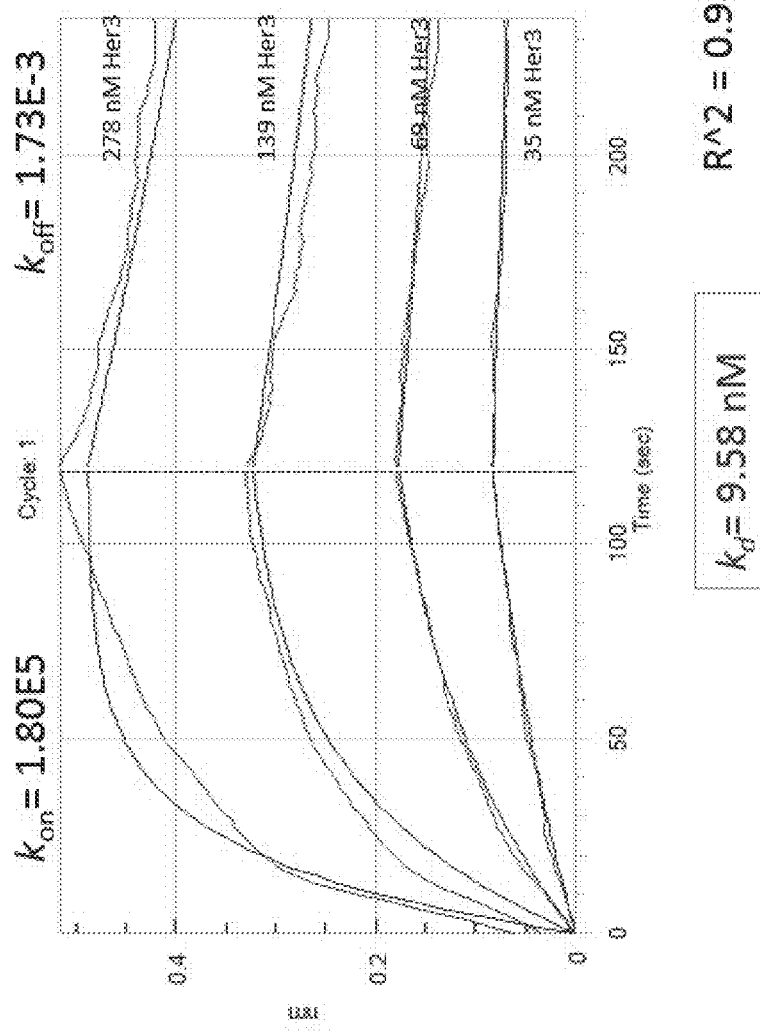
FIG. 8. Representative sensorgram showing the results of analysis of affinity of binding of anti-HER3 antibody clone 10D1 to human HER3. Kon, Koff and $K_D$ are shown.

A representative sensorgram for the analysis of clone 10D1 is shown in FIG. 8. Clone 10D1 was found to bind to human HER3 with an affinity of $K_D$=9.58 nM.

The humanised/optimized 10D1 variants bind to human HER3 with very high affinity. Representative sensorgrams are shown in FIGS. 36A to 36M.

The affinities determined for 10D1 clone variants are shown below:

| Antibody clone | Affinity ($K_D$) |
| --- | --- |
| 10D1_c89 | 72.6 pM |
| 10D1_c90 | <1 pM |
| 10D1_c91 | 176 pM |
| 10D1_11B | 0.41 nM |
| 10D1_c85o | 17.3 nM |

-continued

| Antibody clone | Affinity ($K_D$) |
| --- | --- |
| 10D1_c87 | <1 pM |
| 10D1_c93 | <1 pM |
| 10D1_c76 | <1 pM |
| 10D1_c77 | 1.93 nM |
| 10D1_c78 | <1 pM |
| 10D1_c75 | <1 pM |
| 10D1_c85 | 7.58 nM |
| 10D1_c85o1 | 18.2 nM |

Figure 9:
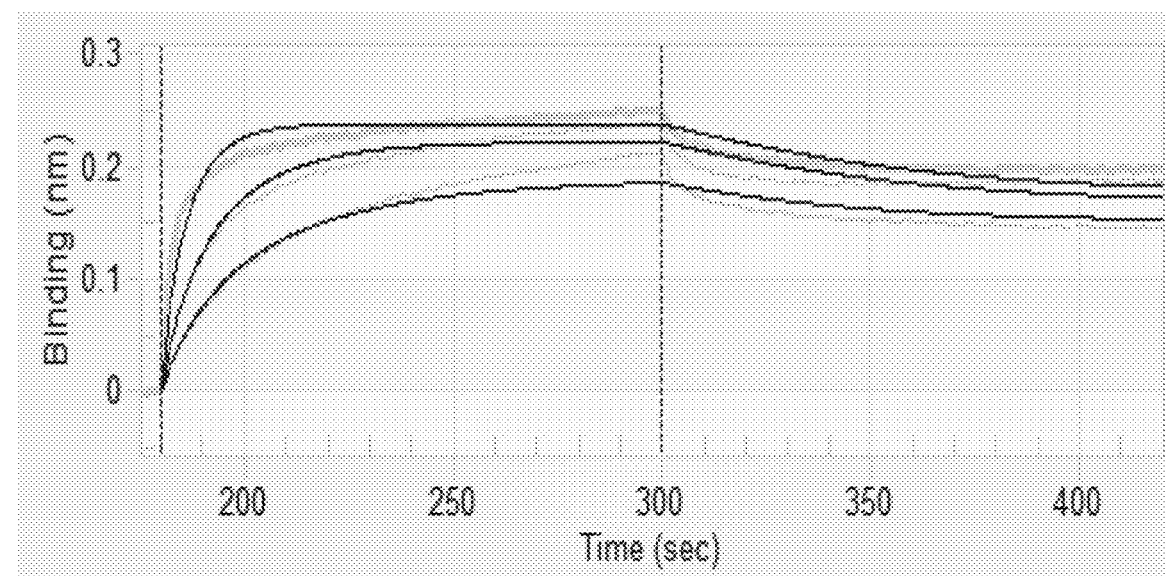
FIG. 9. Representative sensorgram showing the results of analysis of affinity of binding of anti-HER3 antibody clone 4-35-B2 to human HER3.
Figure 10:
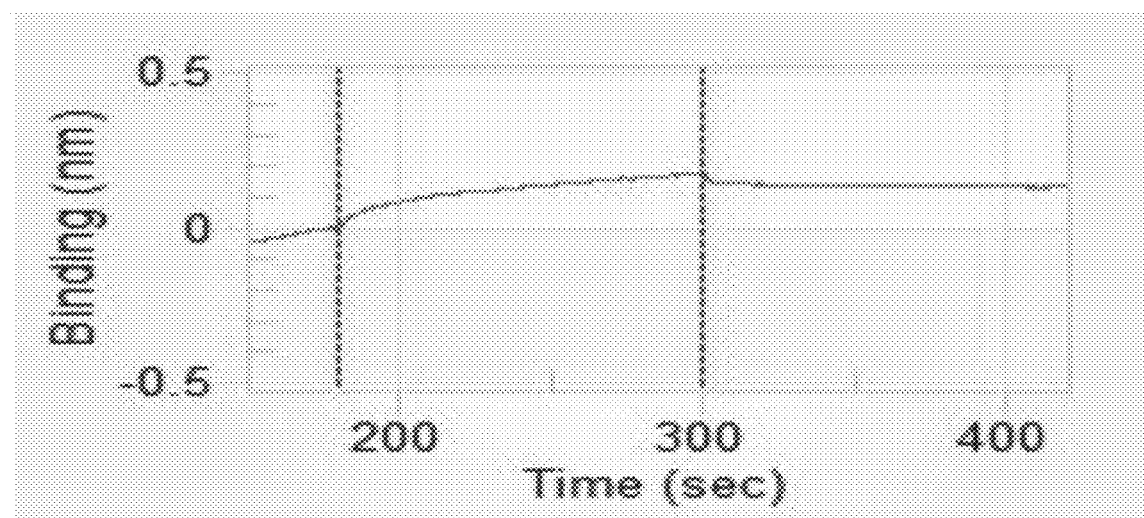
FIG. 10. Representative sensorgram showing the results of analysis of affinity of binding of anti-HER3 antibody clone 4-35-B4 to human HER3.

Clone 4-35-B2 was found to bind to human HER3 with an affinity of $K_D$=80.9 nM (FIG. 9), and clone 4-35-B4 was found to bind to human HER3 with an affinity of $K_D$=50.3 nM (FIG. 10).

3.4 Analysis of Thermostability by Differential Scanning Fluorimetry

Briefly, triplicate reaction mixes of antibodies at 0.2 mg/mL and SYPRO Orange dye (ThermoFisher) were prepared in 25 µL of PBS, transferred to wells of MicroAmp Optical 96-Well Reaction Plates (ThermoFisher), and sealed with MicroAmp Optical Adhesive Film (ThermoFisher). Melting curves were run in a 7500 fast Real-Time PCR system (Applied Biosystems) selecting TAMRA as reporter and ROX as passive reference. The thermal profile included an initial step of 2 min at 25° C. and a final step of 2 min at 99° C., with a ramp rate of 1.2%. The first derivative of the raw data was plotted as a function of temperature to obtain the derivative melting curves. Melting temperatures (Tm) of the antibodies were extracted from the peaks of the derivative curves.

Figure 11:
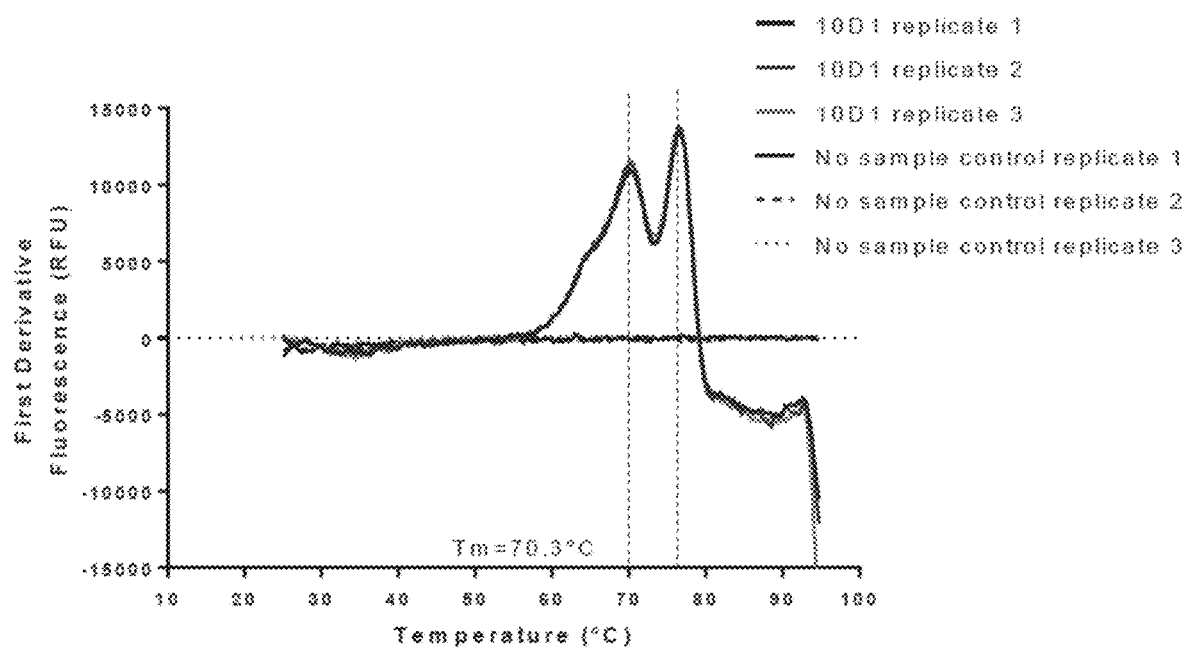
FIG. 11. Graph showing the results of analysis of stability of anti-HER3 antibody clone 10D1 by Differential Scanning Fluorimetry analysis.

The first derivative of the raw data obtained for Differential Scanning Fluorimetry analysis of the thermostability of antibody clone 10D1 is shown in FIG. 11. Three different samples of the antibody were analysed. The Tm was determined to be 70.3° C.

Figure 35A:
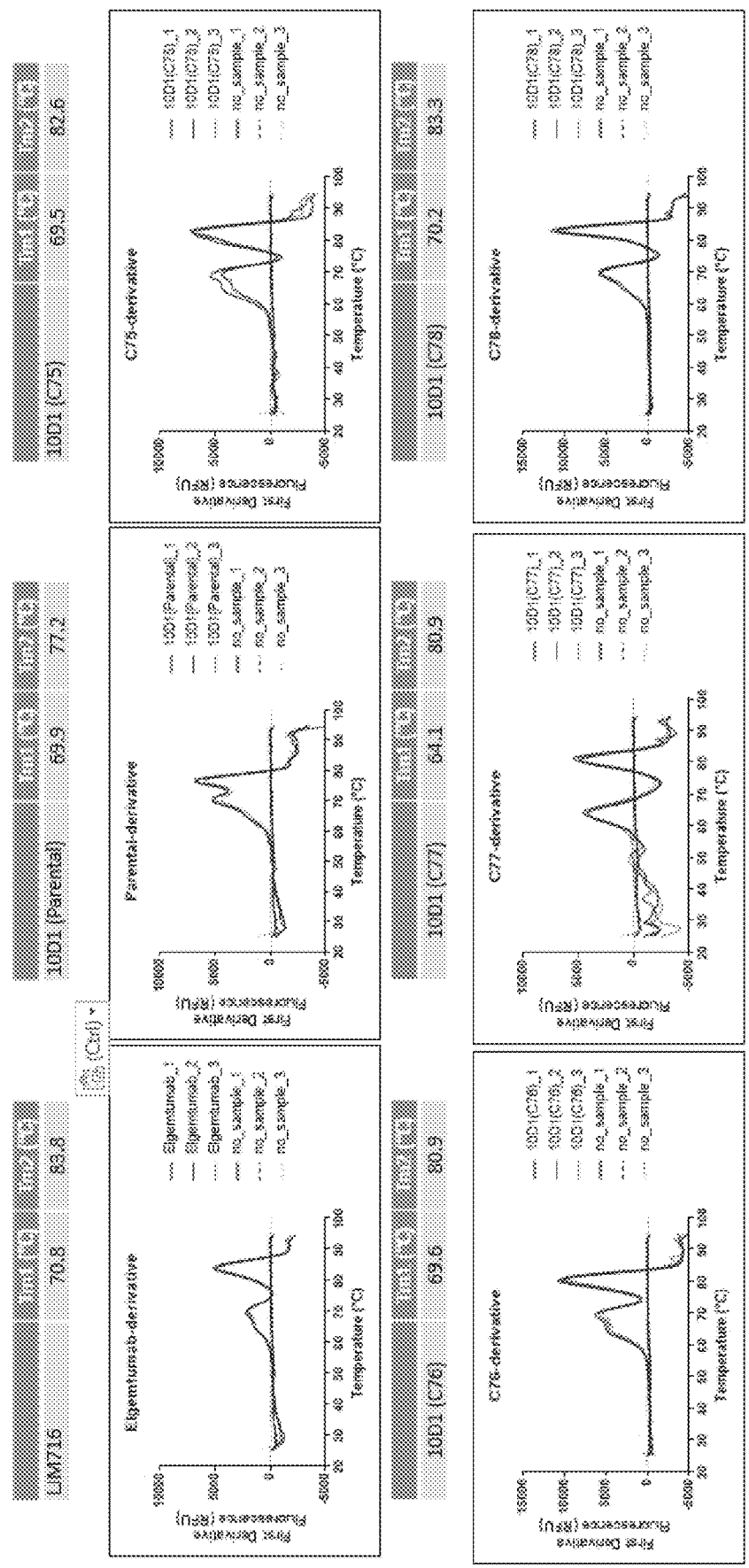
FIGS. 35A to 35C. Graphs showing the results analysis of stability of anti-HER3 antibody 10D1 variant clones by Differential Scanning Fluorimetry analysis. (35A) shows results for anti-HER3 antibody clones LJM716 (also referred to as Elgemtumab), 10D1 (referred to as 10D1 (parental)), 10D1_c75, 10D1_c76, 10D1_c77 and 10D1_c75. (35B) shows results for 10D1_c85o2, 10D1_c87, 10D1_c89, 10D1_11B (referred to as c78_V11B), 10D1_c85 and 10D1_c85o1. (35C) shows results for 10D1_c90, 10D1_c91 and 10D1_c93.
Figure 35B:
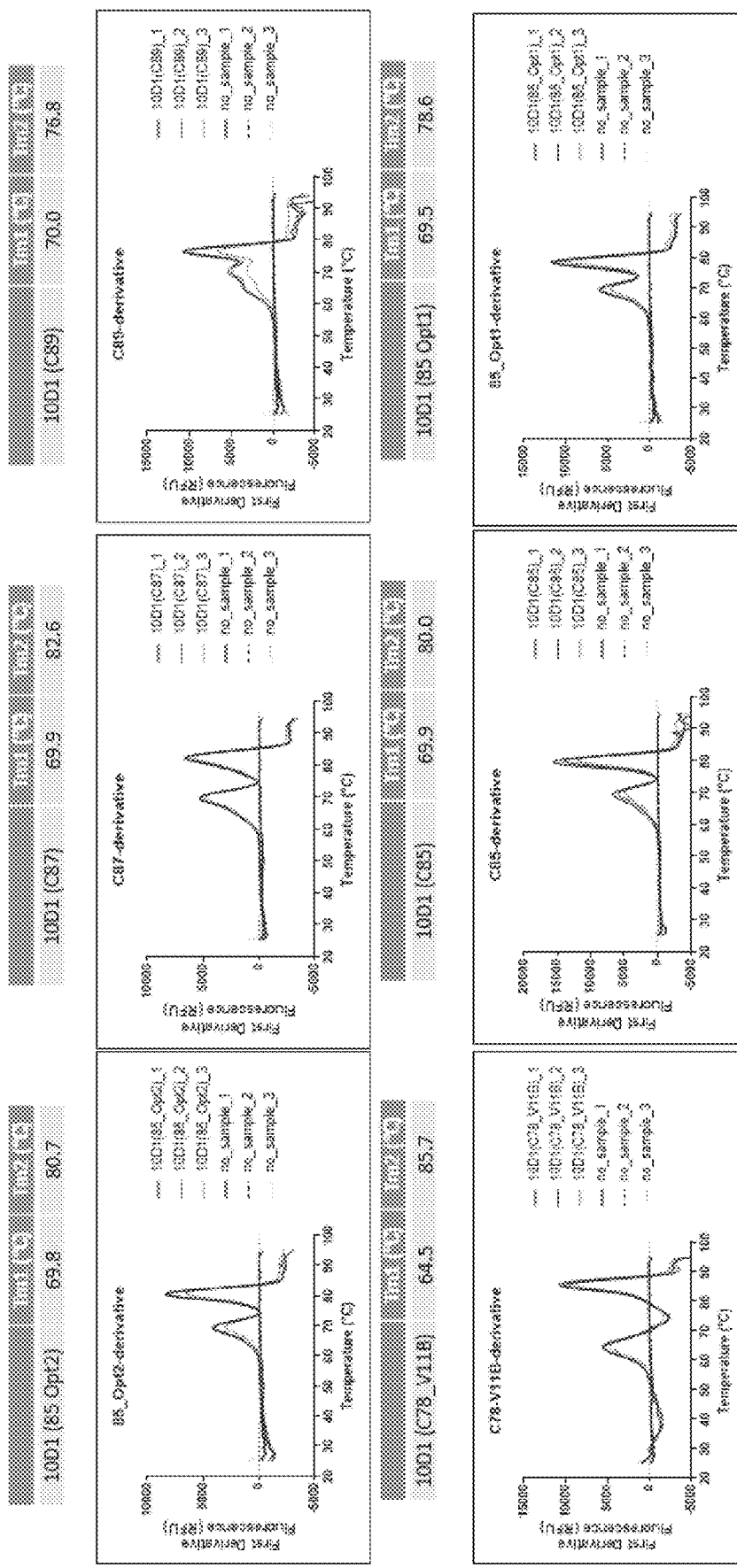
Figure 35C:
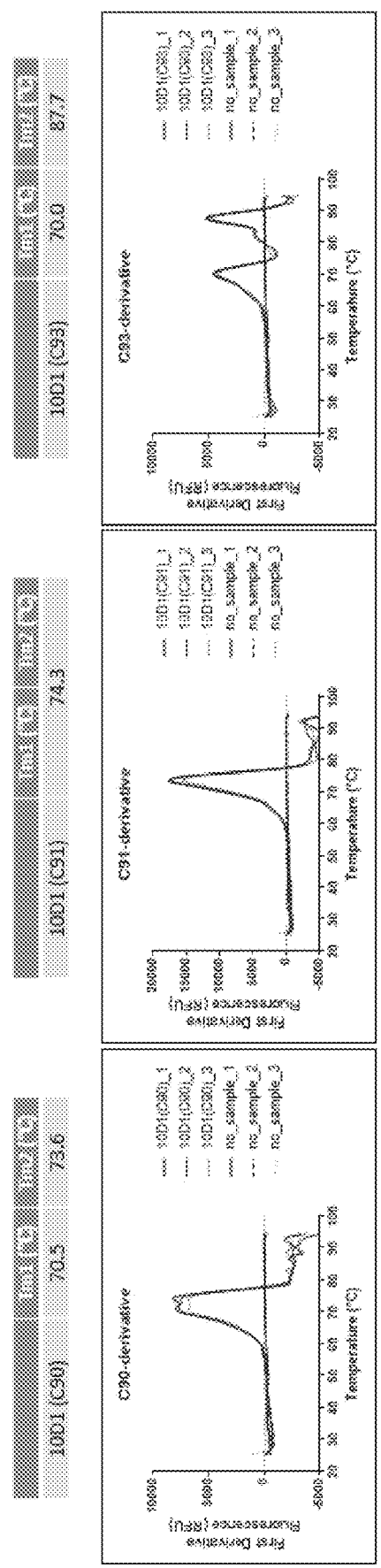
Figure 36A:
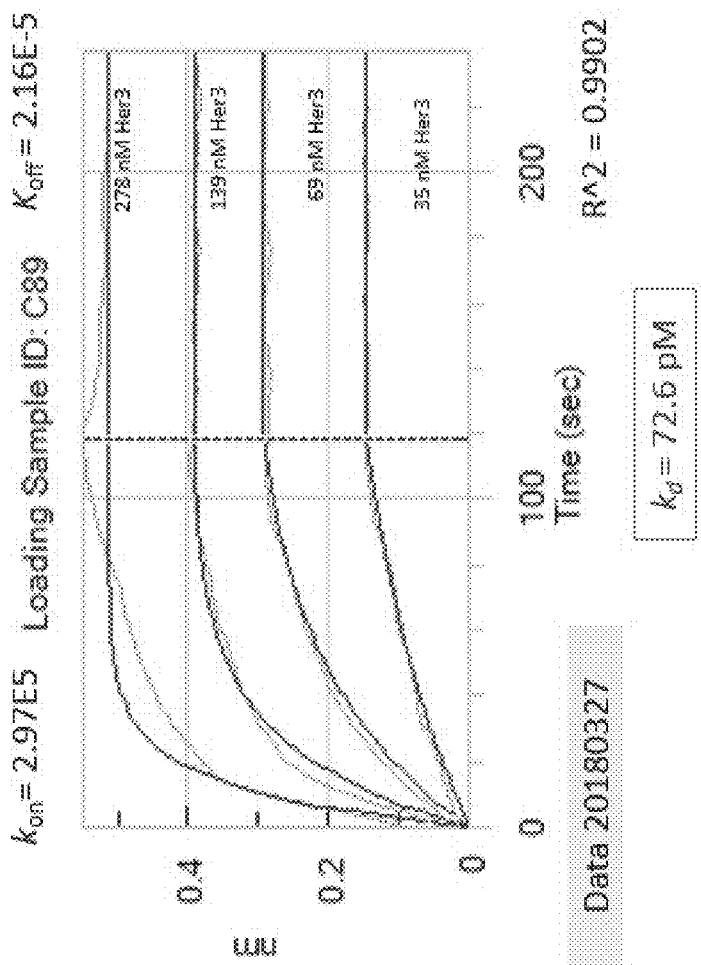
FIGS. 36A to 36M. Representative sensorgrams showing the results of analysis of affinity of anti-HER3 antibody 10D1 variant clones to human HER3. Kon, Koff and $K_D$ are shown. (36A) shows results for clone 10D1_c89, (36B) shows results for clone 10D1_c90, (36C) shows results for clone 10D1_c91, (36D) shows results for clone 10D1_c11B, (36E) shows results for clone 10D1_c85o2, (36F) shows results for clone 10D1_c87, (36G) shows results for clone 10D1_c93, (36H) shows results for clone 10D1_c76, (36I) shows results for clone 10D1_c77, (36J) shows results for clone 10D1_c78, (36K) shows results for clone 10D1_c75, (36L) shows results for clone 10D1_c55, and (36M) shows results for clone 10D1_c85o1.
Figure 36B:
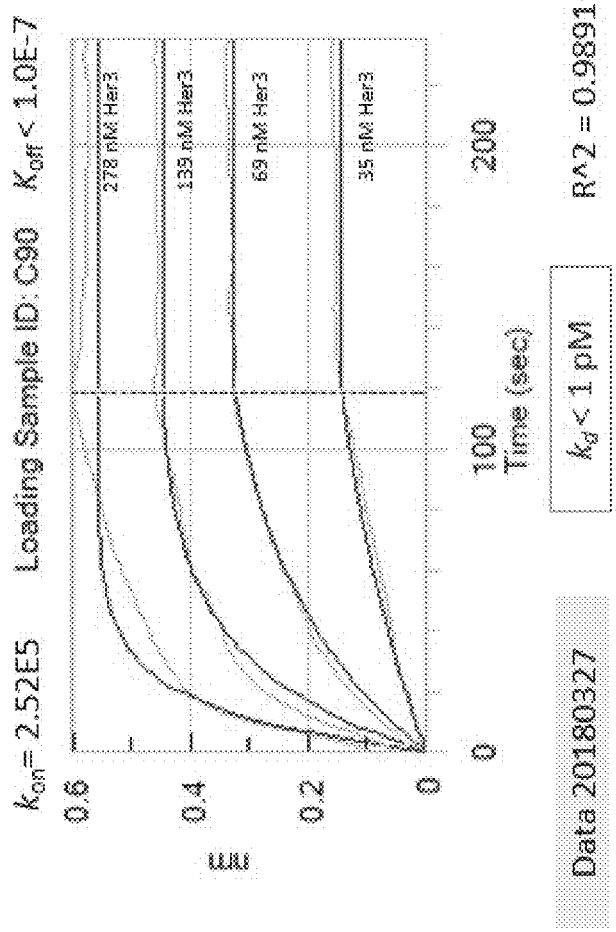
Figure 36C:
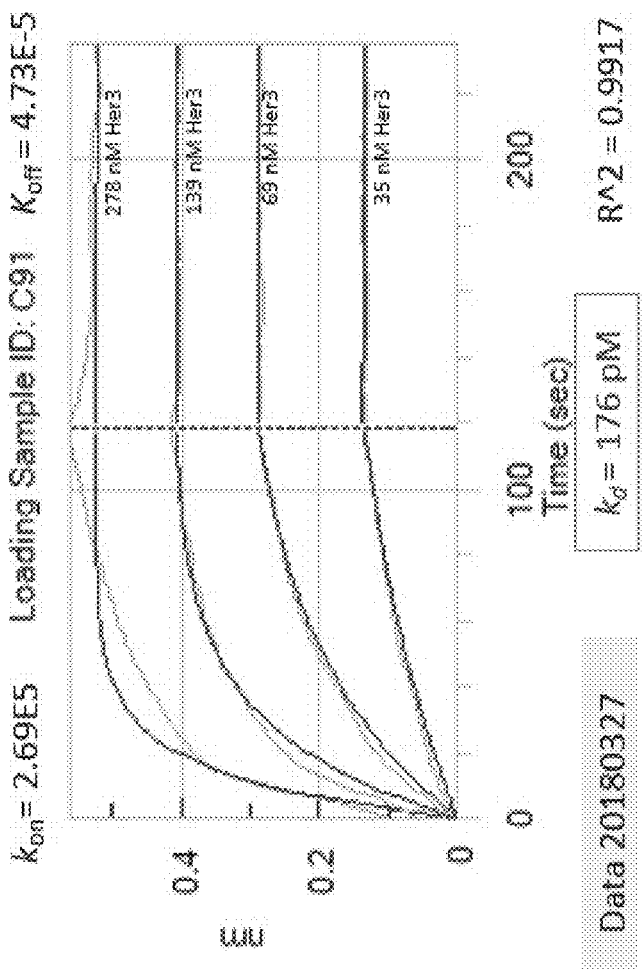
Figure 36D:
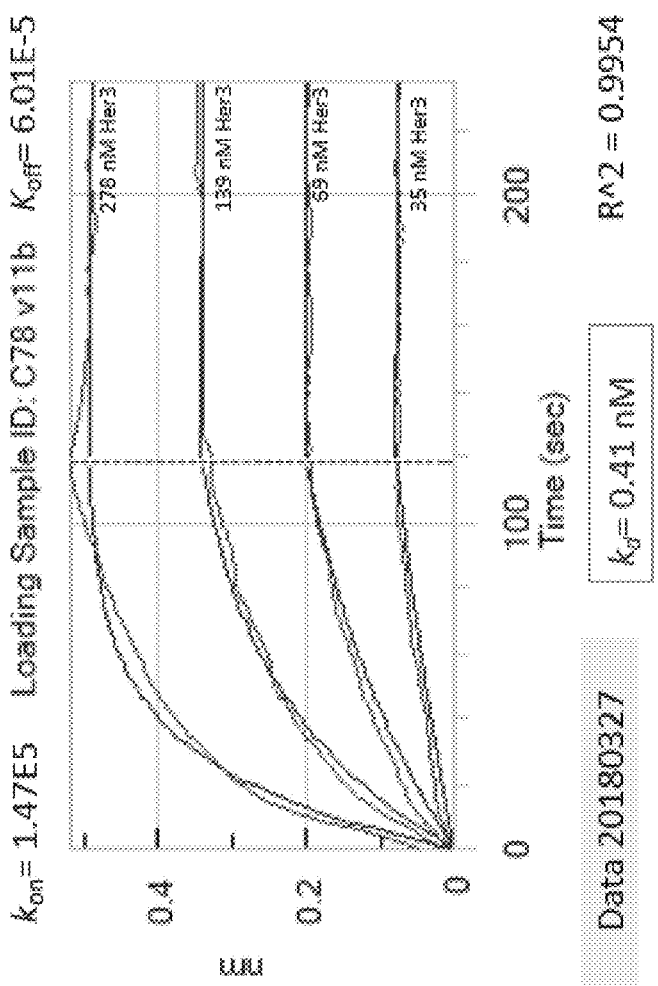
Figure 36E:
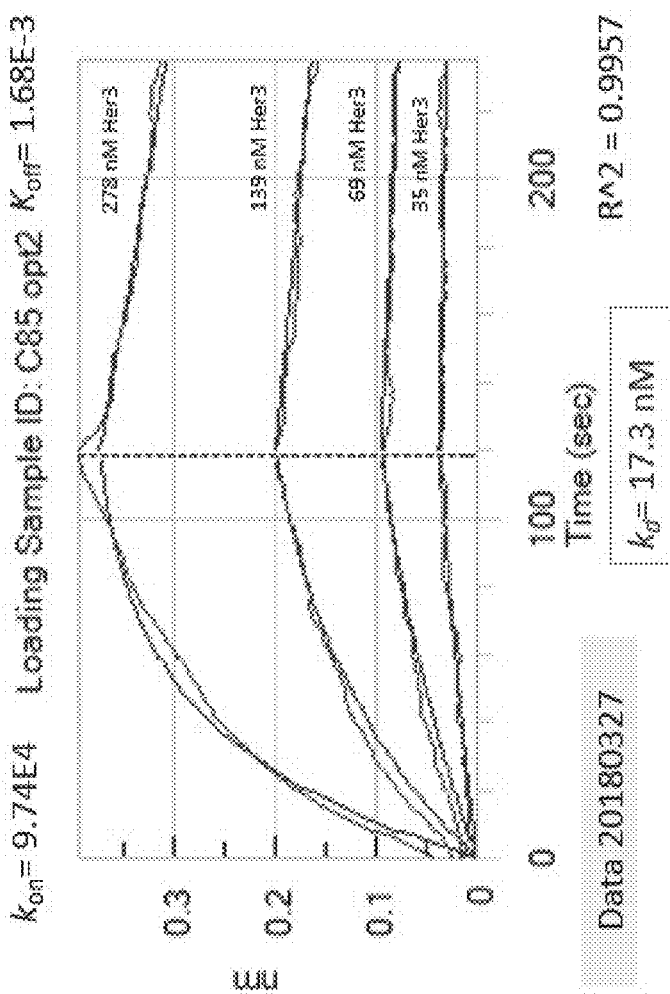
Figure 36F:
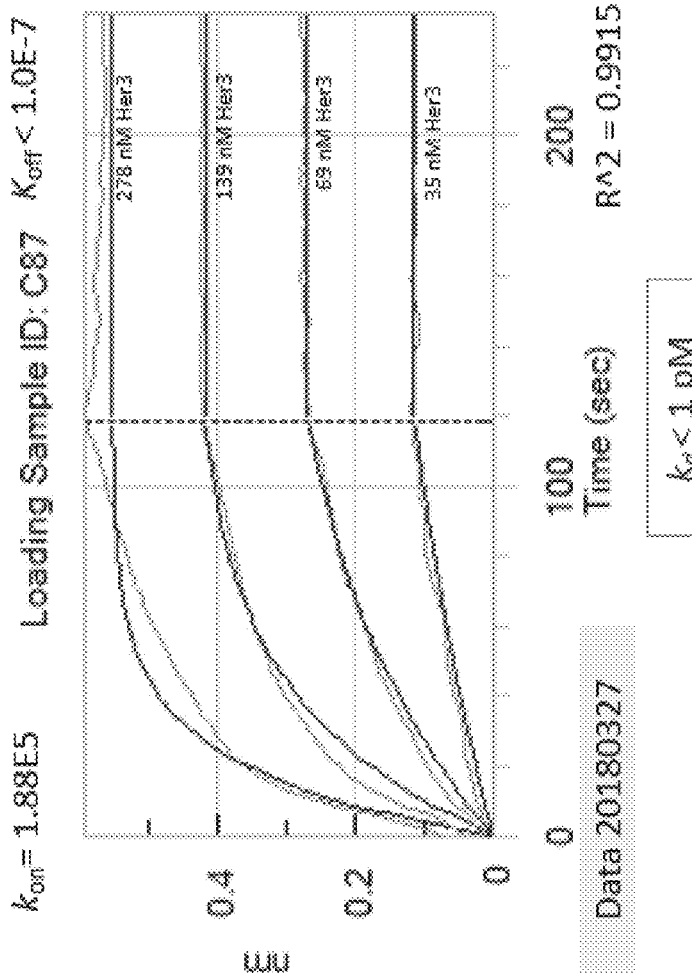
Figure 36G:
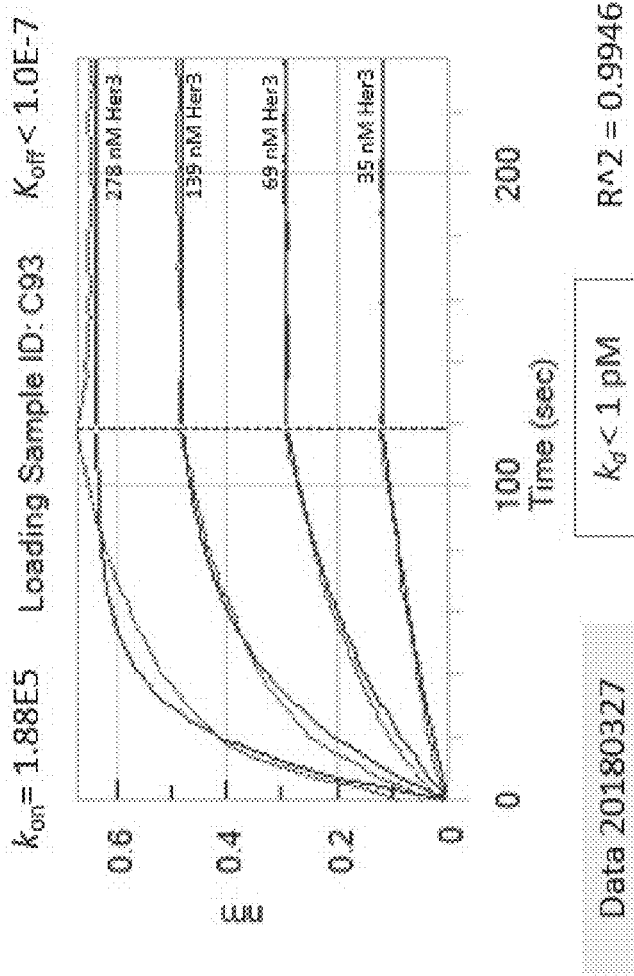
Figure 36H:
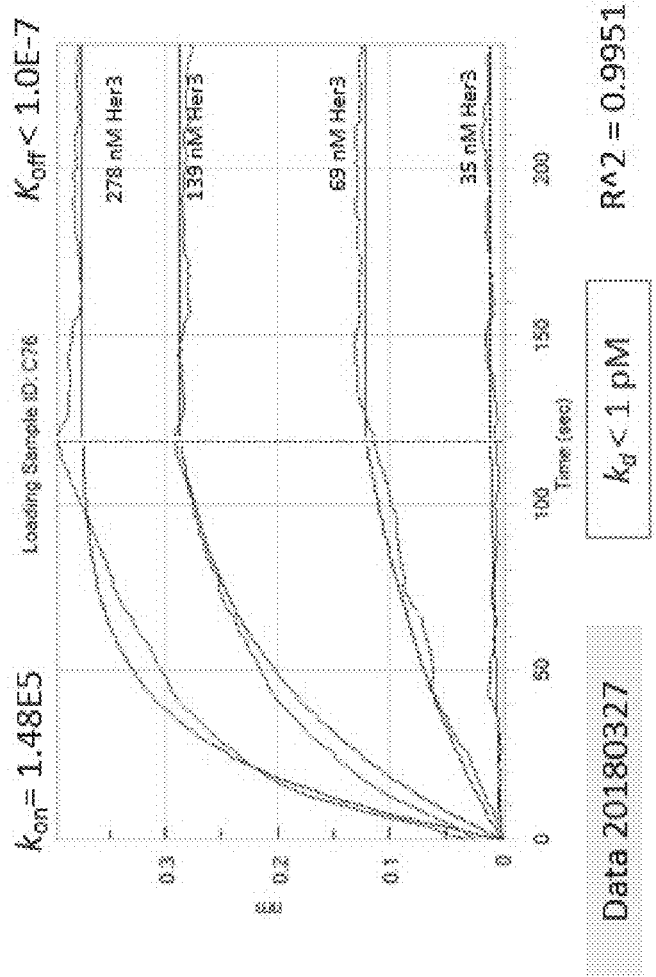
Figure 36I:
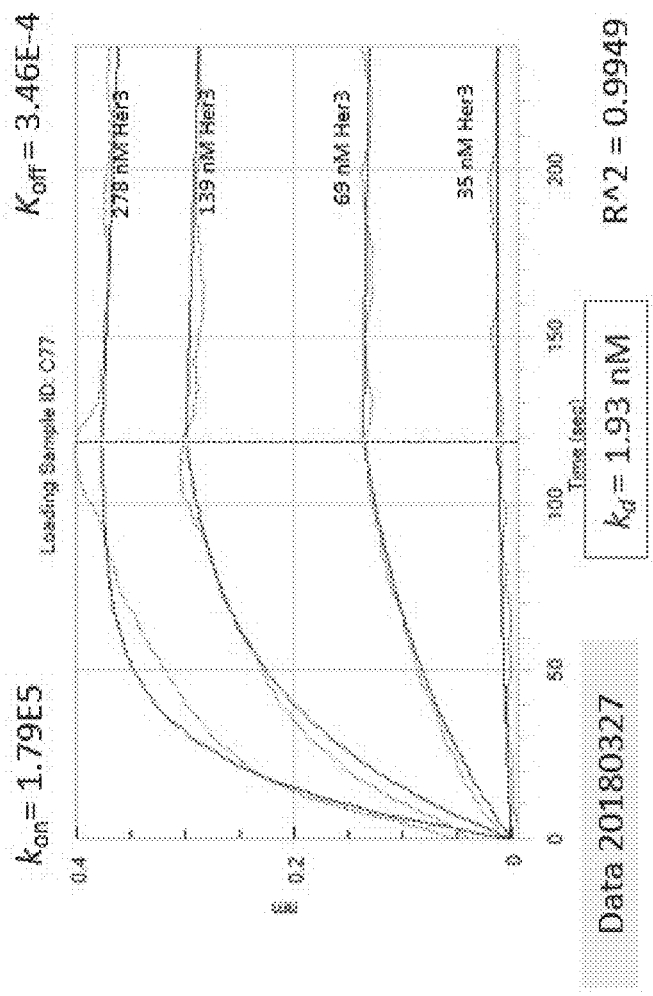
Figure 36J:
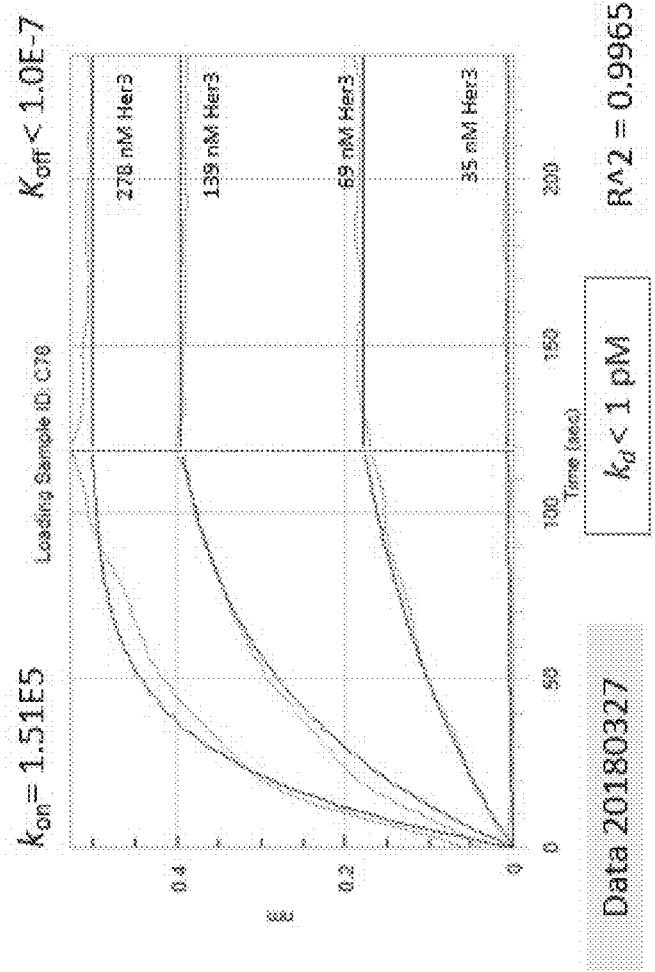
Figure 36K:
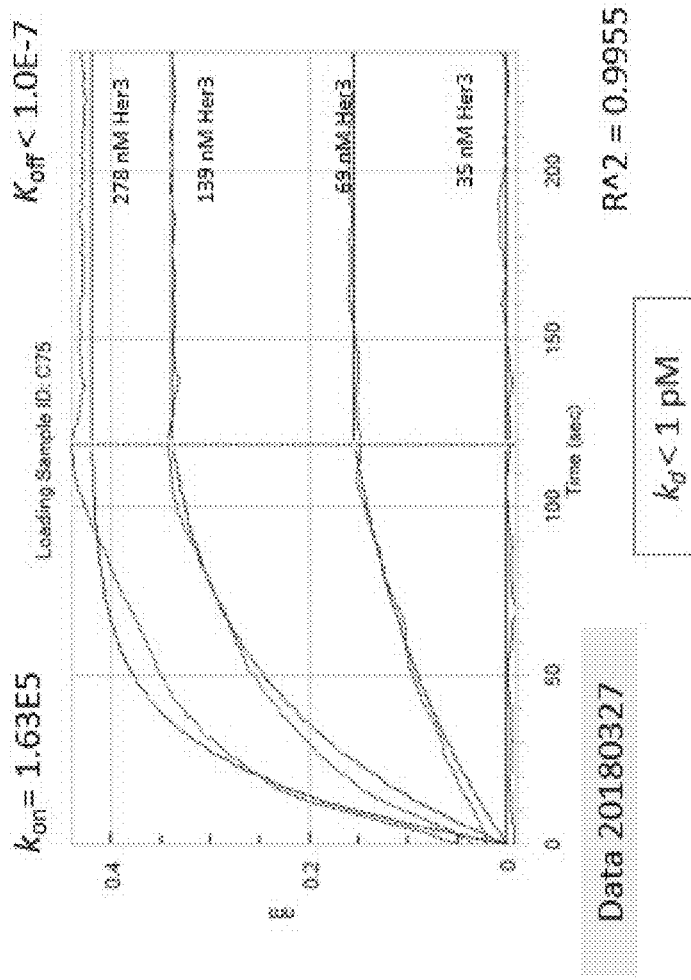
Figure 36L:
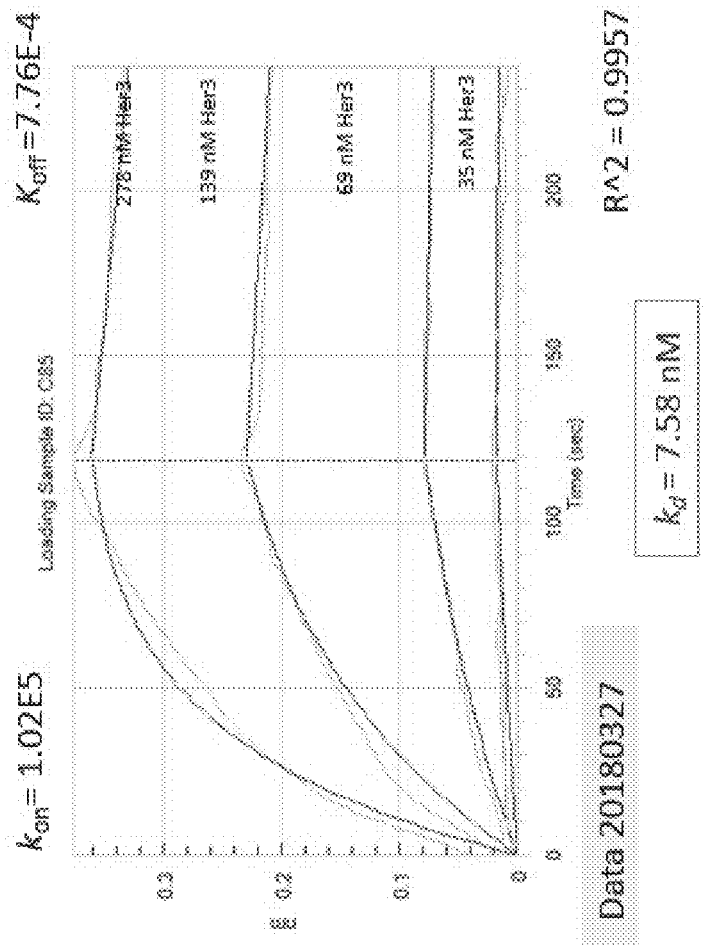
Figure 36M:
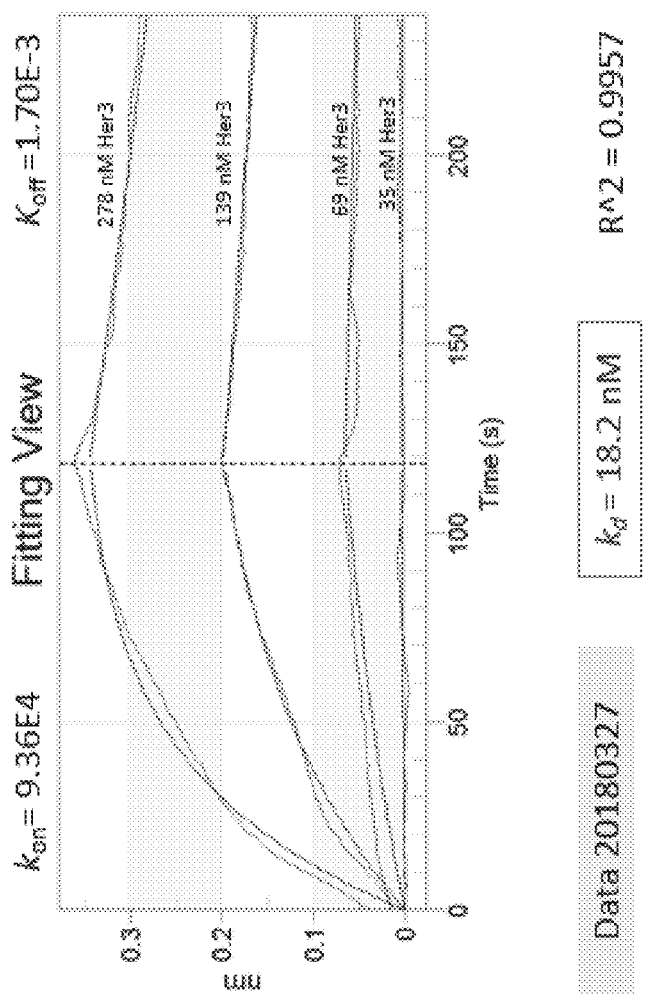

The analysis was also performed for the 10D1 variant clones and LJM716. The first derivative of the raw data and the determined Tms are shown in FIGS. 35A to 35C.

3.5 Analysis of Anti-HER3 Antibody 10D1 Epitope

Anti-HER3 antibody 10D1 was analysed to determine whether it competes with anti-HER3 antibodies MM-121 and/or LJM-716 for binding to HER3. The epitope for MM-121 has been mapped in domain 1 of HER3; it blocks the NRG ligand binding site. The epitope for LJM-716 has been mapped to conformational epitope distributed across domains II and IV, and it locks HER3 in an inactive conformation.

Bio-Layer Interferometry (BLI) experiments were performed using the Octet QK384 system (ForteBio). anti-Penta-HIS (HIS1K) coated biosensor tips (ForteBio, USA) were used to capture His-tagged human HER3 (75 nM; 300 s). Binding by saturating antibody (400 nm; 600 s) was detected, followed by a dissociation step (120 s), followed by detection of binding with competing antibody (300 nM; 300 s), followed by a dissociation step (120 s). The variable region of MM-121 antibody was cloned in the PDZ vector having human IgG2 and IgKappa Fc backbone. The variable region of LJM-716 antibody was cloned in the PDZ vector having human IgG1 and IgKappa Fc backbone.

Figure 14A:
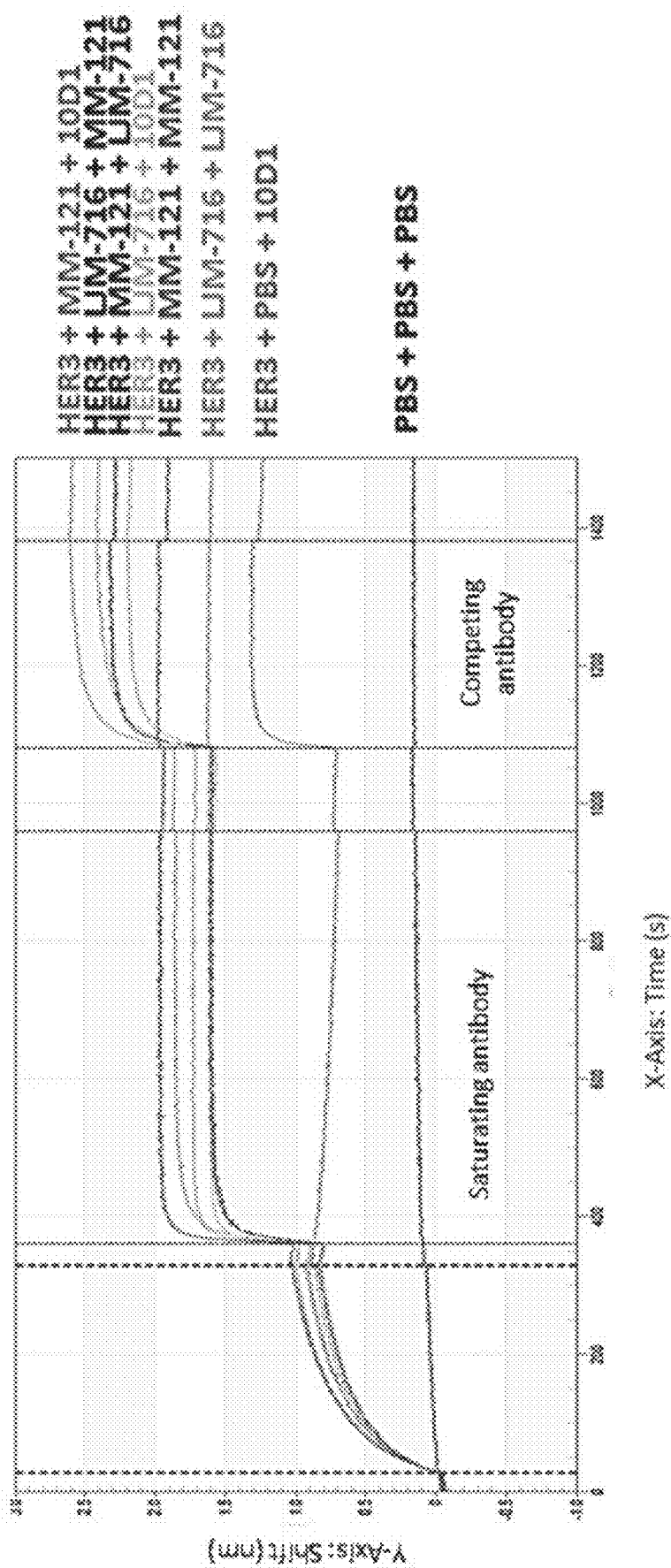
FIGS. 14A and 14B. Representative sensorgram and table showing the results of analysis of competition between different anti-HER3 antibody clones for binding to HER3.
Figures 14B, 15:
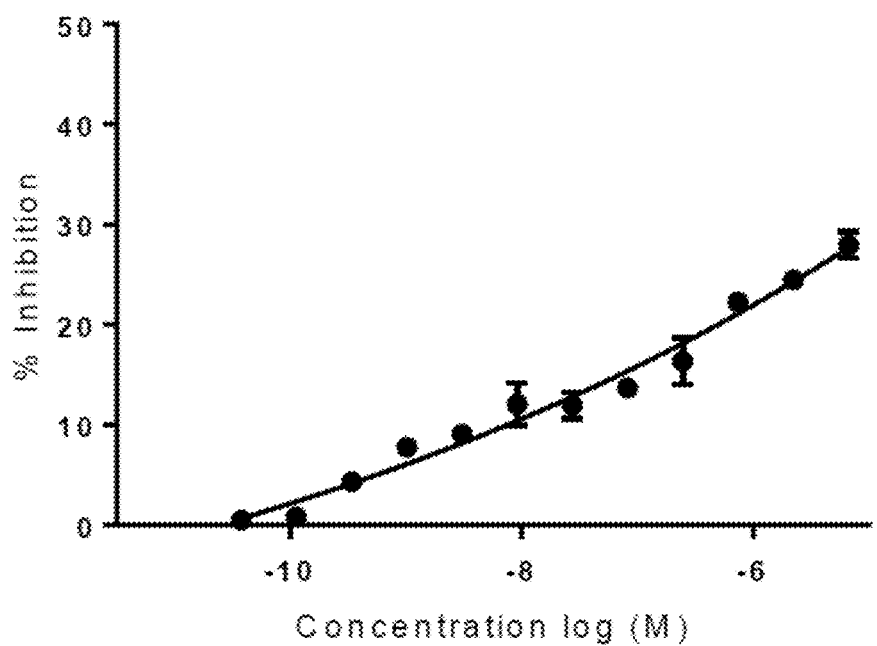
FIG. 15. Graph showing the results of analysis of the inhibition of interaction between HER3 and HER2 by anti-HER3 antibody clone 10D1 as determined by ELISA.

The results of the analysis are shown in FIGS. 14A and 14B. Anti-HER3 antibody was found not to compete with MM-121 and/or LJM-718 for binding to HER3.

10D1 was found to bind a distinct and topologically distant epitope of HER3 than MM-121 and/or LJM-716.

The epitope for 10D1 was mapped using overlapping 15-mer amino acids to cover the entire HER3 extracellular domain. Each unique 15-mer was elongated by a GS linker at C and N-terminals, conjugated to a unique well in 384 well plates, and the plates were incubated with 0.1, 1, 10 and 100 ug/ml of 10D1 antibody for 16 hrs at 4° C. The plates were washed and then incubated for 1 hr at 20° C. with POD-conjugated goat anti-human IgG. Finally POD substrate solution was added to the wells for 20 min. before binding was assessed by measurement of chemiluminescence at 425 nm using a LI-COR Odyssey Imaging System, and quantification and analysis was performed using the PepSlide Analyzer software package. The experiment was performed in duplicate.

The 10D1 epitope was found not to be directly located at a β-hairpin structure of the HER3 dimerisation arm located at domain II, but instead at a dimerisation interface N-terminal to the β-hairpin.

The site of HER3 to which 10D1 and 10D1-derived clones was determined to bind corresponds to positions 218 to 235 of the amino acid sequence of human HER3 (as shown e.g. in SEQ ID NO:1); the amino acid sequence for this region of HER3 is shown in SEQ ID NO:229. Within this region, two consensus binding site motifs were identified, and are shown in SEQ ID NOs:230 and 231.

Binding to this location of HER3 acts to impede HER family heterodimerisation and consequent downstream signalling pathways (see Example 4). Binding is ligand (NRG) independent. The 10D1 binding site is solvent accessible in both the open and closed HER3 conformations, is not conserved between HER3 and other HER family members, and is 100% conserved between human, mouse, rat and monkey HER3 orthologs.

Example 4

Functional Characterisation 4.1 Inhibition of Dimerisation of HER2 and HER3

The anti-HER3 antibodies were analysed for their ability to inhibit heterodimerisation of HER3 and HER2.

Briefly, 96-well plates (Nunc, Denmark) were coated with 0.1 μg/ml His-tagged HER2 protein in PBS for 16 h at 4° C. After blocking for 1 h with 1% BSA in PBS at room temperature, recombinant biotinylated human HER3 protein was added in the presence of different concentrations of anti-HER3 antibody clone 10D1, and plates were incubated for 1 h at room temperature. Plates were subsequently washed three times, and then incubated with HRP-conjugated secondary antibody for 1 h at room temperature. After washing, plates were developed with colorimetric detection substrate 3,3',5,5'-tetramethylbenzidine (Turbo-TMB; Pierce, USA) for 10 min. The reaction was stopped with 2M $H_2SO_4$, and OD was measured at 450 nM.

The results are shown in FIG. 15. Anti-HER3 antibody clone 10D1 was found to inhibit interaction between HER2 and HER3 in a dose-dependent fashion.

In further experiments, inhibition of HER2:HER3 dimerisation was analysed

In further experiments, inhibition of HER2:HER3 dimerisation was evaluated using the PathHunter Pertuzumab Bioassay Kit (DiscoverX) according to the manufacturer's instructions.

Briefly, HER2 and HER3 overexpressing U2OS cells were thawed using 1 ml of pre-warmed CP5 media and 5,000 cells were seeded per well and cultured at 37° C. in 5% $CO_2$ atmosphere for 4 hr. Cells were then treated with an 8-point serial dilution of 10D1F.FcA or Pertuzumab, starting from 25 μg/ml.

After 4 hr incubation, 30 ng/ml of heregulin-β2 was added to each well and the cells were incubated for a further 16 hr. 10 μL of PathHunter bioassay detection reagent 1 was added to wells, and incubated for 15 min at room temperature in the dark. This was followed by addition of 40 μL PathHunter bioassay detection reagent 2, and incubation for 60 min at room temperature in the dark. Plates were then read using Synergy4 Biotek with 1 second delay.

The results are shown in FIG. 65. 10D1F.FcA was found inhibit HER2:HER3 dimerisation with greater efficiency than pertuzumab, as reflected by its lower IC50.

4.2 identification of Cancer Cell Lines for Analysis

The inventors characterised expression of EGFR protein family members by cancer cell lines to identify appropriate cells to investigate inhibition of HER3.

FIG. 16A shows mRNA expression data EGFR family members and ligands by N87, SNU16, HT29, FaDu, A549, HCC95, OvCAR8 and AHCN cells according to the Cancer Cell Line Encyclopaedia (CCLE; Barretina et al., Nature (2012) 483: 603-607 and The Cancer Cell Line Encyclopedia Consortium & The Genomics of Drug Sensitivity in Cancer Consortium, Nature (2015) 528: 84-87). FIG. 16A also shows protein expression data for EGFR, HER2 and HER3 as determined by FlowLogic.

Cell lines used in the experiments were purchased from ATCC and cultured as recommended. Briefly, cell lines maintained in the indicated cell culture medium, supplemented with 10% FBS and 1% Pen/Strep. Cells were cultured at 37° C., in 5% $CO_2$ incubators. Cultured cells were plated at the appropriate seeding density in a 96 well plate: HT29, HCC95, FADU and OvCar8 cells were seeded at 2000 cells/well, NCI-N87 cells were seeded at 5000 cells/well, SNU-16, ACHN and cells were seeded at 1500 cells/well, and A549 cells were seeded at 1200 cells/well.

Figure 16B:
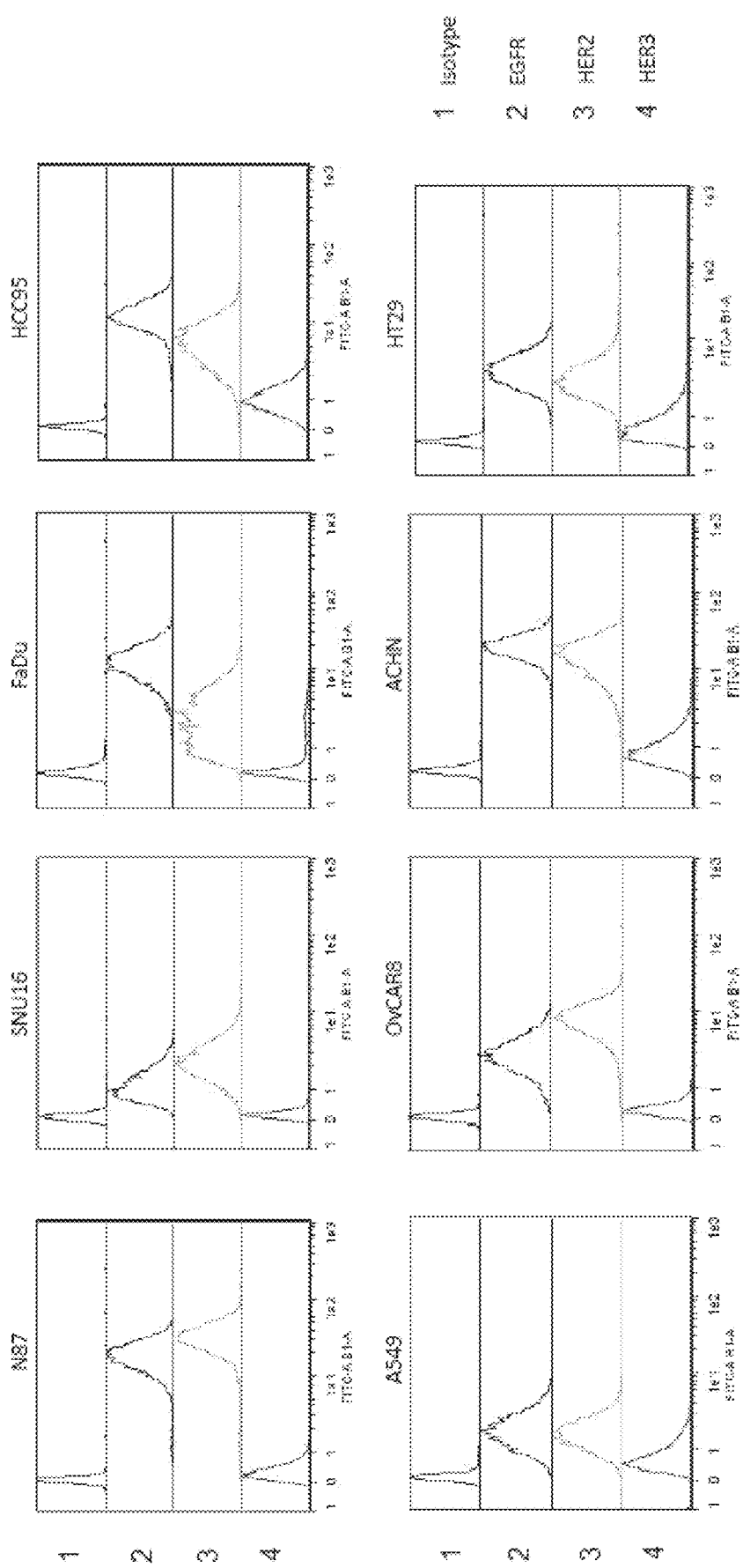

FIG. 16B shows surface expression of EGFR, HER2 and HER3 as determined by flow cytometry. Briefly, 500,000 cells were stained in staining buffer containing 0.5% BSA and 2 mM EDTA with primary antibodies (20 μg/ml) for 1.5 h at 4° C. The secondary Antibody used was anti-human Alexafluor488 at 10 μg/ml for 20 min at 4° C.

4.3 Inhibition of HER3-Mediated Signalling

Anti-HER3 antibody 10D1 was analysed for its ability to inhibit HER-3 mediated signalling in vitro.

Briefly, N87 and FaDu cells were seeded in wells of a 6 well plate with 10% serum at 37° C., 5% $CO_2$. After 16 hrs, cells were starved by culture overnight in 1% FBS cell culture medium (to reduce signalling elicited by growth factors in the serum). On the following day cells were treated with 50 μg/ml anti-HER3 antibody 10D1 for 4 hrs, followed by 15 min stimulation with NRG (100 ng/ml). Proteins were then extracted, quantified using standard Bradford protein assay, fractionated by SDS-PAGE, and transferred to nitrocellulose membranes. The membranes were then blocked and immunoblotted with the following antibodies overnight at 4° C. anti-pHER3, anti-pAKT, pan anti-HER3, pan anti-AKT and anti-beta-actin. The blots were visualized via Bio-Rad Clarity Western ECL substrate, and bands were quantified using densiometric analysis; data were normalized to beta actin controls.

Figure 17:
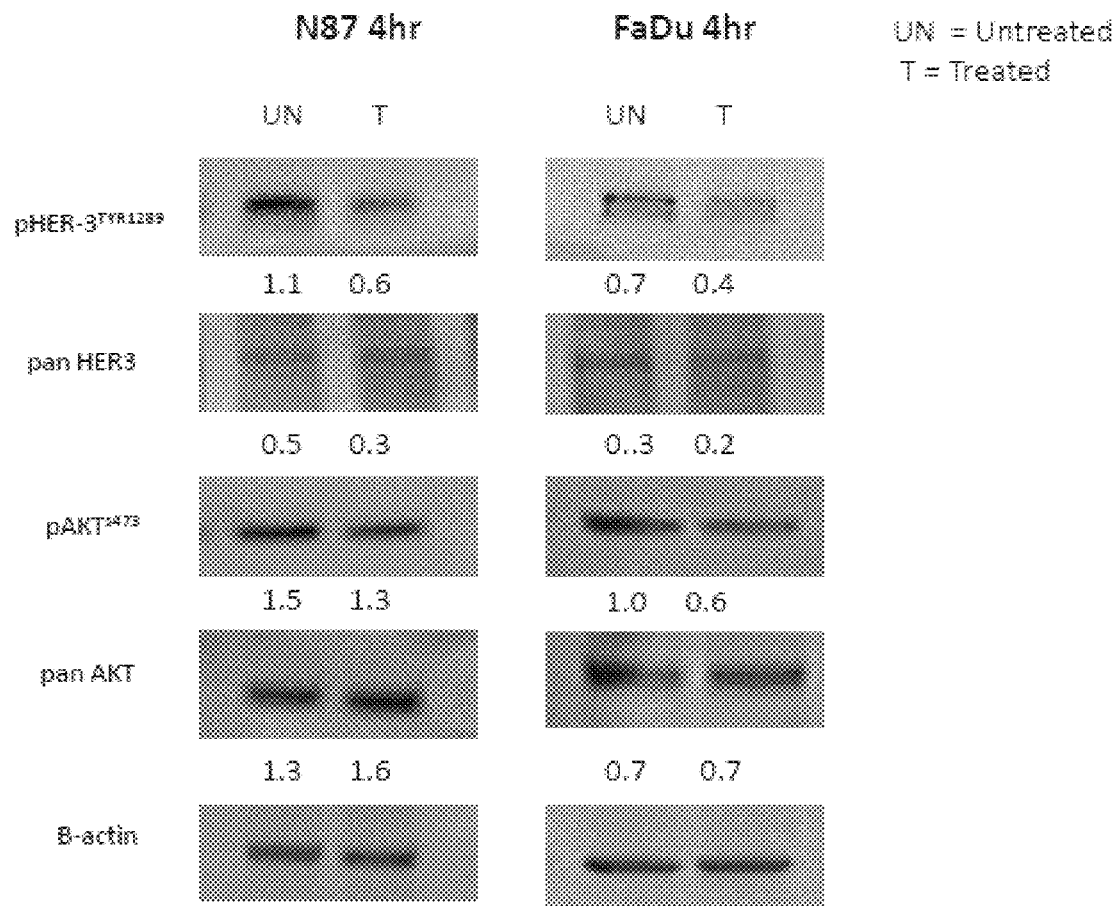
FIG. 17. Images showing the results of analysis of the effect of anti-HER3 antibody clone 10D1 treatment on the HER3-mediated signalling in N87 and FaDu cells by phospho-western blot. UN=untreated; T=treated with anti-HER3 antibody clone 10D1.

The results are shown in FIG. 17. Anti-HER3 antibody 10D1 was found to inhibit HER3 phosphorylation and downstream signalling.

In further experiments the inventors investigated the intracellular signalling pathways affected by anti-HER3 antibody-mediated inhibition of HER3.

FaDu cells were seeded in wells of a 6 well plate with 10% serum at 37° C. 5% $CO_2$. After 16 hrs, cells were starved by culture overnight in 1% FBS cell culture medium. On the following day cells were treated with 50 μg/ml anti-HER3 antibody 10D1 for 4 hrs, followed by 15 min stimulation with NRG (100 ng/ml). Proteins were then extracted, quantified using standard Bradford protein assay, and incubated overnight with pre-blocked Phosphoprotein Antibody Array membrane (Ray Biotech) at 4° C. The membrane was then washed with washing buffer and incubated with detection antibody cocktail for 2 hrs at room temperature, followed by washing and incubation with HRP-Conjugated anti-IgG. After 2 hrs the membrane was washed and probed using the kit detection buffer. Images were captured with Syngene Gbox imaging system, the intensity of each dot/phosphoprotein was measured and percent inhibition was calculated by comparison with intensity measured for cells treated in the same way in the absence of the antibody.

Figure 18:
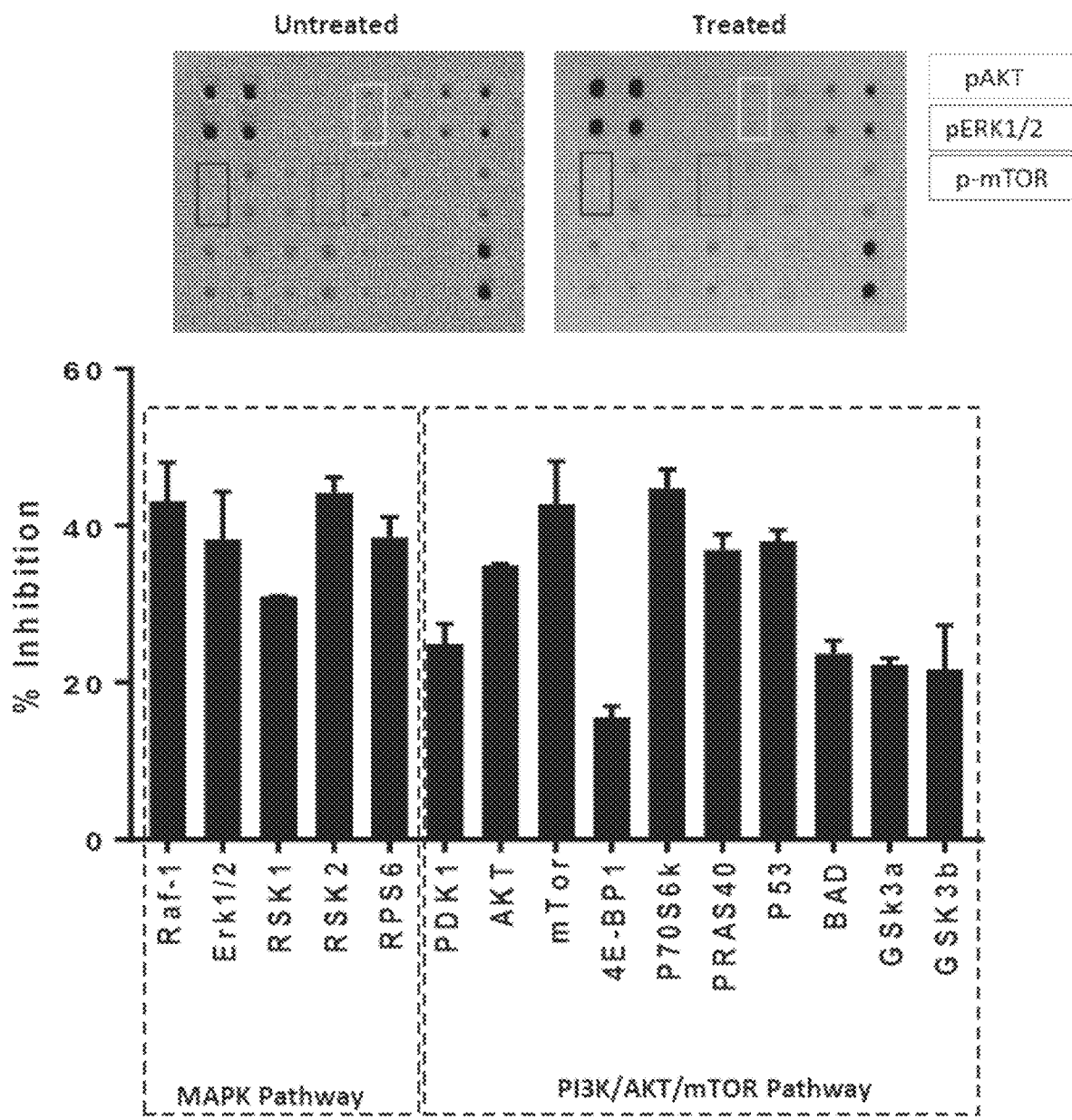
FIG. 18. Images and graph showing the results of analysis of the effect of anti-HER3 antibody clone 10D1 treatment on the HER3-mediated signalling in FaDu cells using the Phosphoprotein Antibody Array assay kit. Untreated=untreated FaDu cells; Treated=FaDu cells treated with anti-HER3 antibody clone 10D1.

The results are shown in FIG. 18. Anti-HER3 antibody 10D1 was found to inhibit PI3K/AKT/mTOR and MAPK signalling.

In further experiments the inventors investigated the effect of treatment with anti-HER3 antibody 10D1 on proliferation of HER3-expressing cells.

Briefly, N87 and FaDu cells were treated with serially diluted concentrations of anti-HER3 antibody 10D1, starting from 100 μg/ml with a 9-point half log dilution. Cell proliferation was measuring using the CCK-8 proliferation assay (Dojindo, Japan) after a period of 5 days, in accordance with the manufacturer's instructions. Briefly 1× CCK-8 solution was added to each well followed by incubation for 2 h at 37° C. The OD was then measured at 450 nm.

Figure 19A:
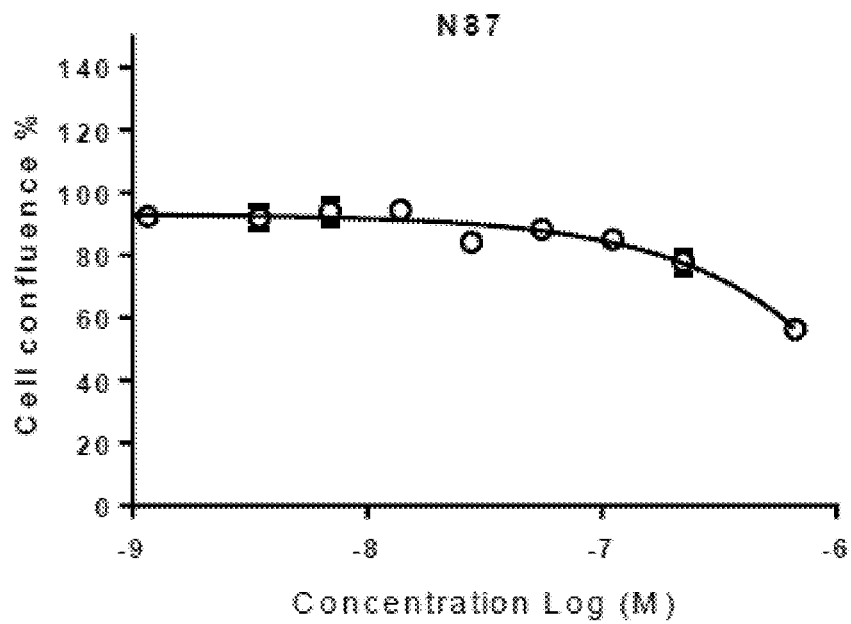
FIGS. 19A and 19B. Graphs showing the percent confluence of cells relative to an untreated control condition (100%), for the indicated cells lines as determined by CCK8 assay, following incubation in the presence of anti-HER3 antibody clone 10D1. (19A) Shows the results obtained for N87 cells, and (19B) shows the results obtained for FaDu cells.
Figure 19B:
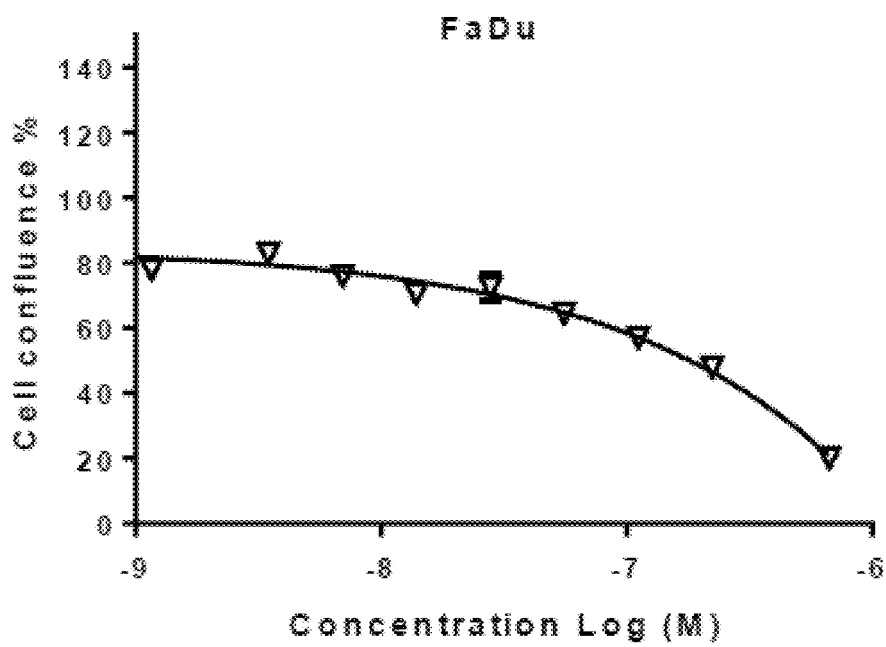

FIGS. 19A and 19B shows the percent cell confluence relative to untreated control cells (data points are averages of three replicates).

Anti-HER3 antibody 10D1 displayed dose-dependent inhibition of cell proliferation by N87 and FaDu cells.

Example 5

Analysis In Vivo 5.1 Pharmacokinetic Analysis

Female NCr nude mice approximately 6-8 weeks old were housed under specific pathogen-free conditions and treated in compliance with the Institutional Animal Care and Use Committee (IACUC) guidelines.

500 μg anti-HER3 antibody was administered and blood was obtained from 3 mice by cardiac puncture at baseline (−2 hr), 0.5 hr, 6 hr, 24 hr, 96 hr, 168 hr and 336 hr after administration. Antibody in the serum was quantified by ELISA.

Figure 49A:
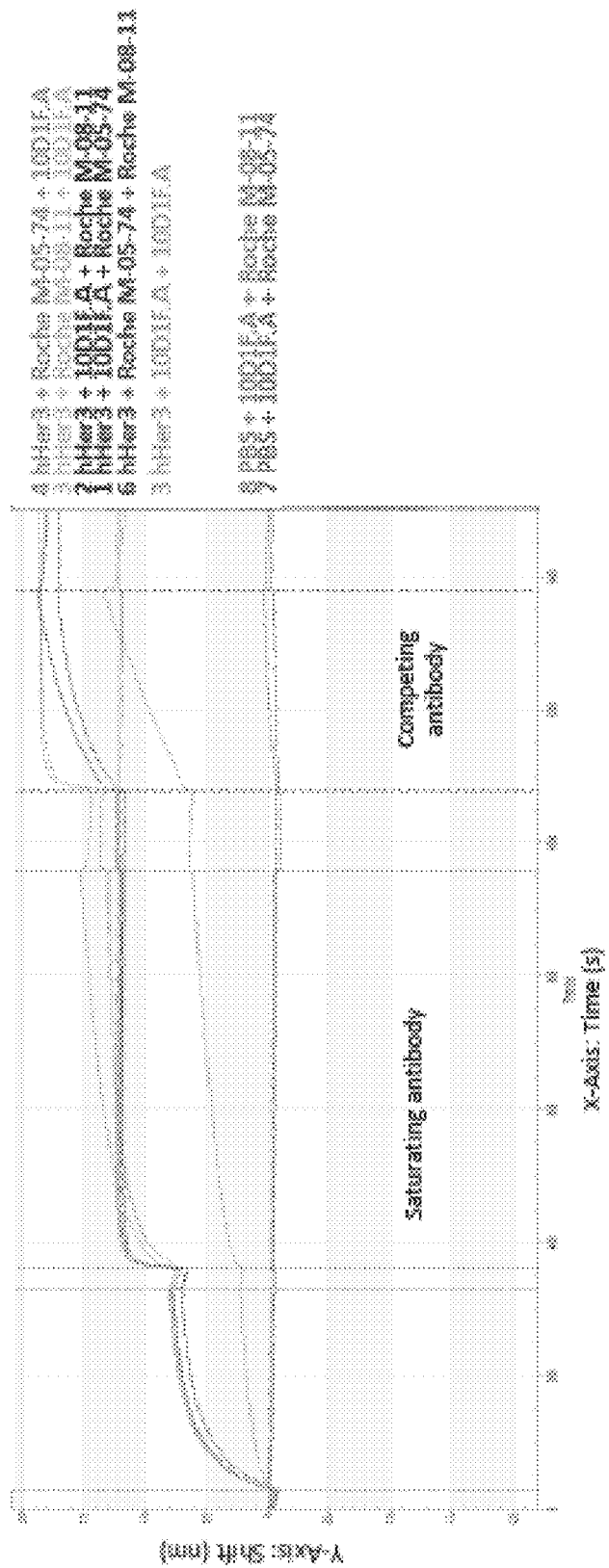
FIGS. 49A and 49B. Representative sensorgram and table showing the results of analysis of competition for binding to HER3 between anti-HER3 antibody clone 10D1F.FcA and anti-HER3 antibodies M-05-74 and M-08-11.
Figures 49B, 50:
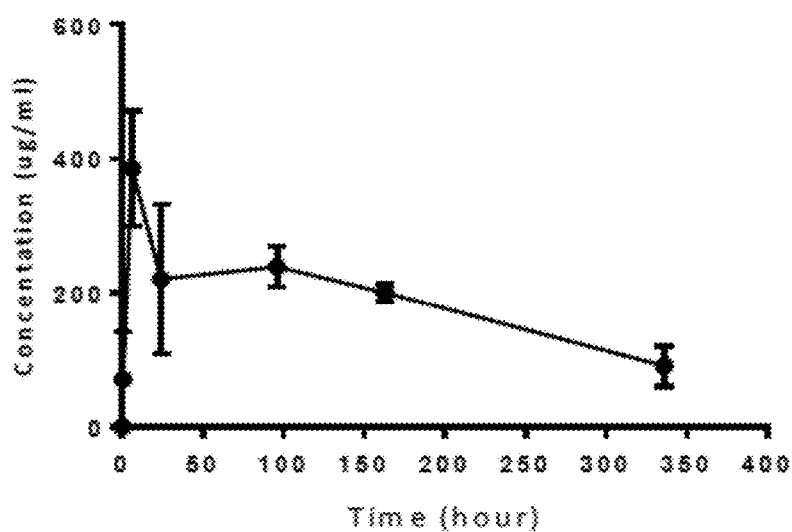
FIG. 50. Graph and tables showing the results of pharmacokinetic analysis of anti-HER3 antibody clone 10D1 in mice.

The results are shown in FIG. 50. Anti-HER3 antibody clone 10D1 was found to have a half-life of 16.3 days in NCr nude mice.

5.2 Safety Immunotoxicity

Anti-HER3 antibody clone 10D1 was analysed in silico for safety and immunogenicity using IMGT DomainGapAlign (Ehrenmann et al., Nucleic Acids Res., 38, D301-307 (2010)) and IEDB deimmunization (Dhanda et al., Immunology. (2018) 153(1):118-132) tools.

Anti-HER3 antibody clone 10D1 had numbers of potential immunogenic peptides few enough to be considered safe, and did not possess any other properties that could cause potential developability issues.

The Table of FIG. 37 provides an overview of the properties of the 10D1 variant clones relevant to safety and developability.

Mice treated with anti-HER3 antibodies in the experiments described in Example 5.3 were monitored for changes in weight and gross necroscopy. No differences were detected in these mice as compared to mice treated with vehicle only.

Hemotoxicity was investigated in an experiment in which 6-8 week old female BALB/c mice (20-25 g) were injected intraperitoneally with a single dose of 1000 μg anti-HER3 10D1 antibody or an equal volume of PBS. Blood samples were obtained at 96 hours post injection and analysed for numbers of different types of white blood cells by flow cytometry and electrolyte indices for $NA^+$, $K^+$, and $Cl^-$.

Figure 51A:
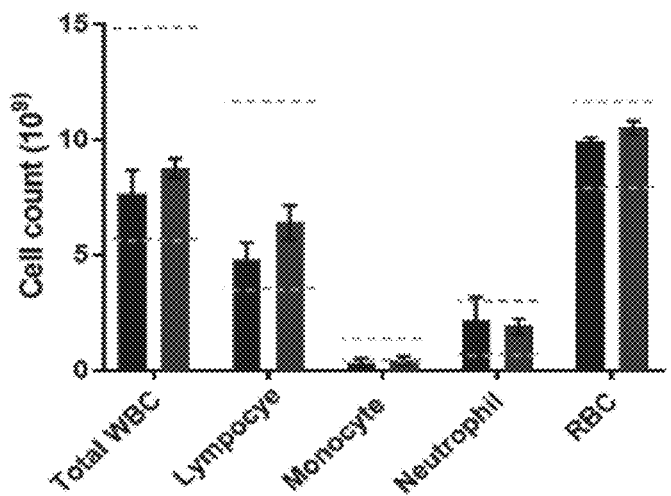
FIGS. 51A to 51F. Graphs showing the effect of anti-HER3 antibody clone 10D1 treatment on blood cell counts (51A), electrolyte indices (51B) and indices of hepatotoxicity, nephrotoxicity and pancreatic toxicity (51C-51F) in mice. Left bars represent vehicle control, right bars represent 10D1 treatment. Dotted lines indicate the end points of the Charles River reference range. Indices of hepatoxicity, nephrotoxicity and pancreatic toxicity include alanine aminotransferase (ALT), aspartate transaminase (AST), blood urea nitrogen (BUN), creatinine (CREA), alkaline phosphatase (ALP), glucose (GLU), calcium (CAL), total bilirubin (BIL), total protein (TPR) and albumin (ALB).
Figure 51B:
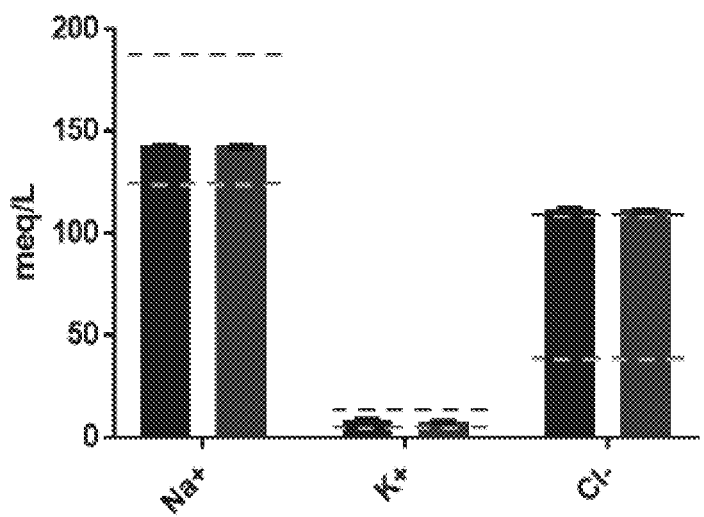
Figure 51C:
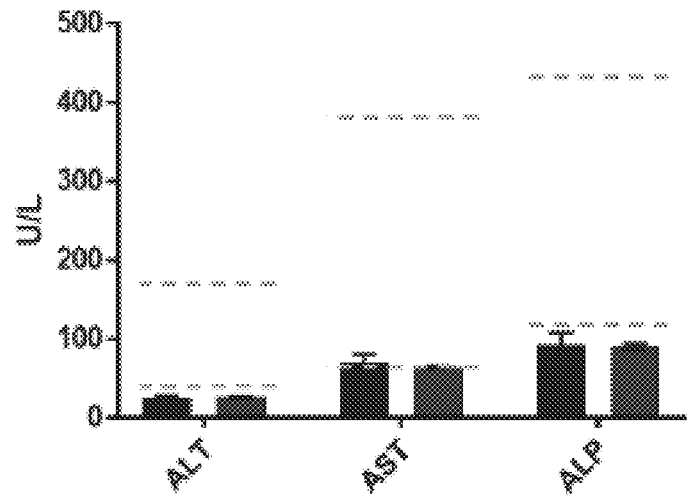
Figure 51D:
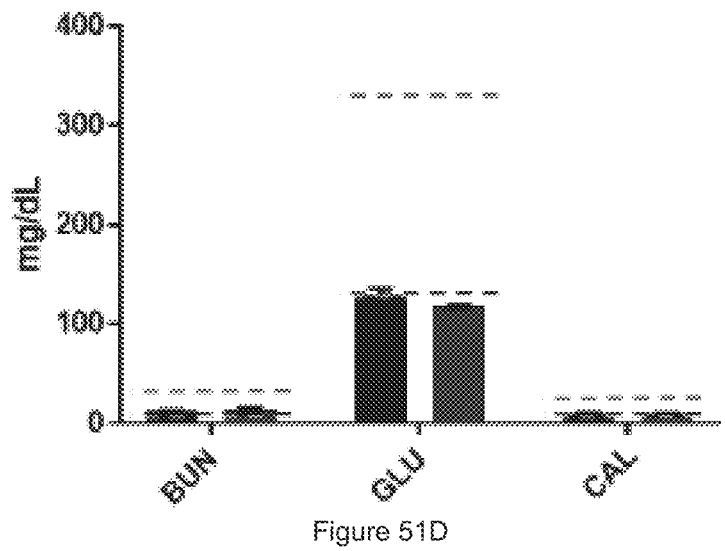
Figure 51E:
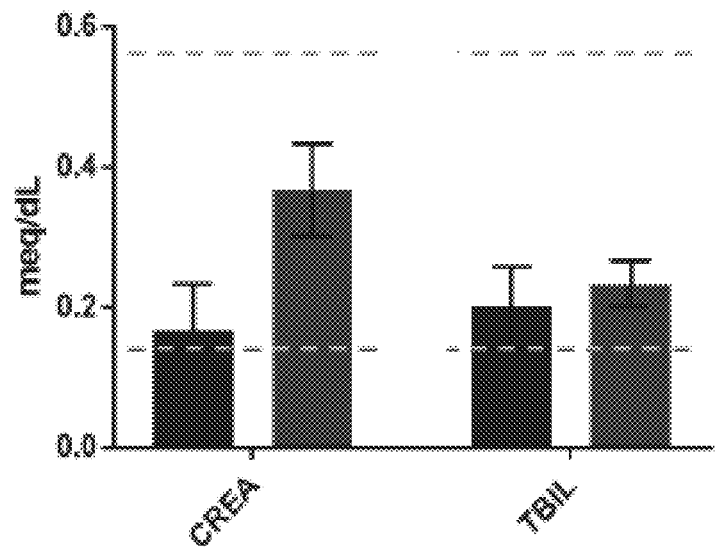
Figure 51F:
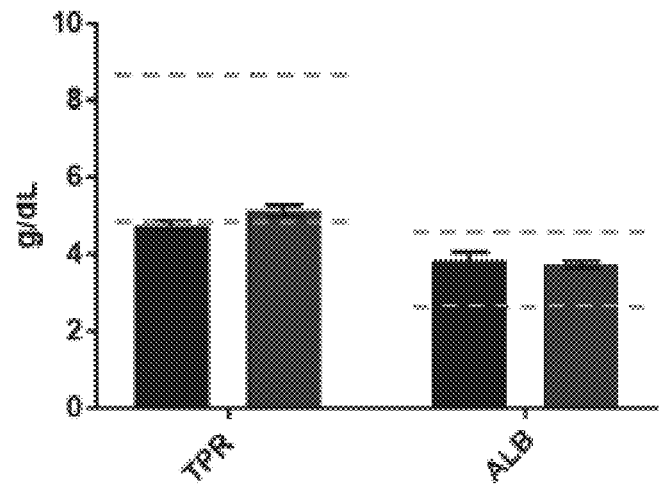

FIGS. 51A and 51B show that the numbers of the different cell types and electrolyte indices were found to be within the Charles River reference range (3 mice) and did not differ significantly from the PBS-treated group (3 mice). Left bars represent vehicle, right bars represent 10D1 treatment, end points of the Charles River reference range indicated with dotted lines. No differences in clinical signs, gross necroscopy or weight were detected between the different groups.

Mice were also analysed for correlates hepatotoxicity, nephrotoxicity and pancreatic toxicity at 96 hours post injection. The levels of alanine aminotransferase (ALT), aspartate transaminase (AST), blood urea nitrogen (BUN), creatinine (CREA), alkaline phosphatase (ALP), glucose (GLU), calcium (CAL), total bilirubin (BIL), total protein (TPR) and albumin (ALB) detected following administration of a single dose of 1000 μg anti-HER3 antibody were found to be within the Charles River reference range and do not differ significantly from the levels of these markers in the PBS-treated group. These are shown in FIGS. 51C to 51F. Left bars represent vehicle, right bars represent 10D1 treatment, end points of the Charles River reference range indicated with dotted lines. 10D1 treatment has no effect on the kidney, liver or pancreatic indices and thus does not affect normal kidney, liver or pancreatic functions.

5.3 Analysis of Efficacy to Treat Cancer In Vivo

Female NCr nude mice approximately 6-8 weeks old were purchased from InVivos (Singapore). Animals were housed under specific pathogen-free conditions and were treated in compliance with the Institutional Animal Care and Use Committee (IACUC) guidelines.

Cell lines used included N87 cells (gastric cancer), FaDu cells (head and neck cancer), OvCAR8 cells (ovarian cancer), SNU16 cells (gastric cancer), HT29 cells (colorectal cancer), A549 cells (lung cancer), HCC95 cells (lung cancer) and AHCN cells (kidney cancer).

Tumor volumes were measured 3 times a week using a digital caliper and calculated using the formula [L×W2/2]. Study End point was considered to have been reaches once the tumors of the control arm measured >1.5 cm in length.

5.3.1 N87 Model

Figure 20:
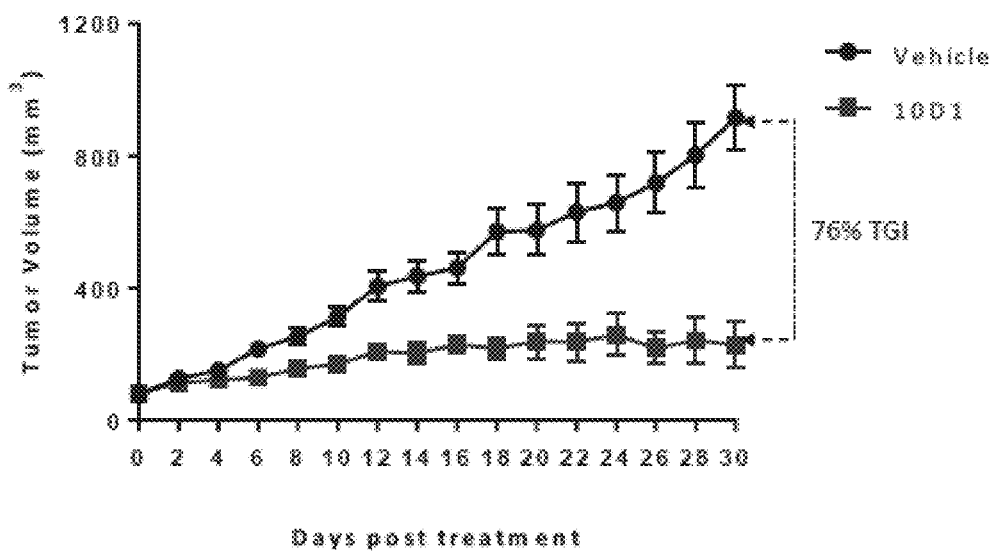
FIG. 20. Graph showing the results of analysis of tumour volume over time in a N87 cell-line derived mouse gastric carcinoma model. Anti-HER3 antibody clone 10D1 was administered IP, biweekly at 500 µg per dose for a total of 10 doses. A control treatment group received an equal volume of PBS (vehicle).

FIG. 20 shows the results obtained in an experiment wherein the anti-cancer effect of anti-HER3 antibody 10D1 ([1] of Example 2.2) was investigated in a N87 cell-line derived mouse gastric carcinoma model. The model was established by subcutaneous injection of 1×10⁶ N87 cells into the right flank (n=6 mice per treatment group).

10D1 was administered IP, biweekly at 500 µg per dose (for a total of 10 doses); a control treatment group received an equal volume of PBS.

Anti-HER3 antibody clone 10D1 was found to be highly potent in this model, and capable of inhibiting tumor growth by 76%.

Figure 21:
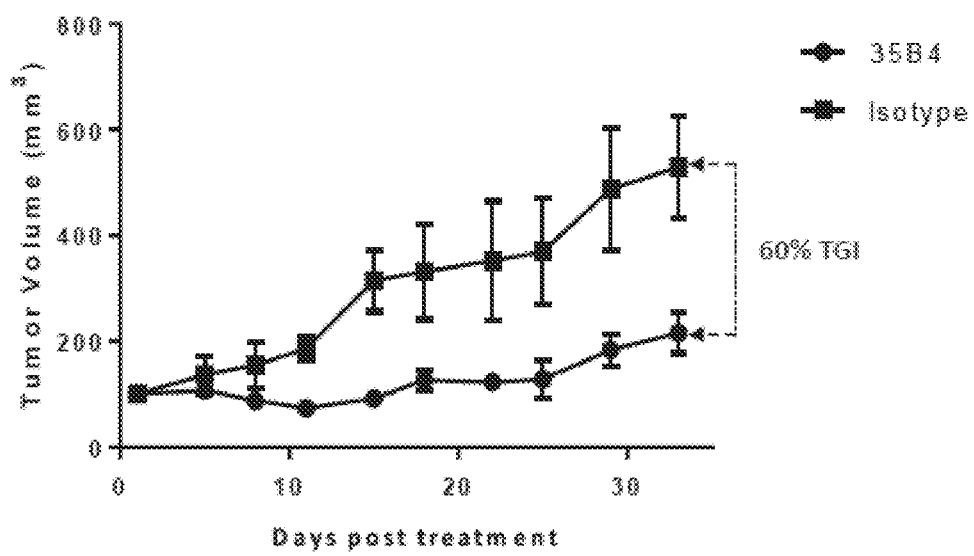
FIG. 21. Graph showing the results of analysis of tumour volume over time in a N87 cell-line derived mouse gastric carcinoma model. Anti-HER3 antibody clone 4-35-B2 was administered IP, weekly at 11 mg/kg per dose for a total of 4 doses. A control treatment group received an equal amount of isotype control antibody (isotype).

FIG. 21 shows the results obtained in a similar experiment in wherein anti-HER3 antibody clone 4-35-B4 was administered weekly IP at a dose of 11 mg/kg (total of 4 doses). Anti-HER3 antibody clone 4-35-B4 was similarly found to be highly potent in this model, and capable of inhibiting tumor growth by 60%.

5.3.2 SNU16 Model

Figure 22:
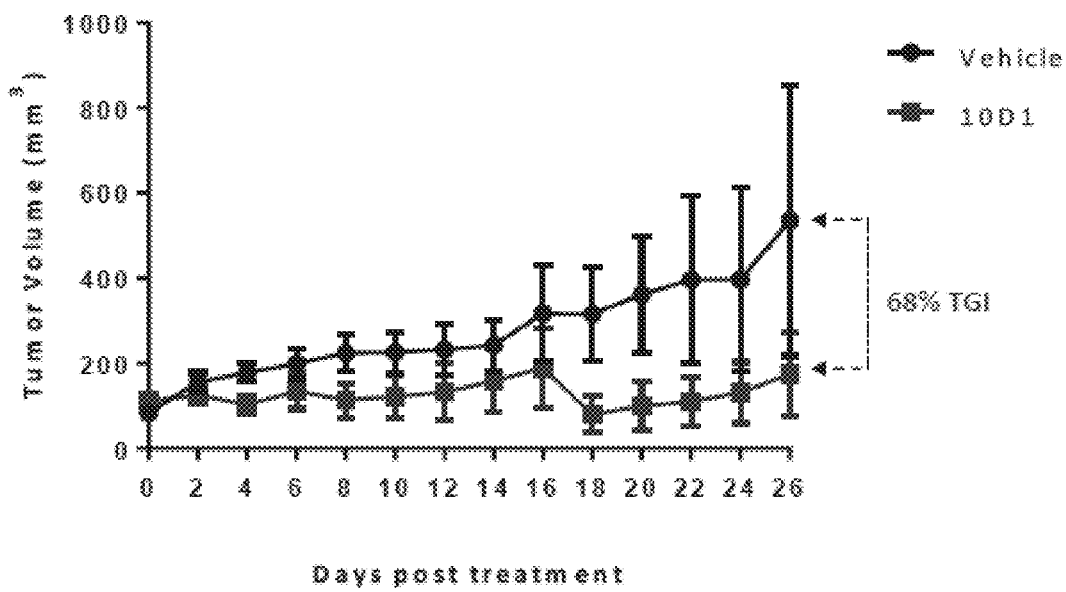
FIG. 22. Graph showing the results of analysis of tumour volume over time in a SNU16 cell-line derived mouse gastric carcinoma model. Anti-HER3 antibody clone 10D1 was administered IP, biweekly at 500 µg per dose for a total of 9 doses. A control treatment group received an equal volume of PBS (vehicle).

FIG. 22 shows the results obtained in an experiment wherein the anti-cancer effect of anti-HER3 antibody 10D1 ([1] of Example 2.2) was investigated in a SNU16 cell-line derived mouse gastric carcinoma model. The model was established by subcutaneous injection of $1\times10^6$ SNU16 cells into the right flank (n=6 mice per treatment group).

10D1 was administered IP, biweekly at 500 µg per dose (for a total of 9 doses); a control treatment group received an equal volume of PBS.

Anti-HER3 antibody clone 10D1 was found to be highly potent in this model, and capable of inhibiting tumor growth by 68%.

5.3.3 FaDu Model

Figure 23:
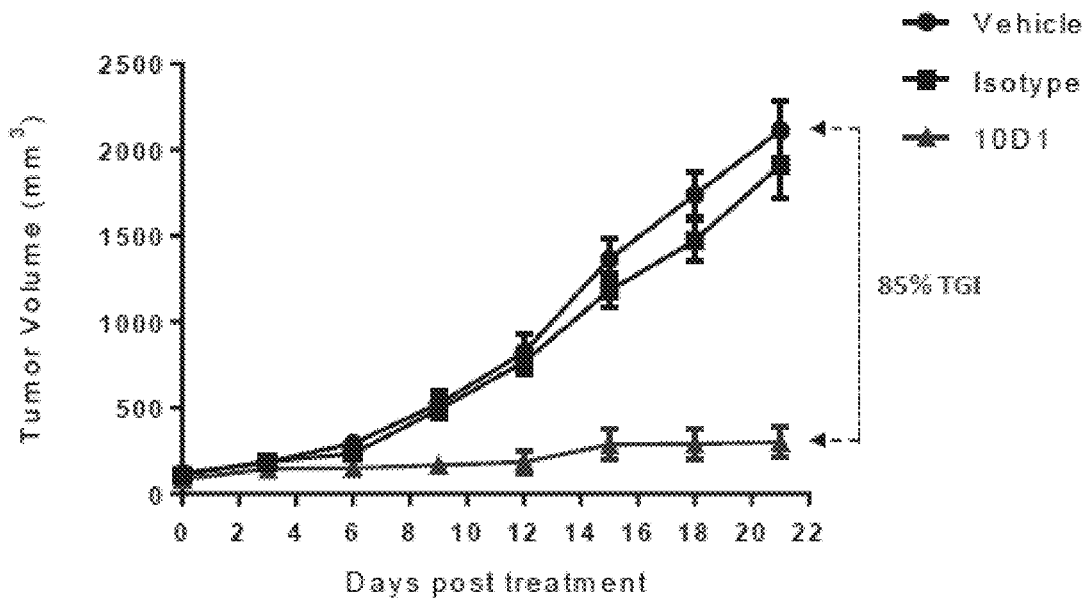
FIG. 23. Graph showing the results of analysis of tumour volume over time in a FaDu cell-line derived mouse model of head and neck squamous cell carcinoma. Anti-HER3 antibody clone 10D1 was administered IP, weekly at 500 µg per dose for a total of 4 doses. Control treatment groups received an equal volume of PBS (vehicle), or the same dose of an isotype control antibody (isotype).

FIG. 23 shows the results obtained in an experiment wherein the anti-cancer effect of anti-HER3 antibody 10D1 ([1] of Example 2.2) was investigated in a FaDu cell-line derived mouse model of head and neck squamous cell carcinoma. The model was established by subcutaneous injection of $1\times10^6$ FaDu cells into the right flanks of female NPG mice (NOD scid gamma phenotype; n=6 mice per treatment group).

10D1 was administered IP, weekly at 500 µg per dose (for a total of 4 doses). Control treatment groups received an equal volume of PBS, or the same dose of an isotype control antibody.

Anti-HER3 antibody clone 10D1 was found to be highly potent in this model, and capable of inhibiting tumor growth by 85%.

Figure 24:
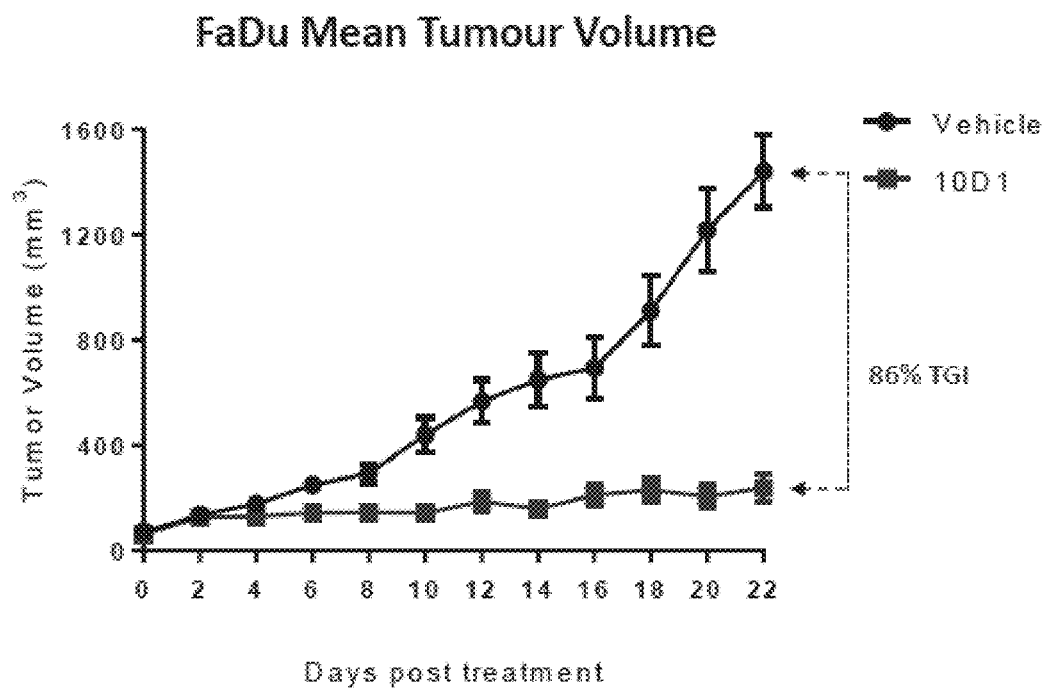
FIG. 24. Graph showing the results of analysis of tumour volume over time in a FaDu cell-line derived mouse model of head and neck squamous cell carcinoma. Anti-HER3 antibody clone 10D1 was administered IP, biweekly at 500 µg per dose for a total of 8 doses. A control treatment group received an equal volume of PBS (vehicle).

FIG. 24 shows the results obtained in an experiment wherein the anti-cancer effect of anti-HER3 antibody 10D1 ([1] of Example 2.2) was investigated in a FaDu cell-line derived mouse model of head and neck squamous cell carcinoma. The model was established by subcutaneous injection of $1\times10^6$ FaDu cells into the right flanks of female NCr nude mice (n=6 mice per treatment group).

10D1 was administered IP, biweekly at 500 µg per dose (for a total of 8 doses); a control treatment group received an equal volume of PBS.

Anti-HER3 antibody clone 10D1 was found to be highly potent in this model, and capable of inhibiting tumor growth by 86%.

5.3.4 OvCAR8 Model

Figure 25:
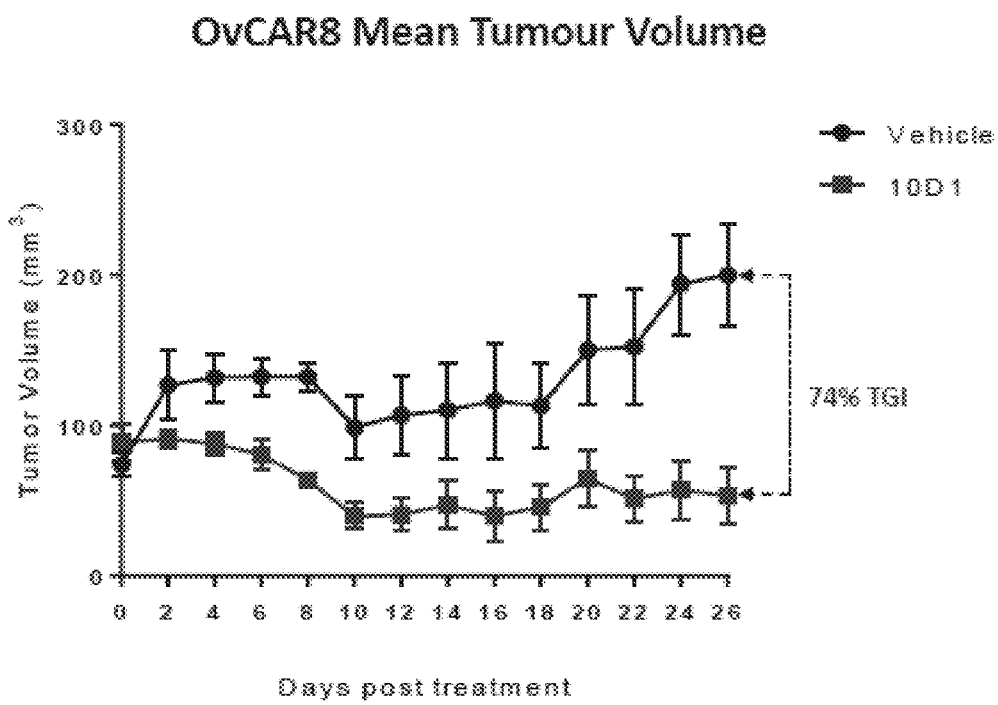
FIG. 25. Graph showing the results of analysis of tumour volume over time in an OvCAR8 cell-line derived mouse model of ovarian carcinoma. Anti-HER3 antibody clone 10D1 was administered IP, biweekly at 500 µg per dose for a total of 9 doses. A control treatment group received an equal volume of PBS (vehicle).

FIG. 25 shows the results obtained in an experiment wherein the anti-cancer effect of anti-HER3 antibody 10D1 ([1] of Example 2.2) was investigated in an OvCAR8 cell-line derived mouse model of ovarian carcinoma. The model was established by subcutaneous injection of $1\times10^6$ OvCAR8 cells into the right flanks of female NCr nude mice (n=6 mice per treatment group).

10D1 was administered IP, biweekly at 500 µg per dose (for a total of 9 doses); a control treatment group received an equal volume of PBS.

Anti-HER3 antibody clone 10D1 was found to be highly potent in this model, and capable of inhibiting tumor growth by ~74%.

5.3.5 HCC-95 Model

Figure 26:
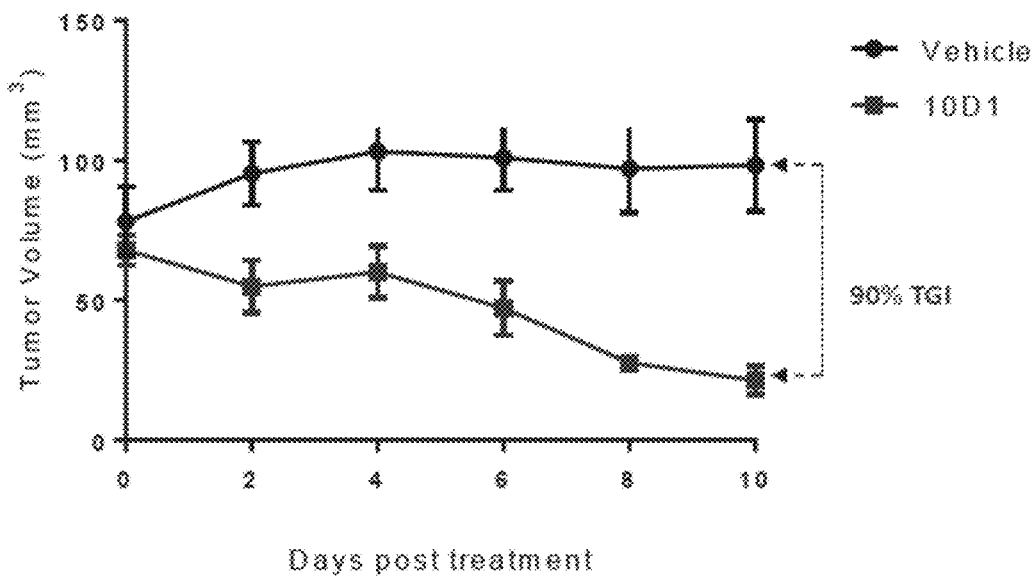
FIG. 26. Graph showing the results of analysis of tumour volume over time in a HCC-95 cell-line derived mouse model of squamous king cell carcinoma. Anti-HER3 antibody clone 10D1 was administered IP, biweekly at 500 µg per dose for a total of 4 doses. A control treatment group received an equal volume of PBS (vehicle).

FIG. 26 shows the results obtained in an experiment wherein the anti-cancer effect of anti-HER3 antibody 10D1 ([1] of Example 2.2) was investigated in a HCC-95 cell-line derived mouse model of squamous cell lung carcinoma. The model was established by subcutaneous injection of $1\times10^6$ HCC-95 cells into the right flanks of female NCr nude mice (n=6 mice per treatment group).

10D1 was administered IP, biweekly at 500 µg per dose (for a total of 4 doses); a control treatment group received an equal volume of PBS.

Anti-HER3 antibody clone 10D1 was found to be highly potent in this model, and capable of inhibiting tumor growth by 90%.

5.3.6 A549 Model

Figure 27:
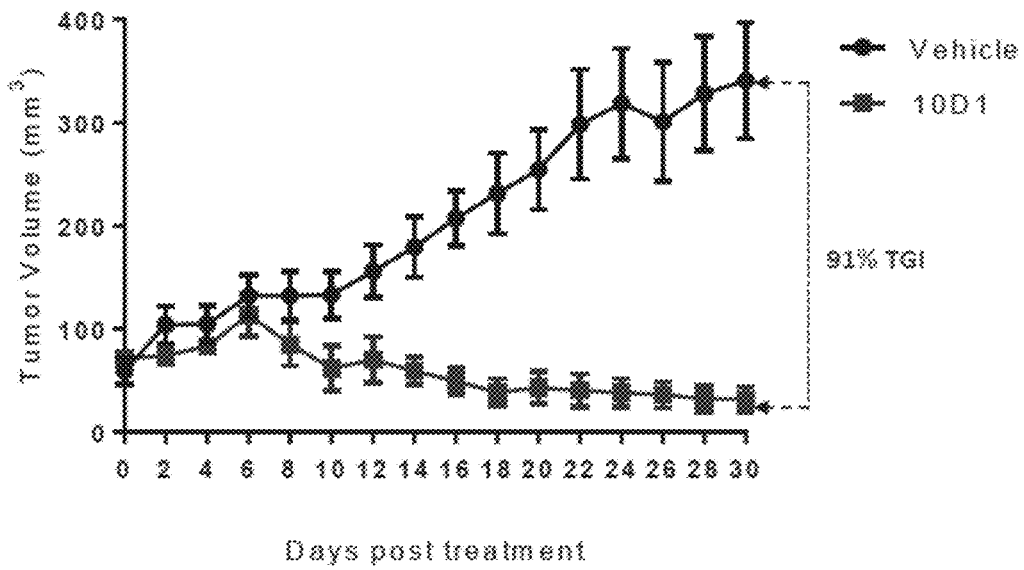
FIG. 27. Graph showing the results of analysis of tumour volume over time in an A549 cell-line derived mouse model of lung adenocarcinoma. Anti-HER3 antibody clone 10D1 was administered IP, biweekly at 500 µg per dose for a total of 10 doses. A control treatment group received an equal volume of PBS (vehicle).

FIG. 27 shows the results obtained in an experiment wherein the anti-cancer effect of anti-HER3 antibody 10D1 ([1] of Example 2.2) was investigated in an A549 cell-line derived mouse model of lung adenocarcinoma. The model was established by subcutaneous injection of $1\times10^6$ A549 cells into the right flanks of female NCr nude mice (n=6 mice per treatment group).

10D1 was administered IP, biweekly at 500 µg per dose (for a total of 10 doses); a control treatment group received an equal volume of PBS.

Anti-HER3 antibody clone 10D1 was found to be highly potent in this model, and capable of inhibiting tumor growth by 91%.

Figure 28:
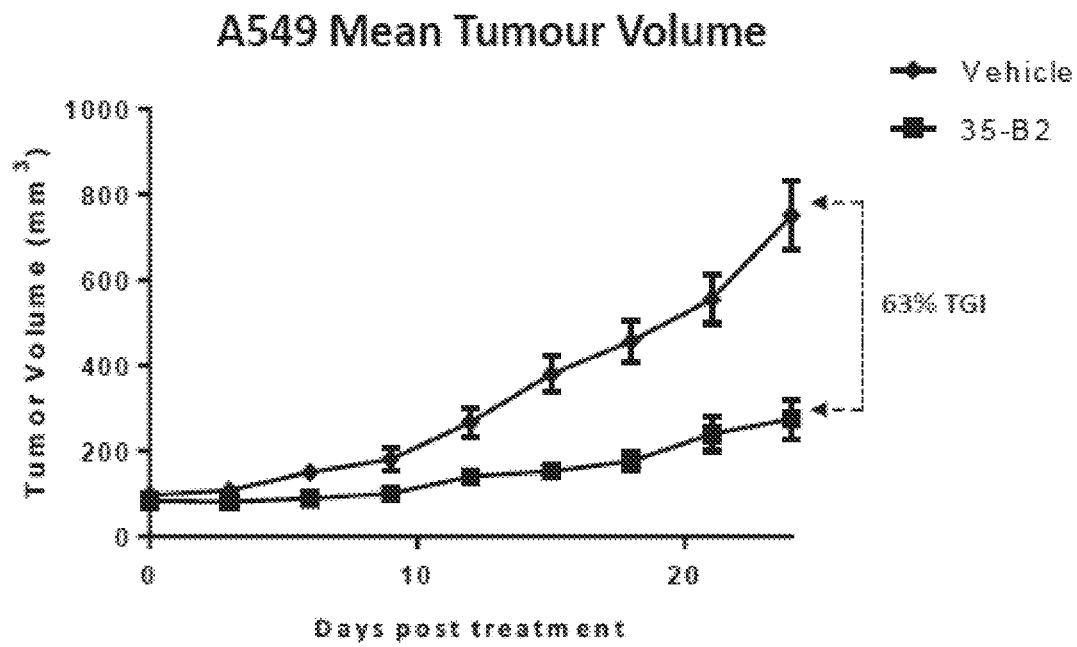
FIG. 28. Graph showing the results of analysis of tumour volume over time in an A549 cell-line derived mouse model of lung adenocarcinoma. Anti-HER3 antibody clone 4-35-B2 was administered IP, biweekly at 500 µg per dose for a total of 4 doses. A control treatment group received an equal volume of PBS (vehicle).

FIG. 28 shows the results obtained in a similar experiment in wherein the anti-cancer effect of anti-HER3 antibody clone 4-35-B2 was investigated in an A549 cell-line derived model established by injection of $1\times10^6$ A549 cells into the right flanks of female NPG mice (NOD scid gamma phenotype). Anti-HER3 antibody clone 4-35-B2 was administered IP weekly at a dose of 500 µg per dose (total of 4 doses). A control treatment group received an equal volume of PBS (6 mice per treatment group).

Anti-HER3 antibody clone 4-35-B2 was similarly found to be highly potent in this model, and capable of inhibiting tumor growth by 63%.

5.3.6 ACHN Model

Figure 29:
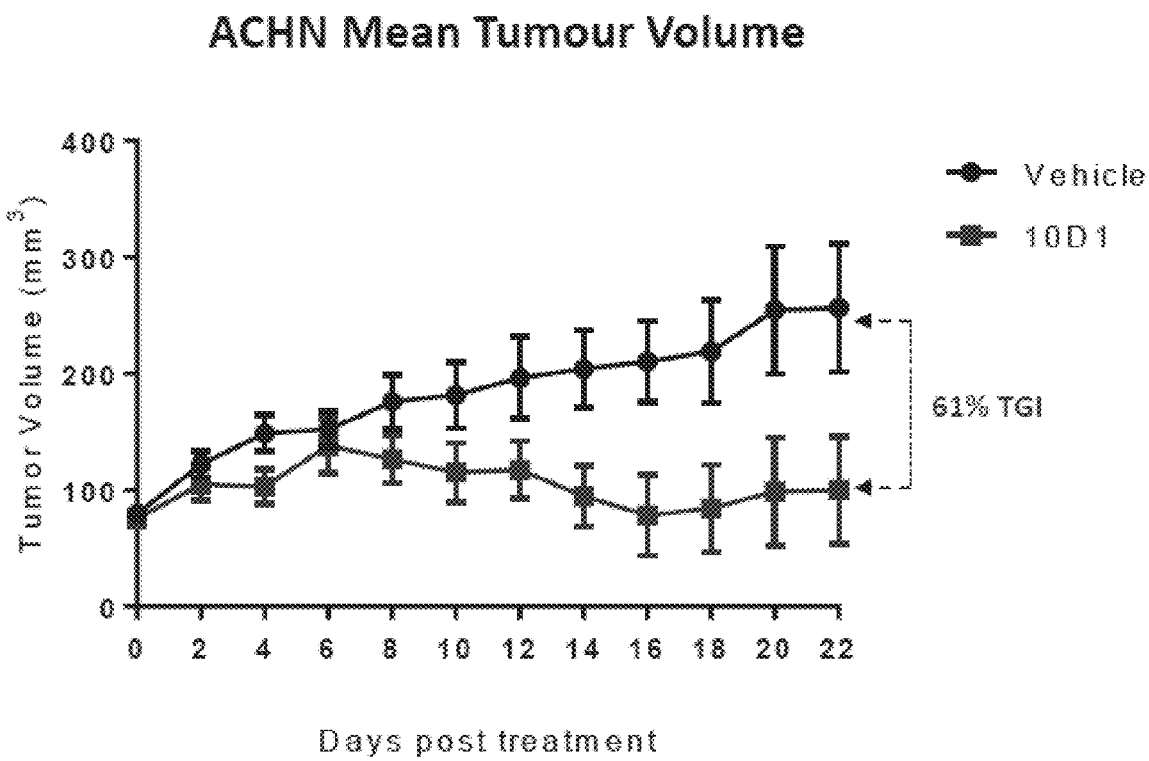
FIG. 29. Graph showing the results of analysis of tumour volume over time in an ACHN cell-line derived mouse model of renal cell carcinoma. Anti-HER3 antibody clone 10D1 was administered IP, biweekly at 500 µg per dose for a total of 7 doses. A control treatment group received an equal volume of PBS (vehicle).
Figure 30:
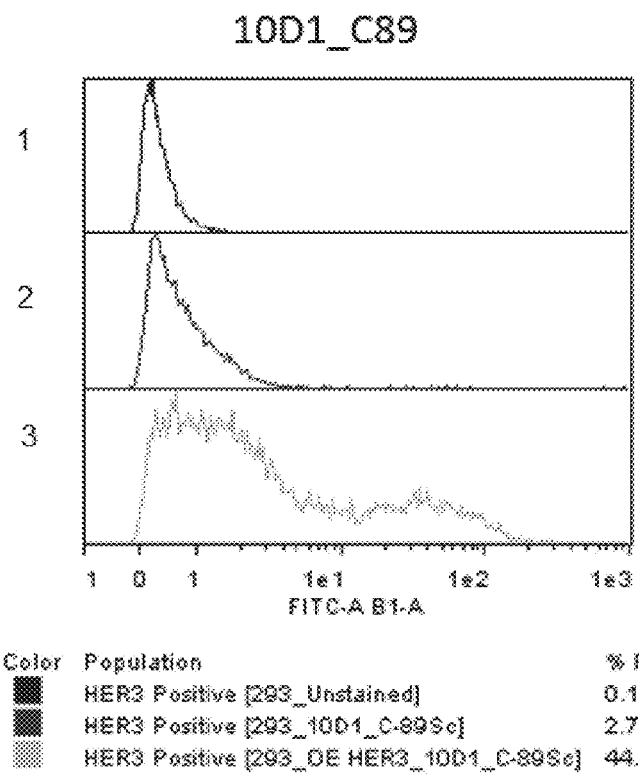
FIG. 30. Histogram showing staining of cells by anti-HER3 antibody clone 10D1_c89 as determined by flow cytometry. Histograms show staining of HEK293 cells (which do not express HER3), or HEK293 HER3 overexpressing cells (HEK293 HER3 O/E).
Figure 31:
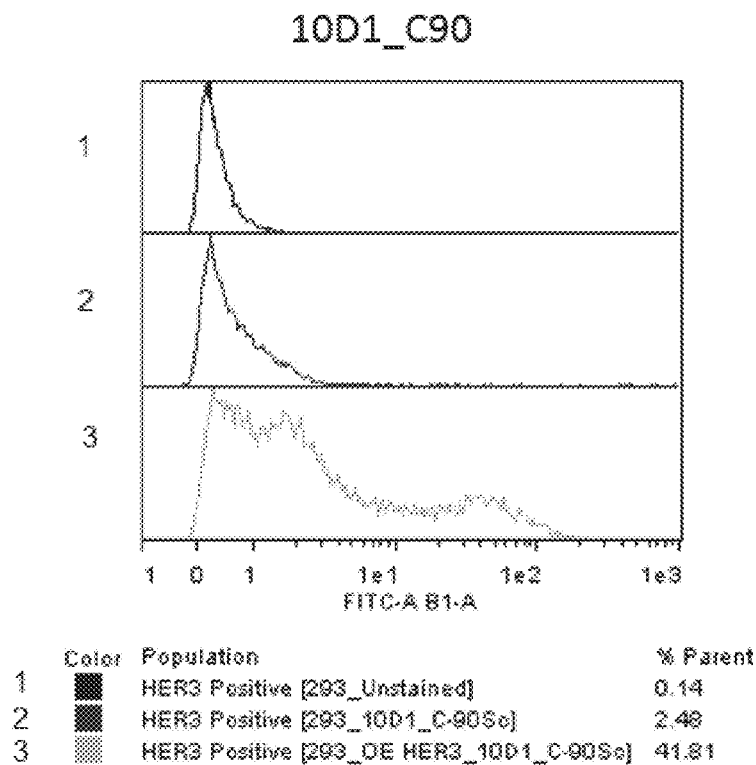
FIG. 31. Histogram showing staining of cells by anti-HER3 antibody clone 10D1_c90 as determined by flow cytometry. Histograms show staining of HEK293 cells (which do not express HER3), or HEK293 HER3 overexpressing cells (HEK293 HER3 O/E).
Figure 32:
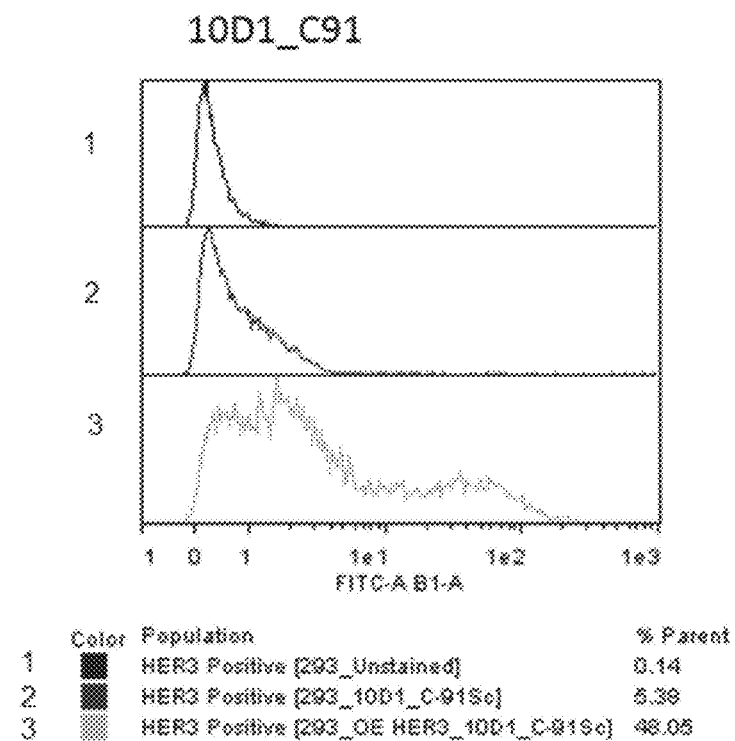
FIG. 32. Histogram showing staining of cells by anti-HER3 antibody clone 10D1_c91 as determined by flow cytometry. Histograms show staining of HEK293 cells (which do not express HER3), or HEK293 HER3 overexpressing cells (HEK293 HER3 O/E).

FIG. 29 shows the results obtained in an experiment wherein the anti-cancer effect of anti-HER3 antibody 10D1 ([1] of Example 2.2) was investigated in an ACHN cell-line derived mouse model of renal cell carcinoma. The model was established by subcutaneous injection of $1\times10^6$ ACHN cells into the right flanks of female NCr nude mice (n=6 mice per treatment group).

10D1 was administered IP, biweekly at 500 µg per dose (for a total of 7 doses); a control treatment group received an equal volume of PBS.

Anti-HER3 antibody clone 10D1 was found to be highly potent in this model, and capable of inhibiting tumor growth by 61%.

5.4 Treatment of Gastric Carcinoma

First in Human

Patients with HER2+ advanced gastric cancer who have failed or cannot receive trastuzumab are treated by intravenous injection of anti-HER3 antibody selected from: 10D1, 10D1_c75, 10D1_c76, 10D1_c77, 10D1_c78v1, 10D1_c78v2, 10D1_11B, 10D1_c85v1, 10D1_c85v2, 10D1_c85o1, 10D1_c85o2, 10D1_c87, 10D1_c89, 10D1_c90, 10D1_c91, 10D1_c92 and 10D1_c93, at a dose calculated in accordance with safety-adjusted 'Minimal Anticipated Biological Effect Level' (MABEL) approach. Patients are monitored for 28 days post-administration.

The patients are then evaluated according to the Common Terminology Criteria for Adverse Events (CTCAE), to determine the safety and tolerability of the treatment, and to determine the pharmacokinetics of the molecules.

Treatment with the anti-HER3 antibodies is found to be safe and tolerable.

Dose Escalation—Monotherapy 12-48 patients with HER2+ advanced gastric cancer who have failed or cannot receive trastuzumab are treated by intravenous injection of anti-HER3 antibody selected from: 10D1, 10D1_c75, 10D1_c76, 10D1_c77, 10D1_c78v1, 10D1_c78v2, 10D1_11B, 10D1_c85v1, 10D1_c85v2, 10D1_c85o1, 10D1_c85o2, 10D1_c87, 10D1_c89, 10D1_c90, 10D1_c91, 10D1_c92 and 10D1_c93 (e.g. 10D1_c89, 10D1_c90 or 10D1_c91; e.g. 10D1_c89), in accordance with a 3+3 model based escalation with overdose control (EWOC) dose escalation.

The patients are then evaluated according to the Common Terminology Criteria for Adverse Events (CTCAE) to determine the safety and tolerability of the treatment, and the pharmacokinetics of the molecules and efficacy of the treatment is evaluated. The maximum tolerated dose (MTD) and maximum administered dose (MAD) are also determined.

Dose Escalation—Combination Therapy 9-18 patients with HER2+ advanced gastric cancer who have failed or trastuzumab are treated by intravenous injection of anti-HER3 antibody selected from: 10D1, 10D1_c75, 10D1_c76, 10D1_c77, 10D1_c78v1, 10D1_c78v2, 10D1_11B, 10D1_c85v1, 10D1_c85v2, 10D1_c85o1, 10D1_c85o2, 10D1_c87, 10D1_c89, 10D1_c90, 10D1_c91, 10D1_c92 and 10D1_c93 (e.g. 10D1_c89, 10D1_c90 or 10D1_c91; e.g. 10D1_c89) in combination with trastuzumab, in accordance with a 3+3 model based escalation with anti-PD-L1 antibody (3 mg/kg).

The patients are then evaluated according to the Common Terminology Criteria for Adverse Events (CTCAE) to determine the safety and tolerability of the treatment, and the pharmacokinetics of the molecules and efficacy of the treatment is evaluated.

Dose Expansion

Patients with HER2+ advanced gastric cancer who have recently failed trastuzumab, and whose tumours have been well-characterised genetically and histologically are treated with anti-HER3 antibody selected from: 10D1, 10D1_c75, 10D1_c76, 10D1_c77, 10D1_c78v1, 10D1_c78v2, 10D1_11B, 10D1_c85v1, 10D1_c85v2, 10D1_c85o1, 10D1_c85o2, 10D1_c87, 10D1_c89, 10D1_c90, 10D1_c91, 10D1_c92, 10D1_c93 (e.g. 10D1_c89, 10D1_c90 or 10D1_c91; e.g. 10D1_c89) in combination with trastuzumab, cisplatin, and either 5-FU or capecitabine The anti-HER3 antibodies are found to be safe and tolerable, to be able to reduce the number/proportion of cancer cells, reduce tumor cell marker expression, increase progression-free survival and increase overall survival.

Example 6

Affinity Matured and Humanised Clones

Humanization of the variable regions of the parental mouse antibody 10D1P was done by CDR grafting. Human framework sequences for grafting were identified by blasting the parental amino acid sequence against the human V domain database and the genes with highest identity to the parental sequence were selected. Upon grafting the mouse CDRs into the selected human frameworks, residues in canonical positions of the framework were back mutated to the parental mouse sequence to preserve antigen binding. A total of 9 humanized variants of 10D1P were designed.

Affinity against human HER3 was increased by two rounds of affinity maturation using yeast display. In the first round, a mixed library of the 9 designed variants was constructed by random mutagenesis and screened by flow cytometry using biotinylated antigen. In the second round, one heavy chain and one light chain clones isolated in the first round were used as template to generate and screen a second library. A total of 10 humanized and affinity matured clones were isolated.

Potential liabilities (immunogenicity, glycosylation sites, exposed reactive residues, aggregation potential) in the variable regions of the designed and isolated humanized variants of 10D1P was assessed using in silico prediction tools. The sequences were deimmunised using EDB deimmunisation tool. The final sequence of 10D1F was selected among the optimized variants based on its developability characteristics as well as in vitro physicochemical and functional properties.

Clone 10D1F comprises VH of SEQ ID NO:36 and VL of SEQ ID NO:83. 10D1F displays 89.9% homology with human heavy chain and 35.3% homology with human light chain.

The antigen-binding molecule comprising 10D1F variable regions and human IgG1 constant regions, and which is comprised of the polypeptides of SEQ ID NOs: 206 and 207, is designated 10D1F.FcA (also sometimes referred to herein as "10D1F.A" or "anti-HER3 clone 10D1_c89 IgG1"—see e.g. [16] of Example 2.2).

Example 7

Fc Engineering

10D1 and 10D1 variants were engineered to comprise mutations in CH2 and/or CH3 regions to increase the potency of the antibodies, e.g. optimise Fc effector function, enhance antibody-dependent cellular cytotoxicity (ADCC) and/or antibody dependent cellular phagocytosis (ADCP), and improve half-life.

The Fc regions of clones 10D1 and 10D1F.FcA were modified to include modifications 'GASDALIE' (G236A, S239D, A330L, I332E) and 'LCKC' (L242C, K334C) in the CH2 region. The GASDALIE substitutions were found to increase affinity for the FcγRIIa (GA) and FcγRIIIa (SDALIE) receptors and enhance ADCP and NK-mediated ADCC (see Example 3.8), whilst decreasing affinity for C1q (AL) and reducing CDC. The LCKC substitutions were found to increase thermal stability of the Fc region by creating a new intramolecular disulphide bridge.

The modified version of 10D1F.FcA heavy chain polypeptide comprising the GASDALIE and LCKC mutations is shown in SEQ ID NO:225. The antigen-binding molecule comprised of the polypeptides of SEQ ID NOs: 225 and 207 is designated 10D1F.FcB (also sometimes referred to herein as "10D1F.B").

A modified version of 10D1 comprising the GASDALIE and LCKC substitutions in CH2 region was prepared and its ability to bind Fc receptor FcγRIIIa was analysed by Bio-Layer Interferometry. The sequence for 10D1 VH-CH1-CH2-CH3 comprising substitutions GASDALIE and LCKC corresponding to G236A, S239D, A330L, I332E and L242C. K334C is shown in SEQ ID NO:227.

Briefly, anti-Penta-HIS (HS1K) coated biosensor tips (Pall ForteBio, USA) were used to capture His-tagged FcγRIIIa (V158) (270 nM) for 120 s. All measurements were performed at 25° C. with agitation at 1000 rpm. Association kinetic measurements for antigen binding were performed by incubating anti-HER3 antibodies at different concentrations (500 nM to 15.6 nM) for 60 s, followed by a 120 s dissociation time by transferring the biosensors into assay buffer (pH 7.2) containing wells. Sensograms were referenced for buffer effects and then fitted using the Octet QK384 user software (Pall ForteBio, USA). Kinetic responses were subjected to a global fitting using a one site binding model to obtain values for association ($K_{on}$), dissociation ($K_{off}$) rate constants and the equilibrium dissociation constant ($K_D$). Only curves that could be reliably fitted with the software ($R^2 > 0.90$) were included in the analysis.

The thermostability of the variant was also analysed by Differential Scanning Fluorimetry analysis as described in Example 3.4.

Figure 38A:
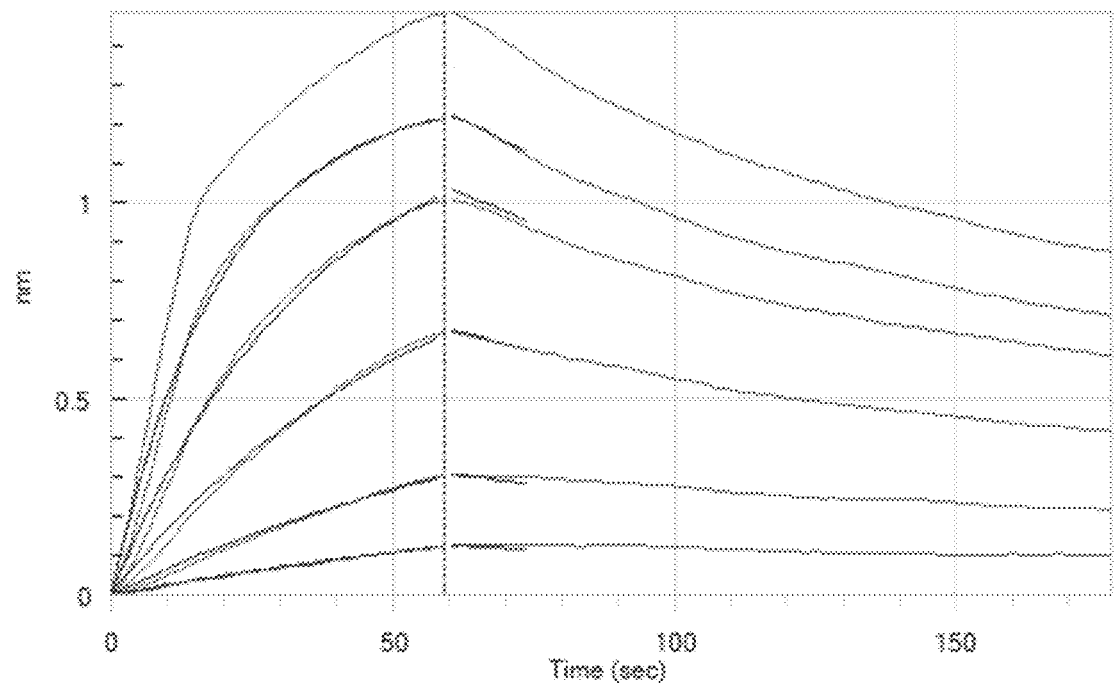
FIGS. 38A and 38B. Bio-Layer Interferometry (38A) and thermostability (38B) analysis of Fc-modified anti-HER3 antibody clone 10D1 comprising GASDALIE and LCKC substitutions in CH2 region. (38A) BLI shows a representative sensorgram showing the results of analysis of affinity of binding to FcγRIIIa by Fc-modified anti-HER3 antibody clone 10D1. Kon, Koff and $K_D$ are shown.
Figure 38B:
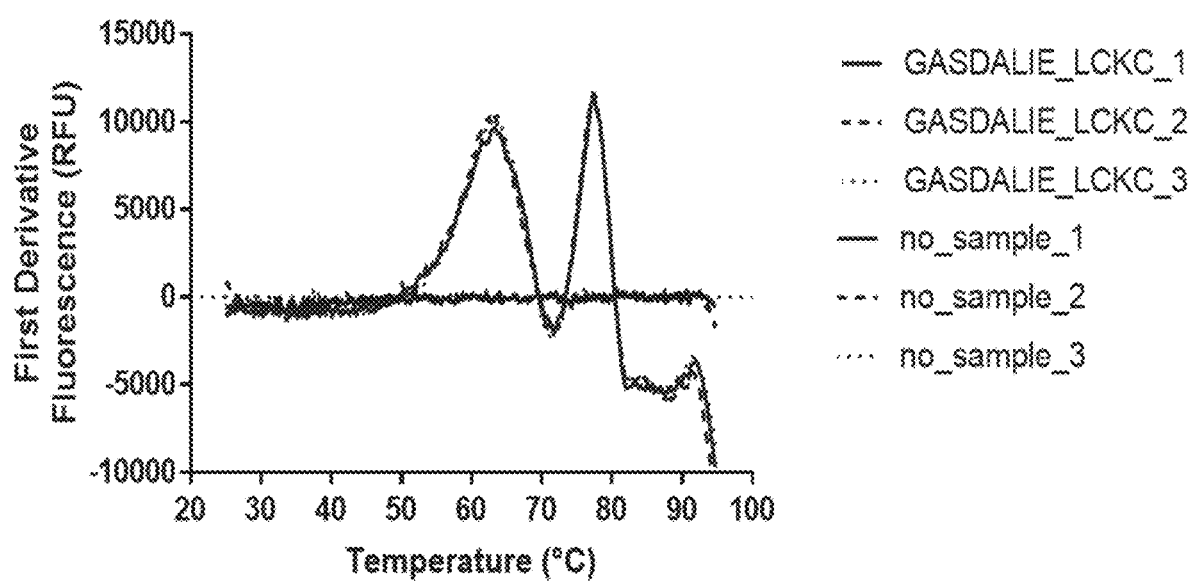

FIGS. 38A and 38B show the BLI analysis and thermostability analysis, respectively, for 10D1 comprising GASDALIE and LCKC Fc substitutions. The Fc engineered 10D1 variant showed significantly improved binding to FcγRIIIa (~9 fold increase in affinity) compared to non-Fc-engineered 10D1 (see FIG. 39A) with thermal stability maintained above 60° C.

A construct for 10D1 comprising the GASD substitutions in CH2 region was also prepared; a sequence of 10D1 VH-CH1-CH2-CH3 comprising substitutions corresponding to G236A and S239D is shown in SEQ ID NO:228.

The affinity of anti-HER3 antibody clone 10D1 ([1] of Example 2.2) and the GASD variant thereof were analysed by Bio-Layer Interferometry for affinity of binding to FcγRIIIa. BLI was performed as described above.

Figure 39A:
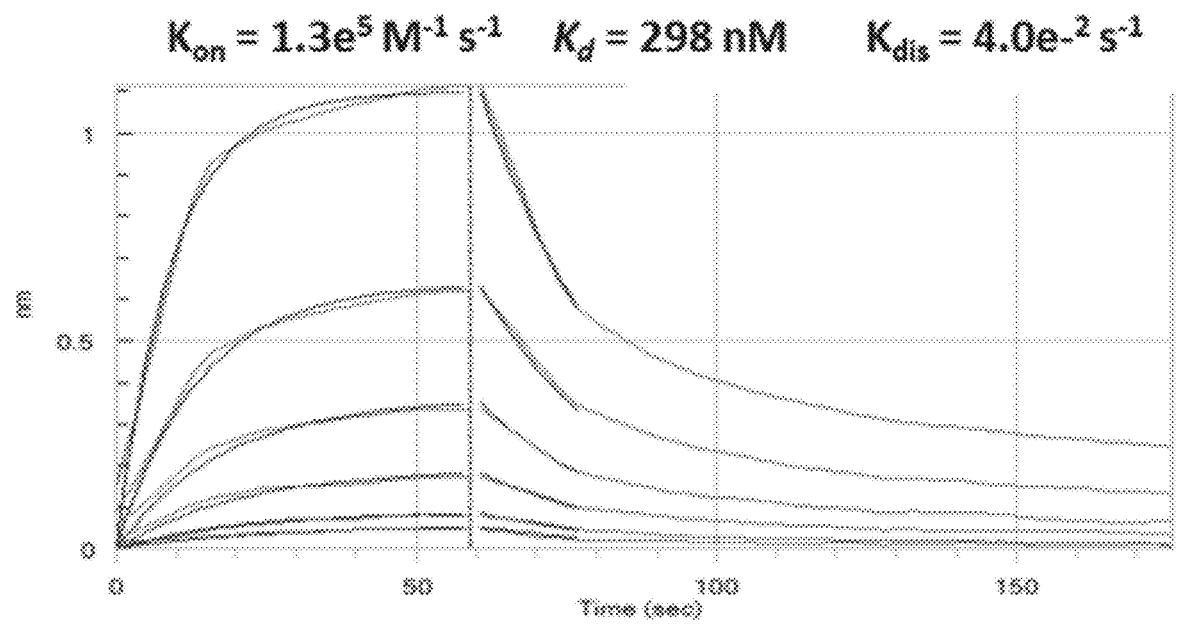
FIGS. 39A and 39B. Representative sensorgrams showing results of analysis of affinity of binding to FcγRIIIa by (39A) non-Fc-modified anti-HER3 antibody clone 10D1 and (39B) Fc-modified anti-HER3 antibody clone 10D1 comprising GASD substitutions in CH2 region. Kon, Koff and $K_D$ are shown.
Figure 39B:
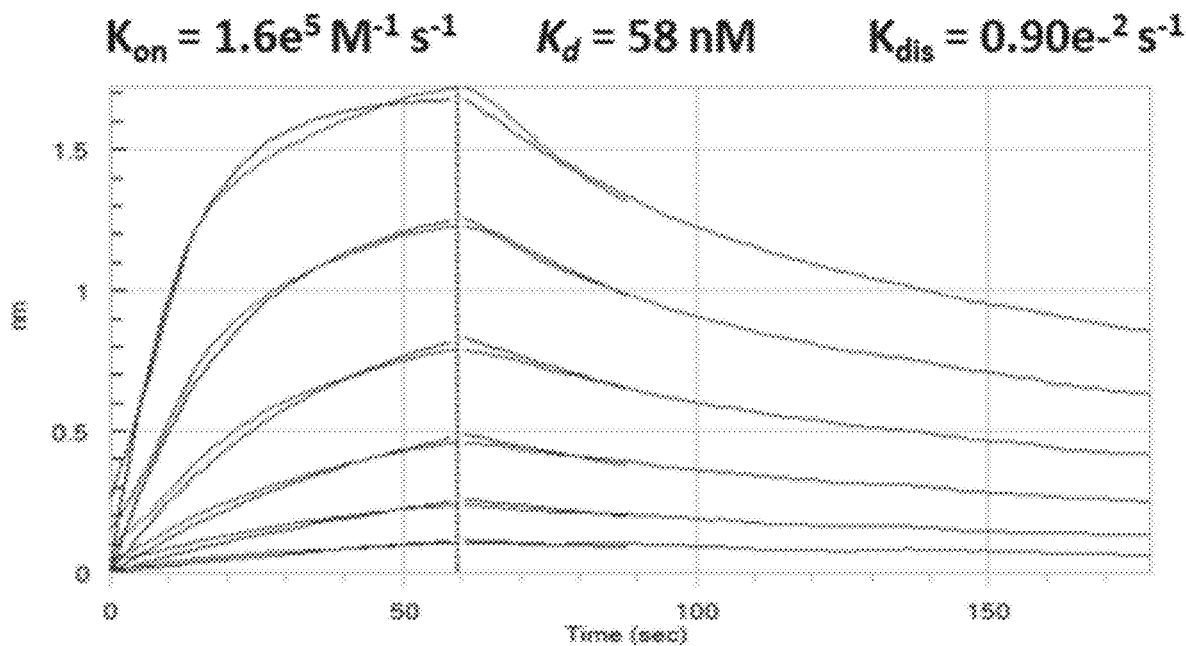

FIGS. 39A and 39B show representative sensorgrams, $K_{on}$, $K_{off}$ and $K_D$ values. As expected, the 10D1 GASD variant (39B) displayed dramatically increased affinity for FcγRIIIa compared to 10D1 (39A).

Figure 40:
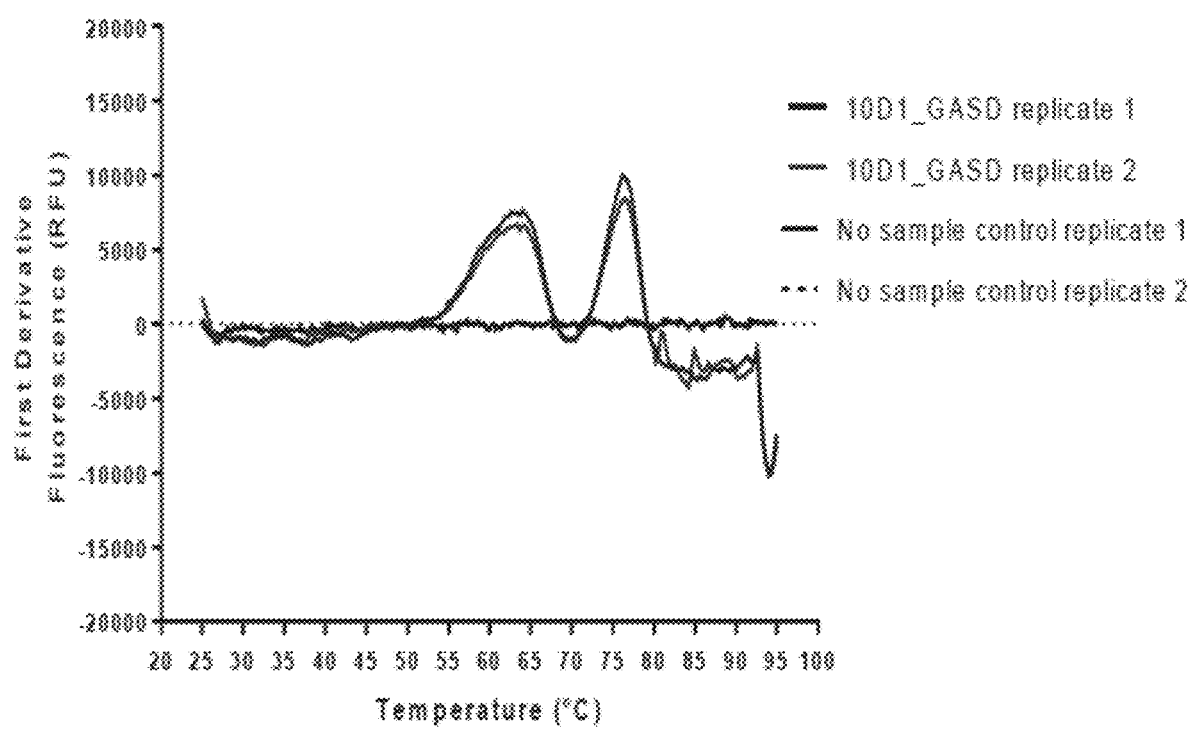
FIG. 40. Graph showing the results of analysis of stability of anti-HER3 antibody alone 10D1 GASD variant by Differential Scanning Fluorimetry analysis.

The thermostability of the 10D1 GASD variant was also analysed by Differential Scanning Fluorimetry analysis as described in Example 3.4. The results are shown in FIG. 40.

Further 10D1F Fc Variant

Another antibody variant was created comprising an N297Q substitution in the CH2 region. A representative sequence for 10D1F VH-CH1-CH2-CH3 comprising the N297Q substitution is shown in SEQ ID NO:226. This 'silent form' prevents both N-linked glycosylation of the Fc region and Fc binding to Fcγ receptors and is used as a negative control.

FIGS. 41A and 41B show the binding affinity of 10D1F hIgG1 Fc variants 10D1F.FcA and 10D1F.FcB to human and mouse Fc receptors, determined as described above. 10D1F.FcB was found to show significantly improved binding to human and mouse Fcγ and FcRn receptors compared to non-modified 10D1F.FcA or commercially available antibodies. ND=$K_D$ Not Determined due to low binding affinity.

Example 8

Characterisation of Humanised and Modified Clones 8.1 Analysis of Cell Surface Antigen-Binding by Flow Cytometry Wildtype (WT) HEK293 cells (which do not express high levels of HER3) and HEK293 cells transfected with vector encoding human HER3 (i.e. HEK293 HER O/E cells) were incubated with 10 μg/ml of humanised anti-HER3 antibody 10D1F.FcA (10D1F), anti-HER3 antibody 10D1 (10D1P) or isotype control antibody at 4° C. for 1.5 hr. The anti-HER3 antibody clone LJM716 (described e.g. in Garner et al., Cancer Res (2013) 73: 6024-6035, and Example 3.5) was included in the analysis as a positive control.

The cells were washed with buffer (PBS with 2 mM EDTA and 0.5% BSA) and resuspended in FITC-conjugated anti-FC antibody (Invitrogen, USA) at 10 μg/ml for 20 min at 4° C. Cells were washed again and resuspended in 200 μL of FACS flow buffer (PBS with 5 mM EDTA) for flow cytometric analysis using MACSQuant 10 (Miltenyi Biotec, Germany). Unstained WT and transfected HEK293 cells were included in the analysis as negative controls. After acquisition, all raw data were analyzed using Flowlogic software. Cells were gated using forward and side scatter profile percentage of positive cells was determined for native and overexpressing cell populations.

Figure 42A:
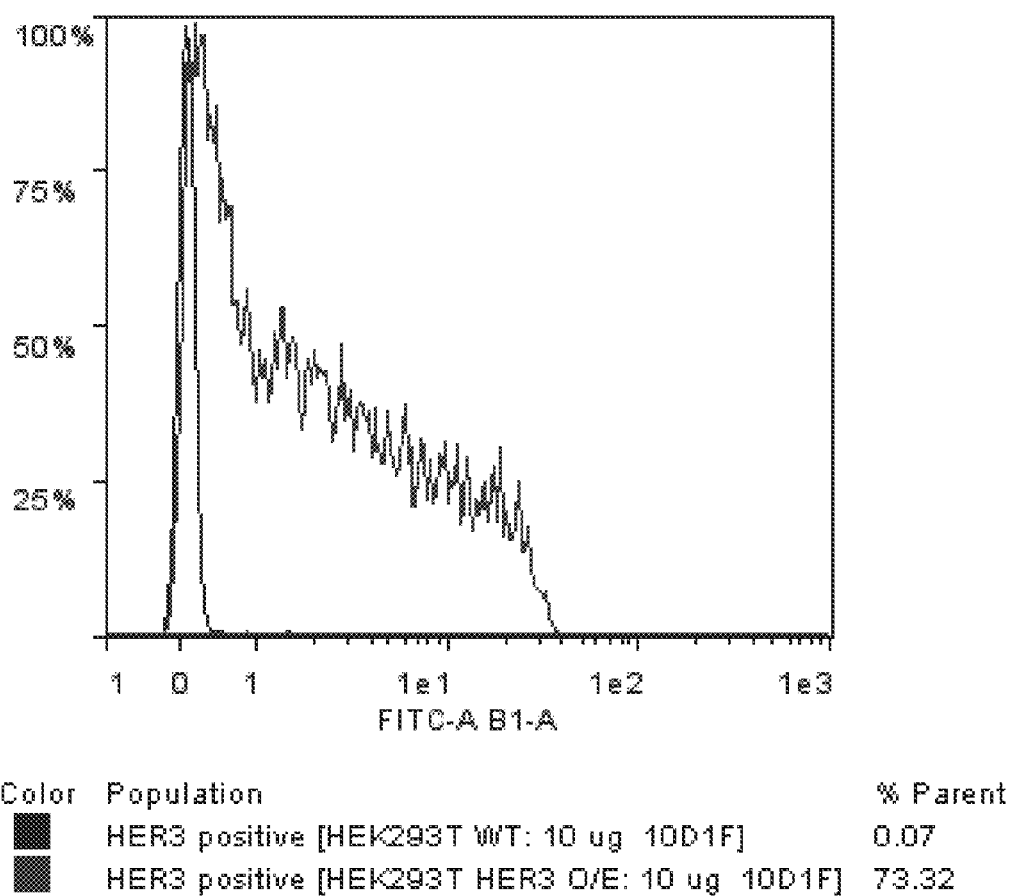
FIGS. 42A and 42B. Histograms showing staining of cells by anti-HER3 antibodies as determined by flow cytometry. Histograms show staining of HEK293 cells (which do not express HER3), or HEK293 HER3 overexpressing cells (HEK293 HER3 O/E) by (42A) anti-HER3 antibody clone 10D1F.FcA and (42B) anti-HER3 antibody clones 10D1 and LJM-716.
Figure 42B:
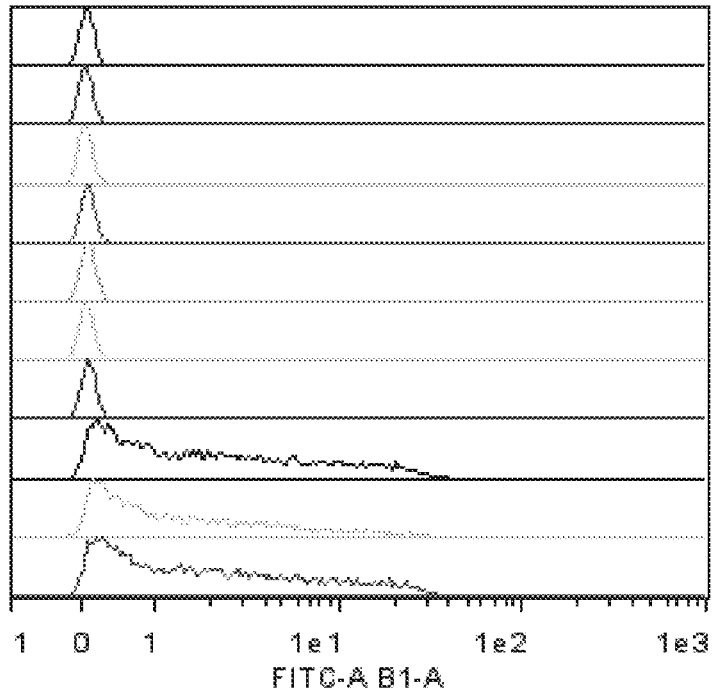

The results are shown in FIGS. 42A and 42B. Anti-HER3 antibody 10D1F.FcA was shown to bind to human HER3 with high specificity (42A). 10D1F.FcA, 10D1P and LJM716 were shown to bind to human HER3-expressing cells to a similar extent (42B).

8.2 ELISAs for Determining Antibody Specificity and Cross-Reactivity

ELISAs were used to confirm the binding specificity of the 10D1F.FcA antibody. The antibodies were analysed for their ability to bind to human HER3 polypeptide as well as human HER1 (EGFR) and human HER2 (Sino Biological Inc., China). Human IgG isotype and an irrelevant antigen were included as negative controls.

ELISAs were carried out according to standard protocols. Plates were coated with 0.1 μg/ml of target polypeptide in phosphate-buffered saline (PBS) for 16 h at 4° C. After blocking for 1 h with 1% BSA in Tris buffer saline (TBS) at room temperature, the anti-HER3 antibody was serially diluted with the highest concentration being 10 μg/ml, and added to the plate. Post 1 h incubation at room temperature, plates were washed three times with TBS containing 0.05% Tween 20 (TBS-T) and were then incubated with a HRP-conjugated anti-His antibody (Life Technologies, Inc., USA) for 1 h at room temperature. After washing, plates were developed with colorimetric detection substrate 3,3',5,5'-tetramethylbenzidine (Turbo-TMB: Pierce, USA) for 10 min. The reaction was stopped with 2M $H_2SO_4$, and OD was measured at 450 nM.

The results are shown in FIG. 43. Anti-HER3 antibody 10D1F.FcA was found not to bind to human HER2 or human HER1 (EGFR) even at high concentrations of the antibody.

The ability of 10D1F.FcA to bind HER4 was analysed using flow cytometry. Wildtype (WT) HEK293 cells (which do not express high levels of HER4) and HEK293 cells transfected with vector encoding human HER4 (i.e. HEK293 HER O/E cells) were incubated with 10 μg/ml of anti-HER3 antibody 10D1F.FcA (10D1F) or isotype control antibody (negative control) at 4° C. for 1.5 hr. The anti-HER3 antibody clones LJM716 (described e.g. in Garner et al., Cancer Res (2013) 73: 6024-6035) and MM-121 (seribantumab), as described in Example 3.5, were included in the analysis as positive control. Also included was a commercial anti-HER4 antibody (Novus, Cat: FAB11311P). Unstained HEK293 cells were included in the analysis as negative controls.

HEK293 cells were incubated with 10 μg/ml of each antibody for 1 hour at 4° C. Flow cytometry was performed as described above. Cells were contacted with FITC-conjugated anti-FC antibody (Invitrogen, USA) at for 30 min at 4° C.

The results are shown in FIG. 44. Anti-HER3 antibody 10D1F.FcA was found not to bind to cell-surface expressed HER4.

In addition, antibody 10D1F.FcA was analysed for its ability to bind to HER3 polypeptide homologues from mouse, rat and monkey (Sino Biological Inc., China), *M. musculus, R. norvegicus* and *M. cynomolgus* HER3 homologues share 91.1, 91.0 and 98.9% sequence identity respectively with human HER3 and the HER3 signalling pathways are conserved between the four species.

ELISAs were performed as above.

Figure 45:
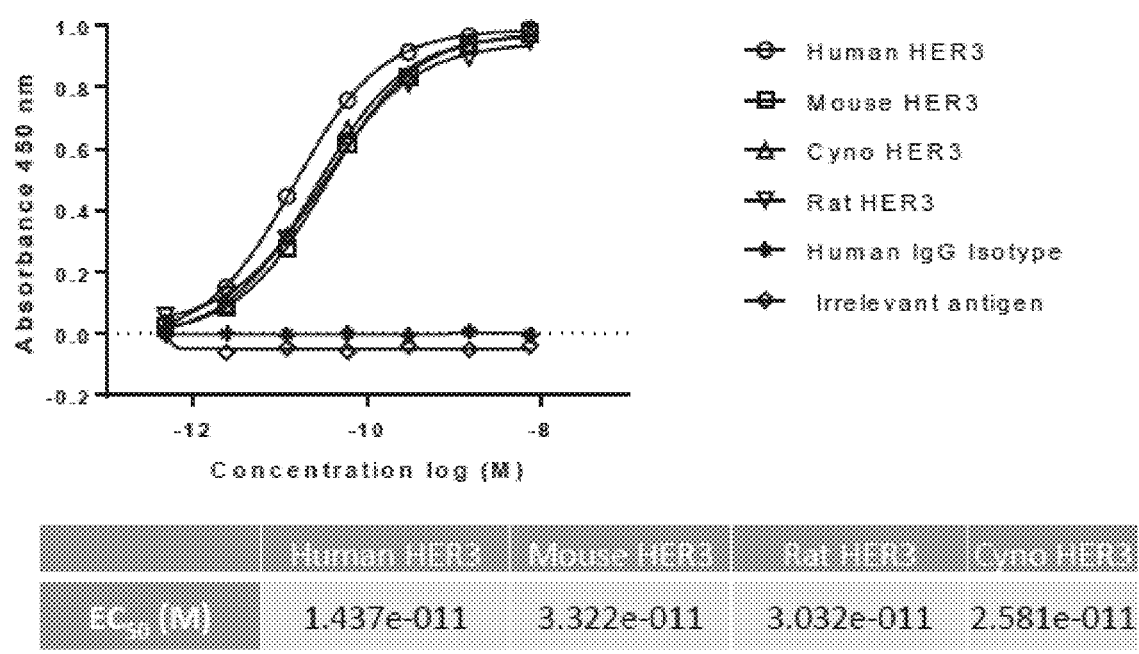
FIG. 45. Graph showing the results of ELISA analysis of binding of anti-HER3 antibody clone 10D1F.FcA to human, mouse, rat and cynomolgus macaque HER3. $EC_{50}$ values are shown.

The results are shown in FIG. 45. 10D1F.FcA antibody was found to bind with high affinity to HER3 cyno, mouse, rat and human orthologs, thus displaying substantial cross-reactivity between species.

8.3 Global Affinity Study Using Octet QK384 System

The anti-HER3 antibody clones 10D1F.FcA and 10D1F.FcB were analysed for binding affinity to human HER3.

Bio-Layer Interferometry (BLI) experiments were performed using the Octet QK384 system (ForteBio). Antibodies (25 nM) were coated onto anti-Human IgG Capture (AHC) Octet sensor tips (Pall ForteBio, USA). Binding was detected using titrated HIS-tagged human HER3 in steps of baseline (60 s), loading (120 s), baseline2 (60 s), association (120 s), dissociation (FcA 120 s, FcB 600 s) and regeneration (15 s). Antigen concentrations are shown in the table in FIGS. 46A and 46B. Sensorgrams were analysed as described in Example 3.3. Values were obtained for association ($K_{on}$), dissociation ($K_{off}$) rate constants and the equilibrium dissociation constant ($K_D$).

Figure 46A:
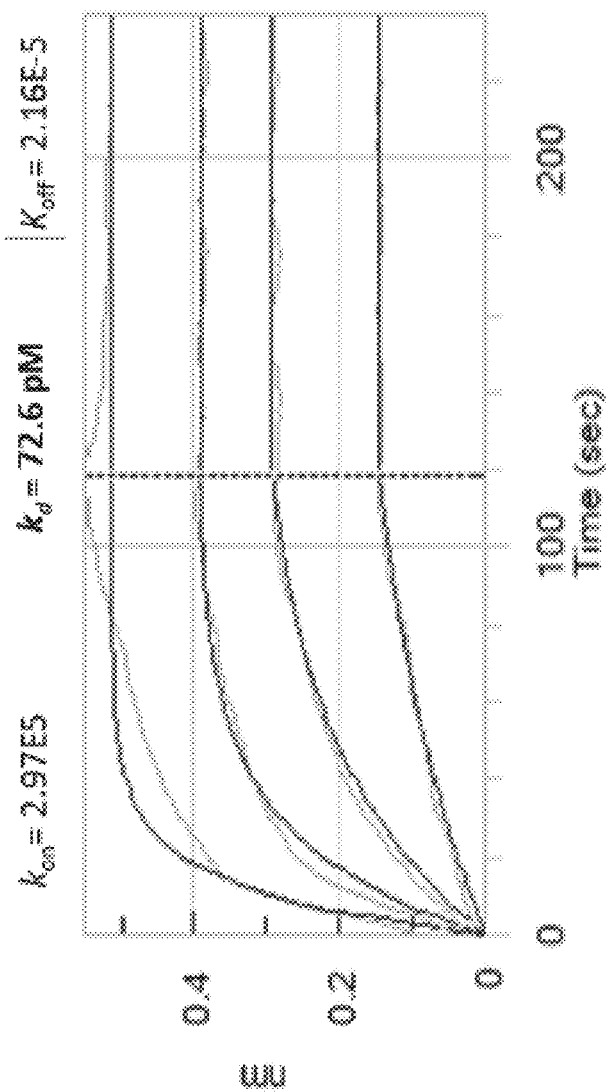
FIGS. 46A and 46B. Representative sensorgrams showing the results of analysis of affinity of binding of anti-HER3 antibody clones (46A) 10D1F.FcA and (46B) 10D1F.FcB to human HER3. Kon, Koff and $K_D$ are shown.
Figure 46B:
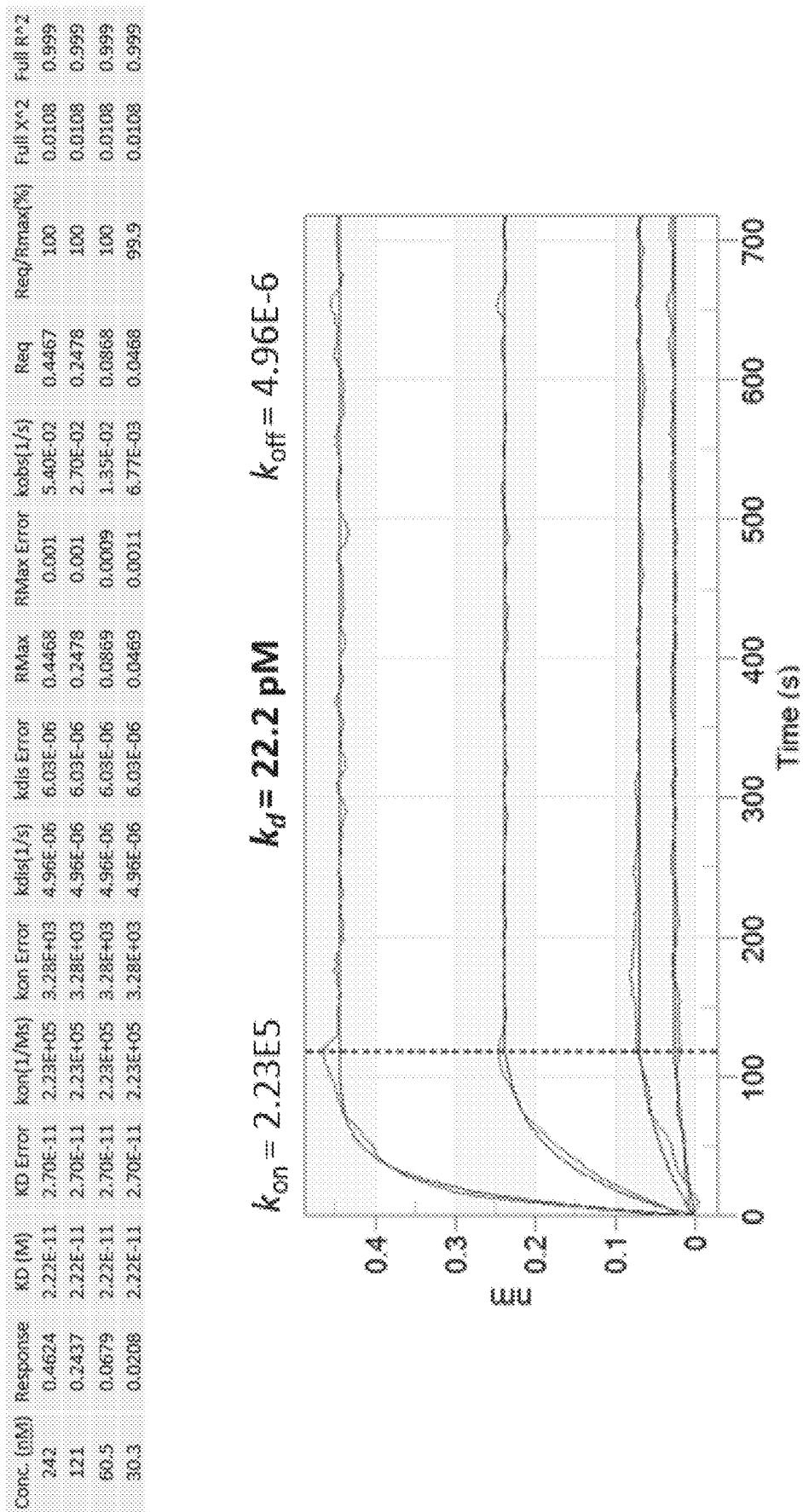

Representative sensorgrams for the analysis of clones 10D1F.FcA and 10D1F.FcB are shown in FIGS. 46A and 46B. 10D1F.FcA binds to human HER3 with a high affinity of $K_D$=72.6 pM (46A). 10D1F.FcB binds to human HER3 with a high affinity of $K_D$=22.2 pM (46B).

8.4 Analysis of Thermostability by Differential Scanning Fluorimetry

Differential Scanning Fluorimetry was performed for antibodies 10D1F.FcA and 10D1F.FcB as described in Example 3.4.

Figure 47A:
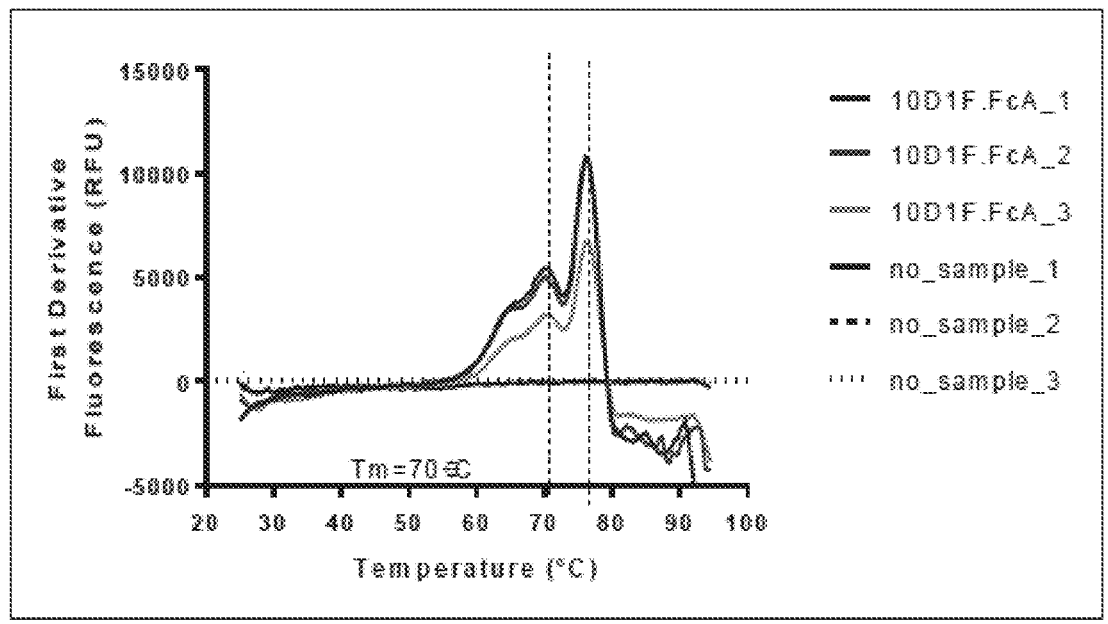
FIGS. 47A and 47B. Graph showing the results of analysis of stability of anti-HER3 antibody clones (47A) 10D1F.FcA and (47B) 10D1F.FcB by Differential Scanning Fluorimetry analysis.

The first derivative of the raw data obtained for Differential Scanning Fluorimetry analysis of the thermostability of antibody clone 10D1F.FcA is shown in FIG. 47A. Three different samples of the antibody were analysed and the Tm was determined to be 70.0° C.

Figure 47B:
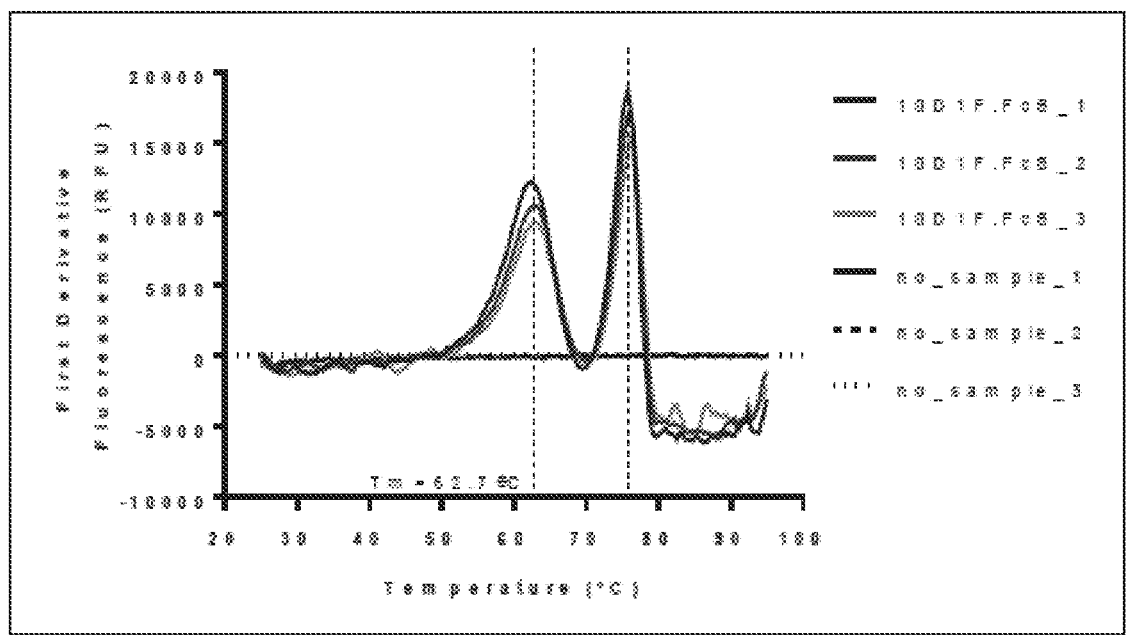

The first derivative of the raw data obtained for Differential Scanning Fluorimetry analysis of the thermostability of antibody clone 10D1F.FcB is shown in FIG. 47B. Three different samples of the antibody were analysed and the Tm was determined to be 62.7° C.

8.5 Antibody Purity Analysis

The purity of antibodies 10D1F.FcA and 10D1F.FcB was analysed by size exclusion chromatography (SEC). 150 µg of 10D1F.FcA in 500 µl PBS pH 7.2 or 150 µg of 10D1F.FcB in 500 µl PBS pH 7.45 was injected on a Superdex 200 10/30 GL column in PBS running buffer at a flow rate of 0.75 min/ml or 0.5 min/ml, respectively, at room temperature and the A280 of flow through was recorded.

Figure 48A:
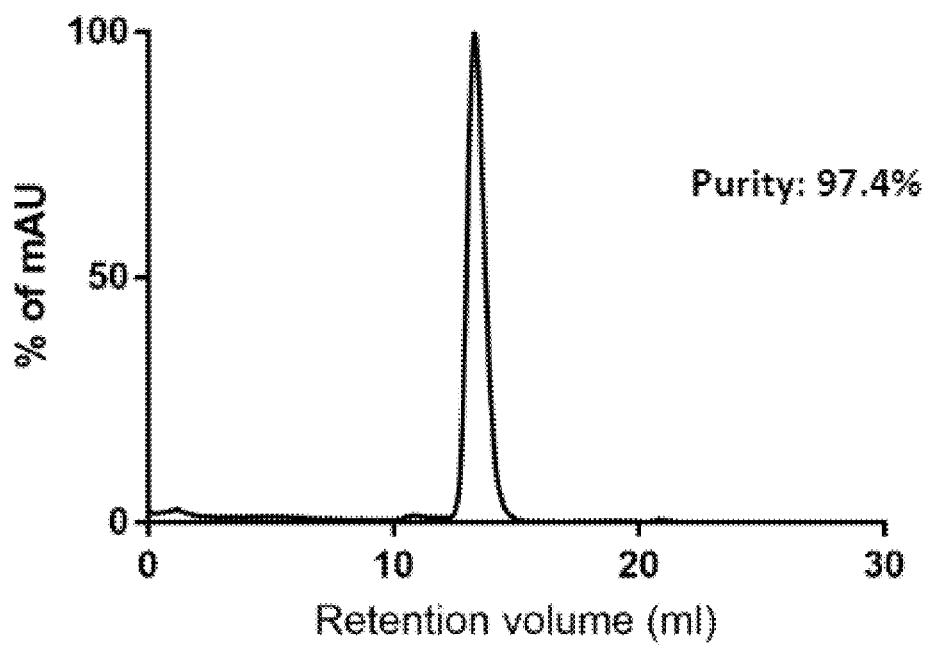
FIGS. 48A and 48B. Graph showing the results of purity analysis of anti-HER3 antibody clones (48A) 10D1F.FcA and (48B) 10D1F.FcB by size exclusion chromatography.
Figure 48B:
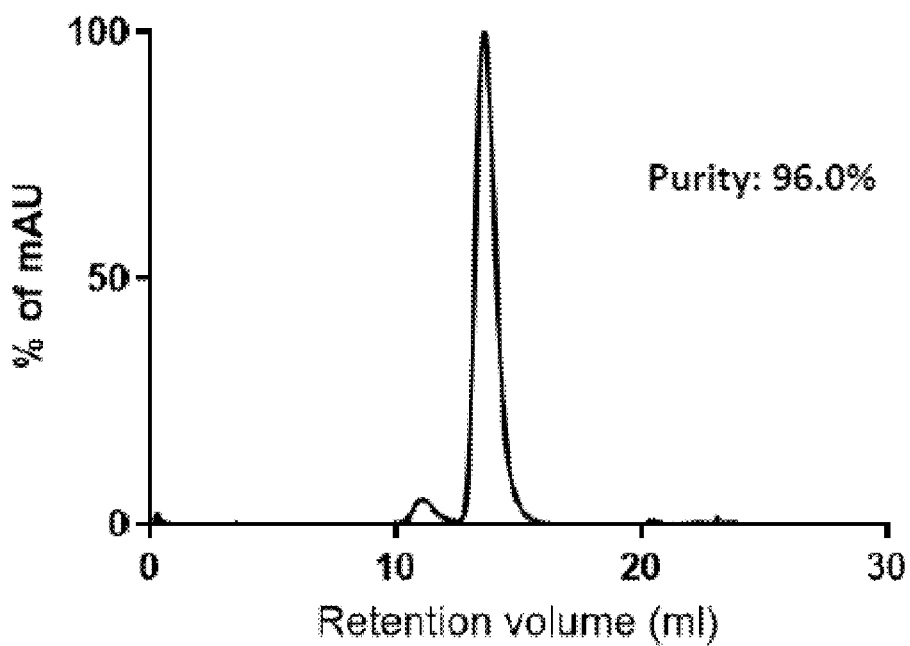

The results are shown in FIGS. 48A (10D1F.FcA) and 48B (10D1F.FcB).

8.6 Analysis of Anti-HER3 Antibody 10D1F.FcA Epitope

Anti-HER3 antibody 10D1F.FcA was analysed to determine whether it competes with anti-HER3 antibodies M-05-74 or M-08-11 (Roche) for binding to HER3. Epitopes of M-05-74 and M-08-11 were both mapped to the β-hairpin structure of the HER3 dimerisation arm located at domain II. M-08-11 does not bind to HER4 whereas M-05-74 recognises the HER4 dimerisation arm. Binding of M-05-74 and M-08-11 to HER3 is ligand (NRG) independent.

BLI experiments were performed as described in Example 3.5 with one alteration: 400 nM of competing antibodies were used. The variable regions of M-05-74 and M-08-11 antibodies were coned in the PDZ vector having human IgG1 and IgKappa Fc backbone.

The results of the analysis are shown in FIGS. 49A and 49B. Anti-HER3 10D1F.FcA antibody was found not to compete with M-05-74 or M-08-11 for binding to HER3. 10D1F.FcA was found to bind a distinct and topologically distant epitope of HER3 compared to M-05-74 and M-08-11. Binding of 10D1F.FcA to HER3 is ligand (NRG) independent.

Conclusions:
Binding of 10D1F.FcA to human HER3 can be achieved in a ligand-independent manner.
10D1F.FcA binding epitope is distinct and topologically distant from that of M-05-74 and M-08-11.

8.7 Inhibition of Dimerisation of HER2-HER3 and EGFR-HER3

Anti-HER3 antibody 10D1F.FcA was analysed for its ability to inhibit heterodimerisation of HER3 and HER2.

Plate-based ELISA dimerisation assays were carried out according to standard protocols. Plates were coated with 1 µg/ml HER2-Fc protein. After blocking and washing, the plate was incubated with different concentrations of candidate antibodies 10D1F.FcA, MM-121, LJM716, Pertuzumab, Roche M05, Roche M08 or isotype control and constant HER3 His 2 µg/ml and NRG 0.1 µg/ml for 1 hour. Plates were then washed and incubated for 1 hour with secondary anti-HIS HRP antibody. Plates were washed, treated with TMB for 10 mins and the reaction was stopped using 2M $H_2SO_4$ stop solution. The absorbance was read at 450 nm.

Figure 52:
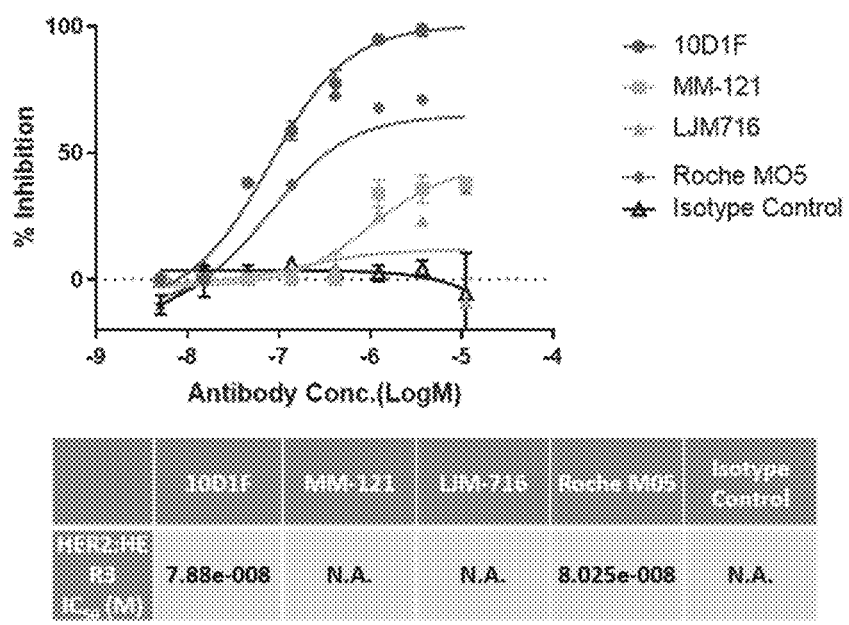
FIG. 52. Graph and table showing the results of analysis of the inhibition of interaction between HER2 and HER3 by anti-HER3 antibody clone 10D1F.FcA and antibodies MM-121, LJM-716 and Roche M05 as determined by ELISA.

The results are shown in FIG. 52. Anti-HER3 antibody clone 10D1F.FcA was found to directly inhibit interaction between HER2 and HER3 in a dose dependent fashion.

In another assay, inhibition of dimerization was detected using PathHunter® Pertuzumab Bioassay Kit (DiscoverX, San Francisco, USA). HER2 and HER3 overexpressing U20S cells were thawed using 1 ml of pre-warmed CP5 media and 5K cells were seeded per at 37° C., 5% $CO_2$ for 4 hrs. Cells were treated with serially diluted concentrations of 10D1F.FcA, Seribantumab, or Pertuzumab starting from 25 µg/ml with an 8-point serial dilution. After 4 hrs incubation, 30 ng/ml of heregulin-µ2 was added to each well and the plates were further incubated for 16 hrs. Following incubation, 10 µL PathHunter bioassay detection reagent 1 was added and incubated for 15 mins at room temperature in the dark, followed by addition of 40 µL PathHunter bioassay detection reagent 2 which was then incubated for 60 mins at room temperature in the dark. Plates were read using Synergy4 Biotek with 1 second delay.

10D1F.FcA was found to have an $EC_{50}$ value of 3.715e-11 for inhibition of HER2-HER3 heterodimerisation. In the same assay, the comparative $EC_{50}$ value for Seribantumab/MM-121 was found to be 6.788e-10 and the comparative $EC_{50}$ value for Pertuzumab was found to be 2.481e-10.

Anti-HER3 antibody 10D1F.FcA was analysed for its ability to inhibit heterodimerisation of EGFR and HER3.

Plate-based ELISA dimerisation assays were performed according to standard protocols. Plate was coated with 1

µg/ml human EGFR-His. After blocking and washing, the plate was incubated with different concentrations of candidate antibodies 10D1F.FcA, MM-121, LJM716, Pertuzumab, or isotype control with constant HER3-biotin 4 µg/ml and NRG 0.1 µg/ml for 1 hour. Plates were then washed and incubated for 1 hour with secondary anti-avidin HRP antibody. Plates were washed, treated with TMB for 10 mins and the reaction was stopped using 2M $H_2SO_4$ stop solution. The absorbance was read at 450 nm.

Figure 53:
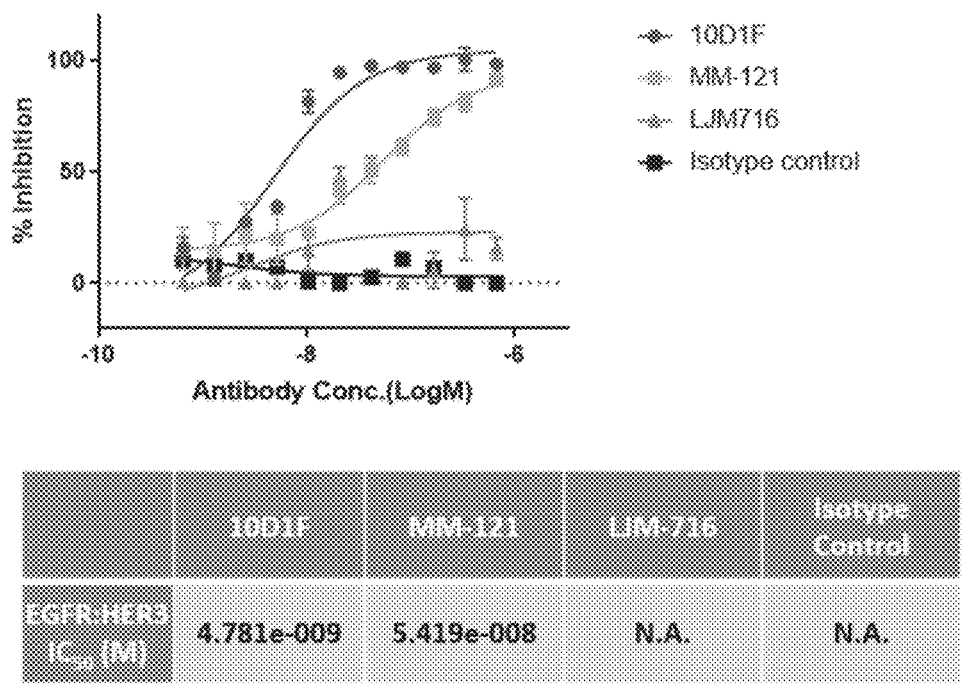
FIG. 53. Graph and table showing the results of analysis of the inhibition of interaction between EGFR and HER3 by anti-HER3 antibody clone 10D1F.FcA and antibodies MM-121 and LJM716, as determined by ELISA.

The results are shown in FIG. 53. Anti-HER3 antibody clone 10D1F.FcA was found to directly inhibit interaction between EGFR and HER3 in a dose dependent fashion.

8.8 Analysis of Ability to Induce ADCC

Anti-HER3 antibody clones 10D1F.FcA and 10D1F.FcB were analysed for their ability to induce antibody-dependent cell-mediated cytotoxicity (ADCC).

Target cells (HEK293 overexpressing HER3) were plated in U-bottom 96-well plates at a density of 20,000 cells/well. Cells were treated with a dilution series (50,000 ng/ml-0.18 ng/ml) of one of 10D1F.FcA, 10D1F.FcB, 10D1F.FcA_N297Q (silent form), LJM-716, Seribantumab (MM-121) or left untreated, and incubated at 37° C. and 5% $CO_2$ for 30 min. Effector cells (Human Natural Killer Cell Line No-GFP-CD16.NK-92; 176V) were added to the plate containing target cells at a density of 60,000 cells/well.

The following controls were included: Target cell maximal LDH release (target cells only), spontaneous release (target cells and effector cells without antibody), background (culture media only). Plates were spun down and incubated at 37° C. and 5% $CO_2$ for 21 hrs.

LDH release assay (Pierce LDH Cytotoxicity Assay Kit); before the assay, 10 µl of Lysis Buffer (10×) were added to target cell maximal LDH release controls and incubated at 37° C. and 5% $CO_2$ for 20 min. After incubation, plates were spun down and 50 µL of the supernatant were transferred to clear flat-bottom 96-well plates. Reactions were started by addition of 50 µl of LDH assay mix containing substrate to the supernatants and incubated at 37° C. for 30 min. Reactions were stopped by addition of 50 µl of stop solution and absorbance was recorded at 490 nm and 680 nm with a BioTek Synergy HT microplate reader.

For data analysis, absorbance from test samples was corrected to background and spontaneous release from target cells and effector cells. Percent cytotoxicity of test samples was calculated relative to target cell maximal LDH release controls and plot as a function of antibody concentration.

Figure 54:
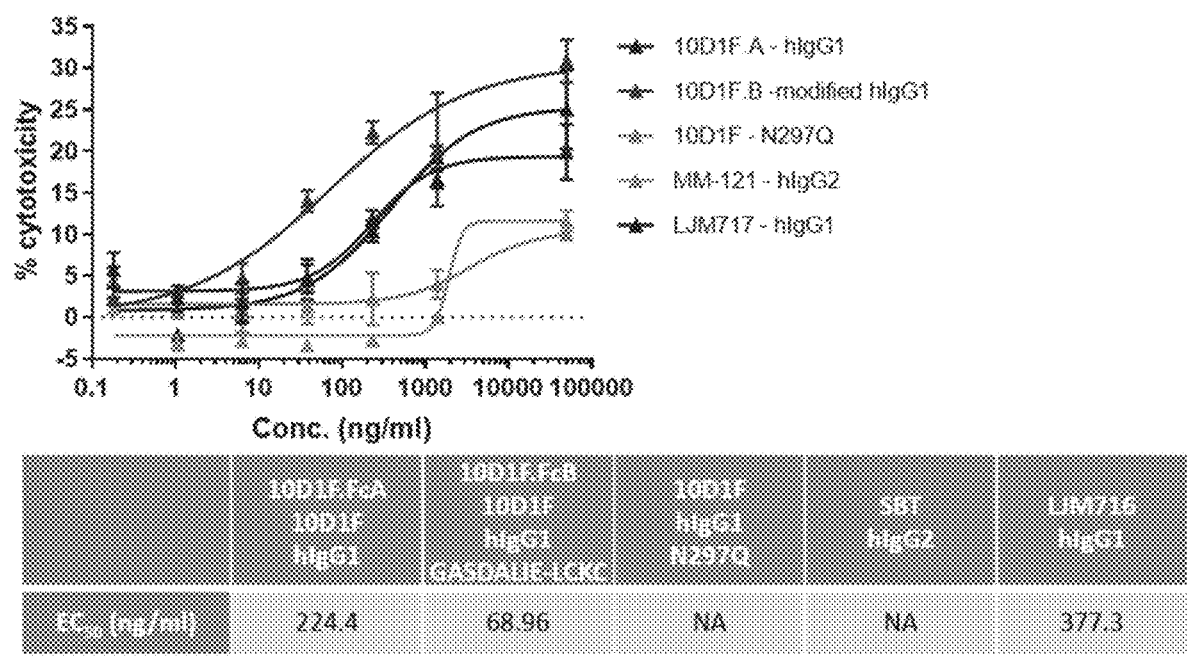
FIG. 54. Graph and table showing the results of analysis of the ability of anti-HER3 antibody clones 10D1F.FcA (10D1F.A), 10D1F.FcB (10D1F.B), 10D1F-hIgG1 (N297Q) and anti-HER3 antibodies LJM-716 and Seribantumab (MM-121), to induce antibody-dependent cell-mediated cytotoxicity (ADCC). $EC_{50}$ values are shown.

The results are shown in FIG. 54. Anti-HER3 antibody 10D1F.FcB was found to induce potent ADCC activity against HER3 overexpressing cells in a dose dependent fashion.

8.9 Inhibition of HER3-Mediated Signalling

Anti-HER3 antibody 10D1F.FcA was analysed for its ability to inhibit HER-3 mediated signalling in vitro in cancer cell lines.

N87, FaDu or OvCAR8 cells were seeded in wells in a 6 well plate with 10% serum overnight at 37° C. with 5% $CO_2$. Cells were starved with 0.2% FBS culture medium for 16 hrs, and were then treated for 0.5 hours with different antibodies at IC50 corresponding to the cell line. Antibodies tested were: 10D1F.FcA (10D1), Seribantumab (SBT), Elegemtumab (LJM), Pertuzumab (PTM), Cetuximab (CTX), and Trastuzumab (TZ).

Before harvesting, cells were stimulated with 100 ng/mi of NRG1. Protein extracted from cell lines was quantified using standard Bradford protein assay. Protein samples (50 µg) were fractionated by SDS-PAGE and transferred to nitrocellulose membrane. Membranes were then blocked and immunoblotted with the indicated antibodies. The results were visualized via Bio-Rad Clarity Western ECL substrate. The blots were quantified using densiometric analysis and data was normalised to beta actin.

Figure 55A:
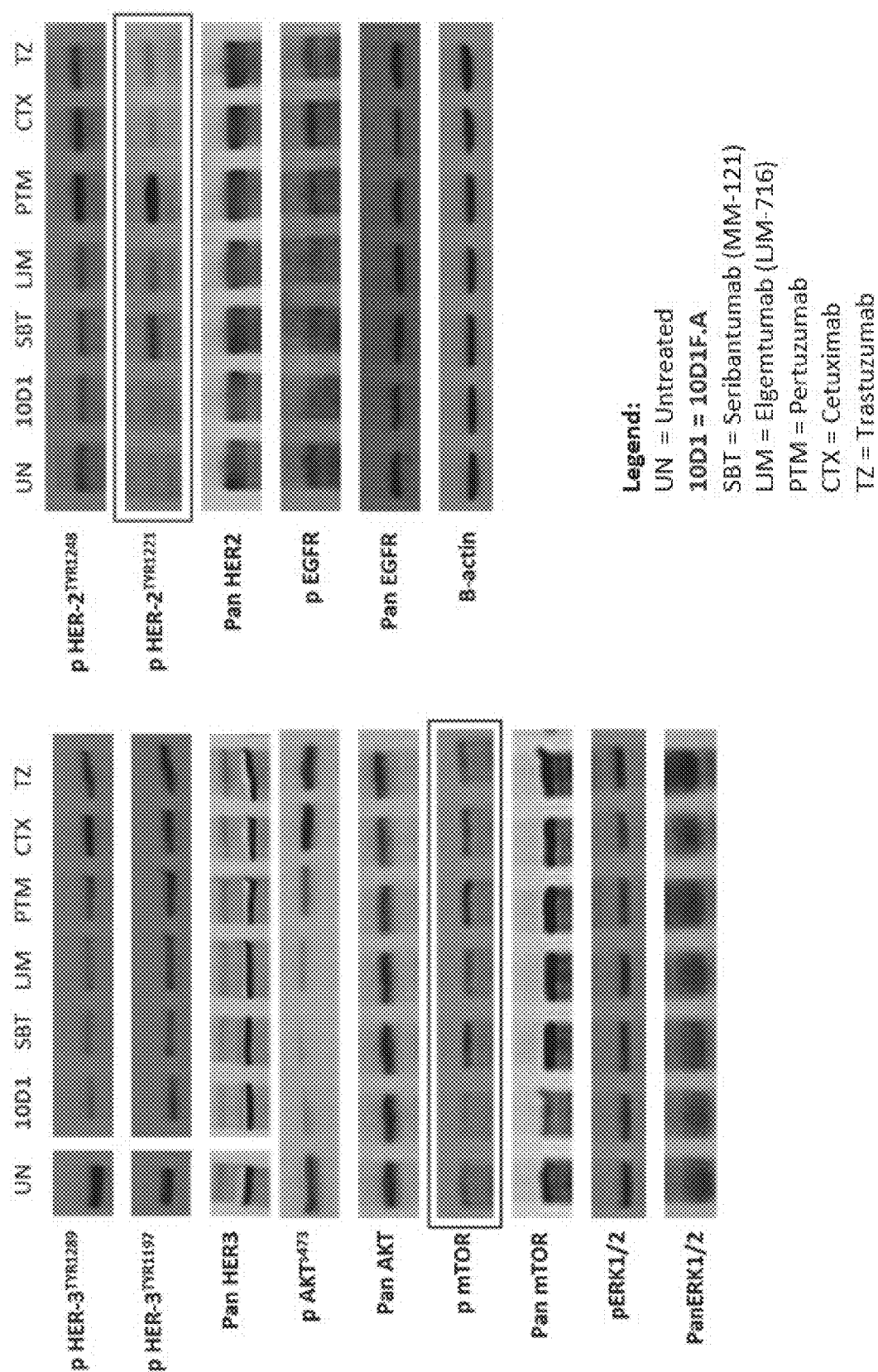
FIGS. 55A to 55C. Images showing the results of analysis of the effect of anti-HER3 antibody treatment on HER3-mediated signalling in (55A) N87, (55B) FaDu and (55C) OvCar8 cells by phospho-western blot.
Figure 55B:
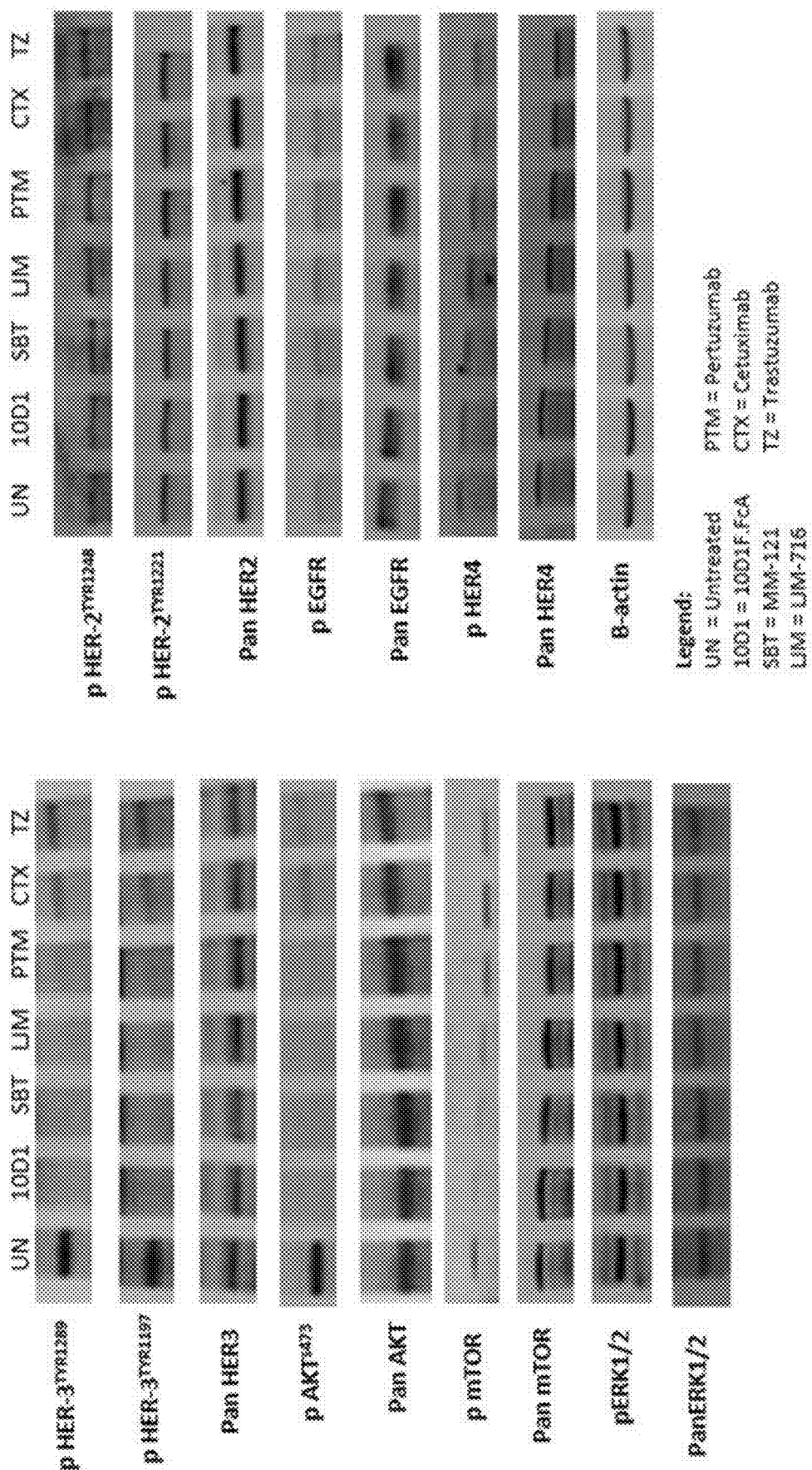
Figure 55C:
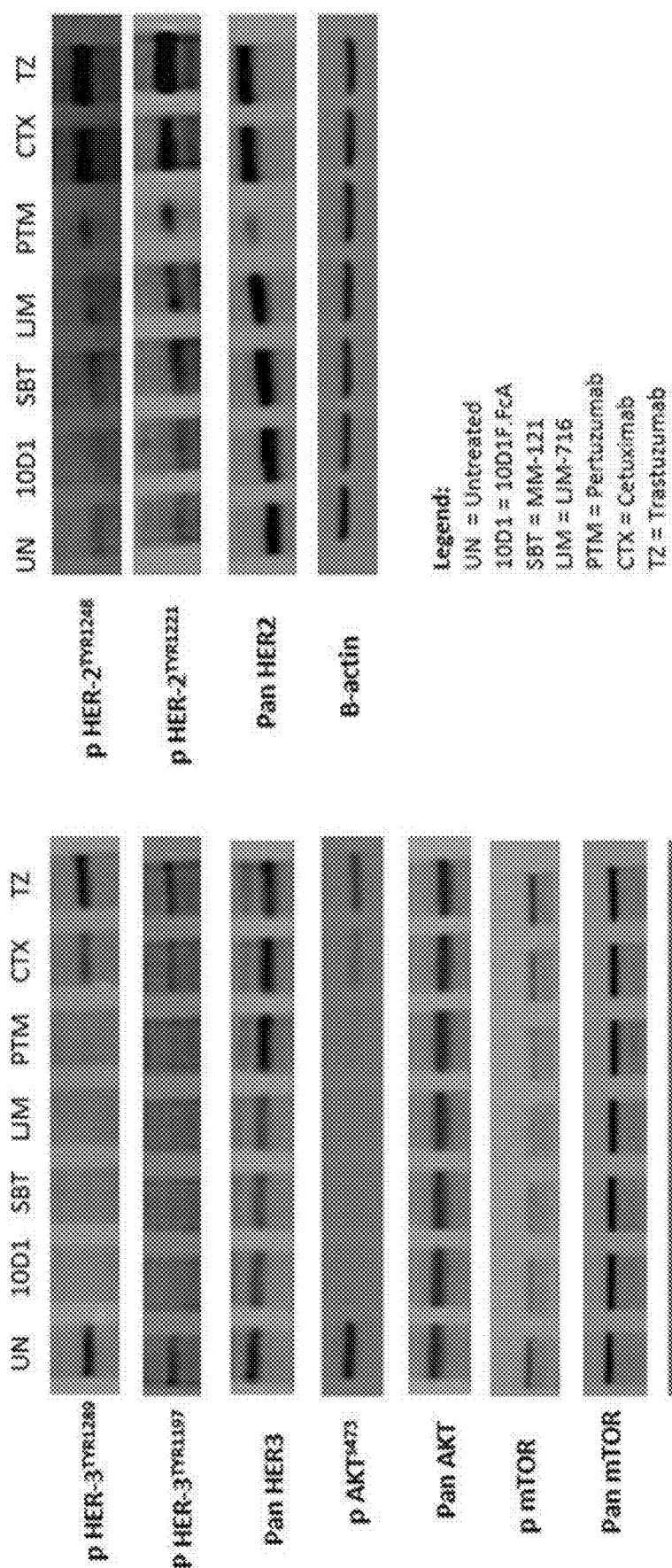

The results are shown in FIGS. 55A to 55C. Anti-HER3 antibody 10D1F.FcA was found to inhibit HER3 phosphorylation and downstream signalling in N87 (55A), FaDu (55B), OvCar8 (55C) and A549 (55D) cell lines.

For the experiments using N87 cells, A549 cells, OvCar8 cells and FaDu cells total RNA was extracted at 16 hrs post antibody treatment was analysed to determine pathway activation based on the level of expression of key signal transduction pathway proteins by gene set enrichment analysis. The results of the analysis are shown in FIGS. 63A to 63D. 10D1F.FcA was the most effective inhibitor of downstream signalling.

Figure 64:
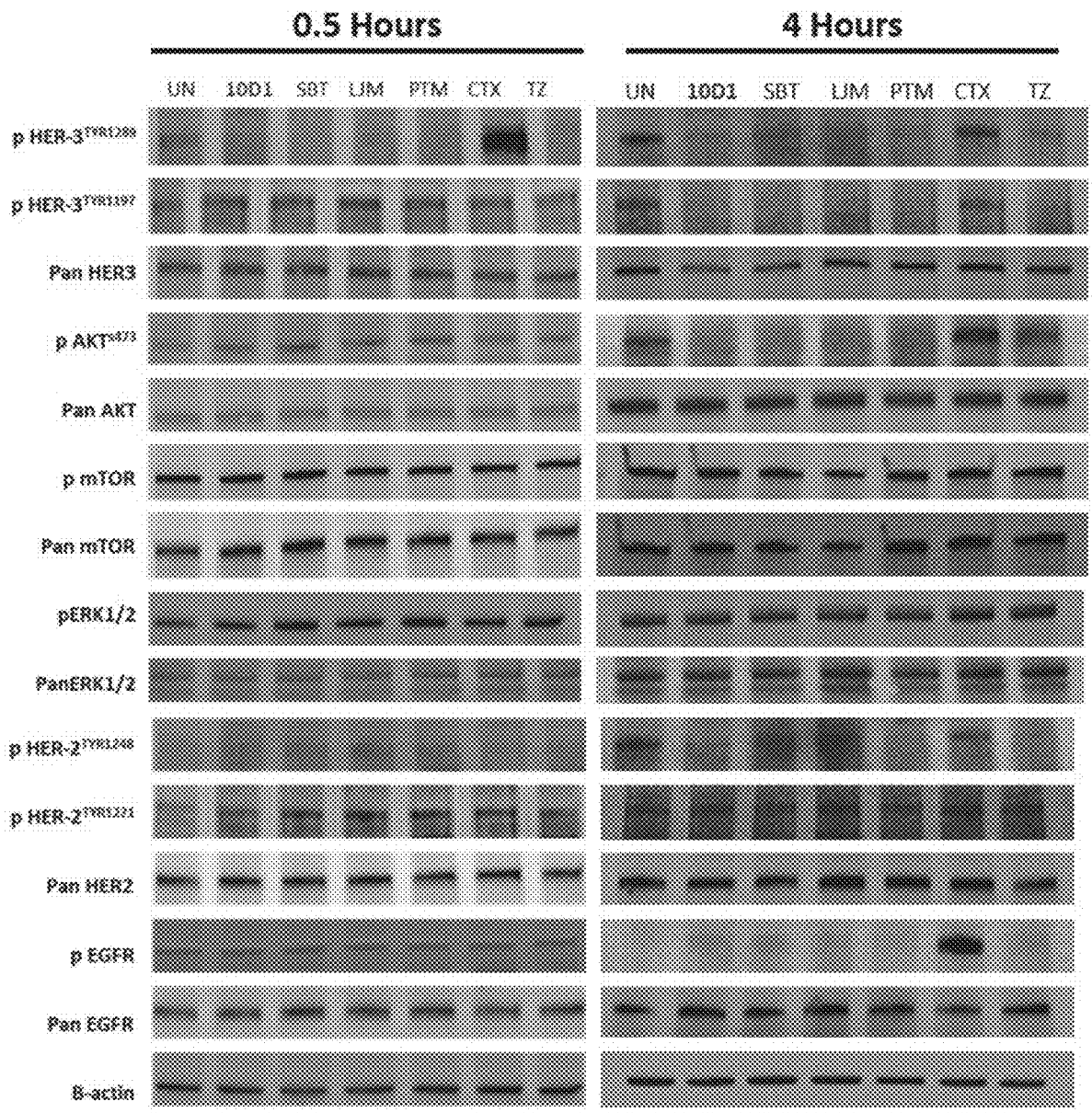
FIG. 64. Images showing the results of analysis of the effect of anti-HER3 antibody treatment on HER3-mediated signalling in A549 cells by phospho-western blot, at the indicated time points.

In further experiments using A549 cells, in vitro phosphorylation assays were performed as above except that the cells were treated for 0.5 hours or 4 hours with the different antibodies. The results are shown in FIG. 64.

Example 9

Analysis of Humanised and Modified Clones In Vitro and In Vivo 9.1 Pharmacokinetic Analysis Mice Female NCr nude mice approximately 6-8 weeks old were housed under specific pathogen-free conditions and treated in compliance with the Institutional Animal Care and Use Committee (IACUC) guidelines.

500 µg anti-HER3 antibody 10D1F.FcA or 10D1F.FcB was administered and blood was obtained from 4 mice by cardiac puncture at baseline (−2 hr), 6 hr, 24 hr, 96 hr, 168 hr and 336 hr after administration. Antibody in the serum was quantified by ELISA.

The parameters for the pharmacokinetic analysis were derived from a non-compartmental model: maximum concentration ($C_{max}$), AUC (0-336 hr), AUC (0-infinity), Half-life ($t_{1/2}$), Clearance (CL), Volume of distribution at steady state ($V_{ss}$).

Figure 56A:
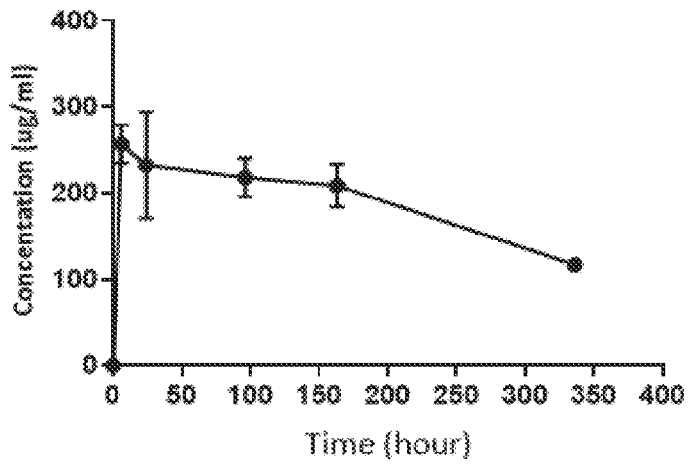
FIGS. 56A and 56B. Graph and tables showing the results of pharmacokinetic analysis of anti-HER3 antibody clones (56A) 10D1F.FcA and (56B) 10D1F.FcB in mice. Parameters: maximum concentration ($C_{max}$), $T_{max}$, AUC (0-336 hr), AUC (0-infinity), Half-life ($t_{1/2}$), Clearance (CL), Volume of distribution at steady state ($V_{ss}$).
Figure 56B:
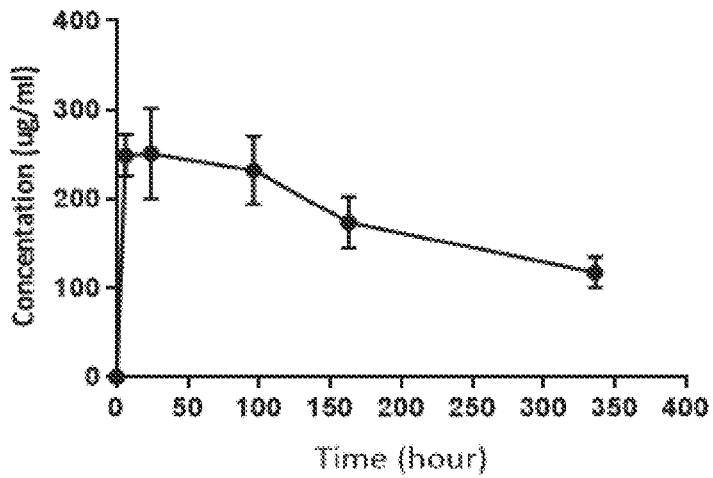

The results are shown in FIGS. 56A and 56B. Anti-HER3 antibody clone 10D1F.FcA was found to have a half-life of 253 hours (56A) and anti-HER3 antibody clone 10D1F.FcB was found to have a half-life of 273 hours (56B) in NCr nude mice.

Rats

10D1F variants were analysed to determine a single dose pharmacokinetic profile in female Sprague Dawley rats with mean weight of 320 g.

Antibody clones 10D1F.FcA and 10D1F.FcB were administered in a single dose of 4 mg (~10 mg/kg), 10 mg (~25 mg/kg), 40 mg (~100 mg/kg) or 100 mg (~250 mg/kg) via tail vein slow i.v. injection. Vehicle was administered as a negative control. Blood from 2 rats per treatment was obtained at baseline (−24 hr), 6 hr, 24 hr, 96 hr, 168 hr and 336 hr after administration. Antibody in the serum was quantified by ELISA.

The parameters for the pharmacokinetic analysis were derived from a non-compartmental model: maximum concentration ($C_{max}$), AUC (0-336 hr), AUC (0-infinity), Half-life ($t_{1/2}$), Clearance (CL), Volume of distribution at steady state ($V_d$).

Figure 57A:
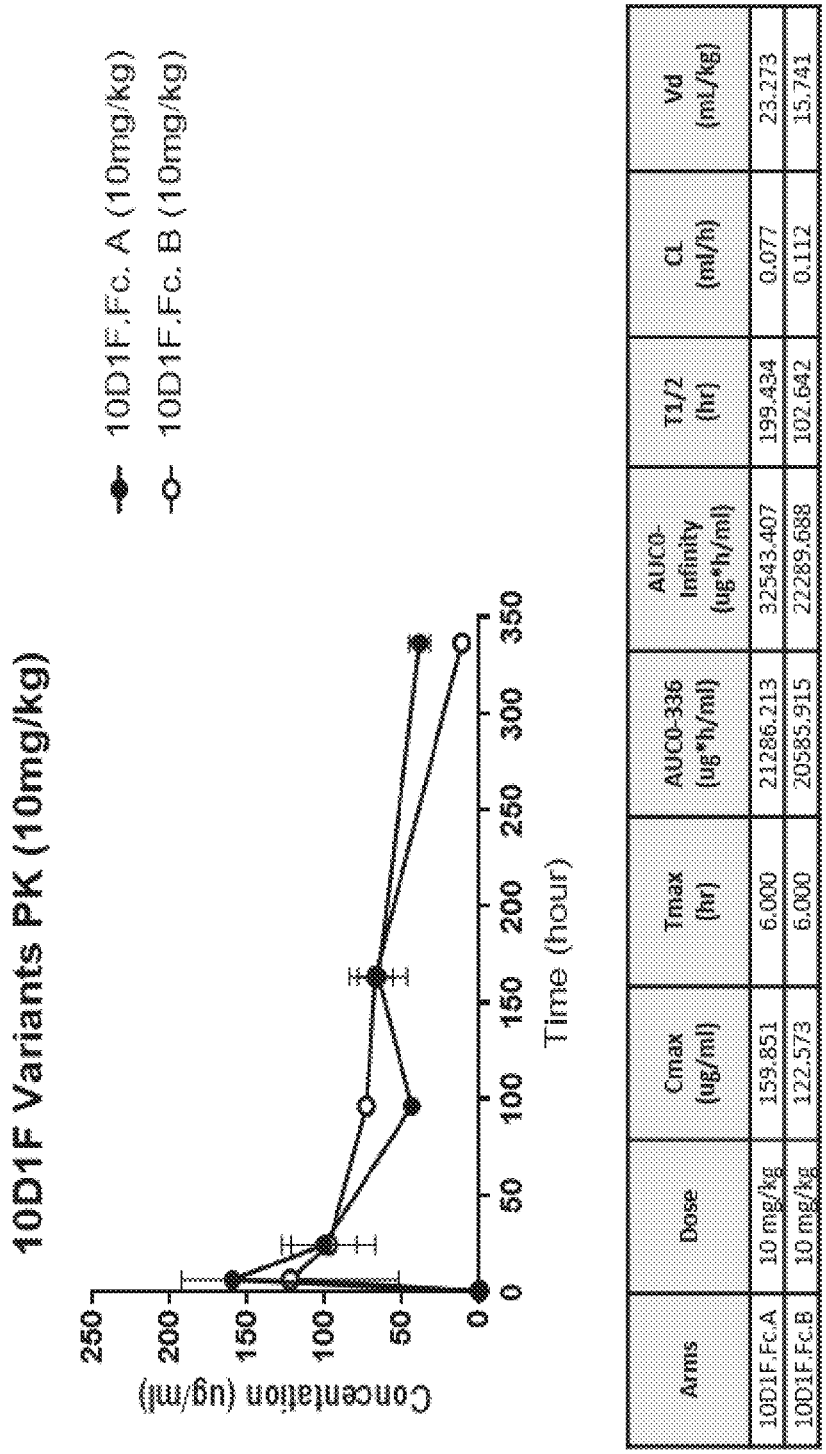
FIGS. 57A to 57D. Graph and tables showing the results of pharmacokinetic analysis of anti-HER3 antibody clones 10D1F.FcA and 10D1F.FcB at (57A) 10 mg/kg, (57B) 25 mg/kg, (57C) 100 mg/kg and (57D) 250 mg/kg in rats. Parameters: maximum concentration ($C_{max}$), $T_{max}$, AUC (0-336 hr), AUC (0-infinity), Half-life ($t_{1/2}$), Clearance (CL), Volume of distribution at steady state ($V_{ss}$).
Figure 57B:
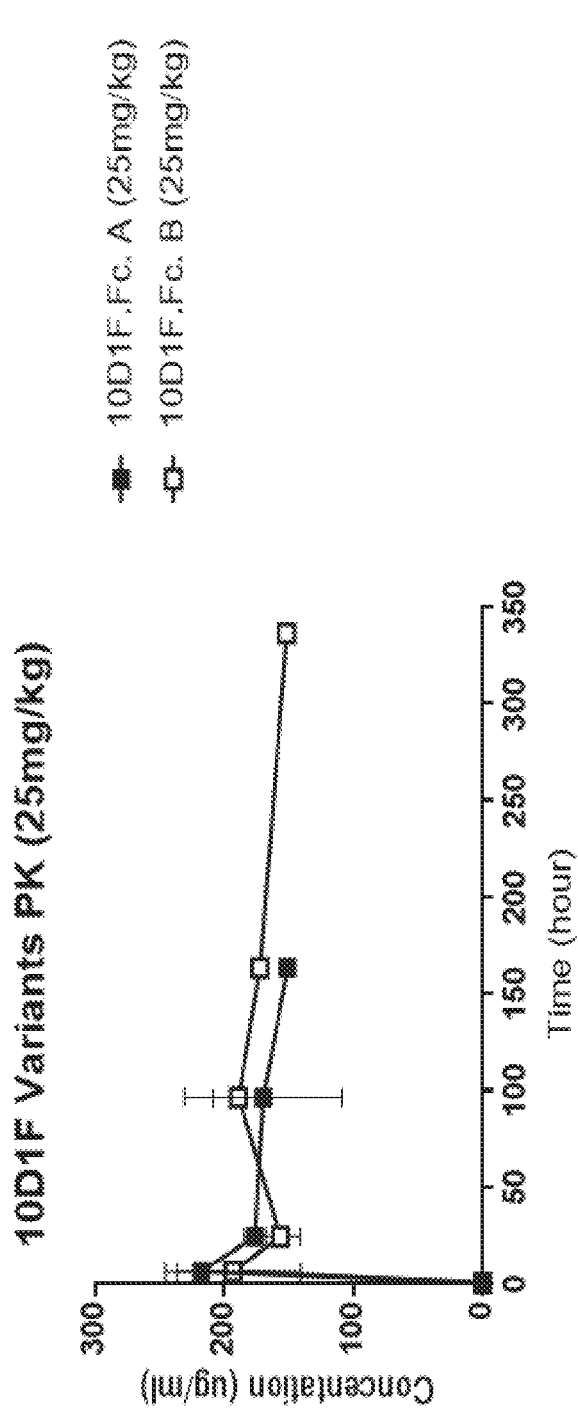
Figure 57C:
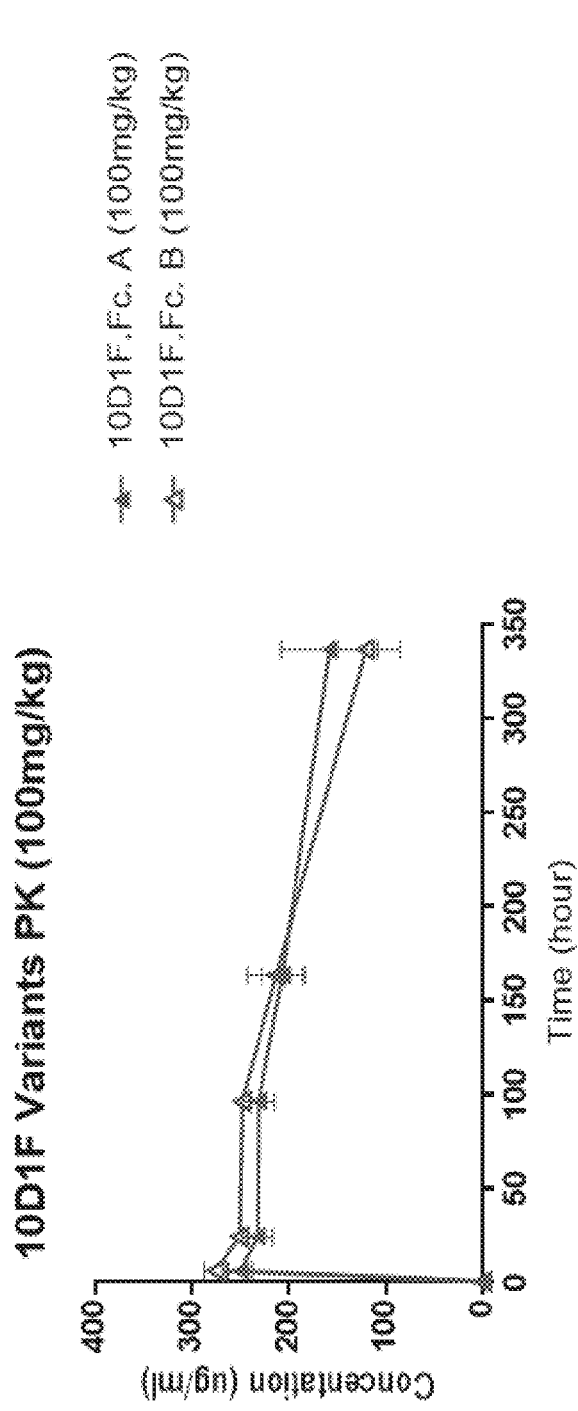
Figure 57D:
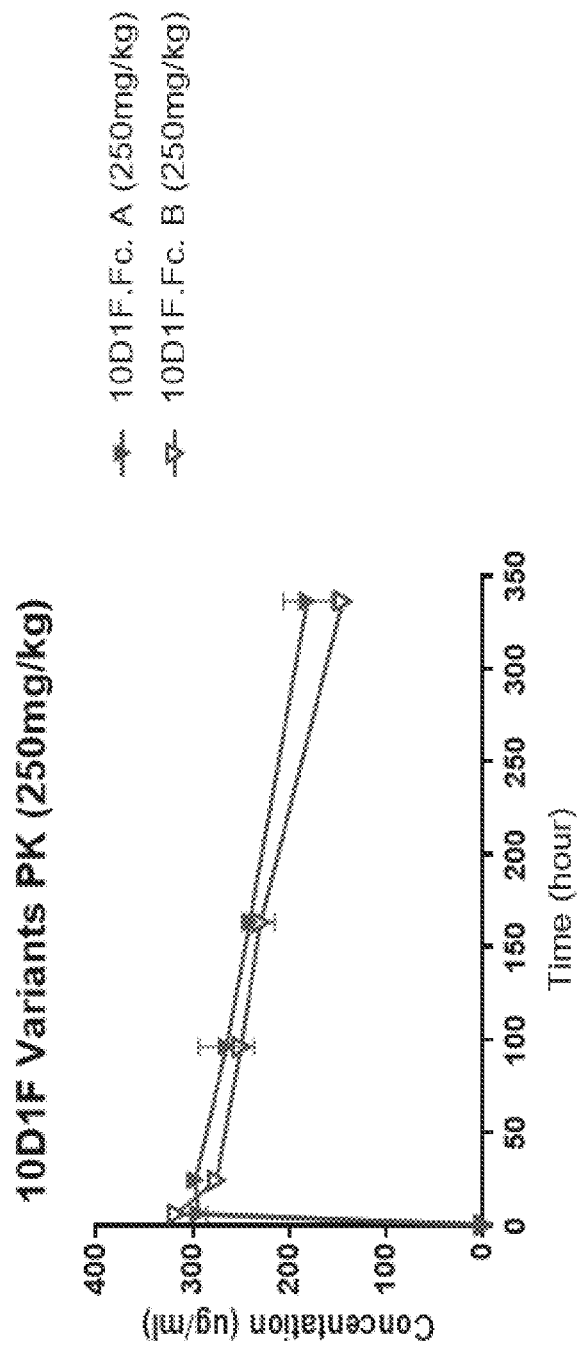

The results are shown in FIGS. 57A (10 mg/kg), 57B (25 mg/kg), 57C (100 mg/kg) and 57D (250 mg/kg).

9.2 Safety Immunotoxicity

The toxicological effects of 10D1F.FcA and 10D1F.FcB were analysed.

Mice 6-8 week old female BALB/c mice (20-25 g) were injected intraperitoneally with a single dose of either 10D1F.FcA and 10D1F.FcB at one of doses: 200 ug (~10 mg/kg), 500 ug (~25 mg/kg), 2 mg (~100 mg/kg), or 5 mg (~250 mg/kg), or an equal volume of PBS. 3 mice were injected with each treatment, 4 mice were injected with PBS control. Blood samples were obtained at 96 hours post injection and analysed for RBC indices (total RBC count, haematocrit, haemoglobin, platelet count, mean corpuscular volume, mean corpuscular haemoglobin, mean corpuscular haemoglobin concentration) and WBC indices (total WBC count, lymphocyte count, neutrophil count, monocyte count). Analysis was performed using a HM5 Hematology Analyser.

Figure 58A:
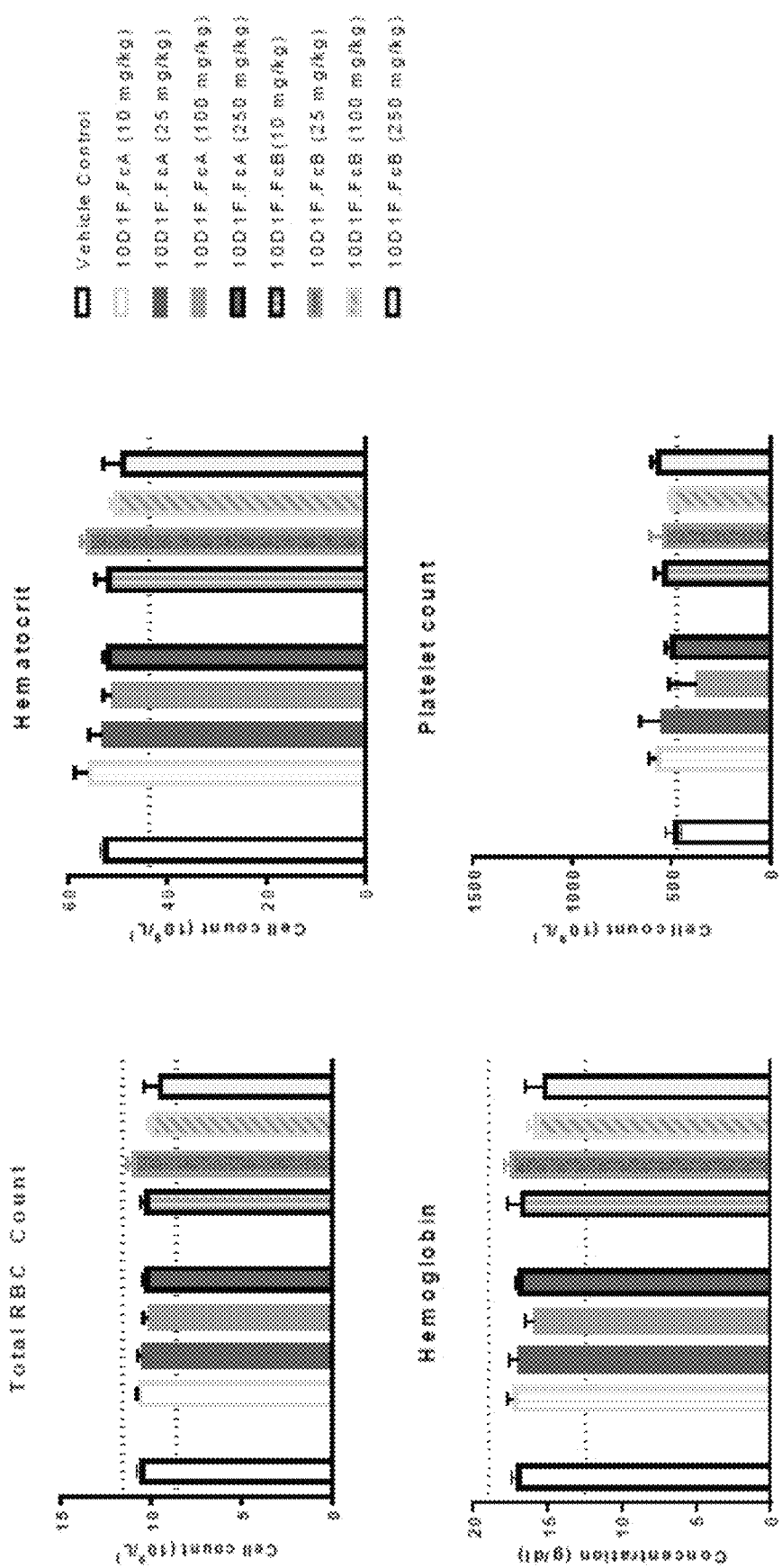
FIGS. 58A to 58F. Graphs showing the effect of treatment of anti-HER3 antibody clone 10D1F.FcA or 10D1F.FcB at 200 ug (~10 mg/kg), 500 ug (~25 mg/kg), 2 mg (~100 mg/kg), or 5 mg (~250 mg/kg) on (58A, 58B) red blood cell indices, (58C) white blood cell indices, (58D) hepatotoxicity, (58E) kidney and pancreatic indices, and (58F) electrolyte indices.
Figure 58B:
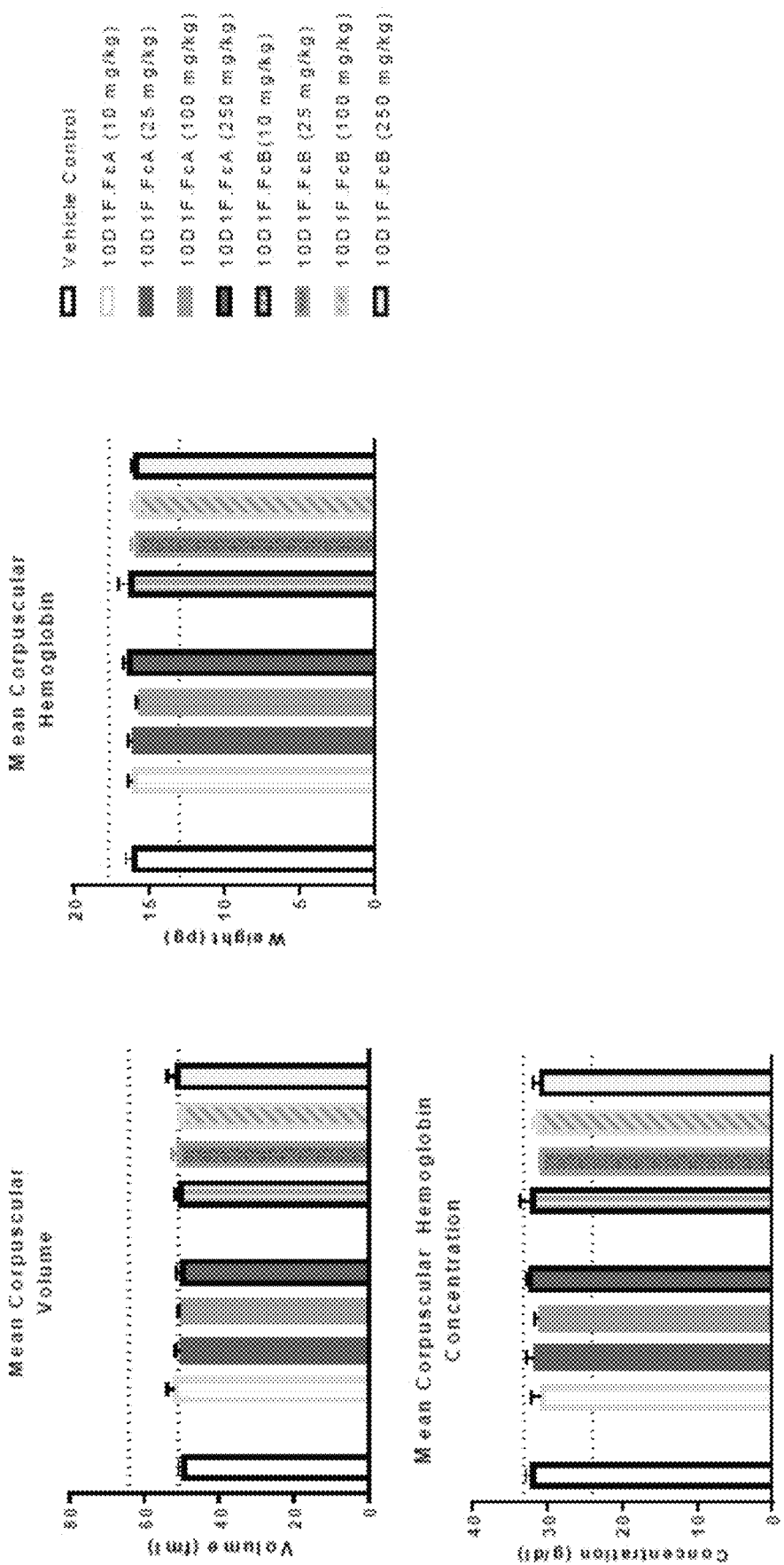
Figure 58C:
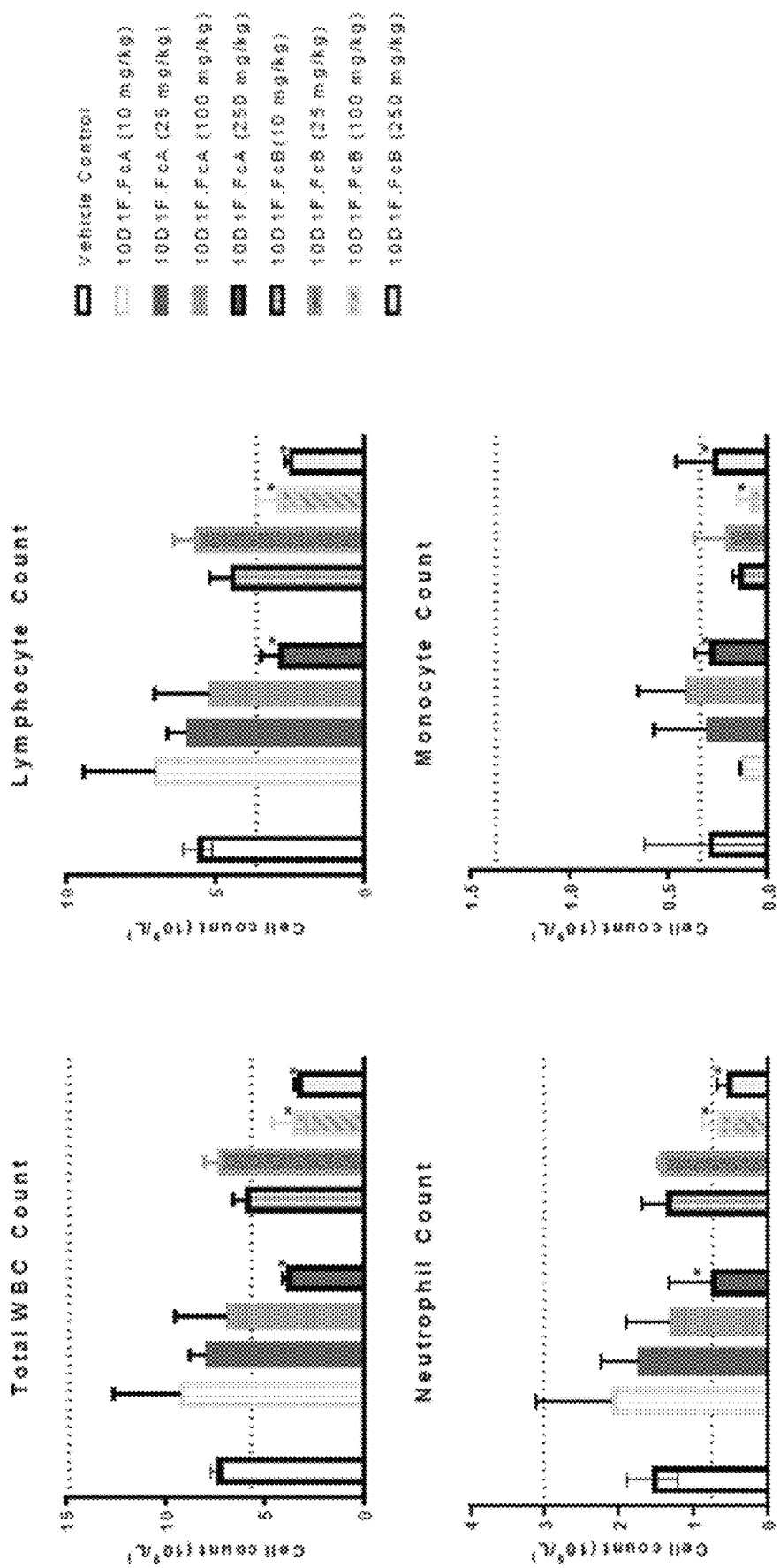

The results are shown in FIGS. 58A, 58B (RBC indices) and 58C (WBC indices). Anti-HER3 antibodies 10D1F.FcA and 10D1F.FcB had no effect on the RBC indices, but were found to have an effect on the WBC indices at higher doses (10D1F.FcA 250 mg/kg, 10D1F.FcB 100 mg/kg, 10D1F.FcB 250 mg/kg).

Figure 58D:
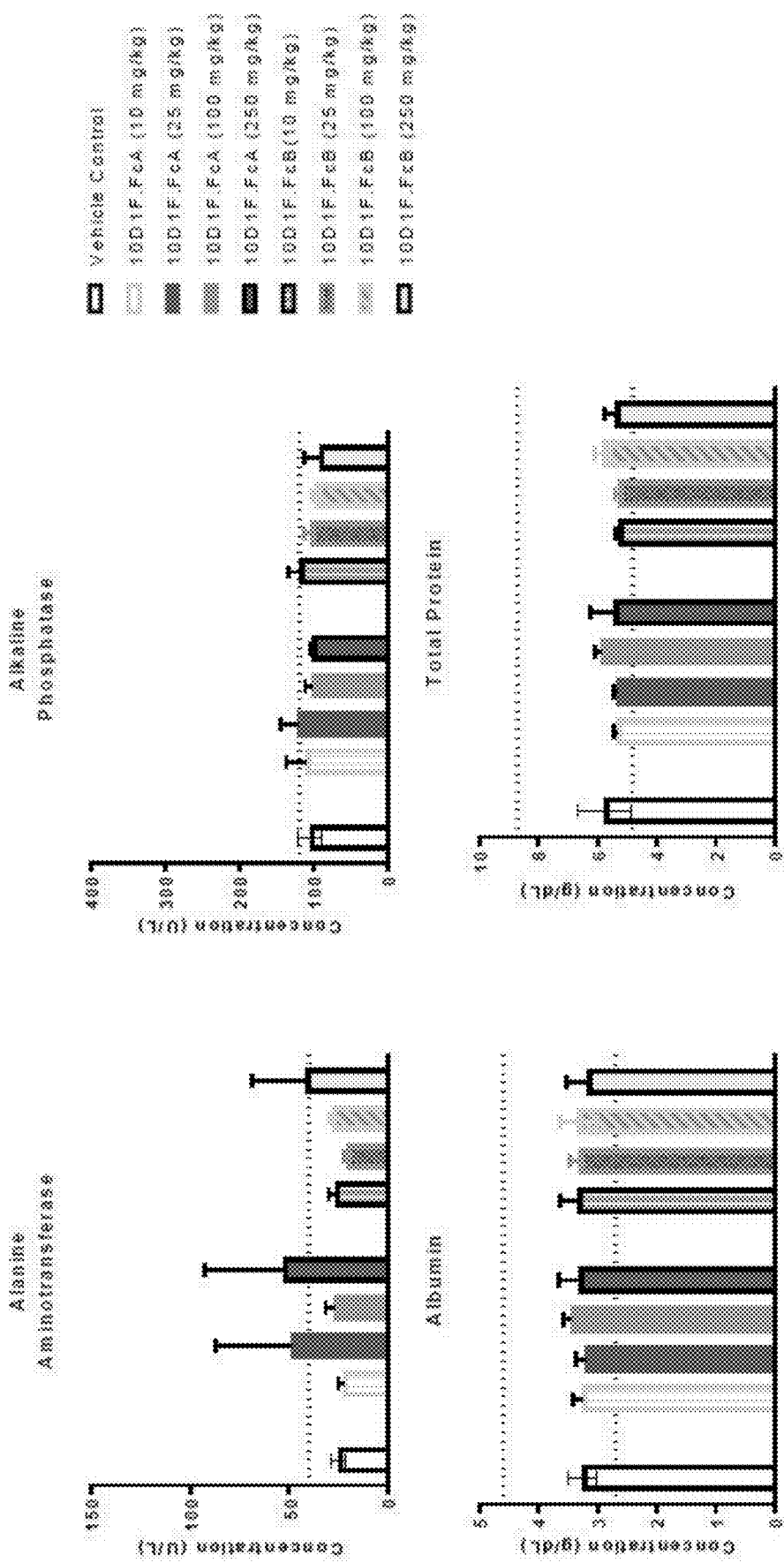
Figure 58E:
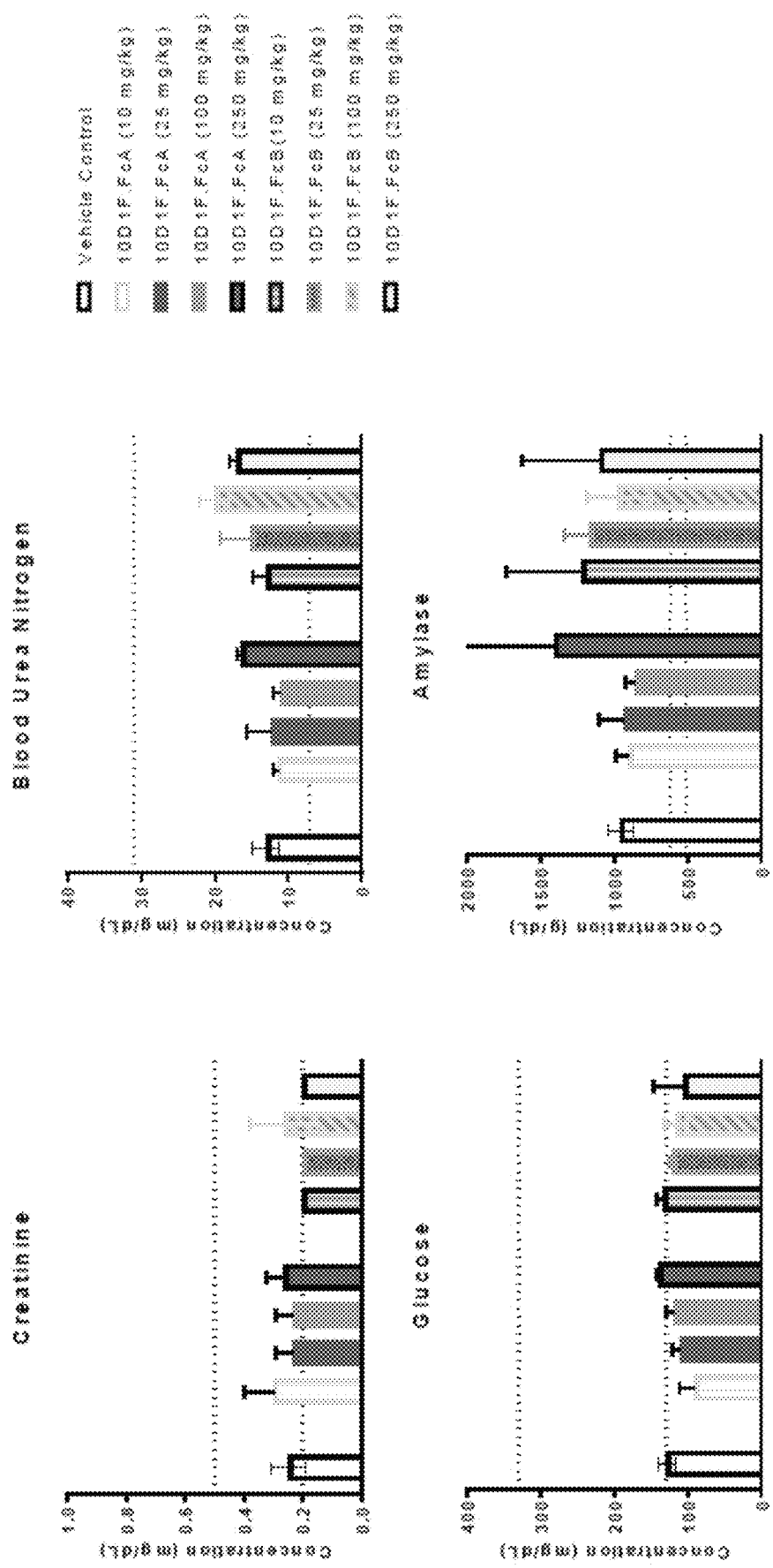
Figure 58F:
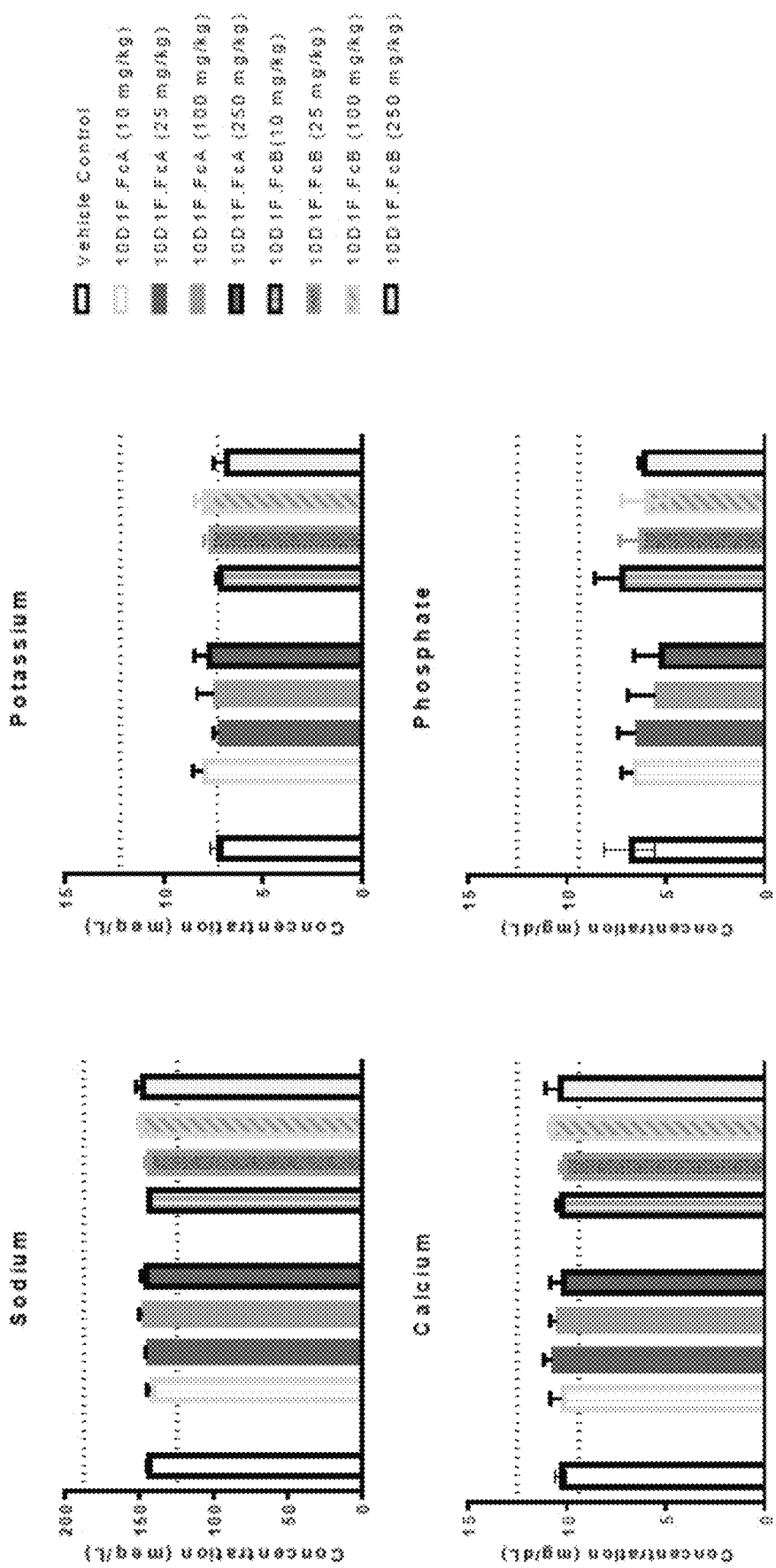
Figure 59A:
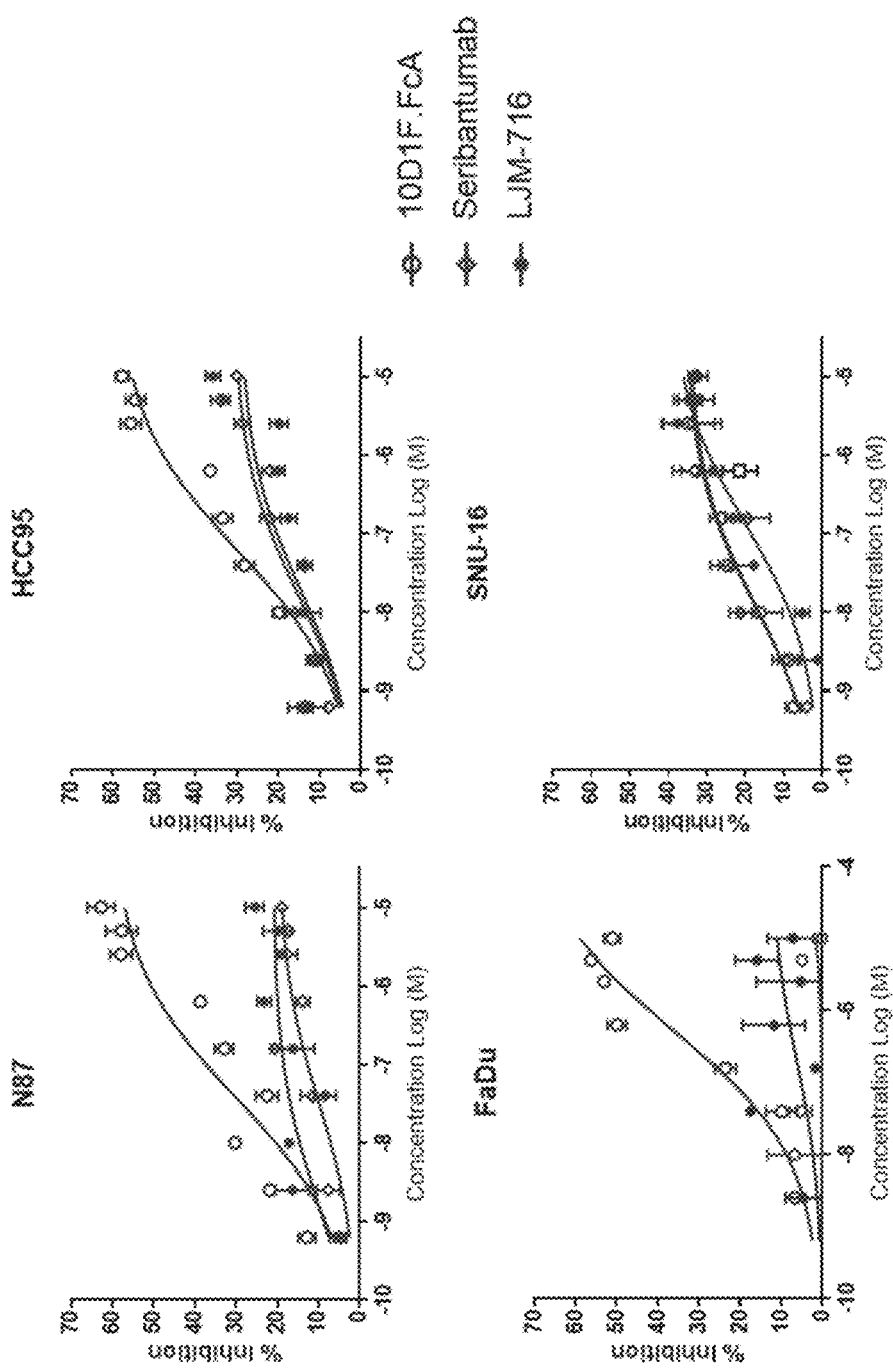
FIGS. 59A to 59D. Graphs showing the effect of treatment anti-HER3 antibody clone 10D1F.FcA on percentage tumour inhibition in in vitro mouse cancer models using N87 cells (gastric cancer), HCC95 cells (lung cancer), FaDu cells (head and neck cancer), SNU-16 cells (gastric cancer), A549 cells (lung cancer), OvCar8 cells (ovarian cancer), ACHN cells (kidney cancer) and HT29 cells (colorectal cancer) in comparison to (59A & 59B) anti-HER3 antibodies seribantumab and LJM-716 and (59C & 59D) EGFR family therapies cetuximab, trastuzumab and pertuzumab.
Figure 59B:
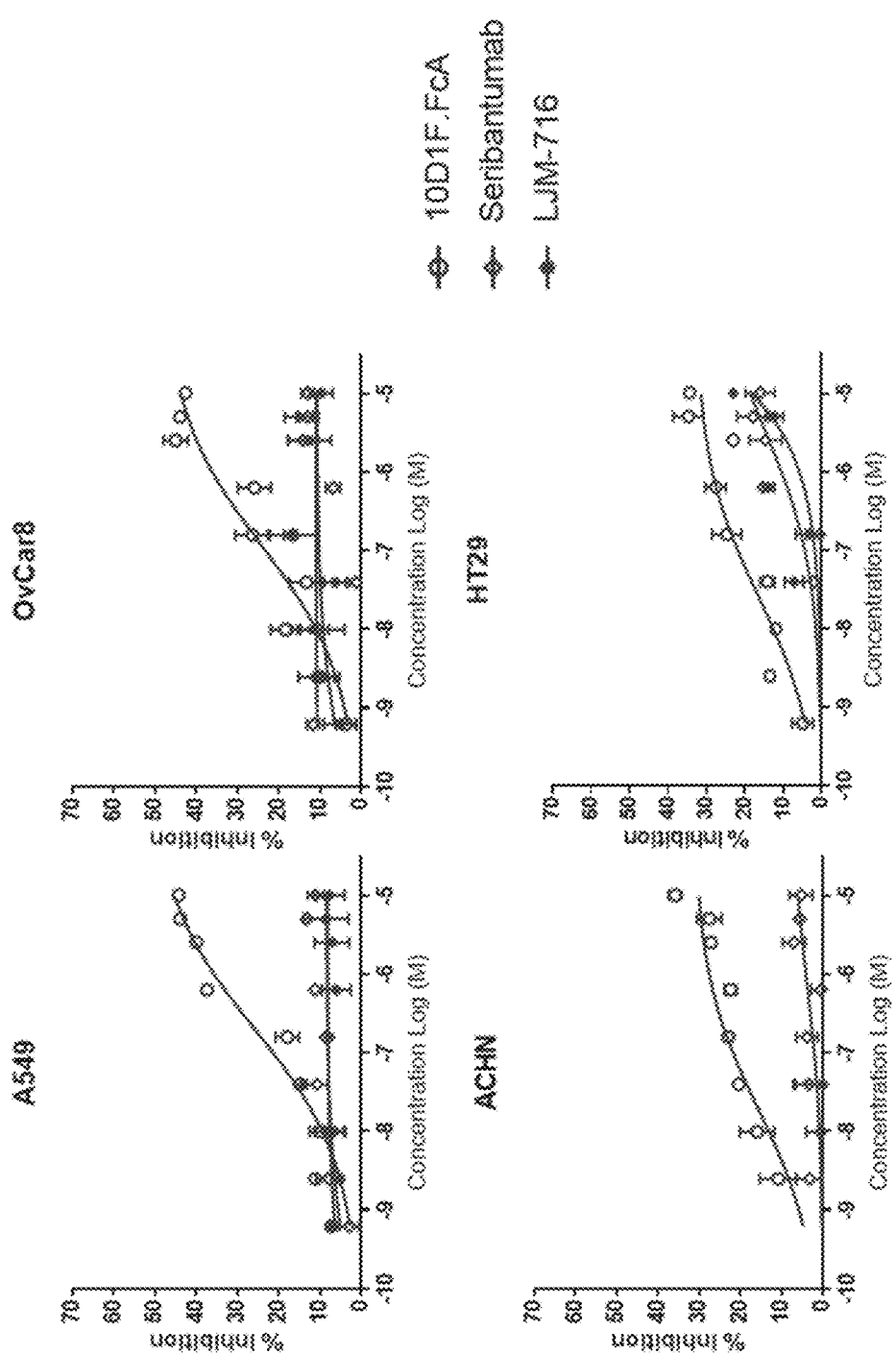
Figure 59C:
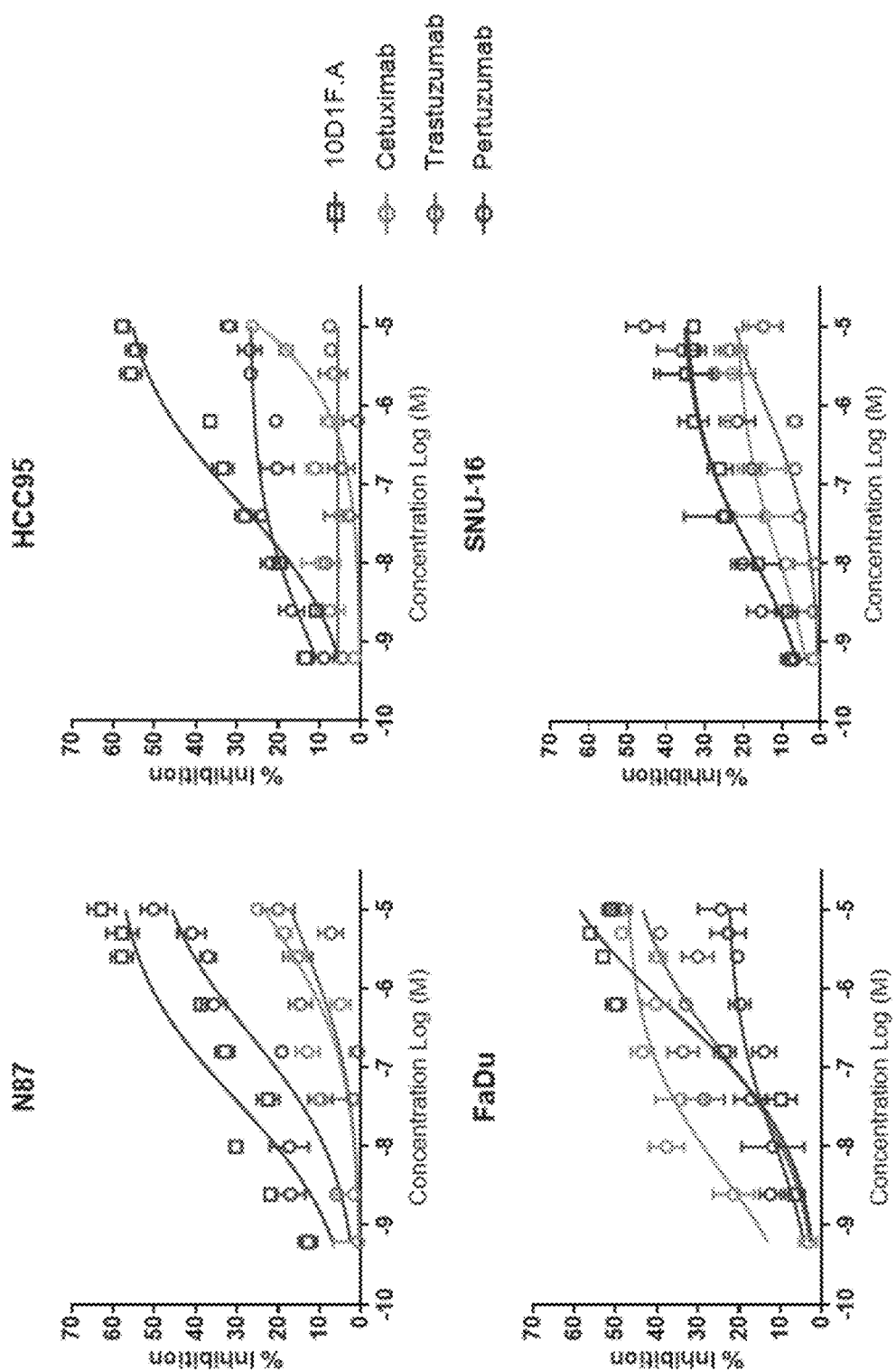
Figure 59D:
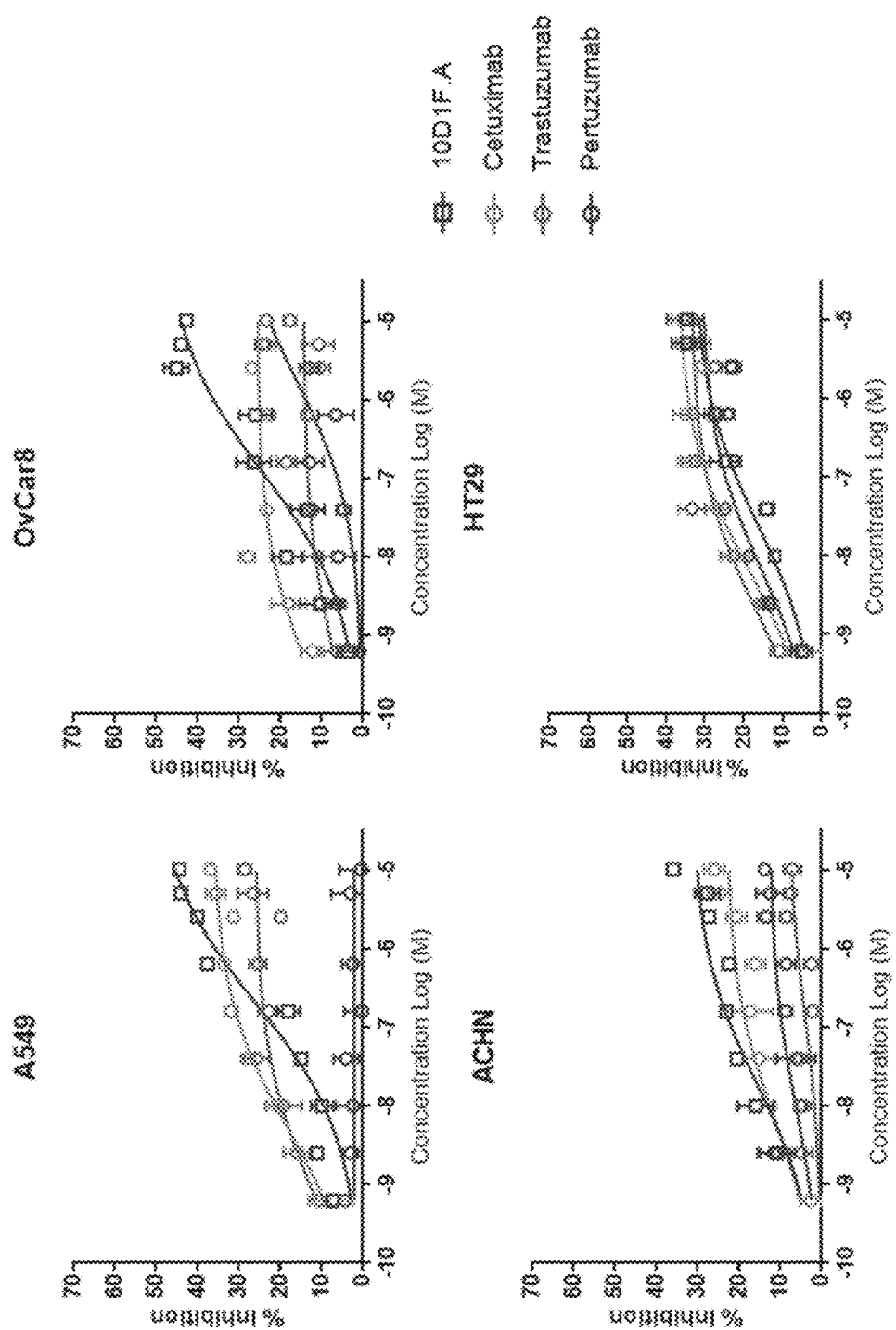

Hepatotoxicity, nephrotoxicity and pancreatic toxicity were also analysed 96 hours post injection. 10D1F.FcA and 10D1F.FcB had no effect on the levels of alanine aminotransferase, alkaline phosphatase, albumin, total protein (liver indices; FIG. 58D), creatine, blood urea nitrogen, glucose or amylase (kidney and pancreatic indices; FIG. 58E). Nor did 10D1F.FcA and 10D1F.FcB have an effect on electrolyte indices sodium, potassium, calcium or phosphate (FIG. 58F).

Mice treated with 10D1F.FcA or 10D1F.FcB showed no abnormalities after 96 hours in weight, behaviour, skin condition, oral examination, stool and wine examination or eye examination. Enlarged spleen (splenomegaly) approximately 1.5 times the normal size was observed in mice treated with higher doses: 10D1F.FcA 250 mg/kg, 10D1F.FcB 100 mg/kg, 10D1F.FcB 250 mg/kg.

A further study was performed in the BALB/c mice to assess the toxicological effects of repeat doses of 500 μg (~25 mg/kg) 10D1F.FcA or 10D1F.FcB. Antibody was administered once a week for four weeks. Blood was obtained 28 days after the first administration. There was no effect observed on RBC, liver, kidney, pancreatic or electrolyte indices for either antibody, no signs of clinical abnormalities and no differences detected in gross necroscopy. Total WBC count, lymphocyte count and neutrophil count was observed to be decreased in mice treated with 10D1F.FcA or 10D1F.FcB but this was not considered to be toxic.

In another study, BALB/c mice were administered with a single dose of 10D1F.FcA or an equal volume of PBS (vehicle control), and analysed after 336 hours. Representative results are shown in FIGS. 69A to 69C.

Rats 6-8 week old female Sprague Dawley rats (400-450 g) were injected intraperitoneally with a single dose of either 10D1F.FcA or 10D1F.FcB antibody at one of doses: 4 mg (~10 mg/kg), 10 mg (~25 mg/kg), 40 mg (~100 mg/kg), 100 mg (~250 mg/kg). Blood was obtained at −24 hours, 6 hours, 24 hours, 96 hours, 168 hours and 336 hours. Up to 366 hours post injection there was no effect on RBC indices, no toxic effect on WBC indices, and no effect on liver, kidney, pancreatic or electrolyte indices. There were no signs of clinical abnormalities and no differences detected in gross necroscopy.

Representative results obtained from rags administered with 250 mg/kg 10D1F.FcA are shown in FIGS. 70A to 70C.

The absence of toxicity signals in rodent toxicology models indicates superior clinical safety for 10D1 and variants.

9.3 Analysis of Efficacy to Treat Cancer In Vitro

Anti-HER3 antibody 10D1F.FcA was analysed for its ability to inhibit tumour growth in vitro in a number of tumour models: N87 cells (gastric cancer), HCC95 cells (lung cancer), FaDu cells (head and neck cancer), SNU-16 cells (gastric cancer). A549 cells (lung cancer), OvCar8 cells (ovarian cancer), ACHN cells (kidney cancer) and HT29 cells (colorectal cancer). 10D1F.FcA efficacy was compared to other anti HER3 antibodies seribantumab (MM-121) and LJM-716, and other EGFR family therapies cetuximab, trastuzumab and pertuzumab.

Cells were treated with serially diluted concentrations of therapeutic antibodies, starting from 1500 ug/ml with a 9-point dilution. Cell viability was measured using CCK-8 cell proliferation assay, 3-5 days post treatment. The percentage of cell inhibition shown is relative to cells treated with only buffer (PBS). Data points indicates average of three replicates.

The results are shown in FIG. 59A to 59D. Anti-HER3 antibody 10D1F.FcA demonstrates superior in vitro tumour inhibition in multiple tumour models compared to other HER3 antibodies (59A & 59B) and EGFR family therapies (59C & 59D).

Figure 77A:
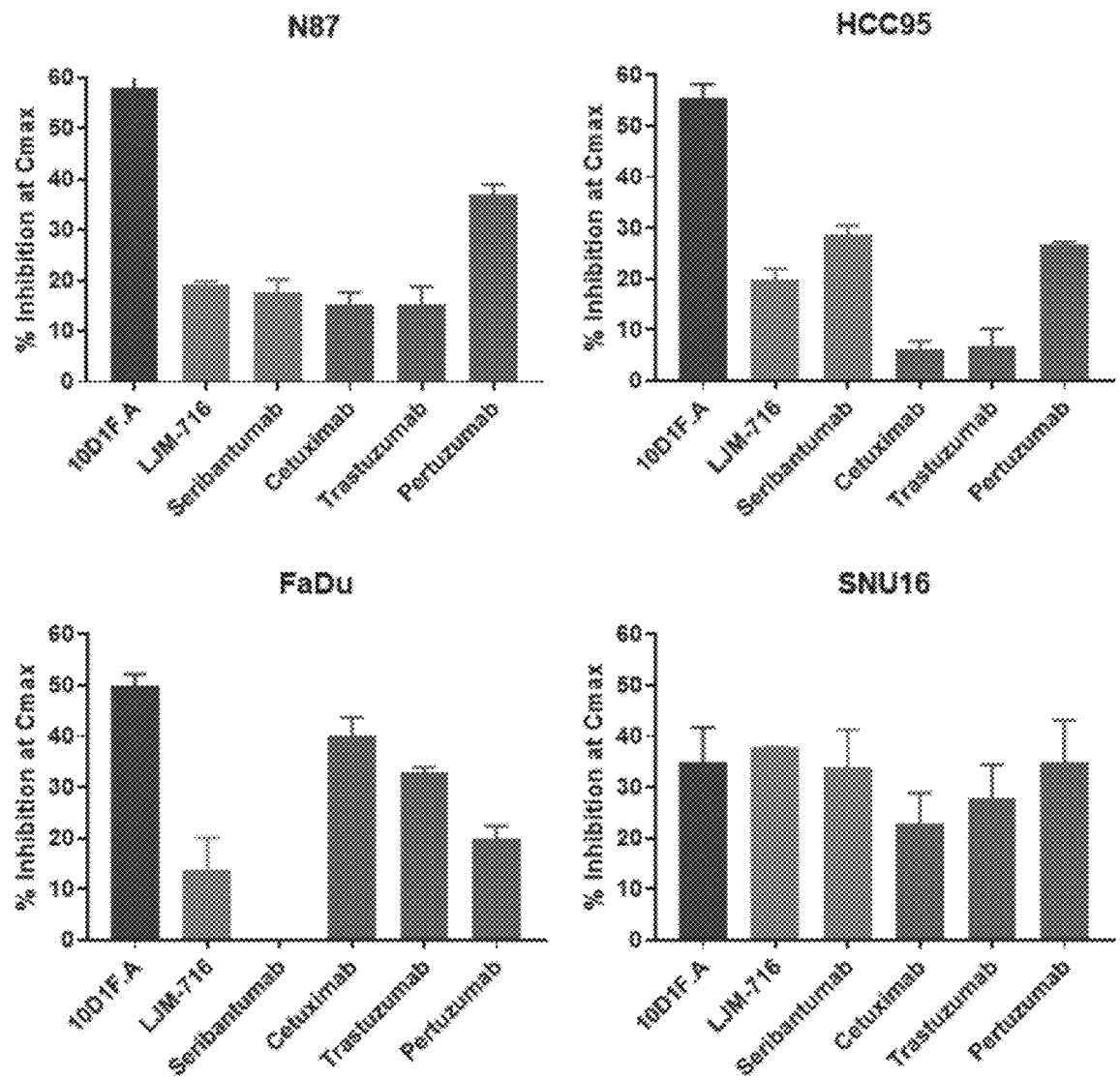
FIGS. 77A and 77B. Bar charts showing the results of analysis of the ability of the indicated anti-ErbB antibodies to inhibit in vitro proliferation of the indicated cancer cell lines at the serum concentrations the antibodies reach at $C_{max}$ following IP administration to mice at 25 mg/kg. 77A and 77B show results obtained using different cell lines.
Figure 77B:
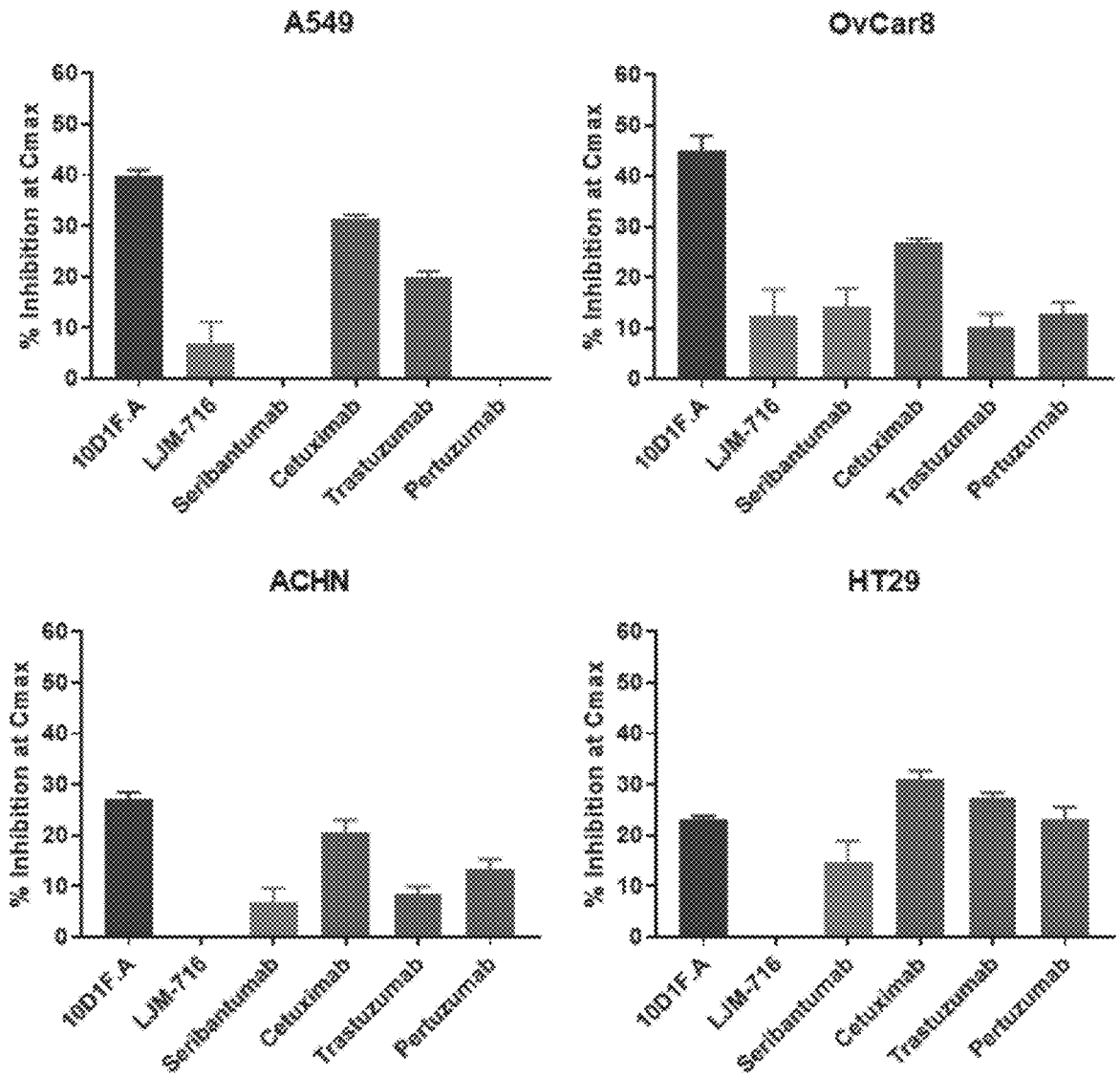

FIGS. 77A and 77B show the ability of different anti-ErbB antibodies to inhibit proliferation of different cancer cell lines in vitro, at the $C_{max}$ concentration they achieve in mice administered IP with 25 mg/kg of the relevant antibody. 10D1F.FcA displays outstanding ability to inhibit growth of a wide variety of different cancer cell types.

9.4 Analysis of Efficacy to Treat Cancer In Vivo

Anti-HER3 antibody clones 10D1F.FcA and 10D1F.FcB were assessed for their effect on tumour growth in in vivo cancer models.

9.4.1 A549 Model

Tumour cells were inserted subcutaneously into the right flanks of female NCr nude mice. Antibodies (25 mg/kg 10D1F.FcA, 10D1F.FcB, Cetuximab, LJM-716 or MM-121; n=6 for each treatment) or vehicle (n=8) were administered biweekly for six weeks.

Figure 60:
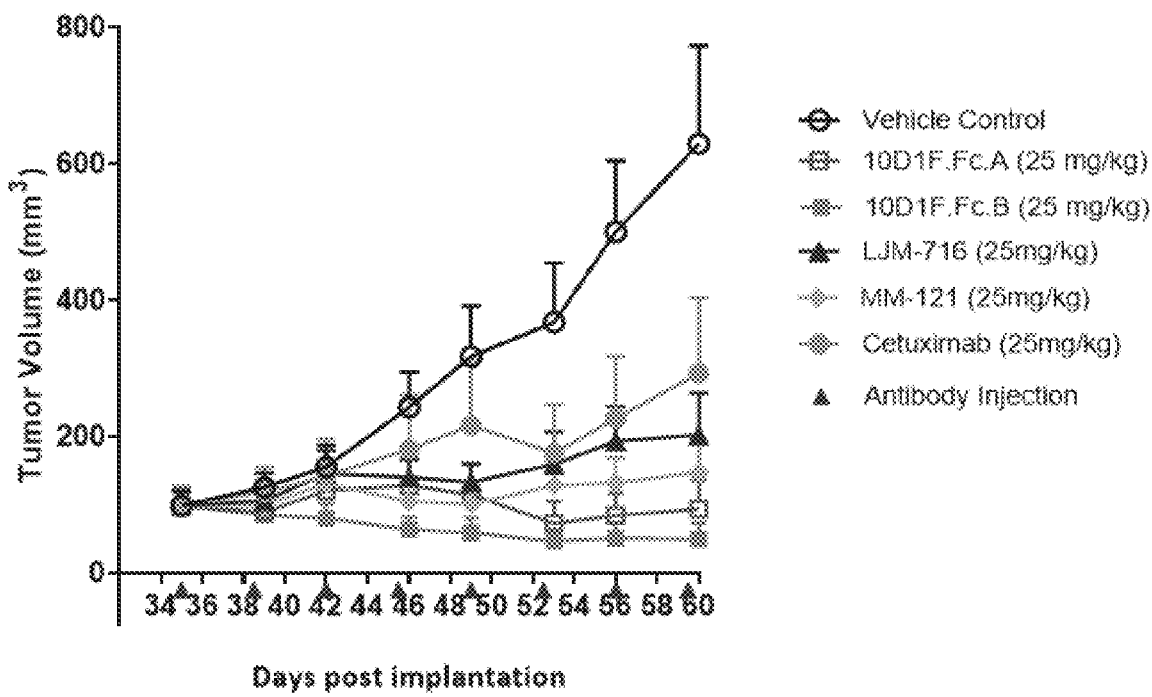
FIG. 60. Graph showing the results of analysis of tumour volume over time in an A549 cell-line derived mouse model of lung adenocarcinoma after biweekly treatment with the indicated concentrations of antibodies for six weeks (n=6, vehicle control n=8). Antibody administration is indicated by triangles along x-axis.

The results are shown in FIG. 60. Anti-HER3 antibody clones 10D1F.FcA and 10D1F.FcB both displayed potent efficacy in the A549 model of lung carcinoma. 10D1F.FcB was found to be particularly potent and made tumours regress.

9.4.2 FaDu Model

Tumour cells were inserted with matrigel subcutaneously into the right flanks of female NCr nude mice. Antibodies (10 and 25 mg/kg 10D1F.FcA and 10D1F.FcB, or 25 mg/kg of Cetuximab, Trastuzumab, Pertuzumab, LJM-716 or MM-121; n=6 for each treatment) or vehicle (n=6) were administered once a week for six weeks.

Figure 61:
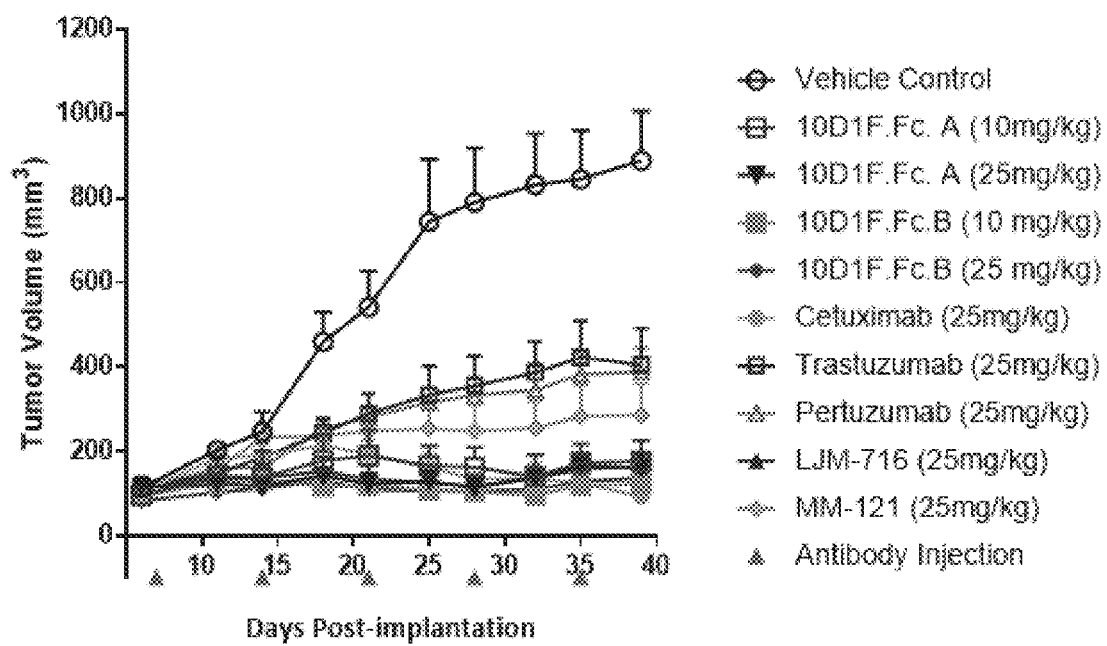
FIG. 61. Graph showing the results of analysis of tumour volume over time in a FaDu cell-line derived mouse model of head and neck squamous cell carcinoma after weekly treatment with the indicated concentrations of antibodies for six weeks (n=6). Antibody administration is indicated by triangles along x-axis.

The results are shown in FIG. 61. Anti-HER3 antibody clones 10D1F.FcA and 10D1F.FcB were both found to be effective to prevent tumour growth in the FaDu model of head and neck cancer.

9.4.3 OvCar8 Model

Tumour cells were inserted with matrigel subcutaneously into the right flanks of female NCr nude mice. Antibodies (10 and 25 mg/kg 10D1F.FcA, or 25 mg/kg Cetuximab, LJM-716 or MM-121; n=6) or vehicle (n=6) were administered once a week for six weeks.

Figure 62:
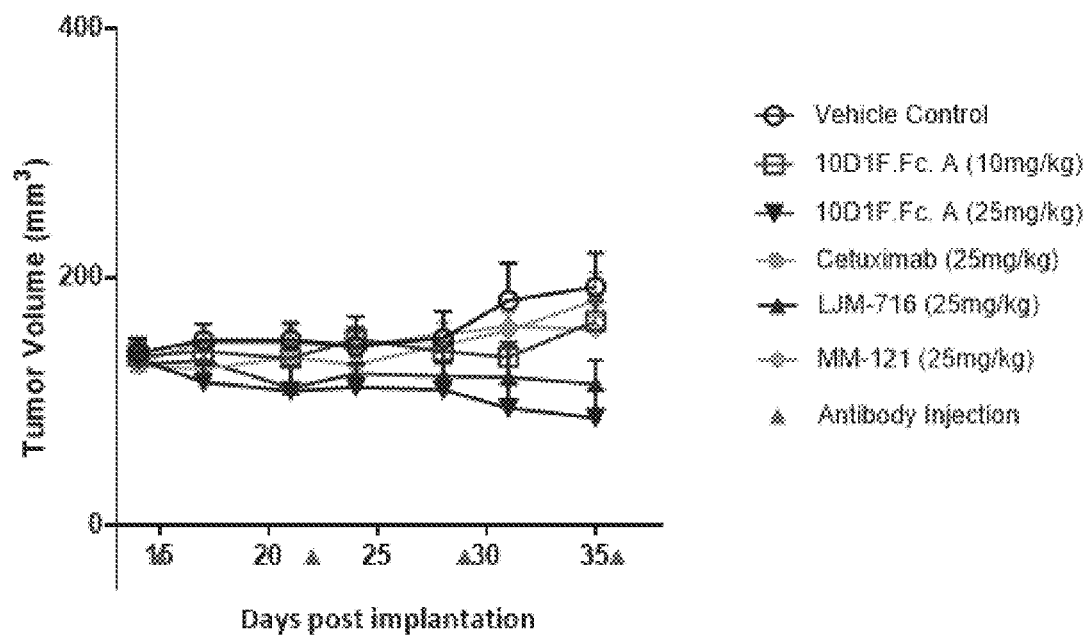
FIG. 62. Graph showing the results of analysis of tumour volume over time in a OvCAR8 cell-line derived mouse model of ovarian carcinoma after weekly treatment with the indicated concentrations of antibodies for six weeks (n=6). Antibody administration is indicated by triangles along x-axis.
Figure 63A:
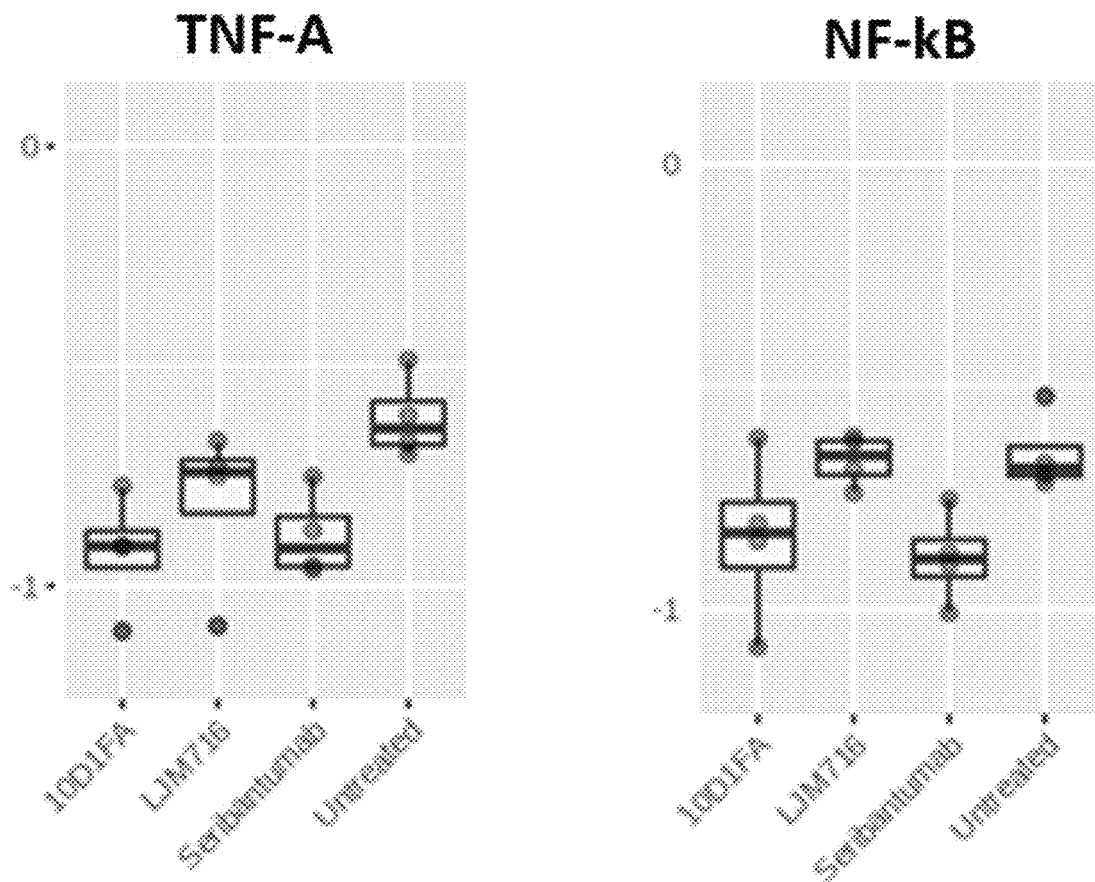
FIGS. 63A to 63D. Box plots showing the results of analysis of pathway activation by gene set enrichment analysis, for cancer cell lines treated with 10D1F.FcA, LJM-716 or seribantumab in in vitro phosphorylation assays. 63A shows the results obtained from N87 cells, 63B shows the results obtained from A549 cells, 63C shows the results obtained from OvCar8 cells and 63D shows the results obtained from FaDu cells.
Figure 63B:
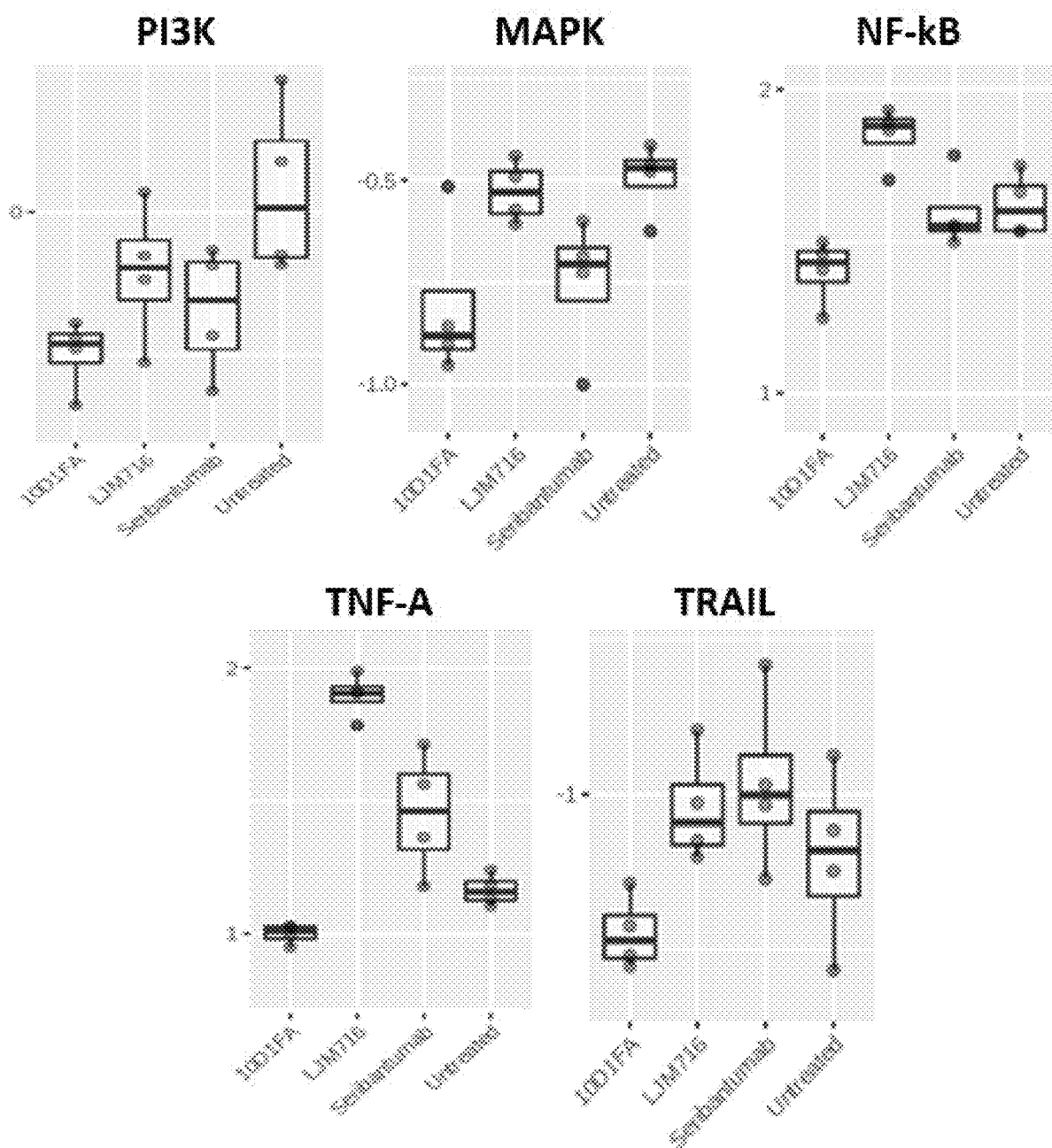
Figure 63C:
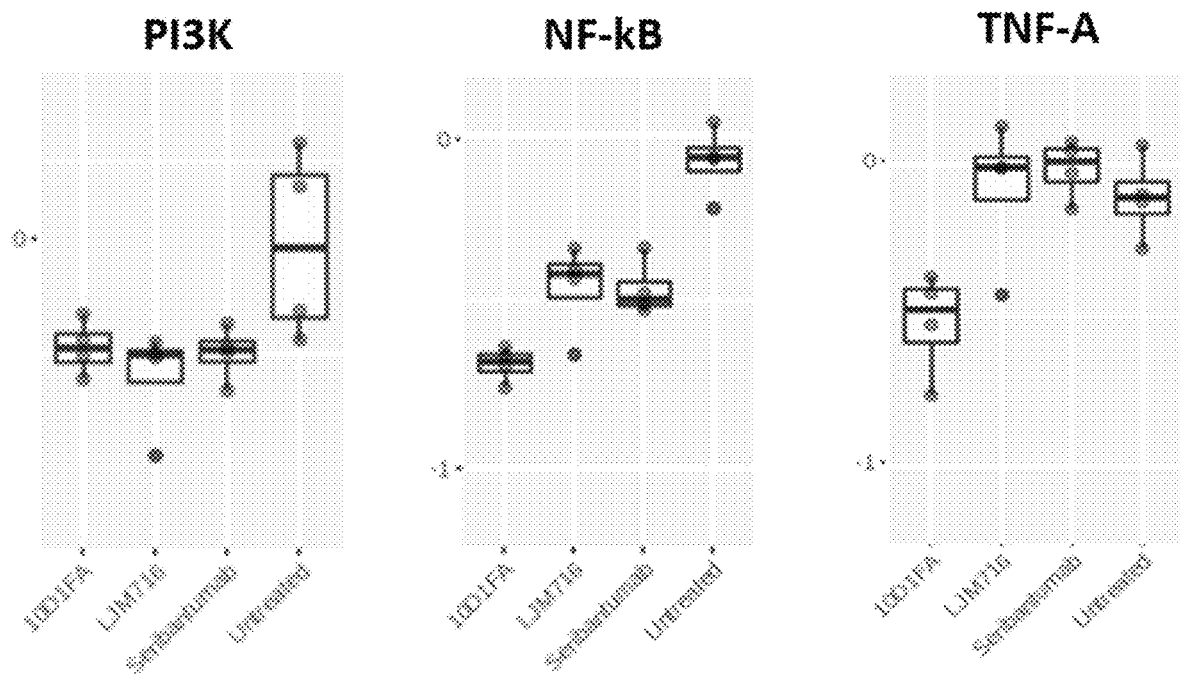
Figure 63D:
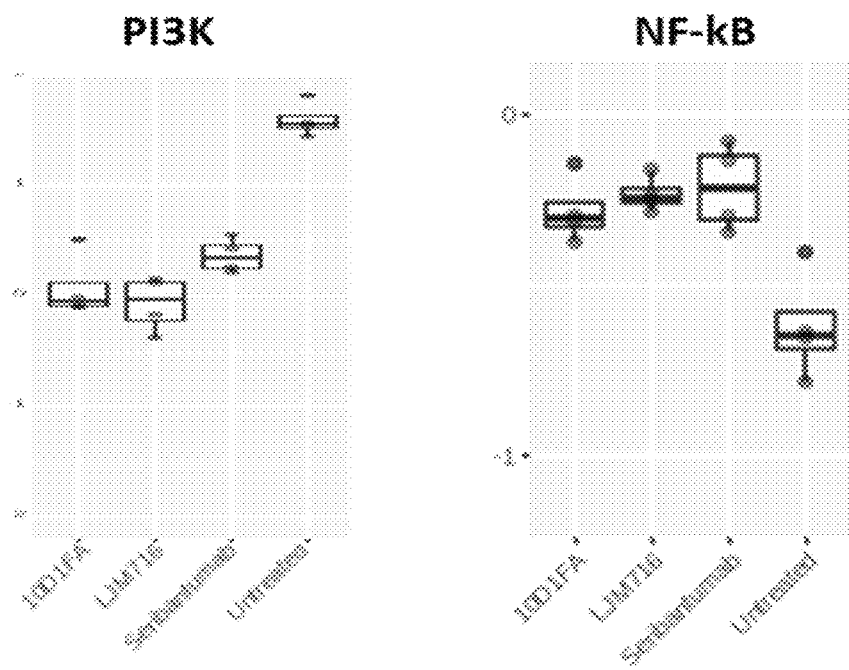

The results are shown in FIG. 62. Anti-HER3 antibody clone 10D1F.FcA was found to be effective at reducing tumour volume at higher dose.

9.4.4 N87 Model

Tumour cells are inserted with matrigel subcutaneously into the right flanks of female NCr nude mice. Antibodies (25 mg/kg 10D1F.FcA, or 50 mg/kg of Trastuzumab, LJM-716 or MM-121; n=6 for each treatment) or vehicle (n=6) were administered biweekly for six weeks.

Figure 74:
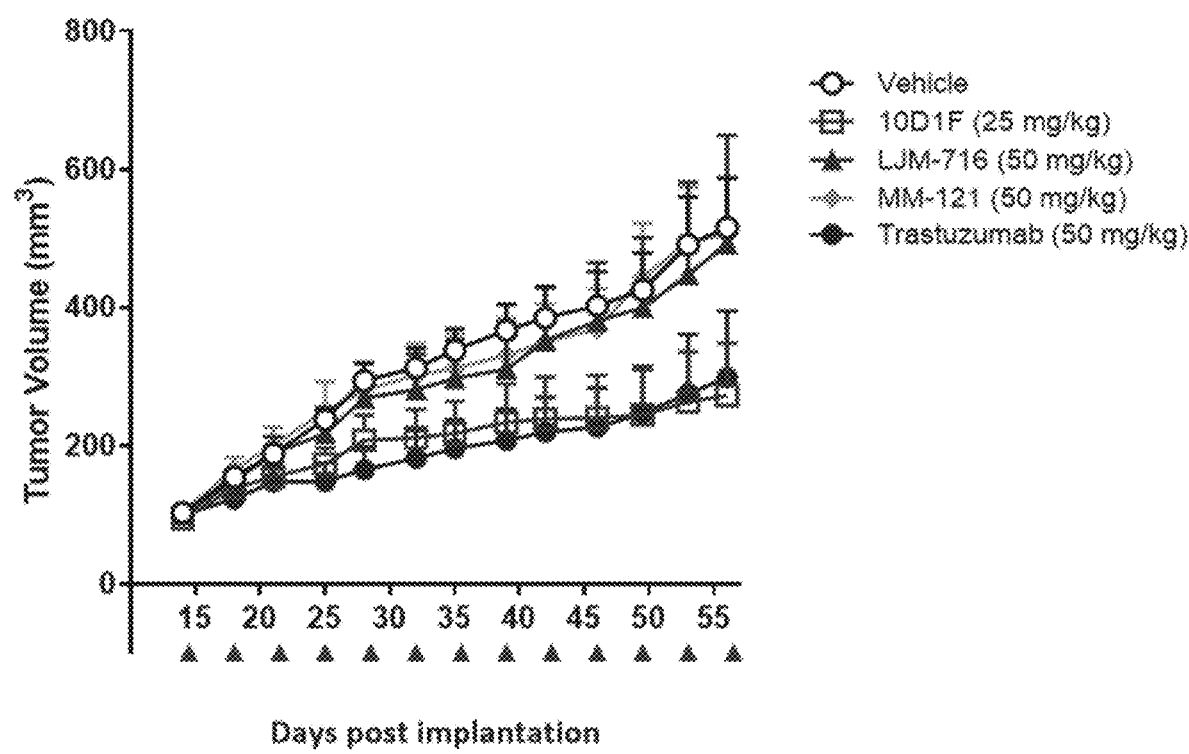
FIG. 74. Graph showing the results of analysis of tumour volume over time in a N87 cell-line derived mouse model of gastric cancer after biweekly treatment with the indicated concentrations of the indicated anti-ErbB antibodies, for six weeks (n=6). Antibody administration is indicated by triangles along x-axis.

The results are shown in FIG. 74. Anti-HER3 antibody 10D1F.FcA and was found to be effective to prevent tumour growth in the N87 model of gastric cancer.

Example 10

Analysis of Inhibition of Proliferation of BRAFV600E Mutant Thyroid Cancer Cell Lines The following cell fines were investigated:

| Cell Line | Type of Cancer | Mutation |
| --- | --- | --- |
| SW1736 | Anaplastic thyroid cancer | BRAF V600E |
| BHT101 | Anaplastic thyroid cancer | BRAF V600E |
| BCPAP | Papillary thyroid cancer | BRAF V600E and p53 mutation |

The cells were investigated for surface expression of EGFR family members by flow cytometry. Briefly, 300,000 cells were incubated with 20 µg/ml of 10D1F.FcA, cetuximab or trastuzumab for 1 hr at 4° C. Alexafluor 488-conjugated anti-human antibody was used at 10 µg/ml as a secondary antibody (40 min at 4° C.).

Figure 66B:
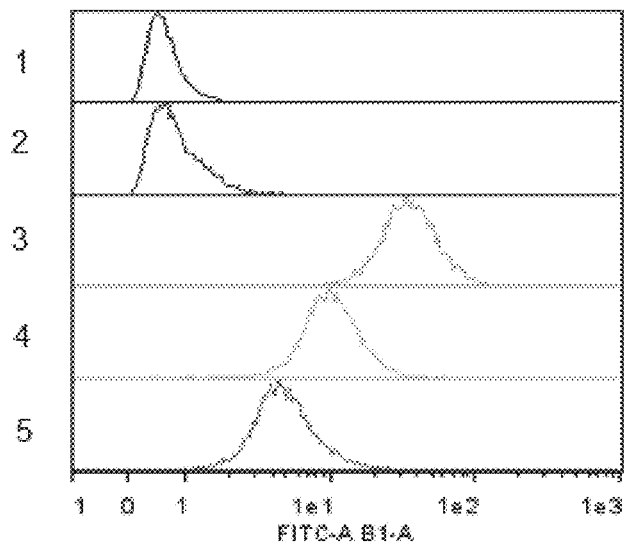
Figure 66C:
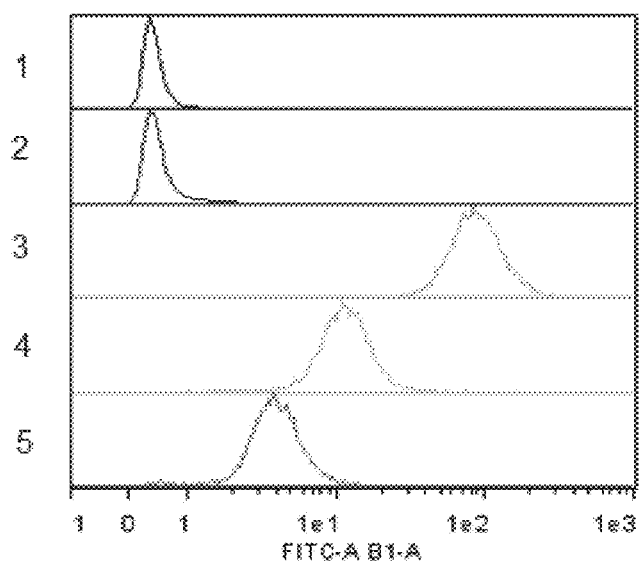

The results are shown in FIG. 66A to 66C. SW1736, BHT101 and BCPAP cells were shown to express EGFR, HER2 and HER3.

The inventors investigated the ability of different HER3-binding antibodies to inhibit in vitro proliferation of different thyroid cancer cell lines harbouring the V600E BRAF mutation.

Briefly, cells of the different cell lines were seeded at a density of $1.5\times10^5$ cells/well, and treated the next day with a 10 point serial dilution starting from 1000 µg/ml of 10D1F.FcA, seribantumab, LJM-716, pertuzumab or isotype control antibody. After 3 days, proliferation was measured using a CCK-8 cell proliferation assay. Percent inhibition of proliferation was calculated relative to cells treated with an equal volume of PBS instead of antibodies.

Figure 67C:
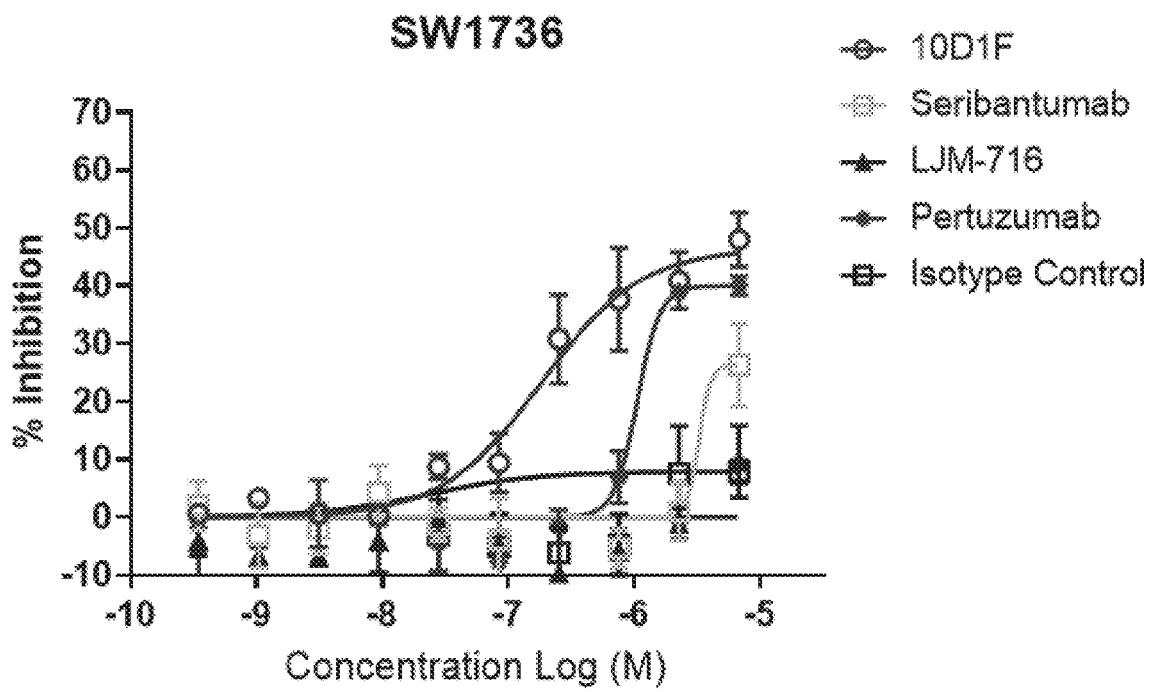

The results are shown in FIGS. 67A to 67C. 10D1F.FcA was found to be more effective at inhibiting proliferation of cell lines harbouring BRAF V600E mutation than any other of the anti-HER3 antibodies analysed.

In further experiments, the ability of a combination of 10D1F.FcA and vemurafenib to inhibit in vitro proliferation of different thyroid cancer cell lines harbouring the V600E BRAF mutation was investigated.

Cells were seeded at a density of $1.5\times10^5$ cells/well, and treated the next day with a 10 point serial dilution starting from 1000 µg/ml of 10D1F.FcA or isotype control antibody, in the presence or absence of 200 nM vemurafenib. After 3 days, proliferation was measured using a CCK-8 cell proliferation assay. Percent inhibition of proliferation was calculated relative to cells treated with an equal volume of PBS instead of antibodies.

Figure 68A:
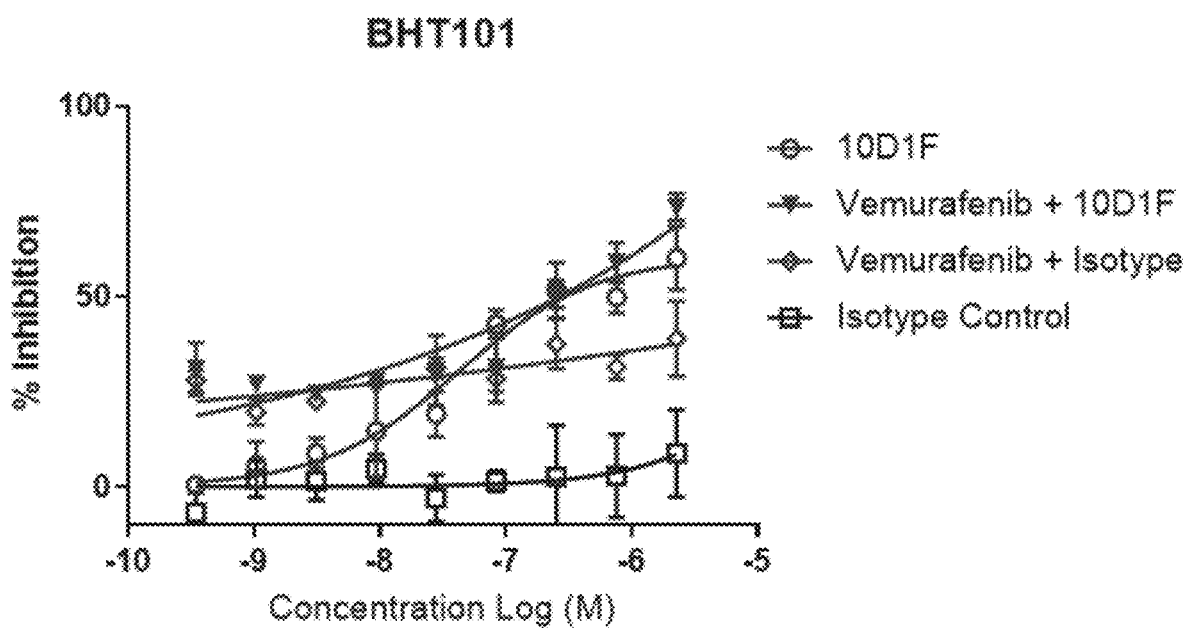
FIGS. 68A to 68C. Graphs showing the results of analysis of the ability of 10D1F.FcA alone, or in combination with vemurafenib, to inhibit proliferation of BRAF$^{V600E}$=mutant thyroid cancer cell lines in vitro. 68A shows the results obtained for BHT101 cells, 68B shows the results obtained for SW1736 cells, and 68C shows the results obtained for BCPAP cells.
Figure 68B:
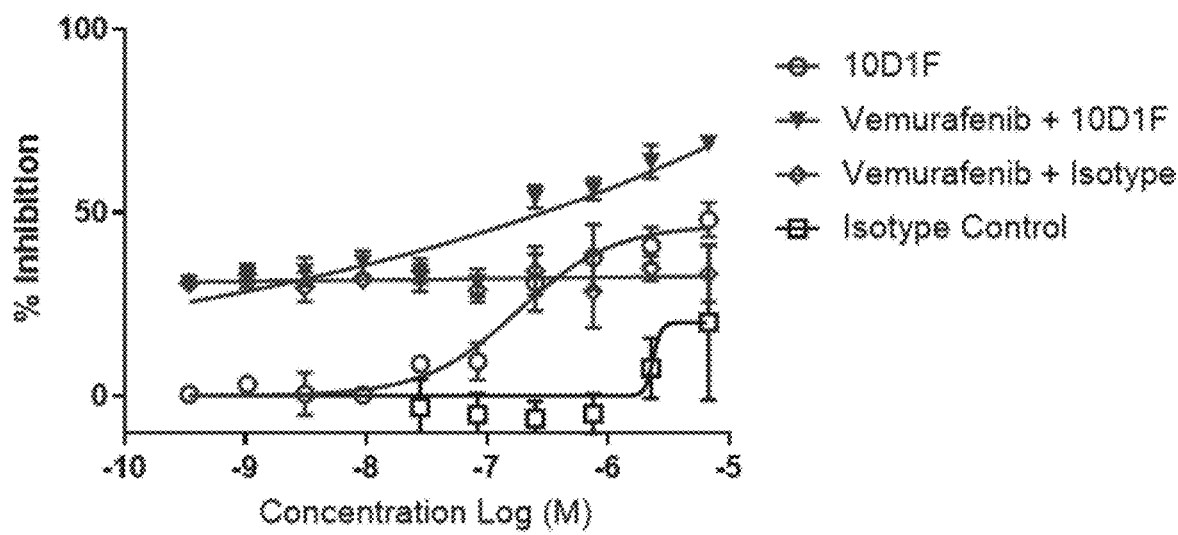
Figure 68C:
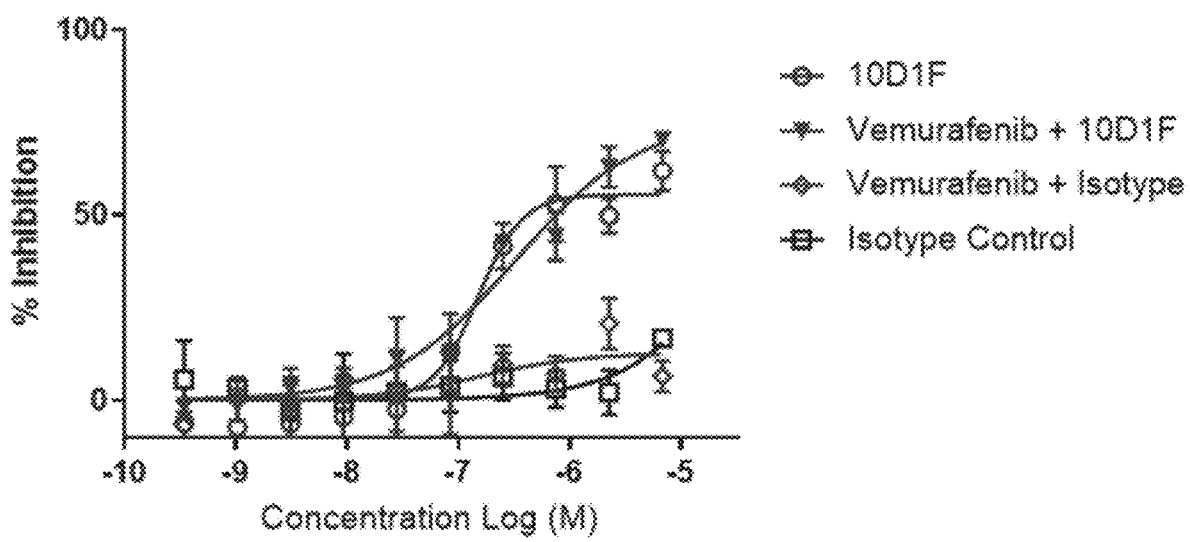

The results are shown in FIGS. 68A to 68C. 10D1F.FcA was found to enhance the ability of vemurafenib to inhibit proliferation of SW1736 and BHT101 cells, which are susceptible to vemurafenib. 10D1F.FcA was also found to be a potent inhibitor of proliferation of vemurafenib-resistant BCPAP cells.

Example 11

Analysis of Inhibition of HER3-Mediated Signalling In Vivo

The inventors investigated the ability of 10D1F.FcA to inhibit HER3-mediated signalling in vivo.

$1\times10^6$ FaDu or OvCar8 cells were introduced subcutaneously into NCr nude mice, to establish ectopic xenograft tumors.

Once tumors had reached a volume of greater than 100 mm$^3$, mice were with treated by biweekly intraperitoneal injection of 10D1F.FcA at a dose of 25 mg/kg, or an equal volume of vehicle (control). After 4 weeks, tumors were harvested. Protein extracts were prepared from the tumors and quantified via Bradford assay, 50 µg samples were fractionated by SDS-PAGE, and analysed by western blot using antibodies in order to determine in vivo phosphorylation of HER3 and AKT, as described in Example 4.3.

Figure 71:
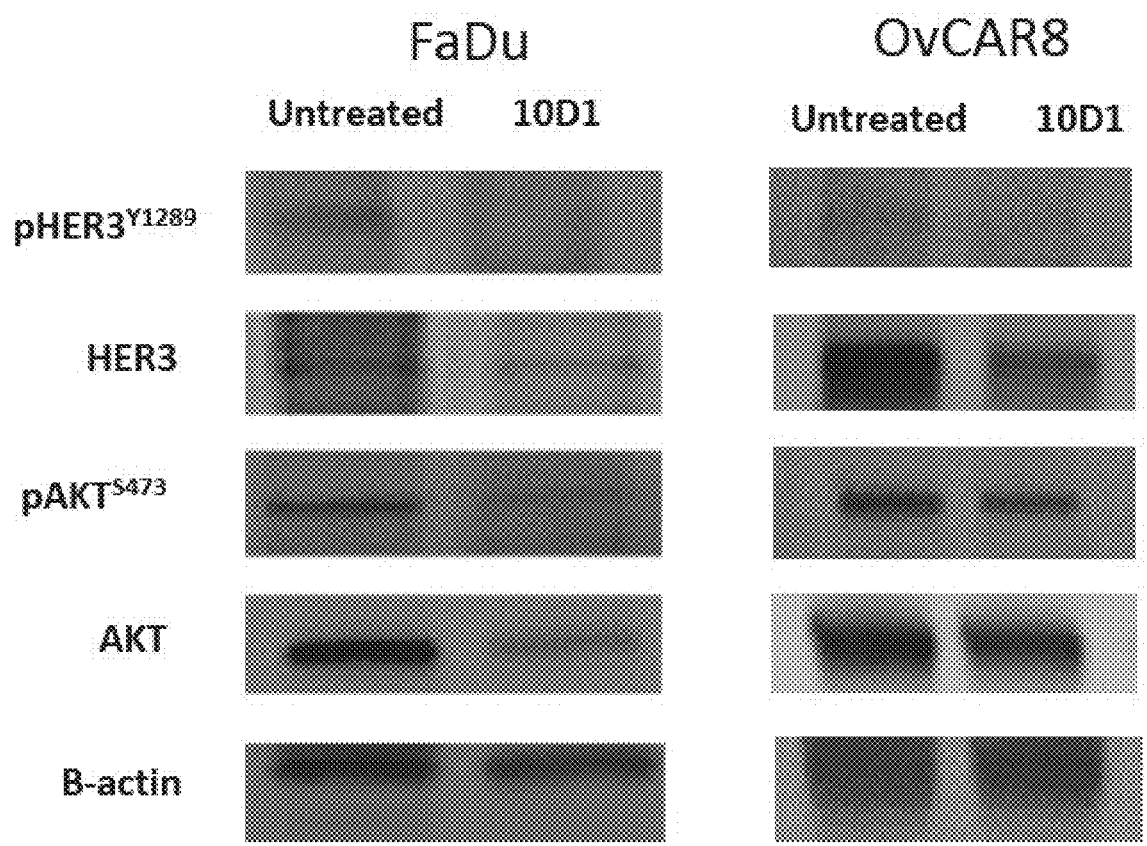
FIG. 71. Images showing the results of analysis of the effect of 10D1F.FcA treatment on HER3-mediated signalling in vivo in cells of FaDu or OvCar3 cell-derived tumors, as determined by phospho-western blot.

The results are shown in FIG. 71. 10D1F.FcA was found to inhibit phosphorylation of HER3 and AKT in tumor cells in vivo.

Example 12

Analysis of Internalisation of Anti-HER3 Antibodies

The inventors investigated internalisation of anti-HER3 antibodies by HER3-expressing cells.

Briefly, 100,000 HEK293 cells engineered to express HER3, HCC95, N87 or OVCAR8 cells were seeded in wells of 96-well tissue culture plates and cultured overnight at 37° C. in 5% CO$_2$. Cells were then treated with 120 nM of 10D1F.FcA, LJM-716, seribantumab or trastuzumab, and 360 nM of pHrodo iFL Green reagent, and incubated at 37° C. in 5% CO$_2$. The cells in culture were imaged every 30 min for 24 hours, in 4 different fields of each well. The maximum signal intensity in the FITC channel of each field was quantified at 24 hours.

Figure 72:
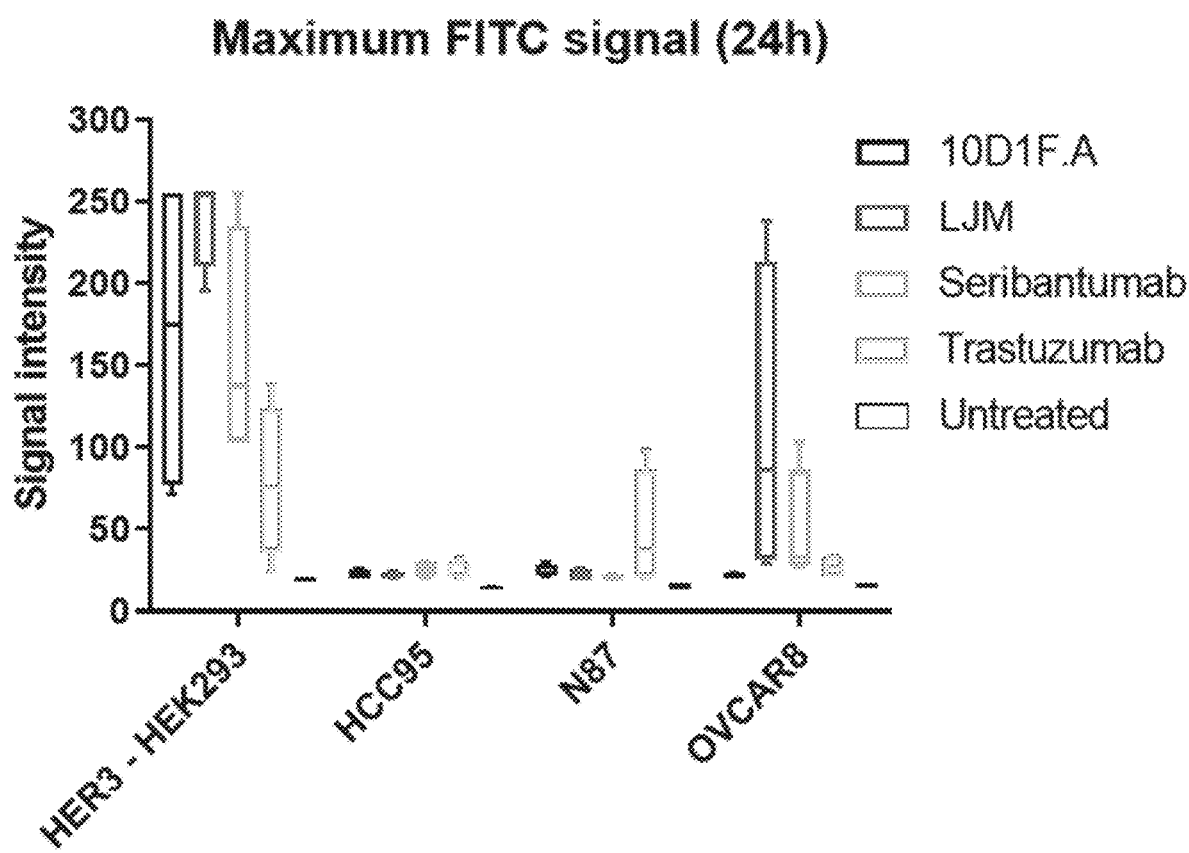
FIG. 72. Box blot showing the results of analysis of internalisation of different anti-ErbB antibodies by the indicated cell lines.

The results are shown in FIG. 72. Modest to moderate internalization of LJM-716 and seribantumab was observed in OvCar8 cells, whereas modest internalization of trastuzumab was observed in N87 cells.

No significant internalization of 10D1F.FcA was observed in HCC95, N87, or OvCar8 cells.

As expected, significant internalization of 10D1F.FcA, LJM-716, and seribantumab was observed in HEK293 cells overexpressing HER3.

In further experiments, antibody internalization was investigated by flow cytometry.

N37 cells were seeded in wells of 96-well tissue culture plates at a density of 50,000 cells/well, and allowed to adhere overnight (37° C., 5% CO$_2$). 10D1F.FcA or trastuzumab were mixed with labelling reagent, and the labelled complexes were added to cells. Samples were harvested at 0 min, 10 min, 30 min, 1 hour, 2 hour and 4.5 hour time points, by aspiration of cell culture medium, washing with PBS and treatment with accutase. Accutase activity was neutralised, and cells were resuspended in FACs buffer and analysed by flow cytometry.

Figure 73A:
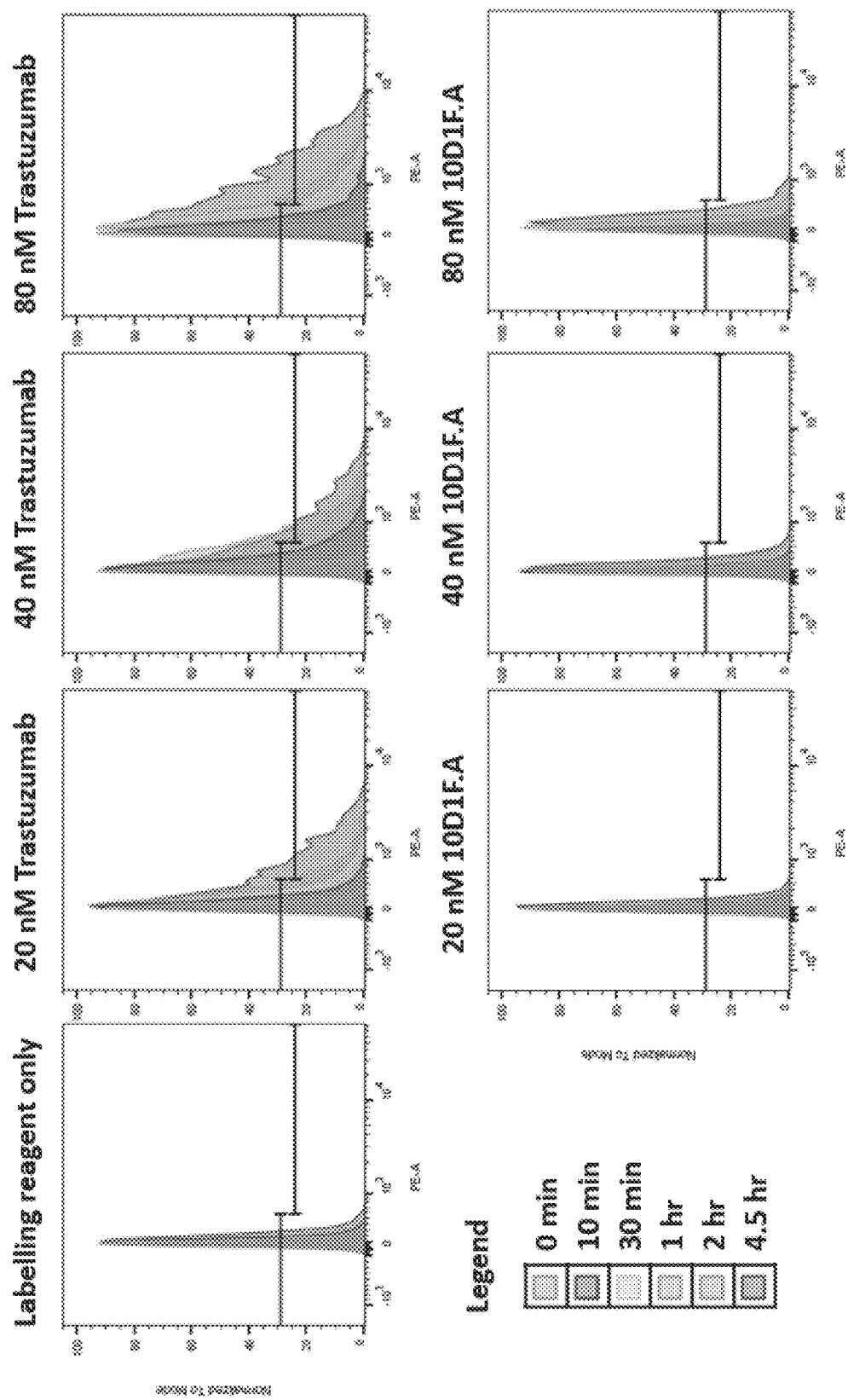

The results are shown in FIGS. 73A and 73B. The cells displayed minimal internalisation of 10D1F.FcA. By contrast, substantial internalisation of anti-HER2 antibody trastuzumab was observed.

Example 13

Use of HER3-Binding Antibodies in Immunohistochemistry

Anti-HER3 antibody 10D1F in mIgG2a format was evaluated for its ability to be used in immunohistochemistry for the detection of human HER3 protein.

Processing of sections was performed using Bond reagents (Leica Biosystems). Arrays of commercially-available frozen tissue sections were obtained. Slides were dried in a desiccator for 10 min and then subjected to the following treatments, with water washes and/or TBS-T rinses between steps: (i) fixation by treatment with 100% acetone for 10 min at room temperature; (ii) endogenous peroxidase blocking by treatment with 3% (v/v) $H_2O_2$ for 15 min at room temperature; (iii) blocking by treatment with 10% goat serum for 30 min at room temperature, (iv) incubation with 10D1F-mIgG2a at 1:250 dilution of a 6.2 mg/ml solution overnight at 4° C., (v) incubation with HRP-polymer conjugated goat anti-mouse antibody for 30 min at room temperature, and (vi) development with Bond Mixed DAB Refine for 5 min at room temperature, followed by rinsing with deionised water and 1× Bond Wash to stop the reaction.

Slides were then dehydrated, mounted in synthetic mounting media and scanned with high resolution.

Figure 75A:
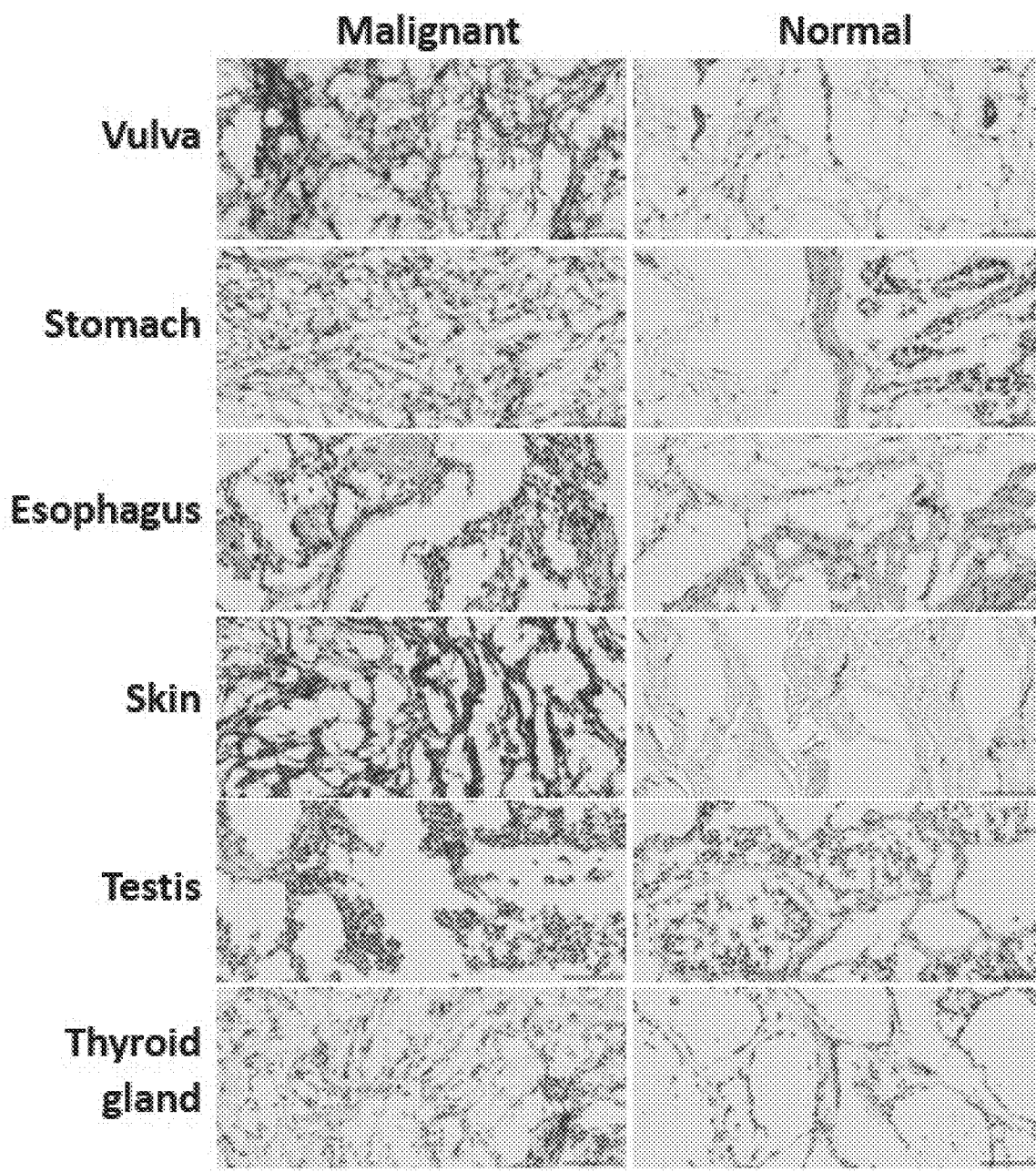
FIGS. 75A and 75B, images showing immunohistochemical staining of malignant and normal human tissues using 10D1F.FcA. 75A and 75B shows staining of different tissues.
Figure 75B:
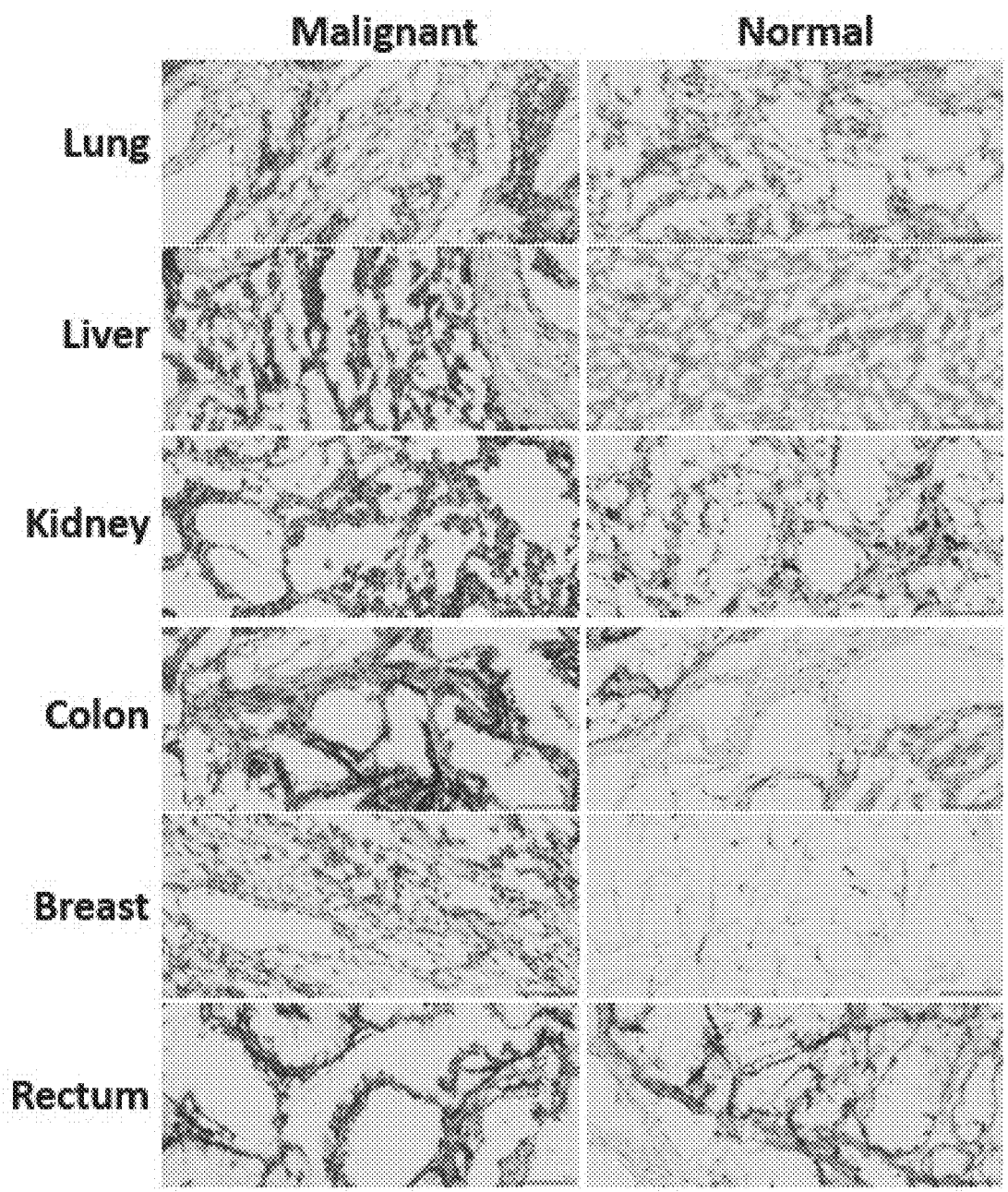

The results are shown in FIGS. 75A and 75B. 10D1F preferentially stained malignant human tissue sections, with low cross-reactivity to normal tissue.

In further experiments, an A549 xenograft tumor was harvested in cold PBS, embedded in OCT cryoembedding medium, frozen in dry-ice and stored at −80° C. 10 μm sections were obtained using a cryostat.

Slides were dried in a desiccator for 10 min and then subjected to the following treatments, with water washes and/or TBS-T rinses between steps: (i) fixation by treatment with 100% acetone for 10 min at room temperature; (ii) endogenous peroxidase blocking by treatment with 3% (v/v) $H_2O_2$ for 15 min at room temperature; (iii) blocking by treatment with 10% goat serum for 30 min at room temperature, (iv) incubation with 10D1F.FcA at 1:50 dilution of 8.8 mg/ml solution, or with 1:200 dilution of Sino Biological rabbit anti-HER3 (Cat. No. 10201-T24) overnight at 4° C., (v) incubation with Invitrogen F(ab')2-Goat anti-Human IgG (H+L) HRP (A24470) (1:500), or HRP-polymer conjugated goat anti-rabbit antibody for 30 min at room temperature, and (vi) development with Bond Mixed DAB Refine for 5 min at room temperature, followed by rinsing with deionised water and 1× Bond Wash to stop the reaction.

Slides were then counterstained with haematoxylin, dehydrated, mounted in synthetic mounting media and scanned with high resolution.

Figure 76:
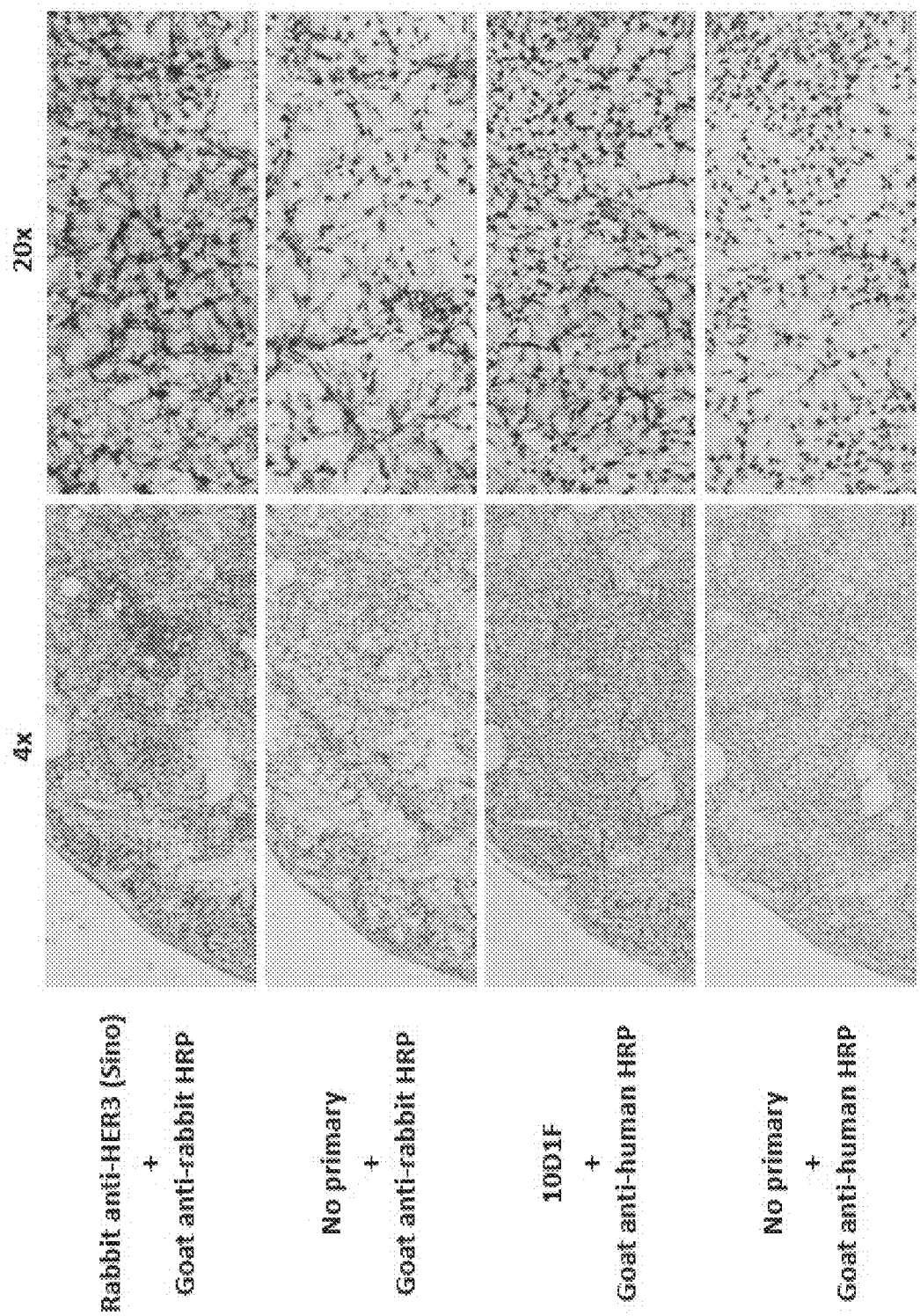
FIG. 76. Images showing immunohistochemical staining of A549 tumor xenograft cryosections by 10D1F or a rabbit polyclonal anti-HER3 antibody, at the indicated magnifications. Secondary-only control stainings are shown.

The results are shown in FIG. 76. 10D1F.FcA displayed specific membrane and cytoplasmic staining of A549 tumor xenograft cryosections.

The invention claimed is:

1. An antigen-binding molecule comprising a heavy chain variable (VH) region and a light chain variable (VL) region, wherein the antigen-binding molecule specifically binds to HER3, wherein binding to HER3 comprises contact with one or more amino acid residues of the region of HER3 shown in SEQ ID NO:229, and wherein the antigen-binding molecule comprises:
   a VH region incorporating the following CDRs:
      HC-CDR1 having the amino acid sequence of SEQ ID NO:43
      HC-CDR2 having the amino acid sequence of SEQ ID NO:46
      HC-CDR3 having the amino acid sequence of SEQ ID NO:51; and
   a VL region incorporating the following CDRs:
      LC-CDR1 having the amino acid sequence of SEQ ID NO:91
      LC-CDR2 having the amino acid sequence of SEQ ID NO:94
      LC-CDR3 having the amino acid sequence of SEQ ID NO:99.

2. The antigen-binding molecule according to claim 1, wherein the antigen-binding molecule comprises:
   (a)
      a VH region having the following CDRs:
         HC-CDR1 having the amino acid sequence of SEQ ID NO:41
         HC-CDR2 having the amino acid sequence of SEQ ID NO:44
         HC-CDR3 having the amino acid sequence of SEQ ID NO:47; and
      a VL region having the following CDRs:
         LC-CDR1 having the amino acid sequence of SEQ ID NO:88

LC-CDR2 having the amino acid sequence of SEQ ID NO:92
LC-CDR3 having the amino acid sequence of SEQ ID NO:95; or (b)
a VH region having the following CDRs:
HC-CDR1 having the amino acid sequence of SEQ ID NO:41
HC-CDR2 having the amino acid sequence of SEQ ID NO:44
HC-CDR3 having the amino acid sequence of SEQ ID NO:47; and
a VL region having the following CDRs:
LC-CDR1 having the amino acid sequence of SEQ ID NO:89
LC-CDR2 having the amino acid sequence of SEQ ID NO:92
LC-CDR3 having the amino acid sequence of SEQ ID NO:95; or (c)
a VH region having the following CDRs:
HC-CDR1 having the amino acid sequence of SEQ ID NO:41
HC-CDR2 having the amino acid sequence of SEQ ID NO:44
HC-CDR3 having the amino acid sequence of SEQ ID NO:47; and
a VL region having the following CDRs:
LC-CDR1 having the amino acid sequence of SEQ ID NO:90
LC-CDR2 having the amino acid sequence of SEQ ID NO:92
LC-CDR3 having the amino acid sequence of SEQ ID NO:96; or (d)
a VH region having the following CDRs:
HC-CDR1 having the amino acid sequence of SEQ ID NO:41
HC-CDR2 having the amino acid sequence of SEQ ID NO:45
HC-CDR3 having the amino acid sequence of SEQ ID NO:47; and
a VL region having the following CDRs:
LC-CDR1 having the amino acid sequence of SEQ ID NO:88
LC-CDR2 having the amino acid sequence of SEQ ID NO:93
LC-CDR3 having the amino acid sequence of SEQ ID NO:95; or (e)
a VH region having the following CDRs:
HC-CDR1 having the amino acid sequence of SEQ ID NO:41
HC-CDR2 having the amino acid sequence of SEQ ID NO:45
HC-CDR3 having the amino acid sequence of SEQ ID NO:49; and
a VL region having the following CDRs:
LC-CDR1 having the amino acid sequence of SEQ ID NO:88
LC-CDR2 having the amino acid sequence of SEQ ID NO:93
LC-CDR3 having the amino acid sequence of SEQ ID NO:95; or (f)
a VH region having the following CDRs:
HC-CDR1 having the amino acid sequence of SEQ ID NO:41
HC-CDR2 having the amino acid sequence of SEQ ID NO:45
HC-CDR3 having the amino acid sequence of SEQ ID NO:50; and
a VL region having the following CDRs:
LC-CDR1 having the amino acid sequence of SEQ ID NO:88
LC-CDR2 having the amino acid sequence of SEQ ID NO:93
LC-CDR3 having the amino acid sequence of SEQ ID NO:95; or (g)
a VH region having the following CDRs:
HC-CDR1 having the amino acid sequence of SEQ ID NO:41
HC-CDR2 having the amino acid sequence of SEQ ID NO:45
HC-CDR3 having the amino acid sequence of SEQ ID NO:48; and
a VL region having the following CDRs:
LC-CDR1 having the amino acid sequence of SEQ ID NO:88
LC-CDR2 having the amino acid sequence of SEQ ID NO:92
LC-CDR3 having the amino acid sequence of SEQ ID NO:95; or (h)
a VH region having the following CDRs:
HC-CDR1 having the amino acid sequence of SEQ ID NO:41
HC-CDR2 having the amino acid sequence of SEQ ID NO:45
HC-CDR3 having the amino acid sequence of SEQ ID NO:48; and
a VL region having the following CDRs:
LC-CDR1 having the amino acid sequence of SEQ ID NO:88
LC-CDR2 having the amino acid sequence of SEQ ID NO:92
LC-CDR3 having the amino acid sequence of SEQ ID NO:97; or (i)
a VH region having the following CDRs:
HC-CDR1 having the amino acid sequence of SEQ ID NO:42
HC-CDR2 having the amino acid sequence of SEQ ID NO:45
HC-CDR3 having the amino acid sequence of SEQ ID NO:48; and
a VL region having the following CDRs:
LC-CDR1 having the amino acid sequence of SEQ ID NO:88
LC-CDR2 having the amino acid sequence of SEQ ID NO:92
LC-CDR3 having the amino acid sequence of SEQ ID NO:95; or (j)
a VH region having the following CDRs:
HC-CDR1 having the amino acid sequence of SEQ ID NO:41
HC-CDR2 having the amino acid sequence of SEQ ID NO:44
HC-CDR3 having the amino acid sequence of SEQ ID NO:47; and a VL region having the following CDRs:
LC-CDR1 having the amino acid sequence of SEQ ID NO:88
LC-CDR2 having the amino acid sequence of SEQ ID NO:92
LC-CDR3 having the amino acid sequence of SEQ ID NO:98.

3. The antigen-binding molecule according to claim 1, wherein the antigen-binding molecule comprises:
(a) a VH region comprising an amino acid sequence having at least 70% sequence identity to the amino acid sequence of SEQ ID NO:24; and a VL region comprising an amino acid sequence having at least 70% sequence identity to the amino acid sequence of SEQ ID NO:74; or
(b) a VH region comprising an amino acid sequence having at least 70% sequence identity to the amino acid sequence of SEQ ID NO:25; and a VL region comprising an amino acid sequence having at least 70% sequence identity to the amino acid sequence of SEQ ID NO:75; or
(c) a VH region comprising an amino acid sequence having at least 70% sequence identity to the amino acid sequence of SEQ ID NO:26; and a VL region comprising an amino acid sequence having at least 70% sequence identity to the amino acid sequence of SEQ ID NO:76; or
(d) a VH region comprising an amino acid sequence having at least 70% sequence identity to the amino acid sequence of SEQ ID NO:27; and a VL region comprising an amino acid sequence having at least 70% sequence identity to the amino acid sequence of SEQ ID NO:77; or
(e) a VH region comprising an amino acid sequence having at least 70% sequence identity to the amino acid sequence of SEQ ID NO:28; and a VL region comprising an amino acid sequence having at least 70% sequence identity to the amino acid sequence of SEQ ID NO:78; or
(f) a VH region comprising an amino acid sequence having at least 70% sequence identity to the amino acid sequence of SEQ ID NO:29; and a VL region comprising an amino acid sequence having at least 70% sequence identity to the amino acid sequence of SEQ ID NO:78; or
(g) a VH region comprising an amino acid sequence having at least 70% sequence identity to the amino acid sequence of SEQ ID NO:30; and a VL region comprising an amino acid sequence having at least 70% sequence identity to the amino acid sequence of SEQ ID NO:78; or
(h) a VH region comprising an amino acid sequence having at least 70% sequence identity to the amino acid sequence of SEQ ID NO:31; and a VL region comprising an amino acid sequence having at least 70% sequence identity to the amino acid sequence of SEQ ID NO:79; or
(i) a VH region comprising an amino acid sequence having at least 70% sequence identity to the amino acid sequence of SEQ ID NO:32; and a VL region comprising an amino acid sequence having at least 70% sequence identity to the amino acid sequence of SEQ ID NO:79; or
(j) a VH region comprising an amino acid sequence having at least 70% sequence identity to the amino acid sequence of SEQ ID NO:33; and a VL region comprising an amino acid sequence having at least 70% sequence identity to the amino acid sequence of SEQ ID NO:80; or
(k) a VH region comprising an amino acid sequence having at least 70% sequence identity to the amino acid sequence of SEQ ID NO:34; and a VL region comprising an amino acid sequence having at least 70% sequence identity to the amino acid sequence of SEQ ID NO:81; or
(l) a VH region comprising an amino acid sequence having at least 70% sequence identity to the amino acid sequence of SEQ ID NO:35; and a VL region comprising an amino acid sequence having at least 70% sequence identity to the amino acid sequence of SEQ ID NO:82; or
(m) a VH region comprising an amino acid sequence having at least 70% sequence identity to the amino acid sequence of SEQ ID NO:36; and a VL region comprising an amino acid sequence having at least 70% sequence identity to the amino acid sequence of SEQ ID NO:83; or
(n) a VH region comprising an amino acid sequence having at least 70% sequence identity to the amino acid sequence of SEQ ID NO:37; and a VL region comprising an amino acid sequence having at least 70% sequence identity to the amino acid sequence of SEQ ID NO:84; or
(o) a VH region comprising an amino acid sequence having at least 70% sequence identity to the amino acid sequence of SEQ ID NO:38; and a VL region comprising an amino acid sequence having at least 70% sequence identity to the amino acid sequence of SEQ ID NO:85; or
(p) a VH region comprising an amino acid sequence having at least 70% sequence identity to the amino acid sequence of SEQ ID NO:39; and a VL region comprising an amino acid sequence having at least 70% sequence identity to the amino acid sequence of SEQ ID NO:86; or
(q) a VH region comprising an amino acid sequence having at least 70% sequence identity to the amino acid sequence of SEQ ID NO:40; and a VL region comprising an amino acid sequence having at least 70% sequence identity to the amino acid sequence of SEQ ID NO:87.

4. A nucleic acid, or a plurality of nucleic acids, encoding an antigen-binding molecule comprising a heavy chain variable (VH) region and a light chain variable (VL) region, wherein the antigen-binding molecule specifically binds to HER3, wherein binding to HER3 comprises contact with one or more amino acid residues of the region of HER3 shown in SEQ ID NO:229, and wherein the antigen-binding molecule comprises:
a VH region incorporating the following CDRs:
HC-CDR1 having the amino acid sequence of SEQ ID NO:43
HC-CDR2 having the amino acid sequence of SEQ ID NO:46
HC-CDR3 having the amino acid sequence of SEQ ID NO:51; and
a VL region incorporating the following CDRs:
LC-CDR1 having the amino acid sequence of SEQ ID NO:91
LC-CDR2 having the amino acid sequence of SEQ ID NO:94
LC-CDR3 having the amino acid sequence of SEQ ID NO:99.

5. The nucleic acid or plurality of nucleic acids according to claim 4, wherein the antigen-binding molecule comprises:
(a)
  a VH region having the following CDRs:
    HC-CDR1 having the amino acid sequence of SEQ ID NO:41
    HC-CDR2 having the amino acid sequence of SEQ ID NO:44
    HC-CDR3 having the amino acid sequence of SEQ ID NO:47; and
  a VL region having the following CDRs:
    LC-CDR1 having the amino acid sequence of SEQ ID NO:88
    LC-CDR2 having the amino acid sequence of SEQ ID NO:92
    LC-CDR3 having the amino acid sequence of SEQ ID NO:95; or
(b)
  a VH region having the following CDRs:
    HC-CDR1 having the amino acid sequence of SEQ ID NO:41
    HC-CDR2 having the amino acid sequence of SEQ ID NO:44
    HC-CDR3 having the amino acid sequence of SEQ ID NO:47; and
  a VL region having the following CDRs:
    LC-CDR1 having the amino acid sequence of SEQ ID NO:89
    LC-CDR2 having the amino acid sequence of SEQ ID NO:92
    LC-CDR3 having the amino acid sequence of SEQ ID NO:95; or
(c)
  a VH region having the following CDRs:
    HC-CDR1 having the amino acid sequence of SEQ ID NO:41
    HC-CDR2 having the amino acid sequence of SEQ ID NO:44
    HC-CDR3 having the amino acid sequence of SEQ ID NO:47; and
  a VL region having the following CDRs:
    LC-CDR1 having the amino acid sequence of SEQ ID NO:90
    LC-CDR2 having the amino acid sequence of SEQ ID NO:92
    LC-CDR3 having the amino acid sequence of SEQ ID NO:96; or
(d)
  a VH region having the following CDRs:
    HC-CDR1 having the amino acid sequence of SEQ ID NO:41
    HC-CDR2 having the amino acid sequence of SEQ ID NO:45
    HC-CDR3 having the amino acid sequence of SEQ ID NO:47; and
  a VL region having the following CDRs:
    LC-CDR1 having the amino acid sequence of SEQ ID NO:88
    LC-CDR2 having the amino acid sequence of SEQ ID NO:93
    LC-CDR3 having the amino acid sequence of SEQ ID NO:95; or
(e)
  a VH region having the following CDRs:
    HC-CDR1 having the amino acid sequence of SEQ ID NO:41
    HC-CDR2 having the amino acid sequence of SEQ ID NO:45
    HC-CDR3 having the amino acid sequence of SEQ ID NO:49; and
  a VL region having the following CDRs:
    LC-CDR1 having the amino acid sequence of SEQ ID NO:88
    LC-CDR2 having the amino acid sequence of SEQ ID NO:93
    LC-CDR3 having the amino acid sequence of SEQ ID NO:95; or
(f)
  a VH region having the following CDRs:
    HC-CDR1 having the amino acid sequence of SEQ ID NO:41
    HC-CDR2 having the amino acid sequence of SEQ ID NO:45
    HC-CDR3 having the amino acid sequence of SEQ ID NO:50; and
  a VL region having the following CDRs:
    LC-CDR1 having the amino acid sequence of SEQ ID NO:88
    LC-CDR2 having the amino acid sequence of SEQ ID NO:93
    LC-CDR3 having the amino acid sequence of SEQ ID NO:95; or
(g)
  a VH region having the following CDRs:
    HC-CDR1 having the amino acid sequence of SEQ ID NO:41
    HC-CDR2 having the amino acid sequence of SEQ ID NO:45
    HC-CDR3 having the amino acid sequence of SEQ ID NO:48; and
  a VL region having the following CDRs:
    LC-CDR1 having the amino acid sequence of SEQ ID NO:88
    LC-CDR2 having the amino acid sequence of SEQ ID NO:92
    LC-CDR3 having the amino acid sequence of SEQ ID NO:95; or
(h)
  a VH region having the following CDRs:
    HC-CDR1 having the amino acid sequence of SEQ ID NO:41
    HC-CDR2 having the amino acid sequence of SEQ ID NO:45
    HC-CDR3 having the amino acid sequence of SEQ ID NO:48; and
  a VL region having the following CDRs:
    LC-CDR1 having the amino acid sequence of SEQ ID NO:88
    LC-CDR2 having the amino acid sequence of SEQ ID NO:92
    LC-CDR3 having the amino acid sequence of SEQ ID NO:97; or
(i)
  a VH region having the following CDRs:
    HC-CDR1 having the amino acid sequence of SEQ ID NO:42
    HC-CDR2 having the amino acid sequence of SEQ ID NO:45
    HC-CDR3 having the amino acid sequence of SEQ ID NO:48; and
  a VL region having the following CDRs:
    LC-CDR1 having the amino acid sequence of SEQ ID NO:88

LC-CDR2 having the amino acid sequence of SEQ ID NO:92
LC-CDR3 having the amino acid sequence of SEQ ID NO:95; or
(j)
  a VH region having the following CDRs:
    HC-CDR1 having the amino acid sequence of SEQ ID NO:41
    HC-CDR2 having the amino acid sequence of SEQ ID NO:44
    HC-CDR3 having the amino acid sequence of SEQ ID NO:47; and
  a VL region having the following CDRs:
    LC-CDR1 having the amino acid sequence of SEQ ID NO:88
    LC-CDR2 having the amino acid sequence of SEQ ID NO:92
    LC-CDR3 having the amino acid sequence of SEQ ID NO:98.

6. The nucleic acid or plurality of nucleic acids according to claim 4, wherein the antigen-binding molecule comprises:
(a) a VH region comprising an amino acid sequence having at least 70% sequence identity to the amino acid sequence of SEQ ID NO:24; and a VL region comprising an amino acid sequence having at least 70% sequence identity to the amino acid sequence of SEQ ID NO:74; or
(b) a VH region comprising an amino acid sequence having at least 70% sequence identity to the amino acid sequence of SEQ ID NO:25; and a VL region comprising an amino acid sequence having at least 70% sequence identity to the amino acid sequence of SEQ ID NO:75; or
(c) a VH region comprising an amino acid sequence having at least 70% sequence identity to the amino acid sequence of SEQ ID NO:26; and a VL region comprising an amino acid sequence having at least 70% sequence identity to the amino acid sequence of SEQ ID NO:76; or
(d) a VH region comprising an amino acid sequence having at least 70% sequence identity to the amino acid sequence of SEQ ID NO:27; and a VL region comprising an amino acid sequence having at least 70% sequence identity to the amino acid sequence of SEQ ID NO:77; or
(e) a VH region comprising an amino acid sequence having at least 70% sequence identity to the amino acid sequence of SEQ ID NO:28; and a VL region comprising an amino acid sequence having at least 70% sequence identity to the amino acid sequence of SEQ ID NO:78; or
(f) a VH region comprising an amino acid sequence having at least 70% sequence identity to the amino acid sequence of SEQ ID NO:29; and a VL region comprising an amino acid sequence having at least 70% sequence identity to the amino acid sequence of SEQ ID NO:78; or
(g) a VH region comprising an amino acid sequence having at least 70% sequence identity to the amino acid sequence of SEQ ID NO:30; and a VL region comprising an amino acid sequence having at least 70% sequence identity to the amino acid sequence of SEQ ID NO:78; or
(h) a VH region comprising an amino acid sequence having at least 70% sequence identity to the amino acid sequence of SEQ ID NO:31; and a VL region comprising an amino acid sequence having at least 70% sequence identity to the amino acid sequence of SEQ ID NO:79; or
(i) a VH region comprising an amino acid sequence having at least 70% sequence identity to the amino acid sequence of SEQ ID NO:32; and a VL region comprising an amino acid sequence having at least 70% sequence identity to the amino acid sequence of SEQ ID NO:79; or
(j) a VH region comprising an amino acid sequence having at least 70% sequence identity to the amino acid sequence of SEQ ID NO:33; and a VL region comprising an amino acid sequence having at least 70% sequence identity to the amino acid sequence of SEQ ID NO:80; or
(k) a VH region comprising an amino acid sequence having at least 70% sequence identity to the amino acid sequence of SEQ ID NO:34; and a VL region comprising an amino acid sequence having at least 70% sequence identity to the amino acid sequence of SEQ ID NO:81; or
(l) a VH region comprising an amino acid sequence having at least 70% sequence identity to the amino acid sequence of SEQ ID NO:35; and a VL region comprising an amino acid sequence having at least 70% sequence identity to the amino acid sequence of SEQ ID NO:82; or
(m) a VH region comprising an amino acid sequence having at least 70% sequence identity to the amino acid sequence of SEQ ID NO:36; and a VL region comprising an amino acid sequence having at least 70% sequence identity to the amino acid sequence of SEQ ID NO:83; or
(n) a VH region comprising an amino acid sequence having at least 70% sequence identity to the amino acid sequence of SEQ ID NO:37; and a VL region comprising an amino acid sequence having at least 70% sequence identity to the amino acid sequence of SEQ ID NO:84; or
(o) a VH region comprising an amino acid sequence having at least 70% sequence identity to the amino acid sequence of SEQ ID NO:38; and a VL region comprising an amino acid sequence having at least 70% sequence identity to the amino acid sequence of SEQ ID NO:85; or
(p) a VH region comprising an amino acid sequence having at least 70% sequence identity to the amino acid sequence of SEQ ID NO:39; and a VL region comprising an amino acid sequence having at least 70% sequence identity to the amino acid sequence of SEQ ID NO:86; or
(q) a VH region comprising an amino acid sequence having at least 70% sequence identity to the amino acid sequence of SEQ ID NO:40; and a VL region comprising an amino acid sequence having at least 70% sequence identity to the amino acid sequence of SEQ ID NO:87.

7. A cell comprising a nucleic acid, or a plurality of nucleic acids, encoding an antigen-binding molecule comprising a heavy chain variable (VH) region and a light chain variable (VL) region, wherein the antigen-binding molecule specifically binds to HER3, wherein binding to HER3 comprises contact with one or more amino acid residues of the region of HER3 shown in SEQ ID NO:229, and wherein the antigen-binding molecule comprises:

a VH region incorporating the following CDRs:
  HC-CDR1 having the amino acid sequence of SEQ ID NO:43
  HC-CDR2 having the amino acid sequence of SEQ ID NO:46
  HC-CDR3 having the amino acid sequence of SEQ ID NO:51; and
a VL region incorporating the following CDRs:
  LC-CDR1 having the amino acid sequence of SEQ ID NO:91
  LC-CDR2 having the amino acid sequence of SEQ ID NO:94
  LC-CDR3 having the amino acid sequence of SEQ ID NO:99.

8. The cell according to claim 7, wherein the antigen-binding molecule comprises:

(a)
  a VH region having the following CDRs:
    HC-CDR1 having the amino acid sequence of SEQ ID NO:41
    HC-CDR2 having the amino acid sequence of SEQ ID NO:44
    HC-CDR3 having the amino acid sequence of SEQ ID NO:47; and
  a VL region having the following CDRs:
    LC-CDR1 having the amino acid sequence of SEQ ID NO:88
    LC-CDR2 having the amino acid sequence of SEQ ID NO:92
    LC-CDR3 having the amino acid sequence of SEQ ID NO:95; or (b)
  a VH region having the following CDRs:
    HC-CDR1 having the amino acid sequence of SEQ ID NO:41
    HC-CDR2 having the amino acid sequence of SEQ ID NO:44
    HC-CDR3 having the amino acid sequence of SEQ ID NO:47; and
  a VL region having the following CDRs:
    LC-CDR1 having the amino acid sequence of SEQ ID NO:89
    LC-CDR2 having the amino acid sequence of SEQ ID NO:92
    LC-CDR3 having the amino acid sequence of SEQ ID NO:95; or (c)
  a VH region having the following CDRs:
    HC-CDR1 having the amino acid sequence of SEQ ID NO:41
    HC-CDR2 having the amino acid sequence of SEQ ID NO:44
    HC-CDR3 having the amino acid sequence of SEQ ID NO:47; and
  a VL region having the following CDRs:
    LC-CDR1 having the amino acid sequence of SEQ ID NO:90
    LC-CDR2 having the amino acid sequence of SEQ ID NO:92
    LC-CDR3 having the amino acid sequence of SEQ ID NO:96; or (d)
  a VH region having the following CDRs:
    HC-CDR1 having the amino acid sequence of SEQ ID NO:41
    HC-CDR2 having the amino acid sequence of SEQ ID NO:45
    HC-CDR3 having the amino acid sequence of SEQ ID NO:47; and
  a VL region having the following CDRs:
    LC-CDR1 having the amino acid sequence of SEQ ID NO:88
    LC-CDR2 having the amino acid sequence of SEQ ID NO:93
    LC-CDR3 having the amino acid sequence of SEQ ID NO:95; or (e)
  a VH region having the following CDRs:
    HC-CDR1 having the amino acid sequence of SEQ ID NO:41
    HC-CDR2 having the amino acid sequence of SEQ ID NO:45
    HC-CDR3 having the amino acid sequence of SEQ ID NO:49; and (f)
  a VH region having the following CDRs:
    HC-CDR1 having the amino acid sequence of SEQ ID NO:41
    HC-CDR2 having the amino acid sequence of SEQ ID NO:45
    HC-CDR3 having the amino acid sequence of SEQ ID NO:50; and
  a VL region having the following CDRs:
    LC-CDR1 having the amino acid sequence of SEQ ID NO:88
    LC-CDR2 having the amino acid sequence of SEQ ID NO:93
    LC-CDR3 having the amino acid sequence of SEQ ID NO:95; or (g)
  a VH region having the following CDRs:
    HC-CDR1 having the amino acid sequence of SEQ ID NO:41
    HC-CDR2 having the amino acid sequence of SEQ ID NO:45
    HC-CDR3 having the amino acid sequence of SEQ ID NO:48; and
  a VL region having the following CDRs:
    LC-CDR1 having the amino acid sequence of SEQ ID NO:88
    LC-CDR2 having the amino acid sequence of SEQ ID NO:92
    LC-CDR3 having the amino acid sequence of SEQ ID NO:95; or (h)
  a VH region having the following CDRs:
    HC-CDR1 having the amino acid sequence of SEQ ID NO:41
    HC-CDR2 having the amino acid sequence of SEQ ID NO:45
    HC-CDR3 having the amino acid sequence of SEQ ID NO:48; and
  a VL region having the following CDRs:
    LC-CDR1 having the amino acid sequence of SEQ ID NO:88
    LC-CDR2 having the amino acid sequence of SEQ ID NO:92
    LC-CDR3 having the amino acid sequence of SEQ ID NO:97; or (i)
  a VH region having the following CDRs:
    HC-CDR1 having the amino acid sequence of SEQ ID NO:42

HC-CDR2 having the amino acid sequence of SEQ ID NO:45
HC-CDR3 having the amino acid sequence of SEQ ID NO:48; and
a VL region having the following CDRs:
LC-CDR1 having the amino acid sequence of SEQ ID NO:88
LC-CDR2 having the amino acid sequence of SEQ ID NO:92
LC-CDR3 having the amino acid sequence of SEQ ID NO:95; or
(j)
a VH region having the following CDRs:
HC-CDR1 having the amino acid sequence of SEQ ID NO:41
HC-CDR2 having the amino acid sequence of SEQ ID NO:44
HC-CDR3 having the amino acid sequence of SEQ ID NO:47; and
a VL region having the following CDRs:
LC-CDR1 having the amino acid sequence of SEQ ID NO:88
LC-CDR2 having the amino acid sequence of SEQ ID NO:92
LC-CDR3 having the amino acid sequence of SEQ ID NO:98.

9. The cell according to claim 7, wherein the antigen-binding molecule comprises:
(a) a VH region comprising an amino acid sequence having at least 70% sequence identity to the amino acid sequence of SEQ ID NO:24; and a VL region comprising an amino acid sequence having at least 70% sequence identity to the amino acid sequence of SEQ ID NO:74; or
(b) a VH region comprising an amino acid sequence having at least 70% sequence identity to the amino acid sequence of SEQ ID NO:25; and a VL region comprising an amino acid sequence having at least 70% sequence identity to the amino acid sequence of SEQ ID NO:75; or
(c) a VH region comprising an amino acid sequence having at least 70% sequence identity to the amino acid sequence of SEQ ID NO:26; and a VL region comprising an amino acid sequence having at least 70% sequence identity to the amino acid sequence of SEQ ID NO:76; or
(d) a VH region comprising an amino acid sequence having at least 70% sequence identity to the amino acid sequence of SEQ ID NO:27; and a VL region comprising an amino acid sequence having at least 70% sequence identity to the amino acid sequence of SEQ ID NO:77; or
(e) a VH region comprising an amino acid sequence having at least 70% sequence identity to the amino acid sequence of SEQ ID NO:28; and a VL region comprising an amino acid sequence having at least 70% sequence identity to the amino acid sequence of SEQ ID NO:78; or
(f) a VH region comprising an amino acid sequence having at least 70% sequence identity to the amino acid sequence of SEQ ID NO:29; and a VL region comprising an amino acid sequence having at least 70% sequence identity to the amino acid sequence of SEQ ID NO:78; or
(g) a VH region comprising an amino acid sequence having at least 70% sequence identity to the amino acid sequence of SEQ ID NO:30; and a VL region comprising an amino acid sequence having at least 70% sequence identity to the amino acid sequence of SEQ ID NO:78; or
(h) a VH region comprising an amino acid sequence having at least 70% sequence identity to the amino acid sequence of SEQ ID NO:31; and a VL region comprising an amino acid sequence having at least 70% sequence identity to the amino acid sequence of SEQ ID NO:79; or
(i) a VH region comprising an amino acid sequence having at least 70% sequence identity to the amino acid sequence of SEQ ID NO:32; and a VL region comprising an amino acid sequence having at least 70% sequence identity to the amino acid sequence of SEQ ID NO:79; or
(j) a VH region comprising an amino acid sequence having at least 70% sequence identity to the amino acid sequence of SEQ ID NO:33; and a VL region comprising an amino acid sequence having at least 70% sequence identity to the amino acid sequence of SEQ ID NO:80; or
(k) a VH region comprising an amino acid sequence having at least 70% sequence identity to the amino acid sequence of SEQ ID NO:34; and a VL region comprising an amino acid sequence having at least 70% sequence identity to the amino acid sequence of SEQ ID NO:81; or
(l) a VH region comprising an amino acid sequence having at least 70% sequence identity to the amino acid sequence of SEQ ID NO:35; and a VL region comprising an amino acid sequence having at least 70% sequence identity to the amino acid sequence of SEQ ID NO:82; or
(m) a VH region comprising an amino acid sequence having at least 70% sequence identity to the amino acid sequence of SEQ ID NO:36; and a VL region comprising an amino acid sequence having at least 70% sequence identity to the amino acid sequence of SEQ ID NO:83; or
(n) a VH region comprising an amino acid sequence having at least 70% sequence identity to the amino acid sequence of SEQ ID NO:37; and a VL region comprising an amino acid sequence having at least 70% sequence identity to the amino acid sequence of SEQ ID NO:84; or
(o) a VH region comprising an amino acid sequence having at least 70% sequence identity to the amino acid sequence of SEQ ID NO:38; and a VL region comprising an amino acid sequence having at least 70% sequence identity to the amino acid sequence of SEQ ID NO:85; or
(p) a VH region comprising an amino acid sequence having at least 70% sequence identity to the amino acid sequence of SEQ ID NO:39; and a VL region comprising an amino acid sequence having at least 70% sequence identity to the amino acid sequence of SEQ ID NO:86; or
(q) a VH region comprising an amino acid sequence having at least 70% sequence identity to the amino acid sequence of SEQ ID NO:40; and a VL region comprising an amino acid sequence having at least 70% sequence identity to the amino acid sequence of SEQ ID NO:87.

10. A method of treating a cancer in a subject, comprising administering to a subject a therapeutically effective amount of an antigen-binding molecule comprising a heavy chain variable (VH) region and a light chain variable (VL) region, wherein the antigen-binding molecule specifically binds to HER3, wherein binding to HER3 comprises contact with one or more amino acid residues of the region of HER3 shown in SEQ ID NO:229, and wherein the antigen-binding molecule comprises:
- a VH region incorporating the following CDRs:
  - HC-CDR1 having the amino acid sequence of SEQ ID NO:43
  - HC-CDR2 having the amino acid sequence of SEQ ID NO:46
  - HC-CDR3 having the amino acid sequence of SEQ ID NO:51; and
- a VL region incorporating the following CDRs:
  - LC-CDR1 having the amino acid sequence of SEQ ID NO:91
  - LC-CDR2 having the amino acid sequence of SEQ ID NO:94
  - LC-CDR3 having the amino acid sequence of SEQ ID NO:99.

11. The method according to claim 10, wherein the antigen-binding molecule comprises:

(a)
- a VH region having the following CDRs:
  - HC-CDR1 having the amino acid sequence of SEQ ID NO:41
  - HC-CDR2 having the amino acid sequence of SEQ ID NO:44
  - HC-CDR3 having the amino acid sequence of SEQ ID NO:47; and
- a VL region having the following CDRs:
  - LC-CDR1 having the amino acid sequence of SEQ ID NO:88
  - LC-CDR2 having the amino acid sequence of SEQ ID NO:92
  - LC-CDR3 having the amino acid sequence of SEQ ID NO:95; or (b)
- a VH region having the following CDRs:
  - HC-CDR1 having the amino acid sequence of SEQ ID NO:41
  - HC-CDR2 having the amino acid sequence of SEQ ID NO:44
  - HC-CDR3 having the amino acid sequence of SEQ ID NO:47; and
- a VL region having the following CDRs:
  - LC-CDR1 having the amino acid sequence of SEQ ID NO:89
  - LC-CDR2 having the amino acid sequence of SEQ ID NO:92
  - LC-CDR3 having the amino acid sequence of SEQ ID NO:95; or (c)
- a VH region having the following CDRs:
  - HC-CDR1 having the amino acid sequence of SEQ ID NO:41
  - HC-CDR2 having the amino acid sequence of SEQ ID NO:44
  - HC-CDR3 having the amino acid sequence of SEQ ID NO:47; and
- a VL region having the following CDRs:
  - LC-CDR1 having the amino acid sequence of SEQ ID NO:90
  - LC-CDR2 having the amino acid sequence of SEQ ID NO:92
  - LC-CDR3 having the amino acid sequence of SEQ ID NO:96; or (d)
- a VH region having the following CDRs:
  - HC-CDR1 having the amino acid sequence of SEQ ID NO:41
  - HC-CDR2 having the amino acid sequence of SEQ ID NO:45
  - HC-CDR3 having the amino acid sequence of SEQ ID NO:47; and
- a VL region having the following CDRs:
  - LC-CDR1 having the amino acid sequence of SEQ ID NO:88
  - LC-CDR2 having the amino acid sequence of SEQ ID NO:93
  - LC-CDR3 having the amino acid sequence of SEQ ID NO:95; or (e)
- a VH region having the following CDRs:
  - HC-CDR1 having the amino acid sequence of SEQ ID NO:41
  - HC-CDR2 having the amino acid sequence of SEQ ID NO:45
  - HC-CDR3 having the amino acid sequence of SEQ ID NO:49; and
- a VL region having the following CDRs:
  - LC-CDR1 having the amino acid sequence of SEQ ID NO:88
  - LC-CDR2 having the amino acid sequence of SEQ ID NO:93
  - LC-CDR3 having the amino acid sequence of SEQ ID NO:95; or (f)
- a VH region having the following CDRs:
  - HC-CDR1 having the amino acid sequence of SEQ ID NO:41
  - HC-CDR2 having the amino acid sequence of SEQ ID NO:45
  - HC-CDR3 having the amino acid sequence of SEQ ID NO:50; and
- a VL region having the following CDRs:
  - LC-CDR1 having the amino acid sequence of SEQ ID NO:88
  - LC-CDR2 having the amino acid sequence of SEQ ID NO:93
  - LC-CDR3 having the amino acid sequence of SEQ ID NO:95; or (g)
- a VH region having the following CDRs:
  - HC-CDR1 having the amino acid sequence of SEQ ID NO:41
  - HC-CDR2 having the amino acid sequence of SEQ ID NO:45
  - HC-CDR3 having the amino acid sequence of SEQ ID NO:48; and
- a VL region having the following CDRs:
  - LC-CDR1 having the amino acid sequence of SEQ ID NO:88
  - LC-CDR2 having the amino acid sequence of SEQ ID NO:92
  - LC-CDR3 having the amino acid sequence of SEQ ID NO:95; or (h)
- a VH region having the following CDRs:
  - HC-CDR1 having the amino acid sequence of SEQ ID NO:41
  - HC-CDR2 having the amino acid sequence of SEQ ID NO:45
  - HC-CDR3 having the amino acid sequence of SEQ ID NO:48; and a VL region having the following CDRs:
- LC-CDR1 having the amino acid sequence of SEQ ID NO:88
- LC-CDR2 having the amino acid sequence of SEQ ID NO:92
- LC-CDR3 having the amino acid sequence of SEQ ID NO:97; or (i)
a VH region having the following CDRs:
- HC-CDR1 having the amino acid sequence of SEQ ID NO:42
- HC-CDR2 having the amino acid sequence of SEQ ID NO:45
- HC-CDR3 having the amino acid sequence of SEQ ID NO:48; and a VL region having the following CDRs:
- LC-CDR1 having the amino acid sequence of SEQ ID NO:88
- LC-CDR2 having the amino acid sequence of SEQ ID NO:92
- LC-CDR3 having the amino acid sequence of SEQ ID NO:95; or (j)
a VH region having the following CDRs:
- HC-CDR1 having the amino acid sequence of SEQ ID NO:41
- HC-CDR2 having the amino acid sequence of SEQ ID NO:44
- HC-CDR3 having the amino acid sequence of SEQ ID NO:47; and a VL region having the following CDRs:
- LC-CDR1 having the amino acid sequence of SEQ ID NO:88
- LC-CDR2 having the amino acid sequence of SEQ ID NO:92
- LC-CDR3 having the amino acid sequence of SEQ ID NO:98.

12. The method according to claim 10, wherein the antigen-binding molecule comprises:

(a) a VH region comprising an amino acid sequence having at least 70% sequence identity to the amino acid sequence of SEQ ID NO:24; and a VL region comprising an amino acid sequence having at least 70% sequence identity to the amino acid sequence of SEQ ID NO:74; or (b) a VH region comprising an amino acid sequence having at least 70% sequence identity to the amino acid sequence of SEQ ID NO:25; and a VL region comprising an amino acid sequence having at least 70% sequence identity to the amino acid sequence of SEQ ID NO:75; or (c) a VH region comprising an amino acid sequence having at least 70% sequence identity to the amino acid sequence of SEQ ID NO:26; and a VL region comprising an amino acid sequence having at least 70% sequence identity to the amino acid sequence of SEQ ID NO:76; or (d) a VH region comprising an amino acid sequence having at least 70% sequence identity to the amino acid sequence of SEQ ID NO:27; and a VL region comprising an amino acid sequence having at least 70% sequence identity to the amino acid sequence of SEQ ID NO:77; or (e) a VH region comprising an amino acid sequence having at least 70% sequence identity to the amino acid sequence of SEQ ID NO:28; and a VL region comprising an amino acid sequence having at least 70% sequence identity to the amino acid sequence of SEQ ID NO:78; or (f) a VH region comprising an amino acid sequence having at least 70% sequence identity to the amino acid sequence of SEQ ID NO:29; and a VL region comprising an amino acid sequence having at least 70% sequence identity to the amino acid sequence of SEQ ID NO:78; or (g) a VH region comprising an amino acid sequence having at least 70% sequence identity to the amino acid sequence of SEQ ID NO:30; and a VL region comprising an amino acid sequence having at least 70% sequence identity to the amino acid sequence of SEQ ID NO:78; or (h) a VH region comprising an amino acid sequence having at least 70% sequence identity to the amino acid sequence of SEQ ID NO:31; and a VL region comprising an amino acid sequence having at least 70% sequence identity to the amino acid sequence of SEQ ID NO:79; or (i) a VH region comprising an amino acid sequence having at least 70% sequence identity to the amino acid sequence of SEQ ID NO:32; and a VL region comprising an amino acid sequence having at least 70% sequence identity to the amino acid sequence of SEQ ID NO:79; or (j) a VH region comprising an amino acid sequence having at least 70% sequence identity to the amino acid sequence of SEQ ID NO:33; and a VL region comprising an amino acid sequence having at least 70% sequence identity to the amino acid sequence of SEQ ID NO:80; or (k) a VH region comprising an amino acid sequence having at least 70% sequence identity to the amino acid sequence of SEQ ID NO:34; and a VL region comprising an amino acid sequence having at least 70% sequence identity to the amino acid sequence of SEQ ID NO:81; or (l) a VH region comprising an amino acid sequence having at least 70% sequence identity to the amino acid sequence of SEQ ID NO:35; and a VL region comprising an amino acid sequence having at least 70% sequence identity to the amino acid sequence of SEQ ID NO:82; or (m) a VH region comprising an amino acid sequence having at least 70% sequence identity to the amino acid sequence of SEQ ID NO:36; and a VL region comprising an amino acid sequence having at least 70% sequence identity to the amino acid sequence of SEQ ID NO:83; or (n) a VH region comprising an amino acid sequence having at least 70% sequence identity to the amino acid sequence of SEQ ID NO:37; and a VL region comprising an amino acid sequence having at least 70% sequence identity to the amino acid sequence of SEQ ID NO:84; or (o) a VH region comprising an amino acid sequence having at least 70% sequence identity to the amino acid sequence of SEQ ID NO:38; and a VL region comprising an amino acid sequence having at least 70% sequence identity to the amino acid sequence of SEQ ID NO:85; or (p) a VH region comprising an amino acid sequence having at least 70% sequence identity to the amino acid sequence of SEQ ID NO:39; and a VL region comprising an amino acid sequence having at least 70% sequence identity to the amino acid sequence of SEQ ID NO:86; or (q) a VH region comprising an amino acid sequence having at least 70% sequence identity to the amino acid sequence of SEQ ID NO:40; and a VL region comprising an amino acid sequence having at least 70% sequence identity to the amino acid sequence of SEQ ID NO:87.

13. The method according to claim 10, wherein the cancer is selected from: a cancer comprising cells expressing an EGFR family member, a cancer comprising cells expressing HER3, a solid tumor, breast cancer, breast carcinoma, ductal carcinoma, gastric cancer, gastric carcinoma, gastric adenocarcinoma, colorectal cancer, colorectal carcinoma, colorectal adenocarcinoma, head and neck cancer, squamous cell carcinoma of the head and neck (SCCHN), lung cancer, lung adenocarcinoma, squamous cell lung carcinoma, ovarian cancer, ovarian carcinoma, ovarian serous adenocarcinoma, kidney cancer, renal cell carcinoma, renal clear cell carcinoma, renal cell adenocarcinoma, renal papillary cell carcinoma, pancreatic cancer, pancreatic adenocarcinoma, pancreatic ductal adenocarcinoma, cervical cancer, cervical squamous cell carcinoma, skin cancer, melanoma, esophageal cancer, esophageal adenocarcinoma, liver cancer, hepatocellular carcinoma, cholangiocarcinoma, uterine cancer, uterine corpus endometrial carcinoma, thyroid cancer, thyroid carcinoma, pheochromocytoma, paraganglioma, bladder cancer, bladder urothelial carcinoma, prostate cancer, prostate adenocarcinoma, sarcoma and thymoma.

* * * * *